(12) United States Patent
Bo et al.

(10) Patent No.: US 7,579,347 B2
(45) Date of Patent: Aug. 25, 2009

(54) VANILLOID RECEPTOR LIGANDS AND THEIR USE IN TREATMENTS

(75) Inventors: Yunxin Y. Bo, Thousand Oaks, CA (US); Partha P. Chakrabarti, Simi Valley, CA (US); Ning Chen, Thousand Oaks, CA (US); Elizabeth M. Doherty, Newbury Park, CA (US); Christopher H. Fotsch, Thousand Oaks, CA (US); Nianhe Han, Thousand Oaks, CA (US); Michael G. Kelly, Thousand Oaks, CA (US); Qingyian Liu, Camarillo, CA (US); Mark Henry Norman, Thousand Oaks, CA (US); Vassil I. Ognyanov, Thousand Oaks, CA (US); Xianghong Wang, Moorpark, CA (US); Jiawang Zhu, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/100,077

(22) Filed: Apr. 5, 2005

(65) Prior Publication Data

US 2005/0227986 A1 Oct. 13, 2005

Related U.S. Application Data

(62) Division of application No. 10/316,295, filed on Dec. 10, 2002.

(60) Provisional application No. 60/339,161, filed on Dec. 10, 2001, provisional application No. 60/344,737, filed on Dec. 21, 2001, provisional application No. 60/383,331, filed on May 22, 2002, provisional application No. 60/402,422, filed on Aug. 8, 2002.

(51) Int. Cl.
| | |
|---|---|
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |
| A61K 31/4427 | (2006.01) |
| A61K 31/4523 | (2006.01) |
| A61K 31/47 | (2006.01) |
| A61K 31/497 | (2006.01) |
| A61K 31/5377 | (2006.01) |
| A61P 29/00 | (2006.01) |
| A61P 25/04 | (2006.01) |

(52) U.S. Cl. ............................... 514/231.5; 514/252.13; 514/307; 514/311; 514/318; 514/336; 546/268.1; 546/193; 546/152; 546/139; 546/112; 546/113; 544/124; 544/360

(58) Field of Classification Search ................ 546/112, 546/113, 139, 152, 184, 193, 268.1; 514/311, 514/336, 307, 318, 231.5, 252.13; 544/124, 544/360

See application file for complete search history.

(56) References Cited

U.S. PATENT DOCUMENTS

| | | | |
|---|---|---|---|
| 3,853,561 A | 12/1974 | Reichel et al. | |
| 3,940,422 A | 2/1976 | Harita et al. | |
| 4,011,236 A | 3/1977 | Grier | |
| 4,536,346 A | 8/1985 | Shepherd et al. | ............ 260/465 |
| 4,753,934 A | 6/1988 | Nickl et al. | |
| 4,847,275 A | 7/1989 | Toda et al. | |
| 4,908,381 A | 3/1990 | Greenwald et al. | |
| 4,927,838 A | 5/1990 | Guthrie et al. | |
| 5,006,548 A * | 4/1991 | Satoh et al. | ................. 514/427 |
| 5,373,019 A | 12/1994 | Zilch et al. | .................. 514/423 |
| 5,453,421 A | 9/1995 | Atwai et al. | |
| 5,510,367 A * | 4/1996 | Cugola et al. | ............... 514/419 |

(Continued)

FOREIGN PATENT DOCUMENTS

EP 0155871 A1 9/1985

(Continued)

OTHER PUBLICATIONS

Fabio et al. J. Med. Chem. 40(6), 841-850, 1997.*

(Continued)

*Primary Examiner*—Venkataraman Balasubramanian
(74) *Attorney, Agent, or Firm*—Richard V. Person

(57) ABSTRACT

Compounds having the general structure

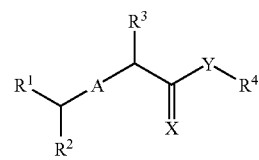

and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

9 Claims, No Drawings

U.S. PATENT DOCUMENTS

| | | | |
|---|---|---|---|
| 5,614,521 | A | 3/1997 | Naruto et al. |
| 5,731,324 | A * | 3/1998 | Fisher et al. .............. 514/320 |
| 5,776,930 | A | 7/1998 | Lynch et al. |
| 5,780,487 | A | 7/1998 | Amer |
| 5,919,776 | A | 7/1999 | Hagmann et al. ........... 514/159 |
| 5,919,811 | A * | 7/1999 | Conti et al. ................. 514/419 |
| 6,150,385 | A | 11/2000 | Thaisrivongs et al. |
| 6,362,210 | B1 | 3/2002 | Hauel et al. ................. 514/396 |
| 6,624,184 | B1 | 9/2003 | Gu et al. |
| 2003/0087922 | A1 | 5/2003 | Bethiel et al. |
| 2005/0009815 | A1 * | 1/2005 | DeVita et al. ............ 514/227.5 |

FOREIGN PATENT DOCUMENTS

| | | |
|---|---|---|
| EP | 0472116 A1 | 2/1992 |
| JP | 63 154663 | 6/1988 |
| JP | 06179660 | 6/1994 |
| WO | WO 9507887 A1 * | 3/1995 |
| WO | WO 97/43241 | 11/1997 |
| WO | WO 00/06153 | 2/2000 |
| WO | WO 00/07993 | 2/2000 |
| WO | WO 01/12621 | 2/2001 |
| WO | WO 01/21577 | 3/2001 |
| WO | WO 01/68652 | 9/2001 |
| WO | WO 01/93682 | 12/2001 |
| WO | WO 02/079197 | 10/2002 |

OTHER PUBLICATIONS

Balsamini et al. J. Med. Chem. 41(6), 808-820, 1998.*

Davis, et al. (2002) 'The Vanilloid Receptor and Vanilloid Receptor-Like Genes: A Hot Topic Getting Hotter', Celltransmissions 18(2): 3-9.

Speranza et al. (2000) 'The Michael Reaction of N-Cinnamoylazoles with Phenols. A Simple Synthesis of 4-Arylchroman-2-ones and 1-Arylbenzo[f]chroman-3-ones' Synthesis 1:123-126.

Zabicky et al. (1961) 'Studies in Absorption Spectra. The Arylacrylic System in the Infrared Region. Part II', Bull. Res. Counc. of Israel 10A:111-119.

Kibble, et al., Society for Neuroscience, "New Drugs 1" 4(12) 1319-1323 (2001).

Pau, et al., Il Farmaco, "Synthesis of 1-methyl-4-(N-aroyl)-piperidinamides with anti-inflammatory and analgesic activities" 53, 233-240 (1998).

Yeung, et al., J Med Chem., "Synthesis of N-(Carbonylamino)-1,2,3,6-tetrahydropyridines with Analgesic, Antiinflammatory ,and Hyperglycemic Activity" 25, 191-195 (1982).

Saraf, et al., Pyatigorsk Pharmaceutical Institute, "Synthesis and Antiallergic Activity in a Series of Cinnamic Acid" 598-602 (1991).

Bansal, et al., Eur J Med Chem., "Synthesis and anti-inflammatory activity of 1-acetyl-5-substitute daryl-3-(β-aminonaphthyl)-2-pyrazolines and β-(substituted aminoethyl amidonaphthaleses" 36, 81-92 (2001).

Kreutzberger, et al., Entzündungshemmende Wirkstoffe III. "(1,2) Synthese and entzündungshemmende Wirksamkeit aromatisch substituierter Benztriazole" 12, 665-667 (1975).

Rajan, et al., Bioorganic & Medicinal Chemistry Letters, "Synthesis and Evaluation of Caffeic Acid Amides as Antioxidants" 11, 215-217 (2001).

Peng, et al., The School of Pharmacy of the U of CA., "The Synthesis of Some 6-N-Substituted Amido Derivatives of 4,6-Diaminoquinaldine and a Study of their in vitro Antibacterial Activity" 78 3703-3708 (1956).

Valenzano, et al., Curr Med Chem., "Current perspectives on the therapeutic utility of VRI antagonists" 11(24) 3185 (2004).

Szallasi, et al., J of Medicinal Chem., "Vanilloid Receptor TRPVI Antagonists as the Next Generation of Painkillers. Are We Putting the Cart before the Horse?" 47(11) 2717-2723 (2004).

JP 60139646, CA 104: 33908 (1986).

Zimmerman, et al., Arch Pharm Med Chem., Phenylamino-Pyrimidine (PAP) Derivatives: A New Class of Potent and Selective Inhibitors of Protein Kinase C (PFC) 329,7, pp. 371-376 (1996).

Lipinski, et al., J. Med Chem., "Pseudosymmetry and Bioisosterism in Biaryl Pyridyl Competitive Histamine H2-Receptor Antagonists" 28, pp. 1628-1636 (1985).

Abstract—Fusco, et al., Gazz Chim Ital., "phenyl-(4-phenyl-pyridin-2-yl)-amine" 98, p. 511 (1968).

Kuzuya, et al., Chem Pharm Bull, "Reactions of 1-Unsubstituted Tautomeric 2-Pyridones with Benzyne" 33, 6, pp. 2313-2322 (1985).

Abstract—Chem Abstracts Service, "4-(4-methoxyphenyl)-2-(1-naphthalenyloxy)" (1998).

Yeung, et al., J Med Chem., "Synthesis of N-(Carbonylamino)-1,2,3,6-tetrahydropyridines with Analgesic, Antiinflammatory, and Hyperglycemic Activity" 25, pp. 191-195 (1982).

Fourchard, et al., Arzneim ForschDrugRes, "Synthesis and Pharmacological Evaluation of (Indol-3-yl)alkylamides as Potent Analgesic Agents" 51, II, pp. 814-824 (2001).

Essawi, M., Dept of Organic Chemistry, "Synthesis and analgesic activity of N-aryl/arylalkyl 3-(1-pyrrolindinyl/piperidinyl)butyramides" 54, 8, pp. 575-579 (1999).

Menciu, et al., J. Med Chem., "New N-(Pyridin-4-yl)-(indol-3-yl)acetamides and Propanamides as Antiallergic Agents" 42, 4, pp. 638-648 (1999).

Hynes, et al., J. of Med Chem., "Synthesis and Evaluation of 6-Arylacetamido-2,4-diaminoquinazolines and Related Compounds as Folic Acid Antagonists" 18, 3, pp. 263-265 (1975).

Peng, et al., J. of the Am. Chem Soc., "The Synthesis of Some 6-N-Substituted Amido Derivatives of 4,6-Diaminoquinaldine and a Study of their in vitro Antibacterial Activity" 78, pp. 3703-3708 (1956).

Abstract—Renzi, et al., Gazz Chim Ital., 3-pyrrolidino-propionic acid-(2,3-dihydro-benzo[1,4]dionix-6-ylamide) 86, pp. 1362-1364 (1956).

Abstract—Bird, et al., J. Chem. Soc. Perkin Trans., "N,3-Diphenyl-3-(4-totyl)propionamid" 1 pp. 2664-2667 (1973).

Abstract—Hardman, J. Am. Chem. Soc., "3-(2-hydroxy-[1]naphthyl)-propionic acid-[1]naphthylamide" 70, p. 2119 (1948).

Abstract—Gaivoronskaya, et al., Pharm Chem J., "N-(1,2,5-trimethylpiperidyl-4)-propanilide" 18, 9 pp. 615-618 (1984).

Abstract—Knunjanz, et al., Acac Sci USSR Div Chem Sci., "3-Brom-3-phenyl-propionsaeure-(naphthyl-(2)-amid)" p. 494 (1960).

Abstract—Smith, Helv Chim Acta, 3-pyrrolidino-butyric acid-(4-chloro-anilide) 42, pp. 1764-1770 (1959).

* cited by examiner

VANILLOID RECEPTOR LIGANDS AND THEIR USE IN TREATMENTS

The present invention is a divisional and claims the benefit of U.S. application Ser. No. 10/316,295 filed on Dec. 10, 2002, U.S. Provisional Application Nos. 60/339,161 filed Dec. 10, 2001, 60/344,737, filed Dec. 21, 2001, 60/383,331, filed May 22, 2002 and 60/402,422, filed Aug. 8, 2002, which are hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resinferatoxin (exogenous activators of VR1), produce desensitization and they have been used for many proof of concept studies in in vivo models of disease (Holzer, 1991, Dray 1992, Szallasi and Blumberg 1999).

VR1 agonists or antagonists have use as analgesics for the treatment of pain of various genesis or aetiology, for example acute, inflammatory and neuropathic pain, dental pain and headache, particularly vascular headache such as migraine, cluster headache and mixed vascular syndromes as well as non-vascular, tension headache. They are also useful as anti-inflammatory agents for the treatment of inflammatory diseases or conditions, for example the treatment of arthritis and rheumatic diseases, osteoarthritis, inflammatory bowel disorders, inflammatory eye disorders (e.g. uvetis), inflammatory or unstable bladder disorders (e.g. cystitis and urinary incontinence), psoriasis and skin complaints with inflammatory components, as well as other chronic inflammatory conditions.

They are, in particular, useful in the treatment of inflammatory pain and associated hyperalgesia and allodynia. They are also useful in the treatment of neuropathic pain and associated hyperalgesia and allodynia, e.g. trigeminal or herpetic neuralgia, diabetic neuropathy pain, causalgia, sympathetically maintained pain and deafferentation syndromes such as brachial plexus avulsion.

They are also indicated for the use in the prophylactic or curative treatment of asthma, of epithelial tissue damage or dysfunction, e.g. spontaneous lesions, of herpes simplex, and in the control of disturbances of visceral motility at respiratory, genitourinary, gastrointestinal or vascular e.g. for treating wounds, burns, allergic skin reactions, pruritis and vitiligo, for the prophylactic or curative treatment of gastrointestinal disorders such as gastric ulceration, duodenal ulcers, inflammatory bowel disease and diarrhea, gastric lesions induced by necrotising agents, for example ethanol or chemotherapeutic agents, hair growth, for the treatment of vasomotor or allergic rhinitis and for the treatment of bronchial disorders or bladder disorders, such as bladder hyperreflexia.

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J., Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201 Hwang-S W. Cho-H. Kwak-J. Lee-S Y. Kang-C J. Jung-J. Cho-S.

Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H. Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Analogously, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure

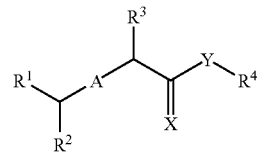

or a pharmaceutically acceptable salt thereof, wherein A, $R^1$, $R^2$, $R^3$, $R^4$, X and Y are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

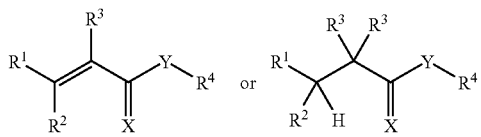

wherein: R¹ is 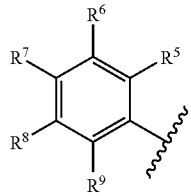

or a naphthyl or saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the naphthyl, heterocycle or fused phenyl ring is substituted by 0, 1, 2 or 3 substituents independently selected from $R^5$, $R^6$ and $R^7$;

$R^2$ is H, hydroxy, halo, $C_{1-6}$alkyl substituted by 0, 1 or 2 substituents selected from $R^{10}$,

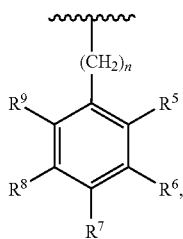

or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$;

or $R^1$ and $R^2$ together are

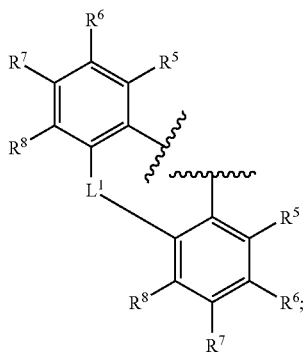

$R^3$ is H or $C_{1-4}$alkyl; or $R^1$ and $R^3$ together are

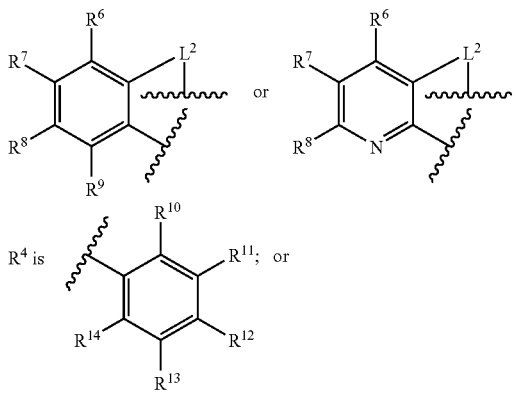

$R^4$ is 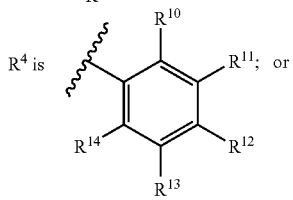

$R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $C_{1-9}$alkyl, $C_{1-4}$haloalkyl, halo, nitro, cyano, —$OR^a$, —$S(=O)_nC_{1-6}$alkyl, —O—$C_{1-4}$haloalkyl, —O—$C_{1-6}$alkyl$NR^aR^a$, —O—$C_{1-6}$alkyl$OR^a$, —O—$C_{1-6}$alkyl$C(=O)OR^a$, —$NR^aR^a$, —$NR^a$—$C_{1-4}$haloalkyl, —$NR^aC_{1-6}$alkyl$NR^aR^a$, —$NR^a$—$C_{1-6}$alkyl$OR^a$, —C(=O)$C_{1-6}$alkyl, —C(=O)O$C_{1-6}$alkyl, —OC(=O)$C_{1-6}$alkyl, —C(=O)$NR^aC_{1-6}$alkyl and —$NR^aC(=O)C_{1-6}$alkyl; or $R^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, $OR^a$, $NR^aR^a$, $C_{1-6}$alkyl and $C_{1-3}$haloalkyl; and saturated carbon atoms may be additionally substituted by =O; except that when $R^1$ is 4-chlorophenyl, 3-bromophenyl, 3-nitrophenyl, 2-nitro-3-chlorophenyl, 3,4-methylenedioxyphenyl, 3-methylthiophenyl or 2,3,4-methoxyphenyl, then $R^4$ is not phenyl substituted by 1 or 2 substituents selected from halo and $C_{1-4}$alkyl; and $R^1$ and $R^4$ are not both 3,4-methylenedioxyphenyl; and when $R^1$ is 4-trifluoromethylphenyl, then $R^4$ is not pyridinyl, 2-methyl-4-aminoquinolinyl or 3,3-dimethyl-1,3-dihydro-indol-2-on-6-yl;

$R^5$ is independently, at each instance, H, $C_{1-9}$alkyl, $C_{1-4}$haloalkyl, halo, nitro, cyano, —O$C_{1-6}$alkyl, —O—$C_{1-4}$haloalkyl, —O—$C_{1-6}$alkyl$NR^aR^a$, —O—$C_{1-6}$alkyl$OR^a$, —$NR^aR^a$, —$NR^a$—$C_{1-4}$haloalkyl, —$NR^a$—$C_{1-6}$alkyl$NR^aR^a$ or —$NR^a$—$C_{1-6}$alkyl$OR^a$; or $R^5$ is a saturated or unsaturated 5- or 6-membered ring heterocycle containing 1, 2 or 3 atoms selected from O, N and S;

$R^6$ is independently, at each instance, H, $C_{1-9}$alkyl, $C_{1-4}$haloalkyl, halo, nitro, cyano, —O$C_{1-6}$alkyl, —O—$C_{1-4}$haloalkyl, —O—$C_{1-6}$alkyl$NR^aR^a$, —O—$C_{1-6}$alkyl$OR^a$, —$NR^aR^a$, —$NR^a$—$C_{1-4}$haloalkyl, —$NR^a$—$C_{1-6}$alkyl$NR^aR^a$ or —$NR^a$—$C_{1-6}$alkyl$OR^a$; or $R^5$ and $R^6$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the bridge are substituted by 0, 1, 2 or 3 substituents selected from halo, $C_{1-6}$alkyl, (=O), —O$C_{1-6}$alkyl, —$NR^aC_{1-6}$alkyl, —$C_{1-6}$ alkylOR$^a$ and $C_{1-6}$alkylNR$^a$R$^a$, and the available N atoms of the bridge are substituted by R$^a$, —$C_{1-6}$alkylOR$^a$ or $C_{1-6}$alkyNR$^a$R$^a$;

R$^7$ is independently, at each instance, H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^a$R$^a$, —O—$C_{1-6}$alkylOR$^a$, —NR$^a$R$^a$, —NR$^a$—$C_{1-4}$haloalkyl, —NR$^a$—$C_{1-6}$alkylNR$^a$R$^a$ or —NR$^a$—$C_{1-6}$alkylOR$^a$;

R$^8$ is independently, at each instance, H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^a$R$^a$, —O—$C_{1-6}$alkylOR$^a$, —NR$^a$R$^a$, —NR$^a$—$C_{1-4}$haloalkyl, —NR$^a$—$C_{1-6}$alkylNR$^a$R$^a$ or —NR$^a$C$_{1-6}$alkylOR$^a$; or R$^7$ and R$^8$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the bridge are substituted by 0, 1, 2 or 3 substituents selected from halo, $C_{1-6}$alkyl, (=O), —O—$C_{1-6}$alkyl, —NR$^a$C$_{1-6}$alkyl, —$C_{1-6}$alkylOR$^a$ and $C_{1-6}$alkylNR$^a$R$^a$, and the available N atoms of the bridge are substituted by R$^a$, —$C_{1-6}$alkylOR$^a$ or $C_{1-6}$alkylNR$^a$R$^a$;

R$^9$ is independently, at each instance, H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^a$R$^a$, —O—$C_{1-6}$alkylOR$^a$, —NR$^a$R$^a$, —NR$^a$—$C_{1-4}$haloalkyl, —NR$^a$C$_{1-6}$alkylNR$^a$R$^a$ or —NR$^a$—$C_{1-6}$alkylOR$^a$;

R$^{10}$ is independently, at each instance, H, $C_{1-9}$alkyl, —$C_{1-3}$alkylOR$^a$, $C_{1-4}$haloalkyl, halo, nitro, cyano, —OR$^a$, —S(=O)$_n$$C_{1-6}$alkyl, —O—$C_{1-4}$haloalkyl, —O—$C_{1-6}$alkylNR$^a$R$^a$, —O—$C_{1-6}$alkylOR$^a$, —O—$C_{1-6}$alkylC(=O)OR$^a$, —NR$^a$R$^a$, —NR$^a$—$C_{1-4}$haloalkyl, —NR$^a$—$C_{1-6}$alkylNR$^a$R$^a$, —NR$^a$—$C_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl or —NR$^a$C(=O)$C_{1-6}$alkyl;

R$^{11}$ is independently, at each instance, H, $C_{1-9}$alkyl, —$C_{1-3}$alkylOR$^a$ $C_{1-4}$haloalkyl, halo, nitro, cyano, —OR$^a$, —S(=O)$_n$$C_{1-6}$alkyl, —O—$C_{1-4}$haloalkyl, —O—$C_{1-6}$alkylNR$^a$R$^a$, —O—$C_{1-6}$alkylR$^c$, —O—$C_{1-6}$alkylOR$^a$, —O—$C_{1-6}$alkylC(=O)OR$^a$, —NR$^a$R$^a$, —NR$^a$—$C_{1-4}$haloalkyl, —NR$^a$—$C_{1-6}$alkylNR$^a$R$^a$, —NR$^a$—$C_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl or —NR$^a$C(=O)$C_{1-6}$alkyl; or R$^{10}$ and R$^{11}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by —H, =O, —OR$^a$, $C_{1-6}$alkylOR$^a$, —$C_{1-6}$alkyl, —NR$^a$R$^a$, —$C_{1-6}$alkylNR$^a$R$^a$, —C(=O)OR$^a$, —C(=O)NR$^a$R$^a$, —$C_{1-3}$alkylC(=O)OR$^a$, —$C_{1-3}$alkylC(=O)NR$^a$R$^a$, —OC(=O)$C_{1-6}$alkyl, —NR$^a$C(=O)$C_{1-6}$alkyl, —$C_{1-3}$alkylOC(=O)$C_{1-6}$alkyl or —$C_{1-3}$alkylNR$^a$C(=O)$C_{1-6}$alkyl, and any nitrogen atoms in the bridge are substituted by H, —$C_{1-6}$alkylOR$^a$, —$C_{1-6}$alkyl, —$C_{1-6}$alkylNR$^a$R$^a$, —$C_{1-3}$alkylC(=O)OR$^a$, —$C_{1-3}$alkylC(=O)NR$^a$R$^a$, —$C_{1-3}$alkylOC(=O)$C_{1-6}$alkyl, —$C_{1-3}$alkylNR$^a$C(=O)$C_{1-6}$alkyl, —C(=O)R$^c$ or —$C_{1-3}$alkylR$^c$; wherein if R$^{10}$, R$^{12}$, R$^{13}$ and R$^{14}$ are all H, then R$^{11}$ is not —O—$C_{1-6}$alkylNR$^a$R$^a$ or —O—$C_{1-6}$alkylOR$^a$;

R$^{12}$ is independently, at each instance, H, $C_{1-9}$alkyl, —$C_{1-3}$alkylOR$^a$, $C_{1-4}$haloalkyl, halo, nitro, cyano, —OR$^a$, —S(=O)$_n$$C_{1-6}$alkyl, —O—$C_{1-4}$haloalkyl, —O—$C_{1-6}$alkyl-NR$^a$R$^a$, —O—$C_{1-6}$alkylOR$^a$, —O—$C_{1-6}$alkylC(=O)OR$^a$, —NR$^a$R$^a$, —NR$^a$—$C_{1-4}$haloalkyl, —NR$^a$—$C_{1-6}$alkylNR$^a$R$^a$, —NR$^a$—$C_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl or —NR$^a$C(=O)$C_{1-6}$alkyl; or R$^{11}$ and R$^{12}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, =O, —OR$^a$, —$C_{1-6}$alkylOR$^a$, —$C_{1-6}$alkyl, —NR$^a$R$^a$, 13 $C_{1-6}$alkylNR$^a$R$^a$, —C(=O)OR$^a$, —C(=O)NR$^a$R$^a$, —$C_{1-3}$alkylC(=O)OR$^a$, —$C_{1-3}$alkylC(=O)NR$^a$R$^a$, —OC(=O)$C_{1-6}$alkyl, —NR$^a$C(=O)$C_{1-6}$alkyl, —$C_{1-3}$alkylOC(=O)$C_{1-6}$alkyl or —$C_{1-3}$alkylNR$^a$C(=O)$C_{1-6}$alkyl, and any nitrogen atoms in the bridge are substituted by H, —$C_{1-6}$alkylOR$^a$, —$C_{1-6}$alkyl, —$C_{1-6}$alkylNR$^a$R$^a$, —$C_{1-3}$alkylC(=O)OR$^a$, —$C_{1-3}$alkylC(=O)NR$^a$R$^a$, —$C_{1-3}$alkylOC(=O)$C_{1-6}$alkyl, —$C_{1-3}$alkylNR$^a$C(=O)$C_{1-6}$alkyl, —C(=O)R$^c$ or —$C_{1-3}$alkylR$^c$;

when R$^1$ is 4-$C_{1-6}$alkylphenyl or 2,4-dimethylphenyl, then R$^{11}$ is $C_{1-9}$alkyl, $C_{1-4}$haloalkyl, halo, nitro, cyano, —OR$^a$, S(=O)OC$_{1-6}$alkyl, —O—$C_{1-4}$haloalkyl, —O—$C_{1-6}$alkylNR$^a$R$^a$, —O—$C_{1-6}$alkylR$^a$, —O—$C_{1-6}$alkylOR$^a$, —O—$C_{1-6}$alkylC(=O)OR$^a$, —NR$^a$R$^a$, —N$^a$—$C_{1-4}$haloalkyl, —NR$^a$—$C_{1-6}$alkylNR$^a$R$^a$, —NR$^a$—$C_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl or —NR$^a$C(=O)$C_{1-6}$alkyl; or R$^{10}$ and R$^{11}$ together are -L$^3$-NR$^a$—, respectively, or -L$^4$-O—, respectively; or R$^{11}$ and R$^{12}$ are —NR$^a$L$^3$-, -L$^3$-NR$^a$—, —O-L$^4$- or -L$^4$-O—; or R$^{12}$ is —NR$^a$R$^b$; or R$^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, OR$^a$, NR$^a$R$^a$, $C_{1-6}$alkyl and $C_{1-3}$haloalkyl; and saturated carbon atoms may be additionally substituted by =O; or R$^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 1, 2 or 3 substituents independently selected from $C_{2-9}$alkyl, $C_{1-4}$haloalkyl, halo, nitro, cyano, —OR$^a$, —S(=O)$_n$$C_{1-6}$alkyl, —O—$C_{1-4}$haloalkyl, —O—$C_{1-6}$alkyl-NR$^a$R$^a$, —O—$C_{1-6}$alkylOR$^a$, —O—$C_{1-6}$alkylC(=O)OR$^a$, —NR$^a$R$^a$, —NR$^a$—$C_{1-4}$haloalkyl, —NR$^a$—$C_{1-6}$alkylNR$^a$R$^a$, —NR$^a$C$_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl and —NR$^a$C(=O)$C_{1-6}$alkyl;

R$^{13}$ is independently, at each instance, H, $C_{1-9}$alkyl, —$C_{1-3}$alkylOR$^a$, $C_{1-4}$haloalkyl, halo, nitro, cyano, —OR$^a$, —S(=O)$_n$$C_{1-6}$alkyl, —O—$C_{1-4}$haloalkyl, —O—$C_{1-6}$alkyl-NR$^a$R$^a$, —O—$C_{1-6}$alkylOR$^a$, —O—$C_{1-6}$alkylC(=O)OR$^a$, —NR$^a$R$^a$, —NR$^a$C$_{1-4}$haloalkyl, —NR$^a$—$C_{1-6}$alkylNR$^a$R$^a$, —NR$^a$—$C_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl or —NR$^a$C(=O)$C_{1-6}$alkyl;

R$^{14}$ is independently, at each instance, H, $C_{1-9}$alkyl, —$C_{1-3}$alkylOR$^a$, $C_{1-4}$haloalkyl, halo, nitro, cyano, —OR$^a$, —S(=O)$_n$$C_{1-6}$alkyl, —O—$C_{1-4}$haloalkyl, —O—$C_{1-6}$alkyl-NR$^a$R$^a$, —O—$C_{1-6}$alkylOR$^a$, —O—$C_{1-6}$alkylC(=O)OR$^a$, —NR$^a$R$^a$, —NR$^a$—$C_{1-4}$haloalkyl, —NR$^a$—$C_{1-6}$alkylNR$^a$R$^a$, —NR$^a$—$C_{1-6}$alkylOR$^a$, —C(=O)$C_{1-6}$alkyl, —C(=O)OC$_{1-6}$alkyl, —OC(=O)$C_{1-6}$alkyl, —C(=O)NR$^a$C$_{1-6}$alkyl or —NR$^a$C(=O)$C_{1-6}$alkyl;

R$^a$ is independently, at each instance, H, phenyl, benzyl or $C_{1-6}$alkyl;

$R^b$ is H, $C_{1-6}$alkyl, —C(=O)$C_{1-6}$alkyl, $C_{1-6}$alkyl-O—$R^a$;

$R^c$ is phenyl substituted by 0, 1 or 2 groups selected from halo, $C_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-3}$haloalkyl, —OR$^a$ and —NR$^a$R$^a$;

$L^1$ is a bond, —CH$_2$CH$_2$— or —CH=CH—;

$L^2$ is NR$^a$, O, S(=O)$_n$, —N=CH—, —CH$_2$NR$^a$—, —CH=N— or —NR$^a$CH$_2$—;

$L^3$ is a 2- or 3-atom, saturated or unsaturated, bridge containing 1, 2 or 3 carbon atoms and 0, 1 or 2 atoms independently selected from O, N and S, wherein the each of the carbon atoms in the bridge is substituted by H, =O, —OR$^a$, —C$_{1-6}$alkylOR, —C$_{1-6}$alkyl, —NR$^a$R$^a$, —C$_{1-6}$alkylNR$^a$R$^a$, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

$L^4$ is a 2- or 3-atom, saturated or unsaturated, bridge containing 1, 2 or 3 carbon atoms and 0 or 1 atoms independently selected from O, N and S, wherein at least one of the carbon atoms in the bridge is substituted by =O, —OR$^a$, —C$_{1-6}$alkylOR$^a$, —C$_{1-6}$alkyl, —NR$^a$R$^a$, —C$_{1-6}$alkylNR$^a$R$^a$, —C(=O)C$_{1-6}$alkyl, —C(=O)NR$^a$R$^a$, —C$_{1-3}$alkylC(=O)OR$^a$, —C$_{1-3}$alkylC(=O)NR$^a$C$_{1-6}$alkyl, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

X is O, S or NR$^a$; or X and R$^2$ together are =N—CH=CH—, =C—O—, =C—S—, or =C—NR$^a$—;

Y is NH or O; and n is independently, at each instance, 0, 1 or 2; with the proviso that when $R^1$ is 4-chlorophenyl, then $R^4$ is not 3-methoxyphenyl.

In another embodiment, in conjunction with the novel compound embodiments above and below, $R^1$ is

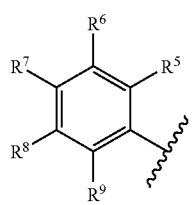

or a naphthyl or saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the naphthyl, heterocycle or fused phenyl ring is substituted by 0, 1, 2 or 3 substituents independently selected from $R^5$, $R^6$ and $R^7$;

$R^2$ is H, hydroxy, halo, $C_{1-6}$alkyl substituted by 0, 1 or 2 substituents selected from $R^{10}$,

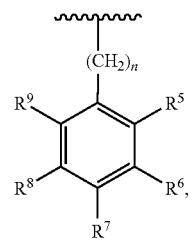

or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$; and $R^3$ is H or $C_{1-4}$alkyl.

In another embodiment, in conjunction with the novel compound embodiments above and below, $R^1$ is

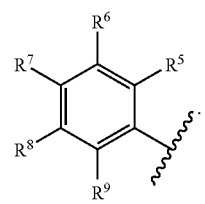

In another embodiment, in conjunction with the novel compound embodiments above and below, $R^7$ is independently, at each instance, $C_{2-9}$alkyl or $C_{1-4}$haloalkyl.

In another embodiment, in conjunction with the novel compound embodiments above and below, $R^1$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the novel compound embodiments above and below, $R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the novel compound embodiments above and below, $R^2$ is

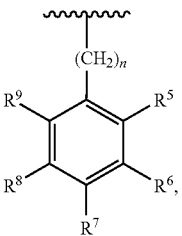

or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the novel compound embodiments above and below, $R^2$ is

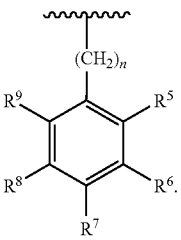

In another embodiment, in conjunction with the novel compound embodiments above and below, $R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the novel compound embodiments above and below, $R^1$ and $R^2$ together are

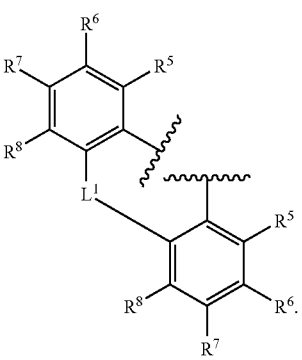

In another embodiment, in conjunction with the novel compound embodiments above and below, $R^1$ and $R^3$ together are

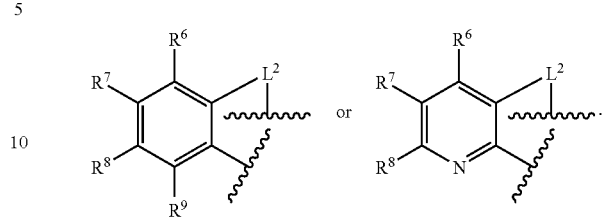

In another embodiment, in conjunction with the novel compound embodiments above and below, X and $R^2$ together are =N—CH=CH—, =C—O—, =C—S—, or =C—NR$^a$—.

In another embodiment, in conjunction with the novel compound embodiments above and below, $R^4$ is

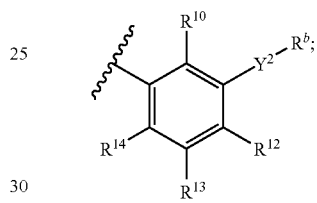

$R^b$ is H, $C_{1-6}$alkyl, —C(=O)$C_{1-6}$alkyl, $C_{1-6}$alkyl-O—$R^a$; and $Y^2$ is —NR$^a$— or —O—.

In another embodiment, in conjunction with the novel compound embodiments above and below, $R^4$ is

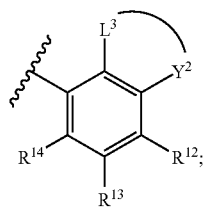

$L^3$ is a 2- or 3-atom, saturated or unsaturated, bridge containing 1, 2 or 3 carbon atoms and 0 or 1 atoms independently selected from O, N and S, wherein the each of the carbon atoms in the bridge is substituted by H, =O, —OR$^a$, —$C_{1-6}$alkylOR$^a$, —$C_{1-6}$alkyl, —NR$^a$R$^a$, —$C_{1-6}$alkylNR$^a$R$^a$, —C(=O)OR$^a$, —C(=O)NR$^a$R$^a$, —$C_{1-3}$alkylC(=O)OR$^a$, —$C_{1-3}$alkylC(=O)NR$^a$R$^a$, —OC(=O)$C_{1-6}$alkyl, —NR$^a$C(=O)$C_{1-6}$alkyl, —$C_{1-3}$alkylOC(=O)$C_{1-6}$alkyl or —$C_{1-3}$alkylNR$^a$C(=O)$C_{1-6}$alkyl, and any nitrogen atoms in the bridge are substituted by H, —$C_{1-6}$alkylOR$^a$, —$C_{1-6}$alkyl, —$C_{1-6}$alkylNR$^a$R$^a$, —$C_{1-3}$alkylC(=O)OR$^a$, —$C_{1-3}$alkylC(=O)NR$^a$R$^a$, —$C_{1-3}$alkylOC(=O)$C_{1-6}$alkyl, —$C_{1-3}$alkylNR$^a$C(=O)$C_{1-6}$alkyl, —C(=O)R$^c$ or —$C_{1-3}$alkylR$^c$;

$R^b$ is H, $C_{1-6}$alkyl, —C(=O)$C_{1-6}$alkyl, $C_{1-6}$alkyl-O—$R^a$; and $Y^2$ is —NR$^b$— or —O—.

In another embodiment, in conjunction with the novel compound embodiments above and below, R⁴ is

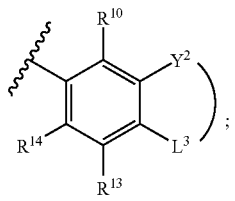

L³ is a 2- or 3-atom, saturated or unsaturated, bridge containing 1, 2 or 3 carbon atoms and 0, 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —NR$^a$R$^a$, —C$_{1-6}$alkylNR$^a$R$^a$, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y² is —NR$^b$— or —O—.

In another embodiment, in conjunction with the novel compound embodiments above and below, R⁴ is

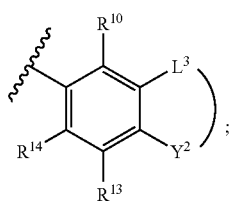

L³ is a 2- or 3-atom, saturated or unsaturated, bridge containing 1, 2 or 3 carbon atoms and 0, 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —NR$^a$R$^a$, —C$_{1-6}$alkylNR$^a$R$^a$, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y² is —NR$^b$ or —O—.

In another embodiment, in conjunction with the novel compound embodiments above and below, R⁴ is

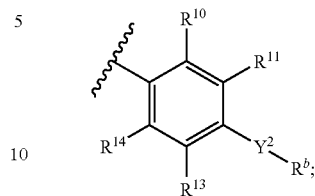

R$^b$ is H, C$_{1-6}$alkyl, —C(=O)C$_{1-6}$alkyl, C$_{1-6}$alkyl-O—R$^a$; and

Y² is —NR$^a$— or —O—.

In another embodiment, in conjunction with the novel compound embodiments above and below, R⁴ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, OR$^a$, NR$^a$R$^a$, C$_{1-6}$alkyl and C$_{1-3}$haloalkyl; and saturated carbon atoms may be additionally substituted by =O.

In another embodiment, in conjunction with the novel compound embodiments above and below, R⁴ is

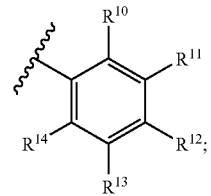

R¹⁰ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkyl-NR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;

R¹¹ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkyl-NR$^a$R$^a$, —O—C$_{1-6}$alkylR$^c$, —O—C$_{1-6}$alkylOR$^a$, OC$_{1-6}$alkylC(=O)OR$^a$, —NR$^a$R$^a$, —NR$^a$—C$_{1-4}$haloalkyl, —NR$^a$C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; C$_{1-6}$alkylNR$^a$R$^a$;

R¹² is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkyl-NR$^a$R$^a$, —O—C$_{1-6}$alkylOR$^a$, —O—C$_{1-6}$alkylC(=O)OR$^a$, —NR$^a$R$^a$, —NR$^a$C$_{1-4}$haloalkyl, —NR$^a$C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;

R¹³ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkyl-NR$^a$R$^a$, —O—C$_{1-6}$alkylOR$^a$, —O—C$_{1-6}$alkylC(=O)OR$^a$, —NR$^a$R$^a$, —NR$^a$C$_{1-4}$haloalkyl, —NR$^a$C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and R$^{14}$ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkyl-NR$^a$R$^a$, —O—C$_{1-6}$alkylOR$^a$, —O—C$_{1-6}$alkylC(=O)OR$^a$, —NR$^a$R$^a$, —NR$^a$C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; wherein one of R$^{10}$ and R$^{12}$ is not H.

In another embodiment, in conjunction with the novel compound embodiments above and below, R$^4$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents selected from halo, C$_{1-4}$haloalkyl, —OR$^a$ and —NR$^a$R$^a$.

Another aspect of the invention relates to a compound having the structure:

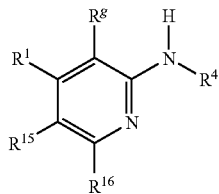

or any pharmaceutically-acceptable salt thereof, wherein:
n is independently, at each instance, 0, 1 or 2.
R$^1$ is

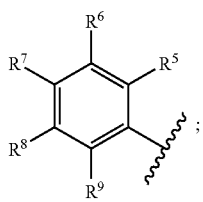

or R$^1$ is a naphthyl substituted by 0, 1, 2 or 3 substituents independently selected from R$^5$; or R$^1$ is R$^e$ substituted by 1, 2 or 3 substituents independently selected from R$^5$;

R$^{15}$ is, independently, in each instance, R$^{10}$, C$_{1-8}$alkyl substituted by 0, 1 or 2 substituents selected from R$^{10}$, —(CH$_2$), phenyl substituted by 0, 1, 2 or 3 substituents independently selected from R$^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{10}$;

R$^{16}$ is, independently, in each instance, H, halo, —NH$_2$, —NHC$_{1-3}$alkyl, —N(C$_{1-3}$alkyl)C$_{1-3}$alkyl or C$_{1-3}$alkyl;

R$^4$ is

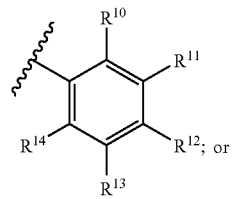

R$^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from C$_{1-9}$alkyl, C$_{1-4}$haloalkyl, halo, nitro, cyano, oxo, —OR$^d$, —S(=O)$_n$C$_{1-6}$alkyl, —OC$_{1-4}$haloalkyl, —OC$_{2-6}$alkylNR$^d$R$^d$, —OC$_{2-6}$alkylOR$^d$, —OC$_{1-6}$alkylC(=O)OR$^d$, —NR$^d$R$^d$, —NR$^d$C$_{1-4}$C$_{1-4}$haloalkyl, —NR$^d$C$_{2-6}$alkylNR$^d$R$^d$, —NR$^d$C$_{2-6}$alkylOR$^d$, —C(=O)C$_{1-6}$alkyl, —C(=O)OC$_{1-6}$alkyl, —OC(=O)C$_{1-6}$alkyl, —C(=O)NR$^d$C$_{1-6}$alkyl and —NR$^d$C(=O)C$_{1-6}$alkyl; and saturated carbon atoms may be additionally substituted by =O; and any nitrogen atoms in the bridge are substituted by H, —C$_{1-6}$alkylOR$^d$, —C$_{1-6}$alkyl, —C$_{1-6}$alkylNR$^d$R$^d$, —C$_{1-3}$alkylC(=O)OR$^d$, —C$_{1-3}$alkylC(=O)NR$^d$R$^d$, —C$_{1-3}$alkylOC(=O)C$_{1-6}$alkyl, —C$_{1-3}$alkylNR$^d$C(=O)C$_{1-6}$alkyl, —C(=O)R$^f$ or —C$_{1-3}$alkylR$^f$; or R$^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, OR$^d$, NR$^d$R$^d$, C$_{1-6}$alkyl and C$_{1-3}$haloalkyl; and saturated carbon atoms may be additionally substituted by =O; but in no instance is R$^4$ 3,5-ditrifluoromethylphenyl or 3-trifluoromethyl-4-fluorophenyl;

R$^5$ is independently, at each instance, H, C$_{1-5}$alkyl, C$_{1-4}$haloalkyl, halo, nitro, cyano, —OC$_{1-6}$alkyl, —OC$_{1-4}$haloalkyl, —OC$_{2-6}$alkylNR$^d$R$^d$, —OC$_{2-6}$alkylOR$^d$, —NR$^d$R$^d$, —NR$^d$C$_{1-4}$haloalkyl, —NR$^d$C$_{2-6}$alkylNR$^d$R$^d$, —NR$^d$C$_{2-6}$alkylOR$^d$, naphthyl, —CO$_2$(C$_{1-6}$alkyl), —C(=O)(C$_{1-6}$alkyl), —C(=O)NR$^d$R$^d$, —NR$^d$C(=O)R$^d$, —NR$^d$C(=O)NR$^d$R$^d$, —NR$^d$CO$_2$(C$_{1-6}$alkyl), —C$_{1-8}$alkylOR$^d$, —C$_{1-6}$alkylNR$^d$R$^d$, —S(=O)$_n$(C$_{1-6}$alkyl), —S(=O)$_2$NR$^d$R$^d$, —NR$^d$S(=O)$_2$(C$_{1-6}$alkyl), —OC(=O)NR$^d$R$^d$, a phenyl ring substituted with 0, 1, 2, or 3 substituents independently selected from R$^{10}$; or R$^5$ is a saturated or unsaturated 5- or 6-membered ring heterocycle containing 1, 2 or 3 atoms selected from O, N and S, substituted with 0, 1, 2, or 3 substituents independently selected from R$^{10}$;

R$^6$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylNR$^d$R$^d$, —OC$_{2-6}$alkylOR$^d$, —NR$^d$R$^d$, —NR$^d$C$_{1-4}$haloalkyl, —NR$^d$C$_{2-6}$alkylNR$^d$R$^d$ or —NR$^d$C$_{2-6}$alkylOR$^d$, —C$_{1-8}$alkylOR$^d$, —C$_{1-6}$alkylNR$^d$R$^d$, —S(C$_{1-6}$alkyl), a phenyl ring substituted with 1, 2, or 3 substituents independently selected from R$^{10}$; or R$^6$ is a saturated or unsaturated 5- or 6-membered ring heterocycle containing 1, 2 or 3 atoms selected from O, N and S substituted with 0, 1, 2, or 3 substituents independently selected from R$^{10}$;

R$^7$ is independently, at each instance, H, C$_{1-8}$alkyl, C$_{1-4}$haloalkyl, halo, —OC$_{1-6}$alkyl, —OC$_{1-4}$haloalkyl, —OC$_{2-6}$ alkylNR$^d$R$^d$, —OC$_{2-6}$alkylOR$^d$, —NR$^d$R$^d$, —NR$^d$C$_{1-4}$haloalkyl, —NR$^d$C$_{2-6}$alkylNR$^d$R$^d$, —NR$^d$C$_{2-6}$alkylOR$^d$, —C$_{1-8}$alkylOR$^d$, —C$_{1-6}$alkylNR$^d$R$^d$ or —S(C$_{1-6}$alkyl); or R$^7$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^8$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylNR$^d$R$^d$, —OC$_{2-6}$alkylOR$^d$, —NR$^d$R$^d$, —NR$^d$C$_4$haloalkyl, —NR$^d$C$_{2-6}$alkylNR$^d$R$^d$, —NR$^d$C$_{2-6}$alkylOR$^d$, —C$_8$alkylOR$^d$, —C$_{1-6}$alkylNR$^d$R$^d$, —S(C$_{1-6}$alkyl), a phenyl ring substituted with 1, 2, or 3 substituents independently selected from R$^{10}$, or R$^8$ is a saturated or unsaturated 5- or 6-membered ring heterocycle containing 1, 2 or 3 atoms selected from O, N and S substituted with 0, 1, 2, or 3 substituents independently selected from R$^{10}$;

R$^9$ is independently, at each instance, H, C$_{1-8}$alkyl, C$_{1-4}$haloalkyl, halo, nitro, cyano, —OC$_{1-6}$alkyl, —OC$_{1-4}$haloalkyl, —OC$_{1-6}$alkylNR$^d$R$^d$, —OC$_{2-6}$alkylOR$^d$, —NR$^d$R$^d$, —NR$^d$C$_{1-4}$haloalkyl, —NR$^d$C$_{2-6}$alkylNR$^d$R$^d$ or —NR$^d$C$_{2-6}$alkylOR$^d$, —CO$_2$(C$_{1-6}$alkyl), —C(=O)(C$_{1-6}$alkyl), —C(=O)NR$^d$R$^d$, —NR$^d$C(=O)(C$_{1-6}$alkyl), —NR$^d$C(=O)NR$^d$R$^d$, —NR$^d$CO$_2$(C$_{1-6}$alkyl), —C$_{1-8}$alkylOR$^d$, —C$_{1-6}$alkylNR$^d$R$^d$, —S(=O)$_n$(C$_{1-6}$alkyl), —S(=O)$_2$NR$^d$R$^d$, —NR$^d$S(=O)$_2$(C$_{1-6}$alkyl), —OC(=O)NR$^d$R$^d$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl; wherein at least one of R$^5$, R$^6$, R$^7$, R$^8$ and R$^9$ is C$_{1-8}$alkyl, C$_{1-4}$haloalkyl, halo, —OC$_{1-4}$haloalkyl, —OC$_{2-6}$alkylNR$^d$R$^d$, —OC$_{2-6}$alkylOR$^d$, —NR$^d$C$_{1-4}$haloalkyl, —NR$^d$C$_{2-6}$alkylNR$^d$R$^d$, —NR$^d$C$_{2-6}$alkylOR$^d$, —C$_{1-8}$alkylOR$^d$, —C$_{1-6}$alkylNR$^d$R$^d$ or —S(C$_{1-6}$alkyl);

R$^{10}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^d$R$^d$, —C(=NR$^d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-8}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^d$R$^d$, —C(=NR$^d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-18}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^d$R$^d$, —C(=NR$^d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-8}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$;

R$^{11}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^d$R$^d$, —C(=NR$_d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-18}$alkyl), —S(=O)$_2$N(R$^d$)C(=O)O(C$_{1-8}$alkyl), —S(=O)$_2$N(R$^d$)C(=O)NR$^d$R$^d$, —NR$_d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^d$R$^d$, —C(=NR$^d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-18}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{11}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^d$R$^d$, C(=NR$^d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-8}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{10}$ and R$^{11}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, =O, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$, and any nitrogen atoms in the bridge are substituted by H, —$C_{1-6}$alkylOR$^d$, —$C_{1-6}$alkyl, —$C_{1-6}$alkylNR$^d$R$^d$, —$C_{1-3}$alkylC(=O)OR$^d$, —$C_{1-3}$alkylC(=O)NR$^d$R$^d$, —$C_{1-3}$alkylOC(=O)$C_{1-6}$alkyl, —$C_{1-3}$alkylNR$^d$C(=O)$C_{1-6}$alkyl, —C(=O)R$^f$ or —$C_{1-3}$alkylR$^f$;

R$^{12}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-18}$alkyl), —S(=O)2N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-18}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{12}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; wherein if R$^{11}$ or R$^{13}$ is CF$_3$, then R$^{12}$ is not F; or R$^{11}$ and R$^{12}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, =O, $C_{1-9}$alkyl, $C_{1-4}$haloalkyl, halo, cyano, nitro, —C(=O)($C_{1-8}$ alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-8}$alkyl), —S(=O)$_2$N(R$^d$)C(=O)NR$_d$R$^d$, —NR$_d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$_d$R$^d$, —NR$^d$C$_{2-6}$alkylNR$^d$R$^d$ and —NR$^d$C$_{2-6}$alkylOR$^d$, and any nitrogen atoms in the bridge are substituted by H, —$C_{1-6}$alkylOR$^d$, —$C_{1-6}$alkyl, —$C_{1-6}$alkylNR$^d$R$^d$, —$C_{1-3}$alkylC(=O)OR$^d$, —$C_{1-3}$alkylC(=O)NR$^d$R$^d$, —$C_{1-3}$alkylOC(=O)$C_{1-6}$alkyl, —$C_{1-3}$alkylNR$^d$C(=O)$C_{1-6}$alkyl, —C(=O)R$^f$ or —$C_{1-3}$alkylR$^f$;

R$^{13}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$ alkyl), —OC(=O)NR$^d$R$^d$, —OC(=O)N(R$^d$)S(=O)$_2$($C_{1-8}$ alkyl), —OC$_{2-6}$alkylNR$^d$R$^d$, —OC$_{2-6}$alkylOR$^d$, —SR, —S(=O)($C_{1-8}$alkyl), —S(=O)$_2$($C_{1-8}$alkyl), —S(=O)$_2$NR$^d$R$^d$, —S(=O)$_2$N(R$^{d)C(=O)(C}$$_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C^{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkyNR$^d$R$^d$ and —NR$^d$C$_{2-6}$alkylOR$^d$; or R$^{13}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R)C(=O)($C_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$;

$R^{14}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or $R^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^d$)S(=O)$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-18}$alkyl), —S(=O)$_2$N(R$^d$)C(=O)O($C_{1-8}$alkyl), —S(=O)$_2$N(R$^d$)C(=O)NR$^d$R$^d$, —N$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or $R^{14}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^d$R$^d$, —C(=NR$^d$)NR$^d$R$^d$, —OR$^d$, —OC(=O)($C_{1-8}$alkyl), —OC(=O)NR$^d$R$^d$, —OC(=O)N(R$^{d)S(=O)}$$_2$($C_{1-8}$alkyl), —OC$_{2-6}$alkylNR$^d$R$^d$, —OC$_{2-6}$alkylOR$^d$, —SR$^d$, —S(=O)($C_{1-8}$alkyl), —S(=O)$_2$($C_{1-8}$alkyl), —S(=O)$_2$NR$^d$R$^d$, —S(=O)$_2$N(R$^d$)C(=O)($C_{1-8}$alkyl), —S(=O)$_2$N(R$^d$)C(=O)O($C_{1-8}$alkyl), —S(=O)$_2$N(R$^d$)C(=O)NR$^d$R$^d$, —NR$^d$R$^d$, —N(R$^d$)C(=O)($C_{1-8}$alkyl), —N(R$^d$)C(=O)O($C_{1-8}$alkyl), —N(R$^d$)C(=O)NR$^d$R$^d$, —N(R$^d$)C(=NR$^d$)NR$^d$R$^d$, —N(R$^d$)S(=O)$_2$($C_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$;

$R^d$ is independently, at each instance, H, phenyl, benzyl or $C_{1-6}$alkyl;

$R^e$ is a heterocycle selected from the group of thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, pyrazol-3-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thidiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 5,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^f$ is phenyl substituted by 0, 1 or 2 groups selected from halo, $C_{1-4}$alkyl, $C_{1-3}$haloalkyl, —$OR^d$ and —$NR^dR^d$; or $R^f$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^d$ and —$NR^dR^d$; and $R^g$ is hydrogen or —$CH_3$.

In another embodiment, in conjunction with the novel compound embodiments above and below, $R^{16}$ is halo, —$NH_2$, —$NHC_{1-3}$alkyl, —$N(C_{1-3}$alkyl$)C_{1-3}$alkyl or $C_{1-3}$alkyl.

In another embodiment, in conjunction with the novel compound embodiments above and below, $R^{10}$ is independently, at each instance, $C_{1-8}$alkyl, $C_{1-4}$haloalkyl, halo, cyano, nitro, —C(=O)($C_{1-8}$alkyl), —C(=O)O($C_{1-8}$alkyl), —C(=O)$NR^dR^d$, —C(=$NR^d$)$NR^dR^d$, —$OR^d$, —OC(=O)($C_{1-8}$alkyl), —OC(=O)$NR^dR^d$, —OC(=O)N($R^d$)S(=O)$_2$($C_{1-8}$alkyl), —$OC_{2-6}$alkyl$NR^dR^d$, —$OC_{2-6}$alkyl$OR^d$, —$SR^d$, —S(=O)($C_{1-8}$alkyl), —S(=O)$_2$($C_{1-8}$alkyl), —S(=O)$_2$$NR^dR^d$, —S(=O)$_2$N($R^d$)C(=O)($C_{1-8}$alkyl), —S(=O)$_2$N($R^d$)C(=O)O($C_{1-8}$alkyl), —S(=O)$_2$N($R^d$)C(=O)$NR^dR^d$, —$NR^dR^d$, —N($R^d$)C(=O)($C_{1-8}$alkyl), —N($R^d$)C(=O)O($C_{1-8}$alkyl), —N($R^d$)C(=O)$NR^dR^d$, —N($R^d$)C(=$NR^d$)$NR^dR^d$, —N($R^d$)S(=O)$_2$($C_{1-8}$alkyl), —N($R^d$)S(=O)$_2$$NR^dR^d$, —$NR^dC_{2-6}$alkyl$NR^dR^d$ and —$NR^dC_{2-6}$alkyl$OR^d$; or $R^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)$NR^dR^d$, —C(=$NR^d$)$NR^dR^d$, —$OR^d$, —OC(=O)($C_{1-8}$alkyl), —OC(=O)$NR^dR^d$, —OC(=O)N($R^d$)S(=O)$_2$($C_{1-8}$alkyl), —$OC_{2-6}$alkyl$NR^dR^d$, —$OC_{2-6}$alkyl$OR^d$, —$SR^d$, —S(=O)($C_{1-8}$alkyl), —S(=O)$_2$($C_{1-8}$alkyl), —S(=O)$_2$$NR^dR^d$, —S(=O)$_2$N($R^d$)C(=O)($C_{1-8}$alkyl), —S(=O)$_2$N($R^d$)C(=O)O($C_{1-8}$alkyl), —S(=O)$_2$N($R^d$)C(=O)$NR^dR^d$, —$NR^dR^d$, —N($R^d$)C(=O)($C_{1-8}$alkyl), —N($R^d$)C(=O)O($C_{1-8}$alkyl), —N($R^d$)C(=O)$NR^dR^d$, —N($R^d$)C(=$NR^d$)$NR^dR^d$, —N($R^d$)S(=O)$_2$($C_{1-8}$alkyl), —N($R^d$)S(=O)$_2$$NR^dR^d$, —$NR^dC_{2-6}$alkyl$NR^dR^d$ and —$NR^dC_{2-6}$alkyl$OR^d$; or $R^{10}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)$NR^dR^d$, —C(=$NR^d$)$NR^dR^d$, —$OR^d$, —OC(=O)($C_{1-8}$alkyl), —OC(=O)$NR^dR^d$, —OC(=O)N($R^d$)S(=O)$_2$($C_{1-8}$alkyl), —$OC_{2-6}$alkyl$NR^dR^d$, —$OC_{2-6}$alkyl$OR^d$, —$SR^d$, —S(=O)($C_{1-8}$alkyl), —S(=O)$_2$($C_{1-8}$alkyl), —S(=O)$_2$$NR^dR^d$, —S(=O)$_2$N($R^d$)C(=O)($C_{1-8}$alkyl), —S(=O)$_2$N($R^d$)C(=O)O($C_{1-8}$alkyl), —S(=O)$_2$N($R^d$)C(=O)$NR^dR^d$, —$NR^dR^d$, —N($R^d$)C(=O)($C_{1-8}$alkyl), —N($R^d$)C(=O)O($C_{1-8}$alkyl), —N($R^d$)C(=O)$NR^dR^d$, —N($R^d$)C(=$NR^d$)$NR^dR^d$, —N($R^d$)S(=O)$_2$($C_{1-8}$alkyl), —N($R^d$)S(=O)$_2$$NR^dR^d$, —$NR^dC_{2-6}$alkyl$NR^dR^d$ and —$NR^dC_{2-6}$alkyl$OR^d$.

In another embodiment, in conjunction with the novel compound embodiments above and below, $R^1$ is

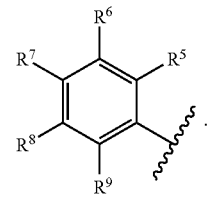

In another embodiment, in conjunction with the novel compound embodiments above and below, $R^7$ is $C_{1-5}$alkyl, halo or $C_{1-4}$haloalkyl.

In another embodiment, in conjunction with the novel compound embodiments above and below, $R^1$ is naphthyl substituted by 0, 1, 2 or 3 substituents independently selected from $R^5$.

In another embodiment, in conjunction with the novel compound embodiments above and below, $R^1$ is $R^e$ substituted by 0, 1, 2 or 3 substituents independently selected from $R^5$.

In another embodiment, in conjunction with the novel compound embodiments above and below, $R^1$ is $R^e$ substituted by 1, 2 or 3 substituents independently selected from $R^5$.

In another embodiment, in conjunction with the novel compound embodiments above and below, $R^4$ is

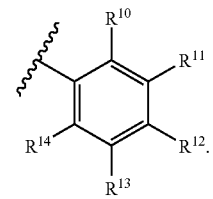

In another embodiment, in conjunction with the novel compound embodiments above and below, $R^{10}$ and $R^{11}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, =O, $C_{1-8}$alkyl, $C_{1-4}$haloalkyl, halo, cyano, nitro, —C(=O)($C_{1-8}$alkyl), —C(=O)O($C_{1-8}$alkyl), —C(=O)$NR^dR^d$, C(=$NR^d$)

$NR^dR^d$, —$OR^d$, —$OC(=O)(C_{1-8}alkyl)$, —$OC(=O)NR^dR^d$, —$OC(=O)N(R^d)S(=O)_2(C_{1-8}alkyl)$, —$OC_{2-6}alkylNR^dR^d$, —$OC_{2-6}alkylOR$, —$SR^d$, —$S(=O)(C_{1-8}alkyl)$, —$S(=O)_2(C_{1-8}alkyl)$, —$S(=O)_2NR^dR^d$, —$S(=O)_2N(R^d)C(=O)(C_8alkyl)$, —$S(=O)_2N(R^d)C(=O)O(C_{1-8}alkyl)$, —$S(=O)_2N(R^d)C(=O)NR^dR^d$, —$NR^dR^d$, —$N(R^d)C(=O)(C_{1-8}alkyl)$, —$N(R^d)C(=O)O(C_{1-8}alkyl)$, —$N(R^d)C(=O)NR^dR^d$, —$N(R^d)C(=NR^d)NR^dR^d$, —$N(R^d)S(=O)_2(C_{1-8}alkyl)$, —$N(R^d)S(=O)_2NR^dR^d$, —$NR^dC_{2-6}alkylNR^dR^d$ and —$NR^dC_{2-6}alkylOR^d$, and any nitrogen atoms in the bridge are substituted by H, —$C_{1-6}alkylOR^d$, —$C_{1-6}alkyl$, —$C_{1-6}alkylNR^dR^d$, —$C_{1-3}alkylC(=O)OR$ —$C_{1-3}alkylC(=O)NR^dR^d$, —$C_{1-3}alkylOC(=O)C_{1-6}alkyl$, —$C_{1-3}alkylNR^dC(=O)C_{1-6}alkyl$, —$C(=O)R^f$ or —$C_{1-3}alkylR^f$; or $R^{11}$ and $R^{12}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, =O, $C_{1-8}alkyl$, $C_{1-4}haloalkyl$, halo, cyano, nitro, —$C(=O)(C_{1-8}alkyl)$, —$C(=O)O(C_{1-8}alkyl)$, —$C(=O)NR^dR^d$, —$C(=NR^d)NR^dR^d$, $OR^d$, —$OC(=O)(C_{1-8}alkyl)$, —$OC(=O)NR^dR^d$, —$OC(=O)N(R^d)S(=O)_2(C_{1-8}alkyl)$, —$OC_{2-6}alkylNR^dR^d$, —$OC_{2-6}alkylOR^d$, —$SR^d$, —$S(=O)(C_{1-8}alkyl)$, —$S(=O)_2(C_{1-8}alkyl)$, —$S(=O)_2NR^dR^d$, —$S(=O)_2N(R^d)C(=O)(C_{1-8}alkyl)$, —$S(=O)_2N(R^d)C(=O)O(C_{1-8}alkyl)$, —$S(=O)_2N(R^d)C(=O)NR^dR^d$, —$NR^dR^d$, —$N(R^d)C(=O)(C_{1-8}alkyl)$, —$N(R^d)C(=O)O(C_{1-8}alkyl)$, —$N(R^d)C(=O)NR^dR^d$, —$N(R^d)C(=NR^d)NR^dR^d$, —$N(R^d)S(=O)_2(C_{1-8}alkyl)$, —$N(R^d)S(=O)_2NR^dR^d$, —$NR^dC_{2-6}alkylNR^dR^d$ and —$NR^dC_{2-6}alkylOR^d$, and any nitrogen atoms in the bridge are substituted by H, —$C_{1-6}alkylOR^d$, —$C_{1-6}alkyl$, —$C_{1-6}alkylNR^dR^d$, —$CR_{1-3}alkylC(=O)OR^d$, —$C_{1-3}alkylC(=O)NR^dR^d$, —$C_{1-3}alkylOC(=O)C_{1-6}alkyl$, —$C_{1-3}alkylNR^dC(=O)C_{1-6}alkyl$, —$C(=O)R^f$ or —$C_{1-3}alkylR^f$.

In another embodiment, in conjunction with the novel compound embodiments above and below, $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $C_{1-9}alkyl$, $C_{1-4}haloalkyl$, halo, nitro, cyano, oxo, —$OR^d$, —$S(=O)_nC_{1-6}alkyl$, —$OC_{1-4}haloalkyl$, —$OC_{2-6}alkylNR^dR^d$, —$OC_{2-6}alkylOR^d$, —$OC_{1-6}alkylC(=O)OR^d$, —$NR^dR^d$, —$NR^dC_{1-4}haloalkyl$, —$NR^dC_{2-6}alkylNR^dR^d$, —$NR^dC_{2-6}alkylOR^d$, —$C(=O)C_{1-6}alkyl$, —$C(=O)OC_{1-6}alkyl$, —$OC(=O)C_{1-6}alkyl$, —$C(=O)NR^dC_{1-6}alkyl$ and —$NR^dC(=O)C_{1-6}alkyl$; and saturated carbon atoms may be additionally substituted by =O; and any nitrogen atoms in the bridge are substituted by H, —$C_{1-6}alkylOR^d$, —$C_{1-6}alkyl$, —$C_{1-6}alkylNR^dR^d$, —$C_{1-3}alkylC(=O)OR^d$, —$C_{1-3}alkylC(=O)NR^dR^d$, —$C_{1-3}alkylOC(=O)C_{1-6}alkyl$, —$C_{1-3}alkylNR^dC(=O)C_{1-6}alkyl$, —$C(=O)R^f$ or —$C_{1-3}alkylR^f$.

In another embodiment, in conjunction with the novel compound embodiments above and below, $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 1, 2 or 3 substituents independently selected from $C_{1-9}alkyl$, $C_{1-4}haloalkyl$, halo, nitro, cyano, oxo, —$OR^d$, —$S(=O)_nC_{1-6}alkyl$, —$OC_{1-4}haloalkyl$, —$OC_{2-6}alkylNR^dR^d$, —$OC_{2-6}alkylOR^d$, —$OC_{1-6}alkylC(=O)OR^d$, —$NR^dR^d$, —$NR^dC_{1-4}haloalkyl$, —$NR^dC_{2-6}alkylNR^dR^d$, —$NR^dC_{2-6}alkylOR^d$, —$C(=O)C_{1-6}alkyl$, —$C(=O)OC_{1-6}alkyl$, —$OC(=O)C_{1-6}alkyl$, —$C(=O)NR^dC_{1-6}alkyl$ and —$NR^dC(=O)C_{1-6}alkyl$; and saturated carbon atoms may be additionally substituted by =O; and any nitrogen atoms in the bridge are substituted by H, —$C_{1-6}alkylOR^d$, —$C_{1-6}alkyl$, —$C_{1-6}alkylNR^dR^d$, —$C_{1-3}alkylC(=O)OR^d$, —$C_{1-3}alkylC(=O)NR^dR^d$, —$C_{1-3}alkylOC(=O)C_{1-6}alkyl$, —$C_{1-3}alkylNR^dC(=O)C_{1-6}alkyl$, —$C(=O)R^f$ or —$C_{1-3}alkylR^f$.

In another embodiment, in conjunction with the novel compound embodiments above and below, $R^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, $OR^d$, $NR^dR^d$, $C_{1-6}alkyl$ and $C_{1-3}haloalkyl$; and saturated carbon atoms may be additionally substituted by =O.

In another embodiment, in conjunction with the novel compound embodiments above and below, $R^4$ is 10-membered bicyclic ring comprising fused 6-membered rings, containing 1, 2, 3 or 4 N atoms with the remainder being carbon atoms, with at least one of the 6-membered rings being aromatic, wherein the carbon atoms are substituted by H, halo, $OR^d$, $NR^dR^d$, $C_{1-6}alkyl$ and $C_{1-3}haloalkyl$; and saturated carbon atoms may be additionally substituted by =O.

Another aspect of the invention relates to a compound having the structure:

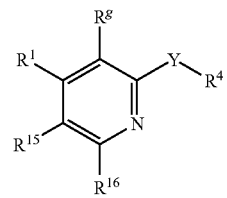

or any pharmaceutically-acceptable salt thereof, wherein:
n is independently, at each instance, 0, 1 or 2;
o is independently, at each instance, 0, 1, 2 or 3;
Y is NH, O or S;
$R^1$ is

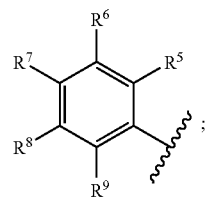

or $R^1$ is a naphthyl substituted by 0, 1, 2 or 3 substituents independently selected from $R^5$; or $R^1$ is $R^e$ substituted by 1, 2 or 3 substituents independently selected from $R^5$;

$R^{15}$ is, independently, in each instance, $R^{10}$, $C_{1-8}alkyl$ substituted by 0, 1 or 2 substituents selected from $R^{10}$, —$(CH_2)_n$phenyl substituted by 0, 1, 2 or 3 substituents independently selected from $R^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{10}$;

$R^{16}$ is, independently, in each instance, H, halo, —$NH_2$, —$NHC_{1-3}$alkyl, —$N(C_{1-3}$alkyl$)C_{1-3}$alkyl or $C_{1-3}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)$R^n$, —C(=O)O$R^n$, —C(=O)N$R^mR^m$, —C(=N$R^m$)N$R^mR^m$, —O$R^m$, —OC(=O)$R^n$, —OC(=O)N$R^mR^m$, —OC(=O)N($R^m$)S(=O)$_2R^n$, —OC$_{2-6}$alkylN$R^mR^m$, —OC$_{2-6}$alkylO$R^m$, —S$R^m$, 'S(=O)$R^n$, —S(=O)$_2R^n$, —S(=O)$_2$N$R^mR^m$, —S(=O)$_2$N($R^m$)C(=O)R, —S(=O)$_2$N($R^m$)C(=O)O$R^n$, —S(=O)$_2$N($R^m$)C(=O)N$R^mR^m$, —N$R^mR^m$, —N($R^m$)C(=O)$R^n$, —N($R^m$)C(=O)O$R^n$, —N($R^m$)C(=O)N$R^mR^m$, —N($R^m$)C(=N$R^m$)N$R^mR^m$, —N($R^m$)S(=O)$_2R^n$, —N($R^m$)S(=O)$_2$N$R^mR^m$, —N$R^mC_{2-6}$alkylN$R^mR^m$, —N$R^mC_{2-6}$alkylO$R^m$, —C(=O)$R^s$, —C(=O)O$R^s$, —C(=O)N$R^mR^s$, —C(=N$R^m$)N$R^mR^s$, —O$R^s$, —OC(=O)$R^s$, —OC(=O)N$R^mR^s$, —OC(=O)N($R^m$)S(=O)$_2R^s$, —OC$_{2-6}$alkylN$R^mR^s$, —OC$_{2-6}$alkylO$R^s$, —S$R^s$, —S(=O)$R^s$, —S(=O)$_2R^s$, —S(=O)$_2$N$R^mR^s$, —S(=O)$_2$N($R^{m)C(=O)Rs}$, —S(=O)$_2$N($R^m$)C(=O)O$R^s$, —S(=O)$_2$N($R^m$)C(=O)N$R^mR^s$, —N$R^mR^s$, —N($R^m$)C(=O)$R^s$, —N($R^m$)C(=O)O$R^s$, —N($R^m$)C(=O)N$R^mR^s$, —N($R^m$)C(=N$R^m$)N$R^mR^s$, —N($R^m$)S(=O)$_2R^s$, —N($R^m$)S(=O)$_2$N$R^mR^s$, —N$R^mC_{2-6}$alkylN$R^mR^s$, —N$R^mC_{2-6}$alkylO$R^s$, and $C_{1-4}$alkyl substituted by 1 or 2 groups selected from $C_{1-2}$haloalkyl, halo, cyano, nitro, —C(=O)$R^n$, —C(=O)O$R^n$, —C(=O)N$R^mR^m$, —C(=N$R^m$)N$R^mR^m$, —O$R^m$, —OC(=O)$R^n$, —OC(=O)N$R^mR^m$, —OC(=O)N($R^m$)S(=O)$_2R^n$, —OC$_{2-6}$alkylN$R^mR^m$, —OC$_{2-6}$alkylO$R^m$, —S$R^m$, —S(=O)$R^n$, —S(=O)$_2R^n$, —S(=O)$_2$N$R^mR^m$, —S(=O)$_2$N($R^m$)C(=O)$R^n$, —S(=O)$_2$N($R^m$)C(=O)O$R^n$, —S(=O)$_2$N($R^m$)C(=O)N$R^mR^m$, —N$R^mR^m$, —N($R^m$)C(=O)$R^n$, —N($R^m$)C(=O)O$R^n$, —N($R^m$)C(=O)N$R^mR^m$, —N($R^m$)C(=N$R^m$)N$R^mR^m$, —N($R^m$)S(=O)$_2R^n$, —N($R^m$)S(=O)$_2$N$R^mR^m$, —N$R^mC_{2-6}$alkylN$R^mR^m$, —N$R^mC_{2-6}$alkylO$R^m$, —C(=O)$R^s$, —C(=O)O$R^s$, —C(=O)N$R^mR^s$, —C(=N$R^m$)N$R^mR^s$, —O$R^s$, —OC(=O)$R^s$, —OC(=O)N$R^mR^s$, —OC(=O)N($R^m$)S(=O)$_2R^s$, —OC$_{2-6}$alkylN$R^mR^s$, —OC$_{2-6}$alkylO$R^s$, —S$R^s$, —S(=O)$R^s$, —S(=O)$_2R^s$, —S(=O)$_2$N$R^mR^s$, —S(=O)$_2$N($R^m$)C(=O)$R^s$, —S(=O)$_2$N($R^m$)C(=O)O$R^s$, —S(=O)$_2$N($R^m$)C(=O)N$R^mR^s$, —N$R^mR^s$, —N($R^m$)C(=O)$R^S$, —N($R^m$)C(=O)O$R^s$, —N($R^m$)C(=O)N$R^mR^s$, —N($R^m$)C(=N$R^m$)N$R^mR^s$, —N($R^m$)S(=O)$_2R^s$, —N($R^m$)S(=O)$_2$N$R^mR^s$, —N$R^mC_{2-6}$alkylN$R^mR^s$, —N$R^mC_{2-6}$alkylO$R^s$; and the ring and bridge carbon atoms are substituted with 0, 1 or 2 =O groups; but in no instance is $R^4$ 3,5-ditrifluoromethylphenyl or 3-trifluoromethyl-4-fluorophenyl;

$R^5$ is independently, at each instance, H, $C_{1-5}$alkyl, $C_{1-4}$haloalkyl, halo, nitro, cyano, —OC$_{1-6}$alkyl, —OC$_{1-4}$haloalkyl, —OC$_{2-6}$alkylN$R^dR^d$, —OC$_{2-6}$alkylO$R^d$, —N$R^dR^d$, —N$R^dC_{1-4}$haloalkyl, —N$R^dC_{2-6}$alkylN$R^dR^d$, —N$R^dC_{2-6}$alkylO$R^d$, naphthyl, —CO$_2$(C$_{1-6}$alkyl), —C(=O)(C$_{1-6}$alkyl), —C(=O)N$R^dR^d$, —N$R^dC$(=O)$R^d$, —N$R^dC$(=O)N$R^dR^d$, —N$R^dCO_2$(C$_{1-6}$alkyl), —$C_{1-8}$alkylO$R^d$, —$C_{1-6}$alkylN$R^dR^d$, —S(=O)$_n$(C$_{1-6}$alkyl), —S(=O)$_2$N$R^dR^d$, —N$R^dS$(=O)$_2$(C$_{1-6}$alkyl), —OC(=O)N$R^dR^d$, a phenyl ring substituted with 0, 1, 2, or 3 substituents independently selected from $R^{10}$; or $R^5$ is a saturated or unsaturated 5- or 6-membered ring heterocycle containing 1, 2 or 3 atoms selected from O, N and S, substituted with 0, 1, 2, or 3 substituents independently selected from $R^{10}$;

$R^6$ is independently, at each instance, H, $C_{1-5}$alkyl, $C_{1-4}$haloalkyl, halo, —OC$_{1-6}$alkyl, —OC$_{1-4}$haloalkyl, —OC$_{2-6}$alkylN$R^dR^d$, —OC$_{2-6}$alkylO$R^d$, —N$R^dR^d$, —N$R^dC_{1-4}$haloalkyl, —N$R^dC_{2-6}$alkylN$R^dR^d$ or —N$R^dC_{2-6}$alkylO$R^d$, —$C_{1-8}$alkylO$R^d$, —$C_{1-6}$alkylN$R^dR^d$, —S(C$_{1-6}$alkyl), a phenyl ring substituted with 1, 2, or 3 substituents independently selected from $R^{10}$; or $R^6$ is a saturated or unsaturated 5- or 6-membered ring heterocycle containing 1, 2 or 3 atoms selected from O, N and S substituted with 0, 1, 2, or 3 substituents independently selected from $R^{10}$;

$R^7$ is independently, at each instance, H, $C_{1-8}$alkyl, $C_{1-4}$haloalkyl, halo, —OC$_{1-6}$alkyl, —OC$_{1-4}$haloalkyl, —OC$_{2-6}$alkylN$R^dR^d$, —OC$_{2-6}$alkylO$R^d$, —N$R^dR^d$, —N$R^dC_{1-4}$haloalkyl, —N$R^dC_{2-6}$alkylN$R^dR^d$, —N$R^dC_{2-6}$alkylO$R^d$, 13 $C_{1-8}$alkylO$R^d$, —$C_{1-6}$alkylN$R^dR^d$ or —S(C$_{1-6}$alkyl); or $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl;

$R^8$ is independently, at each instance, H, $C_{1-5}$alkyl, $C_{1-4}$haloalkyl, halo, —OC$_{1-6}$alkyl, —OC$_{1-4}$haloalkyl, —OC$_{2-6}$alkylN$R^dR^d$, —OC$_{2-6}$alkylO$R^d$, —N$R^dR^d$, —N$R^dC_{1-4}$haloalkyl, —N$R^d$, —C$_{2-6}$alkylN$R^dR^d$, —N$R^dC_{2-6}$alkylO$R^d$, —$C_{1-8}$alkylO$R^d$, —$C_{1-6}$alkylN$R^dR^d$, —S(C$_{1-6}$alkyl), a phenyl ring substituted with 1, 2, or 3 substituents independently selected from $R^{10}$, or $R^8$ is a saturated or unsaturated 5- or 6-membered ring heterocycle containing 1, 2 or 3 atoms selected from O, N and S substituted with 0, 1, 2, or 3 substituents independently selected from $R^{10}$;

$R^9$ is independently, at each instance, H, $C_{1-8}$alkyl, $C_{1-4}$haloalkyl, halo, nitro, cyano, —OC$_{1-6}$alkyl, —OC$_{1-4}$haloalkyl, —OC$_{2-6}$alkylN$R^dR^d$, —OC$_{2-6}$alkylO$R^d$, —N$R^dC_{1-4}$haloalkyl, —N$R^dR^d$ or —N$R^dC_{2-6}$alkylO$R^d$, —CO$_2$(C$_{1-6}$alkyl), —C(=O)(C$_{1-6}$alkyl), —C(=O)N$R^dR^d$, —N$R^dC$(=O)(C$_{1-6}$alkyl), —N$R^dC$(=O)N$R^dR^d$, —N$R^dCO_2$(C$_{1-6}$alkyl), —$C_{1-8}$alkylO$R^d$, —$C_{1-6}$alkylN$R^dR^d$, —S(=O)$_n$(C$_{1-6}$alkyl), —S(=O)$_2$N$R^dR^d$, —N$R^dS$(=O)$_2$(C$_{1-6}$alkyl), —OC(=O)N$R^dR^d$ or a —(C$R^qR^q$)$_o$phenyl wherein the phenyl is substituted with 0, 1, 2, or 3 substituents independently selected from $R^{10}$; or $R^9$ is —(C$R^qR^q$)$_o$Het wherein Het is a saturated or unsaturated 5- or 6-membered ring heterocycle containing 1, 2 or 3 atoms selected from O, N and S substituted with 0, 1, 2, or 3 substituents independently selected from $R^{10}$; or $R^9$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl; wherein at least one of $R^5$, $R^6$, $R^7$, $R^8$ and $R^9$ is $C_{1-8}$alkyl, $C_{1-4}$haloalkyl, halo, —OC$_{1-4}$haloalkyl, —OC$_{2-6}$alkylN$R^dR^d$, —OC$_{2-6}$alkylO$R^d$, —N$R^dC_{1-4}$haloalkyl, —N$R^dC_{2-6}$alkylN$R^dR^d$, —N$R^dC_{2-6}$alkylO$R^d$, —$C_{1-8}$alkylO$R^d$, —$C_{1-6}$alkylN$R^dR^d$ or —S(C$_{1-6}$alkyl);

$R^{10}$ is independently, at each instance, selected from H, $C_{1-8}$alkyl, $C_{1-4}$haloalkyl, halo, cyano, nitro, —C(=O)(C$_{1-8}$alkyl), —C(=O)O(C$_{1-8}$alkyl), —C(=O)N$R^dR^d$, —C(=N$R^d$)N$R^dR^d$, —O$R^d$, —OC(=O)(C$_{1-8}$alkyl), —OC(=O)N$R^dR^d$, —OC(=O)N($R^d$)S(=O)$_2$(C$_{1-8}$alkyl), —OC$_{2-6}$alkylN$R^dR^d$, —OC$_{2-6}$alkylO$R^d$, —S$R^d$, —S(=O)(C$_{1-8}$alkyl), —S(=O)$_2$(C$_{1-8}$alkyl), —S(=O)$_2$N$R^dR^d$, —S(=O)$_2$N($R^d$)C(=O)(C$_{1-8}$alkyl), —S(=O)$_2$N($R^d$)C(=O)O(C$_{1-8}$alkyl), —S(=O)$_2$N($R^d$)C(=O)N$R^dR^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$_d$R$^d$, —C(=NR$^d$)NR$^d$R$^d$, —OR$^d$, —OC(=O)(C$_{1-8}$alkyl), —OC(=O)NR$^d$R$^d$, —OC(=O)N(R$^d$)S(=O)$_2$(C$_{1-8}$alkyl), —OC$_{2-6}$alkylNR$^d$R$^d$, —OC$_{2-6}$alkylOR$^d$, —SR$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-8}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-8}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R$^d$ and —NR$^d$C$_{2-6}$alkylOR$^d$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^d$R$^d$, —C(=NR$^d$)NR$^d$, —OR$^d$, —OC(=O)(C$_{1-8}$alkyl), —OC(=O)NR$^d$R$^d$, —S(=O)(C$_{1-8}$alkyl), —S(=O)$_2$(C$_{1-8}$alkyl), —S(=O)$_2$NR$^d$R$^d$, —S(=O)$_2$N(R$^d$)C(=O)(C$_{1-8}$alkyl), —S(=O)$_2$N(R$^d$)C(=O)O(C$_{1-8}$alkyl), —S(=O)$_2$N(R$^d$)C(=O)NR$^d$R$^d$, —NR$^d$R$^d$, —N(R$^d$)C(=O)(C$_{1-8}$alkyl), —N(R$^d$)C(=O)O(C$_{1-9}$alkyl), —N(R$^d$)C(=O)NR$^d$R$^d$, —N(R$^d$)C(=NR$^d$)NR$^d$R$^d$, —N(R$^d$)S(=O)$_2$(C$_{1-8}$alkyl), —N(R$^d$)S(=O)$_2$NR$^d$R$^d$, —NR$^d$C$_{2-6}$alkylNR$^d$R and —NR$^d$C$_{2-6}$alkylOR$^d$;

R$^d$ is independently, at each instance, H, phenyl, benzyl or C$_{1-6}$alkyl;

R$^e$ is a heterocycle selected from the group of thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, pyrazol-3-yl, pyrazol-5-yl, thiolane, pyrrolidine, tetrahydrofuran, 4,5-dihydrothiophene, 2-pyrroline, 4,5-dihydrofuran, pyridazine, pyrimnidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-1H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^f$ is phenyl substituted by 0, 1 or 2 groups selected from halo, $C_{1-4}$alkyl, $C_{1-3}$haloalkyl, —$OR^d$ and —$NR^dR^d$; or $R^f$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^d$ and —$NR^dR^d$;

$R^l$ is hydrogen or —$CH_3$;

$R^m$ is independently at each instance H or $R^n$;

$R^n$ is independently at each instance $C_{1-8}$alkyl, phenyl or benzyl;

$R^q$ is independently in each instance H, $C_{1-4}$alkyl, $C_{1-4}$haloalkyl, halo, cyano, nitro, —C(=O)$R^n$, —C(=O)O$R^n$, —C(=O)N$R^mR^m$, —C(=N$R^m$)N$R^mR^m$, —O$R^m$, —OC(=O)$R^n$, —OC(=O)N$R^mR^m$, —OC(=O)N($R^m$)S(=O)$_2R^n$, —OC$_{2-6}$alkylN$R^mR^m$, —OC$_{2-6}$alkylO$R^m$, —S$R^m$, —S(=O)$R^n$, —S(=O)$_2R^n$, —S(=)$_2$N$R^mR^m$, —S(=O)$_2$N($R^m$)C(=O)$R^n$, —S(=O)$_2$N($R^m$)C(=O)O$R^n$, —S(=O)$_2$N($R^m$)C(=O)N$R^mR^m$, —N$R^mR^m$, —N($R^m$)C(=O)$R^m$, —N($R^m$)C(=O)O$R^n$, —N($R^m$)C(=O)N$R^mR^m$, —N($R^m$)C(=N$R^m$)N$R^mR^m$, —N($R^m$)S(=O)$_2R^n$, —N($R^m$)S(=O)$_2$N$R^mR^m$, —N$R^mC_{2-6}$alkylN$R^mR^m$ or —N$R^mC_{2-6}$alkylO$R^m$; and $R^s$ is $R^n$ substituted by 0, 1, 2 or 3 substituents independently selected from $R^q$.

In another embodiment, in conjunction with the novel compound embodiments above and below, Y is NH.

In another embodiment, in conjunction with the novel compound embodiments above and below, Y is O.

In another embodiment, in conjunction with the novel compound embodiments above and below, Y is S.

In another embodiment, in conjunction with the novel compound embodiments above and below, $R^1$ is

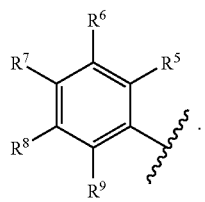

In another embodiment, in conjunction with the novel compound embodiments above and below, $R^7$ is $C_{1-5}$alkyl, halo or $C_{1-4}$haloalkyl.

In another embodiment, in conjunction with the novel compound embodiments above and below, $R^1$ is a naphthyl substituted by 0, 1 or 2 substituents independently selected from $R^5$.

In another embodiment, in conjunction with the novel compound embodiments above and below, $R^1$ is Re substituted by 1, 2 or 3 substituents independently selected from $R^5$;

In another embodiment, in conjunction with the novel compound embodiments above and below, $R^{15}$ is —$(CH_2)_n$phenyl substituted by 0, 1, 2 or 3 substituents independently selected from $R^{10}$.

In another embodiment, in conjunction with the novel compound embodiments above and below, $R^{15}$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^{10}$.

In another embodiment, in conjunction with the novel compound embodiments above and below, $R^{15}$ is $C_{1-8}$alkyl substituted by 0, 1 or 2 substituents selected from $R^{10}$.

In another embodiment, in conjunction with the novel compound embodiments above and below, $R^{15}$ is selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)N$R^dR^d$, —C(=N$R^d$)N$R^dR^d$, —O$R^d$, —OC(=O)($C_{1-8}$alkyl), —OC(=O)N$R^dR^d$, —OC(=O)N($R^d$)S(=O)$_2$($C_{1-8}$alkyl), —OC$_{2-6}$alkylN$R^dR^d$, —OC$_{2-6}$alkylO$R^d$, —S$R^d$, —S(=O)($C_{1-8}$alkyl), —S(=O)$_2$($C_{1-8}$alkyl), —S(=O)$_2$N$R^dR^d$, —S(=O)$_2$N($R^d$)C(=O)($C_{1-8}$alkyl), —S(=O)$_2$N($R^d$)C(=O)O($C_{1-8}$alkyl), —S(=O)$_2$N($R^d$)C(=O)N$R^dR^d$, —N$R^dR^d$, —N($R^d$)C(=O)($C_{1-8}$alkyl), —N(R )C(=O)O($C_{1-8}$alkyl), —N($R^d$)C(=O)N$R^dR^d$, —N($R^d$)C(=N$R^d$)N$R^dR^d$, —N($R^d$)S(=O)$_2$($C_{1-8}$alkyl), —N($R^d$)S(=O)$_2$N$R^dR^d$, —N$R^dC_{2-6}$alkylN$R^dR^d$ and —N$R^dC_{2-6}$alkylO$R^d$; or $R^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)N$R^dR^d$, —C(=N$R^d$)N$R^dR^d$, —O$R^d$, —OC(=O)($C_{1-8}$alkyl), —OC(=O)N$R^dR^d$, —OC(=O)N($R^d$)S(=O)$_2$($C_{1-8}$alkyl), —OC$_{2-6}$alkylN$R^dR^d$, —OC$_{2-6}$alkylO$R^d$, —S$R^d$, —S(=O)($C_{1-8}$alkyl), —S(=O)$_2$($C_{1-8}$alkyl), —S(=O)$_2$N$R^dR^d$, —S(=O)$_2$N($R^d$)C(=O)($C_{1-8}$alkyl), —S(=O)$_2$N($R^d$)C(=O)O($C_{1-8}$alkyl), —S(=O)$_2$N($R^d$)C(=O)N$R^dR^d$, —N$R^dR^d$, —N($R^d$)C(=O)($C_{1-8}$alkyl), —N($R^d$)C(=O)O($C_{1-8}$alkyl), —N($R^d$)C(=O)N$R^dR^d$, —N($R^d$)C(=N$R^d$)N$R^dR^d$, —N($R^d$)S(=O)$_2$($C_{1-8}$alkyl), —N($R^d$)S(=O)$_2$N$R^dR^d$, —N$R^dC_{2-6}$alkylN$R^dR^d$ and —N$R^dC_{2-6}$alkylO$R^d$.

In another embodiment, in conjunction with the novel compound embodiments above and below, $R^{16}$ is, independently, in each instance, halo, —NH$_2$, —NHC$_{1-3}$alkyl, —N(C$_{1-3}$alkyl)C$_{1-3}$alkyl or C$_{1-3}$alkyl.

In another embodiment, in conjunction with the novel compound embodiments above and below, R$^4$ is an unsaturated 6-membered ring containing 0 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$alkylOR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$—NR$'''$C$_{2-6}$alkylNR$'''$R$'''$, —NR$'''$C$_{2-6}$alkylOR$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —N$'''$R$'''$C$_{2-6}$alkylOR$^s$ and C$_{1-4}$alkyl substituted by 1 or 2 groups selected from C$_{1-2}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$OR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=)R$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —NR$'''$C$_{2-6}$alkylNR$'''$R$'''$, —NR$'''$C$_{2-6}$alkylOR$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —NR$'''$C$_{2-6}$alkylOR$^s$; and the ring and bridge carbon atoms are substituted with 0, 1 or 2 =O groups.

In another embodiment, in conjunction with the novel compound embodiments above and below, R$^4$ is a saturated or unsaturated 5- or 6-membered ring containing 1, 2 or 3 atoms selected from O, N and S that is vicinally fused with a saturated or unsaturated 3- or 4-atom bridge containing 0 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$alkylOR$'''$, —SR$'''$, —S(=O)R$''$, —S(=O)$_2$R , —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —NR$'''$C$_{2-6}$alkylNR$'''$R$'''$, —NR$'''$C$_{2-6}$alkylOR$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, NR$'''$C$_{2-6}$ alkylNR$'''$R$^s$, —NR$'''$C$_{2-6}$alkylOR$^s$ and C$_{1-4}$alkyl substituted by 1 or 2 groups selected from C$_{1-2}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$alkylOR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —NR$'''$C$_{2-6}$alkylNR$'''$R$'''$, —NR$'''$C$_{2-6}$alkylOR$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —NR$'''$C$_{2-6}$alkylOR$^s$; and the ring and bridge carbon atoms are substituted with 0, 1 or 2 =O groups; but in no instance is R$^4$ 3,5-ditrifluoromethylphenyl or 3-trifluoromethyl-4-fluorophenyl.

In another embodiment, in conjunction with the novel compound embodiments above and below, R$^4$ is a saturated or unsaturated 6-membered ring containing 0 atoms selected from O, N and S that is vicinally fused with a saturated or unsaturated 3- or 4-atom bridge containing 0 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$alkylOR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —NR$'''$C$_{2-6}$alkylNR$'''$R$'''$, —NR$'''$C$_{2-6}$alkylOR$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, NR$'''$C$_{2-6}$ alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S (=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$; and the ring and bridge carbon atoms are substituted with 0, 1 or 2 =O groups; but in no instance is R$^4$ 3,5-ditrifluoromethylphenyl or 3-trifluoromethyl-4-fluorophenyl.

In another embodiment, in conjunction with the novel compound embodiments above and below, R$^4$ is a saturated or unsaturated 5- or 6-membered ring containing 1, 2 or 3 atoms selected from O, N and S that is vicinally fused with a saturated or unsaturated 3- or 4-atom bridge containing 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R'''—NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$; and the ring and bridge carbon atoms are substituted with 0, 1 or 2 =O groups; but in no instance is R$^4$ 3,5-ditrifluoromethylphenyl or 3-trifluoromethyl-4-fluorophenyl.

In another embodiment, in conjunction with the novel compound embodiments above and below, R$^9$ is H.

In another embodiment, in conjunction with the novel compound embodiments above and below, R$^9$ is independently, at each instance, C$_{1-8}$alkyl, C$_{1-4}$haloalkyl, halo, nitro, cyano, —OC$_{1-6}$alkyl, —OC$_{1-4}$haloalkyl, —OC$_{2-6}$alkylNR$^d$R$^d$, —OC$_{2-6}$alkylOR$^d$, —NR$^d$R$^d$, —NR$^d$C$_{1-4}$haloalkyl, —NR$^d$C$_{2-6}$alkylNR$^d$R$^d$ or —NR$^d$C$_{2-6}$alkylOR$^d$, —CO$_2$(C$_{1-6}$alkyl), —C(=O)(C$_{1-6}$alkyl), —C(=O)NR$^d$R$^d$, —NR$^d$C(=O)(C$_{1-6}$alkyl), —NR$^d$C(=O)NR$^d$R$^d$, —NR$^d$CO$_2$(C$_{1-6}$alkyl), —C$_{1-8}$alkylOR$^d$, —C$_{1-6}$alkylNR$^d$R$^d$, —S(=O)$_n$(C$_{1-6}$alkyl), —S(=O)$_2$NR$^d$R$^d$, —NR$^d$S(=O)$_2$(C$_{1-6}$alkyl) or —OC(=O)NR$^d$R$^d$.

In another embodiment, in conjunction with the novel compound embodiments above and below, R$^9$ is a —(CR$^q$R$^q$)$_o$phenyl wherein the phenyl is substituted with 0, 1, 2, or 3 substituents independently selected from R$^{10}$.

In another embodiment, in conjunction with the novel compound embodiments above and below, R$^9$ is —(CR$^q$R$^q$)$_o$Het wherein Het is a saturated or unsaturated 5- or 6-membered ring heterocycle containing 1, 2 or 3 atoms selected from O, N and S substituted with 0, 1, 2, or 3 substituents independently selected from R$^{10}$; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

Another aspect of the invention relates to a compound having the structure:

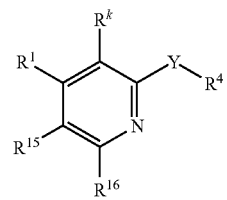

or any pharmaceutically-acceptable salt thereof, wherein:
Y is O or S;
n is independently, at each instance, 0, 1 or 2.
R$^1$ is

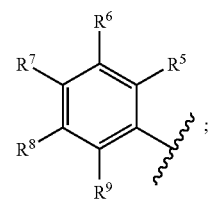

or R$^1$ is a naphthyl substituted by 0, 1, 2 or 3 substituents independently selected from R$^5$; or R$^1$ is R$^i$ substituted by 1, 2 or 3 substituents independently selected from R$^5$;

R$^{15}$ is, independently, in each instance, R$^{10}$, C$_{1-8}$alkyl substituted by 0, 1 or 2 substituents selected from R$^{10}$, —(CH$_2$)$_n$phenyl substituted by 0, 1, 2 or 3 substituents independently selected from R$^{10}$, or a saturated or unsaturated 5- or 6-membered ring heterocycle containing 1, 2 or 3 heteroatoms independently selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, the heterocycle and bridge being substituted by 0, 1, 2 or 3 substituents independently selected from R$^{10}$;

R$^{16}$ is, independently, in each instance, H, halo, —NH$_2$, —NHC$_{1-3}$alkyl, —N(C$_{1-3}$alkyl)C$_{1-3}$alkyl, —OC$_{1-3}$alkyl, —C$_{1-2}$haloalkyl, —OC$_{1-2}$haloalkyl or C$_{1-3}$alkyl;

R$^4$ is

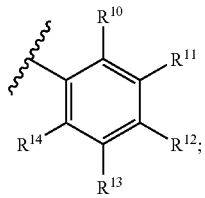

wherein when R$^1$ is bromophenyl, methylphenyl or trifluoromethylphenyl, R$^4$ is not trifluoromethylphenyl or trifluoromethylhalophenyl; or R$^4$ is a saturated or unsaturated 5- or 6-membered ring heterocycle containing 1, 2 or 3 atoms selected from O, N and S, so long as the combination of O and S atoms is not greater than 2, wherein each of the carbon atoms of the heterocycle is substituted by H, C$_{1-9}$alkyl, C$_{1-4}$haloalkyl, halo, cyano, oxo, —OR$^h$, —S(=O)$_n$C$_{1-6}$alkyl, —OC$_{1-4}$haloalkyl, —OC$_{1-6}$alkylNR$^h$R$^h$, —OC$_{2-6}$alkylOR$^h$, —OC$_{1-6}$alkylC(=O)OR$^h$, —NR$^h$R$^h$, —NR$^h$C$_{1-4}$haloalkyl, —NR$^h$C$_{2-6}$alkylNR$^h$R$^h$, —NR$^h$C$_{2-6}$alkylOR$^h$, —C(=O)C$_{1-6}$alkyl, —C(=O)OC$_{1-6}$alkyl, —OC(=O)C$_{1-6}$alkyl, —C(=O)NR$^h$C$_{1-6}$alkyl or —NR$^h$C(=O)C$_{1-6}$alkyl; and saturated carbon atoms may be additionally substituted by =O; and each of the available nitrogen atoms in the heterocycle are substituted by H, —C$_{1-6}$alkylOR$^h$, —C$_{1-6}$alkyl, —C$_{1-6}$alkylNR$^h$R$^h$, —C$_{1-3}$alkylC(=O)OR$^h$, —C$_{1-3}$alkylC(=O)NR$^h$R$^h$, —C$_{1-3}$alkylOC(=O)C$_{1-6}$alkyl, —C$_{1-3}$alkylNR$^h$C(=O)C$_{1-6}$alkyl, —C(=O)R$^j$ or —C$_{1-3}$alkylR$^j$; or R$^4$ is an 8-, 9-, 10- or 11-membered bicyclic ring, containing 0, 1, 2, 3 or 4 N atoms and 0, 1 or 2 atoms selected from S and O with the remainder being carbon atoms, wherein each of the carbon atoms of the ring is substituted by H, C$_{1-9}$alkyl, C$_{1-4}$haloalkyl, halo, cyano, oxo, —OR$^h$, —S(=O)$_n$C$_{1-6}$alkyl, —OC$_{1-4}$haloalkyl, —OC$_{2-6}$alkylNR$^h$R$^h$, —OC$_{2-6}$alkylOR$^h$, —OC$_{1-6}$alkylC(=O)OR$^h$, —NR$^h$R$^h$, —NR$^h$C$_{1-4}$haloalkyl, —NR$^h$C$_{2-6}$alkylNR$^h$R$^h$, —NR$^h$C$_{2-6}$alkylOR$^h$, —C(=O)C$_{1-6}$alkyl, —C(=O)OC$_{1-6}$alkyl, —OC(=O)C$_{1-6}$alkyl, —C(=O)NR$^h$C$_{1-6}$alkyl or —NR$^h$C(=O)C$_{1-6}$alkyl; and saturated carbon atoms may be additionally substituted by =O; and any available nitrogen atoms in the ring are substituted by H, —C$_{1-6}$alkylOR$^h$, —C$_{1-6}$alkyl, —C$_{1-6}$alkylNR$^h$R$^h$, —C$_{1-3}$alkylC(=O)OR$^h$, —C$_{1-3}$alkylC(=O)NR$^h$R$^h$, —C$_{1-3}$alkylOC(=O)C$_{1-6}$alkyl, —C$_{1-3}$alkylNR$^h$C(=O)C$_{1-6}$alkyl, —C(=O)R$^j$ or —C$_{1-3}$alkylR$^j$;

R$^5$ is independently, at each instance, H, C$_{1-5}$alkyl, C$_{1-4}$haloalkyl, halo, nitro, —OC$_{1-6}$alkyl, —OC$_{1-4}$haloalkyl, —OC$_{2-6}$alkylNR$^h$R$^h$, —OC$_{2-6}$alkylOR$^h$, —NR$^h$R$^h$, —NR$^h$C$_{1-4}$haloalkyl, —NR$^h$C$_{2-6}$alkylNR$^h$R$^h$, —NR$^h$C$_{2-6}$alkylOR$^h$, naphthyl, —CO$_2$(C$_{1-6}$alkyl), —C(=O)(C$_{1-6}$alkyl), —C(=O)NR$^h$R$^h$, —NR$^h$C(=O)R$^h$, —NR$^h$C(=O)NR$^h$R$^h$, —NR$^h$CO$_2$(C$_{1-6}$alkyl), —C$_{1-8}$alkylOR$^h$, —C$_{1-6}$alkylNR$^h$R$^h$, —S(=O)$_n$(C$_{1-6}$alkyl), —S(=O)$_2$NR$_h$R$_h$, —NR$^h$S(=O)$_2$(C$_{1-6}$alkyl), —OC(=O)NR$^h$R$^h$, a phenyl ring substituted with 0, 1, 2, or 3 substituents independently selected from R$^{10}$; or R$^5$ is a saturated or unsaturated 5- or 6-membered ring heterocycle containing 1, 2 or 3 atoms selected from O, N and S, substituted with 0, 1, 2, or 3 substituents independently selected from R$^{10}$;

R$^6$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylNR$^h$R$^h$, —OC$_{2-6}$alkylOR$^h$, —NR$^h$R$^h$, —NR$^h$C$_{1-4}$haloalkyl, —NR$^h$C$_{2-6}$alkylNR$^h$R$^h$ or —NR$^h$C$_{2-6}$alkylOR$^h$, —C$_{1-8}$alkylOR$^h$, —C$_{1-6}$alkylNR$^h$R$^h$, —S(C$_{1-6}$alkyl), a phenyl ring substituted with 1, 2, or 3 substituents independently selected from R$^{10}$; or R$^6$ is a saturated or unsaturated 5- or 6-membered ring heterocycle containing 1, 2 or 3 atoms selected from O, N and S substituted with 0, 1, 2, or 3 substituents independently selected from R$^{10}$;

R$^7$ is independently, at each instance, H, C$_{1-8}$alkyl, C$_{1-4}$haloalkyl, bromo, —OC$_{1-6}$alkyl, —OC$_{1-4}$haloalkyl, —OC$_{2-6}$alkylNR$^h$R$^h$, —OC$_{2-6}$alkylOR$^h$, —NR$^h$R$^h$, —NR$^h$C$_{1-4}$haloalkyl, —NR$^h$C$_{2-6}$alkylNR$^h$R$^h$, —NR$^h$C$_{2-6}$alkylOR$^h$, —C$_{1-8}$alkylOR$^h$, —C$_{1-6}$alkylNR$^h$R$^h$ or —S(C$_{1-6}$alkyl); or R$^7$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^8$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylNR$^h$R$^h$, —OC$_{2-6}$alkylOR$^h$, —NR$^h$R$^h$, —NR$^h$C$_{1-4}$haloalkyl, —NR$^h$C$_{2-6}$alkylNR$^h$R$^h$, NR$^h$C$_{2-6}$alkylOR$^h$, —C$_{1-8}$alkylOR$^h$, —C$_{1-6}$alkylNR$^h$R$^h$, —S(C$_{1-6}$alkyl), a phenyl ring substituted with 1, 2, or 3 substituents independently selected from R$^{10}$, or R$^8$ is a saturated or unsaturated 5- or 6-membered ring heterocycle containing 1, 2 or 3 atoms selected from O, N and S substituted with 0, 1, 2, or 3 substituents independently selected from R$^{10}$;

R$^9$ is independently, at each instance, H, C$_{1-8}$alkyl, C$_{1-4}$haloalkyl, halo, nitro, —OC$_{1-4}$haloalkyl, —OC$_{2-6}$alkylNR$^h$R$^h$, —OC$_{2-6}$alkylOR$^h$, —NR$^h$R$^h$, —NR$^h$C$_{1-4}$haloalkyl, —NR$^h$C$_{2-6}$alkylNR$_h$R$^h$ or —NR$^h$C$_{2-6}$alkylOR$^h$, —CO$_2$(C$_{1-6}$alkyl), —C(=O)(C$_{1-6}$alkyl), —C(=O)NR$^h$R$^h$, —NR$^h$C(=O)(C$_{1-6}$alkyl), —NR$^h$C(=O)NR$^h$R$^h$, —NR$^h$CO$_2$(C$_{1-6}$alkyl), —C$_{1-8}$alkylOR$^h$, —C$_{1-6}$alkylNR$^h$R$^h$, —S(=O)$_n$(C$_{1-6}$alkyl), —S(=O)$_2$NR$^h$R$^h$, —NR$^h$S(=O)$_2$(C$_{1-6}$alkyl), —OC(=O)NR$^h$R$^h$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; wherein at least one of R$^5$, R$^6$, R$^7$, R$^8$ and R$^9$ is C$_{1-8}$alkyl, C$_{1-4}$haloalkyl, halo, —OC$_{1-4}$haloalkyl, —OC$_{2-6}$alkylNR$^h$R$^h$, —OC$_{2-6}$alkylOR$^h$, —NR$^h$C$_{1-4}$haloalkyl, —NR$^h$C$_{2-6}$alkylNR$^h$R$^h$, —NR$^h$C$_{2-6}$alkylOR$^h$, —C$_{1-8}$alkylOR$^h$, —C$_{1-6}$alkylNR$^h$R$^h$ or —S(C$_{1-6}$alkyl); or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^{10}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC (=O)NR$^h$R$^h$, —OC(=O)N(R$^h$)S(=O)$_2$(C$_{1-8}$alkyl), —OC$_{2-6}$ alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$; or R$^{10}$ is a saturated or unsaturated 5-, 6- or 7-membered monocyclic or 6-, 7-, 8-, 9-, 10- or 11-membered bicyclic ring containing 1 or 2 atoms selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-3}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$;

R$^{11}$ is independently, at each instance, selected from H, C$_{1-8}$alkyl, C$_{1-4}$haloalkyl, halo, cyano, nitro, —C(=O)O(C$_{1-8}$alkyl), —C(=O)O(C$_{1-8}$alkyl), —C(=O)NR$^h$R$^h$, C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_1$-alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$; or R$^{11}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$;

R$^{12}$ is independently, at each instance, selected from H, C$_{1-8}$alkyl, C$_{1-4}$haloalkyl, halo, cyano, nitro, —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, NR$^h$C$_{2-6}$alkylNR$^h$R$^h$ and —NR$^h$C$_{2-6}$alkylOR$^h$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(Rh)C(=O)O(C$_{1-8}$alkyl), —N(Rh)C(=O)NR$^h$R$^h$, —N(R$^h$)C(=NR$^h$)NR$^h$R$^h$, —N(R$^h$)S(=O)$_2$(C$_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$; or R$^{12}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^h$R$^h$, —C(=NR$^h$)NR$^h$R$^h$, —OR$^h$, —OC(=O)(C$_{1-8}$alkyl), —OC(=O)NR$^h$R$^h$, —OC(=O)N(R$^h$)S(=O)$_2$(C$_{1-8}$alkyl), —OC$_{2-6}$alkylNR$^h$R$^h$, —OC$_{2-6}$alkylOR$^h$, —SR$^h$, —S(=O)(C$_{1-8}$alkyl), —S(=O)$_2$(C$_{1-8}$alkyl), —S(=O)$_2$NR$^h$R$^h$, —S(=O)$_2$N(R$^h$)C(=O)(C$_{1-8}$alkyl), —S(=O)$_2$N(R$^h$)C(=O)O(C$_{1-8}$alkyl), —S(=O)$_2$N(R$^h$)C(=O)NR$^h$R$^h$, —NR$^h$R$^h$, —N(R$^h$)C(=O)(C$_{1-8}$alkyl), —N(R$^h$)C(=O)O(C$_{1-8}$alkyl), —N(R$^h$)C(=O)NR$^h$R$^h$, —N(R$^h$)C(=NR$^h$)NR$^h$R$^h$, —N(R$^h$)S(=O)$_2$(C$_{1-8}$alkyl), —N(Rh)S(=O)$_2$NR$^h$R$^h$, —NR$^h$C$_{2-6}$alkylNR$^h$R$^h$ and —NR$^h$C$_{2-6}$alkylOR$^h$;

R$^{13}$ is independently, at each instance, selected from H, C$_{1-8}$alkyl, C$_{1-4}$haloalkyl, halo, cyano, nitro, —C(=O)(C$_{1-8}$ alkyl), —C(=O)O($C_{1-8}$alkyl), —C(=O)N$R^hR^h$, —C(=NR$^h$)NR$^hR^h$, —OR$^h$, —OC(=O)($C_{1-8}$alkyl), —OC(=O)NR$^hR^h$, —OC(=O)N(R$^h$)S(=O)$_2$($C_{1-8}$alkyl), —OC$_{2-6}$alkylNR$^hR^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^hR^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^hR^h$, —NR$^hR^h$, —N(R$^h$)C(=O)($C_{1-8}$alkyl), —N(R$^h$)C(=O)O($C_{1-8}$alkyl), —N(R$^h$)C(=O)NR$^hR^h$, —N(R$^h$)C(=NR$^h$)NR$^hR^h$ —N(Rh)S(=O)$_2$($C_{1-8}$alkyl), —N(Rh)S(=O)$_2$NR$^hR^h$, —NR$^hC_{2-6}$alkylNR$^hR^h$ and —NR$^hC_{2-6}$alkylOR$^h$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^hR^h$, —C(=NR$^h$)NR$^hR^h$, —OR$^h$, —OC(=O)($C_{1-8}$alkyl), —OC(=O)NR$^hR^h$, —OC(=O)N(R$^h$)S(=O)$_2$($C_{1-8}$alkyl), —OC$_{2-6}$alkylNR$^hR^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$_hR_h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^hR^h$, —NR$^hR^h$, —N(R$^h$)C(=O)($C_{1-8}$alkyl), —N(R$^h$)C(=O)O($C_{1-8}$alkyl), —N(Rh)C(=O)NR$^hR^h$, —N(R$^h$)C(=NR$^h$)NR$^hR^h$, —N(R$^h$)S(=O)$_2$($C_{1-8}$alkyl), —N(R$^h$)S(=O)$_2$NR$^hR^h$, —NR$^hC_{2-6}$alkyl, —NR$^hR^h$ and —NR$^hC_{2-6}$alkylOR$^h$; or R$^{13}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^hR^h$, —C(=NR$^h$)NR$^hR^h$, —OR$^h$, —OC(=O)($C_{1-8}$alkyl), —OC(=O)NR$^hR^h$, —OC(=O)N(R$^h$)S(=O)$_2$($C_{1-8}$alkyl), —OC$_{2-6}$alkylNR$^hR^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^hR^h$, —S(=O)$_2$N(R$^h$)C(=O)($C_{1-8}$alkyl), —S(=O)$_2$N(R$^h$)C(=O)O($C_{1-18}$alkyl), —S(=O)$_2$N(R$^h$)C(=O)NR$^hR^h$, —NR$^hR^h$, —N(R$^h$)C(=O)($C_{1-8}$alkyl), —N(R$^h$)C(=O)O($C_{1-8}$alkyl), —N(R$^h$)C(=O)NR$^hR^h$, —N(R$^h$)C(=NR$^h$)NR$^hR^h$, —N(R$^h$)S(=O)$_2$($C_{1-8}$alkyl), —N(R$^h$)S(=O)$_2$NR$^hR^h$, —NR$^hC_{2-6}$alkylNR$^hR^h$ and —NR$^hC_{2-6}$alkylOR$^h$;

R$^{14}$ is independently, at each instance, selected from H, $C_{1-8}$alkyl, $C_{1-4}$haloalkyl, halo, cyano, nitro, —C(=O)$C_{1-8}$alkyl), —C(=O)O($C_{1-8}$alkyl), —C(=O)NR$^hR^h$, —C(=NR$^h$)NR$^hR^h$, —OR$^h$, —OC(=O)($C_{1-8}$alkyl), —OC(=O)NR$^hR^h$, —OC(=O)N(R$^h$)S(=O)$_2$($C_{1-8}$alkyl), —OC$_{2-6}$alkylNR$^hR^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^hR^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^hR^h$, —NR$^hR^h$, —N(R$^h$)C(=O)($C_{1-8}$alkyl), —N(R$^h$)C(=O)O($C_{1-8}$alkyl), —N(R$^h$)C(=O)NR$^hR^h$, —N(R$^h$)C(=NR$^h$)NR$^hR^h$, —N(R$^h$)S(=O)$_2$($C_{1-8}$alkyl), —N(R$^h$)S(=O)$_2$NR$^hR^h$, —NR$^hC_{2-6}$alkylNR$^hR^h$ and —NR$^hC_{2-6}$alkylOR$^h$; or R$^{14}$ is a saturated or unsaturated 5-, 6- or 7-membered monocyclic or 6-, 7-, 8-, 9-, 10- or 11-membered bicyclic ring containing 1 or 2 atoms selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^hR^h$, —C(=NR$^h$)NR$^hR^h$, —OR$^h$, —OC(=O)($C_{1-8}$alkyl), —OC(=O)NR$^hR^h$, —OC(=O)N(R$^h$)S(=O)$_2$($C_{1-8}$alkyl), —OC$_{2-6}$alkylNR$^hR^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^hR^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^hR^h$, —NR$^hR^h$, —N(R$^h$)C(=O)($C_{1-8}$alkyl), —N(R$^h$)C(=O)O($C_{1-8}$alkyl), —N(R$^h$)C(=O)NR$^hR^h$, —N(R$^h$)C(=NR$^h$)NR$^hR^h$, —N(R$^h$)S(=O)$_2$($C_{1-8}$alkyl), —N(R$^h$)S(=O)$_2$NR$^hR^h$, —NR$^hC_{2-6}$alkylNR$^hR^h$ and —NR$^hC_{2-6}$alkylOR$^h$; or R$^{14}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)NR$^hR^h$, —C(=NR$^h$)NR$^hR^h$, —OR$^h$, —OC(=O)($C_{1-8}$alkyl), —OC(=O)NR$^hR^h$, —OC(=O)N(R$^h$)S(=O)$_2$($C_{1-8}$alkyl), —OC$_{2-6}$alkylNR$^hR^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^hR^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^hR^h$, —NR$^hR^h$, —N(R$^h$)C(=O)($C_{1-8}$alkyl), —N(R$^h$)C(=O)O($C_{1-8}$alkyl), —N(R$^h$)C(=O)NR$^hR^h$, —N(R$^h$)C(=NR$^h$)NR$^hR^h$, —N(R$^h$)S(=O)$_2$($C_{1-8}$alkyl), —N(R$^h$)S(=O)$_2$NR$^hR^h$, —NR$^hC_{2-6}$alkylNR$^hR^h$ and —NR$^hC_{2-6}$alkylOR$^h$;

R$^h$ is independently, at each instance, H, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^i$ is a heterocycle selected from the group of thiophene, pyrrole, 1,3-oxazole, 1,3-thiazol-5-yl, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-3-yl, imidazol-4-yl, 1,2,4-triazole, 1,2,4-triazole, isoxazole, pyrazol-3-yl, pyrazol-4-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazolin-1-yl, 2-imidazolin-2-yl, 2-imidazolin-5-yl, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazol-1-yl, 4,5-dihydro-1H-[1,2,3]triazol-3-yl, 4,5-dihydro-1H-[1,2,3]triazol-5-yl, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]oxadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridazine, 2,3-dihydropyridazine, 2,5-dihydropyridazine, 4,5-dihydropyridazine, 1,2-dihydropyridazine, 1,4-dihydropyrimidin-1-yl, 1,4-dihydropyrimidin-4-yl, 1,4-dihydropyrimidin-5-yl, 1,4-dihydropyrimidin-6-yl, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 2H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^j$ is phenyl substituted by 0, 1 or 2 groups selected from halo, $C_{1-4}$alkyl, $C_{1-3}$haloalkyl, —$OR^h$ and —$NR^hR^h$; or $R^j$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^h$ and —$NR^hR^h$; and $R^k$ is hydrogen or —$CH_3$.

In another embodiment, in conjunction with the novel compound embodiments above and below, $R^1$ is

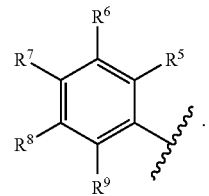

In another embodiment, in conjunction with the novel compound embodiments above and below, $R^7$ is $C_{2-6}$alkyl or $C_{1-4}$haloalkyl.

In another embodiment, in conjunction with the novel compound embodiments above and below, $R^1$ is a naphthyl substituted by 0, 1, 2 or 3 substituents independently selected from $R^5$.

In another embodiment, in conjunction with the novel compound embodiments above and below, $R^1$ is $R^i$ substituted by 1, 2 or 3 substituents independently selected from $R^5$.

In another embodiment, in conjunction with the novel compound embodiments above and below, $R^i$ is substituted by one substituent selected from halo, $C_{1-4}$haloalkyl and $C_{1-5}$alkyl, and additionally by 0, 1 or 2 substituents independently selected from $R^5$.

In another embodiment, in conjunction with the novel compound embodiments above and below, $R^{15}$ is H.

In another embodiment, in conjunction with the novel compound embodiments above and below, $R^{15}$ is $R^{10}$, $C_{1-8}$alkyl substituted by 0, 1 or 2 substituents selected from $R^{10}$, or a saturated or unsaturated 5- or 6-membered ring heterocycle containing 1, 2 or 3 heteroatoms independently selected from N, O and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, the heterocycle and bridge being substituted by 0, 1, 2 or 3 substituents independently selected from $R^{10}$; or $R^{15}$ is —$(CH_2)_n$phenyl substituted by 0, 1, 2 or 3 substituents independently selected from H, $C_{1-8}$alkyl, $C_{1-4}$haloalkyl, halo, cyano, nitro, —$C(=O)(C_{1-8}$alkyl), —$C(=O)O(C_{1-8}$alkyl), —$C(=O)NR^hR^h$, —$C(=NR^h)NR^hR^h$, —$OC(=O)(C_{1-8}$alkyl), —$OC(=O)NR^hR^h$, —$OC(=O)N(R^h)S(=O)_2(C_{1-8}$alkyl), —$OC_{2-6}$alkyl$NR^hR^h$, —$OC_{2-6}$alkyl$OR^h$, —$SR^h$, —$S(=O)(C_{1-8}$alkyl), —$S(=O)_2(C_{1-8}$alkyl), —$S(=O)_2NR^hR^h$, —$S(=O)_2N(R^h)C(=O)(C_{1-8}$alkyl), —$S(=O)_2N(R^h)C(=O)O(C_{1-8}$alkyl), —S(=O)₂N(Rʰ)C(=O)NRʰRʰ, —NRʰRʰ, —N(Rʰ)C(=O)(C₁₋₈alkyl), —N(Rʰ)C(=O)O(C₁₋₈alkyl), —N(Rʰ)C(=O)NRʰRʰ, —N(Rʰ)C(=NRʰ)NRʰRʰ, —N(Rʰ)S(=O)₂(C₁₋₈alkyl), —N(Rʰ)S(=O)₂NRʰRʰ, —NRʰC₂₋₆alkylNRʰRʰ, —NRʰC₂₋₆alkylORʰ, and C₁₋₄alkyl substituted by 0, 1, 2 or 3 groups selected from C₁₋₄haloalkyl, halo, cyano, nitro, —C(=O)(C₁₋₈alkyl), —C(=O)O(C₁₋₈alkyl), —C(=O)NRʰRʰ, —C(=NRʰ)NRʰRʰ, —ORʰ, —OC(=O)(C₁₋₈alkyl), —OC(=O)NRʰRʰ, —OC(=O)N(Rʰ)S(=O)₂(C₁₋₈alkyl), —OC₂₋₆alkylNRʰRʰ, —OC₂₋₆alkylORʰ, —SRʰ, —S(=O)(C₁₋₈alkyl), —S(=O)₂(C₁₋₈alkyl), —S(=O)₂NRʰRʰ, —S(=O)₂N(Rʰ)C(=O)(C₁₋₈alkyl), —S(=O)₂N(Rʰ)C(=O)O(C₁₋₈alkyl), —S(=O)₂N(Rʰ)C(=O)NRʰRʰ, —NRʰRʰ, —N(Rʰ)C(=O)(C₁₋₈alkyl), —N(Rʰ)C(=O)O(C₁₋₈alkyl), —N(Rʰ)C(=O)NRʰRʰ, —N(Rʰ)C(=NRʰ)NRʰRʰ, —N(Rʰ)S(=O)₂(C₁₋₈alkyl), —N(Rʰ)S(=O)₂NRʰRʰ, —NRʰC₂₋₆alkylNRʰRʰ and —NRʰC₂₋₆alkylORʰ.

In another embodiment, in conjunction with the novel compound embodiments above and below, R¹⁶ is H.

In another embodiment, in conjunction with the novel compound embodiments above and below, R¹⁶ is halo, —NHC₁₋₃alkyl, —N(C₁₋₃alkyl)C₁₋₃alkyl, —OC₁₋₃alkyl, —C₁₋₂haloalkyl, —OC₁₋₂haloalkyl or C₁₋₃alkyl.

In another embodiment, in conjunction with the novel compound embodiments above and below, R⁴ is

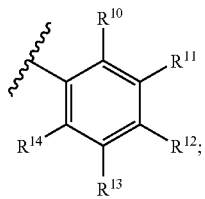

wherein at least one of R¹⁰, R¹¹, R¹², R¹³ and R14 is other than C₁₋₄haloalkyl or halo.

In another embodiment, in conjunction with the novel compound embodiments above and below, at least one of R¹⁰, R¹¹, R¹², R¹³ and R¹⁴ is —ORʰ or —NRʰRʰ.

In another embodiment, in conjunction with the novel compound embodiments above and below, R⁴ is a saturated or unsaturated 5- or 6-membered ring heterocycle containing 1, 2 or 3 atoms selected from O, N and S, so long as the combination of O and S atoms is not greater than 2, wherein each of the carbon atoms of the heterocycle is substituted by H, C₁₋₉alkyl, C₁₋₄haloalkyl, halo, cyano, oxo, —ORʰ, —S(=O)ₙC₁₋₆alkyl, —OC₁₋₄haloalkyl, —OC₂₋₆alkylNRʰRʰ, —OC₂₋₆alkylORʰ, —OC₁₋₆alkylC(=O)ORʰ, —NRʰRʰ, —NRʰC₁₋₄haloalkyl, —NRʰC₂₋₆alkylNRʰRʰ, —NRʰC₂₋₆alkylORʰ, —C(=O)C₁₋₆alkyl, —C(=O)OC₁₋₆alkyl, —OC(=O)C₁₋₆alkyl, —C(=O)NRʰC₁₋₆alkyl or —NRʰC(=O)C₁₋₆alkyl; and saturated carbon atoms may be additionally substituted by =O; and any available nitrogen atoms in the heterocycle are substituted by H, —C₁₋₆alkylORʰ, —C₁₋₆alkyl, —C₁₋₆alkylNRʰRʰ, —C₁₋₃alkylC(=O)ORʰ, —C₁₋₃alkylC(=O)NRʰRʰ, —C₁₋₃alkylOC(=O)C₁₋₆alkyl, —C₁₋₃alkylNRʰC(=O)C₁₋₆alkyl, —C(=O)Rʲ or —C₁₋₃alkylRʲ.

In another embodiment, in conjunction with the novel compound embodiments above and below, R⁴ is a saturated or unsaturated 5- or 6-membered ring heterocycle containing 1 or 2 atoms selected from O, N and S, wherein each of the carbon atoms of the heterocycle is substituted by H, C₁₋₉alkyl, C₁₋₄haloalkyl, halo, cyano, oxo, —ORʰ, —S(=O)ₙC₁₋₆alkyl, —OC₁₋₄haloalkyl, —OC₂₋₆alkylNRʰRʰ, —OC₂₋₆alkylORʰ, —OC₁₋₆alkylC(=O)ORʰ, —NRʰRʰ, —NRʰC₁₋₄haloalkyl, —NRʰC₂₋₆alkylNRʰRʰ, —NRʰC₂₋₆alkylORʰ, —C(=O)C₁₋₆alkyl, —C(=O)OC₁₋₆alkyl, —OC(=O)C₁₋₆alkyl, —C(=O)NRʰC₁₋₆alkyl or —NRʰC(=O)C₁₋₆alkyl; and saturated carbon atoms may be additionally substituted by =O; and any available nitrogen atoms in the bridge are substituted by H, —C₁₋₆alkylORʰ, —C₁₋₆alkyl, —C₁₋₆alkylNRʰRʰ, —C₁₋₃alkylC(=O)ORʰ, —C₁₋₃alkylC(=O)NRʰRʰ, —C₁₋₃alkylOC(=O)C₁₋₆alkyl, —C₁₋₃alkylNRʰC(=O)C₁₋₆alkyl, —C(=O)Rʲ or —C₁₋₃alkylRʲ.

In another embodiment, in conjunction with the novel compound embodiments above and below, R⁴ is an 8-, 9-, 10- or 11-membered bicyclic ring, containing 1, 2, 3 or 4 N atoms and 0, 1 or 2 atoms selected from S and O with the remainder being carbon atoms, wherein each of the carbon atoms of the ring is substituted by H, C₁₋₉alkyl, C₁₋₄haloalkyl, halo, cyano, oxo, —ORʰ, —S(=O)ₙC₁₋₆alkyl, —OC₁₋₄haloalkyl, —OC₁₋₆alkylNRʰRʰ, —OC₂₋₆alkylORʰ, —OC₁₋₆alkylC(=O)ORʰ, —NRʰRʰ, C₁₋₄haloalkyl, —NRʰC₂₋₆alkylNRʰRʰ, —NRʰC₂₋₆alkylORʰ, —C(=O)C₁₋₆alkyl, —C(=O)OC₁₋₆alkyl, —OC(=O)C₁₋₆alkyl, —C(=O)NRʰC₁₋₆alkyl or —NRʰC(=O)C₁₋₆alkyl; and saturated carbon atoms may be additionally substituted by =O; and any available nitrogen atoms in the ring are substituted by H, —C₁₋₆alkylORʰ, —C₁₋₆alkyl, —C₁₋₆alkylNRʰRʰ, —C₁₋₃alkylC(=O)ORʰ, —C₁₋₃alkylC(=O)NRʰRʰ, —C₁₋₃alkylOC(=O)C₁₋₆alkyl, —C₁₋₃alkylNRʰC(=O)C₁₋₆alkyl, —C(=O)Rʲ or —C₁₋₃alkylRʲ.

In another embodiment, in conjunction with the novel compound embodiments above and below, R⁴ is an 8-, 9-, 10- or 11-membered bicyclic ring, containing 0, 1, 2, 3 or 4 N atoms and 0, 1 or 2 atoms selected from S and O with the remainder being carbon atoms, wherein at least one of the carbon atoms of the ring is substituted by C₁₋₉alkyl, C₁₋₄haloalkyl, halo, cyano, oxo, —ORʰ, —S(=O)ₙC₁₋₆alkyl, —OC₁₋₄haloalkyl, —OC₂₋₆alkylNRʰRʰ, —OC₂₋₆alkylORʰ, —OC₁₋₆alkylC(=O)ORʰ, —NRʰRʰ, —NRʰC₁₋₄haloalkyl, —NRʰC₂₋₆alkylNRʰRʰ, —NRʰC₂₋₆alkylORʰ, —C(=O)C₁₋₆alkyl, —C(=O)OC₁₋₆alkyl, —OC(=O)C₁₋₆alkyl, —C(=O)NRʰC₁₋₆alkyl or —NRʰC(=O)C₁₋₆alkyl.

In another embodiment, in conjunction with the novel compound embodiments above and below, R⁵ and R⁹ are each independently selected from H, C₁₋₄haloalkyl, halo, nitro, —OC₁₋₆alkyl, —OC₁₋₄haloalkyl, —OC₂₋₆alkylNRʰRʰ, —OC₂₋₆alkylORʰ, —NRʰRʰ, —NRʰC₁₋₄haloalkyl, —NRʰC₂₋₆alkylNRʰRʰ, —NRʰC₂₋₆alkylORʰ, —CO₂(C₁₋₆alkyl), —C(=O)(C₁₋₆alkyl), —C(=O)NRʰRʰ, —NRʰC(=O)Rʰ, —NRʰC(=O)NRʰRʰ, —NRʰCO₂(C₁₋₆alkyl), —C₁₋₈alkylORʰ, —C₁₋₆alkylNRʰRʰ, —S(=O)ₙ(C₁₋₆alkyl), —S(=O)₂NRʰRʰ, —NRʰS(=O)₂(C₁₋₆alkyl) and —OC(=O)NRʰRʰ.

In another embodiment, in conjunction with the novel compound embodiments above and below, R⁶ and R⁸ are each independently selected from H, C₁₋₅alkyl, C₁₋₄haloalkyl, halo, —OC₁₋₆alkyl, —OC₁₋₄haloalkyl, —OC₂₋₆alkylNRʰRʰ, —OC₂₋₆alkylORʰ, —NRʰC₁₋₄haloalkyl, —NRʰC₂₋₆alkylNRʰRʰ or —NRʰC₂₋₆alkylORʰ, —C₁₋₈alkylORʰ, —C₁₋₆alkylNRʰRʰ and —S(C₁₋₆alkyl).

In another embodiment, in conjunction with the novel compound embodiments above and below, R⁷ is independently, at each instance, C₁₋₈alkyl, C₁₋₄haloalkyl, —OC₁₋₄haloalkyl, —OC₂₋₆alkylNRʰRʰ, —OC₂₋₆alkylORʰ, —NRʰRʰ, —NRʰC₁₋₄haloalkyl, —NRʰC₂₋₆alkylNRʰRʰ, —NRʰC₂₋₆alkylORʰ, —C₁₋₈alkylORʰ-C₁₋₆alkylNRʰRʰ or —S(C₁₋₆alkyl).

In another embodiment, in conjunction with the novel compound embodiments above and below, R¹⁰ and R¹⁴ are each independently selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^h$R$^h$, —C(=NR$^h$)NR$^h$R$^h$, —OR$^h$, —OC(=O)($C_{1-8}$alkyl), —OC(=O)NR$^h$R$^h$, —OC(=O)N(R$^h$)S(=O)$_2$($C_{1-8}$alkyl), —OC$_{2-6}$alkylNR$^h$R$^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^h$R$^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^h$R$^h$, —NR$^h$R$^h$, —N(R$^h$)C(=O)($C_{1-8}$alkyl), —N(R$^h$)C(=O)O($C_{1-8}$alkyl), —N(R$^h$)C(=O)NR$^h$R$^h$, —N(R$^h$)C(=NR$^h$)NR$^h$R$^h$, —N(R$^h$)S(=O)$_2$($C_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$ and $C_{1-4}$alkyl substituted by 0, 1, 2 or 3 groups selected from $C_{1-4}$haloalkyl, halo, cyano, nitro, —C(=O)($C_{1-8}$alkyl), —C(=O)NR$^h$R$^h$, —C(=NR$^h$)NR$^h$R$^h$, —OR$^h$, —OC(=O)($C_{1-8}$alkyl), —OC(=O)NR$^h$R$^h$, —OC(=O)N(R$^h$)S(=O)$_2$($C_{1-8}$alkyl), —OC$_{2-6}$alkylNR$^h$R$^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^h$R$^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^h$R$^h$, —NR$^h$R$^h$, —N(R$^h$)C(=O)($C_{1-8}$alkyl), —N(R$^h$)C(=O)O($C_{1-8}$alkyl), —N(R$^h$)C(=O)NR$^h$R$^h$, —N(R$^h$)C(=NR$^h$)NR$^h$R$^h$, —N(Rh)S(=O)$_2$($C_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$.

In another embodiment, in conjunction with the novel compound embodiments above and below, R$^{11}$ and R$^{13}$ are independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^h$R$^h$, —C(=NR$^h$)NR$^h$R$^h$, —OR$^h$, —OC(=O)($C_{1-8}$alkyl), —OC(=O)NR$^h$R$^h$, —OC(=O)N(R$^h$)S(=O)$_2$($C_{1-8}$alkyl), —OC$_{2-6}$alkylNR$^h$R$^h$, —OC$_{2-6}$alkylOR$^h$, SR$^h$, —S(=O)($C_{1-8}$alkyl), —S(=O)$_2$($C_{1-8}$alkyl), —S(=O)$_2$NR$^h$R$^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^h$R$^h$, NR$^h$R$^h$, —N(R$^h$)C(=O)($C_{1-8}$alkyl), —N(R$^h$)C(=O)O($C_{1-8}$alkyl), —N(R$^h$)C(=O)NR$^h$R$^h$, —N(R$^h$)C(=NR$^h$)NR$^h$R$^h$, —N(R$^h$)S(=O)$_2$($C_{1-8}$alkyl), —N(R$^h$)S(=O)$_2$NR$^h$R$^h$, —NR$^h$C$_{2-6}$alkylNR$^h$R$^h$, —NR$^h$C$_{2-6}$alkylOR$^h$ and $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^h$R$^h$, —C(=NR$^h$)NR$^h$R$^h$, —OR$^h$, —OC(=O)($C_{1-8}$alkyl), —OC(=O)NR$^h$R$^h$, —OC(=O)N(R$^h$)S(=O)$_2$($C_{1-8}$alkyl), —OC$_{2-6}$alkylNR$^h$R$^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^h$R$^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^h$R$^h$, —NR$^h$R$^h$, —N(R$^h$)C(=O)($C_{1-8}$alkyl), —N(R$^h$)C(=O)O($C_{1-8}$alkyl), —N(R$^h$)C(=O)NR$^h$R$^h$, —N(R$^h$)C(=NR$^h$)NR$^h$R$^h$, —N(R$^h$)S(=O)$_2$($C_{1-8}$alkyl), —N(R$^h$)S(=O)$_2$NR$^h$R$^h$, —NR$^h$C$_{2-6}$alkyNR$^h$R$^h$ and —NR$^h$C$_{2-6}$alkylOR$^h$.

In another embodiment, in conjunction with the novel compound embodiments above and below, R$^{12}$ is independently, at each instance, selected from H, $C_{1-8}$alkyl, $C_{1-4}$haloalkyl, halo, cyano, nitro, —C(=O)O($C_{1-8}$alkyl), —C(=O)NR$^h$R$^h$, —C(=NR$^h$)NR$^h$R$^h$, —OR$^h$, —OC(=O)($C_{1-8}$alkyl), —OC(=O)NR$^h$R$^h$, —OC(=O)N(R$^h$)S(=O)$_2$($C_{1-8}$alkyl), —OC$_{2-6}$alkylNR$^h$R$^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^h$R$^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^h$R$^h$, —NR$^h$R$^h$, —N(R$^h$)C(=O)($C_{1-8}$alkyl), —N(R$^h$)C(=O)O($C_{1-8}$alkyl), —N(R$^h$)C(=O)NR$^h$R$^h$, —N(R$^h$)C(=NR$^h$)NR$^h$R$^h$, —N(R$^h$)S(=O)$_2$($C_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$; or R$^{12}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^h$R$^h$, —C(=NR$^h$)NR$^h$R$^h$, —OR$^h$, —OC(=O)($C_{1-8}$alkyl), —OC(=O)NR$^h$R$^h$, —OC(=O)N(R$^h$)S(=O)$_2$($C_{1-8}$alkyl), —OC$_{2-6}$alkylNR$^h$R$^h$, —OC$_{2-6}$alkylOR$^h$, —SR$^h$, —S(=O)($C_{1-8}$alkyl), —S(=O)$_2$($C_{1-8}$alkyl), —S(=O)$_2$NR$^h$R$^h$, —S(=O)$_2$N(R$^h$)C(=O)($C_{1-8}$alkyl), —S(=O)$_2$N(R$^h$)C(=O)O($C_{1-8}$alkyl), —S(=O)$_2$N(R$^h$)C(=O)NR$^h$R$^h$, —NR$^h$R$^h$, —N(R$^h$)C(=O)($C_{1-8}$alkyl), —N(R$^h$)C(=O)O($C_{1-8}$alkyl), —N(R$^h$)C(=O)NR$^h$R$^h$, N(R$^h$)C(=NR$^h$)NR$^h$R$^h$, —N(R$^h$)S(=O)$_2$($C_{1-8}$alkyl), —N(R$^h$)S(=O)$_2$NR$^h$R$^h$, —NR$^h$C$_{2-6}$alkylNR$^h$R$^h$ and —NR$^h$C$_{2-6}$alkylOR$^h$.

In another embodiment, in conjunction with the novel compound embodiments above and below, Y is O.

In another embodiment, in conjunction with the novel compound embodiments above and below, Y is S.

Another aspect of the invention relates to a compound having the structure:

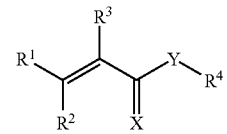

wherein:

X is O, S or NR$^m$;

n is independently, at each instance, 0, 1 or 2;

o is independently, at each instance, 0, 1, 2 or 3;

R$^m$ is independently at each instance H or R$^n$;

R$^n$ is independently at each instance $C_{1-8}$alkyl, phenyl or benzyl;

R$^q$ is independently in each instance H, $C_{1-4}$alkyl, $C_{1-4}$haloalkyl, halo, cyano, nitro, —C(=O)R$^n$, —C(=O)OR$^n$, —C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylNR$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R$^n$, —N(R$^m$)S(=O)$_2$NR$^m$R$^m$, —NR$^m$C$_{2-6}$alkylNR$^m$R$^m$ or —NR$^m$C$_{2-6}$alkylOR$^m$;

R$^s$ is R$^n$ substituted by 0, 1, 2 or 3 substituents independently selected from R$^q$;

R$^3$ is H or $C_{1-4}$alkyl;

R$^5$ is H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^m$R$^m$, —O—$C_{1-6}$alkylOR$^m$, —NR$^m$R$^m$, —NR$^m$—$C_{1-4}$haloalkyl, —NR$^m$—$C_{1-6}$alkylNR$^m$R$^m$, —NR$^m$—$C_{1-6}$alkylOR$^m$, or (CH$_2$)$_n$R$^c$ R$^6$ is, independently at each instance, H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^m$R$^m$, —O—$C_{1-6}$alkylOR$^m$, —NR$^m$R$^m$, —NR$^m$—$C_{1-4}$haloalkyl, —NR$^m$—$C_{1-6}$alkylNR$^m$R$^m$ or —NR$^m$—$C_{1-6}$alkylOR$^m$;

R$^8$ is H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^m$R$^m$, —O—$C_{1-6}$alkylOR$^m$, —NR$^m$R$^m$, —NR$^m$—$C_{1-4}$haloalkyl, —NR$^m$—$C_{1-6}$alkylNR$^m$R$^m$ or —NR$^m$—$C_{1-6}$alkylOR$^m$; and (A) $R^1$ is

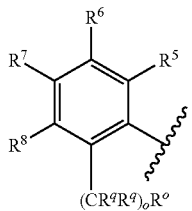

$R^2$ is H, —$OR'''$, halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_2$alkylNR'''R''', —OC$_{2-6}$alkylOR''', —SR''', —S(=O)R$_n$, —S(=O)$_2$R$_n$, —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; and the ring and bridge carbon atoms are substituted with 0, 1 or 2 =O groups;

$R^7$ is $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR''';

$R^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from $R^p$;

$R^p$ is independently at each instance $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', S(=O)$_2$N(R''')C(=O)NR'''R''', —NR'''R''', —N(R''')C(=O)R'', —N(R''')C(=O)OR'', N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; and Y is O or NH; or (B) $R^1$ is

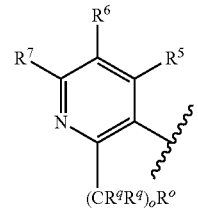

$R^2$ is H, —OR''', halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —C(=O)R^s, —C(=O)OR^s, —C(=O)NR‴R^s, —C(=NR‴)NR‴R^s, —OR^s, —OC(=O)R^s, —OC(=O)NR‴R^s, —OC(=O)N(R‴)S(=O)₂R^s, —OC₂₋₆alkylNR‴R^s, —OC₂₋₆alkylOR^s, —SR^s, —S(=O)R^s, —S(=O)₂R^s, —S(=O)₂NR‴R^s, —S(=O)₂N(R‴)C(=O)R^s, —S(=O)₂N(R‴)C(=O)OR^s, —S(=O)₂N(R‴)C(=O)NR‴R^s, —NR‴R^s, —N(R‴)C(=O)R^s, —N(R‴)C(=O)OR^s, —N(R‴)C(=O)NR‴R^s, —N(R‴)C(=NR‴)NR‴R^s, —N(R‴)S(=O)₂R^s, —N(R‴)S(=O)₂NR‴R^s, —NR‴C₂₋₆alkylNR‴R^s, —NR‴C₂₋₆alkylOR^s and —NR‴C₂₋₆alkylOR‴; and the ring and bridge carbon atoms are substituted with 0, 1 or 2 =O groups;

R⁷ is $C_{1-8}$alkyl, $C_{1-4}$haloalkyl, halo, nitro, cyano, —OC₁₋₆alkyl, —O—C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴ or —NR‴-C₁₋₆alkylOR‴;

R° is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R^p;

R^P is independently at each instance $C_{1-4}$alkyl, $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴ or —NR‴C₂₋₆alkylOR‴; and Y is O or NH; or (C) R¹ is

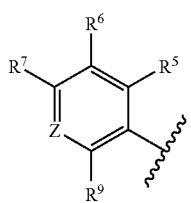

R² is H, —OR‴, halo, $C_{1-3}$haloalkyl or $C_{1-6}$alkyl;

R⁴ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from $C_{1-9}$alkyl, oxo, $C_{1-4}$haloalkyl, halo, nitro, cyano, —OR‴, —S(=O)ₙC₁₋₆alkyl, —O—C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴, —NR‴—C₁₋₆alkylOR‴, —C(=O)C₁₋₆alkyl, —OC(=O)C₁₋₆alkyl, —C(=O)NR‴C₁₋₆alkyl, —NR‴C(=O)C₁₋₆alkyl —C(=O)R^s, —C(=O)OR^s, —C(=O)NR‴R^s, —C(=NR‴)NR‴R^s, —OR^s, —OC(=O)R^s, —OC(=O)NR‴R^s, —OC(=O)N(R‴)S(=O)₂R^s, —OC₂₋₆alkylNR‴R^s, —OC₂₋₆alkylOR^s, —SR^s, —S(=O)R^s, —S(=O)₂R^s, —S(=O)₂NR‴R^s, —S(=O)₂N(R‴)C(=O)R^s, —S(=O)₂N(R‴)C(=O)OR^s, —S(=O)₂N(R‴)C(=O)NR‴R^s, —NR‴R^s, —N(R‴)C(=O)R^s, —N(R‴)C(=O)OR^s, —N(R‴)C(=O)NR‴R^s, —N(R‴)C(=NR‴)NR‴R^s, —N(R‴)S(=O)₂R^s, —N(R‴)S(=O)₂NR‴R^s, —NR‴C₂₋₆alkylNR‴R^s, —NR‴C₂₋₆alkylOR^s and —NR‴C₂₋₆alkylOR‴; wherein R⁴ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

R⁷ is $C_{1-8}$alkyl, $C_{1-5}$haloalkyl, I or Br

R⁹ is H, $C_{1-9}$alkyl, $C_{1-4}$haloalkyl, halo, nitro, cyano, —OC₁₋₆alkyl, —O—C₁₋₄haloalkyl, —O-C₁₋₆alkylNR‴R‴, —O—C₁₋₆alkylOR‴, —NR‴R‴, —NR‴—C₁₋₄haloalkyl, —NR‴—C₁₋₆alkylNR‴R‴, —NR‴—C₁₋₆alkylOR‴, or —(CH₂)ₙR^c;

R⁹ is independently, at each instance, H, $C_{1-9}$alkyl, $C_{1-4}$haloalkyl, halo, nitro, cyano, —OC₁₋₆alkyl, —O-C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴ or —NR‴—C₁₋₆alkylOR‴;

Y is NH; and

Z is CR⁸ or N; or (D) R¹ is

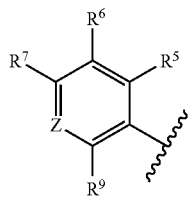

R² is $C_{1-6}$alkyl substituted by 1, 2 or 3 substituents selected from $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴ or —NR‴C$_{2-6}$alkylOR‴; or R$^2$ is —(C(R$^q$)$_2$)$_o$phenyl, wherein the phenyl is substituted by 0, 1, 2 or 3 substituents independently selected from C$_{1-8}$alkyl, C$_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and C$_{1-4}$alkyl substituted by 1 or 2 groups selected from C$_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and —NR‴C$_{2-6}$alkylOR‴; or R$^2$ is —(C(R$^q$)$_2$)$_o$R$^r$, wherein R$^r$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C$_{1-8}$alkyl, C$_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR C$_{2-6}$alkylOR$^s$ and C$_{1-4}$alkyl substituted by 1 or 2 groups selected from C$_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$ R$^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR C$_{2-6}$alkylOR$^s$ and C$_{1-4}$alkyl substituted by 1 or 2 groups selected from C$_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$ R", —S(=O)₂NR'''R''', —S(=O)₂N(R''')C(=O)R",
—S(=O)₂N(R''')C(=O)OR", —S(=O)₂N(R''')C(=O)
NR'''R''', —NR'''R''', —N(R''')C(=O)R", —N(R''')C(=O)
OR", —N(R''')C(=O)NR'''R''', —N(R''')C(=NR''')NR'''R''',
—N(R''')S(=O)₂R", —N(R''')S(=O)₂NR'''R''', —NR'''C₂₋₆
alkylNR'''R''', —C(=O)Rˢ, —C(=O)ORˢ, —C(=O)
NR'''Rˢ, —C(=NR''')NR'''Rˢ, —ORˢ, —OC(=O)Rˢ, —OC
(=O)NR'''Rˢ, —OC(=O)N(R''')S(=O)₂Rˢ, —OC₂₋₆alkyl-
NR'''Rˢ, —OC₂₋₆alkylORˢ, —SRˢ, —S(=O)Rˢ, —S(=O)₂
Rˢ, —S(=O)₂NR'''Rˢ, —S(=O)₂N(R''')C(=O)Rˢ,
—S(=O)₂N(R''')C(=O)ORˢ, —S(=O)₂N(R''')C(=O)
NR'''Rˢ, —NR'''Rˢ, —N(R''')C(=O)Rˢ, —N(R''')C(=O)
ORˢ, —N(R''')C(=O)NR'''Rˢ, —N(R''')C(=NR''')NR'''Rˢ,
—N(R''')S(=O)₂Rˢ, —N(R''')S(=O)₂NR'''Rˢ, —NR'''C₂₋₆
alkylNR'''Rˢ, —NR'''C₂₋₆alkylORˢ and —NR'''C₂₋₆alky-
lOR''', and the ring and bridge carbon atoms are substituted
with 0, 1 or 2=O groups;

R⁷ is C₂₋₈alkyl, C₁₋₅haloalkyl, I, Br;

R⁹ is independently, at each instance, H, C₁₋₉alkyl, C₁₋₄ha-
loalkyl, halo, nitro, cyano, —OC₁₋₆alkyl, —O—C₁₋₄ha-
loalkyl, —O—C₁₋₆alkylNR'''R''', —O—C₁₋₆alkylOR''',
—NR'''R''', —NR'''-C₁₋₄haloalkyl, —NR'''-C₁₋₆alkylNR'''R'''
or —NR'''—C₁₋₆alkylOR''';

Y is NH; and

Z is CR⁸ or N; or (E) R¹ is

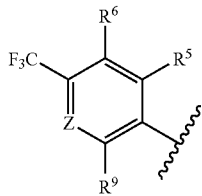

R² is H, —OR''', Cl, C₁₋₃haloalkyl or C₁₋₆alkyl;

R⁴ is a saturated or unsaturated 5- or 6-membered ring
containing 0, 1, 2 or 3 atoms selected from O, N and S, so long
as the combination of O and S atoms is not greater than 1,
wherein the ring is substituted by 0, 1, 2 or 3 substituents
independently selected from C₁₋₈alkyl, C₁₋₄haloalkyl, halo,
cyano, nitro, —C(=O)NR'''R''', —C(=NR''')NR'''R''',
—OR", —OC(=O)R", —OC(=O)NR'''R''', —OC(=O)N
(R''')S(=O)₂R", —OC₂₋₆alkylOR''', —SR", —S(=O)R",
—S(=O)₂R", —S(=O)₂NR'''R''', —S(=O)₂N(R''')C(=O)
R", —S(=O)₂N(R''')C(=O)OR", —S(=O)₂N(R''')C(=O)
NR'''R''', —NR'''R''', —N(R''')C(=O)R", —N(R''')C(=O)
OR", —N(R''')C(=O)NR'''R''', —N(R''')C(=NR''')NR'''R''',
—N(R''')S(=O)₂R", —N(R''')S(=O)₂NR'''R''', —NR'''C₂₋₆
alkylNR'''R''', —NR'''C₂₋₆alkylOR''', —C(=O)Rˢ,
—C(=O)ORˢ, —C(=O)NR'''Rˢ, —C(=NR''')NR'''Rˢ,
—ORˢ, —OC(=O)Rˢ, —OC(=O)NR'''Rˢ, —OC(=O)N
(R''')S(=O)₂Rˢ, —OC₂₋₆alkylNR'''Rˢ, —OC₂₋₆alkylORˢ,
—SRˢ, —S(=O)Rˢ, —S(=O)₂Rˢ, —S(=O)₂NR'''Rˢ,
—S(=O)₂N(R''')C(=O)Rˢ, —S(=O)₂N(R''')C(=O)ORˢ,
—S(=O)₂N(R''')C(=O)NR'''Rˢ, —NR'''Rˢ, —N(R''')C
(=O)Rˢ, —N(R''')C(=O)ORˢ, —N(R''')C(=O)NR'''R,
—N(R''')C(=NR''')NR'''Rˢ, —N(R''')S(=O)₂Rˢ, —N(R''')S
(=O)₂NR'''Rˢ, —NR'''C₂₋₆alkylNR'''Rˢ, —NR'''C₂₋₆alky-
lORˢ and C₁₋₄alkyl substituted by 1 or 2 groups selected from
C₁₋₂haloalkyl, halo, cyano, nitro, —C(=O)R", —C(=O)
NR'''R''', —C(=NR''')NR'''R''', —OR", —OC(=O)R",
—OC(=O)NR'''R''', —OC(=O)N(R''')S(=O)₂R", —OC₂₋₆
alkylNR'''R''', —OC₂₋₆alkylOR''', —SR", —S(=O)R", —S(=O)₂R", —S(=O)₂NR'''R''', —S(=O)₂N(R''')C(=O)
R", —S(=O)₂N(R''')C(=O)OR", —S(=O)₂N(R''')C(=O)
NR'''R''', —NR'''R''', —N(R''')C(=O)R", —N(R''')C(=O)
OR", —N(R''')C(=O)NR'''R''', —N(R''')C(=NR''')NR'''R''',
—N(R''')S(=O)₂R", —N(R''')S(=O)₂NR'''R''', —NR'''C₂₋₆
alkylNR'''R''', —C(=O)Rˢ, —C(=O)ORˢ, —C(=O)
NR'''Rˢ, —C(=NR''')NR'''Rˢ, —ORˢ, —OC(=O)Rˢ, —OC
(=O)NR'''Rˢ, —OC(=O)N(R''')S(=O)₂Rˢ, —OC₂₋₆alkyl-
NR'''Rˢ, —OC₂₋₆alkylORˢ, —SRˢ, —S(=O)Rˢ, —S(=O)₂
Rˢ, —S(=O)₂NR'''Rˢ, —S(=O)₂N(R''')C(=O)Rˢ,
—S(=O)₂N(R''')C(=O)ORˢ, —S(=O)₂N(R''')C(=O)
NR'''Rˢ, —NR'''Rˢ, —N(R''')C(=O)Rˢ, —N(R''')C(=O)
ORˢ, —N(R''')C(=O)NR'''Rˢ, —N(R''')C(=NR''')NR'''Rˢ,
—N(R''')S(=O)₂Rˢ, —N(R''')S(=O)₂NR'''Rˢ, —NR'''C₂₋₆
alkylNR'''Rˢ, —NR'''C₂₋₆alkylORˢ and —NR'''C₂₋₆alky-
lOR'''; wherein R⁴ is not unsubstituted phenyl;

R⁹ is independently, at each instance, H, C₁₋₉alkyl, C₁₋₄ha-
loalkyl, halo, nitro, cyano, —OC₁₋₆alkyl, —O—C₁₋₄ha-
loalkyl, —O—C₁₋₆alkylNR'''R''', —O—C₁₋₆alkylOR''',
—NR'''R''', —NR'''—C₁₋₄haloalkyl, —NR'''—C₁₋₆alkylN-
R'''R''' or —NR'''—C₁₋₆alkylOR''';

Y is NH; and

Z is CR⁸ or N.

In another embodiment, in conjunction with the novel
compound embodiments above and below, 80, wherein:

R¹ is

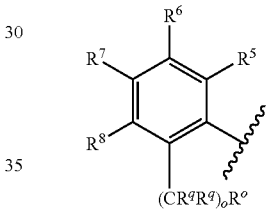

R² is H, —OR''', halo, C₁₋₃haloalkyl or C₁₋₆alkyl;

R⁴ is a saturated or unsaturated 5- or 6-membered ring
containing 0, 1, 2 or 3 atoms selected from O, N and S that is
optionally vicinally fused with a saturated or unsaturated 3-
or 4-atom bridge containing 0, 1, 2 or 3 atoms selected from
O, N and S with the remaining atoms being carbon, so long as
the combination of O and S atoms is not greater than 2,
wherein the ring and bridge are substituted by 0, 1, 2 or 3
substituents independently selected from C₁₋₈alkyl, C₁₋₄ha-
loalkyl, halo, cyano, nitro, —C(=O)R", —C(=O)OR",
—C(=O)NR'''R''', —C(=NR''')NR'''R''', —OR''', —OC
(=O)R", —OC(=O)NR'''R''', —OC(=O)N(R''')S(=O)₂
R", —OC₂₋₆alkylNR'''R''', —OC₂₋₆alkylOR''', —SR''',
—S(=O)R", —S(=O)₂R", —S(=O)₂NR'''R''', —S(=O)₂
N(R''')C(=O)R", —S(=O)₂N(R''')C(=O)OR", —S(=O)₂
N(R''')C(=O)NR'''R''', —NR'''R''', —N(R''')C(=O)R",
—N(R''')C(=O)OR", —N(R''')C(=O)NR'''R''', —N(R''')C
(=NR''')NR'''R''', —N(R''')S(=O)₂R", —N(R''')S(=O)₂
NR'''R''', —NR'''C₂₋₆alkylNR'''R''', —NR'''C₂₋₆alkylOR''',
—C(=O)Rˢ, —C(=O)ORˢ, —C(=O)NR'''Rˢ,
—C(=NR''')NR'''Rˢ, —ORˢ, —OC(=O)Rˢ, —OC(=O)
NR'''Rˢ, —OC(=O)N(R''')S(=O)₂Rˢ, —OC₂₋₆alkylNR'''Rˢ,
—OC₂₋₆alkylORˢ, —SRˢ, —S(=O)Rˢ, —S(=O)₂Rˢ,
—S(=O)₂NR'''Rˢ, —S(=O)₂N(R''')C(=O)Rˢ, —S(=O)₂
N(R''')C(=O)ORˢ, —S(=O)₂N(R''')C(=O)NR'''Rˢ,
—NR'''Rˢ, —N(R''')C(=O)Rˢ, —N(R''')C(=O)Rˢ,
—N(R''')C(=O)NR'''Rˢ, —N(R''')C(=NR''')NR'''Rˢ,
—N(R''')S(=O)₂Rˢ, —N(R''')S(=O)₂NR'''Rˢ, —NR'''C₂₋₆
alkylNR'''Rˢ, —NR'''C₂₋₆alkylORˢ and C₁₋₄alkyl substituted by 1 or 2 groups selected from $C_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and —NR‴C$_{2-6}$alkylOR‴; and the ring and bridge carbon atoms are substituted with 0, 1 or 2=O groups;

R$^7$ is $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR‴R‴, —O—C$_{1-6}$alkylOR‴, —NR‴R‴, —NR‴—C$_{1-4}$haloalkyl, —NR‴—C$_{1-6}$alkylNR‴R‴ or —NR‴—C$_{1-6}$alkylOR‴;

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance $C_{1-8}$alkyl, $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴ or —NR‴C$_{2-6}$alkylOR‴; and Y is O or NH.

In another embodiment, in conjunction with the novel compound embodiments above and below, R$^4$ is a saturated or unsaturated 5- or 6-membered ring containing 0, 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and $C_{1-4}$alkyl substituted by 1 or 2 groups selected from $C_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and —NR‴C$_{2-6}$alkylOR‴; and the ring and bridge carbon atoms are substituted with 0, 1 or 2=O groups.

In another embodiment, in conjunction with the novel compound embodiments above and below, R$^4$ is a phenyl ring that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR‴R$^s$, —C(=NR‴)NR‴R$^s$, —OR$^s$, —OC(=O)R$^s$, —OC(=O)NR‴R$^s$, —OC(=O)N(R‴)S(=O)$_2$R$^s$, —OC$_{2-6}$alkylNR‴R$^s$, —OC$_{2-6}$alkylOR$^s$, —SR$^s$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C (=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; and the bridge carbon atoms are substituted with 0, 1 or 2=O groups.

In another embodiment, in conjunction with the novel compound embodiments above and below, R$^7$ is C$_{1-9}$alkyl, C$_{1-4}$haloalkyl, halo, —OC$_{1-6}$alkyl, —O—C$_{1-4}$haloalkyl, —NR'''R''' or —NR'''—C$_{1-4}$haloalkyl.

In another embodiment, in conjunction with the novel compound embodiments above and below, R$^7$ is C$_{1-5}$alkyl, C$_{1-4}$haloalkyl, I, Br or Cl.

In another embodiment, in conjunction with the novel compound embodiments above and below, R$^7$ is tert-butyl or trifluoromethyl.

In another embodiment, in conjunction with the novel compound embodiments above and below, R$^o$ is a saturated, partially-saturated or unsaturated 5-, 6- or 7-membered monocyclic ring containing 0, 1, 2 or 3 atoms selected from N, O and S, so long as the combination of O and S atoms is not greater than 1, wherein the carbon atoms of the ring are substituted by 0, 1 or 2 oxo groups, wherein the ring is substituted by 0, 1, 2 or 3 substituents independently selected from R$^p$.

In another embodiment, in conjunction with the novel compound embodiments above and below, R$^o$ is a saturated, partially-saturated or unsaturated 6-membered ring containing 0, 1, 2 or 3 N atoms, wherein the carbon atoms of the ring are substituted by 0, 1 or 2 oxo groups, wherein the ring is substituted by 0, 1, 2 or 3 substituents independently selected from R$^p$.

In another embodiment, in conjunction with the novel compound embodiments above and below, Y is O.

In another embodiment, in conjunction with the novel compound embodiments above and below, Y is NH.

In another embodiment, in conjunction with the novel compound embodiments above and below, R$^1$ is

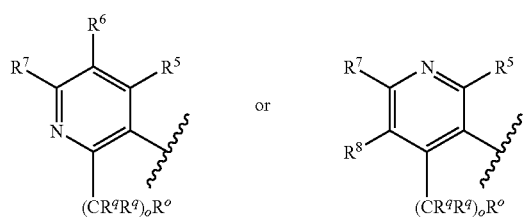

R$^2$ is H, —OR''', halo, C$_{1-3}$haloalkyl or C$_{1-6}$alkyl;

R$^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR'', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; and the ring and bridge carbon atoms are substituted with 0, 1 or 2=O groups;

R$^7$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR'''; [C$_{1-8}$alkyl, C$_{1-5}$haloalkyl, I, Br or Cl]

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; and Y is O or NH.

In another embodiment, in conjunction with the novel compound embodiments above and below, $R^4$ is a saturated or unsaturated 5- or 6-membered ring containing 0, 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR″R$^s$, —C(=NR‴)NR‴R$^s$, —OR$^s$, —OC(=O)R$^s$, —OC(=O)NR″R$^s$, —OC(=O)N(R‴)S(=O)$_2$R$^s$, —OC$_{2-6}$alkylNR″R$^s$, —OC$_{2-6}$alkylOR$^s$, —SR$^s$, —S(=O)R$^s$, —S(=O)$_2$R$^s$, —S(=O)$_2$NR″R$^s$, —S(=O)$_2$N(R‴)C(=O)R$^s$, —S(=O)$_2$N(R‴)C(=O)OR$^s$, —S(=O)$_2$N(R‴)C(=O)NR″R$^s$, —NR″R$^s$, —N(R‴)C(=O)R$^s$, —N(R‴)C(=O)OR$^s$, —N(R‴)C(=O)NR″R$^s$, —N(R‴)C(=NR‴)NR″R$^s$, —N(R‴)S(=O)$_2$R$^s$, —N(R‴)S(=O)$_2$NR″R$^s$, —NR‴C$_{2-6}$alkylNR″R$^s$, —NR‴C$_{2-6}$alkylOR$^s$ and $C_{1-4}$alkyl substituted by 1 or 2 groups selected from $C_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{1-2}$alkylNR‴R‴, —OC$_{2-6}$alkylOR‴, —SR‴, —S(=O)R‴, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —C(=O)R$^s$, —C(=O)OR$^s$, —C(=O)NR″R$^s$, —C(=NR‴)NR″R$^s$, —OR$^s$, —OC(=O)R$^s$, —OC(=O)NR″R$^s$, —OC(=O)N(R‴)S(=O)$_2$R$^s$, —OC$_{2-6}$alkylNR″R$^s$, —OC$_{2-6}$alkylOR$^s$, —SR$^s$, —S(=O)R$^s$, —S(=O)$_2$R$^s$, —S(=O)$_2$NR″R$^s$, —S(=O)$_2$N(R‴)C(=O)R$^s$, —S(=O)$_2$N(R‴)C(=O)OR$^s$, —S(=O)$_2$N(R‴)C(=O)NR″R$^s$, —NR″R$^s$, —N(R‴)C(=O)R$^s$, —N(R‴)C(=O)OR$^s$, —N(R‴)C(=O)NR″R$^s$, —N(R‴)C(=NR‴)NR″R$^s$, —N(R‴)S(=O)$_2$R$^s$, —N(R‴)S(=O)$_2$NR″R$^s$, —NR‴C$_{2-6}$alkylNR″R$^s$, —NR‴C$_{2-6}$alkylOR$^s$ and —NR‴C$_{2-6}$alkylOR‴; and the ring and bridge carbon atoms are substituted with 0, 1 or 2=O groups.

In another embodiment, in conjunction with the novel compound embodiments above and below, $R^4$ is a phenyl ring that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR″R$^s$, —C(=NR‴)NR″R$^s$, —OR$^s$, —OC(=O)R$^s$, —OC(=O)NR″R$^s$, —OC(=O)N(R‴)S(=O)$_2$R$^s$, —OC$_{2-6}$alkylNR″R$^s$, —OC$_{2-6}$alkylOR$^s$, —SR$^s$, —S(=O)R$^s$, —S(=O)$_2$R$^s$, —S(=O)$_2$NR″R$^s$, —S(=O)$_2$N(R‴)C(=O)R$^s$, —S(=O)$_2$N(R‴)C(=O)OR$^s$, —S(=O)$_2$N(R‴)C(=O)NR″R$^s$, —NR″R$^s$, —N(R‴)C(=O)R$^s$, —N(R‴)C(=O)OR$^s$, —N(R‴)C(=O)NR″R$^s$, —N(R‴)C(=NR‴)NR″R$^s$, —N(R‴)S(=O)$_2$R$^s$, —N(R‴)S(=O)$_2$NR″R$^s$, —NR‴C$_{2-6}$alkylNR″R$^s$, —NR‴C$_{2-6}$alkylOR$^s$ and $C_{1-4}$alkyl substituted by 1 or 2 groups selected from $C_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR″R$^s$, —C(=NR‴)NR″R$^s$, —OR$^s$, —OC(=O)R$^s$, —OC(=O)NR″R$^s$, —OC(=O)N(R‴)S(=O)$_2$R$^s$, —OC$_{2-6}$alkylNR″R$^s$, —OC$_{2-6}$alkylOR$^s$, —SR$^s$, —S(=O)R$^s$, —S(=O)$_2$R$^s$, —S(=O)$_2$NR″R$^s$, —S(=O)$_2$N(R‴)C(=O)R$^s$, —S(=O)$_2$N(R‴)C(=O)OR$^s$, —S(=O)$_2$N(R‴)C(=O)NR″R$^s$, —NR″R$^s$, —N(R‴)C(=O)R$^s$, —N(R‴)C(=O)OR$^s$, —N(R‴)C(=O)NR″R$^s$, —N(R‴)C(=NR‴)NR″R$^s$, —N(R‴)S(=O)$_2$R$^s$, —N(R‴)S(=O)$_2$NR″R$^s$, —NR‴C$_{2-6}$alkylNR″R$^s$, —NR‴C$_{2-6}$alkylOR$^s$ and —NR‴C$_{2-6}$alkylOR‴; and the bridge carbon atoms are substituted with 0, 1 or 2=O groups.

In another embodiment, in conjunction with the novel compound embodiments above and below, $R^7$ is $C_{1-8}$alkyl, $C_{1-4}$haloalkyl, halo, —OC$_{1-6}$alkyl, —O—C$_{1-4}$haloalkyl, —NR‴R‴ or —NR‴—C$_{1-4}$haloalkyl.

In another embodiment, in conjunction with the novel compound embodiments above and below, $R^7$ is $C_{1-5}$alkyl, $C_{1-4}$haloalkyl, I, Br or Cl.

In another embodiment, in conjunction with the novel compound embodiments above and below, $R^7$ is tert-butyl or trifluoromethyl.

In another embodiment, in conjunction with the novel compound embodiments above and below, $R^o$ is a saturated, partially-saturated or unsaturated 5-, 6- or 7-membered monocyclic ring containing 0, 1, 2 or 3 atoms selected from N, O and S, so long as the combination of O and S atoms is not greater than 1, wherein the carbon atoms of the ring are substituted by 0, 1 or 2 oxo groups, wherein the ring is substituted by 0, 1, 2 or 3 substituents independently selected from $R^p$.

In another embodiment, in conjunction with the novel compound embodiments above and below, $R^o$ is a saturated, partially-saturated or unsaturated 6-membered ring containing 0, 1, 2 or 3 N atoms, wherein the carbon atoms of the ring are substituted by 0, 1 or 2 oxo groups, wherein the ring is substituted by 0, 1, 2 or 3 substituents independently selected from $R^p$.

In another embodiment, in conjunction with the novel compound embodiments above and below, Y is O.

In another embodiment, in conjunction with the novel compound embodiments above and below, Y is NH.

In another embodiment, in conjunction with the novel compound embodiments above and below, $R^1$ is

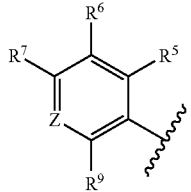

$R^2$ is H, —$OR^m$, halo, $C_{1-3}$haloalkyl or $C_{1-6}$alkyl;

$R^4$ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from $C_{1-9}$alkyl, oxo, $C_{1-4}$haloalkyl, halo, nitro, cyano, —$OR^m$, —$S(=O)_nC_{1-6}$alkyl, —O—$C_{1-4}$haloalkyl, —O—$C_{1-6}$alkyl$NR'''R'''$, —$C_{1-6}$alkyl$OR'''$, —$NR'''R'''$, —$NR'''$—$C_{1-4}$haloalkyl, —$NR'''$—$C_{1-6}$alkyl$NR'''R'''$, —$NR'''$—$C_{1-6}$alkyl$OR'''$, —$C(=O)C_{1-6}$alkyl, —$OC(=O)C_{1-6}$alkyl, —$C(=O)NR'''C_{1-6}$alkyl, —$NR'''C(=O)C_{1-6}$alkyl —$C(=O)R^s$, —$C(=O)OR^s$, —$C(=O)NR'''R^s$, —$C(=NR''')NR'''R^s$, —$OR^s$, —$OC(=O)R^s$, —$OC(=O)NR'''R^s$, —$OC(=O)N(R''')S(=O)_2R^s$, —$OC_{2-6}$alkyl$NR'''R^s$, —$OC_{2-6}$alkyl$OR^s$, —$SR^s$, —$S(=O)R^s$, —$S(=O)_2R^s$, —$S(=O)_2NR'''R^s$, —$S(=O)_2N(R''')C(=O)R^s$, —$S(=O)_2N(R''')C(=O)OR^s$, —$S(=O)_2N(R''')C(=O)NR'''R^s$, —$NR'''R^s$, —$N(R''')C(=O)R^s$, —$N(R''')C(=O)OR^s$, —$N(R''')C(=O)NR'''R^s$, —$N(R''')C(=NR''')NR'''R^s$, —$N(R''')S(=O)_2R^s$, —$N(R''')S(=O)_2NR'''R^s$, —$NR'''C_{2-6}$alkyl$NR'''R^s$, —$NR'''$—$C_{2-6}$alkyl$OR^s$ and $C_{1-4}$alkyl substituted by 1 or 2 groups selected from $C_{1-2}$haloalkyl, halo, cyano, nitro, —$C(=O)R''$, —$C(=O)NR'''R'''$, —$C(=NR''')NR'''R'''$, —$OR'''$, —$OC(=O)R''$, —$OC(=O)NR'''R'''$, —$OC(=O)N(R''')S(=O)_2R''$, —$OC_{2-6}$alkyl$NR'''R'''$, —$OC_{2-6}$alkyl$OR'''$, —$SR'''$, —$S(=O)R''$, —$S(=O)_2R''$, —$S(=O)_2NR'''R'''$, —$S(=O)_2N(R''')C(=O)R''$, —$S(=O)_2N(R''')C(=O)OR''$, —$S(=O)_2N(R''')C(=O)NR'''R'''$, —$N(R''')C(=O)R''$, —$N(R''')C(=O)OR''$, —$N(R''')C(=O)NR'''R'''$, —$N(R''')C(=NR''')NR'''R'''$, —$N(R''')S(=O)_2R''$, —$N(R''')S(=O)_2NR'''R'''$, —$NR'''C_{2-6}$alkyl$NR'''R'''$, —$NR'''C_{2-6}$alkyl$OR'''$; wherein $R^4$ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

$R^7$ is $C_{1-8}$alkyl, $C_{1-5}$haloalkyl, I or Br;

$R^9$ is H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkyl$NR'''R'''$, —O—$C_{1-6}$alkyl$OR'''$, —$NR'''R'''$, —$NR'''$—$C_{1-4}$haloalkyl, —$NR'''$—$C_{1-6}$alkyl$NR'''R'''$ or —$NR'''$—$C_{1-6}$alkyl$OR'''$;

Y is NH; and

Z is $CR^8$ or N.

In another embodiment, in conjunction with the novel compound embodiments above and below, $R^4$ is a heterocycle selected from indole, 3H-indole, benzo[b]furan, benzothiophene, 1H-indazole, benzimidazole, benzthiazole, 1H-benzotriazole, 7-quinoline, 8-quinoline, 1,2,3,4-tetrahydroquinoline, isoquinoline, cinnoline, phthalazine, quinazoline and quinoxaline, wherein the heterocycle is substituted by 0, 1, 2 or 3 substituents independently selected from $C_{1-9}$alkyl, oxo, $C_{1-4}$haloalkyl, halo, nitro, cyano, —$OR^m$, —$S(=O)_nC_{1-6}$alkyl, —O—$C_{1-4}$haloalkyl, —O—$C_{1-6}$alkyl$NR'''R'''$, —O—$C_{1-6}$alkyl$OR'''$, —$NR'''R'''$, —$NR'''$—$C_{1-4}$haloalkyl, —$NR'''$—$C_{1-6}$alkyl$NR'''R'''$, —$NR'''$—$C_{1-6}$alkyl$OR'''$, —$C(=O)C_{1-6}$alkyl, —$OC(=O)C_{1-6}$alkyl, —$C(=O)NR'''C_{1-6}$alkyl, —$NR'''C(=O)C_{1-6}$alkyl —$C(=O)R^s$, —$C(=O)OR^s$, —$C(=O)NR'''R^s$, —$C(=NR''')NR'''R^s$, —$OR^s$, —$OC(=O)R^s$, —$OC(=O)NR'''R^s$, —$OC(=O)N(R''')S(=O)_2R^s$, —$OC_{2-6}$alkyl$NR'''R^s$, —$OC_{2-6}$alkyl$OR^s$, —$SR^s$, —$S(=O)R^s$, —$S(=O)_2R^s$, —$S(=O)_2NR'''R^s$, —$S(=O)_2N(R''')C(=O)R^s$, —$S(=O)_2N(R''')C(=O)OR^s$, —$S(=O)_2N(R''')C(=O)NR'''R^s$, —$NR'''R^s$, —$N(R''')C(=O)R^s$, —$N(R''')C(=O)OR^s$, —$N(R''')C(=O)NR'''R^s$, —$N(R''')C(=NR''')NR'''R^s$, —$N(R''')S(=O)_2R$, —$N(R''')S(=O)_2NR'''R^s$, —$NR'''C_{2-6}$alkyl$NR'''R^s$, —$NR'''C_{2-6}$alkyl$OR^s$ and $C_{1-4}$alkyl substituted by 1 or 2 groups selected from $C_{1-2}$haloalkyl, halo, cyano, nitro, —$C(=O)R''$, —$C(=O)NR'''R'''$, —$C(=NR''')NR'''R'''$, —$OR'''$, —$OC(=O)R''$, —$OC(=O)NR'''R'''$, —$OC(=O)N(R''')S(=O)_2R''$, —$OC_{2-6}$alkyl$NR'''R'''$, —$OC_{2-6}$alkyl$OR'''$, —$SR'''$, —$S(=O)R''$, —$S(=O)_2R''$, —$S(=O)_2NR'''R'''$, —$S(=O)_2N(R''')C(=O)R''$, —$S(=O)_2N(R''')C(=O)OR''$, —$S(=O)_2N(R''')C(=O)NR'''R'''$, —$N(R''')C(=O)R''$, —$N(R''')C(=O)OR''$, —$N(R''')C(=O)NR'''R'''$, —$N(R''')C(=NR''')NR'''R'''$, —$N(R''')S(=O)_2R''$, —$N(R''')S(=O)_2NR'''R'''$, —$C(=O)R^s$, —$C(=O)OR^s$, —$C(=O)NR'''R^s$, —$C(=NR''')NR'''R^s$, —$OR^s$, —$OC(=O)R^s$, —$OC(=O)NR'''R^s$, —$OC(=O)N(R''')S(=O)_2R^s$, —$OC_{2-6}$alkyl$NR'''R^s$, —$OC_{2-6}$alkyl$OR_s$, —$SR^s$, —$S(=O)R^s$, —$S(=O)_2R^s$, —$S(=O)_2NR'''R^s$, —$S(=O)_2N(R''')C(=O)R^s$, —$S(=O)_2N(R''')C(=O)OR^s$, —$S(=O)_2N(R''')C(=O)NR'''R^s$, —$NR'''R^s$, —$N(R''')C(=O)R^s$, —$N(R''')C(=O)OR^s$, —$N(R''')C(=O)NR'''R^s$, —$N(R''')C(=NR''')NR'''R^s$, —$N(R''')S(=O)_2R^s$, —$N(R''')S(=O)_2NR'''R^s$, —$NR'''C_{2-6}$alkyl$NR'''R^s$, —$NR'''C_{2-6}$alkyl$OR^s$ and —$NR'''C_{2-6}$alkyl$OR'''$.

In another embodiment, in conjunction with the novel compound embodiments above and below, $R^4$ is a heterocycle selected from 6-indole, 7-indole, 6-3H-indole, 7-3H-indole, 6-benzo[b]furan, 7-benzo[b]furan, 6-benzothiophene, 7-benzothiophene, 6-1H-indazole, 7-1H-indazole, benzimidazole, benzthiazole, 1H-benzotriazole, 7-quinoline, 8-quinoline, 7-1,2,3,4-tetrahydroquinoline, 8-1,2,3,4-tetrahydroquinoline, isoquinolin-7-yl, isoquinolin-8-yl, 7-cinnoline, 8-cinnoline, phthalazine, 7-quinazoline, 8-quinazoline and quinoxaline, wherein the heterocycle is substituted by 0, 1, 2 or 3 substituents independently selected from $C_{1-9}$alkyl, oxo, $C_{1-4}$haloalkyl, halo, nitro, cyano, —$OR^m$, —$S(=O)_nC_{1-6}$alkyl, —O—$C_{1-4}$haloalkyl, —O—$C_{1-6}$alkyl$NR'''R'''$, —O—$C_{1-6}$alkyl$OR'''$, —$NR'''R'''$, —$NR'''$—$C_{1-4}$haloalkyl, —$NR'''$—$C_{1-6}$alkyl$NR'''R'''$, —$NR'''$—$C_{1-6}$alkyl$OR'''$, —$C(=O)C_{1-6}$alkyl, —$OC(=O)C_{1-6}$alkyl, —$C(=O)NR'''C_{1-6}$alkyl, —$NR'''C(=O)C_{1-6}$alkyl —$C(=O)R^s$, —$C(=O)OR^s$, —$C(=O)NR'''R^s$, —$C(=NR''')NR'''R^s$, —$OR^s$, —$OC(=O)R^s$, —$OC(=O)NR'''R^s$, —$OC(=O)N $(R''')S(\!=\!O)_2R^s$, —$OC_{2\text{-}6}alkylNR'''R^s$, —$OC_{2\text{-}6}alkylOR^s$, —$SR^s$, —$S(\!=\!O)R^s$, —$S(\!=\!O)_2R^s$, —$S(\!=\!O)_2NR'''R^s$, —$S(\!=\!O)_2N(R''')C(\!=\!O)R^s$, —$S(\!=\!O)_2N(R''')C(\!=\!O)OR^s$, —$S(\!=\!O)_2N(R''')C(\!=\!O)NR'''R^s$, —$NR'''R^s$, —$N(R''')C(\!=\!O)R^s$, —$N(R''')C(\!=\!O)OR^s$, —$N(R''')C(\!=\!O)NR'''R^s$, —$N(R''')C(\!=\!NR''')NR'''R^s$, —$N(R''')S(\!=\!O)_2R^s$, —$N(R''')S(\!=\!O)_2NR'''R^s$, —$NR'''C_{2\text{-}6}alkylNR_mR^s$, —$NR'''C_{2\text{-}6}alkylOR^s$ and $C_{1\text{-}4}alkyl$ substituted by 1 or 2 groups selected from $C_{1\text{-}2}haloalkyl$, halo, cyano, nitro, —$C(\!=\!O)R''$, —$C(\!=\!O)NR'''R'''$, —$C(\!=\!NR''')NR'''R'''$, —$OR'''$, —$OC(\!=\!O)R''$, —$OC(\!=\!O)NR'''R'''$, —$OC(\!=\!O)N(R''')S(\!=\!O)_2R''$, —$OC_{2\text{-}6}alkylNR'''R'''$, —$OC_{2\text{-}6}alkylOR'''$, —$SR'''$, —$S(\!=\!O)R''$, —$S(\!=\!O)_2R''$, —$S(\!=\!O)_2NR'''R'''$, —$S(\!=\!O)_2N(R''')C(\!=\!O)R''$, —$S(\!=\!O)_2N(R''')C(\!=\!O)OR''$, —$S(\!=\!O)_2N(R''')C(\!=\!O)NR'''R'''$, —$N(R''')C(\!=\!O)R''$, —$N(R''')C(\!=\!O)OR''$, —$N(R''')C(\!=\!O)NR'''R'''$, —$N(R''')C(\!=\!NR''')NR'''R'''$, —$N(R''')S(\!=\!O)_2R''$, —$N(R''')S(\!=\!O)_2NR'''R'''$, —$C(\!=\!O)R^s$, —$C(\!=\!O)OR^s$, —$C(\!=\!O)NR_mR^s$, —$C(\!=\!NR''')NR_mR^s$, —$OR^s$, —$OC(\!=\!O)R^s$, —$OC(\!=\!O)NR_mR^s$, —$OC(\!=\!O)N(R''')S(\!=\!O)_2R^s$, —$OC_{2\text{-}6}alkylNR_mR^s$, —$OC_{2\text{-}6}alkylOR^s$, —$SR^s$, —$S(\!=\!O)R^s$, —$S(\!=\!O)_2R^s$, —$S(\!=\!O)_2NR_mR^s$, —$S(\!=\!O)_2N(R''')C(\!=\!O)R^s$, —$S(\!=\!O)_2N(R''')C(\!=\!O)OR^s$, —$S(\!=\!O)_2N(R''')C(\!=\!O)NR_mR^s$, $NR_mR^s$, —$N(R''')C(\!=\!O)R^s$, —$N(R''')C(\!=\!O)OR^s$, —$N(R''')C(\!=\!O)NR_mR^s$, —$N(R''')C(\!=\!NR''')NR_mR^s$, —$N(R''')S(\!=\!O)_2R^s$, —$N(R''')S(\!=\!O)_2NR_mR^s$, —$NR'''C_{2\text{-}6}alkylNR_mR^s$, —$NR'''C_{2\text{-}6}alkylOR^s$ and —$NR'''C_{2\text{-}6}alkylOR'''$.

In another embodiment, in conjunction with the novel compound embodiments above and below, $R^9$ is Clgalkyl, $C_{1\text{-}4}haloalkyl$, halo, nitro, cyano, —$OC_{1\text{-}6}alkyl$, —O—$C_{1\text{-}4}haloalkyl$, —O—$C_{1\text{-}6}alkylNR'''R'''$, —O—$C_{1\text{-}6}alkylOR'''$, —$NR'''R'''$, —$NR'''$—$C_{1\text{-}4}haloalkyl$, —$NR'''$—$C_{1\text{-}6}alkylNR'''R'''$ or —$NR'''$—$C_{1\text{-}6}alkylOR'''$.

In another embodiment, in conjunction with the novel compound embodiments above and below, $R^9$ is H.

In another embodiment, in conjunction with the novel compound embodiments above and below, Z is $CR^8$.

In another embodiment, in conjunction with the novel compound embodiments above and below, Z is N.

In another embodiment, in conjunction with the novel compound embodiments above and below, $R^7$ is tert-butyl or trifluoromethyl.

In another embodiment, in conjunction with the novel compound embodiments above and below, $R^1$ is

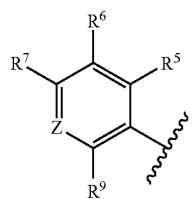

$R^2$ is $C_{1\text{-}6}alkyl$ substituted by 1, 2 or 3 substituents selected from $C_{1\text{-}4}haloalkyl$, halo, cyano, nitro, —$C(\!=\!O)R''$, —$C(\!=\!O)OR''$, —$C(\!=\!O)NR'''R'''$, —$C(\!=\!NR''')NR'''R'''$, —$OR'''$, —$OC(\!=\!O)R''$, —$OC(\!=\!O)NR'''R'''$, —$OC(\!=\!O)N(R''')S(\!=\!O)_2R''$, —$OC_{2\text{-}6}alkylNR'''R'''$, —$OC_{2\text{-}6}alkylOR'''$, —$SR'''$, —$S(\!=\!O)R''$, —$S(\!=\!O)_2R''$, —$S(\!=\!O)_2NR'''R'''$, —$S(\!=\!O)_2N(R''')C(\!=\!O)R''$, —$S(\!=\!O)_2N(R''')C(\!=\!O)OR''$, —$S(\!=\!O)_2N(R''')C(\!=\!O)NR'''R'''$, —$NR'''R'''$, —$N(R''')C(\!=\!O)R''$, —$N(R''')C(\!=\!O)OR''$, —$N(R''')C(\!=\!O)NR'''R'''$, —$N(R''')C(\!=\!NR''')NR'''R'''$, —$N(R''')S(\!=\!O)_2R''$, —$N(R''')S(\!=\!O)_2NR'''R'''$, —$NR'''C_{2\text{-}6}alkylNR'''R'''$ and —$NR'''C_{2\text{-}6}alkylOR'''$; or $R^2$ is

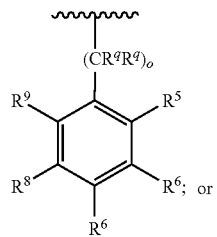

$R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1\text{-}8}alkyl$, $C_{1\text{-}4}haloalkyl$, halo, cyano, nitro, —$C(\!=\!O)R''$, —$C(\!=\!O)OR''$, —$C(\!=\!O)NR'''R'''$, —$C(\!=\!NR''')NR'''R'''$, —$OR'''$, —$OC(\!=\!O)R''$, —$OC(\!=\!O)NR'''R'''$, —$OC(\!=\!O)N(R''')S(\!=\!O)_2R''$, —$OC_{2\text{-}6}alkylNR'''R'''$, —$OC_{2\text{-}6}alkylOR'''$, —$SR'''$, —$S(\!=\!O)R''$, —$S(\!=\!O)_2R''$, —$S(\!=\!O)_2NR'''R'''$, —$S(\!=\!O)_2N(R''')C(\!=\!O)R''$, —$S(\!=\!O)_2N(R''')C(\!=\!O)OR''$, —$S(\!=\!O)_2N(R''')C(\!=\!O)NR'''R'''$, —$NR'''R'''$, —$N(R''')C(\!=\!O)R''$, —$N(R''')C(\!=\!O)OR''$, —$N(R''')C(\!=\!O)NR'''R'''$, —$N(R''')C(\!=\!NR''')NR'''R'''$, —$N(R''')S(\!=\!O)_2R''$, —$N(R''')S(\!=\!O)_2NR'''R'''$, —$NR'''C_{2\text{-}6}alkylNR'''R'''$, —$NR'''C_{2\text{-}6}alkylOR'''$, —$C(\!=\!O)R^s$, —$C(\!=\!O)OR^s$, —$C(\!=\!O)NR_mR^s$, —$C(\!=\!NR''')NR_mR^s$, —$OR^s$, —$OC(\!=\!O)R^s$, —$OC(\!=\!O)NR_mR^s$, —$OC(\!=\!O)N(R''')S(\!=\!O)_2R^s$, —$OC_{2\text{-}6}alkylNR_mR^s$, —$OC_{2\text{-}6}alkylOR^s$, —$SR^s$, —$S(\!=\!O)R^s$, —$S(\!=\!O)_2R^s$, —$S(\!=\!O)_2NR_mR^s$, —$S(\!=\!O)_2N(R''')C(\!=\!O)R^s$, —$S(\!=\!O)_2N(R''')C(\!=\!O)OR^s$, —$S(\!=\!O)_2N(R''')C(\!=\!O)NR'''R^s$, —$NR_mR^s$, —$N(R''')C(\!=\!O)R^s$, —$N(R''')C(\!=\!O)OR^s$, —$N(R''')C(\!=\!O)NR'''R^s$, —$N(R''')C(\!=\!NR''')NR_mR^s$, —$N(R''')S(\!=\!O)_2R^s$, —$N(R''')S(\!=\!O)_2NR_mR^s$, —$NR'''C_{2\text{-}6}alkylNR_mR^s$, —$NR\,C_{2\text{-}6}alkylOR^s$ and $C_{1\text{-}4}alkyl$ substituted by 1 or 2 groups selected from $C_{1\text{-}2}haloalkyl$, halo, cyano, nitro, —$C(\!=\!O)R''$, —$C(\!=\!O)OR''$, —$C(\!=\!O)NR'''R'''$, —$C(\!=\!NR''')NR'''R'''$, —$OR'''$, —$OC(\!=\!O)R''$, —$OC(\!=\!O)$ NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R'', —N(R''')C(=NR''')NR'''R'', —N(R''')S(=O)$_2$R'', —N(R''')S(=O)$_2$NR'''R'', —NR'''C$_{2-6}$alkylNR'''R'', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR''', and the ring and bridge carbon atoms are substituted with 0, 1 or 2 =O groups;

R$^7$ is C$_{2-8}$alkyl, C$_{1-5}$haloalkyl, I, Br;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''-C$_{1-4}$haloalkyl, —NR'''-C$_{1-6}$alkylNR'''R''' or —NR'''—C$_{1-6}$alkylOR''';

Y is NH; and

Z is CR$^8$ or N.

In another embodiment, in conjunction with the novel compound embodiments above and below, R$^2$ is C$_{1-6}$alkyl substituted by 1, 2 or 3 substituents selected from C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' and —NR'''C$_{2-6}$alkylOR''';

In another embodiment, in conjunction with the novel compound embodiments above and below, R$^2$ is —(C(R$^q$)$_2$)$_o$phenyl, wherein the phenyl is substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R'', —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —NR$_m$R$^s$, —N(R''')C(=O)R$^s$, —N(R''')C(=O)OR$^s$, —N(R''')C(=O)NR'''R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)OR'', —C(=O)NR'''R''', —C(=NR''')NR$_m$R''', —OR''', —OC(=O)R'', —OC(=O)

NR'''R''', —OC(=O)N(R''')S(=O)$_2$R'', —OC$_{2-6}$alkylNR$_m$R'', —OC$_{2-6}$alkylOR''', —SR''', —S(=O)R'', 13 S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR$_m$R'', —NR'''R''', —N(R''')C(=O)R'', —N(R''')C(=O)OR'', —N(R''')C(=O)NR'''R''', —N(R''')C(=NR''')NR$_m$R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR'''R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR'''R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and —NR'''C$_{2-6}$alkylOR'''.

In another embodiment, in conjunction with the novel compound embodiments above and below, R$^2$ is —(C(R$^q$)$_2$)$_o$R$^r$, wherein R$^r$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR''', —NR'''C$_{2-6}$alkylNR'''R''', —NR'''C$_{2-6}$alkylOR''', —C(=O)R$^s$, —C(=O)OR$^s$, —C(=O)NR$_m$R$^s$, —C(=NR''')NR'''R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR'''R$^s$, —N(R''')C(=O)R$^s$, —N(R''')C(=O)OR$^s$, —N(R''')C(=O)NR$_m$R$^s$, —N(R''')C(=NR''')NR'''R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR$_m$R''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR'''R$^s$, —NR'''C$_{2-6}$alkylOR$^s$ and —NR'''C$_{2-6}$alkylOR''';

In another embodiment, in conjunction with the novel compound embodiments above and below, $R^4$ is a phenyl ring that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$, and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' and —NR'''C$_{2-6}$alkylOR'''; and the bridge carbon atoms are substituted with 0, 1 or 2=O groups.

In another embodiment, in conjunction with the novel compound embodiments above and below, $R^7$ is tert-butyl or trifluoromethyl.

In another embodiment, in conjunction with the novel compound embodiments above and below, $R^9$ is H.

In another embodiment, in conjunction with the novel compound embodiments above and below, Z is $CR^8$.

In another embodiment, in conjunction with the novel compound embodiments above and below, Z is N.

In another embodiment, in conjunction with the novel compound embodiments above and below, $R^1$ is

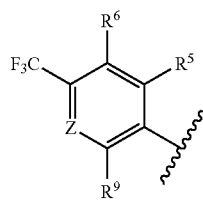

$R^2$ is H, —OR''', Cl, $C_{1-3}$haloalkyl or $C_{1-6}$alkyl;

$R^4$ is a saturated or unsaturated 5- or 6-membered ring containing 0, 1 or 2 atoms selected from O, N and S, so long as the combination of O and S atoms is not greater than 2, wherein the ring is substituted by 0, 1, 2 or 3 substituents independently selected from $C_{1-8}$alkyl, $C_{1-4}$haloalkyl, halo, cyano, nitro, —C(=O)NR'''R''', —C(=NR''')NR'''R''', —OR'', —OC(=O)R'', —OC(=O)NR'''R''', —OC(=O)N(R''')S(=O)$_2$R'', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$^s$, —S(=O)$_2$N(R''')C(=O)R$^s$, —S(=O)$_2$N(R''')C(=O)OR$^s$, —S(=O)$_2$N(R''')C(=O)NR$^s$, —NR'''R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R, —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR$_m$R''' and —NR'''C$_{2-6}$alkylOR'''; wherein $R^4$ is not unsubstituted phenyl;

$R^9$ is independently, at each instance, H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is $CR^8$ or N.

substituted by 1 or 2 groups selected from $C_{1-2}$haloalkyl, halo, cyano, nitro, —C(=O)R'', —C(=O)NR'''R''', —C(=NR''')NR'''R''', —OR''', —OC(=O)R'', —OC(=O) NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR$_m$R''', —NR'''R''', —N(R''')C(=O)R'', —N(R''')C(=O)OR'', —N(R''')C(=O)NR'''R''', —N(R''')C(=NR''')NR$_m$R''', —N(R''')S(=O)$_2$R'', —N(R''')S(=O)$_2$NR'''R''', —NR'''C$_{2-6}$alkylNR'''R''' and —NR'''C$_{2-6}$alkylOR''';

In another embodiment, in conjunction with the novel compound embodiments above and below, Z is $CR^8$.

In another embodiment, in conjunction with the novel compound embodiments above and below, Z is N.

Another aspect of the invention relates to a compound having the structure:

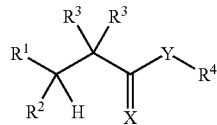

wherein:

X is O, S or NR''';

n is independently, at each instance, 0, 1 or 2;

o is independently, at each instance, 0, 1, 2 or 3;

R''' is independently at each instance H or $R^p$;

R'' is independently at each instance $C_{1-8}$alkyl, phenyl or benzyl;

$R^q$ is independently in each instance H, $C_{1-4}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R, —N(R''')S(=O)$_2$NR'''R''', —NR'''C$_{2-6}$alkylNR'''R''' or —NR'''C$_{2-6}$alkylOR''';

$R^s$ is R'' substituted by 0, 1, 2 or 3 substituents independently selected from $R^q$;

$R^3$ is H or $C_{1-4}$alkyl;

$R^5$ is H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''', —NR'''—$C_{1-6}$alkylOR''', or —(CH$_2$)$_n R^c$ $R^6$ is, independently at each instance, H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR''';

$R^8$ is H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$_R$''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR'''; and (A) $R^1$ is

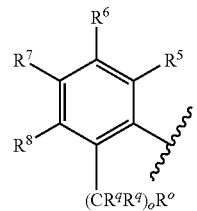

$R^2$ is H, —OR''', halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)$R^1$, —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR$_m$R''', —NR'''C$_{2-6}$alkylNR'''R''', —NR'''C$_{2-6}$alkylOR''', —C(=O)$R^s$, —C(=O)O$R^s$, —C(=O)NR$_m R^s$, —C(=NR''')NR$_m R^s$, —O$R^s$, —OC(=O)$R^s$, —OC(=O)NR$_m R^s$, —OC(=O)N(R''')S(=O)$_2 R^s$, —OC$_{2-6}$alkylNR$_m R^s$, —OC$_{2-6}$alkylO$R^s$, —S$R^s$, —S(=O)$R^s$, —S(=O)$_2 R^s$, —S(=O)$_2$NR$_m R^s$, —S(=O)$_2$N(R''')C(=O)$R^s$, —S(=O)$_2$N(R''')C(=O)O$R^s$, —S(=O)$_2$N(R''')C(=O)NR$_m R^s$, —NR$_m R^s$, —N(R''')C(=O)$R^s$, —N(R''')C(=O)O$R^s$, —N(R''')C(=O)NR$_m R^s$, —N(R''')C(=NR''')NR$_m R^s$, —N(R''')S(=O)$_2 R^s$, —N(R''')S(=O)$_2$NR$_m R^s$, —NR'''C$_{2-6}$alkylNR$_m R^s$, —NR'''C$_{2-6}$alkylO$R^s$ and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR$_m$R''', —N(R''')S(=O)$_2$R'', —N(R''')S(=O)$_2$NR'''R''', —NR'''C$_{2-6}$alkylNR'''R''', —C(=O)$R^s$, —C(=O)O$R^s$, —C(=O)NR$_m R^s$, —C(=NR''')NR$_m R^s$, —O$R^s$, —OC(=O)$R^s$, —OC(=O)NR'''$R^s$, —OC(=O)N(R''')S(=O)$_2 R^s$, —OC$_{2-6}$alkylNR'''$R^s$, —OC$_{2-6}$alkylO$R^s$, —S$R^s$, —S(=O)$R^s$, —S(=O)$_2 R^s$, —S(=O)$_2$NR$_m R^s$, —S(=O)$_2$N(R''')C(=O)$R^s$, —S(=O)$_2$N(R''')C(=O)O$R^s$, —S(=O)$_2$N(R''')C(=O)NR$_m R^s$, —NR$_m R^s$, —N(R''')C(=O)$R^s$, —N(R''')C(=O)O$R^s$, —N(R''')C(=O)NR$_m R^s$, —N(R''')C(=NR''')NR$_m R^s$, —N(R''')S(=O)$_2 R^s$, —N(R''')S(=O)$_2$NR$_m R^s$, —NR'''C$_{2-6}$alkylNR$_m R^s$, —NR'''C$_{2-6}$alkylO$R^s$ and —NR'''C$_{2-6}$alkylOR'''; and the ring and bridge carbon atoms are substituted with 0, 1 or 2=O groups;

$R^7$ is Clgalkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—C$_{1-6}$alkylOR'", —NR'"R'", —NR'"—C$_{1-4}$haloalkyl, —NR'"—C$_{1-6}$alkylNR'"R'" or —NR'"—C$_{1-6}$alkylOR'";

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R", —C(=O)OR", —C(=O)NR'"R'", —C(=NR'")NR'"R'", —OR'", —OC(=O)R", —OC(=O)NR'"R'", —OC(=O)N(R'")S(=O)$_2$R", —OC$_{2-6}$alkylNR'"R'", —OC$_{2-6}$alkylOR'", —SR'", —S(=O)R", —S(=O)$_2$R", —S(=O)$_2$NR'"R'", —S(=O)$_2$N(R'")C(=O)R", —S(=O)$_2$N(R'")C(=O)OR", —S(=O)$_2$N(R'")C(=O)NR'"R'", —NR'"R'", —N(R'")C(=O)R", —N(R'")C(=O)OR", —N(R'")C(=O)NR'"R'", —N(R'")C(=NR'")NR'"R'", —N(R'")S(=O)$_2$R", —N(R'")S(=O)$_2$NR'"R'", —NR'"C$_{2-6}$alkylNR'"R'" or —NR'"C$_{2-6}$alkylOR'"; and Y is O or NH; or (B) R$^1$ is

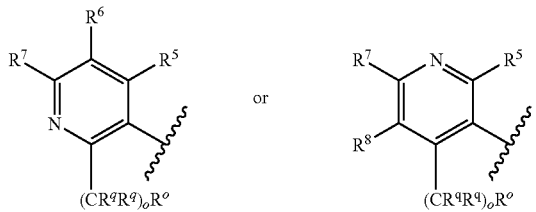

R$^2$ is H, —OR'", halo, C$_{1-3}$haloalkyl or C$_{1-6}$alkyl;

R$^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R", —C(=O)OR", —C(=O)NR'"R'", —C(=NR'")NR'"R'", —O$^{Rm}$, —OC(=O)R", —OC(=O)NR'"R'", —OC(=O)N(R'")S(=O)$_2$R", —OC$_{2-6}$alkylNR'"R'", —OC$_{2-6}$alkylOR'", —SR'", —(=O)R", —S(=O)$_2$R", —S(=O)$_2$NR'"R'", —S(=O)$_2$N(R'")C(=O)R", —S(=O)$_2$N(R'")C(=O)OR", —S(=O)$_2$N(R'")C(=O)NR$_m$R", —NR'"R'", —N(R'")C(=O)R", —N(R'")C(=O)OR", —N(R'")C(=O)NR$_m$R", N(R'")C(=NR'")NR$_m$R", —N(R'")S(=O)$_2$R", —N(R'")S(=O)$_2$NR'"R'", —NR'"C$_{2-6}$alkylNR'"R'", —NR'"C$_{2-6}$alkylOR'", —C(=O)R$^s$, —C(=O)OR$^s$, —C(=O)NR'"R$^s$, —C(=NR'")NR'"R$^s$, —OR$^s$, —OC(=O)R$^s$, —OC(=O)NR'"R$^s$, —OC(=O)N(R'")S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —(=O)$_2$N(R'")C(=O)R$^s$, —S(=O)$_2$N(R'")C(=O)OR$^s$, —S(=O)$_2$N(R'")C(=O)NR$_m$R$^s$, —NR$_m$R$^s$, —N(R'")C(=O)R$^s$, —N(R'")C(=O)OR$^s$, —N(R'")C(=O)NR$_m$R$^s$, —N(R'")C(=NR'")NR$_m$R$^s$, —N(R'")S(=O)$_2$R$^s$, —N(R'")S(=O)$_2$NR$_m$R$^s$, —NR'"C$_{2-6}$alkylNR$_m$R$^s$, —NR'"C$_{2-6}$alkylOR$^s$ and C$_{1-4}$alkyl substituted by 1 or 2 groups selected from C$_{1-2}$haloalkyl, halo, cyano, nitro, —C(=O)R", —C(=O)OR", —C(=O)NR'"R'", —C(=NR'")NR'"R'", —OR'", —OC(=O)R", —OC(=O)NR'"R'", —OC(=O)N(R'")S(=O)$_2$R", —OC$_{2-6}$alkylNR'"R'", —OC$_{2-6}$alkylOR'", —SR'", —S(=O)R", —S(=O)$_2$R", —S(=O)$_2$NR'"R'", —S(=O)$_2$N(R'")C(=O)R", —S(=O)$_2$N(R'")C(=O)OR", —S(=O)$_2$N(R'")C(=O)NR'"R'", —NR'"R'", —N(R'")C(=O)R", —N(R'")C(=O)OR", —N(R'")C(=O)NR'"R'", —N(R'")C(=NR'")NR'"R'", —N(R'")S(=O)$_2$R", —N(R'")S(=O)$_2$NR'"R'", —NR'"C$_{2-6}$alkylNR$_m$R'", —C(=O)R$^s$, —C(=O)OR$^s$, —C(=O)NR$_m$R$^s$, —C(=NR'")NR$_m$R$^s$, —OR$^s$, —OC(=O)R$^3$, —OC(=O)NR'"R$^s$, —OC(=O)N(R'")S(=O)$_2$R$^s$, —OC$_{2-6}$alkylNR'"R$^s$, —OC$_{2-6}$alkylOR$^s$, —SR$^s$, —S(=O)R$^s$, —S(=O)$_2$R$^s$, —S(=O)$_2$NR'"R$^s$, —S(=O)$_2$N(R'")C(=O)R$^s$, —S(=O)$_2$N(R'")C(=O)OR$^s$, —S(=O)$_2$N(R'")C(=O)NR'"R$^s$, —NR'"R$^s$, —N(R'")C(=O)R$^s$, —N(R'")C(=O)OR$^s$, —N(R'")C(=O)NR'"R$^s$, —N(R'")C(=NR'")NR'"R$^s$, —N(R'")S(=O)$_2$R$^s$, —N(R'")S(=O)$_2$NR'"R$^s$, —NR'"C$_{2-6}$alkylNR'"R$^s$, —NR'"C$_{2-6}$alkylORs and —NR'"C$_{2-6}$alkylOR'"; and the ring and bridge carbon atoms are substituted with 0, 1 or 2=O groups;

R$^7$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'"R'", —O—C$_{1-6}$alkylOR'", —NR'"R'", —NR'"—C$_{1-4}$haloalkyl, —NR'"—C$_{1-6}$alkylNR'"R'" or —NR'"—C$_{1-6}$alkylOR'";

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R", —C(=O)OR", —C(=O)NR'"R'", —C(=NR'")NR'"R'", —OR'", —OC(=O)R", —OC(=O)NR'"R'", —OC(=O)N(R'")S(=O)$_2$R", —OC$_{2-6}$alkylNR'"R'", —OC$_{2-6}$alkylOR'", —SR'", —S(=O)R", —S(=O)$_2$R", —S(=O)$_2$NR'"R'", —S(=O)$_2$N(R'")C(=O)R", —S(=O)$_2$N(R'")C(=O)OR", —S(=O)$_2$N(R'")C(=O)NR'"R'", —NR'"R'", —N(R'")C(=O)R", —N(R'")C(=O)OR", —N(R'")C(=O)NR$_m$R", —N(R'")C(=NR'")NR'"R'", —N(R'")S(=O)$_2$R", —N(R'")S(=O)$_2$NR'"R'", —NR'"C$_{2-6}$alkylNR'"R'" or —NR'"C$_{2-6}$alkylOR'"; and Y is O or NH; or (C) R$^1$ is

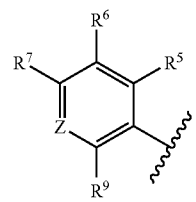

R$^2$ is H, —OR'", halo, C$_{1-3}$haloalkyl or C$_{1-6}$alkyl;

R$^4$ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from C$_{1-9}$alkyl, oxo, C$_{1-4}$haloalkyl, halo, nitro, cyano, —OR''', —S(=O)$_n$C$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''-C$_{1-6}$alkylNR$_m$R''', —NR'''—C$_{1-6}$alkylOR''', —C(=O)C$_{1-6}$alkyl, —OC(=O)C$_{1-6}$alkyl, —C(=O)NR'''C$_{1-6}$alkyl, —NR'''C(=O)C$_{1-6}$alkyl —C(=O)R$^s$, —C(=O)OR$^s$, —C(=O)NR$_m$R$^s$, —C(=NR''')NR'''R$^s$, —OR$^s$, —OC(=O)R$^s$, —OC(=O)NR$_m$R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR'''R$^s$, —N(R''')C(=O)R$^s$, —N(R''')C(=O)OR$^s$, —N(R''')C(=O)NR$_m$R$^s$, —N(R''')C(=NR''')NR'''R$^s$, —N(R''')S(=O)$_2$R$^s$, —N(R''')S(=O)$_2$NR$_m$R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —N(R''')C(=O)R'', —N(R''')C(=O)OR'', —N(R''')C(=O)NR$_m$R''', —N(R''')C(=NR''')NR'''R''', —N(R''')S(=O)$_2$R'', —N(R''')S(=O)$_2$NR'''R''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and —NR'''C$_{2-6}$alkylOR'''; wherein R$^4$ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

R$^7$ is C$_{1-8}$alkyl, C$_{1-5}$haloalkyl, I or Br

R$^9$ is H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', or —(CH$_2$)$_n$R$^c$;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is CR$^8$ or N; or (D) R$^1$ is

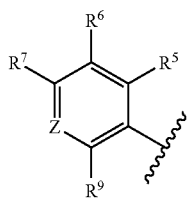

R$^2$ is C$_{1-6}$alkyl substituted by 1, 2 or 3 substituents selected from C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR$_m$R''' or —NR'''C$_{2-6}$alkylOR'''; or R$^2$ is —(C(R$^q$)$_2$)$_o$phenyl, wherein the phenyl is substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR$_m$R''', —NR'''C$_{2-6}$alkylOR''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O) NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NRMC$_{2-6}$alkylOR$^s$ and —NR'''C$_{2-6}$alkylOR'''; or R$^2$ is —(C(R$^q$)$_2$)$_o$R$^r$, wherein R$^r$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)N''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C (=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NRₘRˢ, —C(=NR‴)NRₘRˢ, —ORˢ, —OC(=O)Rˢ, —OC(=O)NRₘRˢ, —OC(=O)N(R‴)S(=O)₂Rˢ, —OC₂₋₆alkylNRₘRˢ, —OC₂₋₆alkylORˢ, —SRˢ, —S(=O)Rˢ, —S(=O)₂Rˢ, —S(=O)₂NRₘRˢ, —S(=O)₂N(R‴)C(=O)Rˢ, —S(=O)₂N(R‴)C(=O)ORˢ, —S(=O)₂N(R‴)C(=O)NRₘRˢ, —NRₘRˢ, —N(R‴)C(=O)Rˢ, —N(R‴)C(=O)ORˢ, —N(R‴)C(=O)NRₘRˢ, —N(R‴)C(=NR‴)NRₘRˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —C(=O)Rˢ, —C(=O)ORˢ, —C(=O)NRₘRˢ, —C(=NR‴)NRₘRˢ, —ORˢ, —OC(=O)Rˢ, —OC(=O)NRₘRˢ, —OC(=O)N(R‴)S(=O)₂Rˢ, —OC₂₋₆alkylNRₘRˢ, —OC₂₋₆alkylORˢ, —SRˢ, —S(=O)Rˢ, —S(=O)₂Rˢ, —S(=O)₂NRₘRˢ, —S(=O)₂N(R‴)C(=O)Rˢ, —S(=O)₂N(R‴)C(=O)ORˢ, —S(=O)₂N(R‴)C(=O)NRₘRˢ, —NRₘRˢ, —N(R‴)C(=O)Rˢ, —N(R‴)C(=O)ORˢ, —N(R‴)C(=O)NRₘRˢ, —N(R‴)C(=NR‴)NRₘRˢ, —N(R‴)S(=O)₂Rˢ, —N(R‴)S(=O)₂NRₘRˢ, —NR‴C₂₋₆alkylNRₘRˢ, —NR‴C₂₋₆alkylORˢ and —NR‴C₂₋₆alkylOR‴;

R⁴ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NRₘRˢ, —C(=NR‴)NRₘRˢ, —ORˢ, —OC(=O)Rˢ, —OC(=O)NRₘRˢ, —OC(=O)N(R‴)S(=O)₂Rˢ, —OC₂₋₆alkylNRₘRˢ, —OC₂₋₆alkylORˢ, —SRˢ, —S(=O)Rˢ, —S(=O)₂Rˢ, —S(=O)₂NRₘRˢ, —S(=O)₂N(R‴)C(=O)Rˢ, —S(=O)₂N(R‴)C(=O)ORˢ, —S(=O)₂N(R‴)C(=O)NRₘRˢ, —NRₘRˢ, —N(R‴)C(=O)Rˢ, —N(R‴)C(=O)ORˢ, N(R‴)C(=O)NRₘRˢ, —N(R‴)C(=NR‴)NRₘRˢ, —N(R‴)S(=O)₂Rˢ, —N(R‴)S(=O)₂NR‴Rˢ, —NR‴C₂₋₆alkylNRₘRˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NRₘRˢ, —C(=NR‴)NRₘRˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)R⁵, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NRₘRˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, and the ring and bridge carbon atoms are substituted with 0, 1 or 2=O groups;

R⁷ is C₂₋₈alkyl, C₁₋₅haloalkyl, I, Br;

R⁹ is independently, at each instance, H, C₁₋₉alkyl, C₁₋₄haloalkyl, halo, nitro, cyano, —OC₁₋₆alkyl, —O—C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴ or —NR‴—C₁₋₆alkylOR‴;

Y is NH; and

Z is CR⁸ or N; or (E) R¹ is

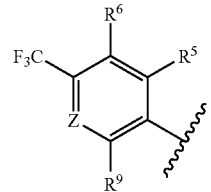

R² is H, —OR‴, Cl, C₁₋₃haloalkyl or C₁₋₆alkyl;

R⁴ is a saturated or unsaturated 5- or 6-membered ring containing 0, 1, 2 or 3 atoms selected from O, N and S, so long as the combination of O and S atoms is not greater than 1, wherein the ring is substituted by 0, 1, 2 or 3 substituents independently selected from C₁₋₈alkyl, C₁₋₄haloalkyl, halo, cyano, nitro, —C(=O)NR‴R‴, —C(=NR‴)NR‴R‴, —OR‴, —OC(=O)R″, OC(=O)NR‴R‴, —OC(=O)N(R‴)S(=O)₂R″, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NRₘR‴, —NR‴C₂₋₆alkylNR‴R‴, —NR‴C₂₋₆alkylOR‴, —C(=O)Rˢ, —C(=O)ORˢ, —C(=O)NRₘRˢ, —C(=NR‴)NRₘRˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)R⁵, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NRₘRˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —C(=O)R$^s$, —C(=O)OR$^s$, —C(=O)NR‴R$^s$, —C(=NR‴)NR‴R$^s$, —OR$^s$, —OC(=O)R$^5$, —OC(=O)NR$_m$R$^s$, —OC(=O)N(R‴)S(=O)$_2$R$^s$, —OC$_{2-6}$alkyl-NR‴R$^s$, —OC$_{2-6}$alkylOR$^s$, —SR$^s$, —S(=O)R$^s$, —S(=O)$_2$R‴, —S(=O)$_2$NR$_m$R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR$_m$R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and —NR‴C$_{2-6}$alkylOR‴; wherein R$^4$ is not unsubstituted phenyl;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR‴R‴, or —O—C$_{1-6}$alkylOR‴, —NR‴R‴, —NR‴—C$_{1-4}$haloalkyl, —NR‴—C$_{1-6}$alkylNR‴R‴ or —NR‴—C$_{1-6}$alkylOR‴;

Y is NH; and

Z is CR$^8$ or N.

In another embodiment, in conjunction with the novel compound embodiments above and below, R$^1$ is

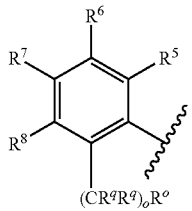

R$^2$ is H, —OR‴, halo, C$_{1-3}$haloalkyl or C$_{1-6}$alkyl;

R$^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR$_m$R$^s$, —C(=NR‴)NR$_m$R$^s$, —OR$^s$, —OC(=O)R$^s$, —OC(=O)NR‴R$^s$, —OC(=O)N(R‴)S(=O)$_2$R$^s$, —OC$_{2-6}$alkylNR$_m$R$^s$, —OC$_{2-6}$alkylOR$^s$, —OC$_{2-6}$alkylOR$^s$, —SR$^5$, —S(=O)R$^s$, —S(=O)$_2$R$^s$, —S(=O)$_2$NR‴R$^s$, —S(=O)$_2$N(R‴)C(=O)R$^s$, —S(=O)$_2$N(R‴)C(=O)OR$^s$, —S(=O)$_2$N(R‴)C(=O)NR‴R$^s$, —NR‴R$^s$, —N(R‴)C(=O)R$^s$, —N(R‴)C(=O)OR$^s$, —N(R‴)C(=O)NR‴R$^s$, —N(R‴)C(=NR‴)NR‴R$^s$, —N(R‴)S(=O)$_2$R$^s$, —N(R‴)S(=O)$_2$NR‴R$^s$, —NR‴C$_{2-6}$alkylNR‴R$^s$, —NR‴C$_{2-6}$alkylOR$^s$ and C$_{1-4}$alkyl substituted by 1 or 2 groups selected from C$_{1-2}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R , —OC$_{2-6}$alkylNR$_m$R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR$_m$R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —C(=O)R$^s$, —C(=O)OR$^s$, —C(=O)NR‴R$^s$, —C(=NR‴)NR$_m$R$^s$, —OR$^s$, —OC(=O)R$^s$, —OC(=O)NR$_m$R$^s$, —OC(=O)N(R‴)S(=O)$_2$R$^s$, —OC$_{2-6}$alkyl-NR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R‴)C(=O)R$^s$, —S(=O)$_2$N(R‴)C(=O)OR$^s$, —S(=O)$_2$N(R‴)C(=O)NR$_m$R$^s$, —NR$_m$R$^s$, —N(R‴)C(=O)R$^s$, —N(R‴)C(=O)OR$^s$, —N(R‴)C(=O)NR$_m$R$^s$, —N(R‴)C(=NR‴)NR$_m$R$^s$, —N(R‴)S(=O)$_2$R$^s$, —N(R‴)S(=O)$_2$NR$_m$R$^s$, —NR$^o$C$_{2-6}$alkylNR$_m$R$^s$, —NR‴C$_{2-6}$alkylOR$^s$ and —NR‴C$_{2-6}$alkylOR‴; and the ring and bridge carbon atoms are substituted with 0, 1 or 2=O groups;

R$^7$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR‴R‴, —O—C$_{1-6}$alkylOR‴, —NR‴R‴, —NR‴—C$_{1-4}$haloalkyl, —NR‴—C$_{1-6}$alkylNR‴R‴ or —NR‴—C$_{1-6}$alkylOR‴;

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴ or —NR‴C$_{2-6}$alkylOR‴; and Y is O or NH.

In another embodiment, in conjunction with the novel compound embodiments above and below, R$^4$ is a saturated or unsaturated 5- or 6-membered ring containing 0, 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)$_2$R″, —OC$_{2-6}$alkylNR‴R‴, —OC$_{2-6}$alkylOR‴, —SR‴, —S(=O)R″, —S(=O)$_2$R″, —S(=O)$_2$NR‴R‴, —S(=O)$_2$N(R‴)C(=O)R″, —S(=O)$_2$N(R‴)C(=O)OR″, —S(=O)$_2$N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)$_2$R″, —N(R‴)S(=O)$_2$NR‴R‴, —NR‴C$_{2-6}$alkylNR‴R‴, —NR‴C$_{2-6}$alkylOR‴, —C(=O)R$^s$, —C(=O)OR$^s$, —C(=O)NR$_m$R$^s$, —C(=NR‴)NR‴R$^s$, —OR$^s$, —OC(=O)

$R^s$, —OC(=O)$NR_mR^s$, —OC(=O)N($R'''$)S(=O)$_2R^s$, —OC$_{2-6}$alkylN$R'''R^s$, —OC$_{2-6}$alkylOR$^s$, —SR$^s$, —S(=O) $R^s$, —S(=O)$_2R^s$, —S(=O)$_2$N$R'''R^s$, —S(=O)$_2$N($R'''$)C (=O)R$^s$, —S(=O)$_2$N($R'''$)C(=O)OR$^s$, —S(=O)$_2$N($R'''$)C (=O)N$R_mR^s$, —N$R'''R^s$, —N($R'''$)C(=O)R$^s$, —N($R'''$)C (=O)OR$^s$, —N($R'''$)C(=O)N$R_mR^s$, —N($R'''$)C(=N$R'''$) N$R_mR^s$, —N($R'''$)S(=O)$_2R^s$, —N($R'''$)S(=O)$_2$N$R_mR^s$, —N$R'''$C$_{2-6}$alkylN$R_mR^s$, —NR$^o$C$_{2-6}$alkylOR$^s$ and C$_{1-4}$alkyl substituted by 1 or 2 groups selected from C$_{1-2}$haloalkyl, halo, cyano, nitro, —C(=O)R$''$, —C(=O)OR$''$, —C(=O) N$R'''R'''$, —C(=N$R'''$)N$R'''R'''$, —OR$'''$, —OC(=O)R$''$, —OC(=O)N$R_mR'''$, —OC(=O)N($R'''$)S(=O)$_2R''$, —OC$_{2-6}$ alkylN$R'''R'''$, —OC$_{2-6}$alkylOR$'''$, —SR$'''$, —S(=O)R$''$, —S(=O)$_2R''$, —S(=O)$_2$N$R'''R'''$, —S(=O)$_2$N($R'''$)C(=O) R$''$, —S(=O)$_2$N($R'''$)C(=O)OR$''$, —S(=O)$_2$N($R'''$)C(=O) N$R'''R'''$, —N$R'''R'''$, —N($R'''$)C(=O)R$''$, —N($R'''$)C(=O) OR$''$, —N($R'''$)C(=O)N$R'''R'''$, —N($R'''$)C(=N$R'''$)N$R'''R'''$, —N($R'''$)S(=O)$_2R''$, —N($R'''$)S(=O)$_2$N$R'''R'''$, —N$R'''$C$_{2-6}$ alkylN$R'''R'''$, —C(=O)R$^s$, —C(=O)OR$^s$, —C(=O) N$R_mR^s$, —C(=N$R'''$)N$R_mR^s$, —OR$^s$, —OC(=O)R$^s$, —OC (=O)N$R_mR^s$, —OC(=O)N($R'''$)S(=O)$_2R^s$, —OC$_{2-6}$alkyl-N$R_mR^s$, —OC$_{2-6}$alkylOR$^s$, —SR$^s$, —S(=O)R$^s$, —S(=O)$_2$ R$^s$, —S(=O)$_2$N$R_mR^s$, —S(=O)$_2$N($R'''$)C(=O)R$^s$, —S(=O)$_2$N($R'''$)C(=O)OR$^s$, —S(=O)$_2$N($R'''$)C(=O) N$R_mR^s$, —N$R_mR^s$, —N($R'''$)C(=O)R$^s$, —N($R'''$)C(=O) OR$^s$, —N($R'''$)C(=O)N$R_mR^s$, —N($R'''$)C(=N$R'''$)N$R_mR^s$, —N($R'''$)S(=O)$_2R^s$, —N($R'''$)S(=O)$_2$N$R'''R^s$, —N$R'''$C$_{2-6}$ alkylN$R'''R^s$, —N$R'''$C$_{2-6}$alkylOR$^s$ and —N$R'''$C$_{2-6}$alky-lOR$'''$; and the ring and bridge carbon atoms are substituted with 0, 1 or 2=O groups.

In another embodiment, in conjunction with the novel compound embodiments above and below, $R^4$ is a phenyl ring that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R$''$, —C(=O)OR$''$, —C(=O) N$R'''R'''$, —C(=N$R'''$)N$R'''R'''$, —OR$'''$, —OC(=O)R$''$, —OC(=O)N$R'''R'''$, —OC(=O)N($R'''$)S(=O)$_2R''$, —OC$_{2-6}$ alkylN$R'''R'''$, —OC$_{2-6}$alkylOR$'''$, —SR$'''$, —S(=O)R$''$, —S(=O)$_2R''$, —S(=O)$_2$N$R'''R'''$, —S(=O)$_2$N($R'''$)C(=O) R$''$, —S(=O)$_2$N($R'''$)C(=O)OR$''$, —S(=O)$_2$N($R'''$)C(=O) N$R'''R'''$, —N$R'''R'''$, —N($R'''$)C(=O)R$''$, —N($R'''$)C(=O) OR$''$, —N($R'''$)C(=O)N$R'''R'''$, —N($R'''$)C(=N$R'''$)N$R'''R'''$, —N($R'''$)S(=O)$_2R''$, —N($R'''$)S(=O)$_2$N$R'''R'''$, —N$R'''$C$_{2-6}$ alkylN$R'''R'''$, —N$R'''$C$_{2-6}$alkylOR$'''$, —C(=O)R$^s$, —C(=O)OR$^s$, —C(=O)N$R_mR^s$, —C(=N$R'''$)N$R_mR^s$, —OR$^s$, —OC(=O)R$^s$, —OC(=O)N$R_mR^s$, —OC(=O)N ($R'''$)S(=O)$_2R^s$, —OC$_{2-6}$alkylN$R_mR^s$, —OC$_{2-6}$alkylOR$^s$, —SR$^s$, —S(=O)R$^s$, —S(=O)$_2R^s$, —S(=O)$_2$N$R_mR^s$, —S(=O)$_2$N($R'''$)C(=O)R$^s$, —S(=O)$_2$N($R'''$)C(=O)OR$^s$, —S(=O)$_2$N($R'''$)C(=O)N$R_mR^s$, —N$R'''R^s$, —N($R'''$)C (=O)R$^s$, —N($R'''$)C(=O)OR$^s$, —N($R'''$)C(=O)N$R_mR^s$, —N($R'''$)C(=N$R'''$)N$R_mR^s$, —N($R'''$)S(=O)$_2R^s$, —N($R'''$)S (=O)$_2$N$R_mR^s$, —N$R'''$C$_{2-6}$alkylN$R_mR^s$, —N$R'''$C$_{2-6}$alky-lOR$^s$ and C$_{1-4}$alkyl substituted by 1 or 2 groups selected from C$_{1-2}$haloalkyl, halo, cyano, nitro, —C(=O)R$''$, —C(=O) OR$''$, —C(=O)N$R'''R'''$, —C(=N$R'''$)N$R'''R'''$, —OR$'''$, —OC(=O)R$''$, —OC(=O)N$R'''R'''$, —OC(=O)N($R'''$)S (=O)$_2R''$, —OC$_{2-6}$alkylN$R'''R'''$, —OC$_{2-6}$alkylOR$'''$, —SR$'''$, —S(=O)R$''$, —S(=O)$_2R''$, —S(=O)$_2$N$R'''R'''$, —S(=O)$_2$N($R'''$)C(=O)R$''$, —S(=O)$_2$N($R'''$)C(=O)OR$''$, —S(=O)$_2$N($R'''$)C(=O)N$R'''R'''$, —N$R'''R'''$, —N($R'''$)C (=O)R$''$, —N($R'''$)C(=O)OR$''$, —N($R'''$)C(=O)N$R'''R'''$, —N($R'''$)C(=N$R'''$)N$R'''R'''$, —N($R'''$)S(=O)$_2R''$, —N($R'''$) S(=O)$_2$N$R_mR^s$, —NR$'''$C$_{2-6}$alkylN$R'''R^s$, —NR$'''$C$_{2-6}$alky-lOR$^s$ and —NR$'''$C$_{2-6}$alkylOR$'''$; and the bridge carbon atoms are substituted with 0, 1 or 2=O groups.

S(=O)$_2$N$R'''R'''$, —N$R'''$C$_{2-6}$alkylN$R'''R'''$, —C(=O)R$^s$, —C(=O)OR$^s$, —C(=O)N$R_mR^s$, —C(=N$R'''$)N$R_mR^s$, —OR$^s$, —OC(=O)R$^s$, —OC(=O)N$R_mR^s$, —OC(=O)N ($R'''$)S(=O)$_2R^s$, —OC$_{2-6}$alkylN$R_mR^s$, —OC$_{2-6}$alkylOR$^s$, —SR$^s$, —S(=O)R$^s$, —S(=O)$_2R^s$, —S(=O)$_2$N$R_mR^s$, —S(=O)$_2$N($R'''$)C(=O)R$^s$, —S(=O)$_2$N($R'''$)C(=O)OR$^s$, —S(=O)$_2$N($R'''$)C(=O)N$R_mR^s$, —N$R_mR^s$, —N($R'''$)C (=O)R$^s$, —N($R'''$)C(=O)OR$^s$, —N($R'''$)C(=O)N$R_mR^s$, —N($R'''$)C(=N$R'''$)N$R'''R^s$, —N($R'''$)S(=O)$_2R^s$, —N($R'''$)S (=O)$_2$N$R_mR^s$, —N$R'''$C$_{2-6}$alkylN$R'''R^s$, —N$R'''$C$_{2-6}$alky-lOR$^s$ and —N$R'''$C$_{2-6}$alkylOR$'''$; and the bridge carbon atoms are substituted with 0, 1 or 2=O groups.

In another embodiment, in conjunction with the novel compound embodiments above and below, $R^7$ is C$_{1-9}$alkyl, C$_{1-4}$haloalkyl, halo, —OC$_{1-6}$alkyl, —O—C$_{1-4}$haloalkyl, —N$R'''R'''$ or —N$R'''$—C$_{1-4}$haloalkyl.

In another embodiment, in conjunction with the novel compound embodiments above and below, $R^7$ is C$_{1-5}$alkyl, C$_{1-4}$haloalkyl, I, Br or Cl.

In another embodiment, in conjunction with the novel compound embodiments above and below, $R^7$ is tert-butyl or trifluoromethyl.

In another embodiment, in conjunction with the novel compound embodiments above and below, $R^o$ is a saturated, partially-saturated or unsaturated 5-, 6- or 7-membered monocyclic ring containing 0, 1, 2 or 3 atoms selected from N, O and S, so long as the combination of O and S atoms is not greater than 1, wherein the carbon atoms of the ring are substituted by 0, 1 or 2 oxo groups, wherein the ring is substituted by 0, 1, 2 or 3 substituents independently selected from $R^p$.

In another embodiment, in conjunction with the novel compound embodiments above and below, $R^o$ is a saturated, partially-saturated or unsaturated 6-membered ring containing 0, 1, 2 or 3 N atoms, wherein the carbon atoms of the ring are substituted by 0, 1 or 2 oxo groups, wherein the ring is substituted by 0, 1, 2 or 3 substituents independently selected from $R^p$.

In another embodiment, in conjunction with the novel compound embodiments above and below, Y is O.

In another embodiment, in conjunction with the novel compound embodiments above and below, Y is NH.

In another embodiment, in conjunction with the novel compound embodiments above and below, $R^1$ is

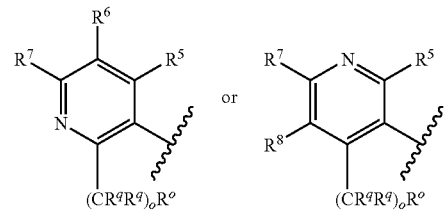

$R^2$ is H, —OR$'''$, halo, C$_{1-3}$haloalkyl or C$_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R$''$, —C(=O)OR$''$, —C(=O)N$R'''R'''$, —C(=N$R'''$)N$R'''R'''$, —OR$'''$, —OC (=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR'''R$^s$, —N(R''')S(=O)$_2$R$^s$, —N(R''')S(=O)$_2$NR''' R$^s$, —NR'''C$_{2-6}$alkylNR'''R$^s$, —NR'''C$_{2-6}$alkylOR$^s$ and —NR'''C$_{2-6}$alkylOR'''; and the ring and bridge carbon atoms are substituted with 0, 1 or 2=O groups;

R$^7$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR'''; [C$_{1-8}$alkyl, C$_{1-5}$haloalkyl, I, Br or Cl]

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR$_m$R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; and Y is O or NH.

In another embodiment, in conjunction with the novel compound embodiments above and below, R$^4$ is a saturated or unsaturated 5- or 6-membered ring containing 0, 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR$_m$R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and —NR'''C$_{2-6}$alkylOR'''; and the ring and bridge carbon atoms are substituted with 0, 1 or 2=O groups.

In another embodiment, in conjunction with the novel compound embodiments above and below, R$^4$ is a phenyl ring that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)

NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR_mR''', —NR'''C_{2-6}alkylNR'''R''', —NR'''C_{2-6}alkylOR''', —C(=O)R^s, —C(=O)OR^s, —C(=O)NR_mR^s, —C(=NR''')NR_mR^s, —OR^s, —OC(=O)R^s, —OC(=O)NR_mR^s, —OC(=O)N(R''')S(=O)₂R^s, —OC_{2-6}alkylNR_mR^s, —OC_{2-6}alkylOR^s, —SR^s, —S(=O)R^s, —S(=O)₂R^s, —S(=O)₂NR_mR^s, —S(=O)₂N(R''')C(=O)R^s, —S(=O)₂N(R''')C(=O)OR^s, —S(=O)₂N(R''')C(=O)NR_mR^s, —NR_mR^s, —N(R''')C(=O)R^s, —N(R''')C(=O)OR^s, N(R''')C(=O)NR_mR^s, —N(R''')C(=NR''')NR_mR^s, —N(R''')S(=O)₂R^s, —N(R''')S(=O)₂NR_mR^s, —NR'''C_{2-6}alkylNR_mR^s, —NR'''C_{2-6}alkylOR^s and C_{1-4}alkyl substituted by 1 or 2 groups selected from C_{1-2}haloalkyl, halo, cyano, nitro, —C(=O)R'', —C(=O)OR'', —C(=O)NR'''R''', —C(=NR''')NR'''R''', —OR'', —OC(=O)R'', —OC(=O)NR'''R''', —OC(=O)N(R''')S(=O)₂R'', —OC_{2-6}alkylNR'''R''', —OC_{2-6}alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C_{2-6}alkylNR'''R''', —C(=O)R^s, —C(=O)OR^s, —C(=O)NR_mR^s, —C(=NR''')NR_mR^s, —OR^s, —OC(=O)R^s, —OC(=O)NR_mR^s, —OC(=O)N(R''')S(=O)₂R^s, —OC_{2-6}alkylNR_mR^s, —OC_{2-6}alkylOR^s, —SR^s, —S(=O)R^s, —S(=O)₂R^s, —S(=O)₂NR_mR^s, —S(=O)₂N(R''')C(=O)R^s, —S(=O)₂N(R''')C(=O)OR^s, —S(=O)₂N(R''')C(=O)NR_mR^s, —NR_mR^s, —N(R''')C(=O)R^s, —N(R''')C(=O)OR^s, —N(R''')C(=O)NR_mR^s, —N(R''')C(=NR''')NR_mR^s, —N(R''')S(=O)₂R^s, —N(R''')S(=O)₂NR_mR^s, —NR'''C_{2-6}alkylNR_mR^s, —NR'''C_{2-6}alkylOR^s and —NR'''C_{2-6}alkylOR'''; and the bridge carbon atoms are substituted with 0, 1 or 2=O groups.

In another embodiment, in conjunction with the novel compound embodiments above and below, $R^7$ is $C_{1-9}$alkyl, $C_{1-4}$haloalkyl, halo, —OC_{1-6}alkyl, —O—C_{1-4}haloalkyl, —NR'''R''' or —NR'''—C_{1-4}haloalkyl.

In another embodiment, in conjunction with the novel compound embodiments above and below, $R^7$ is $C_{1-5}$alkyl, $C_{1-4}$haloalkyl, I, Br or Cl.

In another embodiment, in conjunction with the novel compound embodiments above and below, $R^7$ is tert-butyl or trifluoromethyl.

In another embodiment, in conjunction with the novel compound embodiments above and below, $R^o$ is a saturated, partially-saturated or unsaturated 5-, 6- or 7-membered monocyclic ring containing 0, 1, 2 or 3 atoms selected from N, O and S, so long as the combination of O and S atoms is not greater than 1, wherein the carbon atoms of the ring are substituted by 0, 1 or 2 oxo groups, wherein the ring is substituted by 0, 1, 2 or 3 substituents independently selected from $R^p$.

In another embodiment, in conjunction with the novel compound embodiments above and below, $R^o$ is a saturated, partially-saturated or unsaturated 6-membered ring containing 0, 1, 2 or 3 N atoms, wherein the carbon atoms of the ring are substituted by 0, 1 or 2 oxo groups, wherein the ring is substituted by 0, 1, 2 or 3 substituents independently selected from $R^p$.

In another embodiment, in conjunction with the novel compound embodiments above and below, Y is O.

In another embodiment, in conjunction with the novel compound embodiments above and below, Y is NH.

In another embodiment, in conjunction with the novel compound embodiments above and below, $R^1$ is

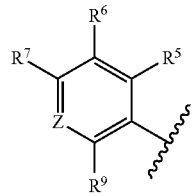

$R^2$ is H, —OR''', halo, $C_{1-3}$haloalkyl or $C_{1-6}$alkyl;

$R^4$ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from $C_{1-9}$alkyl, oxo, $C_{1-4}$haloalkyl, halo, nitro, cyano, —OR''', —S(=O)_mC_{1-6}alkyl, —O—C_{1-4}haloalkyl, —O—C_{1-6}alkylNR'''R''', —O—C_{1-6}alkylOR''', —NR'''R''', —NR'''—C_{1-4}haloalkyl, —NR'''—C_{1-6}alkylNR'''R''', —NR'''-C_{1-6}alkylOR''', —C(=O)C_{1-6}alkyl, —OC(=O)C_{1-6}alkyl, —C(=O)NR'''C_{1-6}alkyl, —NR'''C(=O)C_{1-6}alkyl —C(=O)R^s, —C(=O)OR^s, —C(=O)NR'''R^s, —C(=NR''')NR'''R^s, —OR^s, —OC(=O)R^s, —OC(=O)NR'''R^s, —OC(=O)N(R''')S(=O)₂R^s, —OC_{2-6}alkylNR'''R^s, —OC_{2-6}alkylOR^s, —SR^s, —S(=O)R^s, —S(=O)₂R^s, —S(=O)₂NR'''R^s, —S(=O)₂N(R''')C(=O)R^s, —S(=O)₂N(R''')C(=O)OR^s, —S(=O)₂N(R''')C(=O)NR'''R^s, —NR'''R^s, —N(R''')C(=O)R^s, —N(R''')C(=O)OR^s, —N(R''')C(=O)NR'''R^s, —N(R''')C(=NR''')NR'''R^s, —N(R''')S(=O)₂R^s, —N(R''')S(=O)₂NR'''R^s, —NR'''C_{2-6}alkylNR'''R^s, —NR'''C_{2-6}alkylOR^s and $C_{1-4}$alkyl substituted by 1 or 2 groups selected from $C_{1-2}$haloalkyl, halo, cyano, nitro, —C(=O)R'', —C(=O)NR'''R''', —C(=NR''')NR'''R''', —OR'', —OC(=O)R'', —OC(=O)NR'''R''', —OC(=O)N(R''')S(=O)₂R'', —OC_{2-6}alkylNR'''R''', —OC_{2-6}alkylOR''', —SR''', —S(=O)R'', —S(=O)₂R'', —S(=O)₂NR_mR'', —S(=O)₂N(R''')C(=O)R'', —S(=O)₂N(R''')C(=O)OR'', —S(=O)₂N(R''')C(=O)NR_mR'', —N(R''')C(=O)R'', —N(R''')C(=O)OR'', —N(R''')C(=O)NR'''R''', N(R''')C(=NR''')NR_mR'', —N(R''')S(=O)₂R'', —N(R''')S(=O)₂NR_mR'', —C(=O)R^s, —C(=O)OR^s, —C(=O)NR_mR^s, —C(=NR''')NR_mR^s, —OR^s, —OC(=O)R^s, —OC(=O)NR_mR^s, —OC(=O)N(R''')S(=O)₂R^s, —OC_{2-6}alkylNR_mR^s, —OC_{2-6}alkylOR^s, —SR^s, —S(=O)R^s, —S(=O)₂R^s, —S(=O)₂NR_mR^s, —S(=O)₂N(R''')C(=O)R^s, —S(=O)₂N(R''')C(=O)OR^s, —S(=O)₂N(R''')C(=O)NR_mR^s, —NR_mR^s, —N(R''')C(=O)R^s, —N(R''')C(=O)OR^s, —N(R''')C(=O)NR_mR^s, —N(R''')C(=NR''')NR'''R^s, —N(R''')S(=O)₂R^s, —N(R''')S(=O)₂NR_mR^s, —NR'''C_{2-6}alkylNR_mR^s, —NR'''C_{2-6}alkylOR^s and —NR'''C_{2-6}alkylOR'''; wherein $R^4$ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

$R^7$ is $C_{1-8}$alkyl, $C_{1-5}$haloalkyl, I or Br;

$R^9$ is H, $C_{1-9}$alkyl, $C_{1-4}$haloalkyl, halo, nitro, cyano, —OC_{1-6}alkyl, —O—C_{1-4}haloalkyl, —O—C_{1-6}alkylN- R'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is CR$^8$ or N.

In another embodiment, in conjunction with the novel compound embodiments above and below, R$^4$ is a heterocycle selected from indole, 3H-indole, benzo[b]furan, benzothiophene, 1H-indazole, benzimidazole, benzthiazole, 1H-benzotriazole, 7-quinoline, 8-quinoline, 1,2,3,4-tetrahydroquinoline, isoquinoline, cinnoline, phthalazine, quinazoline and quinoxaline, wherein the heterocycle is substituted by 0, 1, 2 or 3 substituents independently selected from C$_{1-9}$alkyl, oxo, C$_{1-4}$haloalkyl, halo, nitro, cyano, —OR''', —S(=O)$_n$C$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', —C(=O)C$_{1-6}$alkyl, —OC(=O)C$_{1-6}$alkyl, —C(=O)NR'''C$_{1-6}$alkyl, —NR'''C(=O)C$_{1-6}$alkyl —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR'''R$^s$, —N(R''')C(=O)R$^s$, —N(R''')C(=O)OR$^s$, N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR'''R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and —NR'''C$_{2-6}$alkylOR'''.

In another embodiment, in conjunction with the novel compound embodiments above and below, R$^4$ is a heterocycle selected from 6-indole, 7-indole, 6-3H-indole, 7-3H-indole, 6-benzo[b]furan, 7-benzo[b]furan, 6-benzothiophene, 7-benzothiophene, 6-1H-indazole, 7-1H-indazole, benzimidazole, benzthiazole, 1H-benzotriazole, 7-quinoline, 8-quinoline, 7-1,2,3,4-tetrahydroquinoline, 8-1,2,3,4-tetrahydroquinoline, isoquinolin-7-yl, isoquinolin-8-yl, 7-cinnoline, 8-cinnoline, phthalazine, 7-quinazoline, 8-quinazoline and quinoxaline, wherein the heterocycle is substituted by 0, 1, 2 or 3 substituents independently selected from C$_{1-9}$alkyl, oxo, C$_{1-4}$haloalkyl, halo, nitro, cyano, —OR''', —S(=O)$_n$C$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', —C(=O)C$_{1-6}$alkyl, —OC(=O)C$_{1-6}$alkyl, —C(=O)NR'''C$_{1-6}$alkyl, —NR'''C(=O)C$_{1-6}$alkyl —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR$_m$R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR'''R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and —NR'''C$_{2-6}$alkylOR'''.

In another embodiment, in conjunction with the novel compound embodiments above and below, R$^9$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR'''.

In another embodiment, in conjunction with the novel compound embodiments above and below, R$^9$ is H.

In another embodiment, in conjunction with the novel compound embodiments above and below, Z is CR$^8$.

In another embodiment, in conjunction with the novel compound embodiments above and below, Z is N.

In another embodiment, in conjunction with the novel compound embodiments above and below, R$^7$ is tert-butyl or trifluoromethyl.

In another embodiment, in conjunction with the novel compound embodiments above and below, R$^1$ is

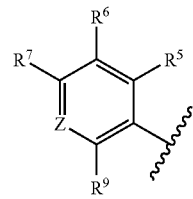

R$^2$ is C$_{1-6}$alkyl substituted by 1, 2 or 3 substituents selected from C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR$_m$R'', —NR'''C$_{2-6}$alkylNR'''R''' and —NR'''C$_{2-6}$alkylOR'''; or $R^2$ is

[chemical structure: a phenyl ring with substituent $(CR^qR^q)_o$ at top (wavy bond), $R^9$ and $R^5$ at ortho positions, $R^8$ and $R^6$ at meta positions, and $R^6$ at para position; labeled "; or"]

$R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)₂R″, —OC$_{2-6}$alkylNR′″R′″, —OC$_{2-6}$alkylOR′″, —SR′″, —S(=O)R″, —S(=O)₂R″, —S(=O)₂NR′″R′″, —S(=O)₂N(R′″)C(=O)R″, —S(=O)₂N(R′″)C(=O)OR″, —S(=O)₂N(R′″)C(=O)NR′″R′″, —NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)₂R″, —N(R′″)S(=O)₂NR′″R′″, —NR′″C$_{2-6}$alkylNR′″R′″, —NR′″C$_{2-6}$alkylOR′″, —C(=O)R^s, —C(=O)OR^s, —C(=O)NR$_m$R^s, —C(=NR′″)NR$_m$R^s, —OR^s, —OC(=O)R^s, —OC(=O)NR$_m$R^s, —OC(=O)N(R′″)S(=O)₂R^s, —OC$_{2-6}$alkylNR$_m$R^s, —OC$_{2-6}$alkylOR^s, —SR^s, —S(=O)R^s, —S(=O)₂R^s, —S(=O)₂NR$_m$R^s, —S(=O)₂N(R′″)C(=O)R^s, —S(=O)₂N(R′″)C(=O)OR^s, —S(=O)₂N(R′″)C(=O)NR$_m$R^s, —NR$_m$R^s, —N(R′″)C(=O)R^s, —N(R′″)C(=O)OR^s, —N(R′″)C(=O)NR$_m$R^s, —N(R′″)C(=NR′″)NR$_m$R^s, —N(R′″)S(=O)₂R^s, —N(R′″)S(=O)₂NR$_m$R^s, —NR′″C$_{2-6}$alkylNR$_m$R^s, —NR′″C$_{2-6}$alkylOR^s and $C_{1-4}$alkyl substituted by 1 or 2 groups selected from $C_{1-2}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)₂R″, —OC$_{2-6}$alkylNR′″R′″, —OC$_{2-6}$alkylOR′″, —SR′″, —S(=O)R″, —S(=O)₂R″, —S(=O)₂NR′″R′″, —S(=O)₂N(R′″)C(=O)R″, —S(=O)₂N(R′″)C(=O)OR″, —S(=O)₂N(R′″)C(=O)NR′″R′″, —NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)₂R″, —N(R′″)S(=O)₂NR$_m$R″, —NR′″C$_{2-6}$alkylNR′″R′″, —C(=O)R^s, —C(=O)OR^s, —C(=O)NR$_m$R^s, —C(=NR′″)NR$_m$R^s, —OR^s, —OC(=O)R^s, —OC(=O)NR′″R^s, —OC(=O)N(R′″)S(=O)₂R^s, —OC$_{2-6}$alkylNR′″R^s, —OC$_{2-6}$alkylOR^s, —SR^s, —S(=O)R^s, —S(=O)₂R^s, —S(=O)₂NR′″R^s, —S(=O)₂N(R′″)C(=O)R^s, —S(=O)₂N(R′″)C(=O)OR^s, —S(=O)₂N(R′″)C(=O)NR′″R^s, —NR′″R^s, —N(R′″)C(=O)R^s, —N(R′″)C(=O)OR^s, —N(R′″)C(=O)NR$_m$R^s, —N(R′″)C(=NR′″)NR$_m$R^s, —N(R′″)S(=O)₂R^s, —N(R′″)S(=O)₂NR$_m$R^s, —NR′″C$_{2-6}$alkylNR$_m$R^s, —NR′″C$_{2-6}$alkylOR^s and —NR′″C$_{2-6}$alkylOR′″, and the ring and bridge carbon atoms are substituted with 0, 1 or 2=O groups;

$R^7$ is $C_{2-8}$alkyl, $C_{1-5}$haloalkyl, I, Br;

$R^9$ is independently, at each instance, H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR′″R′″, —O—C$_{1-6}$alkylOR′″, —NR′″R′″, —NR′″—C$_{1-4}$haloalkyl, —NR′″—C$_{1-6}$alkylNR′″R′″ or —NR′″—C$_{1-6}$alkylOR′″;

Y is NH; and

Z is $CR^8$ or N.

In another embodiment, in conjunction with the novel compound embodiments above and below, $R^2$ is $C_{1-6}$alkyl substituted by 1, 2 or 3 substituents selected from $C_{1-4}$haloalkyl, halo, cyano, nitro, —C(=O)R″, —C(=O)OR″, —C(=O)NR′″R′″, —C(=NR′″)NR$_m$R′″, —OR′″, —OC(=O)R′″, —OC(=O)NR′″R′″, —OC(=O)N(R′″)S(=O)₂R″, —OC$_{2-6}$alkylNR′″R′″, —OC$_{2-6}$alkylOR′″, —SR′″, —S(=O)R″, —S(=O)₂R″, —S(=O)₂NR′″R′″, —S(=O)₂N(R′″)C(=O)R″, —S(=O)₂N(R′″)C(=O)OR″, —S(=O)₂N(R′″)C(=O)NR′″R′″, —NR′″R′″, —N(R′″)C(=O)R″, —N(R′″)C(=O)OR″, —N(R′″)C(=O)NR′″R′″, —N(R′″)C(=NR′″)NR$_m$R′″, —N(R′″)S(=O)₂R″, —N(R′″)S(=O)₂NR′″R′″, —NR′″C$_{2-6}$alkylNR′″R′″ and —NR′″C$_{2-6}$alkylOR′″;

In another embodiment, in conjunction with the novel compound embodiments above and below, $R^2$ is —(C(R^q)₂)$_o$phenyl, wherein the phenyl is substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)₂R″, —OC$_{2-6}$alkylNR′″R′″, —OC$_{2-6}$alkylOR′″, —SR′″, —S(=O)R″, —S(=O)₂R″, —S(=O)₂NR′″R′″, —S(=O)₂N(R′″)C(=O)R″, —S(=O)₂N(R′″)C(=O)OR″, —S(=O)₂N(R′″)C(=O)NR$_m$R′″, —NR′″R′″, —N(R′″)C(=O)R″, —N(R′″)C(=O)OR″, —N(R′″)C(=O)NR′″R′″, —N(R′″)C(=NR′″)NR$_m$R′″, —N(R′″)S(=O)₂R″, —N(R′″)S(=O)₂NR′″R′″, —NR′″C$_{2-6}$alkylNR′″R′″, —NR′″C$_{2-6}$alkylOR′″, —C(=O)R^s, —C(=O)OR^s, —C(=O)NR$_m$R^s, —C(=NR′″)NR″R^s, —OR^s, —OC(=O)R^s, —OC(=O)NR$_m$R^s, —OC(=O)N(R′″)S(=O)₂R^s, —OC$_{2-6}$alkylNR$_m$R^s, —OC$_{2-6}$alkylOR^s, —SR^s, —S(=O)R^s, —S(=O)₂R^s, —S(=O)₂NR$_m$R^s, —S(=O)₂N(R′″)C(=O)R^s, —S(=O)₂N(R′″)C(=O)OR^s, —S(=O)₂N(R′″)C(=O)NR$_m$R^s, —NR$_m$R^s, —N(R′″)C(=O)R^s, —N(R′″)C(=O)OR^s, —N(R′″)C(=O)NR$_m$R^s, —N(R′″)C(=NR′″)NR$_m$R^s, —N(R′″)S(=O)₂R^s, —N(R′″)S(=O)₂NR$_m$R^s, —NR′″C$_{2-6}$alkylNR$_m$R^s, —NR′″C$_{2-6}$alkylOR^s and $C_{1-4}$alkyl substituted by 1 or 2 groups selected from $C_{1-2}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)₂R″, —OC$_{2-6}$alkylNR′″R′″, —OC$_{2-6}$alkylOR′″, —SR′″, —S(=O)R″, —S(=O)₂R″, —S(=O)₂NR′″R′″, —S(=O)₂N(R′″)C(=O)R″, —S(=O)₂N(R′″)C(=O)OR″, —S(=O)₂N(R′″)C(=O)NR′″R′″, —NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)₂R″, —N(R′″)S(=O)₂NR$_m$R′″, —NR′″C$_{2-6}$alkylNR′″R′″, —C(=O)R^s, —C(=O)OR^s, —C(=O)NR$_m$R^s, —C(=NR′″)NR$_m$R^s, —OR^s, —OC(=O)R^s, —OC(=O)NR$_m$R^s, —OC(=O)N(R′″)S(=O)₂R^s, —OC$_{2-6}$alkylNR$_m$R^s, —OC$_{2-6}$alkylOR^s, —SR^s, —S(=O)R^s, —S(=O)₂R^s, —S(=O)₂NR$_m$R^s, —S(=O)₂N(R′″)C(=O)R^s, —S(=O)₂N(R′″)C(=O)OR^s, —NR$_m$R^s, —N(R′″)C(=O)R^s, —N(R′″)C(=O)OR^s, —N(R′″)C(=O)NR$_m$R^s, —N(R′″)C(=NR′″)NR$_m$R^s, —N(R′′′)S(═O)$_2$R$^s$, —N(R′′′)S(═O)$_2$NR$_m$R$^s$, —NR′′′C$_{2-6}$alkylNR$_m$R$^s$, —NR′′′C$_{2-6}$alkylOR$^s$ and —NR′′′C$_{2-6}$alkylOR′′′.

In another embodiment, in conjunction with the novel compound embodiments above and below, R$^2$ is —(C(R$^q$)$_2$)$_o$R$^r$, wherein R$^r$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C$_{1-8}$alkyl, C$_{1-4}$haloalkyl, halo, cyano, nitro, —C(═O)R′′, —C(═O)OR′′, —C(═O)NR′′′R′′′, —C(═NR′′′)NR′′′R′′′, —OR′′′, —OC(═O)R′′, —OC(═O)NR′′′R′′′, —OC(═O)N(R′′′)S(═O)$_2$R′′, —OC$_{2-6}$alkylNR′′′R′′′, —OC$_{2-6}$alkylOR′′′, —SR′′′, —S(═O)R′′, —S(═O)$_2$R′′, —S(═O)$_2$NR′′′R′′′, —S(═O)$_2$N(R′′′)C(═O)R′′, —S(═O)$_2$N(R′′′)C(═O)OR′′, —S(═O)$_2$N(R′′′)C(═O)NR$_m$R′′, —NR′′′R′′′, —N(R′′′)C(═O)R′′, —N(R′′′)C(═O)OR′′, N(R′′′)C(═O)NR$_m$R′′, —N(R′′′)C(═NR′′′)NR$_m$R′′, —N(R′′′)S(═O)$_2$R′′, —N(R′′′)S(═O)$_2$NR$_m$R′′, —NR′′′C$_{2-6}$alkylNR′′′R′′′, —NR′′′C$_{2-6}$alkylOR′′′, —C(═O)R$^s$, —C(═O)OR$^s$, —C(═O)NR$_m$R$^s$, —C(═NR′′′)NR$_m$R$^s$, —OR$^s$, —OC(═O)R$^s$, —OC(═O)NR$_m$R$^s$, —OC(═O)N(R′′′)S(═O)$_2$R$^s$, —OC$_{2-6}$alkylNR$_m$R$^s$, —OC$_{2-6}$alkylOR$^s$, —SR$^s$, —S(═O)$_2$R$^s$, —S(═O)$_2$R$^s$, —S(═O)$_2$NR′′′R$^s$, —S(═O)$_2$N(R′′′)C(═O)R$^s$, —S(═O)$_2$N(R′′′)C(═O)OR$^s$, —S(═O)$_2$N(R′′′)C(═O)NR$_m$R$^s$, —NR$_m$R$^s$, —N(R′′′)C(═O)R$^s$, —N(R′′′)C(═O)OR$^s$, —N(R′′′)C(═O)NR$_m$R$^s$, —N(R′′′)C(═NR′′′)NR$_m$R$^s$, —N(R′′′)S(═O)$_2$R$^s$, —N(R′′′)S(═O)$_2$NR$_m$R$^s$, —NR′′′C$_{2-6}$alkylNR$_m$R$^s$, —NR′′′C$_{2-6}$alkylOR$^s$ and C$_{1-4}$alkyl substituted by 1 or 2 groups selected from C$_{1-2}$haloalkyl, halo, cyano, nitro, —C(═O)R′′, —C(═O)OR′′, —C(═O)NR′′′R′′′, —C(═NR′′′)NR′′′R′′′, —OR′′′, —OC(═O)R′′, —OC(═O)NR′′′R′′′, —OC(═O)N(R′′′)S(═O)$_2$R′′, —OC$_{2-6}$alkylNR′′′R′′′, —OC$_{2-6}$alkylOR′′′, —SR′′′, —S(═O)R′′, —S(═O)$_2$R′′, —S(═O)$_2$NR′′′R′′′, —S(═O)$_2$N(R′′′)C(═O)R′′, —S(═O)$_2$N(R′′′)C(═O)OR′′, —S(═O)$_2$N(R′′′)C(═O)NR′′′R′′′, —NR′′′R′′′, —N(R′′′)C(═O)R′′, —N(R′′′)C(═O)OR′′, —N(R′′′)C(═O)NR′′′R′′′, —N(R′′′)C(═NR′′′)NR$_m$R′′, —N(R′′′)S(═O)$_2$R′′, —N(R′′′)S(═O)$_2$NR$_m$R′′, —NR′′′C$_{2-6}$alkylNR′′′R′′′, —C(═O)R$^s$, —C(═O)OR$^s$, —C(═O)NR$_m$R$^s$, —C(═NR′′′)NR′′′R$^s$, —OR$^s$, —OC(═O)R$^s$, —OC(═O)NR$_m$R$^s$, —OC(═O)N(R′′′)S(═O)$_2$R$^s$, —OC$_{2-6}$alkylNR$_m$R$^s$, —OC$_{2-6}$alkylOR$^s$, —SR$^s$, —S(═O)$_2$R$^s$, —S(═O)$_2$R$^s$, —S(═O)$_2$NR$_m$R$^s$, —S(═O)$_2$N(R′′′)C(═O)R$^s$, —S(═O)$_2$N(R′′′)C(═O)OR$^s$, —S(═O)$_2$N(R′′′)C(═O)NR$_m$R$^s$, —NR$_m$R$^s$, —N(R′′′)C(═O)R$^s$, —N(R′′′)C(═O)OR$^s$, —N(R′′′)C(═O)NR′′′R$^s$, —N(R′′′)C(═NR′′′)NR$_m$R$^s$, —N(R′′′)S(═O)$_2$R$^s$, —N(R′′′)S(═O)$_2$NR$_m$R$^s$, —NR′′′C$_{2-6}$alkylNR$_m$R$^s$, —NR′′′C$_{2-6}$alkylOR$^s$ and —NR′′′C$_{2-6}$alkylOR′′′;

In another embodiment, in conjunction with the novel compound embodiments above and below, R$^4$ is a phenyl ring that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C$_{1-8}$alkyl, C$_{1-4}$haloalkyl, halo, cyano, nitro, —C(═O)R′′, —C(═O)OR′′, —C(═O)NR′′′R′′′, —C(═NR′′′)NR′′′R′′′, —OR′′′, —OC(═O)R′′, —OC(═O)NR$_m$R′′′, —OC(═O)N(R′′′)S(═O)$_2$R′′, —OC$_{2-6}$alkylNR′′′R′′′, —OC$_{2-6}$alkylOR′′′, —SR′′′, —S(═O)R′′, —S(═O)$_2$R′′, —S(═O)$_2$NR′′′R′′′, —S(═O)$_2$N(R′′′)C(═O)R′′, —S(═O)$_2$N(R′′′)C(═O)OR′′, —S(═O)$_2$N(R′′′)C(═O)NR′′′R′′′, —NR′′′R′′′, —N(R′′′)C(═O)R′′, —N(R′′′)C(═O)OR′′, —NR′′′C(═O)NR′′′R′′′, —N(R′′′)C(═NR′′′)NR′′′R′′′, —N(R′′′)S(═O)$_2$R′′, —N(R′′′)S(═O)$_2$NR′′′R′′′, —NR′′′C$_{2-6}$alkylNR′′′R′′′, —NR′′′C$_{2-6}$alkylOR′′′, —C(═O)R$^s$, —C(═O)OR$^s$, —C(═O)NR$_m$R$^s$, —C(═NR′′′)NR$_m$R$^s$, —OR$^s$, —OC(═O)R$^s$, —OC(═O)NR$_m$R$^s$, —OC(═O)N(R′′′)S(═O)$_2$R$^s$, —OC$_{2-6}$alkylNR$_m$R$^s$, —OC$_{2-6}$alkylOR$^s$, —SR$^s$, —S(═O)R$^s$, —S(═O)$_2$R$^s$, —S(═O)$_2$NR$_m$R$^s$, —S(═O)$_2$N(R′′′)C(═O)R$^s$, —S(═O)$_2$N(R′′′)C(═O)OR$^s$, —S(═O)$_2$N(R′′′)C(═O)NR$_m$R$^s$, —NR$_m$R$^s$, —N(R′′′)C(═O)R$^s$, —N(R′′′)C(═O)OR$^s$, —N(R′′′)C(═O)NR′′′R$^s$, —N(R′′′)C(═NR′′′)NR′′′R′′′, —N(R′′′)S(═O)$_2$R′′, —N(R′′′)S(═O)$_2$NR′′′R′′′, —NR′′′C$_{2-6}$alkylNR′′′R′′′, —NR′′′C$_{2-6}$alkylOR′′′ and C$_{1-4}$alkyl substituted by 1 or 2 groups selected from C$_{1-2}$haloalkyl, halo, cyano, nitro, —C(═O)R′′, —C(═O)OR′′, —C(═O)NR′′′R′′′, —C(═NR′′′)NR′′′R′′′, —OR′′′, —OC(═O)R′′, —OC(═O)NR′′′R′′′, —OC(═O)N(R′′′)S(═O)$_2$R′′, —OC$_{2-6}$alkylNR′′′R′′′, —OC$_{2-6}$alkylOR′′′, —SR′′′, —S(═O)R′′, —S(═O)$_2$R′′, —S(═O)$_2$NR′′′R′′′, —S(═O)$_2$N(R′′′)C(═O)R′′, —S(═O)$_2$N(R′′′)C(═O)OR′′, —S(═O)$_2$N(R′′′)C(═O)NR′′′R′′′, —NR′′′R′′′, —N(R′′′)C(═O)R′′, —N(R′′′)C(═O)OR′′, —N(R′′′)C(═O)NR′′′R′′′, —N(R′′′)C(═NR′′′)NR′′′R′′′, —N(R′′′)S(═O)$_2$R′′, —N(R′′′)S(═O)$_2$NR′′′R′′′, —NR′′′C$_{2-6}$alkylNR′′′R′′′, —NR′′′C$_{2-6}$alkylOR′′′, —C(═O)R$^s$, —C(═O)OR$^s$, —C(═O)NR$_m$R$^s$, —C(═NR′′′)NR$_m$R$^s$, —OR$^s$, —OC(═O)R$^s$, —OC(═O)NR$_m$R$^s$, —OC(═O)N(R′′′)S(═O)$_2$R$^s$, —OC$_{2-6}$alkylNR$_m$R$^s$, —OC$_{2-6}$alkylOR$^s$, —SR$^s$, —S(═O)R$^s$, —S(═O)$_2$R$^s$, —S(═O)$_2$NR$_m$R$^s$, —S(═O)$_2$N(R′′′)C(═O)R$^s$, —S(═O)$_2$N(R′′′)C(═O)OR$^s$, —S(═O)$_2$N(R′′′)C(═O)NR$_m$R$^s$, —NR$_m$R$^s$, —N(R′′′)C(═O)R$^s$, —N(R′′′)C(═O)OR$^s$, —N(R′′′)C(═O)NR′′′R$^s$, —N(R′′′)C(═NR′′′)NR′′′R$^s$, —N(R′′′)S(═O)$_2$R$^s$, —N(R′′′)S(═O)$_2$NR′′′R$^s$, —NR′′′C$_{2-6}$alkylNR′′′R$^s$ and —NR′′′C$_{2-6}$alkylOR′′′; and the bridge carbon atoms are substituted with 0, 1 or 2═O groups.

In another embodiment, in conjunction with the novel compound embodiments above and below, R$^7$ is tert-butyl or trifluoromethyl.

In another embodiment, in conjunction with the novel compound embodiments above and below, R$^9$ is H.

In another embodiment, in conjunction with the novel compound embodiments above and below, Z is CR$^8$.

In another embodiment, in conjunction with the novel compound embodiments above and below, Z is N.

In another embodiment, in conjunction with the novel compound embodiments above and below, R$^1$ is

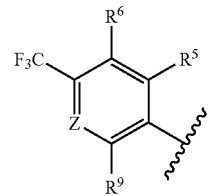

R$^2$ is H, —OR′′′, Cl, C$_{1-3}$haloalkyl or C$_{1-6}$alkyl;

R$^4$ is a saturated or unsaturated 5- or 6-membered ring containing 0, 1, 2 or 3 atoms selected from O, N and S, so long as the combination of O and S atoms is not greater than 2, wherein the ring is substituted by 0, 1, 2 or 3 substituents independently selected from C$_{1-8}$alkyl, C$_{1-4}$haloalkyl, halo, cyano, nitro, —C(═O)NR′′′R′′′, —C(═NR′′′)NR′′′R′′′, —OR′′, —OC(═O)R′′, —OC(═O)NR′′′R′′′, —OC(═O)N(R′′′)S(═O)$_2$R′′, —OC$_{2-6}$alkylOR′′′, —SR′′′, —S(═O)R′′, —S(═O)$_2$R′′, —S(═O)$_2$NR′′′R′′′, —S(═O)$_2$N(R′′′)C(═O)R′′, —S(═O)$_2$N(R′′′)C(═O)OR′′, —S(═O)$_2$N(R′′′)C(═O)NR′′′R′′′, —NR′′′R′′′, —N(R′′′)C(═O)R′′, —N(R′′′)C(═O)OR′′, —N(R′′′)C(═O)NR′′′R′′′, —N(R′′′)C(═NR′′′)NR′′′R′′′, —N(R′′′)S(═O)$_2$R′′, —N(R′′′)S(═O)$_2$NR′′′R′′′, —NR′′′C$_{2-6}$alkylNR′′′R′′′, —NR′′′C$_{2-6}$alkylOR′′′, —C(═O)R$^s$, —C(═O)OR$^s$, —C(═O)NR$_m$R$^s$, —C(═NR′′′)NR$_m$R$^s$, —OR$^s$, —OC(═O)R$^s$, —OC(═O)NR$_m$R$^s$, —OC(═O)N(R′′′)S(═O)$_2$R$^s$, —OC$_{2-6}$alkylNR$_m$R$^s$, —OC$_{2-6}$alkylOR$^s$, —SR$^s$, —S(═O)R$^s$, —S(═O)$_2$R$^s$, —S(═O)$_2$NR$_m$R$^s$, —S(═O)$_2$N(R′′′)C(═O)R$^s$, —S(═O)$_2$N(R′′′)C(═O)OR$^s$, —S(=O)$_2$N(R'''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)NR$_m$R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' and —NR'''C$_{2-6}$alkylOR'''; wherein R$^4$ is not unsubstituted phenyl;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is CR$^8$ or N.

In another embodiment, in conjunction with the novel compound embodiments above and below, R$^4$ is a saturated or unsaturated 5- or 6-membered ring containing 1, 2 or 3 atoms selected from O, N and S, so long as the combination of O and S atoms is not greater than 1, wherein the ring is substituted by 0, 1, 2 or 3 substituents independently selected from C$_{1-8}$alkyl, C$_{1-4}$haloalkyl, halo, cyano, nitro, —C(=O)NR'''R''', —C(=NR''')NR'''R''', —OR'', —OC(=O)R'', —OC(=O)NR'''R''', —OC(=O)N(R''')S(=O)$_2$R'', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR$_m$R$^s$, —C(=NR''')NR$_m$R$^s$, —OR$^s$, —OC(=O)R$^s$, —OC(=O)NR'''R$^s$, —OC(=O)N(R''')S(=O)$_2$R$^s$, —OC$_{2-6}$alkylNR$_m$R$^s$, —OC$_{2-6}$alkylOR$^s$, —SR$^s$, —S(=O)R$^s$, —S(=O)$_2$R$^s$, —S(=O)$_2$NR$_m$R$^s$, —S(=O)$_2$N(R''')C(=O)R$^s$, —S(=O)$_2$N(R''')C(=O)OR$^s$, —S(=O)$_2$N(R''')C(=O)NR$_m$R$^s$, —NR$_m$R$^s$, —N(R''')C(=O)R$^s$, —N(R''')C(=O)OR$^s$, —N(R''')C(=O)NR$_m$R$^s$, —N(R''')C(=NR''')NR$_m$R$^s$, —N(R''')S(=O)$_2$R$^s$, —N(R''')S(=O)$_2$NR$_m$R$^s$, —NR'''C$_{2-6}$alkylNR$_m$R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)NR'''R''', —C(=NR''')NR'''R''', —OR''', —OC(=O)R'', —OC(=O)NR$_m$R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR$_m$R''', —N(R''')C(=NR''')NR$_m$R''', —N(R''')S(=O)$_2$R'', —N(R''')S(=O)$_2$NR'''R''', —NR'''C$_{2-6}$alkylNR'''R''' and —NR'''C$_{2-6}$alkylOR''';

In another embodiment, in conjunction with the novel compound embodiments above and below, Z is CR$^8$.

In another embodiment, in conjunction with the novel compound embodiments above and below, Z is N.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound having the structure:

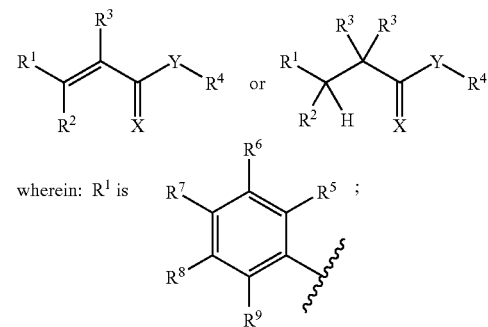

wherein: R$^1$ is

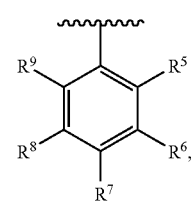

or a naphthyl or saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the naphthyl, heterocycle or fused phenyl ring is substituted by 0, 1, 2 or 3 substituents independently selected from R$^5$, R$^6$ and R$^7$;

R$^2$ is H, hydroxy, halo, C$_{1-6}$alkyl substituted by 0, 1 or 2 substituents selected from R$^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^5$, R$^6$ and R$^7$;

or $R^1$ and $R^2$ together are

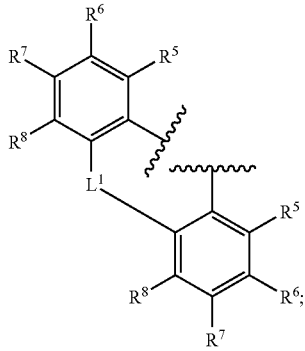

$R^3$ is H or $C_{1-4}$alkyl; or $R^1$ and $R^3$ together are

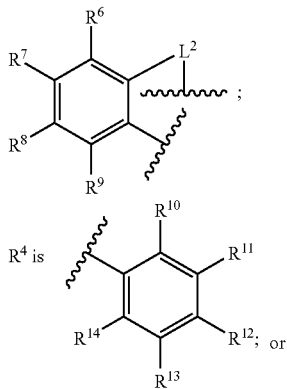

$R^4$ is $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $C_{1-9}$alkyl, $C_{1-4}$haloalkyl, halo, nitro, cyano, —$OR^a$, —$S(=O)_nC_{1-6}$alkyl, —O—$C_{1-4}$haloalkyl, —O—$C_{1-6}$alkyl$NR^aR^a$, —O—$C_{1-6}$alkyl$OR^a$, —O—$C_{1-6}$alkyl$C(=O)OR^a$, —$NR^aR^a$, —$NR^a$—$C_{1-4}$haloalkyl, —$NR^a$—$C_{1-6}$alkyl$NR^aR^a$, —$NR^a$—$C_{1-6}$alkyl$OR^a$, —$C(=O)C_{1-6}$alkyl, —$C(=O)OC_{1-6}$alkyl, —$OC(=O)C_{1-6}$alkyl, —$C(=O)NR^aC_{1-6}$alkyl and —$NR^aC(=O)C_{1-6}$alkyl; or $R^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, $OR^a$, $NR^aR^a$, $C_{1-6}$alkyl and $C_{1-3}$haloalkyl; and saturated carbon atoms may be additionally substituted by =O;

$R^5$ is independently, at each instance, H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkyl$NR^aR^a$, —O—$C_{1-6}$alkyl$OR^a$, —$NR^aR^a$, —$NR^a$—$C_{1-4}$haloalkyl, —$NR^a$—$C_{1-6}$alkylN-$R^aR^a$ or —$NR^a$—$C_{1-6}$alkyl$OR^a$; or $R^5$ is a saturated or unsaturated 5- or 6-membered ring heterocycle containing 1, 2 or 3 atoms selected from O, N and S;

$R^6$ is independently, at each instance, H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkyl$NR^aR^a$, —O—$C_{1-6}$alkyl$OR^a$, —$NR^aR^a$, —$NR^a$—$C_{1-4}$haloalkyl, —$NR^a$—$C_{1-6}$alkylN-$R^aR^a$ or —$NR^a$—$C_{1-6}$alkyl$OR^a$; or $R^5$ and $R^6$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the bridge are substituted by 0, 1, 2 or 3 substituents selected from halo, $C_{1-6}$alkyl, (=O), —$OC_{1-6}$alkyl, —$NR^aC_{1-6}$alkyl, —$C_{1-6}$alkyl$OR^a$ and $C_{1-6}$alkyl$NR^aR^a$, and the available N atoms of the bridge are substituted by $R^a$, —$C_{1-6}$alkyl$OR^a$ or $C_{1-6}$alkyl$NR^aR^a$;

$R^7$ is independently, at each instance, H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkyl$NR^aR^a$, —O—$C_{1-6}$alkyl$R^a$, —$NR^aR^a$, —$NR^a$—$C_{1-4}$haloalkyl, —$NR^a$—$C_{1-6}$alkylN-$R^aR^a$ or —$NR^a$—$C_{1-6}$alkyl$OR^a$;

$R^8$ is independently, at each instance, H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkyl$NR^aR^a$, —O—$C_{1-6}$alkyl$OR^a$, —$NR^aR^a$, —$NR^a$—$C_{1-4}$haloalkyl, —$NR^a$—$C_{1-6}$alkylN-$R^aR^a$ or —$NR^a$—$C_{1-6}$alkyl$OR^a$; or $R^7$ and $R^8$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the bridge are substituted by 0, 1, 2 or 3 substituents selected from halo, $C_{1-6}$alkyl, (=O), —O—$C_{1-6}$alkyl, —$NR^aC_{1-6}$alkyl, —$C_{1-6}$alkyl$OR^a$ and $C_{1-6}$alkyl$NR^aR^a$, and the available N atoms of the bridge are substituted by $R^a$, —$C_{1-6}$alkyl$OR^a$ or $C_{1-6}$alkyl$NR^aR^a$;

$R^9$ is independently, at each instance, H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkyl$NR^aR^a$, —O—$C_{1-6}$alkyl$OR^a$, —$NR^aR^a$, —$NR^a$—$C_{1-4}$haloalkyl, —$NR^a$—$C_{1-6}$alkylN-$R^aR^a$ or —$NR^a$—$C_{1-6}$alkyl$OR^a$;

$R^{10}$ is independently, at each instance, H, $C_{1-9}$alkyl, —$C_{1-3}$alkyl$OR^a$, $C_{1-4}$haloalkyl, halo, nitro, cyano, —$OR^a$, —$S(=O)_nC_{1-6}$alkyl, —O—$C_{1-4}$haloalkyl, —O—$C_{1-6}$alkyl-$NR^aR^a$, —O—$C_{1-6}$alkyl$OR^a$, —O—$C_{1-6}$alkyl$C(=O)OR^a$, —$NR^aR^a$, —$NR^a$—$C_{1-4}$haloalkyl, —$NR^a$—$C_{1-6}$alkylN-$R^aR^a$, —$NR^a$—$C_{1-6}$alkyl$OR^a$, —$C(=O)C_{1-6}$alkyl, —$C(=O)OC_{1-6}$alkyl, —$OC(=O)C_{1-6}$alkyl, —$C(=O)$ $NR^aC_{1-6}$alkyl or —$NR^aC(=O)C_{1-6}$alkyl;

$R^{11}$ is independently, at each instance, H, $C_{1-9}$alkyl, —$C_{1-3}$alkyl$OR^a$, $C_{1-4}$haloalkyl, halo, nitro, cyano, —$OR^a$, —$S(=O)_nC_{1-6}$alkyl, —O—$C_{1-4}$haloalkyl, —O—$C_{1-6}$alkyl-$NR^aR^a$, —O—$C_{1-6}$alkyl$R^c$, —O—$C_{1-6}$alkyl$OR^a$, —O—$C_{1-6}$alkyl$C(=O)OR^a$, —$NR^aR^a$, —$NR^a$—$C_{1-4}$haloalkyl, —$NR^a$—$C_{1-6}$alkyl$NR^aR^a$, —$NR^a$—$C_{1-6}$alkyl$OR^a$, —$C(=O)C_{1-6}$alkyl, —$C(=O)OC_{1-6}$alkyl, —$OC(=O)C_{1-6}$alkyl, —$C(=O)NR^aC_{1-6}$alkyl or —$NR^aC(=O)C_{1-6}$alkyl; or $R^{10}$ and $R^{11}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, =O, —$OR^a$, —$C_{1-6}$alkyl$OR^a$, —$C_{1-6}$alkyl, —$NR^aR^a$, —$C_{1-6}$alkyl$NR^aR^a$, —$C(=O)OR^a$, —$C(=O)NR^aR^a$, —$C_{1-3}$alkyl$C(=O)OR^a$, —$C_{1-3}$alkyl$C(=O)NR^aR^a$, —$OC(=O)C_{1-6}$alkyl, —$NR^aC(=O)C_{1-6}$alkyl, —$C_{1-3}$alkyl$OC(=O)C_{1-6}$alkyl or —$C_{1-3}$alkyl$NR^aC(=O)C_{1-6}$alkyl, and any nitrogen atoms in the bridge are substituted by H, —$C_{1-6}$alkyl$OR^a$, —$C_{1-6}$alkyl$NR^aR^a$, —$C_{1-3}$alkyl$C(=O)OR^a$, —$C_{1-3}$alkyl$C(=O)NR^aR^a$, —$C_{1-3}$alkyl$OC$ —C(═O)C$_{1-6}$alkyl, —C$_{1-3}$alkylNR$^a$C(═O)C$_{1-6}$alkyl, C(═O)R$^c$ or —C$_{1-3}$alkylR$^c$; wherein if R$^{10}$, R$^{12}$, R$^{13}$ and R$^{14}$ are all H, then R$^{11}$ is not —O—C$_{1-6}$alkylNR$^a$R$^a$ or —O—C$_{1-6}$alkylOR$^a$;

R$^{12}$ is independently, at each instance, H, C$_{1-9}$alkyl, —C$_{1-3}$alkylOR$^a$, C$_{1-4}$haloalkyl, halo, nitro, cyano, —OR$^a$, —S(═O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(═O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(═O)C$_{1-6}$alkyl, —C(═O)OC$_{1-6}$alkyl, —OC(═O)C$_{1-6}$alkyl, —C(═O)NR$^a$C$_{1-6}$alkyl or —NR$^a$C(═O)C$_{1-6}$alkyl; or R$^{11}$ and R$^{12}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the bridge is substituted by H, ═O, —OR$^a$, —C$_{1-6}$alkylOR$^a$, —C$_{1-6}$alkyl, —NR$^a$R$^a$, —C$_{1-6}$alkylNR$^a$R$^a$, —C(═O)OR$^a$, —C(═O)NR$^a$R$^a$, —C$_{1-3}$alkylC(═O)OR$^a$, —C$_{1-3}$alkylC(═O)NR$^a$R$^a$, —OC(═O)C$_{1-6}$alkyl, —NR$^a$C(═O)C$_{1-6}$alkyl, —C$_{1-3}$alkylOC(═O)C$_{1-6}$alkyl or —C$_{1-3}$alkylNR$^a$C(═O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(═O)OR$^a$, —C$_{1-3}$alkylC(═O)NR$^a$R$^a$, —C$_{1-3}$alkylOC(═O)C$_{1-6}$alkyl, —C$_{1-3}$alkylNR$^a$C(═O)C$_{1-6}$alkyl, —C(═O)R$^c$ or —C$_{1-3}$alkylR$^c$;

R$^{13}$ is independently, at each instance, H, C$_{1-9}$alkyl, —C$_{1-3}$alkylOR$^a$, C$_{1-4}$haloalkyl, halo, nitro, cyano, OR$^a$, —S(═O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(═O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(═O)C$_{1-6}$alkyl, —C(═O)OC$_{1-6}$alkyl, —OC(═O)C$_{1-6}$alkyl, —C(═O)NR$^a$C$_{1-6}$alkyl or —NR$^a$C(═O)C$_{1-6}$alkyl;

R$^{14}$ is independently, at each instance, H, C$_{1-9}$alkyl, —C$_{1-3}$alkylOR$^a$, C$_{1-4}$haloalkyl, halo, nitro, cyano, —OR$^a$, —S(═O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(═O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(═O)C$_{1-6}$alkyl, —C(═O)OC$_{1-6}$alkyl, —OC(═O)C$_{1-6}$alkyl, —C(═O)NR$^a$C$_{1-6}$alkyl or —NR$^a$C(═O)C$_{1-6}$alkyl;

R$^a$ is independently, at each instance, H, phenyl, benzyl or C$_{1-6}$alkyl;

R$^c$ is phenyl substituted by 0, 1 or 2 groups selected from halo, C$_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, C$_{1-3}$haloalkyl, —OR$^a$ and —NR$^a$R$^a$;

L$^1$ is a bond, —CH$_2$CH$_2$— or —CH═CH—;

L$^2$ is NR$^a$, O, S(═O)$_n$, —N═CH—, —CH$_2$NR$^a$—, —CH═N— or —NR$^a$CH$_2$—;

X is O, S or NR$^a$; or X and R$^2$ together are ═N—CH═CH—, ═C—O—, ═C—S—, or ═C—NR$^a$;

Y is NH or O; and n is independently, at each instance, 0, 1 or 2; with the proviso that when R$^1$ is 4-chlorophenyl, then R$^4$ is not 3-methoxyphenyl.

In another embodiment, in conjunction with the method of treatment embodiments above and below, R$^1$ is

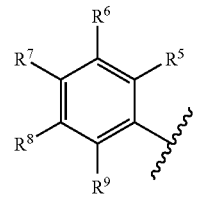

or a naphthyl or saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the naphthyl, heterocycle or fused phenyl ring is substituted by 0, 1, 2 or 3 substituents independently selected from R$^5$, R$^6$ and R$^7$;

R$^2$ is H, hydroxy, halo, C$_{1-6}$alkyl substituted by 0, 1 or 2 substituents selected from R$^{10}$,

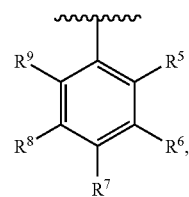

or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^5$, R$^6$ and R$^7$; and R$^3$ is H or C$_{1-4}$alkyl.

In another embodiment, in conjunction with the method of treatment embodiments above and below, R$^1$ is

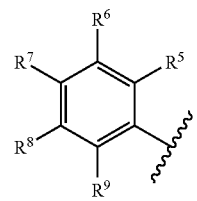

In another embodiment, in conjunction with the method of treatment embodiments above and below, R$^7$ is independently, at each instance, C$_{2-9}$alkyl or C$_{1-4}$haloalkyl.

In another embodiment, in conjunction with the method of treatment embodiments above and below, R$^1$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^5$, R$^6$ and R$^7$.

In another embodiment, in conjunction with the method of treatment embodiments above and below, $R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the method of treatment embodiments above and below, $R^2$ is

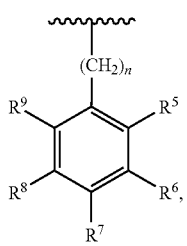

or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the method of treatment embodiments above and below, $R^2$ is

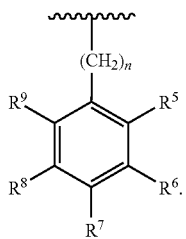

In another embodiment, in conjunction with the method of treatment embodiments above and below, $R^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $R^5$, $R^6$ and $R^7$.

In another embodiment, in conjunction with the method of treatment embodiments above and below, $R^1$ and $R^2$ together are

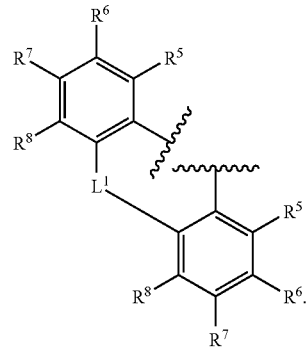

In another embodiment, in conjunction with the method of treatment embodiments above and below, $R^1$ and $R^3$ together are

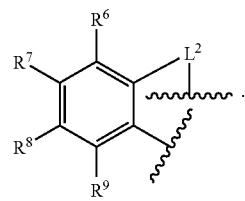

In another embodiment, in conjunction with the method of treatment embodiments above and below, X and $R^2$ together are =N—CH=CH—, =C—O—, =C—S—, or =C—NR$^a$—.

In another embodiment, in conjunction with the method of treatment embodiments above and below, $R^4$ is

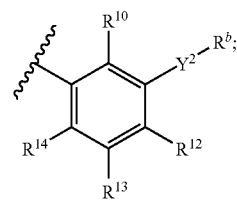

$R^b$ is H, $C_{1-6}$alkyl, —C(=O)$C_{1-6}$alkyl, $C_{1-6}$alkyl-O—R$^a$; and $Y^2$ is —NR$^a$— or —O—.

In another embodiment, in conjunction with the method of treatment embodiments above and below, $R^4$ is

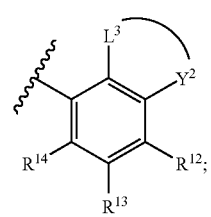

$L^3$ is a 2- or 3-atom, saturated or unsaturated, bridge containing 1, 2 or 3 carbon atoms and 0 or 1 atoms independently selected from O, N and S, wherein the each of the carbon atoms in the bridge is substituted by H, =O, —OR$^a$, —C$_{1-6}$alkylOR$^a$, —C$_{1-6}$alkyl, —NR$^a$R$^a$, —C$_{1-6}$alkylNR$^a$R$^a$, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y$^2$ is —NR$^b$— or —O—.

In another embodiment, in conjunction with the method of treatment embodiments above and below, R$^4$ is

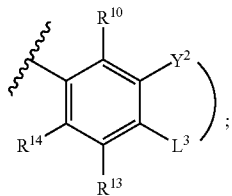

L$^3$ is a 2- or 3-atom, saturated or unsaturated, bridge containing 1, 2 or 3 carbon atoms and 0, 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —NR$^a$R$^a$, —C$_{1-6}$alkylNR$^a$R$^a$, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y$^2$ is —NR$^b$— or —O—.

In another embodiment, in conjunction with the method of treatment embodiments above and below, R$^4$ is

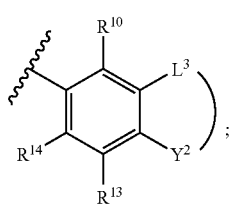

L$^3$ is a 2- or 3-atom, saturated or unsaturated, bridge containing 1, 2 or 3 carbon atoms and 0, 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —NR$^a$R$^a$, —C$_{1-6}$alkylNR$^a$R$^a$, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-6}$alkylNR$^a$R$^a$, —C$_{1-3}$alkylC(=O)OR$_a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y$^2$ is —NR$^b$— or —O—.

In another embodiment, in conjunction with the method of treatment embodiments above and below, R$^4$ is

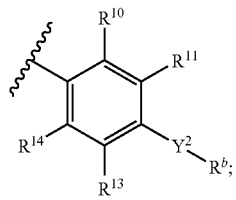

R$^b$ is H, C$_{1-6}$alkyl, —C(=O)C$_{1-6}$alkyl, C$_{1-6}$alkyl-O—R$^a$; and

Y$^2$ is —NR$^a$— or —O—.

In another embodiment, in conjunction with the method of treatment embodiments above and below, R$^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, OR$^a$, NR$^a$R$^a$, C$_{1-6}$alkyl and C$_{1-3}$haloalkyl; and saturated carbon atoms may be additionally substituted by =O.

In another embodiment, in conjunction with the method of treatment embodiments above and below, R$^4$ is

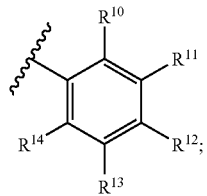

R$^{10}$ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;

R$^{11}$ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylR$^c$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; C$_{1-6}$alkylNR$^a$R$^a$;

R$^{12}$ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;

$R^{13}$ is independently, at each instance, H, $C_{1-9}$alkyl, —$C_{1-3}$alkylOR$^a$, $C_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; and $R^{14}$ is independently, at each instance, H, $C_{1-9}$alkyl, —$C_{1-3}$alkylOR$^a$, $C_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl; wherein one of $R^{10}$ and $R^{12}$ is not H.

In another embodiment, in conjunction with the method of treatment embodiments above, $R^4$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents selected from halo, $C_{1-4}$haloalkyl, —OR$^a$ and —NR$^a$R$^a$.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to compound description embodiments above—each seperately and alternatively.

Another aspect of the invention involves a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound having the structure:

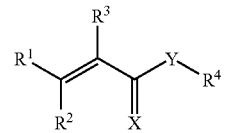

wherein:
X is O, S or NR$^m$;
n is independently, at each instance, 0, 1 or 2;
o is independently, at each instance, 0, 1, 2 or 3;
R$^m$ is independently at each instance H or R$^n$;
R$^n$ is independently at each instance $C_{1-8}$alkyl, phenyl or benzyl;
R$^q$ is independently in each instance H, $C_{1-4}$alkyl, $C_{1-4}$haloalkyl, halo, cyano, nitro, —C(=O)R$^n$, —C(=O)OR$^n$, —C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylNR$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R$^n$, —N(R$^m$)S(=O)$_2$NR$^m$R$^m$, —NR$^m$C$_{2-6}$alkylNR$^m$R$^m$ or —NR$^m$C$_{2-6}$alkylOR$^m$;
R$^s$ is R$^n$ substituted by 0, 1, 2 or 3 substituents independently selected from R$^q$;
R$^3$ is H or $C_{1-4}$alkyl;
R$^5$ is H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR$^m$R$^m$, —O—C$_{1-6}$alkylOR$^m$, —NR$^m$R$^m$, —NR$^m$—C$_{1-4}$haloalkyl, —NR$^m$—C$_{1-6}$alkylNR$^m$R$^m$, —NR$^m$—C$_{1-6}$alkylOR$^m$, or —(CH$_2$)$_n$R$^c$
R$^6$ is, independently at each instance, H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR$^m$R$^m$, —O—C$_{1-6}$alkylOR$^m$, —NR$^m$R$^m$, —NR$^m$—C$_{1-4}$haloalkyl, —NR$^m$—C$_{1-6}$alkylNR$^m$R$^m$ or —NR$^m$—C$_{1-6}$alkylOR$^m$;
R$^8$ is H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR$^m$R$^m$, —O—C$_{1-6}$alkylOR$^m$, —NR$^m$R$^m$, —NR$^m$—C$_{1-4}$haloalkyl, —NR$^m$—C$_{1-6}$alkylNR$^m$R$^m$ or —NR$^m$—C$_{1-6}$alkylOR$^m$; and (A) R$^1$ is

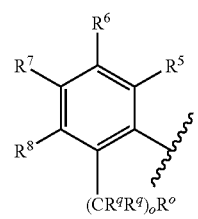

R$^2$ is H, —OR$^m$, halo, $C_{1-3}$haloalkyl or $C_{1-6}$alkyl;
R$^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R", —C(=O)OR", —C(=O)NR'''R''', —C(=NR''')NR'''R''', —OR''', —OC(=O)R''', —OC(=O)NR'''R''', —OC(=O)N(R''')S(=O)$_2$R", —OC$_{2-6}$alkylNR'''R''', —OC$_{2-6}$alkylOR''', —SR''', —S(=O)R", —S(=O)$_2$R", —S(=O)$_2$NR'''R''', —S(=O)$_2$N(R''')C(=O)R", —S(=O)$_2$N(R''')C(=O)OR", —S(=O)$_2$N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)$_2$R", —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R", —C(=O)OR", —C(=O)NR'''R''', —C(=NR''')NR'''R''', —OR''', —OC(=O)R''', —OC(=O)NR'''R''', —OC(=O)N(R''')S(=O)$_2$R", —OC$_{2-6}$alkylNR'''R''', —OC$_{2-6}$alkylOR''', —SR''', —S(=O)R", —S(=O)$_2$R", —S(=O)$_2$NR'''R''', —S(=O)$_2$N(R''')C(=O)R", —S(=O)$_2$N(R''')C(=O)OR", —S(=O)$_2$N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)$_2$R", —N(R''')S(=O)$_2$NR'''R''', —NR'''C$_{2-6}$alkylNR'''R''', —C(=O)R$^a$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; and the ring and bridge carbon atoms are substituted with 0, 1 or 2=O groups;

$R^7$ is $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR''';

$R^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from $R^p$;

$R^p$ is independently at each instance $C_{1-8}$alkyl, $C_{1-4}$haloalkyl, halo, cyano, nitro, —C(=O)R", —C(=O)OR", —C(=O)NR'''R''', —C(=NR''')NR'''R''', —OR''', —OC(=O)R''', —OC(=O)NR'''R''', —OC(=O)N(R''')S(=O)$_2$R", —OC$_{2-6}$alkylNR'''R''', —OC$_{2-6}$alkylOR''', —SR''', —S(=O)R", —S(=O)$_2$R", —S(=O)$_2$NR'''R''', —S(=O)$_2$N(R''')C(=O)R", —S(=O)$_2$N(R''')C(=O)OR", —S(=O)$_2$N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)$_2$R", —N(R''')S(=O)$_2$NR'''R''', —NR'''C$_{2-6}$alkylNR'''R''' or —NR'''C$_{2-6}$alkylOR'''; and Y is O or NH; or (B) $R^1$ is

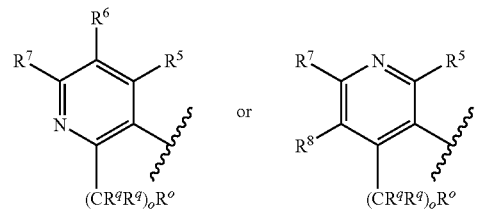

$R^2$ is H, —OR''', halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R", —C(=O)OR", —C(=O)NR'''R''', —C(=NR''')NR'''R''', —OR''', —OC(=O)R''', —OC(=O)NR'''R''', —OC(=O)N(R''')S(=O)$_2$R", —OC$_{2-6}$alkylNR'''R''', —OC$_{2-6}$alkylOR''', —SR''', —S(=O)R", —S(=O)$_2$R", —S(=O)$_2$NR'''R''', —S(=O)$_2$N(R''')C(=O)R", —S(=O)$_2$N(R''')C(=O)OR", —S(=O)$_2$N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)$_2$R", —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R", —C(=O)OR", —C(=O)NR'''R''', —C(=NR''')NR'''R''', —OR''', —OC(=O)R''', —OC(=O)NR'''R''', —OC(=O)N(R''')S(=O)$_2$R", —OC$_{2-6}$alkylNR'''R''', —OC$_{2-6}$alkylOR''', —SR''', —S(=O)R", —S(=O)$_2$R", —S(=O)$_2$NR'''R''', —S(=O)$_2$N(R''')C(=O)R", —S(=O)$_2$N(R''')C(=O)OR", —S(=O)$_2$N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)$_2$R", —N(R''')S(=O)$_2$NR'''R", —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$ alkylNR'''R$^s$, —NR'''C$_{2-6}$alkylOR$^s$ and —NR'''C$_{2-6}$alkylOR'''; and the ring and bridge carbon atoms are substituted with 0, 1 or 2=O groups;

R$^7$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; and Y is O or NH; or (C) R$^1$ is

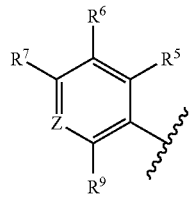

R$^2$ is H, —OR''', halo, C$_{1-3}$haloalkyl or C$_{1-6}$alkyl;

R$^4$ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from C$_{1-9}$alkyl, oxo, C$_{1-4}$haloalkyl, halo, nitro, cyano, —OR''', —S(=O)$_n$C$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', —C(=O)C$_{1-6}$alkyl, —OC(=O)C$_{1-6}$alkyl, —C(=O)NR''C$_{1-6}$alkyl, —NR'''C(=O)C$_{1-6}$alkyl —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)NR'''R''', —C(=NR''')NR'''R''', —OR''', —OC(=O)R'', —OC(=O) NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(Rm)S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; wherein R$^4$ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

R$^7$ is C$_{1-8}$alkyl, C$_{1-5}$haloalkyl, I or Br

R$^9$ is H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', or —(CH$_2$)$_n$R$^c$;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is CR$^8$ or N; or (D) R$^1$ is

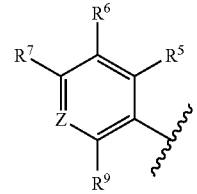

R$^2$ is C$_{1-6}$alkyl substituted by 1, 2 or 3 substituents selected from C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R)C(=O)NR'''R''', —NR'''R''', —N(R)C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; or R$^2$ is —(C(R$^q$)$_2$)$_o$phenyl, wherein the phenyl is substituted by 0, 1, 2 or 3 substituents independently selected from C$_{1-8}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C₂₋₆alkylNR'''R''', —NR'''C₂₋₆alkylOR''', —C(=O)Rˢ, —C(=O)ORˢ, —C(=O)NR'''Rˢ, —C(=NR''')NR'''Rˢ, —ORˢ, —OC(=O)Rˢ, —OC(=O)NR'''Rˢ, —OC(=O)N(R''')S(=O)₂Rˢ, —OC₂₋₆alkylNR'''Rˢ, —OC₂₋₆alkylORˢ, —S(=O)Rˢ, —S(=O)Rˢ, —S(=O)₂Rˢ, —S(=O)₂NR'''Rˢ, —S(=O)₂N(R''')C(=O)Rˢ, —S(=O)₂N(R''')C(=O)ORˢ, —S(=O)₂N(R''')C(=O)NR'''Rˢ, —NR'''Rˢ, —N(R''')C(=O)Rˢ, —N(R''')C(=O)ORˢ, —N(R''')C(=O)NR'''Rˢ, —N(R''')C(=NR''')NR'''Rˢ, —N(R''')S(=O)₂Rˢ, —N(R''')S(=O)₂NR'''Rˢ, —NR'''C₂₋₆alkylNR'''Rˢ, —NR'''C₂₋₆alkylORˢ and C₁₋₄alkyl substituted by 1 or 2 groups selected from C₁₋₂haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)₂R'', —OC₂₋₆alkylNR'''R''', —OC₂₋₆alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C₂₋₆alkylNR'''R''', —C(=O)Rˢ, —C(=O)ORˢ, —C(=O)NR'''Rˢ, —C(=NR''')NR'''Rˢ, —ORˢ, —OC(=O)Rˢ, —OC(=O)NR'''Rˢ, —OC(=O)N(R''')S(=O)₂Rˢ, —OC₂₋₆alkylNR'''Rˢ, —OC₂₋₆alkylORˢ, —SRˢ, —S(=O)Rˢ, —S(=O)₂Rˢ, —S(=O)₂NR'''Rˢ, —S(=O)₂N(R''')C(=O)Rˢ, —S(=O)₂N(R''')C(=O)ORˢ, —S(=O)₂N(R''')C(=O)NR'''Rˢ, —NR'''Rˢ, —N(R''')C(=O)Rˢ, —N(R''')C(=O)ORˢ, —N(R''')C(=O)NR'''Rˢ, —N(R''')C(=NR''')NR'''Rˢ, —N(R''')S(=O)₂Rˢ, —N(R''')S(=O)₂NR'''Rˢ, —NR'''C₂₋₆alkylNR'''Rˢ, —NR'''C₂₋₆alkylORˢ and —NR'''C₂₋₆alkylOR'''; or R² is —(C(Rᵍ)₂)ₒRʳ, wherein Rʳ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C₁₋₈alkyl, C₁₋₄haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)₂R'', —OC₂₋₆alkylNR'''R''', —OC₂₋₆alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C₂₋₆alkylNR'''R''', —NR'''C₂₋₆alkylOR''', —C(=O)Rˢ, —C(=O)ORˢ, —C(=O)NR'''Rˢ, —C(=NR''')NR'''Rˢ, —ORˢ, —OC(=O)Rˢ, —OC(=O)NR'''Rˢ, —OC(=O)N(R''')S(=O)₂Rˢ, —OC₂₋₆alkylNR'''Rˢ, —OC₂₋₆alkylORˢ, —SRˢ, —S(=O)Rˢ, —S(=O)₂Rˢ, —S(=O)₂NR'''Rˢ, —S(=O)₂N(R''')C(=O)Rˢ, —S(=O)₂N(R''')C(=O)ORˢ, —S(=O)₂N(R''')C(=O)NR'''Rˢ, —NR'''Rˢ, —N(R''')C(=O)Rˢ, —N(R''')C(=O)ORˢ, —N(R''')C(=O)NR'''Rˢ, —N(R''')C(=NR''')NR'''Rˢ, —N(R''')S(=O)₂Rˢ, —N(R''')S(=O)₂NR'''Rˢ, —NR'''C₂₋₆alkylNR'''Rˢ, —NR'''C₂₋₆alkylORˢ and C₁₋₄alkyl substituted by 1 or 2 groups selected from C₁₋₂haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)₂R'', —OC₂₋₆alkylNR'''R''', —OC₂₋₆alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C₂₋₆alkylNR'''R''', —C(=O)Rˢ, —C(=O)ORˢ, —C(=O)NR'''Rˢ, —C(=NR''')NR'''Rˢ, —ORˢ, —OC(=O)Rˢ, —OC(=O)NR'''Rˢ, —OC(=O)N(R''')S(=O)₂Rˢ, —OC₂₋₆alkylNR'''Rˢ, —OC₂₋₆alkylORˢ, —SRˢ, —S(=O)Rˢ, —S(=O)₂Rˢ, —S(=O)₂NR'''Rˢ, —S(=O)₂N(R''')C(=O)Rˢ, —S(=O)₂N(R''')C(=O)ORˢ, —S(=O)₂N(R''')C(=O)NR'''Rˢ, —NR'''Rˢ, —N(R''')C(=O)Rˢ, —N(R''')C(=O)ORˢ, —N(R''')C(=O)NR'''Rˢ, —N(R''')C(=NR''')NR'''Rˢ, —N(R''')S(=O)₂Rˢ, —N(R''')S(=O)₂NR'''Rˢ, —NR'''C₂₋₆alkylNR'''Rˢ, —NR'''C₂₋₆alkylORˢ and —NR'''C₂₋₆alkylOR''';

R⁴ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C₁₋₈alkyl, C₁₋₄haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)₂R'', —OC₂₋₆alkylNR'''R''', —OC₂₋₆alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C₂₋₆alkylNR'''R''', —NR'''C₂₋₆alkylOR''', —C(=O)Rˢ, —C(=O)ORˢ, —C(=O)NR'''Rˢ, —C(=NR''')NR'''Rˢ, —ORˢ, —OC(=O)Rˢ, —OC(=O)NR'''Rˢ, —OC(=O)N(R''')S(=O)₂Rˢ, —OC₂₋₆alkylNR'''Rˢ, —OC₂₋₆alkylORˢ, —SRˢ, —S(=O)Rˢ, —S(=O)₂Rˢ, —S(=O)₂NR'''Rˢ, —S(=O)₂N(R''')C(=O)Rˢ, —S(=O)₂N(R''')C(=O)ORˢ, —S(=O)₂N(R''')C(=O)NR'''Rˢ, —NR'''Rˢ, —N(R''')C(=O)Rˢ, —N(R''')C(=O)ORˢ, —N(R''')C(=O)NR'''Rˢ, —N(R''')C(=NR''')NR'''Rˢ, —N(R''')S(=O)₂Rˢ, —N(R''')S(=O)₂NR'''Rˢ, —NR'''C₂₋₆alkylNR'''Rˢ, —NR'''C₂₋₆alkylORˢ and C₁₋₄alkyl substituted by 1 or 2 groups selected from C₁₋₂haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)₂R'', —OC₂₋₆alkylNR'''R''', —OC₂₋₆alkylOR''', —SR''', —S(=O)R'', —S(=O)₂R'', —S(=O)₂NR'''R''', —S(=O)₂N(R''')C(=O)R'', —S(=O)₂N(R''')C(=O)OR'', —S(=O)₂N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)₂R'', —N(R''')S(=O)₂NR'''R''', —NR'''C₂₋₆alkylNR'''R''', —C(=O)Rˢ, —C(=O)ORˢ, —C(=O)NR'''Rˢ, —C(=NR''')NR'''Rˢ, —ORˢ, —OC(=O)Rˢ, —OC(=O)NR'''Rˢ, —OC(=O)N(R''')S(=O)₂Rˢ, —OC₂₋₆alkylNR'''Rˢ, —OC₂₋₆alkylORˢ, —SRˢ, —S(=O)Rˢ, —S(=O)₂Rˢ, —S(=O)₂NR'''Rˢ, —S(=O)₂N(R''')C(=O)Rˢ, —S(=O)₂N(R''')C(=O)ORˢ, —S(=O)₂N(R''')C(=O)NR'''Rˢ, —NR'''Rˢ, —N(R''')C(=O)Rˢ, —N(R''')C(=O)ORˢ, —N(R''')C(=O)NR'''Rˢ, —N(R''')C(=NR''')NR'''Rˢ, —N(R''')S(=O)₂Rˢ, —N(R''')S(=O)₂NR'''Rˢ, —NR'''C₂₋₆ alkylNR'''R$^s$, —NR'''C$_{2-6}$alkylOR$^s$ and —NR'''C$_{2-6}$alkylOR''', and the ring and bridge carbon atoms are substituted with 0, 1 or 2=O groups;

R$^7$ is C$_{2-8}$alkyl, C$_{1-5}$haloalkyl, I, Br;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is CR$^8$ or N; or (E) R$^1$ is

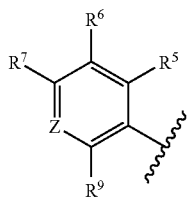

R$^2$ is H, —OR''', Cl, C$_{1-3}$haloalkyl or C$_{1-6}$alkyl;

R$^4$ is a saturated or unsaturated 5- or 6-membered ring containing 0, 1, 2 or 3 atoms selected from O, N and S, so long as the combination of O and S atoms is not greater than 1, wherein the ring is substituted by 0, 1, 2 or 3 substituents independently selected from C$_{1-8}$alkyl, C$_{1-4}$haloalkyl, halo, cyano, nitro, —C(=O)NR'''R''', —C(=NR''')NR'''R''', —OR'', —OC(=O)R'', —OC(=O)NR'''R''', —OC(=O)N(R''')S(=O)$_2$R'', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR)NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and C$_{1-4}$alkyl substituted by 1 or 2 groups selected from C$_{1-2}$haloalkyl, halo, cyano, nitro, —C(=O)R'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; wherein R$^4$ is not unsubstituted phenyl;

R$^7$ is C$_{2-6}$alkyl, C$_{1-5}$haloalkyl, I or Br;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_6$alkylNR'''R''' or —NR'''—C$_{1-6}$alkylOR''';

Y is NH; and

Z is CR$^8$ or N.

Another aspect of the invention involves a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound having the structure:

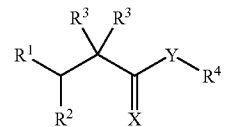

wherein:

X is O, S or NR''';

n is independently, at each instance, 0, 1 or 2;

o is independently, at each instance, 0, 1, 2 or 3;

R''' is independently at each instance H or R'';

R'' is independently at each instance C$_{1-8}$alkyl, phenyl or benzyl;

R$^q$ is independently in each instance H, C$_{1-4}$alkyl, C$_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR''';

R$^s$ is R'' substituted by 0, 1, 2 or 3 substituents independently selected from R$^q$;

R$^3$ is H or C$_{1-4}$alkyl;

R$^5$ is H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', or —(CH$_2$)$_n$R$^c$ $R^6$ is, independently at each instance, H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR''';

$R^8$ is H, $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR'''; and (A) $R^1$ is

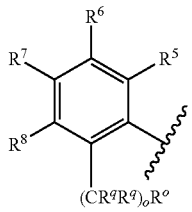

$R^2$ is H, —OR''', halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R''', —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; and the ring and bridge carbon atoms are substituted with 0, 1 or 2=O groups;

$R^7$ is $C_{1-9}$alkyl, $C_{1-4}$haloalkyl, halo, nitro, cyano, —$OC_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR''';

$R^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from $R^p$;

$R^p$ is independently at each instance $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; and Y is O or NH; or (B) $R^1$ is

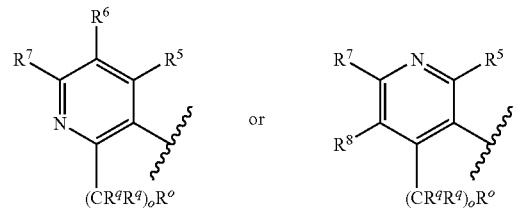

$R^2$ is H, —OR''', halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —NR$'''$C$_{2-6}$alkylOR$^s$ and C$_{1-4}$alkyl substituted by 1 or 2 groups selected from C$_{1-2}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —O—C$_{2-6}$alkylNR$'''$R$'''$, —OC$_{2-6}$alkylOR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —NR$'''$C$_{2-6}$alkylNR$'''$R$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —NR$'''$C$_{2-6}$alkylOR$^s$ and —NR$'''$C$_{2-6}$alkylOR$'''$; and the ring and bridge carbon atoms are substituted with 0, 1 or 2=O groups;

R$^7$ is C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$'''$R$'''$, —O—C$_{1-6}$alkylOR$'''$, —NR$'''$R$'''$, —NR$'''$—C$_{1-4}$haloalkyl, —NR$'''$—C$_{1-6}$alkylNR$'''$R$'''$ or —NR$'''$—C$_{1-6}$alkylOR$'''$;

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance C$_{1-8}$alkyl, C$_{1-4}$haloalkyl, halo, cyano, nitro, —C(=O)R$''$, —C(=O)OR$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$alkylOR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —NR$'''$C$_{2-6}$alkylNR$'''$R$'''$ or —NR$'''$C$_{2-6}$alkylOR$'''$; and Y is O or NH; or (C) R$^1$ is

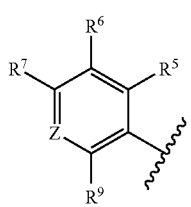

R$^2$ is H, —OR$'''$, halo, C$_{1-3}$haloalkyl or C$_{1-6}$alkyl;

R$^4$ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from C$_{1-9}$alkyl, oxo, C$_{1-4}$haloalkyl, halo, nitro, cyano, —OR$'''$, —S(=O)$_n$C$_{1-6}$alkyl, —O—C$_{1-4}$haloalkyl, —O—C$_{1-6}$alkylNR$'''$R$'''$, —O—C$_{1-6}$alkylOR$'''$, —NR$'''$R$'''$, —NR$'''$—C$_{1-4}$haloalkyl, —NR$'''$—C$_{1-6}$alkylNR$'''$R$'''$, —NR$'''$—C$_{1-6}$alkylOR$'''$, —C(=O)C$_{1-6}$alkyl, —OC(=O)C$_{1-6}$alkyl, —C(=O)NR$'''$C$_{1-6}$alkyl, —NR$'''$C(=O)C$_{1-6}$alkyl, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —NR$'''$C$_{2-6}$alkylOR$^s$ and C$_{1-4}$alkyl substituted by 1 or 2 groups selected from C$_{1-2}$haloalkyl, halo, cyano, nitro, —C(=O)R$''$, —C(=O)NR$'''$R$'''$, —C(=NR$'''$)NR$'''$R$'''$, —OR$'''$, —OC(=O)R$''$, —OC(=O)NR$'''$R$'''$, —OC(=O)N(R$'''$)S(=O)$_2$R$''$, —OC$_{2-6}$alkylNR$'''$R$'''$, —OC$_{2-6}$alkylOR$'''$, —SR$'''$, —S(=O)R$''$, —S(=O)$_2$R$''$, —S(=O)$_2$NR$'''$R$'''$, —S(=O)$_2$N(R$'''$)C(=O)R$''$, —S(=O)$_2$N(R$'''$)C(=O)OR$''$, —S(=O)$_2$N(R$'''$)C(=O)NR$'''$R$'''$, —N(R$'''$)C(=O)R$''$, —N(R$'''$)C(=O)OR$''$, —N(R$'''$)C(=O)NR$'''$R$'''$, —N(R$'''$)C(=NR$'''$)NR$'''$R$'''$, —N(R$'''$)S(=O)$_2$R$''$, —N(R$'''$)S(=O)$_2$NR$'''$R$'''$, —C(=O)R$^s$, —C(=O)OR$^s$, —C(=O)NR$'''$R$^s$, —C(=NR$'''$)NR$'''$R$^s$, —OR$^s$, —OC(=O)R$^s$, —OC(=O)NR$'''$R$^s$, —OC(=O)N(R$'''$)S(=O)$_2$R$^s$, —OC$_{2-6}$alkylNR$'''$R$^s$, —OC$_{2-6}$alkylOR$^s$, —SR$^s$, —S(=O)R$^s$, —S(=O)$_2$R$^s$, —S(=O)$_2$NR$'''$R$^s$, —S(=O)$_2$N(R$'''$)C(=O)R$^s$, —S(=O)$_2$N(R$'''$)C(=O)OR$^s$, —S(=O)$_2$N(R$'''$)C(=O)NR$'''$R$^s$, —NR$'''$R$^s$, —N(R$'''$)C(=O)R$^s$, —N(R$'''$)C(=O)OR$^s$, —N(R$'''$)C(=O)NR$'''$R$^s$, —N(R$'''$)C(=NR$'''$)NR$'''$R$^s$, —N(R$'''$)S(=O)$_2$R$^s$, —N(R$'''$)S(=O)$_2$NR$'''$R$^s$, —NR$'''$C$_{2-6}$alkylNR$'''$R$^s$, —NR$'''$C$_{2-6}$alkylOR$^s$ and —NR$'''$C$_{2-6}$alkylOR$'''$; wherein R$^4$ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

R$^7$ is C$_{1-8}$alkyl, C$_{1-5}$haloalkyl, I or Br

R$^9$ is H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$'''$R$'''$, —O—C$_{1-6}$alkylOR$'''$, —NR$'''$R$'''$, —NR$'''$—C$_{1-4}$haloalkyl, —NR$'''$—C$_{1-6}$alkylNR$'''$R$'''$, —NR$'''$—C$_{1-6}$alkylOR$'''$, or —(CH$_2$)$_n$R$^c$;

R$^9$ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$'''$R$'''$, —O—C$_{1-6}$alkylOR$'''$, —NR$'''$R$'''$, —NR$'''$—C$_{1-4}$haloalkyl, —NR$'''$—C$_{1-6}$alkylNR$'''$R$'''$ or —NR$'''$—C$_{1-6}$alkylOR$'''$;

Y is NH; and

Z is CR$^8$ or N; or (D) R¹ is

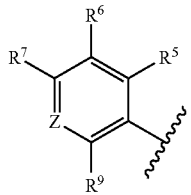

R² is C₁₋₆alkyl substituted by 1, 2 or 3 substituents selected from C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴ or —NR‴C₂₋₆alkylOR‴; or R² is —(C(R)₂)ₒphenyl, wherein the phenyl is substituted by 0, 1, 2 or 3 substituents independently selected from C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴Rˢ, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and —NR‴C₂₋₆alkylOR‴;

R² is —(C(Rᵍ)ₒRʳ, wherein Rʳ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and —NR‴C₂₋₆alkylOR‴;

R⁴ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NRʳRˢ, —C(=NR‴)

$NR'''R^s$, $-OR^s$, $-OC(=O)R^s$, $-OC(=O)NR'''R^s$, $-OC(=O)N(R''')S(=O)_2R^s$, $-OC_{2-6}$alkyl$NR'''R^s$, $-OC_{2-6}$alkyl$OR^s$, $-SR^s$, $-S(=O)R^s$, $-S(=O)_2R^s$, $-S(=O)_2NR'''R^s$, $-S(=O)_2N(R''')C(=O)R^s$, $-S(=O)_2N(R''')C(=O)OR^s$, $-S(=O)_2N(R''')C(=O)NR'''R^s$, $-NR'''R^s$, $-N(R''')C(=O)R^s$, $-N(R''')C(=O)OR^s$, $-N(R''')C(=O)NR'''R^s$, $-N(R''')C(=NR''')NR'''R^s$, $-N(R''')S(=O)_2R^s$, $-N(R''')S(=O)_2NR'''R^s$, $-NR'''C_{2-6}$alkyl$NR'''R^s$, $-NR'''C_{2-6}$alkyl$OR^s$ and $C_{1-4}$alkyl substituted by 1 or 2 groups selected from $C_{1-2}$haloalkyl, halo, cyano, nitro, $-C(=O)R''$, $-C(=O)OR''$, $-C(=O)NR'''R'''$, $-C(=NR''')NR'''R'''$, $-OR'''$, $-OC(=O)R''$, $-OC(=O)NR'''R'''$, $-OC(=O)N(R''')S(=O)_2R''$, $-OC_{2-6}$alkyl$NR'''R'''$, $-OC_{2-6}$alkyl$OR'''$, $-SR'''$, $-S(=O)R''$, $-S(=O)_2R''$, $-S(=O)_2NR'''R'''$, $-S(=O)_2N(R''')C(=O)R''$, $-S(=O)_2N(R''')C(=O)OR''$, $-S(=O)_2N(R''')C(=O)NR'''R'''$, $-NR'''R'''$, $-N(R''')C(=O)R''$, $-N(R''')C(=O)OR''$, $-N(R''')C(=O)NR'''R'''$, $-N(R''')C(=NR''')NR'''R'''$, $-N(R''')S(=O)_2R''$, $-N(R''')S(=O)_2NR'''R'''$, $-NR'''C_{2-6}$alkyl$NR'''R'''$, $-C(=O)R^s$, $-C(=O)OR^s$, $-C(=O)NR'''R^s$, $-C(=NR''')NR'''R^s$, $-OR^s$, $-OC(=O)R^s$, $-OC(=O)NR'''R^s$, $-OC(=O)N(R''')S(=O)_2R^s$, $-OC_{2-6}$alkyl$NR'''R^s$, $-OC_{2-6}$alkyl$OR^s$, $-SR^s$, $-S(=O)R^s$, $-S(=O)_2R^s$, $-S(=O)_2NR'''R^s$, $-S(=O)_2N(R''')C(=O)R^s$, $-S(=O)_2N(R''')C(=O)OR^s$, $-S(=O)_2N(R''')C(=O)NR'''R^s$, $-NR'''R^s$, $-N(R''')C(=O)R^s$, $-N(R''')C(=O)OR^s$, $-N(R''')C(=O)NR'''R^s$, $-N(R''')C(=NR''')NR'''R^s$, $-N(R''')S(=O)_2R^s$, $-N(R''')S(=O)_2NR'''R^s$, $-NR'''C_{2-6}$alkyl$NR'''R^s$, $-NR'''C_{2-6}$alkyl$OR^s$ and $-NR'''C_{2-6}$alkyl$OR'''$, and the ring and bridge carbon atoms are substituted with 0, 1 or 2 =O groups;

$R^7$ is $C_{2-8}$alkyl, $C_{1-5}$haloalkyl, I, Br;

$R^9$ is independently, at each instance, H, $C_{1-9}$alkyl, $C_{1-4}$haloalkyl, halo, nitro, cyano, $-OC_{1-6}$alkyl, $-O-C_{1-4}$haloalkyl, $-O-C_{1-6}$alkyl$NR'''R'''$, $-O-C_{1-6}$alkyl$OR'''$, $-NR'''R'''$, $-NR'''-C_{1-4}$haloalkyl, $-NR'''-C_{1-6}$alkyl$NR'''R'''$ or $-NR'''-C_{1-6}$alkyl$OR'''$;

Y is NH; and

Z is $CR^8$ or N; or (E) $R^1$ is

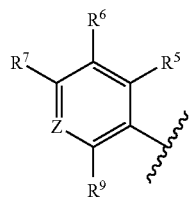

$R^2$ is H, $-OR'''$, Cl, $C_{1-3}$haloalkyl or $C_{1-6}$alkyl;

$R^4$ is a saturated or unsaturated 5- or 6-membered ring containing 0, 1, 2 or 3 atoms selected from O, N and S, so long as the combination of O and S atoms is not greater than 1, wherein the ring is substituted by 0, 1, 2 or 3 substituents independently selected from $C_{1-8}$alkyl, $C_{1-4}$haloalkyl, halo, cyano, nitro, $-C(=O)NR'''R'''$, $-C(=NR''')NR'''R'''$, $-OR''$, $-OC(=O)R''$, $-OC(=O)NR'''R'''$, $-OC(=O)N(R''')S(=O)_2R''$, $-OC_{2-6}$alkyl$OR'''$, $-SR'''$, $-S(=O)R''$, $-S(=O)_2R''$, $-S(=O)_2NR'''R'''$, $-S(=O)_2N(R''')C(=O)R''$, $-S(=O)_2N(R''')C(=O)OR''$, $-S(=O)_2N(R''')C(=O)NR'''R'''$, $-NR'''R'''$, $-N(R''')C(=O)R''$, $-N(R''')C(=O)OR''$, $-N(R''')C(=O)NR'''R'''$, $-N(R''')C(=NR''')NR'''R'''$, $-N(R''')S(=O)_2R''$, $-N(R''')S(=O)_2NR'''R'''$, $-NR'''C_{2-6}$alkyl$NR'''R'''$, $-NR'''C_{2-6}$alkyl$OR'''$, $-C(=O)R^s$, $-C(=O)OR^s$, $-C(=O)NR'''R^s$, $-C(=NR''')NR'''R^s$, $-OR^s$, $-OC(=O)R^s$, $-OC(=O)NR'''R^s$, $-OC(=O)N(R''')S(=O)_2R^s$, $-OC_{2-6}$alkyl$NR'''R^s$, $-OC_{2-6}$alkyl$OR^s$, $-SR^s$, $-S(=O)R^s$, $-S(=O)_2R^s$, $-S(=O)_2NR'''R^s$, $-S(=O)_2N(R''')C(=O)R^s$, $-S(=O)_2N(R''')C(=O)OR^s$, $-S(=O)_2N(R''')C(=O)NR'''R^s$, $-NR'''R^s$, $-N(R''')C(=O)R^s$, $-N(R''')C(=O)OR^s$, $-N(R''')C(=O)NR'''R^s$, $-N(R''')C(=NR''')NR'''R^s$, $-N(R''')S(=O)_2R^s$, $-N(R''')S(=O)_2NR'''R^s$, $-NR'''C_{2-6}$alkyl$NR'''R^s$, $-NR'''C_{2-6}$alkyl$OR^s$ and $-NR'''C_{2-6}$alkyl$OR'''$; wherein $R^4$ is not unsubstituted phenyl;

$R^7$ is $C_{2-6}$alkyl, $C_{1-5}$haloalkyl, I or Br;

$R^9$ is independently, at each instance, H, $C_{1-9}$alkyl, $C_{1-4}$haloalkyl, halo, nitro, cyano, $-OC_{1-6}$alkyl, $-O-C_{1-4}$haloalkyl, $-O-C_{1-6}$alkyl$NR'''R'''$, $-O-C_{1-6}$alkyl$OR'''$, $-NR'''R'''$, $-NR'''-C_{1-4}$haloalkyl, $-NR'''-C_{1-6}$alkyl$NR'''R'''$ or $-NR'''-C_{1-6}$alkyl$OR'''$;

Y is NH; and

Z is $CR^8$ or N.

Another aspect of the invention involves a pharmaceutical composition comprising a compound according to any of the above embodiments and a pharmaceutically-acceptable diluent or carrier.

Another aspect of the invention involves the use of any of the above compound embodiments as a medicament.

Another aspect of the invention relates to the use of a compound according the any one of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Another aspect of the invention relates to the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, wherein the medicament contains a compound having the structure:

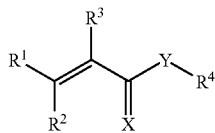

wherein:

X is O, S or NR''';

n is independently, at each instance, 0, 1 or 2;

o is independently, at each instance, 0, 1, 2 or 3;

$R'''$ is independently at each instance H or $R''$;

$R''$ is independently at each instance $C_{1-8}$alkyl, phenyl or benzyl;

$R^q$ is independently in each instance H, $C_{1-4}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR''';

$R^s$ is $R''$ substituted by 0, 1, 2 or 3 substituents independently selected from $R^q$;

$R^3$ is H or $C_{1-4}$alkyl;

$R^5$ is H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''', —NR'''—C$_{1-6}$alkylOR''', or —(CH$_2$)$_n$R$^c$ $R^6$ is, independently at each instance, H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

$R^8$ is H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR'''; and (A) $R^1$ is

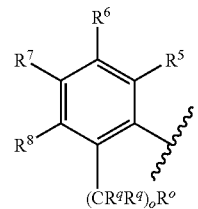

$R^2$ is H, —OR''', halo, $C_{1-3}$haloalkyl or $C_{1-6}$alkyl;

$R^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)R'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O) NR'''R$^s$, —NR'''R$^s$, —N(R''')C(=O)R$^s$, —N(R''')C(=O) OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; and the ring and bridge carbon atoms are substituted with 0, 1 or 2=O groups;

$R^7$ is $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR'''R''', —O—$C_{1-6}$alkylOR$^m$, —NR$^m$R$^m$, —NR$^m$—$C_{1-4}$haloalkyl, —NR$^m$—$C_{1-6}$alkylNR$^m$R$^m$ or —NR$^m$—$C_{1-6}$alkylOR$^m$;

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from R$^p$;

R$^p$ is independently at each instance $C_{1-8}$alkyl, $C_{1-4}$haloalkyl, halo, cyano, nitro, —C(=O)R$^n$, —C(=O)OR$^n$, —C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylNR$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R, —N(R$^m$)S(=O)$_2$NR$^m$R$^m$, —NR$^m$C$_{2-6}$alkylNR$^m$R$^m$ or —NR$^m$C$_{2-6}$alkylOR$^m$; and Y is O or NH; or (B) R$^1$ is

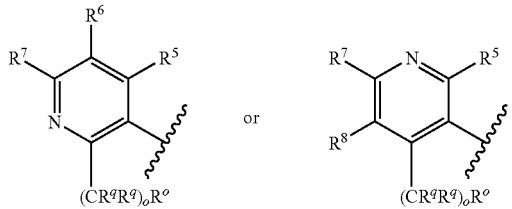

R$^2$ is H, —OR$^m$, halo, $C_{1-3}$haloalkyl or $C_{1-6}$alkyl;

R$^4$ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R$^n$, —C(=O)OR$^n$, —C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylNR$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R$^n$, —N(R$^m$)S(=O)$_2$NR$^m$R$^m$, —NR$^m$C$_{2-6}$alkylNR$^m$R$^m$, —NR$^m$C$_{2-6}$alkylOR$^m$, —C(=O)R$^s$, —C(=O)OR$^s$, —C(=O)NR$^m$R$^s$, —C(=NR$^m$)NR$^m$R$^s$, —OR$^s$, —OC(=O)R$^s$, —OC(=O)NR$^m$R$^s$, —OC(=O)N(R$^m$)S(=O)$_2$R$^s$, —OC$_{2-6}$alkylNR$^m$R$^s$, —OC$_{2-6}$alkylOR$^s$, —SR$^s$, —S(=O)R$^s$, —S(=O)$_2$R$^s$, —S(=O)$_2$NR$^m$R$^s$, —S(=O)$_2$N(R$^m$)C(=O)R$^s$, —S(=O)$_2$N(R$^m$)C(=O)OR$^s$, —S(=O)$_2$N(R$^m$)C(=O)NR$^m$R$^s$, —NR$^m$R$^s$, —N(R$^m$)C(=O)R$^s$, —N(R$^m$)C(=O)OR$^s$, —N(R$^m$)C(=O)NR$^m$R$^s$, —N(R$^m$)C(=NR$^m$)NR$^m$R$^s$, —N(R$^m$)S(=O)$_2$R$^s$, —N(R$^m$)S(=O)$_2$NR$^m$R$^s$, —NR$^m$C$_{2-6}$alkylNR$^m$R$^s$, —NR$^m$C$_{2-6}$alkylOR$^s$ and $C_{1-4}$alkyl substituted by 1 or 2 groups selected from $C_{1-2}$haloalkyl, halo, cyano, nitro, —C(=O)R$^n$, —C(=O)OR$^n$, —C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylN-R$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R$^n$, —N(R$^m$)S(=O)$_2$NR$^m$R$^m$, —NR$^m$C$_{2-6}$alkylNR$^m$R$^m$, —C(=O)R$^s$, —C(=O)OR$^s$, —C(=O)NR$^m$R$^s$, —C(=NR$^m$)NR$^m$R$^s$, —OR$^s$, —OC(=O)R$^s$, —OC(=O)NR$^m$R$^s$, —OC(=O)N(R$^m$)S(=O)$_2$R$^s$, —OC$_{2-6}$alkylNR$^m$R$^s$, —OC$_{2-6}$alkylOR$^s$, —SR$^s$, —S(=O)R$^s$, —S(=O)$_2$R$^s$, —S(=O)$_2$NR$^m$R$^s$, —S(=O)$_2$N(R$^m$)C(=O)R$^s$, —S(=O)$_2$N(R$^m$)C(=O)OR$^s$, —S(=O)$_2$N(R$^m$)C(=O)NR$^m$R$^s$, —NR$^m$R$^s$, —N(R$^m$)C(=O)R$^s$, —N(R$^m$)C(=O)OR$^s$, —N(R$^m$)C(=O)NR$^m$R$^s$, —N(R$^m$)C(=NR$^m$)NR$^m$R$^s$, —N(R$^m$)S(=O)$_2$R$^s$, —N(R$^m$)S(=O)$_2$NR$^m$R$^s$, —NR$^m$C$_{2-6}$R$^m$C$_{2-6}$alkylOR$^s$ and —NR$^m$C$_{2-6}$alkylOR$^m$; and the ring and bridge carbon atoms are substituted with 0, 1 or 2=O groups;

R$^7$ is $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR$^m$R$^m$, —O—$C_{1-6}$alkylOR$^m$, —NR$^m$R$^m$, —NR$^m$—$C_{1-4}$haloalkyl, —NR$^m$—$C_{1-6}$alkylNR$^m$R$^m$ or —NR$^m$—$C_{1-6}$alkylOR$^m$;

R$^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups,- wherein the ring is substituted by 0, 1, 2 or 3 substituents independently selected from R$^p$;

R$^p$ is independently at each instance $C_{1-8}$alkyl, $C_{1-4}$haloalkyl, halo, cyano, nitro, —C(=O)R$^n$, —C(=O)=OR$^n$, C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylNR$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R$^n$, —N(R$^m$)S(=O)$_2$NR$^m$R$^m$, —NR$^m$C$_{2-6}$alkylNR$^m$R$^m$ or —NR$^m$C$_{2-6}$alkylOR$^m$; and Y is O or NH; or (C) R$^1$ is

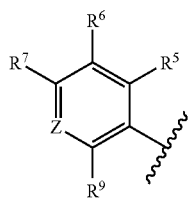

R$^2$ is H, —OR$^m$, halo, $C_{1-3}$haloalkyl or $C_{1-6}$alkyl;

R$^4$ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from $C_{1-9}$alkyl, oxo, $C_{1-4}$haloalkyl, halo, nitro, cyano, —OR$^m$, —S(=O)$_n$$C_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''', —NR'''—$C_{1-6}$alkylOR''', —C(=O)$C_{1-6}$alkyl, —OC(=O)$C_{1-6}$alkyl, —C(=O)NR'''$C_{1-6}$alkyl, —NR'''C(=O)$C_{1-6}$alkyl —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; wherein R$^4$ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

R$^7$ is $C_{1-8}$alkyl, $C_{1-5}$haloalkyl, I or Br

R$^9$ is H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''', —NR'''—$C_{1-6}$alkylOR''', or —(CH$_2$)$_n$R$^c$;

R$^9$ is independently, at each instance, H, $C_{1-9}$alkyl, $C_{1-4}$haloalkyl, halo, nitro, cyano, —OC$_{1-6}$alkyl, —O—$C_{1-4}$haloalkyl, —O—$C_{1-6}$alkylNR'''R''', —O—$C_{1-6}$alkylOR''', —NR'''R''', —NR'''—$C_{1-4}$haloalkyl, —NR'''—$C_{1-6}$alkylNR'''R''' or —NR'''—$C_{1-6}$alkylOR''';

Y is NH; and

Z is CR$^8$ or N; or (D) R$^1$ is

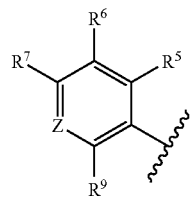

R$^2$ is $C_{1-6}$alkyl substituted by 1, 2 or 3 substituents selected from $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)NR'''S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''' or —NR'''C$_{2-6}$alkylOR'''; or R$^2$ is —(C(R$^q$)$_2$)$_o$phenyl, wherein the phenyl is substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —NR'''C$_{2-6}$alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and $C_{1-4}$alkyl substituted by 1 or 2 groups selected from $C_{1-2}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C(=O)R'', —N(R''')C(=O)OR'', —N(R''')C(=O)NR'''R''', —N(R''')C(=NR''')NR'''R''', —N(R''')S(=O)$_2$R'', —N(R''')S(=O)$_2$NR'''R''', —NR'''C$_{2-6}$alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)$_2$R$^s$, —OC$_{2-6}$alkylNR'''R$^s$, —OC$_{2-6}$alkylOR$^s$, —SR$^s$, —S(=O)R$^s$, —S(=O)$_2$R$^s$, —S(=O)$_2$NR'''R$^s$, —S(=O)$_2$N(R''')C(=O)R$^s$, —S(=O)$_2$N(R''')C(=O)OR$^s$, —S(=O)$_2$N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)$_2$R$^s$, —N(R''')S(=O)$_2$NR'''R$^s$, —NR'''C$_{2-6}$alkylNR'''R$^s$, —NR'''C$_{2-6}$alkylOR$^s$ and —NR'''C$_{2-6}$alkylOR'''; or R$^2$ is —(C(R$^q$)$_2$)$_o$R$^r$, wherein R$^r$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from $C_{1-8}$alkyl, $C_{1-4}$haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)$_2$R'', —OC$_{2-6}$alkylNR'''R''', —OC$_{2-6}$alkylOR''', —SR''', —S(=O)R'', —S(=O)$_2$R'', —S(=O)$_2$NR'''R''', —S(=O)$_2$N(R''')C(=O)R'', —S(=O)$_2$N(R''')C(=O)OR'', —S(=O)$_2$N(R''')C(=O)NR'''R''', —NR'''R''', —N(R''')C (=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and —NR‴C₂₋₆alkylOR‴;

R⁴ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and —NR‴C₂₋₆alkylOR‴, and the ring and bridge carbon atoms are substituted with 0, 1 or 2=O groups;

R⁷ is C₂₋₈alkyl, C₁₋₅haloalkyl, I, Br;

R⁹ is independently, at each instance, H, C₁₋₉alkyl, C₁₋₄haloalkyl, halo, nitro, cyano, —OC₁₋₆alkyl, —O—C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴ or —NR‴—C₁₋₆alkylOR‴;

Y is NH; and

Z is CR⁸ or N; or (E) R¹ is

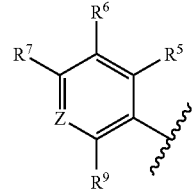

R² is H, —OR‴, Cl, C₁₋₃haloalkyl or C₁₋₆alkyl;

R⁴ is a saturated or unsaturated 5- or 6-membered ring containing 0, 1, 2 or 3 atoms selected from O, N and S, so long as the combination of O and S atoms is not greater than 1, wherein the ring is substituted by 0, 1, 2 or 3 substituents independently selected from C₁₋₈alkyl, C₁₋₄haloalkyl, halo, cyano, nitro, —C(=O)NR‴R‴, —C(=NR‴)NR‴R‴, —OR″, —OC(=O)R″, —OC(=O)NR‴R‴, —OC(=O)N(R‴)S(=O)₂R″, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R", —S(=O)₂NR'''R''', —S(=O)₂N(R''')C(=O)R", —S(=O)₂N(R''')C(=O)OR", —S(=O)₂N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)₂R", —N(R''')S(=O)₂NR'''R''', —NR'''C₂₋₆alkylNR'''R''', —C(=O)R^s, —C(=O)OR^s, —C(=O)NR'''R^s, —C(=NR''')NR'''R^s, —OR^s, —OC(=O)R^s, —OC(=O)NR'''R^s, —OC(=O)N(R''')S(=O)₂R^s, —OC₂₋₆alkylNR'''R^s, —OC₂₋₆alkylOR^s, —SR^s, —S(=O)R^s, —S(=O)₂R^s, —S(=O)₂NR'''R^s, —S(=O)₂N(R''')C(=O)R^s, —S(=O)₂N(R''')C(=O)OR^s, —S(=O)₂N(R''')C(=O)NR'''R^s, —NR'''R^s, —N(R''')C(=O)R^s, —N(R''')C(=O)OR^s, —N(R''')C(=O)NR'''R^s, —N(R''')C(=NR''')NR'''R^s, —N(R''')S(=O)₂R^s, —N(R''')S(=O)₂NR'''R^s, —NR'''C₂₋₆alkylNR'''R^s, —NR'''C₂₋₆alkylOR^s and —NR'''C₂₋₆alkylOR'''; wherein R⁴ is not unsubstituted phenyl;

R⁷ is C₂₋₆alkyl, C₁₋₅haloalkyl, I or Br;

R⁹ is independently, at each instance, H, C₁₋₉alkyl, C₁₋₄haloalkyl, halo, nitro, cyano, —OC₁₋₆alkyl, —O—C₁₋₄haloalkyl, —O—C₁₋₆alkylNR'''R''', —O—C₁₋₆alkylOR''', —NR'''R''', —NR'''—C₁₋₄haloalkyl, —NR'''—C₁₋₆alkylNR'''R''' or —NR'''—C₁₋₆alkylOR''';

Y is NH; and

Z is CR⁸ or N.

Another aspect of the invention relates to the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, wherein the medicament contains a compound having the structure:

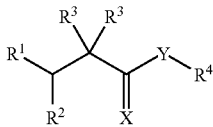

wherein:

X is O, S or NR''';

n is independently, at each instance, 0, 1 or 2;

o is independently, at each instance, 0, 1, 2 or 3;

R''' is independently at each instance H or R";

R" is independently at each instance C₁₋₈alkyl, phenyl or benzyl;

R^q is independently in each instance H, C₁₋₄alkyl, C₁₋₄haloalkyl, halo, cyano, nitro, —C(=O)R", —C(=O)OR", —C(=O)NR'''R''', —C(=NR''')NR'''R''', —OR''', —OC(=O)R", —OC(=O)NR'''R''', —OC(=O)N(R''')S(=O)₂R", —OC₂₋₆alkylNR'''R''', —OC₂₋₆alkylOR''', —SR''', —S(=O)R", —S(=O)₂R", —S(=O)₂NR'''R''', —S(=O)₂N(R''')C(=O)R", —S(=O)₂N(R''')C(=O)OR", —S(=O)₂N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)₂R", —N(R''')S(=O)₂NR'''R''', —NR'''C₂₋₆alkylNR'''R''' or —NR'''C₂₋₆alkylOR''';

R^s is R" substituted by 0, 1, 2 or 3 substituents independently selected from R^q;

R³ is H or C₁₋₄alkyl;

R⁵ is H, C₁₋₉alkyl, C₁₋₄haloalkyl, halo, nitro, cyano, —OC₁₋₆alkyl, —O—C₁₋₄haloalkyl, —O—C₁₋₆alkylNR'''R''', —O—C₁₋₆alkylOR''', —NR'''R''', —NR'''—C₁₋₄haloalkyl, —NR'''—C₁₋₆alkylNR'''R''', —NR'''—C₁₋₆alkylOR''', or —(CH₂)ₙR^c;

R⁶ is, independently at each instance, H, C₁₋₉alkyl, C₁₋₄haloalkyl, halo, nitro, cyano, —OC₁₋₆alkyl, —O—C₁₋₄haloalkyl, —O—C₁₋₆alkylNR'''R''', —O—C₁₋₆alkylOR''', —NR'''R''', —NR'''—C₁₋₄haloalkyl, —NR'''—C₁₋₆alkylNR'''R''' or —NR'''—C₁₋₆alkylOR''';

R⁸ is H, C₁₋₉alkyl, C₁₋₄haloalkyl, halo, nitro, cyano, —OC₁₋₆alkyl, —O—C₁₋₄haloalkyl, —O—C₁₋₆alkylNR'''R''', —O—C₁₋₆alkylOR''', —NR'''R''', —NR'''—C₁₋₄haloalkyl, —NR'''—C₁₋₆alkylNR'''R''' or —NR'''—C₁₋₆alkylOR'''; and (A) R¹ is

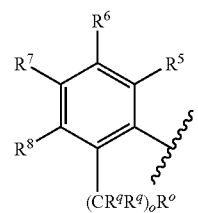

R² is H, —OR''', halo, C₁₋₃haloalkyl or C₁₋₆alkyl;

R⁴ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C₁₋₈alkyl, C₁₋₄haloalkyl, halo, cyano, nitro, —C(=O)R", —C(=O)OR", —C(=O)NR'''R''', —C(=NR''')NR'''R''', —OR''', —OC(=O)R", —OC(=O)NR'''R''', —OC(=O)N(R''')S(=O)₂R", —OC₂₋₆alkylNR'''R''', —OC₂₋₆alkylOR''', —SR''', —S(=O)R", —S(=O)₂R", —S(=O)₂NR'''R''', —S(=O)₂N(R''')C(=O)R", —S(=O)₂N(R''')C(=O)OR", —S(=O)₂N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)₂R", —N(R''')S(=O)₂NR'''R''', —NR'''C₂₋₆alkylNR'''R''', —NR'''C₂₋₆alkylOR''', —C(=O)R^s, —C(=O)OR^s, —C(=O)NR'''R^s, —C(=NR''')NR'''R^s, —OR^s, —OC(=O)R^s, —OC(=O)NR'''R^s, —OC(=O)N(R''')S(=O)₂R^s, —OC₂₋₆alkylNR'''R^s, —OC₂₋₆alkylOR^s, —SR^s, —S(=O)R^s, —S(=O)₂R^s, —S(=O)₂NR'''R^s, —S(=O)₂N(R''')C(=O)R^s, —S(=O)₂N(R''')C(=O)OR^s, —S(=O)₂N(R''')C(=O)NR'''R^s, —NR'''R^s, —N(R''')C(=O)R^s, —N(R''')C(=O)OR^s, —N(R''')C(=O)NR'''R^s, —N(R''')C(=NR''')NR'''R^s, —N(R''')S(=O)₂R^s, —N(R''')S(=O)₂NR'''R^s, —NR'''C₂₋₆alkylNR'''R^s, —NR'''C₂₋₆alkylOR^s and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —O—C₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and —NR‴C₂₋₆alkylOR‴; and the ring and bridge carbon atoms are substituted with 0, 1 or 2=O groups;

R⁷ is C₁₋₉alkyl, C₁₋₄haloalkyl, halo, nitro, cyano, —OC₁₋₆alkyl, —O—C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴ or —NR‴—C₁₋₆alkylOR‴;

Rᵒ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from Rᵖ;

Rᵖ is independently at each instance C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴ or —NR‴C₂₋₆alkylOR‴; and Y is O or NH; or (B) R¹ is

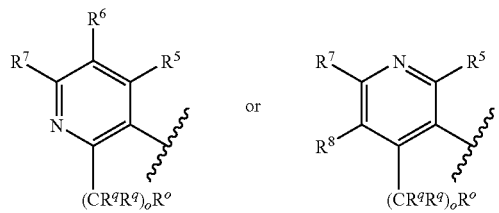

R² is H, —OR‴, halo, C₁₋₃haloalkyl or C₁₋₆alkyl;

R⁴ is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —NR‴C₂₋₆alkylOR‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and C₁₋₄alkyl substituted by 1 or 2 groups selected from C₁₋₂haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴, —C(=O)Rˢ, —C(=O)ORˢ, —C(=O)NR‴Rˢ, —C(=NR‴)NR‴Rˢ, —ORˢ, —OC(=O)Rˢ, —OC(=O)NR‴Rˢ, —OC(=O)N(R‴)S(=O)₂Rˢ, —OC₂₋₆alkylNR‴Rˢ, —OC₂₋₆alkylORˢ, —SRˢ, —S(=O)Rˢ, —S(=O)₂Rˢ, —S(=O)₂NR‴Rˢ, —S(=O)₂N(R‴)C(=O)Rˢ, —S(=O)₂N(R‴)C(=O)ORˢ, —S(=O)₂N(R‴)C(=O)NR‴Rˢ, —NR‴Rˢ, —N(R‴)C(=O)Rˢ, —N(R‴)C(=O)ORˢ, —N(R‴)C(=O)NR‴Rˢ, —N(R‴)C(=NR‴)NR‴Rˢ, —N(R‴)S(=O)₂Rˢ, —N(R‴)S(=O)₂NR‴Rˢ, —NR‴C₂₋₆alkylNR‴Rˢ, —NR‴C₂₋₆alkylORˢ and —NR‴C₂₋₆alkylOR‴; and the ring and bridge carbon atoms are substituted with 0, 1 or 2=O groups;

R⁷ is C₁₋₉alkyl, C₁₋₄haloalkyl, halo, nitro, cyano, —OC₁₋₆alkyl, —O—C₁₋₄haloalkyl, —O—C₁₋₆alkylNR‴R‴, —O—C₁₋₆alkylOR‴, —NR‴R‴, —NR‴—C₁₋₄haloalkyl, —NR‴—C₁₋₆alkylNR‴R‴ or —NR‴—C₁₋₆alkylOR‴;

Rᵒ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from Rᵖ;

Rᵖ is independently at each instance C₁₋₈alkyl, C₁₋₄haloalkyl, halo, cyano, nitro, —C(=O)R″, —C(=O)OR″, —C(=O)NR‴R‴, —C(=NR‴)NR‴R‴, —OR‴, —OC(=O)R″, —OC(=O)NR‴R‴, —OC(=O)N(R‴)S(=O)₂R″, —OC₂₋₆alkylNR‴R‴, —OC₂₋₆alkylOR‴, —SR‴, —S(=O)R″, —S(=O)₂R″, —S(=O)₂NR‴R‴, —S(=O)₂N(R‴)C(=O)R″, —S(=O)₂N(R‴)C(=O)OR″, —S(=O)₂N(R‴)C(=O)NR‴R‴, —NR‴R‴, —N(R‴)C(=O)R″, —N(R‴)C(=O)OR″, —N(R‴)C(=O)NR‴R‴, —N(R‴)C(=NR‴)NR‴R‴, —N(R‴)S(=O)₂R″, —N(R‴)S(=O)₂NR‴R‴, —NR‴C₂₋₆alkylNR‴R‴ or —NR‴C₂₋₆alkylOR‴; and Y is O or NH; or (C) R¹ is

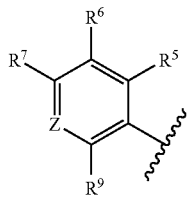

R² is H, —ORᵐ, halo, C₁₋₃haloalkyl or C₁₋₆alkyl;

R⁴ is a saturated, partially-saturated or unsaturated 8-, 9-, 10 or 11-membered bicyclic heterocycle containing 1, 2, 3, 4 or 5 atoms selected from O, N and S, so long as the combination of O and S atoms is not greater than 2, but excluding quinolin-6-yl, 4,5,6,7-tetrahydro-benzo[b]thiophen-2-yl, benzothiazol-2-yl, 2,3-dihydro-benzo[1,4]dioxin-6-yl, wherein the heterocycle is substituted by 0, 1, 2 or 3 substituents independently selected from C₁₋₉alkyl, oxo, C₁₋₄haloalkyl, halo, nitro, cyano, —ORᵐ, —S(═O)ₙC₁₋₆alkyl, —O—C₁₋₄haloalkyl, —O—C₁₋₆alkylNRᵐRᵐ, —O—C₁₋₆alkylORᵐ, —NRᵐRᵐ, —NRᵐ—C₁₋₄haloalkyl, —NRᵐ—C₁₋₆alkylNRᵐRᵐ, —NRᵐ—C₁₋₆alkylORᵐ, —C(═O)C₁₋₆alkyl, —OC(═O)C₁₋₆alkyl, —C(═O)NRᵐC₁₋₆alkyl, —NRᵐC(═O)C₁₋₆alkyl —C(═O)Rˢ, —C(═O)ORˢ, —C(═O)NRᵐRˢ, —C(═NRᵐ)NRᵐRˢ, —ORˢ, —OC(═O)Rˢ, —OC(═O)NRᵐRˢ, —OC(═O)N(Rᵐ)S(═O)₂Rˢ, —OC₂₋₆alkylNRᵐRˢ, —OC₂₋₆alkylORˢ, —SRˢ, —S(═O)Rˢ, —S(═O)₂Rˢ, —S(═O)₂NRᵐRˢ, —S(═O)₂N(Rᵐ)C(═O)Rˢ, —S(═O)₂N(Rᵐ)C(═O)ORˢ, —S(═O)₂N(Rᵐ)C(═O)NRᵐRˢ, —NRᵐRˢ, —N(Rᵐ)C(═O)Rˢ, —N(Rᵐ)C(═O)ORˢ, —N(Rᵐ)C(═O)NRᵐRˢ, —N(Rᵐ)C(═NRᵐ)NRᵐRˢ, —N(Rᵐ)S(═O)₂Rˢ, —N(Rᵐ)S(═O)₂NRᵐRˢ, —NRᵐC₂₋₆alkylNRᵐRᵐ, —NRᵐC₂₋₆alkylORˢ and C₁₋₄alkyl substituted by 1 or 2 groups selected from C₁₋₂haloalkyl, halo, cyano, nitro, —C(═O)Rⁿ, —C(═O)NRᵐRᵐ, —C(═NRᵐ)NRᵐRᵐ, —ORᵐ, —OC(═O)Rⁿ, —OC(═O)NRᵐRᵐ, —OC(═O)N(Rᵐ)S(═O)₂Rⁿ, —OC₂₋₆alkylNRᵐRᵐ, —OC₂₋₆alkylORᵐ, —SRᵐ, —S(═O)Rⁿ, —S(═O)₂Rⁿ, —S(═O)₂NRᵐRᵐ, —S(═O)₂N(Rᵐ)C(═O)Rⁿ, —S(═O)₂N(Rᵐ)C(═O)ORⁿ, —S(═O)₂N(Rᵐ)C(═O)NRᵐRᵐ, —N(Rᵐ)C(═O)Rⁿ, —N(Rᵐ)C(═O)ORⁿ, —N(Rᵐ)C(═O)NRᵐRᵐ, —N(Rᵐ)C(═NRᵐ)NRᵐRᵐ, —N(Rᵐ)S(═O)₂Rⁿ, —N(Rᵐ)S(═O)₂NRᵐRᵐ, —C(═O)Rˢ, —C(═O)ORˢ, —C(═O)NRᵐRˢ, —C(═NRᵐ)NRᵐRˢ, —ORˢ, —OC(═O)Rˢ, —OC(═O)NRᵐRˢ, —OC(═O)N(Rᵐ)S(═O)₂Rˢ, —OC₂₋₆alkylNRᵐRˢ, —OC₂₋₆alkylORˢ, —SRˢ, —S(═O)Rˢ, —S(═O)₂Rˢ, —S(═O)₂NRᵐRˢ, —S(═O)₂N(Rᵐ)C(═O)Rˢ, —S(═O)₂N(Rᵐ)C(═O)ORˢ, —S(═O)₂N(Rᵐ)C(═O)NRᵐRˢ, —NRᵐRˢ, —N(Rᵐ)C(═O)Rˢ, —N(Rᵐ)C(═O)ORˢ, —N(Rᵐ)C(═O)NRᵐRˢ, —N(Rᵐ)C(═NRᵐ)NRᵐRˢ, —N(Rᵐ)S(═O)₂Rˢ, —N(Rᵐ)S(═O)₂NRᵐRˢ, —NRᵐC₂₋₆alkylNRᵐRˢ, —NRᵐC₂₋₆alkylORˢ and —NRᵐC₂₋₆alkylORᵐ; wherein R⁴ is not 2-aminocarbonylmethyl-2,3-dihydro-benzo[1,4]dioxin-8-yl, 2-cyanomethyl-2,3-dihydro-benzo[1,4]dioxin-8-yl, quinolin-3-yl, 3H-quinazolin-4-on-3-yl, benzo[1,3]dioxol-5-yl, 3,3-dimethyl-1,3-dihydro-indol-2-on-6-yl or 4,4-dimethyl-3,4-dihydro-1H-quinolin-2-on-7-yl;

R⁷ is C₁₋₈alkyl, C₁₋₅haloalkyl, I or Br

R⁹ is H, C₁₋₉alkyl, C₁₋₄haloalkyl, halo, nitro, cyano, —OC₁₋₆alkyl, —O—C₁₋₄haloalkyl, —O—C₁₋₆alkylNRᵐRᵐ, —O—C₁₋₆alkylORᵐ, —NRᵐRᵐ, —NRᵐ—C₁₋₄haloalkyl, —NRᵐ—C₁₋₆alkylNRᵐRᵐ, —NRᵐ—C₁₋₆alkylORᵐ, or —(CH₂)ₙRᶜ;

R⁹ is independently, at each instance, H, C₁₋₉alkyl, C₁₋₄haloalkyl, halo, nitro, cyano, —OC₁₋₆alkyl, —O—C₁₋₄haloalkyl, —O—C₁₋₆alkylNRᵐRᵐ, —O—C₁₋₆alkylORᵐ, —NRᵐRᵐ, —NRᵐ—C₁₋₄haloalkyl, —NRᵐ—C₁₋₆alkylNRᵐRᵐ or —NRᵐ—C₁₋₆alkylORᵐ;

Y is NH; and

Z is CR⁸ or N; or (D) R¹ is

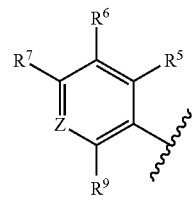

R² is C₁₋₆alkyl substituted by 1, 2 or 3 substituents selected from C₁₋₄haloalkyl, halo, cyano, nitro, —C(═O)Rⁿ, —C(═O)ORⁿ, —C(═O)NRᵐRᵐ, —C(═NRᵐ)NRᵐRᵐ, —ORᵐ, —OC(═O)Rⁿ, —OC(═O)NRᵐRᵐ, —OC(═O)N(Rᵐ)S(═O)₂Rⁿ, —OC₂₋₆alkylNRᵐRᵐ, —OC₂₋₆alkylORᵐ, —SRᵐ, —S(═O)Rⁿ, —S(═O)₂Rⁿ, —S(═O)₂NRᵐRᵐ, —S(═O)₂N(Rᵐ)C(═O)Rⁿ, —S(═O)₂N(Rᵐ)C(═O)ORⁿ, —S(═O)₂N(Rᵐ)C(═O)NRᵐRᵐ, —NRᵐRᵐ, —N(Rᵐ)C(═O)Rⁿ, —N(Rᵐ)C(═O)ORⁿ, —N(Rᵐ)C(═O)NRᵐRᵐ, —N(Rᵐ)C(═NRᵐ)NRᵐRᵐ, —N(Rᵐ)S(═O)₂Rⁿ, —N(Rᵐ)S(═O)₂NRᵐRᵐ, —NRᵐC₂₋₆alkylNRᵐRᵐ or —NRᵐC₂₋₆alkylORᵐ; or R² is —(C(Rᵠ)₂)ₒphenyl, wherein the phenyl is substituted by 0, 1, 2 or 3 substituents independently selected from C₁₋₈alkyl, C₁₋₄haloalkyl, halo, cyano, nitro, —C(═O)Rⁿ, —C(═O)ORⁿ, —C(═O)NRᵐRᵐ, —C(═NRᵐ)NRᵐRᵐ, —ORᵐ, —OC(═O)Rⁿ, —OC(═O)NRᵐRᵐ, —OC(═O)N(Rᵐ)S(═O)₂Rⁿ, —OC₂₋₆alkylNRᵐRᵐ, —OC₂₋₆alkylORᵐ, —SRᵐ, —S(═O)Rⁿ, —S(═O)₂Rⁿ, —S(═O)₂NRᵐRᵐ, —S(═O)₂N(Rᵐ)C(═O)Rⁿ, —S(═O)₂N(Rᵐ)C(═O)ORⁿ, —S(═O)₂N(Rᵐ)C(═O)NRᵐRᵐ, —NRᵐRᵐ, —N(Rᵐ)C(═O)Rⁿ, —N(Rᵐ)C(═O)ORⁿ, —N(Rᵐ)C(═O)NRᵐRᵐ, —N(Rᵐ)C(═NRᵐ)NRᵐRᵐ, —N(Rᵐ)S(═O)₂Rⁿ, —N(Rᵐ)S(═O)₂NRᵐRᵐ, —NRᵐC₂₋₆alkylNRᵐRᵐ, —NRᵐC₂₋₆alkylORᵐ, —C(═O)Rˢ, —C(═O)ORˢ, —C(═O)NRᵐRˢ, —C(═NRᵐ)NRᵐRˢ, —ORˢ, —OC(═O)Rˢ, —OC(═O)NRᵐRˢ, —OC(═O)N(Rᵐ)S(═O)₂Rˢ, —OC₂₋₆alkylNRᵐRˢ, —OC₂₋₆alkylORˢ, —SRˢ, —S(═O)Rˢ, —S(═O)₂Rˢ, —S(═O)₂NRᵐRˢ, —S(═O)₂N(Rᵐ)C(═O)Rˢ, —S(═O)₂N(Rᵐ)C(═O)ORˢ, —S(═O)₂N(Rᵐ)C(═O)NRᵐRˢ, —NRᵐRˢ, —N(Rᵐ)C(═O)Rˢ, —N(Rᵐ)C(═O)ORˢ, —N(Rᵐ)C(═O)NRᵐRˢ, —N(Rᵐ)C(═NRᵐ)NRᵐRˢ, —N(Rᵐ)S(═O)₂Rˢ, —N(Rᵐ)S(═O)₂NRᵐRˢ, —NRᵐC₂₋₆alkylNRᵐRˢ, —NRᵐC₂₋₆alkylORˢ and C₁₋₄alkyl substituted by 1 or 2 groups selected from C₁₋₂haloalkyl, halo, cyano, nitro, —C(═O)Rⁿ, —C(═O)ORⁿ, —C(═O)NRᵐRᵐ, —C(═NRᵐ)NRᵐRᵐ, —ORᵐ, —OC(═O)Rⁿ, —OC(═O)NRᵐRᵐ, —OC(═O)N(Rᵐ)S(═O)₂Rⁿ, —OC₂₋₆alkylNRᵐRᵐ, —OC₂₋₆alkylORᵐ, —SRᵐ, —S(═O)Rⁿ, —S(═O)₂Rⁿ, —S(═O)₂NRᵐRᵐ, —S(═O)₂N(Rᵐ)C(═O)Rⁿ, —S(═O)₂N(Rᵐ)C(═O)ORⁿ, —S(═O)₂N(Rᵐ)C(═O)NRᵐRᵐ, —NRᵐRᵐ, —N(Rᵐ)C(═O)Rⁿ, —N(Rᵐ)C(═O)ORⁿ, —N(Rᵐ)C(═O)NRᵐRᵐ, —N(Rᵐ)C(═NRᵐ)NRᵐRᵐ, —N(Rᵐ)S(═O)₂Rⁿ, —N(Rᵐ)S(═O)₂NRᵐRᵐ, —NRᵐC₂₋₆alkylNRᵐRᵐ, —C(═O)Rˢ, —C(═O)ORˢ, —C(═O)NRᵐRˢ, —C(═NRᵐ)NRᵐRˢ, —ORˢ, —OC(═O)Rˢ, —OC(═O)NRᵐRˢ, —OC(═O)N(Rᵐ)S(═O)₂Rˢ, —OC₂₋₆ alkyl- NR'''R^s, —OC_{2-6}alkylOR^s, —SR^s, —S(=O)R^s, —S(=O)_2 R^s, —S(=O)_2NR'''R^s, —S(=O)_2N(R''')C(=O)R^s, —S(=O)_2N(R''')C(=O)OR^s, —S(=O)_2N(R''')C(=O) NR'''R^s, —NR'''R^s, —N(R''')C(=O)R^s, —N(R''')C(=O) OR^s, —N(R''')C(=O)NR'''R^s, —N(R''')C(=NR''')NR'''R^s, —N(R''')S(=O)_2R^s, —N(R''')S(=O)_2NR'''R^s, —NR'''C_{2-6} alkylNR'''R^s, —NR'''C_{2-6}alkylOR^s and —NR'''C_{2-6}alkylOR'''; or R^2 is —(C(R^q)_2)_oR^r, wherein R^r is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from C_{1-8}alkyl, C_{1-4}haloalkyl, halo, cyano, nitro, —C(=O)R'', —C(=O)OR'', —C(=O)NR'''R''', —C(=NR''')NR'''R''', —OR''', —OC(=O)R'', —OC(=O)NR'''R''', —OC(=O)N(R''')S(=O)_2R'', —OC_{2-6}alkylNR'''R''', —OC_{2-6}alkylOR''', —SR''', —S(=O)R'', —S(=O)_2R'', —S(=O)_2NR'''R''', —S(=O)_2N(R''')C(=O)R'', —S(=O)_2N(R''')C(=O)OR'', —S(=O)_2N(R''')C(=O)NR'''R''', —NR'''R''', —N(R''')C (=O)R'', —N(R''')C(=O)OR'', —N(R''')C(=O)NR'''R''', —N(R''')C(=NR''')NR'''R''', —N(R''')S(=O)_2R'', —N(R''') S(=O)_2NR'''R''', —NR'''C_{2-6}alkylNR'''R''', —NR'''C_{2-6}alkylOR''', —C(=O)R^s, —C(=O)OR^s, —C(=O)NR'''R^s, —C(=NR''')NR'''R^s, —OR^s, —OC(=O)R^s, —OC(=O) NR'''R^s, —OC(=O)N(R''')S(=O)_2R^s, —OC_{2-6}alkylNR'''R^s, —OC_{2-6}alkylOR^s, —SR^s, —S(=O)R^s, —S(=O)_2R^s, —S(=O)_2NR'''R^s, —S(=O)_2N(R''')C(=O)R^s, —S(=O)_2N (R''')C(=O)OR^s, —S(=O)_2N(R''')C(=O)NR'''R^s, —NR'''R^s, —N(R''')C(=O)R^s, —N(R''')C(=O)OR^s, —N(R''')C(=O)NR'''R^s, —N(R''')C(=NR''')NR'''R^s, —N(R''')S(=O)_2R^s, —N(R''')S(=O)_2NR'''R^s, —NR'''C_{2-6} alkylNR'''R^s, —NR'''C_{2-6}alkylOR^s and C_{1-4}alkyl substituted by 1 or 2 groups selected from C_{1-2}haloalkyl, halo, cyano, nitro, —C(=O)R'', —C(=O)OR'', —C(=O)NR'''R''', —C(=NR''')NR'''R''', —OR''', —OC(=O)R'', —OC(=O) NR'''R''', —OC(=O)N(R''')S(=O)_2R'', —OC_{2-6}alkylNR'''R''', —OC_{2-6}alkylOR''', —SR''', —S(=O)R'', —S(=O)_2 R'', —S(=O)_2NR'''R''', —S(=O)_2N(R''')C(=O)R'', —S(=O)_2N(R''')C(=O)OR'', —S(=O)_2N(R''')C(=O) NR'''R''', —NR'''R''', —N(R''')C(=O)R'', —N(R''')C(=O) OR'', —N(R''')C(=O)NR'''R''', —N(R''')C(=NR''')NR'''R''', —N(R''')S(=O)_2R'', —N(R''')S(=O)_2NR'''R''', —NR'''C_{2-6} alkylNR'''R''', —C(=O)R^s, —C(=O)OR^s, —C(=O) NR'''R^s, —C(=NR''')NR'''R^s, —OR^s, —OC(=O)R^s, —OC (=O)NR'''R^s, —OC(=O)N(R''')S(=O)_2R^s, —OC_{2-6}alkyl-NR'''R^s, —OC_{2-6}alkylOR^s, —SR^s, —S(=O)R^s, —S(=O)_2 R^s, —S(=O)_2NR'''R^s, —S(=O)_2N(R''')C(=O)R^s, —S(=O)_2N(R''')C(=O)OR^s, —S(=O)_2N(R''')C(=O) NR'''R^s, —NR'''R^s, —N(R''')C(=O)R^s, —N(R''')C(=O) OR^s, —N(R''')C(=O)NR'''R^s, —N(R''')C(=NR''')NR'''R^s, —N(R''')S(=O)_2R^s, —N(R''')S(=O)_2NR'''R^s, —NR'''C_{2-6} alkylNR'''R^s, —NR'''C_{2-6}alkylOR^s and —NR'''C_{2-6}alkylOR''';

R^4 is a saturated or unsaturated 5- or 6-membered ring containing 0, 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from C_{1-8}alkyl, C_{1-4}haloalkyl, halo, cyano, nitro, —C(=O)R'', —C(=O)OR'', —C(=O)NR'''R''', —C(=NR''')NR'''R''', —OR''', —OC (=O)R'', —OC(=O)NR'''R''', —OC(=O)N(R''')S(=O)_2 R'', —OC_{2-6}alkylNR'''R''', —OC_{2-6}alkylOR''', —SR''', —S(=O)R'', —S(=O)_2R'', —S(=O)_2NR'''R''', —S(=O)_2 N(R''')C(=O)R'', —S(=O)_2N(R''')C(=O)OR'', —S(=O)_2 N(R''')C(=O)NR'''R''', —NR'''R''', —N(R''')C(=O)R'', —N(R''')C(=O)OR'', —N(R''')C(=O)NR'''R''', —N(R''')C (=NR''')NR'''R''', —N(R''')S(=O)_2R'', —N(R''')S(=O)_2 NR'''R''', —NR'''C_{2-6}alkylNR'''R''', —NR'''C_{2-6}alkylOR''', —C(=O)R^s, —C(=O)OR^s, —C(=O)NR'''R^s, —C(=NR''')NR'''R^s, —OR^s, —OC(=O)R^s, —OC(=O) NR'''R^s, —OC(=O)N(R''')S(=O)_2R^s, —OC_{2-6}alkylNR'''R^s, —OC_{2-6}alkylOR^s, —SR^s, —S(=O)R^s, —S(=O)_2R^s, —S(=O)_2NR'''R^s, —S(=O)_2N(R''')C(=O)R^s, —S(=O)_2 N(R''')C(=O)OR^s, —S(=O)_2N(R''')C(=O)NR'''R^s, —NR'''R^s, —N(R''')C(=O)R^s, —N(R''')C(=O)OR^s, —N(R''')C(=O)NR'''R^s, —N(R''')C(=NR''')NR'''R^s, —N(R''')S(=O)_2R^s, —N(R''')S(=O)_2NR'''R^s, —NR'''C_{2-6} alkylNR'''R^s, —NR'''C_{2-6}alkylOR^s and C_{1-4}alkyl substituted by 1 or 2 groups selected from C_{1-2}haloalkyl, halo, cyano, nitro, —C(=O)R'', —C(=O)OR'', —C(=O)NR'''R''', —C(=NR''')NR'''R''', —OR''', —OC(=O)R'', —OC(=O) NR'''R''', —OC(=O)N(R''')S(=O)_2R'', —OC_{2-6}alkylN-R'''R''', —OC_{2-6}alkylOR''', —SR''', —S(=O)R'', —S(=O)_2 R'', —S(=O)_2NR'''R''', —S(=O)_2N(R''')C(=O)R'', —S(=O)_2N(R''')C(=O)OR'', —S(=O)_2N(R''')C(=O) NR'''R''', —NR'''R''', —N(R''')C(=O)R'', —N(R''')C(=O) OR'', —N(R''')C(=O)NR'''R''', —N(R''')C(=NR''')NR'''R''', —N(R''')S(=O)_2R'', —N(R''')S(=O)_2NR'''R''', —NR'''C_{2-6} alkylNR'''R''', —C(=O)R^s, —C(=O)OR^s, —C(=O) NR'''R^s, —C(=NR''')NR'''R^s, —OR^s, —OC(=O)R^s, —OC (=O)NR'''R^s, —OC(=O)N(R''')S(=O)_2R^s, —OC_{2-6}alkyl-NR'''R^s, —OC_{2-6}alkylOR^s, —SR^s, —S(=O)R^s, —S(=O)_2 R^s, —S(=O)_2NR'''R^s, —S(=O)_2N(R''')C(=O)R^s, —S(=O)_2N(R''')C(=O)OR^s, —S(=O)_2N(R''')C(=O) NR'''R^s, —NR'''R^s, —N(R''')C(=O)R^s, —N(R''')C(=O) OR^s, —N(R''')C(=O)NR'''R^s, —N(R''')C(=NR''')NR'''R^s, —N(R''')S(=O)_2R^s, —N(R''')S(=O)_2NR'''R^s, —NR'''C_{2-6} alkylNR'''R^s, —NR'''C_{2-6}alkylOR^s and —NR'''C_{2-6}alkylOR''', and the ring and bridge carbon atoms are substituted with 0, 1 or 2=O groups;

R^7 is C_{2-8}alkyl, C_{1-5}haloalkyl, I, Br;

R^9 is independently, at each instance, H, C_{1-9}alkyl, C_{1-4}haloalkyl, halo, nitro, cyano, —OC_{1-6}alkyl, —O—C_{1-4}haloalkyl, —O—C_{1-6}alkylNR'''R''', —O—C_{1-6}alkylOR''', —NR'''R''', —NR'''—C_{1-4}haloalkyl, —NR'''—C_{1-6}alkylN-R'''R''' or —NR'''—C_{1-6}alkylOR''';

Y is NH; and

Z is CR^8 or N; or (E) R^1 is

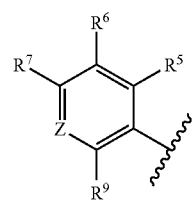

R^2 is H, —OR''', Cl, C_{1-3}haloalkyl or C_{1-6}alkyl;

R^4 is a saturated or unsaturated 5- or 6-membered ring containing 0, 1, 2 or 3 atoms selected from O, N and S, so long as the combination of O and S atoms is not greater than 1, wherein the ring is substituted by 0, 1, 2 or 3 substituents independently selected from C_{1-8}alkyl, C_{1-4}haloalkyl, halo, cyano, nitro, —C(=O)NR'''R''', —C(=NR''')NR'''R''', —OR", —OC(=O)R", —OC(=O)NR'''R''', —OC(=O)N(R''')S(=O)₂R", —OC₂₋₆alkylOR''', —SR''', —S(=O)R''', —S(=O)₂R", —S(=O)₂NR'''R''', —S(=O)₂N(R''')C(=O)R", —S(=O)₂N(R''')C(=O)OR", —S(=O)₂N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)₂R", —N(R''')S(=O)₂NR'''R''', —NR'''C₂₋₆alkylNR'''R''', —NR'''C₂₋₆alkylOR''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)₂R$^s$, —OC₂₋₆alkylNR'''R$^s$, —OC₂₋₆alkylOR$^s$, —SR$^s$, —S(=O)R$^s$, —S(=O)₂R$^s$, —S(=O)₂NR'''R$^s$, —S(=O)₂N(R''')C(=O)R$^s$, —S(=O)₂N(R''')C(=O)OR$^s$, —S(=O)₂N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NRr)NR'''R$^s$, —N(R''')S(=O)₂R$^s$, —N(R''')S(=O)₂NR'''R$^s$, —NR'''C₂₋₆alkylNR'''R$^s$, —NR'''C₂₋₆alkylOR$^s$ and C₁₋₄alkyl substituted by 1 or 2 groups selected from C₁₋₂haloalkyl, halo, cyano, nitro, —C(=O)R", —C(=O)NR'''R''', —C(=NR''')NR'''R''', —OR''', —OC(=O)R", —OC(=O)NR'''R''', —OC(=O)N(R''')S(=O)₂R", —OC₂₋₆alkylNR'''R''', —OC₂₋₆alkylOR''', —SR''', —S(=O)R''', —S(=O)₂R", —S(=O)₂NR'''R''', —S(=O)₂N(R''')C(=O)R", —S(=O)₂N(R''')C(=O)OR", —S(=O)₂N(R''')C(=O)NR'''R''', —NR'''R''', —N(R''')C(=O)R", —N(R''')C(=O)OR", —N(R''')C(=O)NR'''R''', —N(R''')C(=NR''')NR'''R''', —N(R''')S(=O)₂R", —N(R''')S(=O)₂NR'''R''', —NR'''C₂₋₆alkylNR'''R''', —C(=O)R$^s$, —C(=O)OR$^s$, —C(=O)NR'''R$^s$, —C(=NR''')NR'''R$^s$, —OR$^s$, —OC(=O)R$^s$, —OC(=O)NR'''R$^s$, —OC(=O)N(R''')S(=O)₂R$^s$, —OC₂₋₆alkylNR'''R$^s$, —OC₂₋₆alkylOR$^s$, —SR$^s$, —S(=O)R$^s$, —S(=O)₂R$^s$, —S(=O)₂NR'''R$^s$, —S(=O)₂N(R''')C(=O)R$^s$, —S(=O)₂N(R''')C(=O)OR$^s$, —S(=O)₂N(R''')C(=O)NR'''R$^s$, —NR'''R$^s$, —N(R''')C(=O)R$^s$, —N(R''')C(=O)OR$^s$, —N(R''')C(=O)NR'''R$^s$, —N(R''')C(=NR''')NR'''R$^s$, —N(R''')S(=O)₂R$^s$, —N(R''')S(=O)₂NR'''R$^s$, —NR'''C₂₋₆alkylNR'''R$^s$, —NR'''C₂₋₆alkylOR$^s$ and —NR'''C₂₋₆alkylOR'''; wherein $R^4$ is not unsubstituted phenyl;

$R^7$ is $C_{2-6}$alkyl, $C_{1-5}$haloalkyl, I or Br;

$R^9$ is independently, at each instance, H, $C_{1-9}$alkyl, $C_{1-4}$haloalkyl, halo, nitro, cyano, —OC$_{1-6}$alkyl, —O—C$_{1-4}$haloalkyl, —O—C$_{1-6}$alkylNR'''R''', —O—C$_{1-6}$alkylOR''', —NR'''R''', —NR'''—C$_{1-4}$haloalkyl, —NR'''—C$_{1-6}$alkylNR'''R''' or —NR'''—C$_{1-6}$alkylOR''';

Y is NH; and

Z is $CR^8$ or N.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alkyl" means an alkyl group comprising from α to β carbon atoms in a branched, cyclical or linear relationship or any combination of the three. The alkyl groups described in this section may also contain a double or triple bond. Examples of $C_{1-6}$alkyl include, but are not limited to the following:

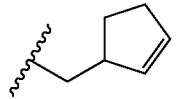

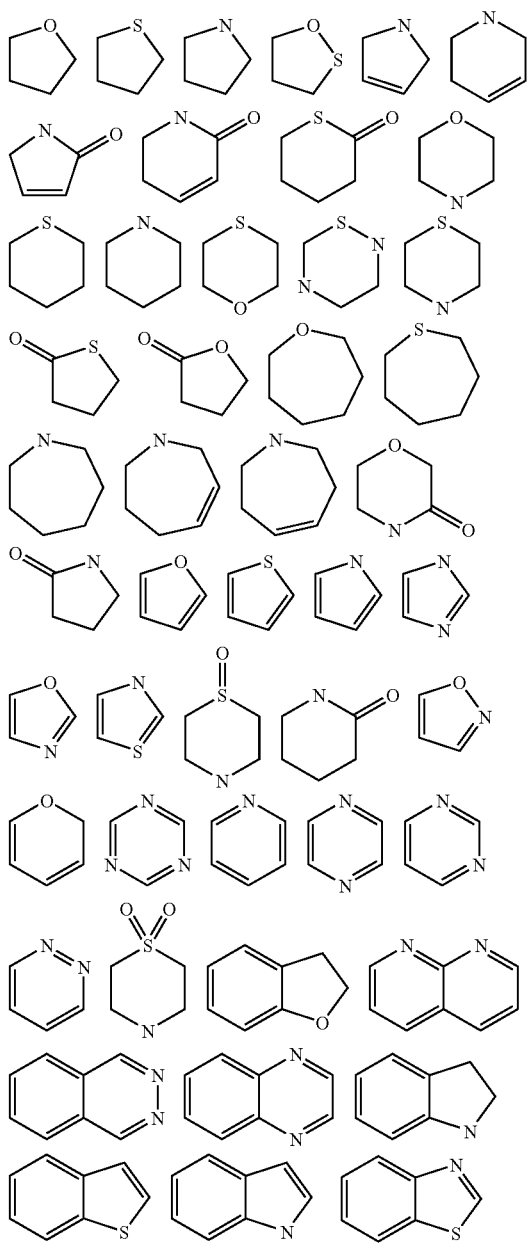

"Halo" means a halogen atoms selected from F, Cl, Br and I.

"$C_{\alpha-\beta}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

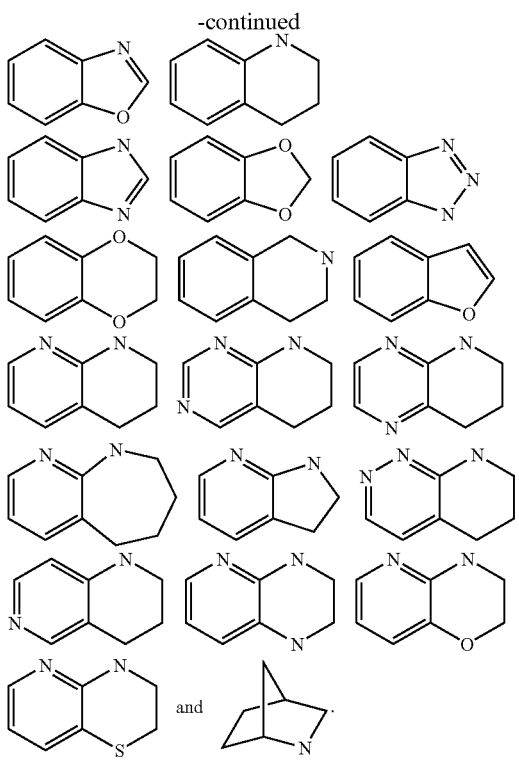

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

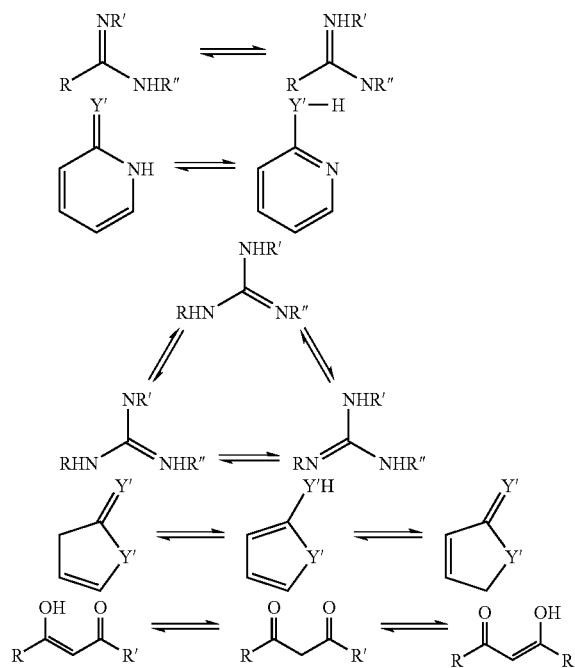

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Experimental

General

Unless otherwise noted, all materials were obtained from commercial suppliers and used without further purification. All parts are by weight and temperatures are in Degrees centigrade unless otherwise indicated. All compounds showed NMR spectra consistent with their assigned structures. Melting points were determined on a Buchi apparatus and are uncorrected. Mass spectral data was determined by electrospray ionization technique. All examples were purified to >95% purity as determined by high-performance liquid chromatography (HPLC). Unless otherwise stated, reactions were run at room temperature.

The following abbreviations are used:

| | |
|---|---|
| aq. - | aqueous |
| cond - | concentrated |
| DMF - | N,N-dimethylformamide |
| $Et_2O$ - | diethyl ether |
| EtOAc - | ethyl acetate |
| EtOH - | ethyl alcohol |
| h - | hour |
| min - | minutes |
| MeOH - | methyl alcohol |
| satd - | saturated |
| THF - | tetrahydrofuran |

EXAMPLE 1

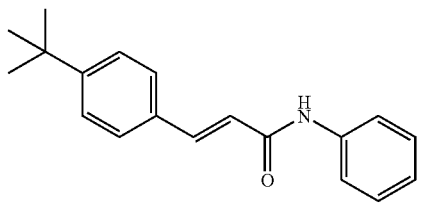

(2E)-3-[4-(tert-Butyl)phenyl]—N-phenylprop-2-enamide. To a 10 mL glass vial was added 4-tert-butyl-trans-cinnamic acid (200 mg, 0.98 mmol, EMKA-Chemie) followed by $CH_2Cl_2$ (5 mL), 1-[3-(dimethylamino)propyl]-3-ethylcarbodiimide hydrochloride (225 mg, 1.17 mmol, Bachem) and aniline (98 uL, 100 mg, 1.08 mmol, Aldrich). The reaction mixture was magnetically stirred at 25° C. for 24 h. EtOAc was added (60 mL) and the mixture washed successively with 1 N NaOH (2×20 mL), 1 N HCl (20 mL), water (20 mL) and satd NaCl (20 mL), dried over $MgSO_4$, filtered and concentrated. Recrystallization from hexane and $CH_2Cl_2$ provided the title product as white crystals. MP 141° C. MS (ESI, pos. ion) m/z: 280 (M+1).

EXAMPLE 2

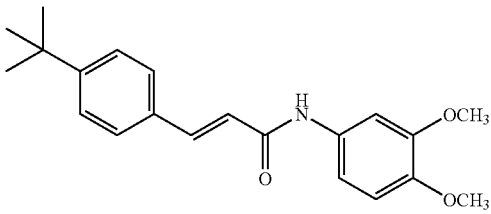

(2E)—N-(3,4-Dimethoxyphenyl)-3-[4-(tert-butyl)phenyl]prop-2-enamide. To a 20 mL round-bottomed flask equipped with reflux condenser and drying tube was added 4-tert-butyl-trans-cinnamic acid (200 mg, 0.98 mmol, EMKA-Chemie) followed by $CH_2Cl_2$ (5 mL), oxalyl chloride (90 uL, 130 mg, 1.03 mmol, Aldrich) and DMF (1 uL). The reaction mixture was magnetically stirred and heated at reflux for 30 min. The reaction mixture was concentrated in vacuo and the residue dissolved in acetone (2 mL). The solution was added to a mixture of 3,4-dimethoxyaniline (180 mg, 1.17 mmol, Aldrich), potassium carbonate (200 mg), water (2 mL) and acetone (2 mL), magnetically stirred at 25° C. in a 10 mL glass vial. The reaction mixture was stirred at 25° C. for 16 h then diluted with EtOAc (60 mL) and washed successively with 1 N HCl (20 mL), 1 N NaOH (20 mL), water (20 mL) and satd NaCl (20 mL), dried over $MgSO_4$, filtered and concentrated. Recrystallization from hexane and $CH_2Cl_2$ provided the title product as a yellow solid. MP 115-116° C. MS (ESI, pos. ion) m/z: 340 (M+1).

EXAMPLE 3

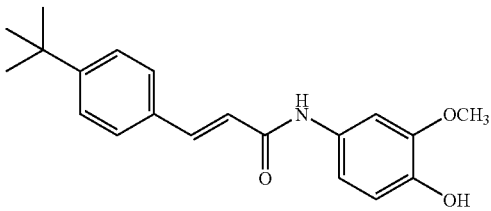

(2E)-3-[4-(tert-Butyl)phenyl]-N-(4-hydroxy-3-methoxyphenyl)prop-2-enamide

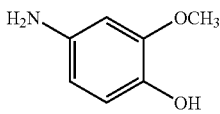

(a). 4-Amino-2-methoxyphenol. To a round-bottomed flask was added 4-nitroguaiacol (500 mg, 3.0 mmol, Aldrich) and anhydrous EtOH (50 mL). The solution was stirred magnetically under $N_2$ and treated with 10% Pd on carbon (200 mg, Aldrich). The suspension was purged with $H_2$ and then stirred at 25° C. under 1 atm $H_2$ for 16 h. The suspension was purged with $N_2$, filtered through Celite and concentrated in vacuo to provide a dark solid. The solid was washed with 1:1 $CH_2Cl_2$:hexane and dried in vacuo to provide the title product as pale brown crystals. MS (ESI, pos. ion) m/z: 140 (M+1).

(b). (2E)-3-[4-(tert-Butyl)phenyl]-N-(4-hydroxy-3-methoxyphenyl)prop-2-enamide. Analogous to the procedure used to prepare Example 2, 4-amino-2-methoxyphenol, Example 3(a), (164 mg, 1.18 mmol) and 4-t-butyl-trans-cinnamic acid (200 mg, 0.98 mmol, EMKA—Chemie) provided, after recrystallization of the crude product from $CH_2Cl_2$ and hexane, the title product as brown crystals. MP 203-204° C. MS (ESI, pos. ion) nm/z: 326 (M+1).

EXAMPLE 4

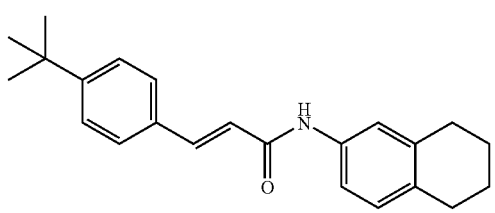

(2E)-3-[4-(tert-Butyl)phenyl]-N-(2-5,6,7,8-tetrahydronaphthyl)prop-2-enamide

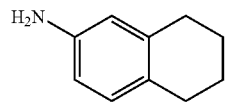

(a). 2-5,6,7,8-Tetrahydronaphthylamine. To a round-bottomed flask was added 6-amino-1,2,3,4-tetrahydronaphthalene (500 mg, 3.10 mmol, Maybridge), triethylsilane (2.50 mL, 15.5 mmol, Aldrich) and trifluoroacetic acid (5.0 mL, 66 mmol, Aldrich). The reaction mixture was magnetically stirred vigorously, at 25° C., for 2 h. The solvents were removed in vacuo and the residue dissolved in EtOAc (50 mL) and extracted with 1 N HCl (100 mL, then 50 mL). The combined aqueous acidic extract was washed with EtOAc (50 mL) then basified with 5 N NaOH, at 0° C., to pH 10. The mixture was extracted with $CH_2Cl_2$ (3×50 mL), the combined organic extract washed with water (50 mL), satd NaCl (50 mL), dried over $Na_2SO_4$, filtered and concentrated in vacuo to provide the title product as a brown oil. MS (ESI, pos. ion) m/z: 148 (M+1).

(b). (2E)-3-[4-(tert-Butyl)phenyl]-N-(2-5,6,7,8-tetrahydronaphthyl)prop-2-enamide. Analogous to the procedure used to prepare Example 2, 2-5,6,7,8-tetrahydronaphthylamine, Example 4(a), (173 mg, 1.18 mmol) and 4-t-butyl-trans-cinnamic acid (200 mg, 0.98 mmol, EMKA-Chemie) provided, after purification by silica gel chromatography (4:1 hexane:EtOAc) followed by re-crystallization from $CH_2Cl_2$ and hexane, the title product as white crystals. MP 198-199° C. MS (ESI, pos. ion) m/z: 334 (M+1).

EXAMPLE 5

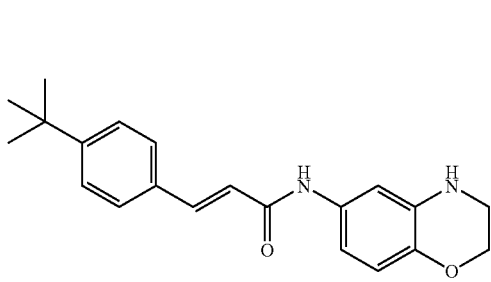

(2E)-N-(2H,3H,4H-Benzo[3,4-e]1,4-oxazaperhydroin-6-yl)-3-[4-(tert-butyl)phenyl]prop-2-enamide

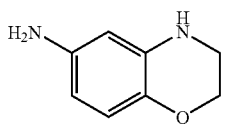

(a) 2H,3H,4H-Benzo[e]1,4-oxazaperhydroine-6-ylamine. To a round-bottomed flask was added 2-amino-4-nitrophenol (1.0 g, 6.5 mmol, Aldrich), potassium carbonate (1.8 g, 13 mmol), DMF (5 mL) and 1,2-dibromoethane (0.59 mL, 6.9 mmol, Aldrich). The mixture was magnetically stirred and heated in a 125° C. oil bath, under $N_2$, for 2.5 h. After allowing to cool to 25° C., the reaction mixture was diluted with EtOAc (100 mL), washed with 1 N NaOH (3×50 mL), water (50 mL), satd NaCl (50 mL), dried over $Na_2SO_4$, filtered and concentrated to provide a dark residue [MS (ESI, pos. ion) m/z: 181 (M+1)]. The crude product was dissolved in EtOH (100 mL), the solution was purged with $N_2$, treated with 10% Pd on carbon (450 mg, Aldrich), purged with $H_2$ then magnetically stirred under 1 atm $H_2$ for 2 h. After purging again with $N_2$, the suspension was filtered through Celite and concentrated in vacuo. Purification by silica gel chromatography (95:5 $CH_2Cl_2$:2 M $NH_3$ in EtOH) provided the title product as a viscous brown oil. MS (ESI, pos. ion) m/z: 151 (M+1).

(b) (2E)-N-(2H,3H,4H-Benzo[3,4-e]1,4-oxazaperhydroin-6-yl)-3-[4-(tert-butyl)phenyl]prop-2-enamide. Analogous to the procedure used to prepare Example 2, 2H,3H,4H-benzo[e]1,4-oxazaperhydroine-6-ylamine, Example 5(a), (176 mg, 1.18 mmol) and 4-t-butyl-trans-cinnamic acid (200 mg, 0.98 mmol, EMKA-Chemie) provided, after purification by silica gel chromatography (step gradient, 6:3:1 $CH_2Cl_2$:hexane:EtOAc then 9:1 hexane:EtOAc) the title product as a yellow solid. MP 108-114° C. MS (ESI, pos. ion) m/z: 337 (M+1).

EXAMPLE 6

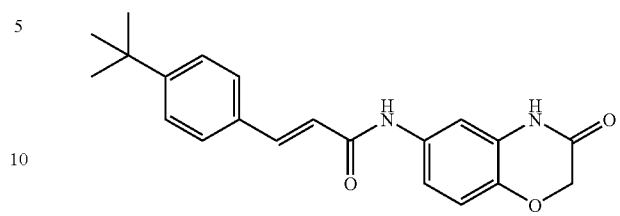

(2E)-3-[4-(tert-Butyl)phenyl]—N-(3-oxo(2H,4H-benzo[3,4-e]1,4-oxazaperhydroin-6-yl))prop-2-enamide

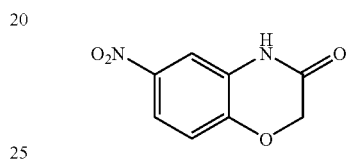

(a) 6-Nitro-2H,4H-benzo[e]1,4-oxazaperhydroin-3-one. A mixture of 4-nitro-2-aminophenol (4.6 g, 30 mmol, Aldrich), benzyltrimethylammonium chloride (6.8 g, 30 mmol, Aldrich) and solid $NaHCO_3$ (12.6 g, 150 mmol) in chloroform (100 mL) was magnetically stirred at 0° C. in a round-bottomed flask and treated dropwise with chloroacetyl chloride (2.9 mL, 33 mmol, Aldrich) over a period of 30 min. After the addition was complete, the reaction mixture was stirred at 0° C. for 1 h, then at 50° C. overnight. The solvent was removed in vacuo and the residue treated with water (50 mL), collected by filtration and washed with water. The solid was recrystallized from EtOH to provide 6-nitro-2H,4H-benzo[e]1,4-oxazaperhydroin-3-one. MS (ESI, neg. ion) m/z: 193 (M-1).

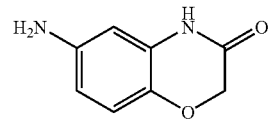

(b) 6-Amino-2H,4H-benzo[e]1,4-oxazaperhydroin-3-one. To a suspension of 6-nitro-2H,4H-benzo[e]1,4-oxazaperhydroin-3-one, Example 6(a), (0.50 g, 2.6 mmol) and CuCl (0.77 g, 7.8 mmol, Aldrich) in anhydrous MeOH (25 mL), magnetically stirred at 25° C. in a round-bottomed flask, was added potassium borohydride (0.98 g, 18 mmol, Aldrich) in portions. The reaction mixture was stirred at 25° C. for 0.5 h, then the solvent was removed in vacuo and the residue suspended in water (30 mL) and extracted with EtOAc (5×20 mL). The combined organic extracts were washed with satd NaCl, dried over $Na_2SO_4$, filtered and concentrated in vacuo to provide the title product as a brown solid.
MS (ESI, pos. ion) m/z: 165 (M+1).

(c) (2E)-3-[4-(tert-Butyl)phenyl]-N-(3-oxo(2H,4H-benzo[3,4-e]1,4-oxazaperhydroin-6-yl))prop-2-enamide. Analogous to the procedure used to prepare Example 1, 6-amino-2H,4H-benzo[e]1,4-oxazaperhydroin-3-one, Example 6(b), (207 mg, 1.26 mmol) and 4-tert-butyl-trans-cinnamic acid (258 mg, 1.26 mmol EMKA-Chemie) provided, after recrystallization from EtOAc and hexane, the title compound as a pale yellow solid. MP>280° C. MS (ESI, pos. ion) m/z: 351 (M+1).

Example 7

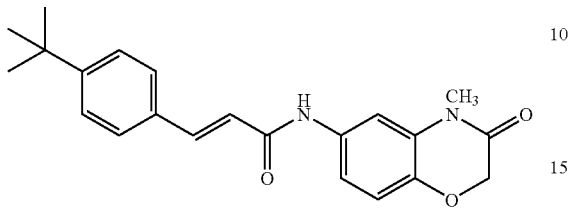

(2E)-3-[4-(tert-Butyl)phenyl]-N-(4-methyl-3-oxo (2H-benzo[3,4-e]1,4-oxazaperhydroin-6-yl))prop-2-enamide

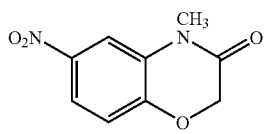

(a) 4-Methyl-6-nitro-2H-benzo[e]1,4-oxazaperhydroin-3-one. A mixture of 6-nitro-2H,4H-benzo[e]1,4-oxazaperhydroin-3-one, Example 6(a), (970 mg, 25 mmol), benzyltrimethylammonium chloride (114 mg, 0.50 mmol, Aldrich) and iodomethane (0.47 mL, 7.5 mmol, Aldrich) in CH$_2$Cl$_2$ (20 mL) was stirred magnetically in a 100 mL round-bottomed flask and treated with CsOH monohydrate (4.2 g, 25 mmol, Aldrich). The reaction mixture was stirred at 25° C. for 1 h, treated with water (5 mL) and extracted with CH$_2$Cl$_2$ (3×50 mL). The combined organic extract was washed with water (5 mL), satd NaCl (5 mL), dried over Na$_2$SO$_4$, filtered and concentrated in vacuo. The residue was purified by silica gel chromatography (9:1 hexane:EtOAc) to provide the title product.

MS (ESI, pos. ion) m/z: 209 (M+1).

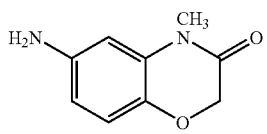

(b) 6-Amino-4-methyl-2H-benzo[e]1,4-oxazaperhydroin-3-one. To a solution of 4-methyl-6-nitro-2H-benzo[e]1,4-oxazaperhydroin-3-one, Example 7(a), (700 mg, 3.4 mmol) and NiCl$_2$·6H$_2$O (400 mg, 1.7 mmol, Aldrich) in MeOH (10 mL), magnetically stirred in a 100 mL round-bottomed flask at 25° C., was added NaBH4 (190 mg, 5.1 mmol, Aldrich) in portions. The reaction mixture was stirred for 30 min then concentrated in vacuo. Purification by silica gel chromatography (CH$_2$Cl$_2$/EtOAc) provided the title product. MS (ESI, pos. ion) m/z: 179 (M+1).

(c) (2E)-3-[4-(tert-Butyl)phenyl]—N-(4-methyl-3-oxo (2H-benzo[3,4-e]1,4-oxazaperhydroin-6-yl))prop-2-enamide. Analogous to the procedure used to prepare Example 1, 4-tert-butyl-trans-cinnamic acid (200 mg, 1.0 mmol, EMKA-Chemie) and 6-amino-4-methyl-2H-benzo[e]1,4-oxazaperhydroin-3-one, Example 7(b), (180 mg, 1.0 mmol) provided, after purification by silica gel chromatography (4:1 CH$_2$Cl$_2$: EtOAc), the title product as a pale yellow solid. MP 201-203° C. MS (ESI, pos. ion) m/z: 365 (M+1).

EXAMPLE 8

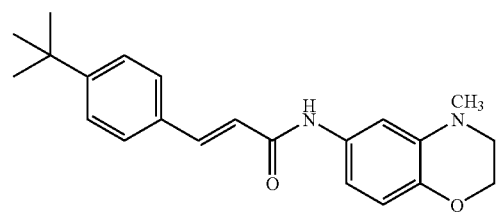

(2E)-3-[4-(tert-Butyl)phenyl]-N-(4-methyl(2H,3H-benzo[3,4-e]1,4-oxazaperhydroin-6-yl))prop-2-enamide To a solution of lithium aluminum hydride (2.0 mL, 2.0 mmol, 1.0 M in THF, Aldrich), magnetically stirred at 0° C. in a round-bottomed flask under N$_2$, was added 6-amino-4-methyl-2H-benzo[e]1,4-oxazaperhydroin-3-one, Example 7b, (180 mg, 1.0 mmol). The reaction mixture was allowed to warm to 25° C. and stirred at that temperature for 1 h. The reaction was quenched by the dropwise addition of 20% H$_2$O/THF (1.2 mnL), followed by 5 N NaOH (0.2 mL). The mixture was stirred at 25° C. for 30 min, then filtered and washed with EtOAc.

The filtrate was dried over Na$_2$SO$_4$, filtered and concentrated in vacuo [MS (ESI, pos. ion) m/z: 165 (M+1)]. Analogous to the procedure used to prepare Example 1, the crude product and 4-tert-butyl-trans-cinnamic acid provided the title compound as a pale yellow solid. MP 186-188° C. MS (ESI, pos. ion) m/z: 351 (M+1).

EXAMPLE 9

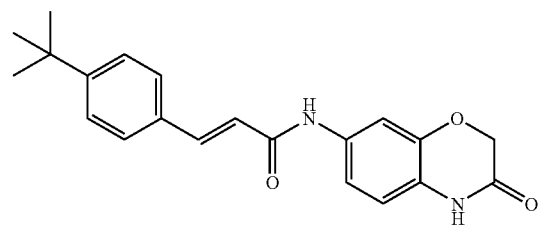

(2E)-3-[4-(tert-Butyl)phenyl]-N-(3-oxo(2H,4H-benzo[e]1,4-oxazaperhydroin-7-yl))prop-2-enamide

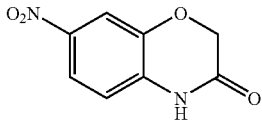

(a) 7-Nitro-2H,4H-benzo[e]1,4-oxazaperhydroin-3-one. Analogous to the procedure used for the preparation of 6-nitro-2H,4H-benzo[e]1,4-oxazaperhydroin-3-one, Example 6(a), 5-nitro-2-aminophenol (4.6 g, 30 mmol, Aldrich) and chloroacetyl chloride (2.9 mL, 33 mmol, Aldrich) provided, after recrystallization from EtOH, 7-nitro-2H,4H-benzo[e]1,4-oxazaperhydroin-3-one.

MS (ESI, neg. ion) m/z: 193 (M−1).

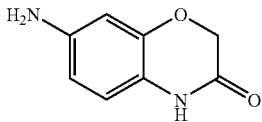

(b) 7-Amino-2H,4H-benzo[e]1,4-oxazaperhydroin-3-one. A mixture of 7-nitro-2H,4H-benzo[e]1,4-oxazaperhydroin-3-one, Example 9(a), (970 mg, 5.0 mmol) and 10% Pd on carbon (100 mg, Aldrich) in MeOH (20 mL) was magnetically stirred in a round-bottomed flask under 1 atm H$_2$ for 2 h. The mixture was purged with N$_2$ and filtered through a pad of Celite. Concentration in vacuo provided the title product. MS (ESI, pos. ion) n/z: 165 (M+1).

(c) (2E)-3-[4-(tert-Butyl)phenyl]-N-(3-oxo(2H,4H-benzo[e]1,4-oxazaperhydroin-7-yl))prop-2-enamide. Analogous to the procedure used to prepare Example 1, 4-tert-butyl-trans-cinnamic acid (200 mg, 1.0 mmol, EMKA-Chemie) and 7-amino-2H,4H-benzo[e]1,4-oxazaperhydroin-3-one, Example 9(b), (164 mg, 1.0 mmol) provided, after purification by silica gel chromatography (4:1 CH$_2$Cl$_2$:EtOAc), the title product as a pale yellow solid. MP 226-227° C. MS (ESI, pos. ion) m/z: 351 (M+1).

EXAMPLE 10

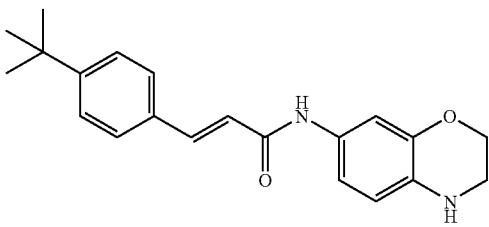

(2E)-N-(2H,3H,4H-Benzo[e]1,4-oxazaperhydroin-7-yl)-3-[4-(tert-butyl)phenyl]prop-2-enamide To a solution of borane-THF complex (2.5 mL, 2.5 mmol, 1.0 M in THF, Aldrich), magnetically stirred at 0° C. under N$_2$ in a round-bottomed flask equipped with a reflux condenser, was added 7-amino-2H,4H-benzo[e]1,4-oxazaperhydroin-3-one, Example 9(b), (160 mg, 1.0 mmol). The reaction mixture was stirred at reflux for 2 h, then treated with EtOH (0.5 mL) and reflux continued for an additional 1 h. The mixture was treated with cond HCl (0.5 mL) and reflux continued for an additional 1 h. The solvent was removed in vacuo and the residue treated with 1 N NaOH (5 mL) and extracted with CH$_2$Cl$_2$ (3×20 mL). The combined organic extracts were washed with satd NaCl, dried over Na$_2$SO$_4$, filtered and concentrated in vacuo to provide the crude aniline [MS (ESI, pos. ion) m/z: 151 (M+1)]. Analogous to the procedure used to prepare Example 1, 4-tert-butyl-trans-cinnamic acid (200 mg, 1.0 mmol, EMKA-Chemie) and the crude aniline, after purification by silica gel chromatography (85:15 CH$_2$Cl$_2$:EtOAc), provided the title product as a pale yellow solid. MP 186-188° C. MS (ESI, pos. ion) m/z: 337 (M+1).

EXAMPLE 11

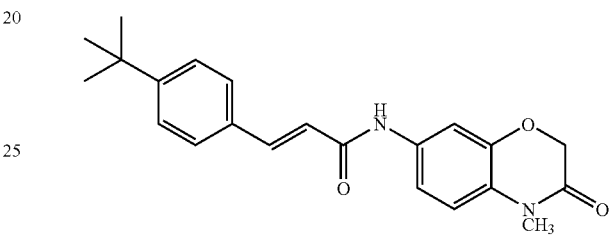

(2E)-3-[4-(tert-Butyl)phenyl]-N-(4-methyl-3-oxo(2H-benzo[e]1,4-oxazaperhydroin-7-yl))prop-2-enamide

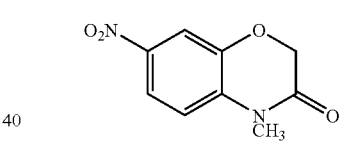

(a) 4-Methyl-7-nitro-2H-benzo[e]1,4-oxazaperhydroin-3-one. Analogous to the procedure used to prepare Example 7(a), 7-nitro-2H,4H-benzo[e]1,4-oxazaperhydroin-3-one, Example 9(a), (970 mg, 25 mmol), benzyltrimethyl-ammonium chloride (110 mg, 0.50 mmol, Aldrich), iodomethane (0.47 mL, 7.5 mmol, Aldrich) and CsOH hydrate (4.2 g, 25 mmol, Aldrich), after purification by silica gel chromatography (9:1 hexane:EtOAc), provided the title product. MS (ESI, neg. ion) m/z: 207 (M−1).

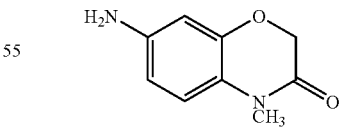

(b) 7-Amino-4-methyl-2H-benzo[e]1,4-oxazaperhydroin-3-one. Analogous to the procedure used to prepare Example 3(a), 4-methyl-7-nitro-2H-benzo[e]1,4-oxazaperhydroin-3-one, Example 11(a), (1.0 g, 5.0 mmol) provided, after recrystallization from EtOH, the title product. MS (ESI, pos. ion) m/z: 179 (M+1).

(c) (2E)-3-[4-(tert-Butyl)phenyl]-N-(4-methyl-3-oxo(2H-benzo[e]1,4-oxazaperhydroin-7-yl))prop-2-enamide. Analogous to the procedure used to prepare Example 1, 4-tert-butyl-trans-cinnamic acid (200 mg, 1.0 mmol, EMKA-Chemie) and 7-amino-4-methyl-2H-benzo[e]1,4-oxazaperhydroin-3-one, Example 11b, (164 mg, 1.0 mmol) provided, after purification by silica gel chromatography (85:15 CH$_2$Cl$_2$:EtOAc), the title product as a pale yellow solid. MP 194-195° C. MS (ESI, pos. ion) m/z: 365 (M+1).

EXAMPLE 12

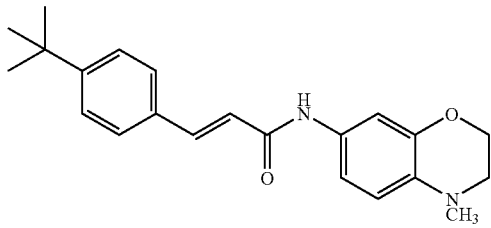

(2E)-3-[4-(tert-Butyl)phenyl]-N-(4-methyl(2H,3H-benzo[e]1,4-oxazaperhydroin-7-yl))prop-2-enamide Analogous to the procedure used for the preparation of Example 10, 7-amino-4-methyl-2H-benzo[e]1,4-oxazaperhydroin-3-one, Example 11(b), (180 mg, 1.0 mmol) and 4-tert-butyl-trans-cinnamic acid (200 mg, 1.0 mmol, EMKA-Chemie) provided, after purification by silica gel chromatography (85:15 CH$_2$Cl$_2$:EtOAc), the title product as a pale yellow solid. MP 232-233° C. MS (ESI, pos. ion) m/z: 351 (M+1).

EXAMPLE 13

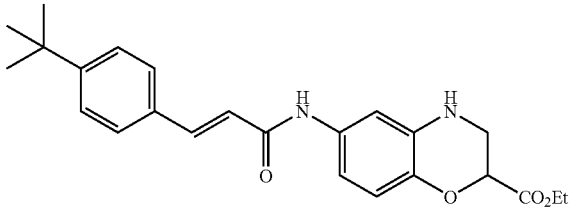

Ethyl 6-{(2E)-3-[4-(tert-butyl)phenyl]prop-2-enoylamino}-2H,3H,4H-benzo[e]1,4-oxazaperhydroine-2-carboxylate

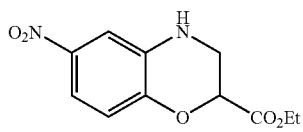

(a) Ethyl 6-nitro-2H,3H,4H-benzo[e]1,4-oxazaperhydroine-2-carboxylate. A solution of ethyl 2,3-dibromopropionate (4.8 mL, 33 mmol, Aldrich) in acetone (10 mL, Aldrich) was added to a mixture of 2-amino-4-nitrophenol (4.6 g, 30 mmol, Aldrich) in 80 mL of acetone in a 150 mL round-bottomed flask at 25° C. After the addition, the mixture was stirred at 60° C. for 48 h. The solvent was removed in vacuo, and the residue was treated with water (30 mL) and extracted with CH$_2$Cl$_2$ (3×50 mL). The combined organic phases were washed with satd NaCl (10 mL), dried over Na$_2$SO$_4$, filtered and concentrated in vacuo. The residue was purified by silica gel chromatography (9:1 CH$_2$Cl$_2$:EtOAc) to give the title product. MS (ESI, pos. ion) m/z: 253 (M+1).

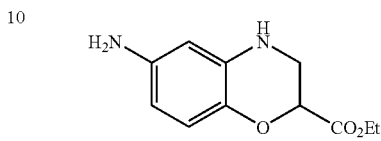

(b) Ethyl 6-amino-2H,3H,4H-benzo[e]1,4-oxazaperhydroine-2-carboxylate Analogous to the procedure used to prepare Example 3(a), ethyl 6-nitro-2H,3H,4H-benzo[e]1,4-oxazaperhydroine-2-carboxylate, Example 13(a), (1.3 g, 5.0 mmol) provided the title product. MS (ESI, pos. ion) m/z: 223 (M+1).

(c). Analogous to the procedure used to prepare Example 1, 4-tert-butyl-trans-cinnamic acid (1.3 g, 6.4 mmol, EMKA-Chemie) and ethyl 6-amino-2H,3H,4H-benzo[e]1,4-oxazaperhydroine-2-carboxylate, Example 13(b), (1.4 g, 6.4 mmol) provided, after purification by silica gel chromatography (85:15 CH$_2$Cl$_2$:EtOAc), the title product as a pale yellow solid. MP 207-208° C. MS (ESI, pos. ion) m/z: 409 (M+1).

EXAMPLE 14

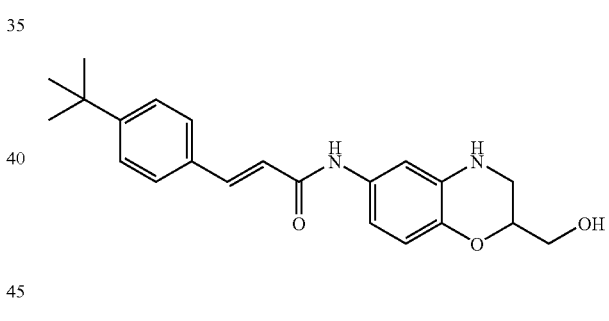

(2E)-3-[4-(tert-Butyl)phenyl]-N-[2-(hydroxymethyl)(2H,3H,4H-benzo[3,4-e]1,4-oxazaperhydroin-6-yl)]prop-2-enamide A solution of ethyl 6-{(2E)-3-[4-(tert-butyl)phenyl]prop-2-enoylamino}-2H,3H,4H-benzo[e]1,4-oxazaperhydroine-2-carboxylate, Example 13, (410 mg, 1.0 mmol) in THF (5 mL, Aldrich), magnetically stirred in a round-bottomed flask under N$_2$ at 0° C., was treated with lithium borohydride (1.5 mL, 3.0 mmol, 2.0 M in THF, Aldrich). The reaction mixture was allowed to warm to 25° C., and stirred at that temperature for 3 h. The reaction was quenched by the addition of satd NH$_4$Cl (5 mL), stirred for 30 min at 25° C. and extracted with EtOAc (2×15 mL). The combined organic extract was washed with satd NaCl, dried over Na$_2$SO$_4$, filtered and concentrated in vacuo. Purification by silica gel chromatography (1:1 CH$_2$Cl$_2$:EtOAc) provided the title product as a pale yellow solid. MP 165-167° C. MS (ESI, pos. ion) m/z: 367 (M+1).

EXAMPLE 15

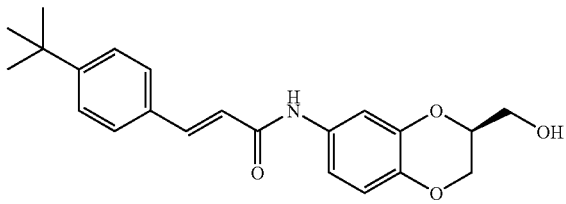

(2E)-N-[(3S)-3-(Hydroxymethyl)(2H,3H-benzo[e]1,4-dioxan-6-yl)]-3-[4-tert-butyl)phenyl]prop-2-enamide

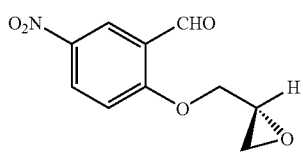

(a) 2-[((2R)Oxiran-2-yl)methoxy]-5-nitrobenzaldehyde. A mixture of (R)-glycidyl tosylate (1.1 g, 5 mmol, Aldrich), 2-hydroxy-5-nitrobenzaldehyde (840 mg, 5.0 mmol, Aldrich) and solid K₂CO₃ (1.4 g, 10 mmol) in DMF (5 mL, Aldrich) was magnetically stirred in a round-bottomed flask at 100° C. under N₂ for 30 min. The reaction mixture was allowed to cool to 25° C., water (20 mL) was added, and the mixture was extracted with EtOAc (3×30 mL). The combined extracts were washed with water (2×20 mL), satd NaCl (10 mL), dried over Na₂SO₄, filtered and concentrated in vacuo. Purification by silica gel chromatography (4:1 hexane:EtOAc) provided the title product. MS (ESI, pos. ion) m/z: 224 (M+1).

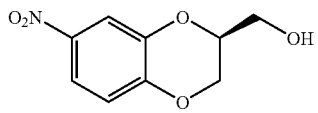

(b) ((2S)-7-Nitro-2H,3H-benzo[e]1,4-dioxan-2-yl)methan-1-ol. To a solution of 2-[((2R)oxiran-2-yl)methoxy]-5-nitrobenzaldehyde, Example 15(a), (670 mg, 3.0 mmol) in CH₂Cl₂ (10 mL), magnetically stirred in a round-bottomed flask at 0° C., was added 86% m-chloroperbenzoic acid (350 mg, 2.0 mmol, Aldrich). The reaction mixture was allowed to warm to 25° C. and stirred at that temperature for 18 h. The mixture was then diluted with CH₂Cl₂ (20 mL), washed with 10% Na₂S₂O₃ (3 mL), NaHCO₃ (3×5 mL), satd NaCl (3 mL), dried over Na₂SO₄, filtered and concentrated in vacuo. The resulting residue was treated with MeOH (20 mL) and 1 N NaOH (6 mL) and stirred at 25° C. for 16 h. The reaction mixture was diluted with water (10 mL) and extracted with EtOAc (3×10 mL). The combined organic extracts were washed with satd NaCl, dried over Na₂SO₄, filtered and concentrated in vacuo. Purification by silica gel chromatography (3:2 hexane:EtOAc) provided the product. MS (ESI, pos. ion) m/z: 212 (M+1).

(c) (2E)-N-[(3S)-3-(Hydroxymethyl)(2H,3H-benzo[e]1,4-dioxan-6-yl)]-3-[4-(tert-butyl)phenyl]prop-2-enamide. A mixture of ((2S)-7-nitro-2H,3H-benzo[e]1,4-dioxan-2-yl)methan-1-ol, Example 15(b), (110 mg, 0.5 mmol) and 10% Pd on carbon (20 mg, Aldrich) in MeOH (5 mL), in a round-bottomed flask, was magnetically stirred under 1 atm H₂ for 2 h. The mixture was purged with N₂, filtered through a pad of Celite and concentrated in vacuo to provide the crude aniline [MS (ESI, pos. ion) m/z: 182 (M+1)]. Analogous to the procedure used to prepare Example 1, 4-tert-butyl-trans-cinnamic acid (102 mg, 0.5 mmol, EMKA Chemie) and the crude aniline, provided the title product as a white solid. MP 169-171° C. MS (ESI, pos. ion) m/z: 368 (M+1).

EXAMPLE 16

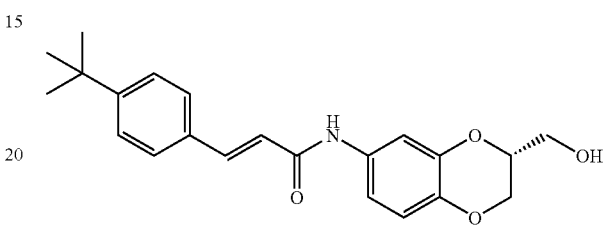

(2E)-N-[(3R)-3-(Hydroxymethyl)(2H,3H-benzo[e]1,4-dioxan-6-yl)]-3-[4-(tert-butyl)phenyl]prop-2-enamide Analogous to the procedure described for Example 15, the title product was prepared starting from (S)-glycidyl tosylate (Aldrich), 2-hydroxy-5-nitrobenzaldehyde (Aldrich) and 4-tert-butyl-trans-cinnamic acid (EMKA Chemie). MP 170-171° C. MS (ESI, pos. ion) m/z: 368 (M+1).

EXAMPLE 17

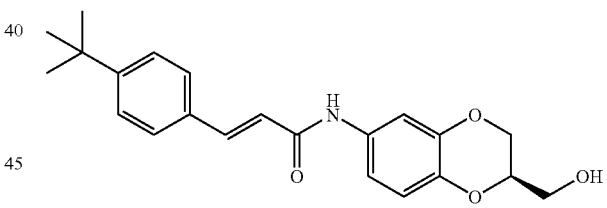

(2E)-N-[(2R)-2-(Hydroxymethyl)(2H,3H-benzo[3,4-e]1,4-dioxan-6-yl)]-3-[4-(tert-butyl)phenyl]prop-2-enamide

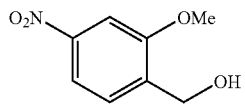

(a) (2-Methoxy-4-nitrophenyl)methan-1-ol. To a solution of 2-methoxy-4-nitrobenzoic acid (2.0 g, 10 mmol, Aldrich) in THF (30 mL), magnetically stirred at 0° C. under N₂ in a round-bottomed flask equipped with a reflux condenser, was added borane-THF complex (30 mL, 30 mmol, 1.0 M in THF, Aldrich). The reaction mixture was stirred at reflux overnight. The reaction was quenched by the careful addition of MeOH (5 mL), followed by 1 N NaOH (30 mL). The mixture was extracted with EtOAc (2×50 mL), the combined organic extracts were washed with satd NaCl, dried over Na$_2$SO$_4$, filtered and concentrated in vacuo to give the product. MS (ESI, neg. ion) m/z: 182 (M−1).

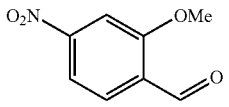

(b) 2-Methoxy-4-nitrobenzaldehyde. A mixture of (2-methoxy-4-nitrophenyl)methan-1-ol, Example 17(a), (1.6 g, 8.9 mmol) and MnO$_2$ (15 g, 180 mmol, Aldrich) in 1:1 hexane: CH$_2$Cl$_2$ (60 mL) was magnetically stirred at 40° C. for 3 h. The solid was removed by filtration and washed with CH$_2$Cl$_2$. The filtrate was concentrated in vacuo and the residue was recrystallized from EtOAc and hexane to give the title product. MS (ESI, neg. ion) m/z: 180 (M−1).

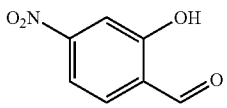

(c) 2-Hydroxy-4-nitrobenzaldehyde. To a solution of 2-methoxy-4-nitrobenzaldehyde, Example 17(b), (190 mg, 1.0 mmol) in CH$_2$Cl$_2$ (5 mL), magnetically stirred at −78° C. in a round-bottomed flask, was added BBr$_3$ (0.19 mL, 2.0 mmol, Aldrich). The reaction mixture was allowed to warm to 25° C. and stirred at that temperature for 2 h. The reaction mixture was then cooled to −78° C., and treated with MeOH (5 mL). The mixture was allowed to warm to 25° C., stirred at that temperature for 30 min, then concentrated in vacuo. Purification by silica gel chromatography (3:2 hexane: EtOAc) provided 2-hydroxy-4-nitrobenzaldehyde. MS (ESI, neg. ion) m/z: 166 (M−1).

(d) (2E)-N-[(2R)-2-(Hydroxymethyl)(2H,3H-benzo[3,4-e]1,4-dioxan-6-yl)]-3-[4-(tert-butyl)phenyl]prop-2-enamide. Analogous to the procedure described for Example 15, the title product was obtained as a white solid from 2-hydroxy-4-nitrobenzaldehyde, Example 17(c), (S)-glycidyl tosylate (Aldrich) and 4-tert-butyl-trans-cinnamic acid (EMKA-Chemie). MP 159-160° C. MS (ESI, pos. ion) m/z: 368 (M+1).

EXAMPLE 18

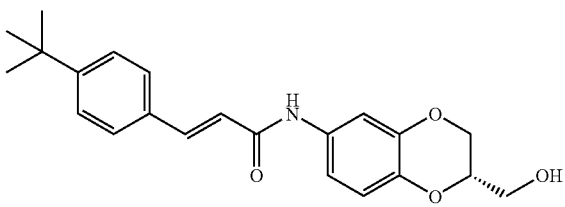

(2E)-N-[(2S)-2-(Hydroxymethyl)(2H,3H-benzo[3,4-e]1,4-dioxan-6-yl)]-3-[4-(tert-butyl)phenyl]prop-2-enamide Analogous to the procedure described for Example 15, the title product was prepared starting from 2-hydroxy-4-nitrobenzaldehyde, Example 17(c), (R)-glycidyl tosylate (Aldrich) and 4-tert-butyl-trans-cinnamic acid (EMKA Chemie). MP 169-170° C. MS (ESI, pos. ion) m/z: 368 (M+1).

EXAMPLE 19

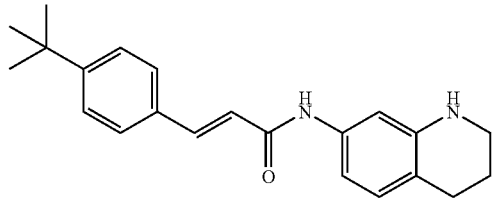

(2E)-3-[4-(tert-Butyl)phenyl]-N-(7-1,2,3,4-tetrahydroquinolyl)prop-2-enamide

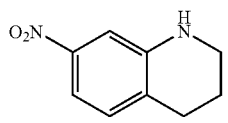

(a) 7-Nitro-1,2,3,4-tetrahydroquinoline. To a round-bottomed flask equipped with magnetic stirring was added 1,2,3,4-tetrahydroquinoline (6.3 mL, 50 mmol, Aldrich) and 96% H$_2$SO$_4$ (42 mL). The mixture was stirred until all of the amine had dissolved, then cooled to 0° C. and treated with KNO$_3$ (5.9 g, 59 mmol) in portions. The reaction mixture was allowed to warm to 25° C. and stirred overnight at that temperature. The mixture was then cooled to 0° C. and neutralized with solid NaOH followed by 5 N NaOH until pH 11 was reached. The mixture was extracted with CH$_2$Cl$_2$ and the extract was dried over Na$_2$SO$_4$, filtered and concentrated in vacuo. Purification by silica gel chromatography (8:1 hexane: EtOAc) provided 7-nitro-1,2,3,4-tetrahydroquinoline as an orange solid. MS (ESI, pos. ion) m/z 179 (M+1).

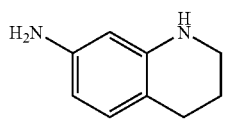

(b) 7-1,2,3,4-Tetrahydroquinolylamine. Analogous to the procedure used to prepare Example 3(a), 7-nitro-1,2,3,4-tetrahydroquinoline, Example 19(a), (0.35 g, 2.0 mmol) provided the aniline as a pale gray oil. MS (ESI, pos. ion) m/z: 149 (M+1).

(c) (2E)-3-[4-(tert-Butyl)phenyl]-N-(7-1,2,3,4-tetrahydroquinolyl)prop-2-enamide. Analogous to the procedure used to prepare Example 1, 7-1,2,3,4-tetrahydroquinolylamine, Example 19(b), (280 mg, 1.9 mmol) and 4-tert-butyl-trans-cinnamic acid (0.33 g, 1.6 mmol, EMKA-Chemie) provided, after purification by silica gel chromatography (3:1 hexane:

EtOAc) then recrystallization from EtOAc and hexane, the title product as a yellow solid. MP 225-227° C. MS (ESI, pos. ion) m/z: 335 (M+1).

EXAMPLE 20

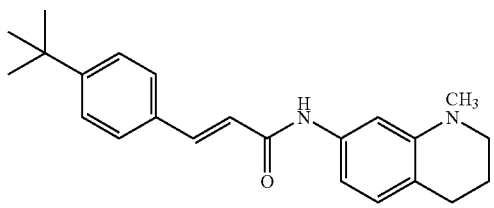

(2E)-3-[4-(tert-Butyl)phenyl]-N-(1-methyl(7-1,2,3,4-tetrahydroquinolyl))-prop-2-enamide

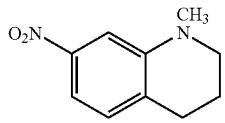

(a) 1-methyl-7-nitro-1,2,3,4-tetrahydroquinoline. To a solution of 7-nitro-1,2,3,4-tetrahydro-quinoline, Example 19(a), (0.36 g, 2 mmol) in DMF (10 mL), magnetically stirred under $N_2$ at 0° C. in a 15 mL round-bottomed flask, was added sodium hydride (0.12 g, 3 mmol, 60% dispersion in mineral oil, Aldrich). After stirring for 10 min, the reaction mixture was treated with iodomethane (0.24 mL, 4 mmol, Aldrich) dropwise. The reaction mixture was stirred at 0° C. for 1 h, at 25° C. for an additional 1 h, then partitioned between EtOAc and satd NaCl. The aqueous layer was extracted with EtOAc (40 mL) and the combined organic extract was dried over $Na_2SO_4$, filtered and concentrated in vacuo. Purification by silica gel chromatography (7:1 hexane:EtOAc) provided the product as an orange oil. MS (ESI, pos. ion) m/z: 193 (M+1).

(b) (2E)-3-[4-(tert-Butyl)phenyl]-N-(1-methyl(7-1,2,3,4-tetrahydroquinolyl))-prop-2-enamide. Analogous to the procedure described for Example 19, steps (b)-(c), 1-methyl-7-nitro-1,2,3,4-tetrahydroquinoline, Example 20(a), (240 mg, 1.3 mmol) and 4-tert-butyl-trans-cinnamic acid (0.23 g, 1.1 mmol, EMKA-Chemie) provided, after purification by silica gel chromatography (4:1 hexane:EtOAc) then recrystallization from EtOAc and hexane, the title product as a yellow solid. MP 200-202° C. MS (ESI, pos. ion) m/z: 349 (M+1).

EXAMPLE 21

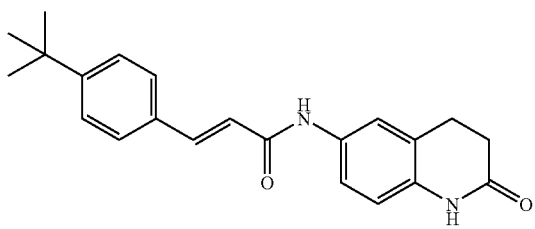

(2E)-3-[4-(tert-Butyl)phenyl]-N-(2-oxo(6-1,3,4-trihydroquinolyl))prop-2-enamide

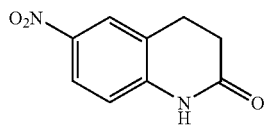

(a) 6-Nitro-1,3,4-trihydroquinolin-2-one. To a round-bottomed flask equipped with magnetic stirring was added 3,4-dihydro-2(1H)-quinolinone (1.47 g, 10 mmol, Aldrich) and 96% $H_2SO_4$ (8.3 mL). The mixture was stirred until all of the material was dissolved, then cooled to 0° C. and treated with $KNO_3$ (1.2 g, 11.7 mmol) in portions. The reaction mixture was allowed to warm to 25° C. and stirred at that temperature overnight. The mixture was basified to pH 9 with 35% NaOH, resulting in a precipitate. The solid was collected by filtration, washed with water and dried in vacuo at 50° C. to provide the title product as a yellow solid. MS (ESI, pos. ion) m/z: 193 (M+1).

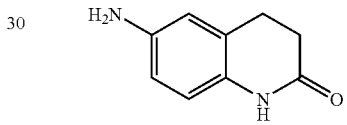

(b) 6-Amino-1,3,4-trihydroquinolin-2-one. Analogous to the procedure used to prepare Example 3(a), 6-nitro-1,3,4-trihydroquinolin-2-one, Example 21(a), (1.7 g, 8.9 mmol) was converted to the title product as a tan solid. MS (ESI, pos. ion) m/z: 163 (M+1).

(c) (2E)-3-[4-(tert-Butyl)phenyl]-N-(2-oxo(6-1,3,4-trihydroquinolyl))prop-2-enamide. Analogous to the procedure used to prepare Example 1, 6-amino-1,3,4-trihydroquinolin-2-one, Example 21(b), (0.68 g, 4.2 mmol) and 4-tert-butyl-trans-cinnamic acid (0.86 g, 4.2 mmol, EMKA-Chemie) provided, after recrystallization from MeOH, the title product as a pale yellow solid. MP 275-276° C. MS (ESI, pos. ion) m/z: 349 (M+1).

EXAMPLE 22

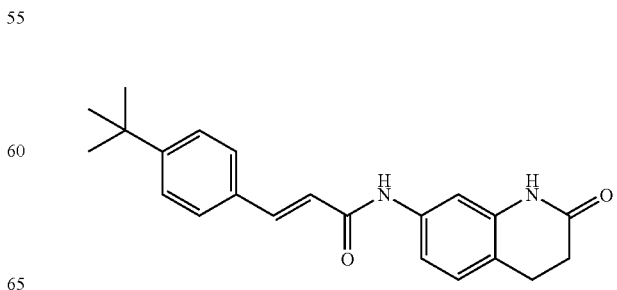

(2E)-3-[4-(tert-Butyl)phenyl]-N-(2-oxo(7-1,3,4-tri-hydroquinolyl))prop-2-enamide

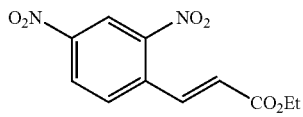

(a) Ethyl 3-(2,4-dinitrophenyl)prop-2-enoate. A suspension of sodium hydride (2.0 g, 50 mmol, 60% dispersion in mineral oil, Aldrich) in anhydrous THF (100 mL) was magnetically stirred under $N_2$ at 25° C. and treated dropwise with triethyl phosphonoacetate (10 mL, 11 g, 51 mmol, Aldrich). The reaction mixture was stirred for 1 h at 25° C. then treated with 2,4-dinitrobenzaldehyde (9.0 g, 46 mmol, Aldrich) in portions. After stirring overnight at 25° C., the reaction was quenched by the addition of water (50 mL) and concentrated in vacuo to remove the THF. The remaining aqueous mixture was extracted with EtOAc (2×150 mL). The combined organic extract was washed with water (4×100 mL), satd NaCl (75 mL), dried over $Na_2SO_4$, filtered and concentrated in vacuo. Purification by silica gel chromatography (1:4 hexane:EtOAc) provided the title product as a dark oil.

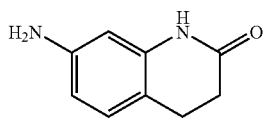

(b) 7-Amino-1,3,4-trihydroquinolin-2-one. Ethyl 3-(2,4-dinitrophenyl)prop-2-enoate, Example 22(a), (3.0 g, 11 mmol) was dissolved in glacial acetic acid (240 mL), treated with 10% Pd on carbon (2.4 g, Aldrich) and hydrogenated on a Parr shaker apparatus at 65° C., under 60 psi $H_2$, for 3 h. The reaction mixture was allowed to cool to 25° C., purged with $N_2$, filtered through Celite and the filtercake washed with acetic acid (200 mL) and EtOH (200 mL). The combined filtrate was concentrated in vacuo, then treated with 1 N NaOH (150 mL) and extracted with EtOAc (3×100 mL). The combined organic extract was washed with satd NaCl (50 mL), dried over $Na_2SO_4$, filtered and concentrated in vacuo. Purification by silica gel chromatography (EtOAc) provided the title product as a pale yellow solid. MS (ESI, pos. ion) m/z: 163 (M+1).

(c) (2E)-3-[4-(tert-Butyl)phenyl]-N-(2-oxo(7-1,3,4-trihydroquinolyl))prop-2-enamide. Analogous to the procedure used to prepare Example 1, 7-amino-1,3,4-trihydroquinolin-2-one, Example 22(b), (300 mg, 1.8 mmol) and 4-tert-butyl-trans-cinnamic acid (370 mg, 1.8 mmol, EMKA-Chemie) provided the title product as white crystals. MP 288-290° C. MS (ESI, pos. ion) m/z: 349 (M+1).

EXAMPLE 23

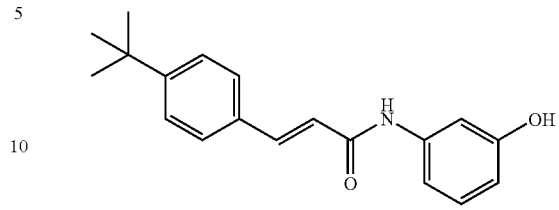

(2E)-3-[4-(tert-Butyl)phenyl]-N-(3-hydroxyphenyl)prop-2-enamide. To a round-bottomed flask equipped with magnetic stirring was added 4-tert-butyl-trans-cinnamic acid (530 mg, 2.43 mmol, EMKA-Chemie), $CH_2Cl_2$ (10 mL), and DMF (10 uL, Aldrich) under $N_2$. The solution was treated dropwise with oxalyl chloride (3.0 mL, 6.0 mmol, 2.0 M in $CH_2Cl_2$, Aldrich) then stirred at 25° C. for 1 h. The reaction mixture was concentrated in vacuo and treated with 3-aminophenol (265 mg, 2.43 mmol, Aldrich), THF (20 mL) and satd $K_2CO_3$ (15 mL). The reaction mixture was stirred at 25° C. overnight, then acidified to pH~4.5 with 1 N HCl. The mixture was extracted with EtOAc (2×30 mL), the combined organic extract was dried and concentrated in vacuo. Purification by silica gel chromatography (2:1 hexane:EtOAc) provided the title product as an oil. MS (ESI, pos. ion) m/z: 296 (M+1).

EXAMPLE 24

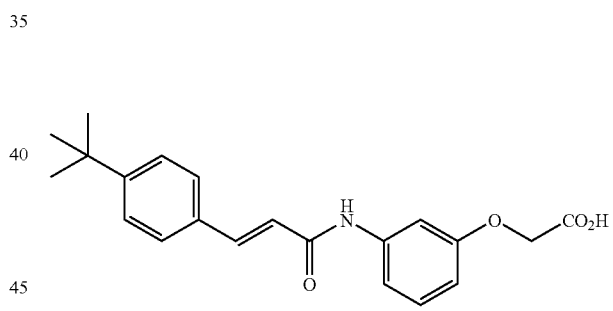

2-(3-{(2E)-3-[4-(tert-Butyl)phenyl]prop-2-enoylamino}phenoxy)acetic acid

To a round-bottomed flask equipped with magnetic stirring was added (2E)-3-[4-(tert-butyl)phenyl]-N-(3-hydroxyphenyl)prop-2-enamide, Example 23, (120 mg, 0.407 mmol), THF (10 mL), tert-butyl bromoacetate (60 uL, 0.407 mmol, Aldrich) and 5 N NaOH (10 mL). The reaction mixture was stirred at 25° C. overnight. The mixture was extracted with EtOAc (20 mL), the organic extract washed with water (20 mL), dried over $Na_2SO_4$, filtered and concentrated in vacuo. The resulting residue was treated with trifluoroacetic acid (10 mL), stirred at 25° C. for 2 h, then concentrated in vacuo. Purification by silica gel chromatography (1:2 hexane:EtOAc) provided the title product as an off-white solid. MP 166-172° C. MS (ESI, pos. ion) m/z: 354 (M+1).

EXAMPLE 25

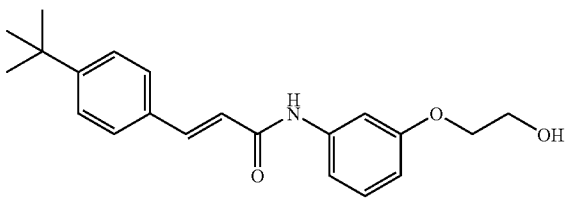

(2E)-3-[4-(tert-Butyl)phenyl]-N-[3-(2-hydroxyethoxy)phenyl]prop-2-enamide

To a round-bottomed flask, equipped with magnetic stirring and reflux condenser, was added (2E)-3-[4-(tert-butyl)phenyl]-N-(3-hydroxyphenyl)prop-2-enamide, Example 23, (200 mg, 0.68 mmol), THF (10 mL), 2-bromoethanol (200 uL, 2.80 mmol, Aldrich) and 5 N NaOH (10 mL). The reaction mixture was stirred at reflux for 5 h. After allowing to cool to 25° C., the mixture was extracted with EtOAc (20 mL). The organic extract was washed with water (20 mL), dried over $Na_2SO_4$, filtered and concentrated in vacuo. Purification by silica gel chromatography (2:1 hexane:EtOAc) provided the title product as a colorless oil. MS (ESI, pos. ion) m/z: 340 (M+1).

EXAMPLE 26

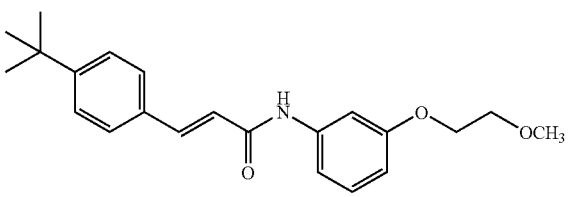

(2E)-3-[4-(tert-Butyl)phenyl]-N-[3-(2-methoxyethoxy)phenyl]prop-2-enamide

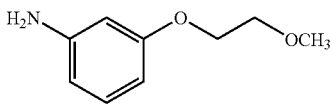

(a) 3-(2-Methoxyethoxy)phenylamine. To a round-bottomed flask equipped with magnetic stirring was added 3-aminophenol (1.2 g, 11 mmol, Aldrich), THF (15 mL) and sodium hydride (440 mg, 11 mmol, 60% in mineral oil, Aldrich) at 0° C. The reaction mixture was allowed to stir at 0° C. for 30 min, then 2-bromoethyl methyl ether (1.0 mL, 11 mmol, Aldrich) was added dropwise. The reaction mixture was stirred at 25° C. overnight, then cooled to 0° C. and quenched with satd NaCl (10 mL). The mixture was extracted with EtOAc (20 mL) and the organic phase was washed with water (20 mL), dried over $Na_2SO_4$, filtered and concentrated in vacuo to provide the title product. MS (ESI, pos. ion) m/z: 168 (M+1).

(b) (2E)-3-[4-(tert-Butyl)phenyl]-N-[3-(2-methoxyethoxy)phenyl]prop-2-enamide. Analogous to the procedure used to prepare Example 2, 3-(2-methoxyethoxy)phenylamine, Example 26(a), (350 mg, 2.45 mmol) and 4-tert-butyl-trans-cinnamic acid (500 mg, 2.45 mmol, EMKA-Chemie) provided, after purification by silica gel chromatography (5:1 hexane:EtOAc), the title product as a colorless oil. MS (ESI, pos. ion) m/z: 354 (M+1).

EXAMPLE 27

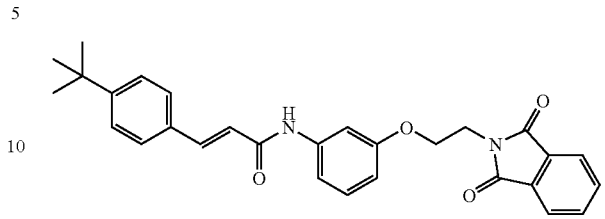

(2E)-3-[4-(tert-Butyl)phenyl]-N-{3-[2-(1,3-dioxobenzo[c]azolin-2-yl)ethoxy]phenyl}prop-2-enamide

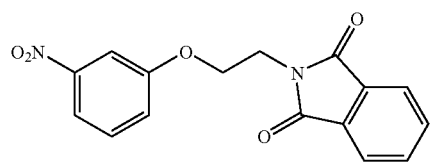

(a) 2-[2-(3-Nitrophenoxy)ethyl]benzo[c]azoline-1,3-dione. To a round-bottomed flask, equipped with magnetic stirring, an addition funnel and a reflux condenser, was added 3-nitrophenol (2.0 g, 14 mmol, Fluka), triphenylphosphine (4.9 g, 19 mmol, Aldrich) and DMF (20 mL). A solution of N-[2-hydroxyethyl]phthalimide (2.7 mg, 14 mmol, Aldrich) and diethyl azodicarboxylate (3.3 g, 19 mmol, Aldrich) in DMF (20 mL) was added dropwise through the addition funnel at 25° C. The reaction mixture was stirred at 60° C. for 12 h. The reaction mixture was concentrated in vacuo, dissolved in EtOAc (55 mL), and washed with satd NaCl (20 mL) and water (20 mL). The organic phase was dried over $Na_2SO_4$, filtered and concentrated in vacuo. Purification by silica gel chromatography (2:1 hexane:EtOAc) provided the title product. MS (ESI, pos. ion) m/z: 313 (M+1).

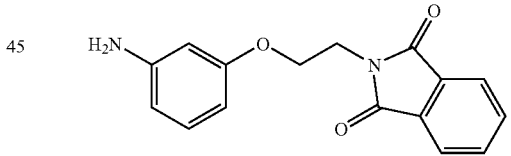

(b) 2-[2-(3-Aminophenoxy)ethyl]benzo[c]azoline-1,3-dione. In a round-bottomed flask, equipped with magnetic stirring, a solution of 2-[2-(3-nitrophenoxy)ethyl]benzo[c]azoline-1,3-dione, Example 27(a), (1.9 g, 6.1 mmol) in 0.5% acetic acid in EtOAc (10 mL), under $N_2$, was treated with 10% Pd on carbon (500 mg, Aldrich). The suspension was purged with $H_2$ and stirred under 1 atm $H_2$ at 25° C. overnight. The suspension was purged with $N_2$ and filtered through a pad of Celite. The solvent was removed in vacuo to provide the title product.

(c) (2E)-3-[4-(tert-Butyl)phenyl]-N-{3-[2-(1,3-dioxobenzo[c]azolin-2-yl)ethoxy]phenyl}prop-2-enamide. Analogous to the procedure used to prepare Example 2, 2-[2-(3-aminophenoxy)ethyl]benzo[c]azoline-1,3-dione, Example 27(b), (1.7 g, 6.1 mmol) and 4-tert-butyl-trans-cinnamic acid (1.2 g, 6.0 mmol, EMKA-Chemie) provided, after purification by silica gel chromatography (3:1 hexane: EtOAc), the title product as an off-white film. MS (ESI, pos. ion) m/z: 469 (M+1).

EXAMPLE 28

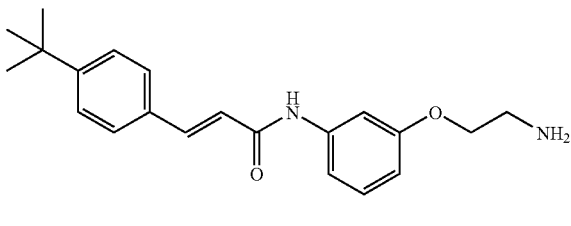

(2E)-N-[3-(2-Aminoethoxy)phenyl]-3-[4-(tert-butyl)phenyl]prop-2-enamide

To a round-bottomed flask equipped with magnetic stirring was added Example 27, (2E)-3-[4-(tert-butyl)phenyl]-N-{3-[2-(1,3-dioxobenzo[c]azolin-2-yl)ethoxy]phenyl}prop-2-enamide, (856 mg, 1.83 mmol), EtOH (15 mL) and hydrazine (574 uL, 18.3 mmol, Aldrich). The reaction mixture was stirred at 25° C. for 2 h. The mixture was concentrated in vacuo, the residue dissolved in EtOAc (40 mL), washed with 10% $K_2CO_3$ (15 mL), water (15 mL), dried over $Na_2SO_4$, filtered and concentrated in vacuo. Purification by silica gel chromatography (step gradient, EtOAc followed by 1:1 EtOAc:EtOH) provided the title product as an oil. MS (ESI, pos. ion) m/z: 339 (M+1).

EXAMPLE 29

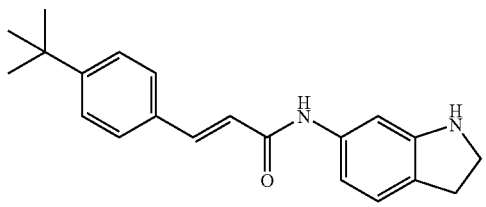

(2E)-3-[4-(tert-Butyl)phenyl]-N-indolin-6-ylprop-2-enamide

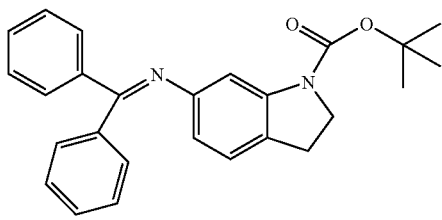

(a) tert-Butyl 6-(1-aza-2,2-diphenylvinyl)indolinecarboxylate. To a solution of benzophenone imine (0.91 g, 5.0 mmol, Aldrich) in $CH_2Cl_2$ (35 mL), magnetically stirred at 25° C. in a round-bottomed flask, was added a solution of 6-aminoindoline dihydrochloride (1.04 g, 5.0 mmol, Biosynth AG) in $CH_2Cl_2$ (40 mL). The reaction mixture was stirred at 25° C. for 12 h, then diluted with $CH_2Cl_2$ (30 mL), washed with water (30 mL), satd NaCl (30 mL), dried over $MgSO_4$, filtered and concentrated in vacuo. The crude product [MS (ESI, pos. ion) m/z: 299 (M+1)] was dissolved in 1,4-dioxane and treated with di-tert-butyl dicarbonate (8.0 mL, 8.0 mmol, 1.0 M in THF, Aldrich) and 5 N aq. $Na_2CO_3$ (5 mL). The reaction mixture was magnetically stirred at 25° C. until complete, then diluted with water (30 mL), and extracted with EtOAc (3×30 mL). The combined organic extract was washed with satd NaCl (30 mL), dried over $MgSO_4$, filtered and concentrated in vacuo. Purification by silica gel chromatography (4:1 hexane EtOAc) provided the title product. MS (ESI, pos. ion) m/z: 399 (M+1).

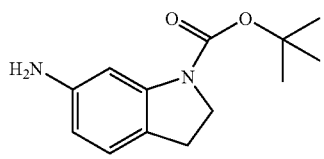

(b) tert-Butyl 6-aminoindolinecarboxylate. In a round-bottomed flask, a solution of tert-butyl 6-(1-aza-2,2-diphenylvinyl)indolinecarboxylate, Example 29(a), (0.80 g, 2.0 mmol) in 1,4-dioxane (10 mL) was treated with 1 N aq. HCl (10 mL). The reaction mixture was magnetically stirred overnight at 25° C., then diluted with water (20 mL) and extracted with ethyl ether (30 mL). The aqueous phase was treated with 5 N NaOH (10 mL) and extracted with ethyl ether (3×30 mL). The combined organic extracts were dried over $MgSO_4$, filtered and concentrated in vacuo. Purification by silica gel chromatography (3:2 hexane EtOAc) provided the title product. MS (ESI, pos. ion) m/z: 235 (M+1).

(c) (2E)-3-[4-(tert-Butyl)phenyl]-N-indolin-6-ylprop-2-enamide. Analogous to the procedure used to prepare Example 1, tert-butyl 6-aminoindoline-carboxylate, Example 29(b), (230 mg, 1.0 mmol) and 4-tert-butyl cinnamic acid (200 mg, 1.0 mmol, EMKA-Chemie) provided, after purification by silica gel chromatography (7:3 hexane EtOAc), a crude product which was dissolved in $CH_2Cl_2$ (5 mL) and treated with 4 N HCl in dioxane (5 mL, Aldrich). The reaction mixture was magnetically stirred at 25° C. for 1 h, then washed with 5 N NaOH (15 mL), satd NaCl (15 mL), dried over $MgSO_4$, filtered and concentrated in vacuo. Purification by silica gel chromatography (55:45 hexane EtOAc) provided the title product. MP 153-167° C. MS (ESI, pos. ion) m/z: 321 (M+1).

EXAMPLE 30

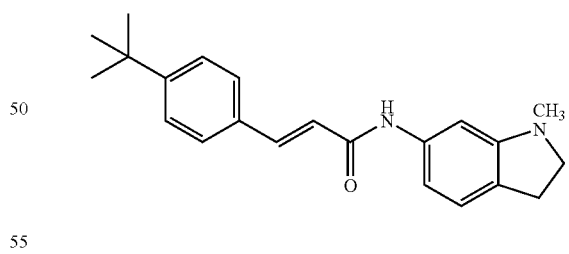

(2E)-3-[4-(tert-Butyl)phenyl]-N-(1-methylindolin-6-yl)prop-2-enamide

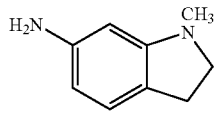

(a) 1-Methylindoline-6-ylamine. To a round-bottomed flask was added 6-nitroindoline (1.64 g, 10.0 mmol, Aldrich), 37% aq. formaldehyde (2.35 g, 30.0 mmol, Aldrich) and THF (40 mL). The reaction mixture was magnetically stirred at 25° C. and treated with sodium cyanoborohydride (1.89 g, 30.0 mmol, Aldrich). The reaction mixture was allowed to stir at 25° C. for 30 min, then washed with satd $Na_2CO_3$. The aqueous phase was extracted with ethyl ether, the organic phases combined and concentrated in vacuo to a residue. Analogous to the procedure of Goswami, P.; Chowdhury, P.; Indian J Chem, Sect B, 1997, 36 (2), 185-186, the crude residue was dissolved in tetrahydrofuran (60 mL) and added to Zn dust (0.43 g, 6.6 mmol, Aldrich) and $AlCl_3.6H_2O$ (9.6 g, 40 mmol, Aldrich) in water (2 mL), magnetically stirred at 25° C. The reaction mixture was stirred at 25° C. for 16 h, then filtered. The filtrate was added to cold water (300 mL) and extracted with $CH_2Cl_2$ (3×100 mL). The combined organic extract was concentrated in vacuo to provide the title product as a brown solid. MS (ESI, pos. ion) m/z: 149 (M+1).

(b) (2E)-3-[4-(tert-Butyl)phenyl]-N-(1-methylindolin-6-yl)prop-2-enamide. Analogous to the procedure used to prepare Example 1, 1-methylindoline-6-ylamine, Example 30(a), (150 mg, 1.0 mmol) and 4-tert-butyl-trans-cinnamic acid (200 mg, 1.0 mmol, EMKA-Chemie) provided the title product as an amorphous yellow solid. MS (ESI, pos. ion) m/z: 335 (M+1).

EXAMPLE 31

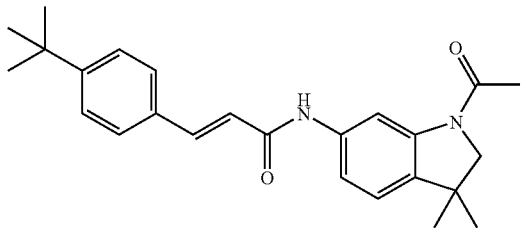

(2E)-N-(1-Acetyl-3,3-dimethylindolin-6-yl)-3-[4-(tert-butyl)phenyl]prop-2-enamide

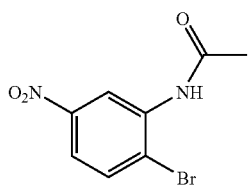

(a) N-(2-Bromo-5-nitrophenyl)acetamide. A solution of 2-bromo-5-nitroaniline (43 g, 0.20 mol, Aldrich) in glacial acetic acid (1.3 L), magnetically stirred at 25° C., was treated with acetic anhydride (20 mL, 0.21 mol). The reaction mixture was allowed to stir at 25° C. overnight, then quenched by pouring into water (6 L). The precipitate was collected by filtration, washed with water, and dried in vacuo to provide the title product as an off white solid. MS (ESI, pos. ion) m/z: 259, 262 (M+1, M+3).

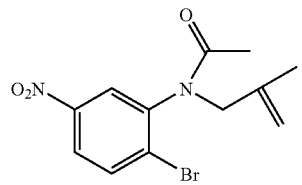

(b) N-(2-Bromo-5-nitrophenyl)-N-(2-methylprop-2-enyl)acetamide. To a flame-dried round-bottomed flask, equipped with magnetic stirring and an addition funnel, was added N-(2-bromo-5-nitrophenyl)acetamide, Example 31(a), (48 g, 0.19 mol), solid potassium carbonate (103 g, 744 mmol) and anhydrous DMF (830 mL). The resulting solution was stirred at 25° C. and treated dropwise, through the addition funnel, with a solution of 3-bromo-2-methylpropene (38 mL, 380 mmol, Aldrich) in anhydrous DMF (100 mL) over 45 min. The reaction mixture was stirred at 25° C. overnight, then filtered and treated with satd $NaHCO_3$. The organic layer was removed and the aqueous layer was extracted with EtOAc (3×150 mL). The combined organic extracts were washed with water (4×70 mL), satd NaCl (70 mL), dried over $MgSO_4$, filtered and concentrated in vacuo to provide the title product as a golden solid. MS (ESI, pos. ion) m/z: 313, 315 (M+1, M+3).

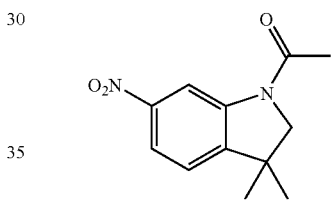

(c). 1-Acetyl-3,3-dimethyl-6-nitroindoline. To a flame-dried round-bottomed flask, equipped with magnetic stirring, was added N-(2-bromo-5-nitrophenyl)-N-(2-methylprop-2-enyl)acetamide, Example 31(b), (55 g, 0.18 mol), tetraethylammonium chloride hydrate (30.8 g, 186 mmol, Aldrich), sodium formate (14.4 g, 212 mmol, Aldrich), sodium acetate (36.3 g, 443 mmol) and anhydrous DMF (443 mL). The resulting solution was purged with $N_2$ and treated with palladium (II) acetate (3.97 g, 17.7 mmol, Aldrich). The reaction mixture was stirred in an oil bath at 80° C. for 15 h, then allowed to cool to 25° C. and filtered through a pad of Celite. The Celite was washed with EtOAc and the combined filtrate was washed with satd $NaHCO_3$ (500 mL). The aqueous layer was extracted with EtOAc (3×100 mL) and the combined organic extract was washed with water (4×100 mL), satd NaCl (2×100 mL), dried over $MgSO_4$, filtered and concentrated in vacuo to provide 1-acetyl-3,3-dimethyl-6-nitroindoline as a brown solid. MS (ESI, pos. ion) m/z: 235 (M+1).

(d) (2E)-N-(1-Acetyl-3,3-dimethylindolin-6-yl)-3-[4-(tert-butyl)phenyl]prop-2-enamide. To a solution of 1-acetyl-3,3-dimethyl-6-nitroindoline, Example 31(c), (110 mg, 0.47 mmol) in ethyl ether (3 mL), magnetically stirred in a round-bottomed flask at 0° C., was added tin (II) chloride dihydrate (0.67 g, 2.96 mmol, Aldrich) and cond HCl (0.3 mL). The reaction mixture was stirred at 0° C. for 10 min, allowed to warm to 25° C. then stirred at that temperature overnight. The reaction mixture was washed with 10 N NaOH (10 mL), extracted with EtOAc and concentrated in vacuo. Analogous to the procedure used to prepare Example 1, the crude product and 4-tert-butyl-trans-cinnamic acid (92 mg, 0.45 mmol, EMKA-Chemie) provided, after purification by silica gel chromatography (2:3 hexane:EtOAc), the title product. MP 121° C. MS (ESI, pos. ion) m/z: 391 (M+1).

EXAMPLE 32

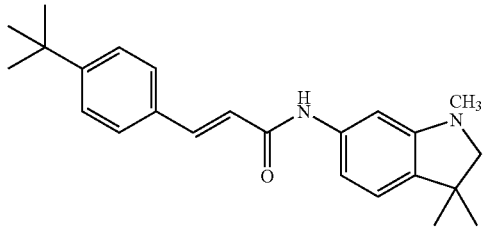

(2E)-3-[4-(tert-Butyl)phenyl]-N-(1,3,3-trimethylindolin-6-yl)prop-2-enamide

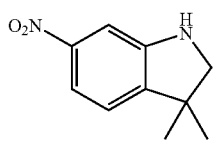

(a) 3,3-Dimethyl-6-nitroindoline. To a round-bottomed flask, equipped with magnetic stirring and a reflux condenser, was added 1-acetyl-3,3-dimethyl-6-nitroindoline, Example 31(c), (1.73 g, 7.39 mmol) and EtOH (20 mL). The solution was treated with 12 N HCl (20 mL) then stirred and heated at reflux for 2 h. The reaction mixture was cooled to 0° C., providing a precipitate which was collected by filtration and dried in vacuo to afford the title product as an off-white solid. MS (ESI, pos. ion) m/z: 193 (M+1).

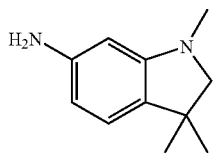

(b) 1,3,3-Trimethylindoline-6-ylamine. A solution of 3,3-dimethyl-6-nitroindoline, Example 32(a), (0.23 g, 1.2 mmol) in anhydrous DMF (15 mL) was magnetically stirred at 25° C. and treated with sodium hydride (0.14 g, 3.6 mmol, 60% dispersion in mineral oil, Aldrich), followed by iodomethane (0.17, 1.3 mmol, Aldrich). The reaction mixture was stirred at 25° C. for 3 h, then quenched with water (40 mL) and extracted with EtOAc (3×30 mL). The combined extract was concentrated in vacuo to provide a residue [MS (ESI, pos. ion) m/z: 207 (M+1)] which was immediately dissolved in ethyl ether (5 mL), magnetically stirred at 0° C., and treated with tin (II) chloride dihydrate (1.7 g, 7.5 mmol, Aldrich) and cond HCl (0.8 mL). The reaction mixture was stirred at 0° C. for 10 min, allowed to warm to 25° C., then stirred at that temperature overnight. The reaction mixture was washed with 10 N NaOH (20 mL) and extracted with EtOAc (3×50 mL). The combined extracts were concentrated in vacuo and purified by silica gel chromatography to provide the title product. MS (ESI, pos. ion) m/z: 177 (M+1).

(c) (2E)-3-[4-(tert-Butyl)phenyl]-N-(1,3,3-trimethylindolin-6-yl)prop-2-enamide. Analogous to the procedure used to prepare Example 1, 1,3,3-trimethylindoline-6-ylamine, Example 32(b), (176 mg, 1.0 mmol) and 4-tert-butyl-trans-cinnamic acid (200 mg, 1.0 mmol, EMKA-Chemie) provided, after purification by silica gel chromatography (3:2 hexane:EtOAc), the title product. MP 90-101° C. MS (ESI, pos. ion) m/z: 363 (M+1).

EXAMPLE 33

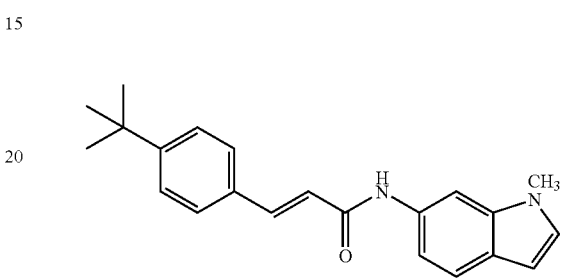

(2E)-3-[4-(tert-Butyl)phenyl]-N-(1-methylindol-6-yl)prop-2-enamide

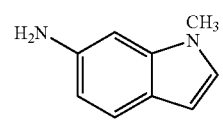

(a) 1-Methylindole-6-ylamine. To a round-bottomed flask was added 6-nitroindole (0.81 g, 5.0 mmol, Aldrich) and anhydrous DMF (40 mL). The solution was stirred magnetically and treated with sodium hydride (0.40 g, 10 mmol, 60% dispersion in mineral oil, Aldrich) followed by iodomethane (0.71 gm 10 mmol, Aldrich). Stirring was continued at 25° C. for 30 min, then the reaction mixture was quenched by the addition of water (75 mL) and extracted with EtOAc. The organic extract was concentrated in vacuo to provide a residue which was dissolved in EtOH (40 mL), treated with 10% Pd on carbon (400 mg, Aldrich), purged with $H_2$ and magnetically stirred under 1 atm $H_2$ for 4 h. The suspension was purged with $N_2$, filtered through a pad of Celite and concentrated in vacuo. Purification by silica gel chromatography (50:50 hexane:EtOAc) provided the aniline. MS (ESI, pos. ion) m/z: 147 (M+1).

(b) (2E)-3-[4-(tert-Butyl)phenyl]-N-(1-methylindol-6-yl)prop-2-enamide. Analogous to the procedure used to prepare Example 1, 1-methylindole-6-ylamine, Example 33(a), (150 mg, 1.0 mmol) and 4-tert-butyl-trans-cinnamic acid (200 mg, 1.0 mmol), after purification by silica gel chromatography (65:35 hexane:EtOAc), provided the title product as a yellow solid. MP 95° C. MS (ESI, pos. ion) m/z: 333 (M+1).

EXAMPLE 34

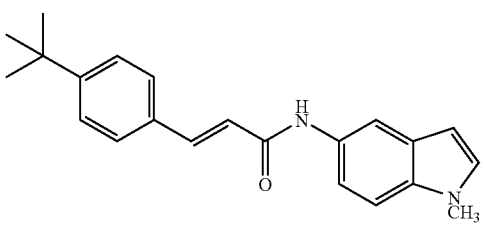

(2E)-3-[4-(tert-Butyl)phenyl]-N-(1-methylindol-5-yl)prop-2-enamide

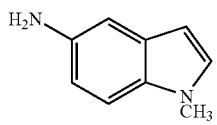

(a) 1-Methylindole-5-ylamine. To a round-bottomed flask was added 5-nitroindole (0.81 g, 5.0 mmol, Aldrich) and anhydrous DMF (40 mL). The solution was stirred magnetically and treated with sodium hydride (0.40 g, 10 mmol, 60% dispersion in mineral oil, Aldrich) followed by iodomethane (0.71 gm 10 mmol, Aldrich). Stirring was continued at 25° C. for 30 min, then the reaction mixture was quenched by the addition of water (75 mL) and extracted with EtOAc. The organic extract was concentrated in vacuo to provide a crude residue. Analogous to the procedure of Goswami, P.; Chowdhury, P.; *Indian J Chem, Sect B,* 1997, 36 (2), 185-186, the crude residue was dissolved in THF (40 mL) and added to Zn dust (0.22 g, 3.3 mmol, Aldrich) and $AlCl_3.6H_2O$ (4.78 g, 19.8 mmol, Aldrich) in water (1 mL), magnetically stirred at 25° C. The reaction mixture was stirred at 25° C. for 16 h, then filtered. The filtrate was added to cold water (300 mL) and extracted with $CH_2Cl_2$ (3×100 mL). The combined organic extract was concentrated in vacuo to provide the title product. MS (ESI, pos. ion) m/z: 147 (M+1).

(b) (2E)-3-[4-(tert-Butyl)phenyl]-N-(1-methylindol-5-yl)prop-2-enamide. Analogous to the procedure used to prepare Example 1, 1-methylindole-5-ylamine, Example 34(a), (150 mg, 1.0 mmol) and 4-tert-butyl-trans-cinnamic acid (200 mg, 1.0 mmol, EMKA-Chemie) provided, after purification by silica gel chromatography (65:35 hexane:EtOAc), the title product as a crystalline yellow solid. MP 171° C. MS (ESI, pos. ion) m/z: 333 (M+1).

EXAMPLE 35

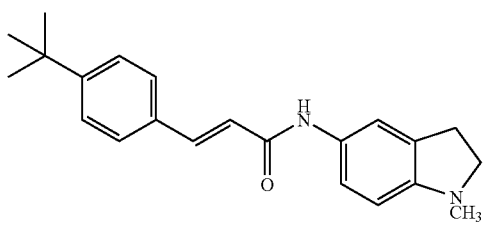

(2E)-3-[4-(tert-Butyl)phenyl]-N-(1-methylindolin-5-yl)prop-2-enamide

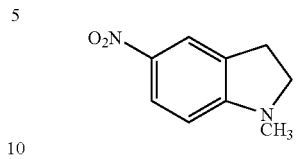

(a) 1-Methyl-5-nitroindoline. To a round-bottomed flask equipped with magnetic stirring was added 5-nitroindoline (0.82, 5.0 mmol, Aldrich), iodomethane (0.71g, 5.0 mmol, Aldrich), sodium hydroxide (0.24, 6 mmol) and DMF (20 mL). The reaction mixture was stirred at 25° C. for 3 h, diluted with water (50 mL), extracted with EtOAc (3×40 mL) and the combined extracts were concentrated in vacuo. Purification by silica gel chromatography 97:3 hexane:EtOAc) provided the title product. MS (ESI, pos. ion) m/z: 179 (M+1).

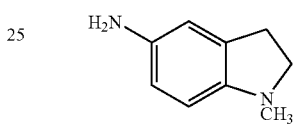

(b) 1-Methylindoline-5-ylamine. To a solution of 1-methyl-5-nitroindoline, Example 35(a), (0.55 g, 3.1 mmol) in ethyl ether (20 mL), magnetically stirred in a round-bottomed flask at 0° C., was added tin (II) chloride dihydrate (4.5 g, 20 mmol, Aldrich) and cond HCl (2.5 mL). The reaction mixture was stirred at 0° C. for 10 min, allowed to warm to 25° C. then stirred at that temperature overnight. The reaction mixture was washed with 10N NaOH (30 mL) and the aqueous phase extracted with EtOAc (3×20 mL). The combined organic extracts were concentrated in vacuo. Purification by silica gel chromatography (55:45 hexane:EtOAc) provided the aniline. MS (ESI, pos. ion) m/z: 149 (M+1).

(c) (2E)-3-[4-(tert-Butyl)phenyl]-N-(1-methylindolin-5-yl)prop-2-enamide. Analogous to the procedure used to prepare Example 1, 1-methylindoline-5-ylamine, Example 35(b), (150, 1.0 mmol) and 4-tert-butyl-trans-cinnamic acid (200 mg, 1.0 mmol, EMKA-Chemie) provided, after purification by silica gel chromatography (60:40 hexane:EtOAc), the title product as a crystalline yellow solid. MP 194° C. MS (ESI, pos. ion) m/z: 335 (M+1).

EXAMPLE 36

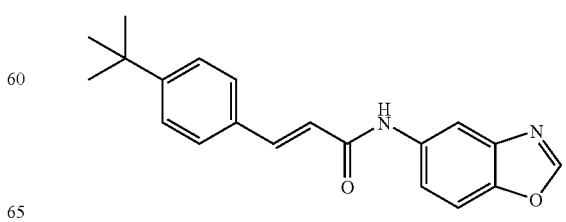

(2E)-N-Benzoxazol-5-yl-3-[4-(tert-butyl)phenyl]
prop-2-enamide

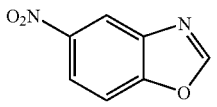

(a) 5-Nitrobenzoxazole. Following the procedure of A. R. Katritzky et al. *Heterocycles* 1995, 41, 345, to a round-bottomed flask was added 2-amino-4-nitrophenol (5.0 g, 32 mmol, Aldrich), trimethyl orthoformate (20 mL, 180 mmol, Aldrich) and p-toluenesulfonic acid monohydrate (300 mg, 1.6 mmol, Aldrich). The reaction mixture was magnetically stirred in a 95° C. oil bath for 1 h, and then allowed to cool to 25° C. The mixture was cooled to 0° C. to provide a precipitate which was collected by filtration, washed with cold toluene, pentane, then dried in vacuo to afford the title product as a dark brown powder.

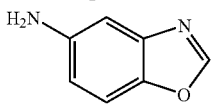

(b) Benzoxazole-5-ylamine. Analogous to the procedure used to prepare Example 3(a), 5-nitrobenzoxazole, Example 36(a), (2.4 g, 15 mmol) provided, after purification by silica gel chromatography (step gradient, 7:3 then 4.5:5.5 then 3:7 hexane:EtOAc), the title product. MS (ESI, pos. ion) m/z: 135 (M+1).

(c) (2E)-N-Benzoxazol-5-yl-3-[4-(tert-butyl)phenyl]prop-2-enamide. Analogous to the procedure used to prepare Example 1, benzoxazole-5-ylamine, Example 36(b), (530 mg, 4.0 mmol) and 4-tert-butyl-trans-cinnamic acid (820 mg, 4.0 mmol, EMKA-Chemie) provided, after twice being purified by silica gel chromatography (7:3 hexane:EtOAc then 1.25% MeOH in $CH_2Cl_2$), the title product as white crystals. MP 177° C. MS (ESI, pos. ion) m/z: 321 (M+1).

EXAMPLE 37

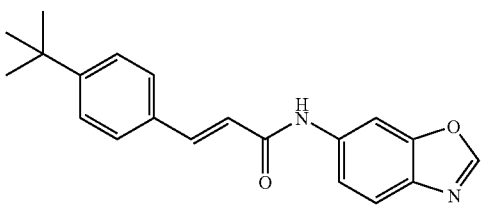

(2E)-N-Benzoxazol-6-yl-3-[4-(tert-butyl)phenyl]
prop-2-enamide

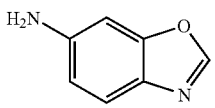

(a) Benzoxazole-6-ylamine. Analogous to the procedure described for the preparation of Example 36, steps (a)-(b), 2-amino-5-nitrophenol (5.0 g, 32 mmol, Aldrich) provided the title product as a pale tan solid. MS (ESI, pos. ion) m/z: 135 (M+1).

(b) (2E)-N-Benzoxazol-6-yl-3-[4-(tert-butyl)phenyl]prop-2-enamide. Analogous to the procedure used to prepare Example 1, benzoxazole-6-ylamine, Example 37(a), (1.8 g, 13 mmol) and 4-tert-butyl-trans-cinnamic acid (2.7 g, 13 mmol, EMKA-Chemie) provided, after purification by silica gel chromatography (6:4:0.2 $CH_2Cl_2$:hexane:MeOH), the title product as a tan solid. MP 147-148° C. MS (ESI, pos. ion) m/z: 321 (M+1).

EXAMPLE 38

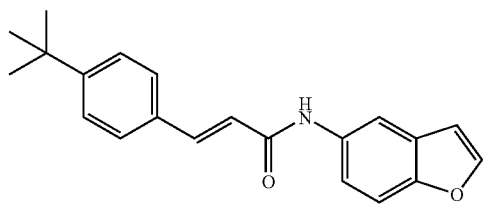

(2E)-N-Benzo[b]furan-5-yl-3-[4-(tert-butyl)phenyl]
prop-2-enamide

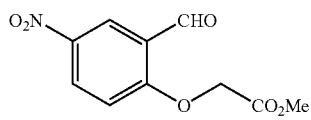

(a) Methyl 2-(2-formyl-4-nitrophenoxy)acetate. To a round-bottomed flask was added a suspension of 2-hydroxy-5-nitrobenzaldehyde (10 g, 60 mmol, Aldrich) in anhydrous EtOH (180 mL). The suspension was treated with KOH (4.4 g, 66 mmol) and heated under $N_2$ with magnetic stirring in a 65° C. oil bath for 45 min. The reaction mixture was allowed to cool to 25° C. and concentrated in vacuo. Anhydrous DMF (180 mL) was added, and the reaction flask was cooled in an ice bath and charged with methyl bromoacetate (10 mL, 110 mL, Aldrich). The reaction mixture was stirred for 3.5 h at 25° C., then the solvent was removed in vacuo. Water (200 mL) was added, and the mixture was extracted with EtOAc (3×50 mL). The combined organic extract was washed with 1 M $H_3PO_4$, satd $NaHCO_3$, and satd NaCl. After drying over $MgSO_4$, the organic layer was filtered and concentrated in vacuo. The residue was recrystallized from $CH_2Cl_2$ and hexane to afford the title product as a pale yellow solid. MS (ESI, pos. ion) m/z: 240 (M+1).

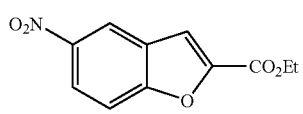

(b) Ethyl 5-nitrobenzo[d]furan-2-carboxylate. To a 250 mL round-bottomed flask was added methyl 2-(2-formyl-4-nitrophenoxy)acetate, Example 38(a), (5.3 g, 22 mmol), EtOH (110 mL) and 1,8-diazabicyclo[5.4.0]undec-7-ene (3.7 g, 24 mmol, Aldrich). The reaction mixture was magnetically stirred at 25° C. for 20 h, then concentrated to approximately half of its volume in vacuo. After cooling the mixture in an ice bath for 20 min, a precipitate formed which was collected by filtration and washed with ice cold EtOH. The resulting pale yellow solid was dried in vacuo to provide the title product. MS (ESI, pos. ion) m/z: 253 (M+$H_2O$).

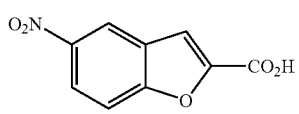

(c) 5-Nitrobenzo[b]furan-2-carboxylic acid. To a 250 mL round-bottomed flask was added ethyl 5-nitrobenzo[d]furan-2-carboxylate, Example 38(b), (1.0 g, 4.3 mmol), EtOH (10 mL), and KOH (610 mg, 11 mmol) in 10 mL of $H_2O$. The reaction mixture was stirred at 25° C. for 24 h, then treated with 1 M $H_3PO_4$ (200 mL) and saturated with solid NaCl. The aqueous layer was extracted with EtOAc (3×70 mL), and the combined organic extracts were washed with satd NaCl, dried over $MgSO_4$, filtered and concentrated in vacuo to provide the title product as a yellowish-white powder. MS (ESI, pos. ion) m/z: 225 (M+$H_2O$).

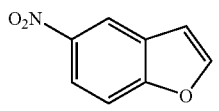

(d). 5-Nitrobenzofuran. To a 100 mL round-bottomed flask was added 5-nitrobenzo[b]furan-2-carboxylic acid, Example 38(c), (860 mg, 4.2 mmol), copper (830 mg, 13 mmol, Aldrich), and quinoline (38 mL, Aldrich). The reaction flask was placed in a 185° C. oil bath and magnetically stirred for 20 min under $N_2$. After allowing to cool to 25° C., the mixture was filtered through a 1" pad of Celite. To the filtrate was added 10% aq. HCl (300 mL) and the aqueous layer was extracted with $Et_2O$ (3×100 mL). The combined ethereal layers were washed with 10% HCl (4×200 mL, 1×100 mL), satd $NaHCO_3$ (200 mL), and satd NaCl (100 mL), dried over $MgSO_4$, filtered and concentrated in vacuo. Purification by silica gel chromatography (10:0.25 hexanes:EtOAc) provided 5-nitrobenzofuran as a white solid.

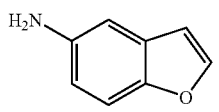

(e) Benzo[b]furan-5-ylamine. To a 150 mL round-bottomed flask was added 5-nitrobenzofuran, Example 38(d), (270 mg, 1.7 mmol) and ethyl ether (16 mL). The mixture was magnetically stirred at 0° C. under $N_2$ and treated with a solution of tin (II) chloride dihydrate (3.4 g, 15 mmol, Aldrich) in 12 M aq. HCl (2 mL). The reaction mixture was stirred at 0° C. for 10 min, then allowed to warm to 25° C. and stirred at that temperature for 20 h. Water and 2 N NaOH (pH>10) were added followed by Celite (10 g). The mixture was filtered through a pad of Celite and the filtrate extracted with EtOAc. The organic extract was washed with 2 N NaOH, satd NaCl, dried over $K_2CO_3$, filtered and concentrated in vacuo to provide the title product as a pale yellow oil. MS (ESI, pos. ion) m/z: 134 (M+1).

(f) (2E)-N-Benzo[b]furan-5-yl-3-[4-(tert-butyl)phenyl]prop-2-enamide. Analogous to the procedure used to prepare Example 1, benzo[b]furan-5-ylamine, Example 38(e), (230 mg, 1.7 mmol) and 4-tert-butyl-trans-cinnamic acid (350 mg, 1.7 mmol, EMKA-Chemie) provided, after purification by silica gel chromatography (9:1 hexane:EtOAc), the title product as white crystals. MP 149-150° C. MS (ESI, pos. ion) m/z: 320 (M+1).

EXAMPLE 39

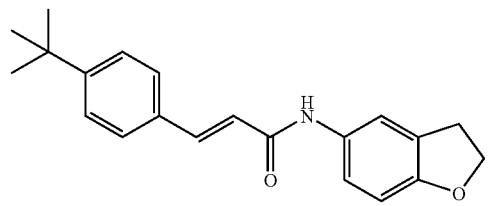

(2E)-3-[4-(tert-Butyl)phenyl]-N-(2,3-dihydrobenzo[b]furan-5-yl)prop-2-enamide

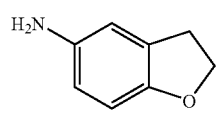

(a) 2,3-Dihydrobenzo[b]furan-5-ylamine. To a 150 mL round-bottomed flask was added 5-nitrobenzofuran, Example 38(d), (250 mg, 1.5 mmol), EtOAc (16 mL) and 10% Pd on carbon (33 mg, Aldrich). The suspension was stirred at 25° C. under 1 atm $H_2$ for 24 h, then purged with $N_2$, filtered through Celite and concentrated in vacuo to provide the aniline as a red-brown solid. MS (ESI, pos. ion) m/z: 136 (M+1).

(b) (2E)-3-[4-(tert-Butyl)phenyl]-N-(2,3-dihydrobenzo[b]furan-5-yl)prop-2-enamide. Analogous to the procedure used to prepare Example 1, 2,3-dihydrobenzo[b]furan-5-ylamine, Example 39(a), (240 mg, 1.8 mmol) and 4-tert-butyl-trans-cinnamic acid (370 mg, 1.8 mmol, EMKA-Chemie) provided the crude title product. The product was purified by silica gel chromatography (9:1:0.25 hexane:EtOAc:MeOH) to provide 45 mg of the title product and additional impure fractions. The impure fractions were combined and concentrated in vacuo. The residue was dissolved in MeOH (25 mL), treated with 5 N NaOH (10 mL) and stirred for 1 h. The mixture was diluted with 5 N NaOH (100 mL) and extracted with EtOAc. The organic phase was washed with 5 N NaOH (2×), 5% citric acid, satd NaCl, dried over $MgSO_4$, filtered and concentrated in vacuo. Purification by silica gel chromatography (8:1:0.5 hexane:EtOAc: 2 M $NH_3$ in MeOH) provided an additional the title product as a white solid. MP 175-176° C. MS (ESI, pos. ion) m/z: 322 (M+1).

EXAMPLE 40

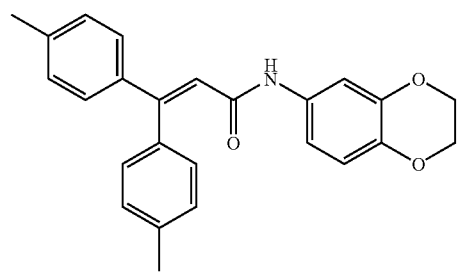

175

N-(2H,3H-Benzo[3,4-e]1,4-dioxan-6-yl)-3,3-bis(4-methylphenyl)prop-2-enamide

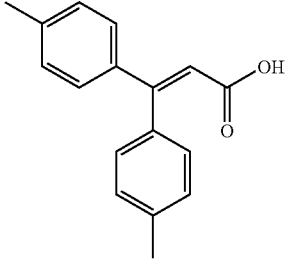

(a) 3,3-Bis(4-methylphenyl)prop-2-enoic acid. Triethyl phosphonoacetate (2.0 mL, 10 mmol, Aldrich) was added dropwise to a suspension of NaH (0.44 g, 11 mmol, 60% dispersion in mineral oil, Aldrich) in anhydrous THF (16 mL), magnetically stirred at 0° C. under Ar, in a round-bottomed flask equipped with a reflux condenser. The reaction mixture was allowed to warm to 25° C. then stirred at that temperature for 0.5 h. 4,4'-Dimethylbenzophenone (2.1 g, 10 mmol, Aldrich) was added in one portion and the reaction mixture stirred and heated at reflux for 48 h. After allowing to cool to 25° C., the reaction mixture was quenched with H$_2$O (30 mL) and extracted with Et$_2$O (4×10 mL). The combined organic extract was washed with H$_2$O (5 mL), dried over MgSO$_4$, filtered and concentrated in vacuo to an oily residue. The residue was dissolved in 1,4-dioxane (2.5 mL), treated with H$_2$O (7 mL) and KOH (1.1 g, 20 mmol), then stirred and heated at reflux under Ar for 18 h. The reaction mixture was allowed to cool to 25° C., diluted with H$_2$O (50 mL) and washed with Et$_2$O (10 mL). The aqueous phase was acidified with 1 N HCl and extracted with chloroform. The combined chloroform extracts were washed with satd NaCl, dried over MgSO$_4$, filtered and concentrated in vacuo to provide the acid as a white solid. MS (ESI, pos. ion) m/z: 253 (M+1).

(b) N-(2H,3H-Benzo[3,4-e]1,4-dioxan-6-yl)-3,3-bis(4-methylphenyl)prop-2-enamide. Analogous to the procedure used to prepare Example 1, 3,3-bis(4-methylphenyl)prop-2-enoic acid, Example 40(a), (0.50 g, 2.0 mmol) and 1,4-benzodioxan-6-amine (0.33 g, 2.2 mmol, Aldrich) provided, after purification by silica gel chromatography (chloroform), the title product as a yellow solid. MP 163-164° C. MS (ESI, pos. ion) m/z: 386 (M+1).

EXAMPLE 41

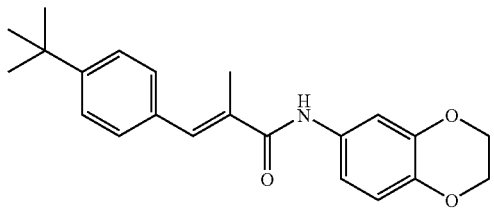

176

(2E)-N-(2H,3H-Benzo[3,4-e]1,4-dioxan-6-yl)-3-[4-(tert-butyl)phenyl]-2-methylprop-2-enamide

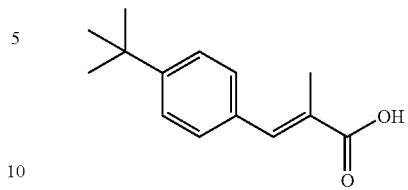

(a) (2E)-3-[4-(tert-Butyl)phenyl]-2-methylprop-2-enoic acid. Analogous to the procedure described for the preparation of Example 40, step (a), triethyl 2-phosphonopropionate (2.4 g, 10 mmol, Aldrich) and 4-tert-butylbenzaldehyde (1.6 g, 10 mmol, Aldrich) provided the title product as a yellow solid. MS (ESI, pos. ion) m/z: 219 (M+1).

(b) (2E)-N-(2H,3H-Benzo[3,4-e]1,4-dioxan-6-yl)-3-[4-(tert-butyl)phenyl]-2-methylprop-2-enamide. Analogous to the procedure used to prepare Example 1, (2E)-3-[4-(tert-butyl)phenyl]-2-methylprop-2-enoic acid, Example 41(a), (0.44 g, 2.0 mmol) and 1,4-benzodioxan-6-amine (0.33 g, 2.2 mmol, Aldrich) provided, after purification by silica gel chromatography (chloroform), the title product as an off-white solid. MP 157-158° C. MS (ESI, pos. ion) m/z: 352 (M+1).

EXAMPLE 42

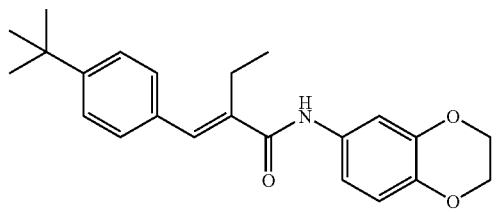

(2E)-N-(2H,3H-Benzo[3,4-e]1,4-dioxan-6-yl)-3-[4-(tert-butyl)phenyl]-2-ethylprop-2-enamide

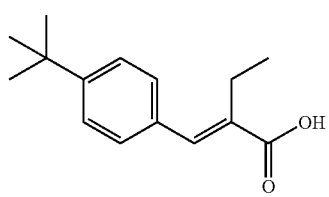

(a) (2E)-3-[4-(tert-Butyl)phenyl]-2-ethylprop-2-enoic acid. Analogous to the procedure described for the preparation of Example 40, step (a), triethyl 2-phosphonobutyrate (2.5 g, 10 mmol, Aldrich) and 4-tert-butylbenzaldehyde (1.6 g, 10 mmol, Aldrich) provided the title product as a white solid. MS (ESI, pos. ion) m/z: 233 (M+1).

(b) (2E)-N-(2H,3H-Benzo[3,4-e]1,4-dioxan-6-yl)-3-[4-(tert-butyl)phenyl]-2-ethylprop-2-enamide. Analogous to the procedure used to prepare Example 1, (2E)-3-[4-(tert-butyl)phenyl]-2-ethylprop-2-enoic acid, Example 42(a), (0.46 g, 2.0 mmol) and 1,4-benzodioxan-6-amine (0.33 g, 2.2 mmol, Aldrich) provided, after purification by silica gel chromatography (chloroform), the title product as a white solid. MP 133-134° C. MS (ESI, pos. ion) m/z: 366 (M+1).

EXAMPLE 43

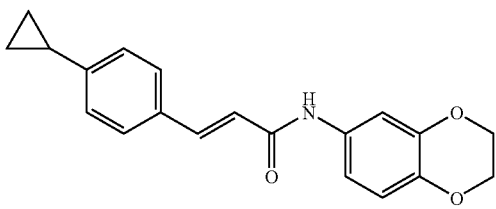

(2E)-N-(2H,3H-Benzo[3,4-e]1,4-dioxan-6-yl)-3-(4-cyclopropylphenyl)prop-2-enamide

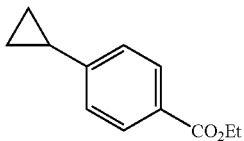

(a) Ethyl 4-cyclopropylbenzoate. To a round-bottomed flask under N₂ was added zinc dust (0.80 g, 12.5 mmol, Aldrich), cuprous chloride (1.23 g, 12.5 mmol, Aldrich) and Et₂O (2 mL). The mixture was magnetically stirred and heated at reflux for 30 min. The suspension was treated with ethyl 4-vinylbenzoate (0.85 g, 4.82 mmol, Apin) followed by methylene diiodide (1.68 g, 6.27 mmol, Aldrich) and reflux was continued for 24 h. The reaction mixture was allowed to cool to 25° C., filtered, concentrated in vacuo and purified by silica gel chromatography (9:1 hexane:EtOAc) to provide the title product. MS (ESI, pos. ion) m/z: 191 (M+1).

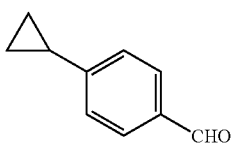

(b) 4-Cyclopropylbenzaldehyde. Ethyl 4-cyclopropylbenzoate, Example 43(a), (316 mg, 1.66 mmol) was transferred to a round-bottomed flask and treated with lithium aluminum hydride (0.30 mL, 3.0 mmol, 1.0 M in THF, Aldrich) under N₂. The reaction mixture was magnetically stirred at 25° C. for 1 h, then quenched by the dropwise addition of H₂O (0.5 mL) followed by 20% aq. KOH (3 mL). The suspension was filtered and the aqueous phase extracted with EtOAc. The organic extract was concentrated in vacuo and the crude alcohol was redissolved in anhydrous CH₂Cl₂ (2 mL). In a separate round-bottomed flask, a solution of oxalyl chloride (2.0 mL, 4.0 mmol, 2.0 M in CH₂Cl₂, Aldrich) was magnetically stirred under N₂ at −78° C. and treated dropwise with a solution of anhydrous dimethyl sulfoxide (4.0 mL, 56 mmol, Aldrich) in anhydrous CH₂Cl₂ (2 mL). The reaction mixture was stirred at −78° C. for 5 min then treated dropwise with the solution of crude alcohol in CH₂Cl₂. The reaction mixture was stirred an additional 5 min at −78° C., treated with triethylamine (2.0 mL, 14 mmol), allowed to warm to 25° C. and stirred at that temperature for 1 h. The reaction was quenched by the addition of H₂O and the mixture was extracted with Et₂O. The organic extract was concentrated in vacuo to provide 230 mg (95% over two steps) of the title product.

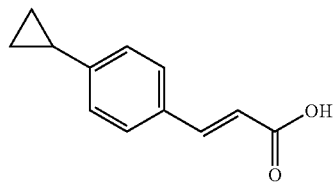

(c) (2E)-3-(4-Cyclopropylphenyl)prop-2-enoic acid. Analogous to the procedure described for Example 40, step (a), 4-cyclopropylbenzaldehyde, Example 43(b), (0.23 g, 1.6 mmol) and triethyl phosphonoacetate (0.35 g, 1.6 mmol, Aldrich) provided the title product. MS (ESI, pos. ion) m/z: 189 (M+1).

(d) (2E)-N-(2H,3H-Benzo[3,4-e]1,4-dioxan-6-yl)-3-(4-cyclopropylphenyl)prop-2-enamide. Analogous to the procedure used to prepare Example 1, (2E)-3-(4-cyclopropylphenyl)prop-2-enoic acid, Example 43(c), (130 mg, 0.69 mmol) and 1,4-benzodioxan-6-amine (104 mg, 0.69 mmol, Aldrich) provided, after purification by silica gel chromatography (65:35 hexane:EtOAc), the title product as a clear glass. MS (ESI, pos. ion) m/z: 322 (M+1).

EXAMPLE 44

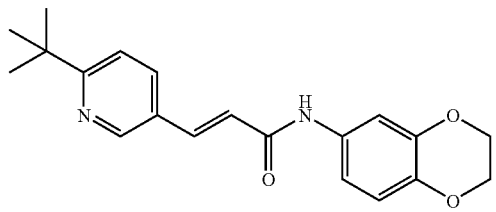

(2E)-N-(2H,3H-Benzo[3,4-e]1,4-dioxan-6-yl)-3-[6-(tert-butyl)(3-pyridyl)]-prop-2-enamide

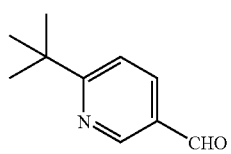

(a) 6-(tert-Butyl)pyridine-3-carbaldehyde. Analogous to the procedure of Rybakova, et al. *Zh. Org. Khim.* 1995, 31(5), 670-673, pyridine-3-methanol (2.18 g, 20.0 mmol, Aldrich), trimethylacetic acid (10.2 g, 100 mmol, Aldrich), silver nitrate (0.68 gm 4.0 mmol, Aldrich), and 10% aq. sulfuric acid (20 mL) were combined in a round-bottomed flask. The reaction mixture was magnetically stirred and treated with a solution of ammonium persulfate (9.1 g, 40 mmol, Aldrich) in H₂O (40 mL). Evolution of gas was observed and the reaction mixture was stirred at 25° C. for 2 h. The reaction mixture was basified to pH 9 by the addition of aq. ammonium hydroxide then extracted with EtOAc. The organic extract was washed with H₂O, dried over Na₂SO₄, filtered and concentrated in vacuo. Purification of the crude product by silica gel chromatography (70:30 hexane:EtOAc) provided the title product. MS (ESI, pos. ion) m/z: 164 (M+1).

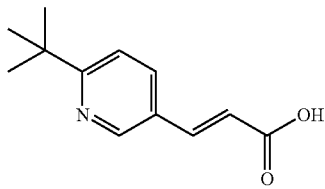

(b) (2E)-3-[6-(tert-Butyl)(3-pyridyl)]prop-2-enoic acid. Analogous to the procedure described for Example 40, step (a), 6-(tert-butyl)pyridine-3-carbaldehyde, Example 44(a), (0.55 g, 3.4 mmol) and triethyl phosphonoacetate (0.76 g, 3.4 mmol, Aldrich) provided the title product. MS (ESI, pos. ion) m/z: 206 (M+1).

(c) (2E)-N-(2H,3H-Benzo[3,4-e]1,4-dioxan-6-yl)-3-[6-(tert-butyl)(3-pyridyl)]prop-2-enamide. Analogous to the procedure used to prepare Example 1, (2E)-3-[6-(tert-butyl)(3-pyridyl)]prop-2-enoic acid, Example 44(b), (200 mg, 1.0 mmol) and 1,4-benzodioxan-6-amine (150 mg, 1.0 mmol, Aldrich) provided, after purification by silica gel chromatography (60:40 hexane:EtOAc), the title product as a clear glass. MS (ESI, pos. ion) m/z: 339 (M+1).

EXAMPLE 45

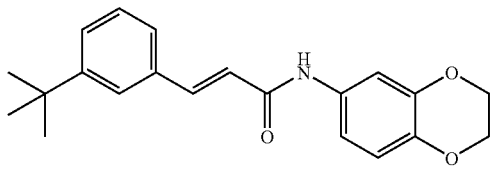

(2E)-N-(2H,3H-Benzo[3,4-e]1,4-dioxan-6-yl)-3-[3-(tert-butyl)phenyl]prop-2-enamide

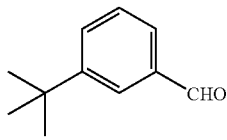

(a) 3-(tert-Butyl)benzaldehyde. To a round-bottomed flask equipped with magnetic stirring was added 1-tert-butyl-3-methylbenzene (1 g, 6.8 mmol, Wiley), ammonium cerium (IV) nitrate (17.5 g, 29.7 mmol, Aldrich) and 50% aq. acetic acid (150 mL). The reaction mixture was stirred and heated at 90° C. for 1.5 h. The reaction mixture was allowed to cool to 25° C. and extracted with 10% EtOAc in hexane. The organic extract was concentrated in vacuo to provide the crude aldehyde.

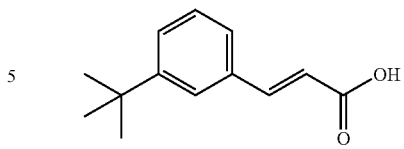

(b) (2E)-3-[3-(tert-Butyl)phenyl]prop-2-enoic acid. Analogous to the procedure described for Example 40, step (a), 3-(tert-butyl)benzaldehyde, Example 45(a), (320 mg, 2.0 mmol) and triethyl phosphonoacetate (250 mg, 2.0 mmol, Aldrich) provided the title product. MS (ESI, pos. ion) m/z: 205 (M+1).

(c) (2E)-N-(2H,3H-Benzo[3,4-e]1,4-dioxan-6-yl)-3-[3-(tert-butyl)phenyl]prop-2-enamide. Analogous to the procedure used to prepare Example 1, (2E)-3-[3-(tert-butyl)phenyl]prop-2-enoic acid, Example 45(b), (200 mg, 1.0 mmol) and 1,4-benzodioxan-6-amine (150 mg, 1.0 mmol, Aldrich) provided, after purification by silica gel chromatography (60:40 hexane:EtOAc), the title product. MP 168° C. MS (ESI, pos. ion) m/z: 338 (M+1).

EXAMPLE 46

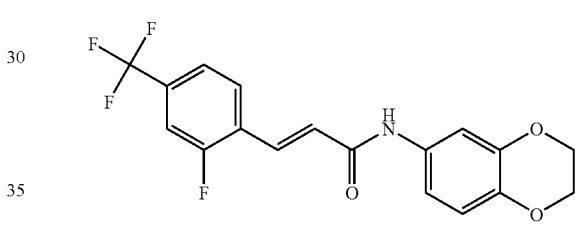

(2E)-N-(2H,3H-Benzo[3,4-e]1,4-dioxan-6-yl)-3-[2-fluoro-4-(trifluoromethyl)-phenyl]prop-2-enamide

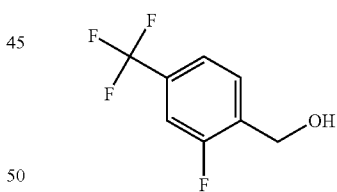

(a) [2-Fluoro-4-(trifluoromethyl)phenyl]methan-1-ol. To a round-bottomed flask, equipped with magnetic stirring and a reflux condenser, was added 2-fluoro-4-(trifluoromethyl) benzoic acid (5.0 g, 24 mmol, ABCR) and borane-THF complex (72 mL, 72 mmol, 1.0 M in THF, Aldrich) at 0° C. under N₂. The reaction mixture was warmed to 65° C. and stirred at that temperature for 2 h. The reaction mixture was allowed to cool to 25° C. and the solvent was removed in vacuo. The resulting residue was dissolved in CH₂Cl₂ (100 mL) and washed with satd Na₂CO₃ (100 mL). The aqueous phase was back-extracted with CH₂Cl₂ (4×80 mL). The combined organic extract was washed with satd NaCl (200 mL), dried over Na₂SO₄, filtered and concentrated in vacuo. Purification by silica gel chromatography (gradient: 0-10% EtOAc in hexane) provided the title product as a colorless oil.

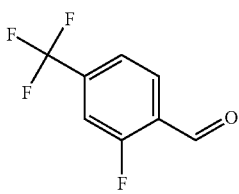

(b) 2-Fluoro-4-(trifluoromethyl)benzaldehyde. To a solution of [2-fluoro-4-(trifluoromethyl)phenyl]methan-1-ol, Example 46(a), (4.4 g, 23 mmol) in $CH_2Cl_2$ (100 mL) was added ground pyridinium dichromate (38.4 g, 102 mmol, Fluka). The reaction mixture was stirred at 25° C. overnight, then filtered through Celite. The Celite pad was washed with $CH_2Cl_2$ (2×50 mL) and the combined filtrate was concentrated in vacuo. Purification by silica gel chromatography (gradient: 0-5% EtOAc in hexane) provided the title product as a white slurry.

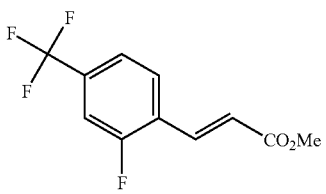

(c) Methyl (2E)-3-[2-fluoro-4-(trifluoromethyl)phenyl]prop-2-enoate. 2-Fluoro-4-(trifluoromethyl)benzaldehyde, Example 46(b), (900 mg, 4.7 mmol) in $CH_2Cl_2$ (5 mL) was added via cannula to a solution of carbomethoxymethylene triphenylphosphorane (2.0 g, 6.1 mmol, Aldrich) in $CH_2Cl_2$ (15 mL), magnetically stirred in a round-bottomed flask at 0° C. The reaction mixture was allowed to warm to 25° C. and stirred at this temperature under $N_2$ overnight. The solvent was removed in vacuo and the crude material purified by silica gel chromatography (gradient: 0-5% EtOAc in hexane) to provide the title product as a white solid.

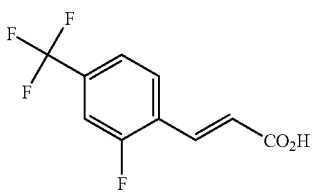

(d) (2E)-3-[2-Fluoro-4-(trifluoromethyl)phenyl]prop-2-enoic acid. Methyl (2E)-3-[2-fluoro-4-(trifluoromethyl)phenyl]prop-2-enoate, Example 46(c), (1.6 g, 6.3 mmol) was treated with lithium hydroxide monohydrate (530 mg, 12.6 mmol, Aldrich) in wet EtOH (15 mL) and magnetically stirred in a round-bottomed flask at 25° C. overnight. The reaction mixture was acidified to pH <2 with 10% aq. HCl and extracted with EtOAc (3×50 mL). The combined extracts were washed with satd NaCl (100 mL), dried over $Na_2SO_4$, filtered and concentrated in vacuo to provide the acid as a white solid.

(e) (2E)-N-(2H,3H-Benzo[3,4-e]1,4-dioxan-6-yl)-3-[2-fluoro-4-(trifluoromethyl)phenyl]prop-2-enamide. Analogous to the procedure used to prepare Example 1, (2E)-3-[2-fluoro-4-(trifluoromethyl)phenyl]prop-2-enoic acid, Example 46(d), (200 mg, 0.85 mmol) and 1,4-benzodioxan-6-amine (193 mg, 1.28 mmol, Aldrich) provided, after purification by silica gel chromatography (gradient: 0-20% EtOAc in hexane) and recrystallization from EtOAc and hexane, the title product as a yellow crystalline solid. MP 174-175° C. MS (ESI, pos. ion) m/z: 368 (M+1).

EXAMPLE 47

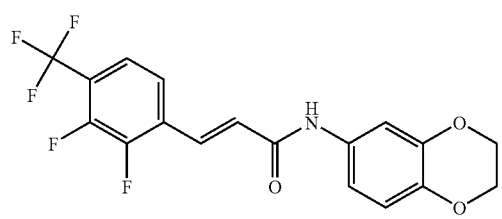

(2E)-N-(2H,3H-Benzo[3,4-e]1,4-dioxan-6-yl)-3-[2,3-difluoro-4-(trifluoro-methyl)phenyl]prop-2-enamide. Analogous to the procedure used to prepare Example 46, steps (b)-(e), the title product was obtained from 2,3-difluoro-4-(trifluoromethyl)benzyl alcohol (ABCR) and 1,4-benzodioxan-6-amine (Aldrich) as a crystalline yellow solid. MP 169-170° C. MS (ESI, pos. ion) m/z: 386 (M+1).

EXAMPLE 48

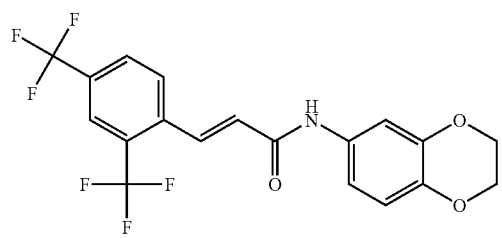

(2E)-N-(2H,3H-Benzo[3,4-e]1,4-dioxan-6-yl)-3-[2,4-bis(trifluoromethyl)-phenyl]prop-2-enamide. Analogous to the procedure used to prepare Example 46, steps (b)-(e), the title product was obtained from 2,4-bis(trifluoromethyl)benzyl alcohol (Avocado) and 1,4-benzodioxan-6-amine (Aldrich) as a crystalline yellow solid. MP 204-205° C. MS (ESI, pos. ion) m/z: 418 (M+1).

EXAMPLE 49

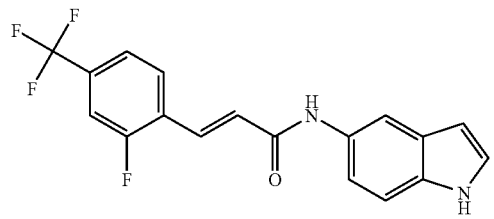

(2E)-3-[2-Fluoro-4-(trifluoromethyl)phenyl]-N-indol-5-ylprop-2-enamide

Analogous to the procedure used to prepare Example 46, steps (a)-(e), the title product was obtained from 2-fluoro-4-(trifluoromethyl)benzoic acid (ABCR) and 5-aminoindole (Aldrich) as a crystalline yellow solid. MP 203-205° C. MS (ESI, pos. ion) m/z: 349 (M+1).

EXAMPLE 50

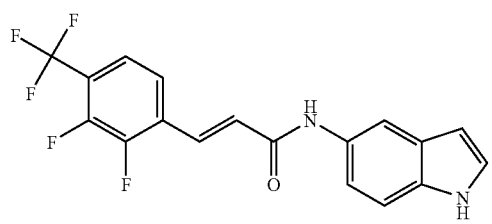

(2E)-3-[2,3-Difluoro-4-(trifluoromethyl)phenyl]-N-indol-5-ylprop-2-enamide

Analogous to the procedure used to prepare Example 46, steps (b)-(e), the title product was obtained from 2,3-difluoro-4-(trifluoromethyl)benzyl alcohol (ABCR) and 5-aminoindole (Aldrich) as a crystalline yellow solid. MP 220-222° C. MS (ESI, pos. ion) m/z: 367 (M+1).

EXAMPLE 51

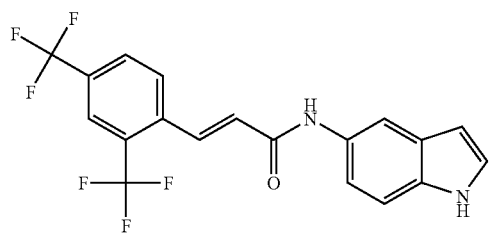

(2E)-3-[2,4-Bis(trifluoromethyl)phenyl]-N-indol-5-ylprop-2-enamide

Analogous to the procedure used to prepare Example 46, steps (b)-(e), the title product was obtained from 2,4-bis(trifluoromethyl)benzyl alcohol (Avocado) and 5-aminoindole (Aldrich) as a crystalline yellow solid. MP 207-209° C. MS (ESI, pos. ion) m/z: 399 (M+1).

EXAMPLE 52

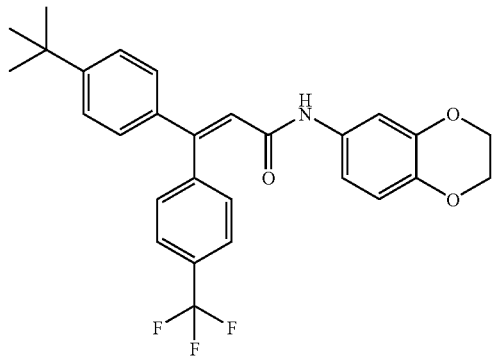

N-(2H,3H-Benzo[e]1,4-dioxan-6-yl)(2Z)-3-[4-(tert-butyl)phenyl]-3-[4-(trifluoromethyl)phenyl]prop-2-enamide

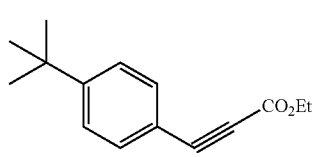

(a). Ethyl 3-[4-(tert-butyl)phenyl]prop-2-ynoate. To a 1 L round-bottomed flask was added (4-tert-butyl)phenylacetylene (33.8 g, 214 mmol, GFS Chemicals) and anhydrous THF (220 mL). The solution was magnetically stirred, purged with $N_2$ and cooled to −78° C., then n-butyllithium (136 mL, 2.5 M in hexanes, Aldrich) was added slowly. After the addition was complete, the mixture was gradually warmed to 0° C. and stirred magnetically for 30 min. The reaction mixture was cooled to −78° C. again and ethyl chloroformate (28.6 mL, 299.2 mmol, Aldrich) was added. After allowing to warm to 25° C. and stirring overnight, the reaction was quenched with 1:1 satd $NaHCO_3$:satd $NH_4Cl$ (200 mL) and extracted with $Et_2O$ (1000 mL). The organic phase was dried over $Na_2SO_4$, filtered and concentrated in vacuo to afford a yellow oil. Purification by silica gel chromatography (gradient: 0.5%-3% EtOAc/hexane) provided ethyl 3-[4-(tert-butyl)phenyl]prop-2-ynoate as a pale yellow oil. MS (ESI, pos. ion) m/z: 231 (M+1).

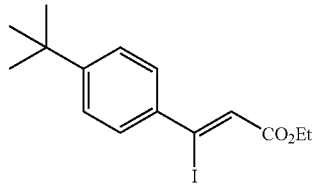

(b). Ethyl (2Z)-3-[4-(tert-butyl)phenyl]-3-iodoprop-2-enoate. According to the procedure of E. Piers et al., *Can. J. Chem.* 1994, 72, 1816, to a 150 mL round-bottomed flask equipped with a reflux condenser and magnetic stirring was added ethyl 3-[4-(tert-butyl)phenyl]prop-2-ynoate, Example 52(a), (15 g, 65 mmol), sodium iodide (31 g, 209 mmol, Aldrich) and glacial acetic acid (48 mL, 830 mmol). The reaction mixture was purged with $N_2$ and the flask immersed in a pre-heated 115° C. oil bath. The reaction mixture was magnetically stirred at 115° C. for 4 h, then allowed to cool to 25° C. and treated with $H_2O$ (200 mL). The aqueous phase was extracted with $Et_2O$ (500 mL). The organic layer was washed with satd $Na_2CO_3$ until the evolution of $CO_2$ ceased, then washed with 1 M $Na_2S_2O_3$ (100 mL), satd NaCl, dried over $Na_2SO_4$, filtered, and concentrated in vacuo to provide ethyl (2Z)-3-[4-(tert-butyl)phenyl]-3-iodoprop-2-enoate as a yellow oil. MS (ESI, pos. ion) m/z: 359 (M+1).

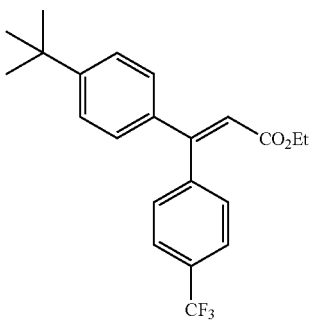

(c) Ethyl (2Z)-3-[4-(tert-butyl)phenyl]-3-[4-(trifluoromethyl)phenyl]prop-2-enoate. To a 100 mL round-bottomed flask equipped with a reflux condenser and magnetic stirring was added ethyl (2Z)-3-[4-(tert-butyl)phenyl]-3-iodoprop-2-enoate, Example 52(b), (0.75 g, 2.1 mmol), 4-trifluoromethylphenylboronic acid (0.60 g, 3.1 mmol, Aldrich), tetrakis(triphenylphosphine)palladium (0) (0.24 g, 0.21 mmol, Aldrich), toluene (10 mL), EtOH (2 mL), and 2 M aq. $Na_2CO_3$ (2 mL). The reaction mixture was magnetically stirred at 80° C. under $N_2$ overnight, allowed to cool to 25° C. and diluted with EtOAc (50 mL). The organic layer was separated, washed with $H_2O$, satd NaCl (50 mL), dried over $Na_2SO_4$, filtered and concentrated to afford a brown oil. Purification by silica gel chromatography (gradient: 1.5%-2% EtOAc/hexane) provided the title product as a white solid. MS (ESI, pos. ion) m/z: 377 (M+1).

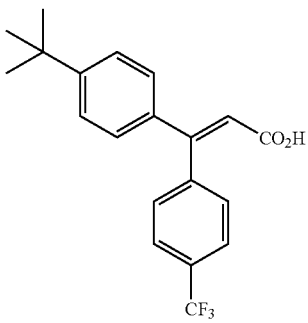

(d) (2Z)-3-[4-(tert-Butyl)phenyl]-3-[4-(trifluoromethyl)phenyl]prop-2-enoic acid. To a 50 mL round-bottomed flask equipped with a reflux condenser was added ethyl (2Z)-3-[4-(tert-butyl)phenyl]-3-[4-(trifluoromethyl)phenyl]prop-2-enoate, Example 52(c), (0.74 g, 2.0 mmol), 1,4-dioxane (3 mL), KOH (0.66 g, 12 mmol) and $H_2O$ (1.5 mL). The reaction mixture was heated and magnetically stirred under reflux overnight then diluted with $H_2O$ (20 mL) and acidified with 1 N HCl. The aqueous mixture was extracted with $CH_2Cl_2$ (3×100 mL). The organic phase was dried over $Na_2SO_4$, filtered and concentrated in vacuo to provide the title product as a white solid. MS (ESI, pos. ion) m/z: 349 (M+1).

(e) N-(2H,3H-Benzo[e]1,4-dioxan-6-yl)(2Z)-3-[4-(tert-butyl)phenyl]-3-[4-(trifluoromethyl)phenyl]prop-2-enamide. Analogous to the procedure used to prepare Example 1, (2Z)-3-[4-(tert-butyl)phenyl]-3-[4-(trifluoromethyl)phenyl]prop-2-enoic acid, Example 52(d), (0.15 g, 0.43 mmol) and 1,4-benzodioxan-6-amine (0.07 g, 0.43 mmol, Aldrich) provided, after purification by silica gel chromatography (gradient: 10%-18% EtOAc/hexane), the title product as a pale yellow solid. MP 150-151° C. MS (ESI, pos. ion) m/z: 482 (M+1).

EXAMPLE 53

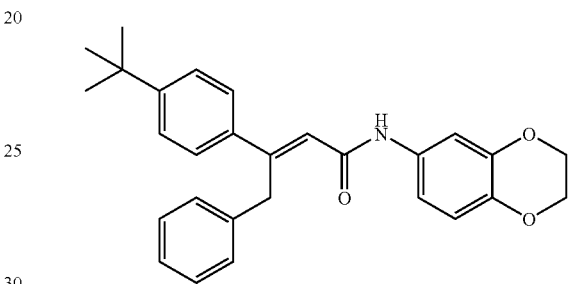

(2E)-N-(2H,3H-Benzo[e]1,4-dioxan-6-yl)-3-[4-(tert-butyl)phenyl]-4-phenylbut-2-enamide

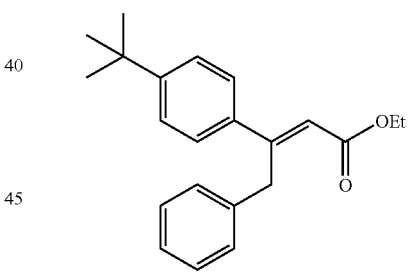

(a) Ethyl (2E)-3-[4-(tert-butyl)phenyl]-4-phenylbut-2-enoate. A solution of ethyl (2Z)-3-[4-(tert-butyl)phenyl]-3-iodoprop-2-enoate, Example 52(b), (710 mg, 2.0 mmol) in anhydrous DMF (4 mL) was added dropwise to benzylzinc bromide (12 mL, 6.0 mmol, 0.5 M solution in THF, Aldrich) magnetically stirred under Ar at 0° C. in a round-bottomed flask. The mixture was treated with bis(acetonitrile)dichloropalladium (II) (78 mg, 0.30 mmol, Aldrich) in one portion. The reaction mixture was then magnetically stirred for 16 h at 25° C., diluted with $Et_2O$ (100 mL) and washed with 1N HCl (25 mL) and satd NaCl (25 mL). The organic phase was dried over $MgSO_4$, filtered and concentrated in vacuo and the residue purified by silica gel chromatography (49:1 hexane:EtOAc) to provide the title product as a colorless oil. MS (ESI, pos. ion) m/z: 323 (M+1).

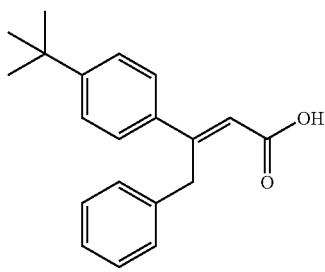

(b) (2E)-3-[4-(tert-Butyl)phenyl]-4-phenylbut-2-enoic acid. Ethyl (2E)-3-[4-(tert-butyl)phenyl]-4-phenylbut-2-enoate, Example 53(a), (530 mg, 1.8 mmol) was treated with KOH (0.22 g, 4.0 mmol), H₂O (4 mL) and 1,4-dioxane (2 mL), then magnetically stirred under reflux for 16 h. The reaction mixture was diluted with H₂O (50 mL), acidified with 1 N HCl and extracted with chloroform. The combined organic extract was washed with satd NaCl, dried over MgSO₄, filtered and concentrated in vacuo. The resulting residue was crystallized from EtOAc and hexane to provide the title product as a white solid.

(c) (2E)-N-(2H,3H-Benzo[e]1,4-dioxan-6-yl)-3-[4-(tert-butyl)phenyl]-4-phenylbut-2-enamide. Analogous to the procedure used to prepare Example 1, (2E)-3-[4-(tert-butyl)phenyl]-4-phenylbut-2-enoic acid, Example 53(b), (250 mg, 0.85 mmol) and 1,4-benzodioxan-6-amine (140 mg, 0.93 mmol, Aldrich) provided, after purification by silica gel chromatography (chloroform), the title product as off-white needles. MP 97-99° C. MS (ESI, pos. ion) m/z: 428 (M+1).

EXAMPLE 54

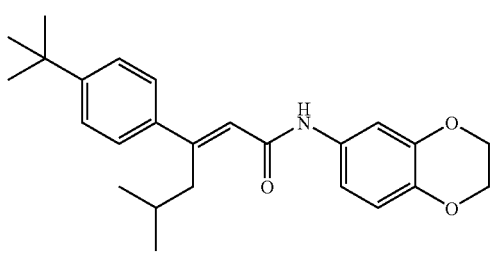

(2E)-N-(2H,3H-Benzo[e]1,4-dioxan-6-yl)-3-[4-(tert-butyl)phenyl]-5-methylhex-2-enamide Analogous to the procedure used to prepare Example 53, starting from 3-methylbutylzinc bromide (Aldrich), ethyl (2Z)-3-[4-(tert-butyl)phenyl]-3-iodoprop-2-enoate, Example 52(b), and 1,4-benzodioxan-6-amine (Aldrich), the title product was obtained as an off-white solid. MP 123° C. MS (ESI, pos. ion) m/z: 394 (M+1).

EXAMPLE 55

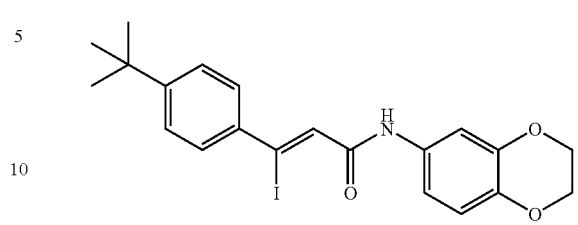

N-(2H,3H-Benzo[e]1,4-dioxan-6-yl)(2Z)-3-[4-(tert-butyl)phenyl]-3-iodoprop-2-enamide (a) 3-[4-(tert-Butyl)phenyl]prop-2-ynoic acid. To a round-bottomed flask equipped with magnetic stirring and a reflux condenser was added a solution of ethyl 3-[4-(tert-butyl)phenyl]prop-2-ynoate, Example 52(a), (4.6 g, 20 mmol) in 1,4-dioxane (5 mL). The solution was treated with H₂O (15 mL) and KOH (2.2 g, 40 mmol) then stirred and heated at reflux under Ar for 18 h. After allowing to cool to 25° C., the mixture was diluted with H₂O (200 mL) and washed with Et₂O (50 mL). The aqueous phase was separated, acidified with 1 N HCl and extracted with chloroform. The chloroform extract was washed with satd NaCl, dried over MgSO₄, filtered and concentrated in vacuo. Crystallization from EtOAc and hexane provided the title product as white needles. MS (ESI, pos. ion) m/z: 203 (M+1).

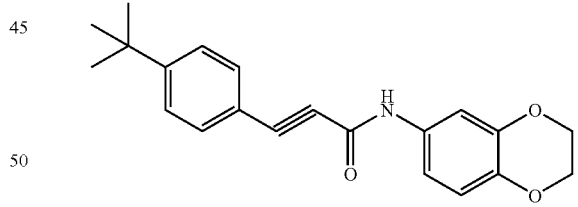

(b) N-(2H,3H-Benzo[e]1,4-dioxan-6-yl)-3-[4-(tert-butyl)phenyl]prop-2-ynamide. Analogous to the procedure used to prepare Example 1, 3-[4-(tert-butyl)phenyl]prop-2-ynoic acid, Example 55(a), (404 mg, 2.0 mmol) and 1,4-benzodioxan-6-amine (330 mg, 2.2 mmol, Aldrich) provided the title product as a white solid. MP 199° C. MS (ESI, pos. ion) m/z: 336 (M+1).

(c) N-(2H,3H-Benzo[e]1,4-dioxan-6-yl)(2Z)-3-[4-(tert-butyl)phenyl]-3-iodoprop-2-enamide. Analogous to the procedure described for the preparation of Example 52(b), N-(2H,3H-benzo[e]1,4-dioxan-6-yl)-3-[4-(tert-butyl)phenyl]prop-2-ynamide, Example 55(b), (0.335 g, 1.0 mmol), sodium iodide (0.48 g, 3.2 mmol, Aldrich) and glacial acetic acid (0.73 mL) provided, after purification by silica gel chromatography (chloroform), the title product as yellow crystals. MP 164° C. MS (ESI, pos. ion) m/z: 464 (M+1).

EXAMPLE 56

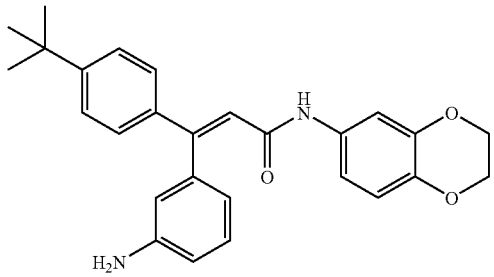

(2E)-N-(2H,3H-Benzo[e]1,4-dioxan-6-yl)-3-(3-aminophenyl)-3-[4-(tert-butyl)phenyl]prop-2-enamide Analogous to the procedure used to prepare Example 52, step (c), 3-aminophenylboronic acid (0.23 g, 1.5 mmol, Avocado) and N-(2H,3H-benzo[e]1,4-dioxan-6-yl)(2Z)-3-[4-(tert-butyl)phenyl]-3-iodoprop-2-enamide, Example 55, (0.46 g, 1.0 mmol) provided the title product as off-white crystals. MP 140° C. MS (ESI, pos. ion) m/z: 429 (M+1).

EXAMPLE 57

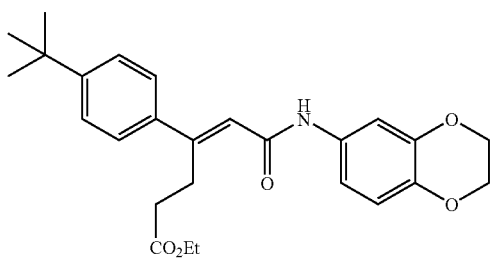

Ethyl (4E)-5-(N-(2H,3H-benzo[e]1,4-dioxan-6-yl)carbamoyl)-4-[4-(tert-butyl)phenyl]pent-4-enoate Analogously to the procedure used to prepare Example 53, step (a), 3-ethoxy-3-oxopropylzinc bromide (6.0 mL, 3.0 mmol, 0.5 M in THF, Aldrich) and N-(2H,3H-benzo[e]1,4-dioxan-6-yl)(2Z)-3-[4-(tert-butyl)phenyl]-3-iodoprop-2-enamide, Example 55, (0.46 g, 1.0 mmol) provided the title product as a pale yellow solid. MP 104-105° C. MS (ESI, pos. ion) m/z: 438 (M+1).

EXAMPLE 58

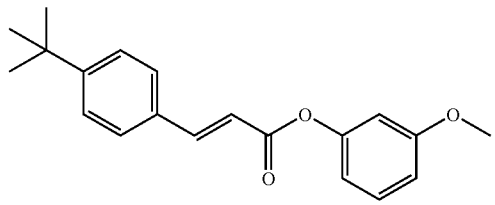

3-Methoxyphenyl (2E)-3-[4-(tert-butyl)phenyl]prop-2-enoate. To a 100 mL round-bottomed flask equipped with magnetic stirring was added 4-tert-butyl-trans-cinnamic acid (500 mg, 2.45 mmol, EMKA-Chemie), CH$_2$Cl$_2$ (10 mL), and DMF (10 uL) under N$_2$. The solution was treated dropwise with oxalyl chloride (4.0 mL, 8.0 mmol, 2.0 M in CH$_2$Cl$_2$, Aldrich) then stirred at 25° C. for 1 h. The reaction mixture was concentrated in vacuo and the residue treated with 3-methoxyphenol (269 uL, 2.45 mmol, Aldrich), THF (20 mL) and satd K$_2$CO$_3$ (15 mL). The reaction mixture was stirred at 25° C. overnight, then acidified to pH 4.5 with 1 N HCl. The mixture was extracted with EtOAc (2×30 mL), the combined organic extract was dried and concentrated in vacuo. Purification by silica gel chromatography (5:1 hexane: EtOAc) provided the title product as a white solid. MP 83° C. MS (ESI, pos. ion) m/z: 311 (M+1).

EXAMPLE 60

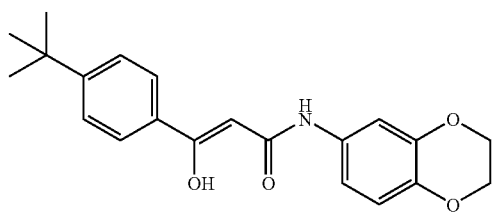

N-(2H,3H-Benzo[3,4-e]1,4-dioxan-6-yl)(2Z)-3-[4-(tert-butyl)phenyl]-3-hydroxyprop-2-enamide

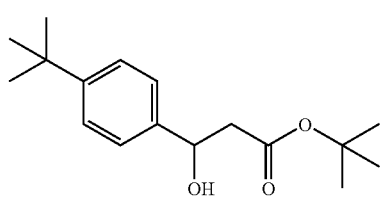

(a) tert-Butyl 3-[4-(tert-butyl)phenyl]-3-hydroxypropanoate. To a round-bottomed flask equipped with magnetic stirring was added N,N-diisopropylamine (10.4 mL, 74.0 mmol, Aldrich) and anhydrous THF (20 mL). The solution was stirred at −78° C. under N$_2$ and treated dropwise with n-butyllithium (30.0 mL, 75.0 mmol, 2.5 M in hexane, Aldrich). After stirring for 10 min at −78° C., the reaction mixture was treated with t-butyl acetate (10.8 mL, 80.1 mmol, Aldrich). After stirring 30 min at −78° C., the enolate was added via cannula to a solution of 4-t-butylbenzaldehyde (10.0 g, 61.6 mmol, Fluka) in anhydrous THF (100 mL), stirred under $N_2$ at −78° C. The reaction mixture was allowed to warm to 0° C. with stirring over 3 h, then quenched with satd $NH_4Cl$ and concentrated in vacuo to remove the THF. The resulting mixture was diluted with satd $NH_4Cl$ (100 mL) and extracted with $Et_2O$ (200 mL). The organic extract was washed with $H_2O$ (100 mL), satd NaCl (50 mL), dried over $MgSO_4$, filtered and concentrated in vacuo to provide the title product as a white solid. MS (ESI, pos. ion) m/z: 261 (M+1−$H_2O$).

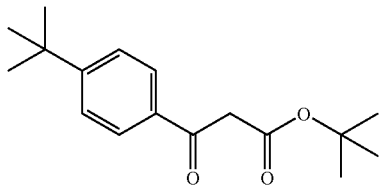

(b) tert-butyl 3-[4-(tert-butyl)phenyl]-3-oxopropanoate. tert-Butyl 3-[4-(tert-butyl)phenyl]-3-hydroxypropanoate, Example 60(a), (5.0 g, 18 mmol) was dissolved in $CH_2Cl_2$ (100 mL), magnetically stirred in a round-bottomed flask at 0° C., and treated with pyridinium chlorochromate (5.8 g, 27 mmol, Aldrich) in portions. The reaction mixture was allowed to warm to 25° C. and stirred at that temperature for 5 h. The mixture was filtered through a pad of Celite, the filtercake washed with $CH_2Cl_2$ (3×100 mL) and the combined filtrate was concentrated in vacuo. Purification by silica gel chromatography (1:1 hexane:EtOAc) provided the title product as a dark oil. MS (ESI, pos. ion) m/z: 277 (M+1).

(c) N-(2H,3H-Benzo[3,4-e]1,4-dioxan-6-yl)(2Z)-3-[4-(tert-butyl)phenyl]-3-hydroxyprop-2-enamide. According to the procedure of Wiseman et al., *J. Org. Chem.* 1991, 56, 1713-1718, to a round-bottomed flask equipped with magnetic stirring and a reflux condenser was added tert-butyl 3-[4-(tert-butyl)phenyl]-3-oxopropanoate, Example 60(b), (640 mg, 2.3 mmol), 1,4-benzodioxan-6-amine (350 mg, 2.3 mmol, Aldrich) and anhydrous toluene (20 mL). The mixture was stirred and heated at 130° C. for 2 h. Upon allowing to cool to 25° C., a precipitate was observed. Hexane (20 mL) was added to the suspension and the precipitate collected by filtration, washed with hexane (20 mL) and dried in vacuo at 60° C. to provide the title product as a pale grey solid. MP 161° C. MS (ESI, pos. ion) m/z: 354 (M+1).

EXAMPLE 61

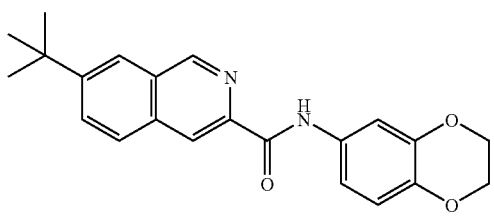

N-(2H,3H-Benzo[3,4-e]1,4-dioxan-6-yl)[7-(tert-butyl)(3-isoquinolyl)]-carboxamide

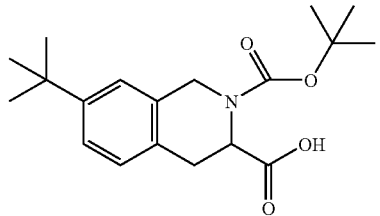

(a) 2-[(tert-Butyl)oxycarbonyl]-7-(tert-butyl)-1,2,3,4-tetrahydroisoquinoline-3-carboxylic acid. According to the procedure of D. Ma, et al., *Bioorg. Med. Chem. Lett.* 1998, 8(18), 2447-2450, to a 250 mL round-bottomed flask, equipped with magnetic stirring and reflux condenser, was added N-Boc-(p-tert-butyl)-S-phenylalanine (5.0 g, 15.6 mmol, Bachem), formaldehyde (50 mL, 37 wt. % in $H_2O$, Aldrich) and cond HCl (30 mL). The reaction mixture was stirred and heated at 90° C. for 4 h. The solvents were removed in vacuo to provide 3.6 g of a residue [MS (ESI, pos. ion) m/z: 234 (M+1)] which was dissolved in THF (140 mL) and treated with 5% aq. $K_2CO_3$ (140 mL) and di-t-butyl dicarbonate (4.8 g, 22 mmol, Aldrich). The reaction mixture was stirred at 25° C. overnight, then acidified to pH 5 with 1 N HCl. The mixture was extracted with EtOAc (300 mL), the organic phase washed with satd NaCl (100 mL) and $H_2O$ (120 mL), dried over $Na_2SO_4$, filtered and concentrated in vacuo. Purification by silica gel chromatography (2:1 hexane:EtOAc) provided the title product. MS (ESI, pos. ion) m/z: 334 (M+1).

(b) N-(2H,3H-Benzo[3,4-e]1,4-dioxan-6-yl)[7-(tert-butyl)(3-1,2,3,4-tetrahydroisoquinolyl)]carboxamide hydrochloride. To a 250 mL round-bottomed flask equipped with magnetic stirring was added 2-[(tert-butyl)oxycarbonyl]-7-(tert-butyl)-1,2,3,4-tetrahydroisoquinoline-3-carboxylic acid, Example 61(a), (1.5 g, 4.65 mmol), DMF (15 mL), 1,4-benzodioxan-6-amine (700 mg, 4.65 mmol, Aldrich), dimethylaminopropyl-3-ethylcarbodiimide hydrochloride (1.25 g, 6.5 mmol, Aldrich) and N,N-diisopropylethylamine (2.5 mL, 13.95 mmol, Aldrich). The reaction mixture was stirred at 25° C. overnight then concentrated in vacuo. The residue was dissolved in EtOAc (35 mL), washed with $H_2O$ (2×15 mL), dried over $Na_2SO_4$, filtered and concentrated in vacuo. Purification by silica gel chromatography (3:1 hexane:EtOAc) provided a product [MS (ESI, pos. ion) m/z: 467 (M+1)] which was treated with 4.0 N HCl in 1,4 dioxane (10 mL, Aldrich) and stirred at 25° C. for 1 h. The solvent was removed in vacuo to provide the title product as the hydrochloride salt. MP 134° C. MS (ESI, pos. ion) m/z: 367 (M+1).

(c) N-(2H,3H-Benzo[3,4-e]1,4-dioxan-6-yl)[7-(tert-butyl)(3-isoquinolyl)]-carboxamide. Analogous to the procedure of E. D. Cox; T. J. Hagen; R. M. McKernan; J. M. Cook, *Med. Chem. Rest.* 1995, 5(9), 710-718, N-(2H,3H-benzo[3,4-e]1,4-dioxan-6-yl)[7-(tert-butyl)(3-1,2,3,4-tetrahydroisoquinolyl)]carboxamide hydrochloride, Example 61(b), was suspended in EtOAc (55 mL), washed with 10% $NaHCO_3$ (20 mL) and $H_2O$ (10 mL), dried over $Na_2SO_4$, filtered and concentrated in vacuo. The resulting residue (80 mg, 0.22 mmol) was dissolved in toluene (10 mL) and treated with manganese dioxide (110 mg, 1.1 mmol). The reaction mixture was magnetically stirred at 70° C. under $N_2$ for 1.5 h, filtered through Celite and concentrated in vacuo. Purification by silica gel chromatography (8:1 hexane:EtOAc) provided the title product as a yellow solid. MP 154-157° C. MS (ESI, pos. ion) m/z: 363 (M+1).

EXAMPLE 63

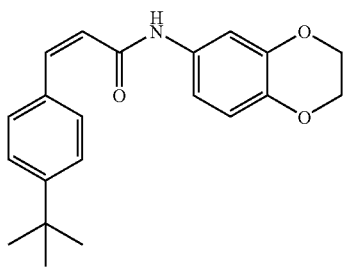

N-(2H,3H-Benzo[3,4-e]1,4-dioxan-6-yl)(2Z)-3-[4-(tert-butyl)phenyl]prop-2-enamide

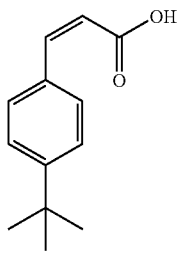

(a) (2Z)-3-[4-(tert-Butyl)phenyl]prop-2-enoic acid. Potassium bis(trimethylsilyl)amide (6.1 mL, 3.05 mmol, 0.5 M in toluene, Aldrich) was added dropwise with stirring to a mixture of diphenylphosphonoacetic acid ethyl ester (0.98 g, 3.05 mmol, TCI-US) and 18-crown-6 (3.35 g, 12.7 mmol, Aldrich) in anhydrous THF (20 mL), magnetically stirred at −78° C. under Ar. The reaction mixture was stirred at −78° C. for 0.5 h then treated dropwise with a solution of 4-tert-butylbenzaldehyde (0.42 mL, 2.54 mmol, Aldrich) in anhydrous THF (5 mL). The mixture was stirred at −78° C. for 1 h, quenched with satd NH$_4$Cl (5 mL), warmed to 25° C., diluted with H$_2$O (50 mL) and extracted with EtOAc (2×50 mL). The combined organic extracts were washed with satd NaCl, dried over MgSO$_4$, filtered and concentrated in vacuo to provide a brown viscous oil. [MS (ESI, pos. ion) m/z: 233 (M+1)] The oil (0.83 g) was dissolved in THF (5 mL) and MeOH (5 mL), magnetically stirred in a round-bottomed flask at 25° C., and treated with 1 N LiOH (10 mL). The reaction mixture was stirred at 25° C. for 18 h, the organic solvents removed in vacuo, and the aqueous phase was washed with Et$_2$O, acidified with 10% citric acid and extracted with EtOAc (3×10 mL). The combined organic extracts were dried over MgSO$_4$, filtered and concentrated in vacuo to provide the title product as a white solid. MS (ESI, pos. ion) m/z: 205 (M+1).

(b) N-(2H,3H-Benzo[3,4-e]1,4-dioxan-6-yl)(2Z)-3-[4-(tert-butyl)phenyl]prop-2-enamide. Analogous to the procedure used to prepare Example 1, (2Z)-3-[4-(tert-butyl)phenyl]prop-2-ynyl]prop-2-enoic acid, Example 63(a), (0.46 g, 2.3 mmol) and 1,4-benzodioxan-6-amine (0.38 g, 2.58 mmol, Aldrich) provided the title product as a white solid. MP 114-116° C. MS (ESI, pos. ion) m/z: 338 (M+1).

EXAMPLE 64

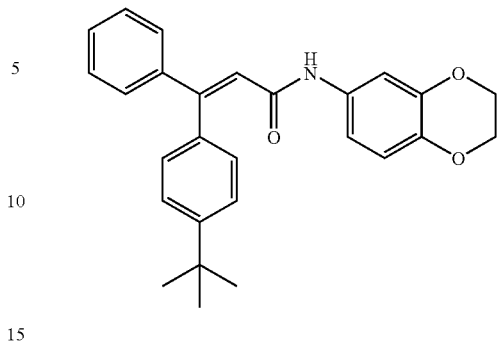

N-(2H,3H-Benzo[e]1,4-dioxan-6-yl)(2Z)-3-[4-(tert-butyl)phenyl]-3-phenylprop-2-enamide N-(2H,3H-Benzo[e]1,4-dioxan-6-yl)-3-[4-(tert-butyl)phenyl]prop-2-ynamide, Example 55(b), (0.34 g, 1.0 mmol) was dissolved in anhydrous EtOAc (50 mL) in a 100 mL round-bottomed flask equipped with reflux condenser and magnetic stirring under dry nitrogen atmosphere. To this solution was added iodobenzene (0.20 g, 1.0 mmol, Aldrich) and bis(dibenzylideneacetone)palladium (0.080 g, 0.14 mmol, Acros), followed by diethylamine (0.34 mL, 3.3 mmol, Aldrich) and formic acid (0.098 mL, 2.6 mmol, Aldrich). The reaction mixture was heated under reflux for 20 h, cooled to room temperature, washed with 1 N HCl (2×5 mL), 1 N NaOH (2×5 mL), satd NaCl (5 mL) and dried over Na$_2$SO$_4$. The organic solution was filtered and concentrated to afford a brown oil which was purified by silica gel chromatography (20% EtOAc/hexane) to give the title compound as a pale yellow solid. MP 80-82° C. MS (ESI, pos. ion) m/z: 414 (M+1).

EXAMPLE 65

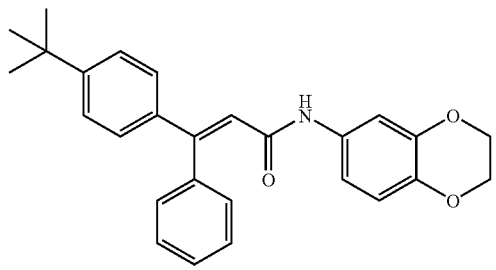

(2E)-N-(2H,3H-Benzo[e]1,4-dioxan-6-yl)-3-[4-(tert-butyl)phenyl]-3-phenylprop-2-enamide

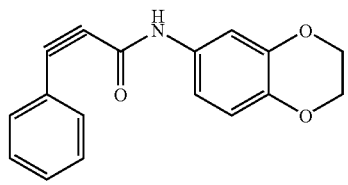

(a). N-(2H,3H-Benzo[e]1,4-dioxan-6-yl)-3-phenylprop-2-ynamide. Analogous to the procedure used to prepare Example 1, phenylpropiolic acid (5.8 g, 140 mmol, Aldrich) and 1,4-benzodioxan-6-amine (6.65 g, 44 mmol, Aldrich)

provided, after recrystallization from EtOAc and hexane, the title compound as a white solid. MP 132° C. MS (ESI, pos. ion) m/z: 280 (M+1).

(b). (2E)-N-(2H,3H-Benzo[e]1,4-dioxan-6-yl)-3-[4-(tert-butyl)phenyl]-3-phenylprop-2-enamide. Analogous to the procedure used to prepare Example 64, 1-tert-butyl-4-iodobenzene (0.26 g, 1.0 mmol, Aldrich) and N-(2H,3H-benzo[e]1,4-dioxan-6-yl)-3-phenylprop-2-ynamide, Example 65(a), (0.28 g, 1.0 mmol) provided, after recrystallization from EtOAc and hexane, the title compound as an off-white solid. MP 139° C. MS (ESI, pos. ion) m/z: 414 (M+1).

EXAMPLE 66

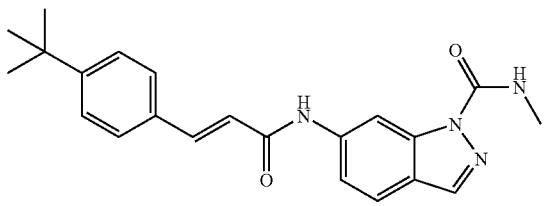

(2E)-3-[4-(tert-Butyl)phenyl]-N-[1-(N-methylcarbamoyl)(1H-indazol-6-yl)]prop-2-enamide. To a round-bottomed flask, equipped with a magnetic stir bar, was added (2E)-N-(1H-indazol-6-yl)-3-[4-(tert-butyl)phenyl]prop-2-enamide, Example 155, (61 mg, 0.19 mmol), THF (8 mL) and isocyanatomethane (54 mg, 0.96 mmol, Carbolabs). The reaction mixture was stirred at room temperature for 8 h. The reaction mixture was diluted with EtOAc (10 mL), washed with water (8 mL), dried over Na$_2$SO$_4$, filtered and concentrated in vacuo. Purification by silica gel chromatography (40:20:1 hexane:EtOAc:MeOH) provided the title product as an off-white solid. MP 208-209° C. MS (ESI, pos. ion) m/z: 377 (M+1).

EXAMPLE 67

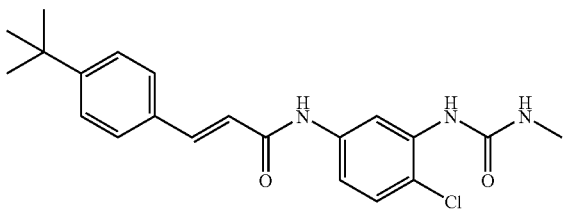

(2E)-3-[4-(tert-Butyl)phenyl]-N-{4-chloro-3-[(methylamino)carbonylamino]-phenyl}prop-2-enamide

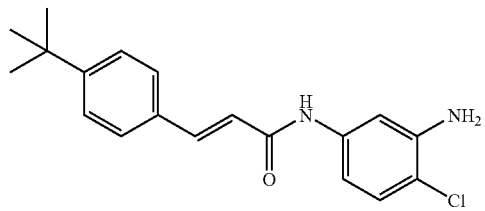

(a) (2E)-N-(3-Amino-4-chlorophenyl)-3-[4-(tert-butyl)phenyl]prop-2-enamide. To a round-bottomed flask equipped with a magnetic stir bar, was added (2E)-3-[4-(tert-butyl)phenyl]-N-(4-chloro-3-nitrophenyl)prop-2-enamide, Example 156, (250 mg, 0.69 mmol), EtOH (8 mL), indium (800 mg, 6.9 mmol, Aldrich) and satd NH$_4$Cl (10 mL). The reaction mixture was stirred at reflux for 5 h. The solvents were removed in vacuo, the residue was dissolved in EtOAc (20 mL), washed with water (20 mL), dried over Na$_2$SO$_4$, filtered and concentrated in vacuo to yield the title product. MS (ESI, pos. ion) m/z: 329 (M+1).

(b) (2E)-3-[4-(tert-Butyl)phenyl]-N-{4-chloro-3-[(methylamino)-carbonylamino]phenyl}prop-2-enamide. According to the procedure used to prepare Example 66, (2E)-N-(3-amino-4-chlorophenyl)-3-[4-(tert-butyl)phenyl]prop-2-enamide, Example 67(a), (90 mg, 0.27 mmol) and isocyanatomethane (156 mg, 2.7 mmol, Carbolabs) provided, after purification by silica gel chromatography (2:1 hexane:EtOAc), the title product as an off-white solid. MP 120-122° C. MS (ESI, pos. ion) m/z: 386 (M+1).

EXAMPLE 68

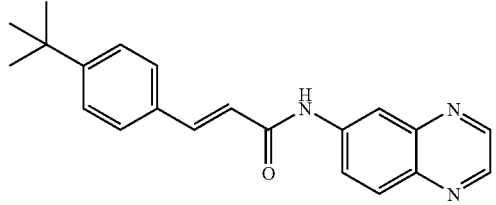

(2E)-3-[4-(tert-Butyl)phenyl]-N-quinoxalin-6-yl-prop-2-enamide

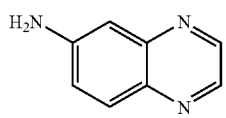

(a) Quinoxaline-6-ylamine. To a round-bottomed flask equipped with magnetic stirring was added 4-nitro-1,2-phenylenediamine (1.0 g, 6.5 mmol, Aldrich), acetonitrile (10 mL) and glyoxal (2.2 mL, 19 mmol, 40 wt. % in water, Aldrich). The reaction mixture was allowed to stir at 50° C. for 12 h, then concentrated in vacuo to yield 1.1 g crude 6-nitro-quinoxaline. The crude product was dissolved in methanol, treated with 10% Pd/C (10 mg, Aldrich) and stirred under H$_2$ (1 atm) at 25° C. overnight. The reaction mixture was filtered through Celite and the filtrate was concentrated in vacuo to provide the title product. MS (ESI, pos. ion) m/z: 146 (M+1).

(b) (2E)-3-[4-(tert-Butyl)phenyl]-N-quinoxalin-6-ylprop-2-enamide. Analogous to the procedure used to prepare Example 2, 4-tert-butyl-trans-cinnamic acid (100 mg, 0.40 mmol, EMKA-Chemie) and quinoxaline-6-ylamine, Example 68(a), (71 mg, 0.40 mmol) provided, after purification by silica gel chromatography (1:2 hexane:EtOAc), the title product as a yellow solid. MP 229-230° C. MS (ESI, pos. ion) m/z: 332 (M+1).

EXAMPLE 69

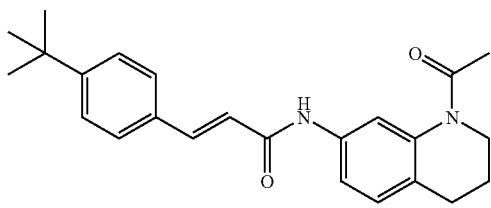

(2E)-N-(1-acetyl(7-1,2,3,4-tetrahydroquinolyl))-3-[4-(tert-butyl)phenyl]prop-2-enamide

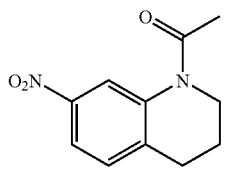

(a) 1-Acetyl-7-nitro-1,2,3,4-tetrahydroquinoline. A mixture of 7-nitro-1,2,3,4-tetrahydroquinoline, Example 19(a), (0.36 g, 2.0 mmol) and acetic anhydride (3.5 mL, 37 mmol, Aldrich) in a 15 mL round-bottomed flask, was heated at reflux for 1.5 h. The reaction mixture was concentrated in vacuo and the residue was partitioned between EtOAc and 30% ammonium hydroxide. The aqueous layer was extracted with EtOAc (10 mL) and the combined organic layers were dried over $Na_2SO_4$, filtered and concentrated in vacuo to give the title compound as a yellow solid. MS (ESI, pos. ion) m/z: 221 (M+1).

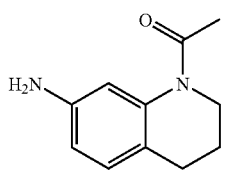

(b) 1-Acetyl-7-amino-1,2,3,4-tetrahydroquinoline. Analogous to the procedure used to prepare Example 3, step (a), 1-acetyl-7-nitro-1,2,3,4-tetrahydroquinoline, Example 69(a), (0.44 g, 2.0 mmol) was converted to the title product. MS (ESI, pos. ion) m/z: 191 (M+1).

(c) (2E)-N-(1-acetyl(7-1,2,3,4-tetrahydroquinolyl))-3-[4-(tert-butyl)phenyl]prop-2-enamide. According to the procedure used to prepare Example 1, 4-tert-butyl-trans-cinnamic acid (0.41 g, 2.0 mmol, EMKA Chemie) and 1-acetyl-7-amino-1,2,3,4-tetrahydroquinoline, Example 69(b), (370 mg, 2.0 mmol) provided, after purification by silica gel chromatography (1:1 hexane:EtOAc), the title compound as an amorphous white solid. MS (ESI, pos. ion) m/z: 377 (M+1).

EXAMPLE 70

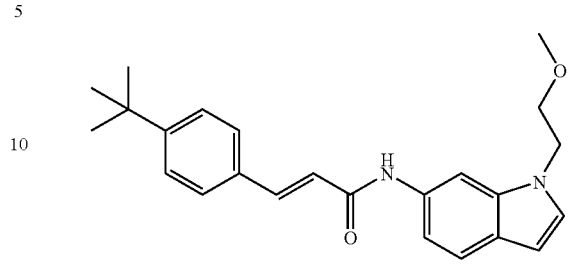

(2E)-3-[4-(tert-Butyl)phenyl]-N-[1-(2-methoxyethyl)indol-6-yl]prop-2-enamide

To a round-bottomed flask was added, (2E)-3-[4-(tert-butyl)phenyl]-N-indol-6-ylprop-2-enamide, Example 189, (320 mg, 1.0 mmol) and anhydrous DMF (20 mL). The solution was stirred magnetically and treated with sodium hydride (0.10 g, 2.5 mmol, 60% dispersion in mineral oil, Aldrich) followed by 2-bromoethyl methyl ether (140 mg, 1.0 mmol, Aldrich). Stirring was continued at 25° C. for 2 h, then the reaction mixture was quenched by the addition of water (50 mL) and extracted with EtOAc. The organic extract was concentrated in vacuo. Purification by silica gel chromatography (60:40 hexane:EtOAc) provided the title compound as a yellow solid. MP 133° C. MS (ESI, pos. ion) m/z: 377 (M+1).

EXAMPLE 71

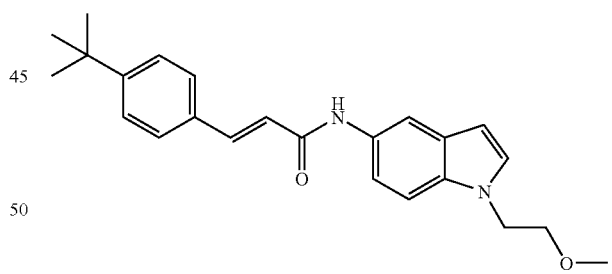

(2E)-3-[4-(tert-Butyl)phenyl]-N-[1-(2-methoxyethyl)indol-5-yl]prop-2-enamide

Analogous to the procedure used to prepare Example 70, 2-bromoethyl methyl ether (140 mg, 1.0 mmol, Aldrich) and (2E)-3-[4-(tert-butyl)phenyl]-N-indol-5-ylprop-2-enamide, Example 161, (320 mg, 0.01 mmol) provided, after purification by silica gel chromatography (65:35 hexane:EtOAc), the title compound as a pale yellow solid. MP 138° C. MS (ESI, pos. ion) m/z: 377 (M+1).

EXAMPLE 72

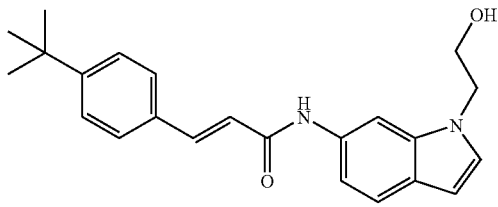

(2E)-3-[4-(tert-Butyl)phenyl]-N-[1-(2-hydroxyethyl)indol-6-yl]prop-2-enamide

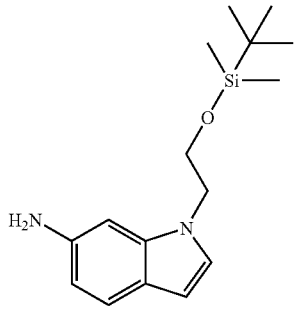

(a) 1-[2-(1,1,2,2-Tetramethyl-1-silapropoxy)ethyl]indole-6-ylamine. Analogous to the procedure used to prepare Example 33, step (a), 6-nitroindole (0.49 g, 3.0 mmol, Aldrich) and (2-bromoethoxy)-tert-butyldimethylsilane (0.72 g, 3.0 mmol, Aldrich) provided the title product. MS (ESI, pos. ion) m/z: 291 (M+1).

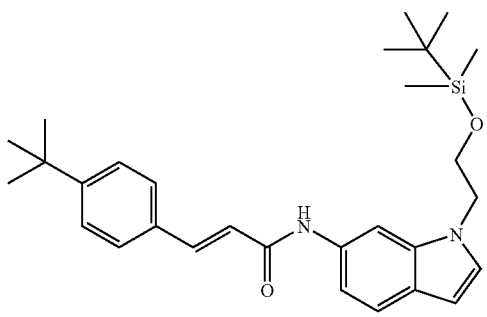

(b) (2E)-3-[4-(tert-Butyl)phenyl]-N-{1-[2-(1,1,2,2-tetramethyl-1-silapropoxy)ethyl]indol-6-yl}prop-2-enamide. Analogous to the procedure used to prepare Example 1, 4-tert-butyl-trans-cinnamic acid (200 mg, 1.0 mmol, EMKA-Chemie) and 1-[2-(1,1,2,2-tetramethyl-1-silapropoxy)ethyl]indole-6-ylamine, Example 72(a), (290 mg, 1.0 mmol) provided the title product. MS (ESI, pos. ion) m/z: 477 (M+1).

(c) (2E)-3-[4-(tert-Butyl)phenyl]-N-[1-(2-hydroxyethyl)indol-6-yl]prop-2-enamide. (2E)-3-[4-(tert-Butyl)phenyl]-N-{1-[2-(1,1,2,2-tetramethyl-1-silapropoxy)ethyl]indol-6-yl}prop-2-enamide, Example 72(b), (420 mg, 0.88 mmol) was transferred to a round-bottomed flask and treated with tetrabutylammonium fluoride (2.0 mL, 2.0 mmol, 1.0 M in THF, Aldrich) under N₂. The reaction mixture was magnetically stirred at 25° C. for 2 h. The reaction mixture was diluted with water (25 mL) and extracted with EtOAc. The organic extract was concentrated in vacuo. Purification by silica gel chromatography (30:70 hexane:EtOAc) provided the title compound as a yellow solid. MP 178° C. MS (ESI, pos. ion) m/z: 363 (M+1).

EXAMPLE 73

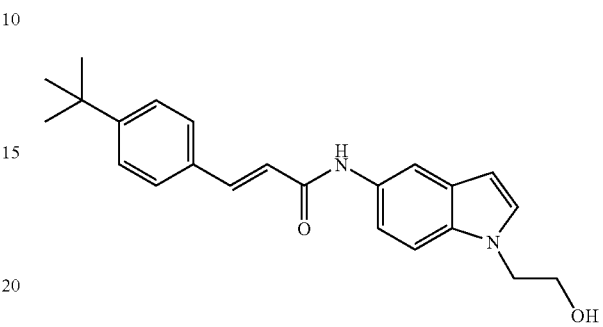

(2E)-3-[4-(tert-Butyl)phenyl]-N-[1-(2-hydroxyethyl)indol-5-yl]prop-2-enamide

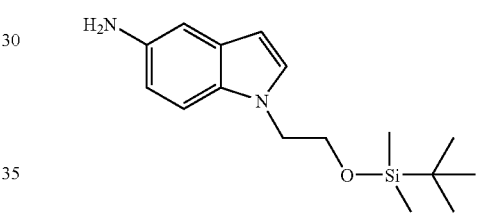

(a) 1-[2-(1,1,2,2-Tetramethyl-1-silapropoxy)ethyl]indole-5-ylamine. According to the procedure used to prepare Example 33, step (a), 5-nitroindole (0.49 g, 3.0 mmol, Aldrich) and (2-bromoethoxy)-tert-butyldimethylsilane (0.72 g, 3.0 mmol, Aldrich) provided the title product. MS (ESI, pos. ion) m/z: 291 (M+1).

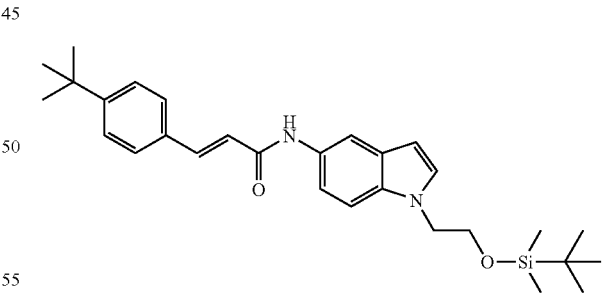

(b) (2E)-3-[4-(tert-Butyl)phenyl]-N-{1-[2-(1,1,2,2-tetramethyl-1-silapropoxy)ethyl]indol-5-yl}prop-2-enamide. According to the procedure used to prepare Example 1, 4-tert-butyl-trans-cinnamic acid (100 mg, 0.50 mmol, EMKA-Chemie) and 1-[2-(1,1,2,2-tetramethyl-1-silapropoxy)ethyl]indole-5-ylamine, Example 73(a), (145 mg, 0.50 mmol) provided the title product. MS (ESI, pos. ion) m/z: 477 (M+1).

(c) (2E)-3-[4-(tert-Butyl)phenyl]-N-[1-(2-hydroxyethyl)indol-5-yl]prop-2-enamide. According to the procedure used to prepare Example 72, step (c), (2E)-3-[4-(tert-butyl)phenyl]-N-{1-[2-(1,1,2,2-tetramethyl-1-silapropoxy)ethyl]indol-5-yl}prop-2-enamide, Example 73(b), (130 mg, 0.27 mmol) and tetrabutylammonium fluoride(1.0 mL, 1.0 mmol, 1.0 M in THF, Aldrich) provided, after purification by silica gel chromatography (30:70 hexane:EtOAc), the title compound as a pale yellow solid. MP 182° C. MS (ESI, pos. ion) m/z: 363 (M+1).

EXAMPLE 74

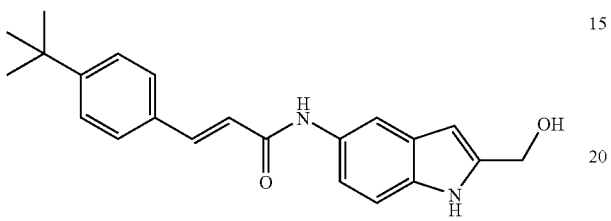

(2E)-3-[4-(tert-Butyl)phenyl]-N-[2-(hydroxymethyl)indol-5-yl]prop-2-enamide

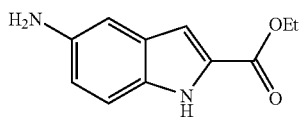

(a) Ethyl 5-aminoindole-2-carboxylate. Analogous to the procedure used to prepare Example 3, step (a), ethyl 5-nitroindole-2-carboxylate (2.3 g, 9.9 mmol, Acros) provided the title product. MS (ESI, pos. ion) m/z: 205 (M+1).

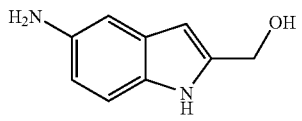

(b) (5-Aminoindol-2-yl)methan-1-ol. Ethyl 5-aminoindole-2-carboxylate, Example 74(a), (1.5 g, 7.3 mmol) was transferred to a round-bottomed flask and treated with lithium aluminum hydride (10 mL, 10 mmol, 1.0 M in THF, Aldrich) under N₂. The reaction mixture was magnetically stirred at 25° C. for 1 h, then quenched by the dropwise addition of H₂O (0.5 mL) followed by 20% aq. KOH (30 mL). The suspension was filtered and the aqueous phase extracted with EtOAc. The organic extract was concentrated in vacuo. Purification of the crude product by silica gel chromatography (20:80 hexane:EtOAc) provided the title product. MS (ESI, pos. ion) m/z: 163 (M+1).

(c) (2E)-3-[4-(tert-Butyl)phenyl]-N-[2-(hydroxymethyl)indol-5-yl]prop-2-enamide. Analogous to the procedure used to prepare Example 1, 4-tert-butyl-trans-cinnamic acid (200 mg, 1.0 mmol, EMKA-Chemie) and (5-aminoindol-2-yl)methan-1-ol, Example 74(b), (160 mg, 1.0 mmol) provided, after purification by silica gel chromatography (40:60 hexane:EtOAc), the title product as a pale tan amorphous solid. MS (ESI, pos. ion) m/z: 349 (M+1).

EXAMPLE 75

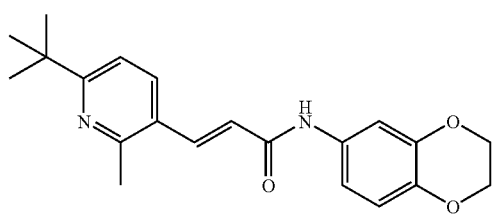

(2E)-N-(2H,3H-Benzo[3,4-e]1,4-dioxan-6-yl)-3-[6-(tert-butyl)-2-methyl(3-pyridyl)]prop-2-enamide

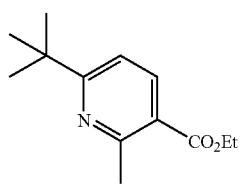

(a) Ethyl 6-(tert-butyl)-2-methylpyridine-3-carboxylate. Analogous to the procedure used to prepare Example 44, step (a), ethyl 2-methylnicotinate (8.3 g, 50 mmol, Aldrich), trimethylacetic acid (26 g, 250 mmol, Aldrich), silver nitrate (1.7 g, 10 mmol, Aldrich), 10% aq. sulfuric acid (50 mL) and ammonium persulfate (23 g, 100 mmol, Aldrich) provided, after purification by silica gel chromatography (80:20 hexane:EtOAc), the title product. MS (ESI, pos. ion) m/z: 222 (M+1).

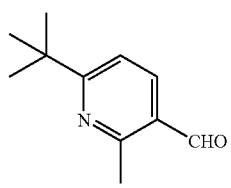

(b) 6-(tert-Butyl)-2-methylpyridine-3-carbaldehyde. Analogous to the procedure used to prepare Example 43, step (b), ethyl 6-(tert-butyl)-2-methylpyridine-3-carboxylate, Example 75(a), (5.2 g, 23 mmol) provided the title product. MS (ESI, pos. ion) m/z: 178 (M+1).

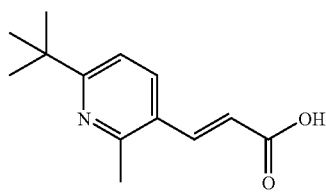

(c) (2E)-3-[6-(tert-Butyl)-2-methyl(3-pyridyl)]prop-2-enoic acid. Analogous to the procedure used to prepare Example 40, step (a), 6-(tert-butyl)-2-methylpyridine-3-carbaldehyde, Example 75(b), (3.0 g, 17 mmol) and triethyl phosphonoacetate (4.0 g, 18 mmol, Aldrich) provided the title product. MS (ESI, 10 pos. ion) m/z: 220 (M+1).

(d) (2E)-N-(2H,3H-Benzo[3,4-e]1,4-dioxan-6-yl)-3-[6-(tert-butyl)-2-methyl(3-pyridyl)]prop-2-enamide. Analogous to the procedure used to prepare Example 1, (2E)-3-[6-(tert-butyl)-2-methyl(3-pyridyl)]prop-2-enoic acid, Example 75(c), (110 mg, 0.50 mmol) and 1,4-benzodioxan-6-amine (76 mg, 0.50 mmol, Aldrich) provided, after purification by silica gel chromatography (55:45 hexane:EtOAc), the title compound as a yellow amorphous solid. MS (ESI, pos. ion) m/z: 353 (M+1).

EXAMPLE 76

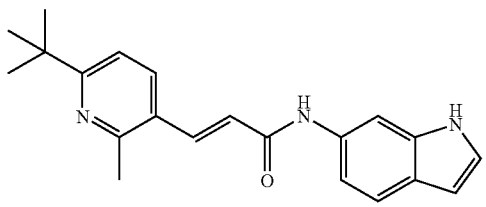

(2E)-3-[6-(tert-Butyl)-2-methyl(3-pyridyl)]-N-indol-6-ylprop-2-enamide

Analogous to the procedure used to prepare Example 1, (2E)-3-[6-(tert-butyl)-2-methyl(3-pyridyl)]prop-2-enoic acid, Example 75(c), (220 mg, 1.0 mmol) and 6-aminoindole (130 mg, 1.0 mmol, Lancaster) provided, after purification by silica gel chromatography (55:45 hexane:EtOAc), the title compound as a yellow solid. MP 182° C. MS (ESI, pos. ion) m/z: 334 (M+1).

EXAMPLE 77

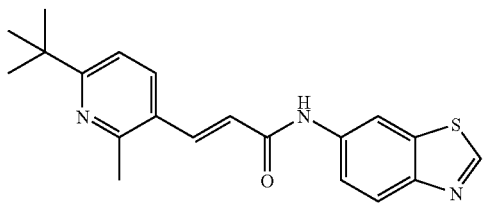

(2E)-N-Benzothiazol-6-yl-3-[6-(tert-butyl)-2-methyl(3-pyridyl)]prop-2-enamide

Analogous to the procedure used to prepare Example 1, (2E)-3-[6-(tert-butyl)-2-methyl(3-pyridyl)]prop-2-enoic acid, Example 75(c), (220 mg, 1.0 mmol) and 6-aminobenzothiazole (150 mg, 1.0 mmol, Lancaster) provided, after purification by silica gel chromatography (55:45 hexane:EtOAc), the title compound as a pale yellow amorphous solid. MS (ESI, pos. ion) m/z: 352 (M+1).

EXAMPLE 78

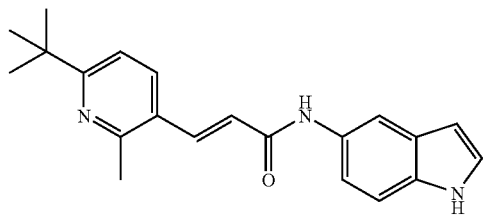

(2E)-3-[6-(tert-Butyl)-2-methyl(3-pyridyl)]-N-indol-5-ylprop-2-enamide

Analogous to the procedure used to prepare Example 1, (2E)-3-[6-(tert-butyl)-2-methyl(3-pyridyl)]prop-2-enoic acid, Example 75(c), (0.88 g, 4.0 mmol) and 5-aminoindole (0.53 g, 4.0 mmol, Lancaster) provided, after purification by silica gel chromatography (55:45 hexane:EtOAc), the title compound as a yellow amorphous solid. MS (ESI, pos. ion) m/z: 334 (M+1).

EXAMPLE 79

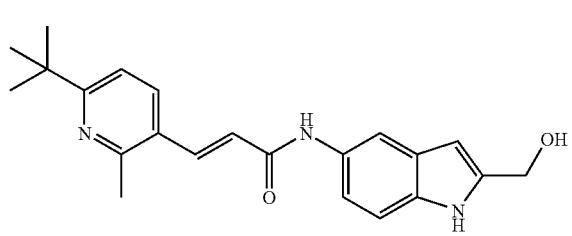

(2E)-3-[6-(tert-Butyl)-2-methyl(3-pyridyl)]-N-[2-(hydroxymethyl)indol-5-yl]prop-2-enamide Analogous to the procedure used to prepare Example 1, (2E)-3-[6-(tert-butyl)-2-methyl(3-pyridyl)]prop-2-enoic acid, Example 75(c), (10 mg, 0.50 mmol) and (5-aminoindol-2-yl)methan-1-ol, Example 74(b), (81, 0.50 mmol) provided, after purification by silica gel chromatography (25:75 hexane:EtOAc), the title compound as a pale yellow solid. MP 213° C. MS (ESI, pos. ion) m/z: 364 (M+1).

EXAMPLE 80

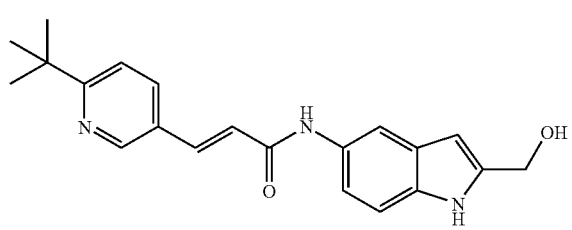

(2E)-3-[6-(tert-Butyl)(3-pyridyl)]-N-[2-(hydroxymethyl)indol-5-yl]prop-2-enamide Analogous to the procedure used to prepare Example 1, (2E)-3-[6-(tert-butyl)(3-pyridyl)]prop-2-enoic acid, Example 44(b), (41 mg, 0.20 mmol) and (5-aminoindol-2-yl)methan-1-ol, Example 74(b), (32 mg, 0.20 mmol) provided, after purification by silica gel chromatography (20:80 hexane:EtOAc), the title compound as a yellow amorphous solid. MS (ESI, pos. ion) m/z: 350 (M+1).

EXAMPLE 81

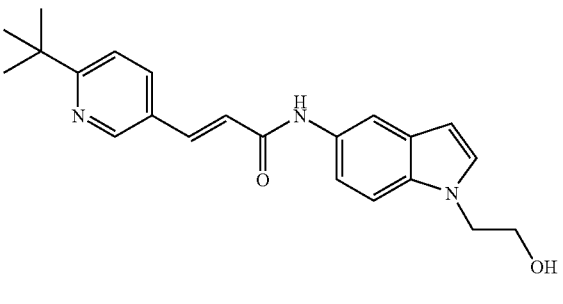

(2E)-3-[6-(tert-Butyl)(3-pyridyl)]-N-[1-(2-hydroxyethyl)indol-5-yl]prop-2-enamide

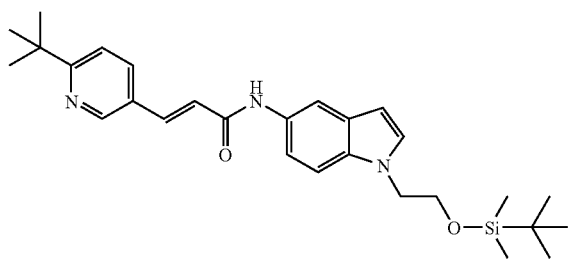

(a) (2E)-3-[6-(tert-butyl)(3-pyridyl)]-N-{1-[2-(1,1,2,2-tetramethyl-1-silapropoxy)ethyl]indol-5-yl}prop-2-enamide. Analogous to the procedure used to prepare Example 1, (2E)-3-[6-(tert-butyl)(3-pyridyl)]prop-2-enoic acid, Example 44(b), (41 mg, 0.20 inmol) and 1-[2-(1,1,2,2-tetramethyl-1-silapropoxy)ethyl]indole-5-ylamine, Example 73(a), (60 mg, 0.20 mmol) provided the title product. MS (ESI, pos. ion) m/z: 478 (M+1).

(b) (2E)-3-[6-(tert-Butyl)(3-pyridyl)]-N-[1-(2-hydroxyethyl)indol-5-yl]prop-2-enamide. Analogous to the procedure used to prepare Example 72, step (c), (2E)-3-[6-(tert-butyl)(3-pyridyl)]-N-{1-[2-(1,1,2,2-tetramethyl-1-silapropoxy)ethyl]indol-5-yl}prop-2-enamide, Example 81(a), (75 mg, 0.16 mmol) and tetrabutylammonium fluoride (0.50 mL, 0.50 mmol, 1.0 M in THF, Aldrich) provided, after purification by silica gel chromatography (20:80 hexane:EtOAc), the title compound as a yellow amorphous solid. MS (ESI, pos. ion) m/z: 364 (M+1).

EXAMPLE 82

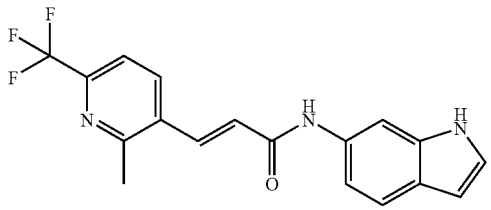

(2E)-N-Indol-6-yl-3-[2-methyl-6-(trifluoromethyl)(3-pyridyl)]prop-2-enamide

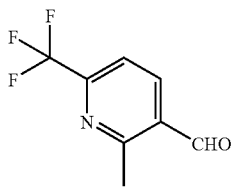

(a) 2-Methyl-6-(trifluoromethyl)pyridine-3-carbaldehyde. Analogous to the procedure used to prepare Example 43, step (b), 2-methyl-6-(trifluoromethyl)pyridine-3-carboxylic acid (5.0 g, 24 mmol, Oakwood) provided the title product. MS (ESI, pos. ion) m/z: 190 (M+1).

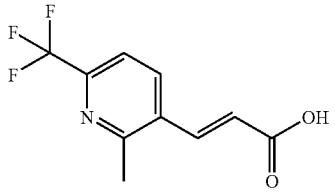

(b) (2E)-3-[2-Methyl-6-(trifluoromethyl)(3-pyridyl)]prop-2-enoic acid. Analogous to the procedure used to prepare Example 40, step (a), 2-methyl-6-(trifluoromethyl)pyridine-3-carbaldehyde, Example 82(a), (3.7 g, 20 mmol) and triethyl phosphonoacetate (4.5 g, 20 mmol, Aldrich) provided the title product. MS (ESI, pos. ion) m/z: 232 (M+1).

(c) (2E)-N-Indol-6-yl-3-[2-methyl-6-(trifluoromethyl)(3-pyridyl)]prop-2-enamide. Analogous to the procedure used to prepare Example 1, (2E)-3-[2-methyl-6-(trifluoromethyl)(3-pyridyl)]prop-2-enoic acid, Example 82(b), (58 mg, 0.25 mmol) and 6-aminoindole (33 mg, 0.25 mmol, Lancaster) provided, after purification by silica gel chromatography (55:45 hexane:EtOAc), the title compound as a yellow solid. MP 223° C. MS (ESI, pos. ion) m/z: 346 (M+1).

EXAMPLE 83

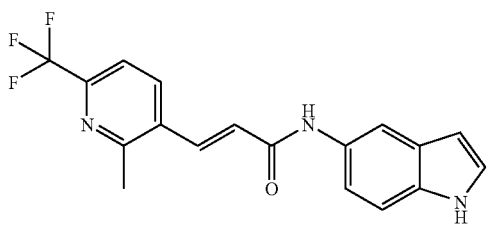

(2E)-N-Indol-5-yl-3-[2-methyl-6-(trifluoromethyl)(3-pyridyl)]prop-2-enamide

Analogous to the procedure used to prepare Example 1, (2E)-3-[2-methyl-6-(trifluoromethyl)(3-pyridyl)]prop-2-enoic acid, Example 82(b), (120 mg, 0.50 mmol) and 5-aminoindole (66 mg, 0.50 mmol, Aldrich) provided, after purification by silica gel chromatography (55:45 hexane:EtOAc), the title compound as a yellow solid. MP 231° C. MS (ESI, pos. ion) m/z: 346 (M+1).

EXAMPLE 84

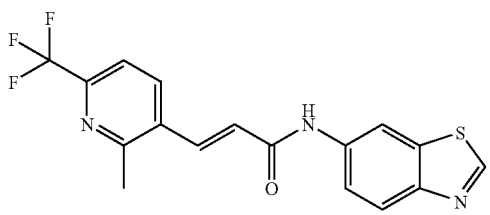

(2E)-N-Benzothiazol-6-yl-3-[2-methyl-6-(trifluoromethyl)(3-pyridyl)]prop-2-enamide Analogous to the procedure used to prepare Example 1, (2E)-3-[2-methyl-6-(trifluoromethyl)(3-pyridyl)]prop-2-enoic acid, Example 82(b), (120 mg, 0.50 mmol) and 6-aminobenzothiazole (75 mg, 0.50 mmol, Lancaster) provided, after purification by silica gel chromatography (55:45 hexane:EtOAc), the title compound as a white solid. MP 196° C. MS (ESI, pos. ion) m/z: 364 (M+1).

EXAMPLE 85

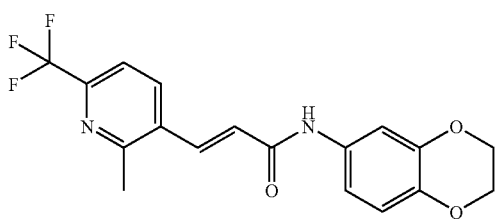

(2E)-N-(2H,3H-Benzo[3,4-e]1,4-dioxan-6-yl)-3-[2-methyl-6-(trifluoromethyl)-(3-pyridyl)]prop-2-enamide Analogous to the procedure used to prepare Example 1, (2E)-3-[2-methyl-6-(trifluoromethyl)(3-pyridyl)]prop-2-enoic acid, Example 82(b), (120 mg, 0.50 mmol) and 1,4-benzodioxan-6-amine (76 mg, 0.50 mmol, Aldrich) provided, after purification by silica gel chromatography (55:45 hexane:EtOAc), the title compound as a yellow solid. MP 186° C. MS (ESI, pos. ion) m/z: 365 (M+1).

EXAMPLE 86

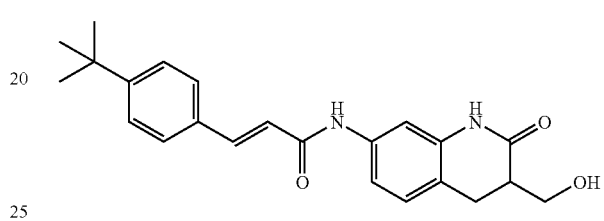

(2E)-3-[4-(tert-butyl)phenyl]-N-[3-(hydroxymethyl)-2-oxo(7-1,3,4-trihydroquinolyl)]prop-2-enamide

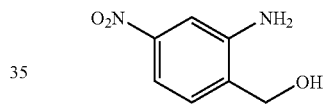

(a) (2-Amino-4-nitrophenyl)methan-1-ol. To a solution of 4-nitroanthranilic acid (910 mg, 5.0 mmol, Aldrich) in THF (15 mL), magnetically stirred at 0° C., was added borane-tetrahydrofuran complex (15 mL, 15 mmol, 1.0 M in THF, Aldrich) dropwise. The reaction mixture was heated to reflux overnight. The mixture was then cooled to 0° C. and treated dropwise with MeOH (5 mL) followed by 1 N NaOH (30 mL). After stirring for 30 min at room temperature, the mixture was extracted with EtOAc (2×50 mL). The combined organic phases were washed with satd NaCl (20 mL), dried over $Na_2SO_4$, filtered and concentrated in vacuo. Purification by silica gel chromatography (50% EtOAc/hexane) followed by recrystallization from EtOAc/hexane provided the title product. MS (ESI, pos. ion) m/z: 169 (M+1).

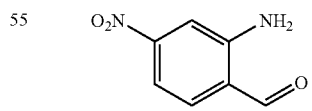

(b) 2-Amino-4-nitrobenzaldehyde. A mixture of 2-amino-4-nitrophenyl)methan-1-ol, Example 86(a), (336 mg, 2.0 mmol) and $MnO_2$ (3.48 g, 40.0 mmol, Aldrich) in $CH_2Cl_2$/hexane (1:1, 10 mL) was stirred at room temperature for 1 h. The suspension was filtered and washed with $CH_2Cl_2$. The filtrate was concentrated in vacuo to give the crude product. MS (ESI, pos. ion) m/z: 167 (M+1).

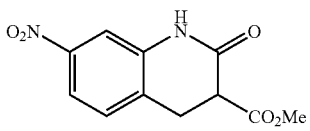

(c) Methyl 7-nitro-2-oxo-1,3,4-trihydroquinoline-3-carboxylate. A mixture of 2-amino-4-nitrobenzaldehyde, Example 86(b), (1.66 g, 10.0 mmol), dimethyl malonate (1.37 mL, 12.0 mmol, Aldrich), copper (11) acetate (100 mg, 0.5 mmol, Aldrich) and potassium acetate (99 mg, 1.0 mmol, Bayer) in acetic acid (20 mL) was stirred at 110° C. for 48 h. Most of the solvent was removed in vacuo and the resulting precipitate was collected by filtration, washed with EtOAc and dried in vacuo to give the title product. MS (ESI, pos. ion) m/z: 248 (M+1)

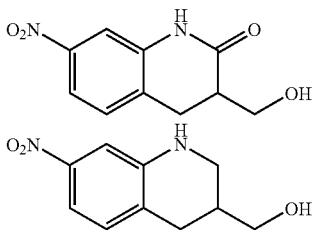

(d) 3-(Hydroxymethyl)-7-nitro-1,3,4-trihydroquinolin-2-one and (7-nitro-3-1,2,3,4-tetrahydroquinolyl)methan-1-ol. To a solution of methyl 7-nitro-2-oxo-1,3,4-trihydroquinoline-3-carboxylate, Example 86(c), (1.23 g, 5.0 mmol) in THF (50 mL) was added LiBH$_4$ (12.5 mL, 25.0 mmol, 2.0 M in THF, Aldrich). The reaction mixture was stirred at 40° C. for 18 h, then quenched by the careful addition of satd NH$_4$Cl (20 mL). The mixture was stirred at room temperature for 30 min, then extracted with EtOAc (2×50 mL). The combined organic phases were washed with satd NaCl (10 mL), dried over Na$_2$SO$_4$, filtered and concentrated in vacuo. Purification by silica gel chromatography (50% EtOAc/CH$_2$Cl$_2$) provided 3-(hydroxymethyl)-7-nitro-1,3,4-trihydroquinolin-2-one [MS (ESI, pos. ion) m/z: 223 (M+1)] and (7-nitro-3-1,2,3,4-tetrahydroquinolyl)methan-1-ol [MS (ESI, pos. ion) m/z: 209 (M+1)].

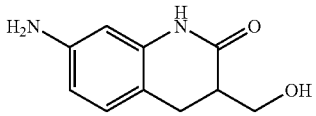

(e) 7-Amino-3-(hydroxymethyl)-1,3,4-trihydroquinolin-2-one. Analogous to the procedure used to prepare Example 3, step (a), 3-(hydroxymethyl)-7-nitro-1,3,4-trihydroquinolin-2-one, Example 86(d), (66 mg, 0.30 mmol) provided, after purification by silica gel chromatography (10% MeOH/CH$_2$Cl$_2$), the title compound. MS (ESI, pos. ion) m/z: 193 (M+1).

(f) (2E)-3-[4-(tert-Butyl)phenyl]-N-[3-(hydroxymethyl)-2-oxo(7-1,3,4-trihydroquinolyl)]prop-2-enamide. Analogous to the procedure used to prepare Example 1, 4-tert-butyl-trans-cinnamic acid (67 mg, 0.33 inmol, EMKA-Chemie) and 7-amino-3-(hydroxymethyl)-1,3,4-trihydroquinolin-2-one, Example 86(e), (52 mg, 0.27 mmol) provided, after purification by silica gel chromatography (10% MeOH/EtOAc), the title compound as a pale yellow solid. MP 201-203° C. MS (ESI, pos. ion) m/z: 379 (M+1).

EXAMPLE 87

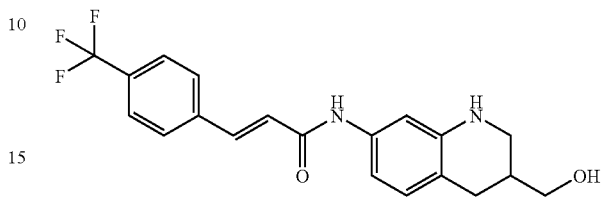

(2E)-N-[3-(Hydroxymethyl)(7-1,2,3,4-tetrahydroquinolyl)]-3-[4-(trifluoromethyl)phenyl]prop-2-enamide

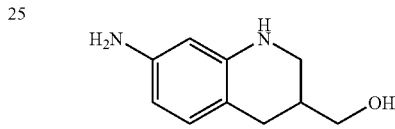

(a) (7-Amino-3-1,2,3,4-tetrahydroquinolyl)methan-1-ol. Analogous to the procedure used to prepare Example 3, step (a), (7-nitro-3-1,2,3,4-tetrahydroquinolyl)methan-1-ol, Example 86(d), (140 mg, 0.68 mmol) provided, after purification by silica gel chromatography (10% MeOH/CH$_2$Cl$_2$), the title compound. MS (ESI, pos. ion) m/z: 179 (M+1).

(b) (2E)-N-[3-(Hydroxymethyl)(7-1,2,3,4-tetrahydroquinolyl)]-3-[4-(trifluoromethyl)phenyl]prop-2-enamide. Analogous to the procedure used to prepare Example 1, trans-4-(trifluoromethyl)cinnamic acid (120 mg, 0.55 mmol, Aldrich) and (7-amino-3-1,2,3,4-tetrahydroquinolyl)methan-1-ol, Example 87(a), (98 mg, 0.55 mmol) provided, after purification by silica gel chromatography (10% MeOH/EtOAc), the title compound as a pale yellow solid. MP 176-179° C. MS (ESI, pos. ion) m/z: 377 (M+1).

EXAMPLE 88

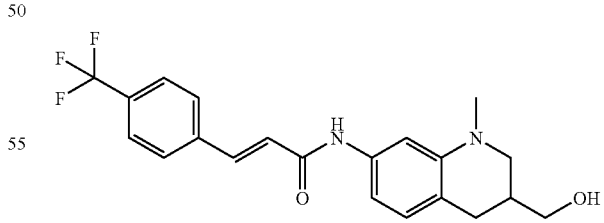

(2E)-N-[3-(hydroxymethyl)-1-methyl(7-1,2,3,4-tetrahydroquinolyl)]-3-[4-(trifluoromethyl)phenyl]prop-2-enamide A mixture of (2E)-N-[3-(hydroxymethyl)(7-1,2,3,4-tetrahydroquinolyl)]-3-[4-(trifluoromethyl)phenyl]prop-2-enamide, Example 87, (75 mg, 0.20 mmol), iodomethane (0.014 mL, 0.22 mmol, Aldrich) and NaHCO₃ (84 mg, 1.0 mmol) in DMF (1.0 mL, Aldrich) was stirred for 4 h at room temperature. Water (5 mL) was added and the mixture was extracted with EtOAc (2×20 mL). The combined organic phases were washed with water (5 mL), satd NaCl (5 mL), dried over Na₂SO₄, filtered and concentrated in vacuo. Purification by silica gel chromatography (60% EtOAc/CH₂Cl₂) provided the title product as a white solid. MP 167-169° C. MS (ESI, pos. ion) m/z: 391 (M+1).

EXAMPLE 89

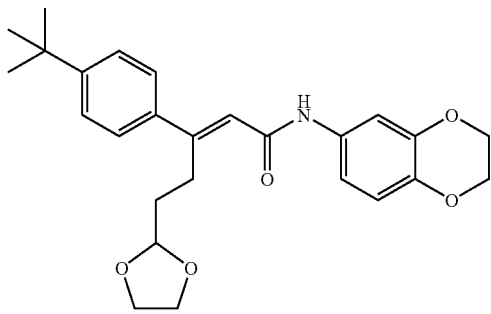

(2E)-N-(2H,3H-Benzo[e]1,4-dioxan-6-yl)-3-[4-(tert-butyl)phenyl]-5-(1,3-dioxolan-2-yl)pent-2-enamide Analogous to the procedure used to prepare Example 53(a), (1,3-dioxolan-2-ylethyl)zinc bromide (3.0 mL, 1.5 mmol, 0.5 M THF solution, Rieke) and N-(2H,3H-benzo[e]1,4-dioxan-6-yl)(2Z)-3-[4-(tert-butyl)phenyl]-3-iodoprop-2-enamide, Example 55, (0.23 g, 0.50 mmol) provided, after purification by silica gel chromatography (gradient: 30%-35% EtOAc/hexane), the title product as an amorphous white solid. MS (ESI, pos. ion) m/z: 438 (M+1).

EXAMPLE 90

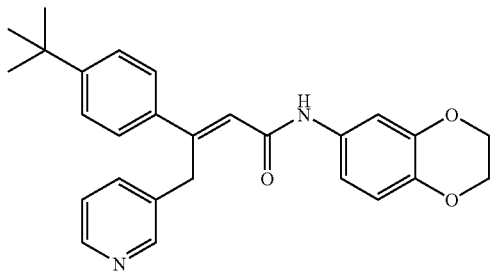

(2E)-N-(2H,3H-Benzo[e]1,4-dioxan-6-yl)-3-[4-(tert-butyl)phenyl]-4-(3-pyridyl)but-2-enamide

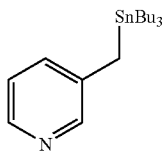

(a). 3-(Tributylstannanylmethyl)pyridine. Analogous to the procedure of Kaiser, E. M. and Petty, J. D. Synthesis 1975, 705-706, to a 50 mL round-bottomed flask equipped with magnetic stirring was added lithium diisopropylamide (5.2 mL, 10 mmol, 2.0 M in heptane/THF/ethylbenzene, Aldrich) at 0° C. under nitrogen, followed by hexamethylphosphoramide (1.8 mL, 10 mmol, Aldrich). The mixture was stirred for 15 min, then treated with a solution of 3-picoline (1.0 mL, 10 mmol, Aldrich) in THF (4 mL) over 5 min. The reaction mixture was stirred for 30 min, then a solution of tributyltin chloride (2.8 mL, 10 mmol, Aldrich) in THF (6 mL) was added. The resulting solution was gradually warmed to room temperature and concentrated in vacuo. Purification by silica gel chromatography (gradient: 2%-5% EtOAc/hexane) provided the title product as a colorless oil. MS (ESI, pos. ion) m/z: 382 (M+1).

(b) (2E)-N-(2H,3H-Benzo[e]1,4-dioxan-6-yl)-3-[4-(tert-butyl)phenyl]-4-(3-pyridyl)but-2-enamide. To a 50 mL round-bottomed flask, equipped with magnetic stirring, was added 3-(tributylstannanylmethyl)pyridine, Example 90(a), (0.37 g, 0.97 mmol), N-(2H,3H-benzo[e]1,4-dioxan-6-yl)(2Z)-3-[4-(tert-butyl)phenyl]-3-iodoprop-2-enamide, Example 55, (0.30 g, 0.65 mmol), 1-methyl-2-pyrrolidinone (2.5 mL, Aldrich), and tetrakis(triphenylphosphine)-palladium (0) (75 mg, 0.06 mmol, Aldrich). The reaction mixture was stirred at 110° C. overnight, then diluted with EtOAc (100 mL), washed with satd NaHCO₃, water and satd NaCl. The organic phase was dried over Na₂SO₄, filtered and concentrated in vacuo. Purification by silica gel chromatography (25%-45% EtOAc/hexane) was followed by reverse phase preparative HPLC (CH₃CN/H₂O with 0.1% TFA). The fractions containing desired product were neutralized with NaHCO₃. The mixture was extracted with CH₂Cl₂ and the organic phase concentrated in vacuo to provide the title product as an amorphous white solid. MS (ESI, pos. ion) m/z: 429 (M+1).

EXAMPLE 91

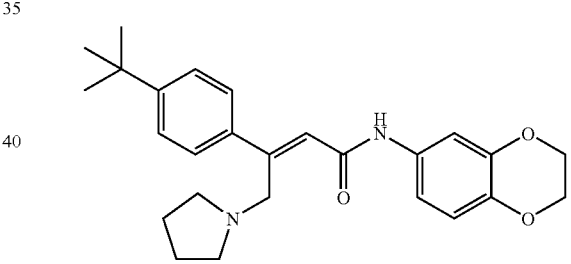

N-(2H,3H-Benzo[e]1,4-dioxan-6-yl)(2Z)-3-[4-(tert-butyl)phenyl]-4-pyrrolidinylbut-2-enamide

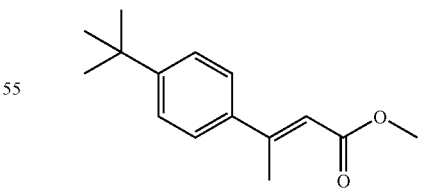

(a). Methyl (2E)-3-[4-(tert-butyl)phenyl]but-2-enoate. To a 100 mL round-bottomed flask purged with N₂ was added 1-bromo-4-tert-butylbenzene (2.34 g, 11.0 mmol, Aldrich), methyl crotonate (1.08 mL, 10 mmol, Aldrich), N-methyldicyclohexylamine (3.31 mL, 15 mmol, Aldrich), palladium acetate (0.045 g, 0.20 mmol, Aldrich), tetraethylammonium chloride (1.66 g, 10.0 mmol, Fluka), and N,N-dimethylacetamide (40 mL, Aldrich). The reaction mixture was magnetically stirred at 100° C. overnight, then allowed to cool to 25° C., diluted with Et₂O, and filtered through Celite. The solution was washed with H₂O (3×), dried over MgSO₄, filtered, and concentrated in vacuo. Purification by silica gel chromatography (gradient: 0.5%-3% dichloromethane in hexane) provided the title product as a colorless oil. MS (ESI, pos. ion) m/z: 233 (M+1).

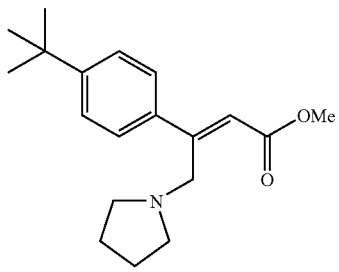

(b) Methyl (2Z)-3-[4-(tert-butyl)phenyl]-4-pyrrolidinylbut-2-enoate. A solution of methyl (2E)-3-[4-(tert-butyl)phenyl]but-2-enoate, Example 91(a), (0.37 g, 1.6 mmol) in CCl₄ (15 mL), magnetically stirred in a 50 mL round-bottomed flask under N₂, was treated with N-bromosuccinimide (0.31 g, 1.75 mmol, Aldrich) and 2,2'-azobisisobutyronitrile (5 mg, 0.03 mmol, Aldrich). The reaction mixture was magnetically stirred under reflux overnight, then allowed to cool to 25° C. The solid was filtered. The filtrate was concentrated in vacuo to afford a yellow oil [MS (ESI, pos. ion) m/z: 311, 313 (M+1, M+3)]. To a solution of the yellow oil in THF (5 mL), was added pyrrolidine (0.16 mL, 1.9 mmol, Aldrich) and N,N-diisopropylethylamine (0.33 mL, 1.9 mmol, Aldrich). The reaction mixture was magnetically stirred at room temperature overnight, then concentrated in vacuo. The residue was treated with water and extracted with dichloromethane (3×). The organic phase was dried over Na₂SO₄, filtered and concentrated in vacuo to afford a yellow oil. Purification by silica gel chromatography (gradient: 4%-20% EtOAc/hexane) provided the title product as a pale yellow oil. MS (ESI, pos. ion) m/z: 302 (M+1).

(c). N-(2H,3H-Benzo[e]1,4-dioxan-6-yl)(2Z)-3-[4-(tert-butyl)phenyl]-4-pyrrolidinylbut-2-enamide. To a 50 mL round-bottomed flask charged with methyl (2Z)-3-[4-(tert-butyl)phenyl]-4-pyrrolidinylbut-2-enoate, Example 91(b), (188 mg, 0.62 mmol) was added THF (2 mL), MeOH (0.2 mL), H₂O (1 mL), and lithium hydroxide monohydrate (54 mg, 1.25 mmol, Aldrich). The reaction mixture was magnetically stirred at room temperature overnight. The excess lithium hydroxide was removed by filtration. The mixture was purified by reverse phase preparative HPLC (CH₃CN/H₂O with 0.1% TFA), concentrated in vacuo, then treated with an excess of HCl in Et₂O. Concentration in vacuo provided a pale yellow solid 0.15 g [MS (ESI, pos. ion) m/z: 288 (M+1)]. Analogous to the procedure used to prepare Example 1, the solid (77 mg) and 1,4-benzodioxan-6-amine (61 mg, 0.40 mmol, Aldrich) provided the crude title product. Purification by silica gel chromatography (gradient: 1-5% MeOH in CH₂Cl₂) was followed by reverse phase preparative HPLC (CH₃CN/H₂O with 0.1% TFA). The fractions containing desired product were neutralized with NaHCO₃. The mixture was extracted with CH₂Cl₂ and the organic phase concentrated in vacuo to provide the title product as a pale yellow oil. MS (ESI, pos. ion) m/z: 421 (M+1).

EXAMPLE 92

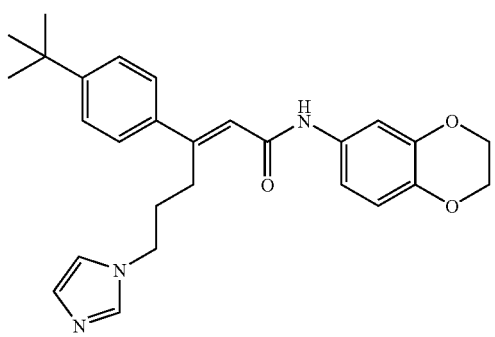

(2E)-N-(2H,3H-Benzo[e]1,4-dioxan-6-yl)-3-[4-(tert-butyl)phenyl]-6-imidazolylhex-2-enamide

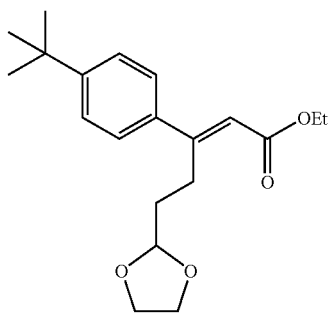

(a). Ethyl (2E)-3-[4-(tert-butyl)phenyl]-5-(1,3-dioxolan-2-yl)pent-2-enoate. Analogous to the procedure used to prepare Example 53(a), starting from (1,3-dioxolan-2-ylethyl)zinc bromide (0.5 M THF solution, 40 mL, 20 mmol, Rieke) and ethyl (2Z)-3-[4-(tert-butyl)phenyl]-3-iodoprop-2-enoate, Example 52(b), (3.58 g, 10.0 mmol), the title product was obtained as a colorless oil. MS (ESI, pos. ion) m/z: 333 (M+1).

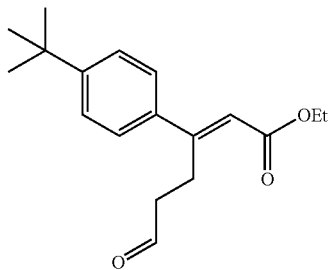

(b). Ethyl (2E)-3-[4-(tert-butyl)phenyl]-6-oxohex-2-enoate. To a round-bottomed flask was added ethyl (2E)-3-[4-(tert-butyl)phenyl]-5-(1,3-dioxolan-2-yl)pent-2-enoate, Example 92(a), (2.7 g, 8.1 mmol), THF (3 mL), and 5 N HCl (12 mL). The reaction mixture was initially stirred at room temperature for 24 h, then heated to 40° C. overnight. The pH was adjusted to ~5-6 by the addition of NaHCO₃ and the mixture was extracted with EtOAc. The combined organic extract was dried over Na₂SO₄, filtered, and concentrated in vacuo. Purification by silica gel chromatography (5% EtOAc/hexane) provided the title product as a white solid. MS (ESI, pos. ion) m/z: 289 (M+1).

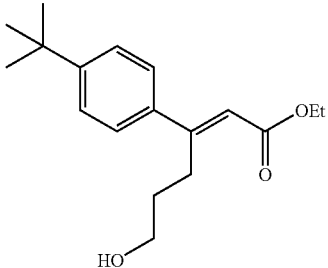

(c). Ethyl (2E)-3-[4-(tert-butyl)phenyl]-6-hydroxyhex-2-enoate. To solution of ethyl (2E)-3-[4-(tert-butyl)phenyl]-6-oxohex-2-enoate, Example 92(b), (1.5 g, 5.3 mmol) in MeOH (18 mL), magnetically stirred at 0° C. in a 100 mL round-bottomed flask, was added sodium borohydride (0.40 g, 11 mmol, Aldrich). The mixture was allowed to gradually warm up to room temperature over 2 h, then quenched with water (20 mL) and extracted with EtOAc (4×). The organic extract was dried over Na₂SO₄, filtered, and concentrated in vacuo. Purification by silica gel chromatography (15% EtOAc/hexane) provided the title product as a colorless oil in quantitative yield. MS (ESI, pos. ion) m/z: 291 (M+1).

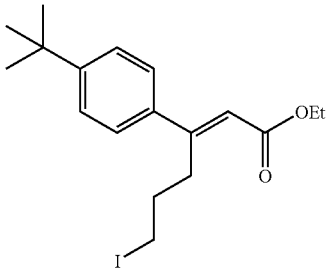

(d). Ethyl (2E)-3-[4-(tert-butyl)phenyl]-6-iodohex-2-enoate. To a 100 mL round-bottomed flask charged with ethyl (2E)-3-[4-(tert-butyl)phenyl]-6-hydroxyhex-2-enoate, Example 92(c), (0.80 g, 2.7 mmol) and CH₂Cl₂ (10 mL) at room temperature, was added triphenylphosphine (0.87 g, 3.3 mmol, Aldrich), imidazole (0.22 g, 3.3 mmol, Aldrich), and I₂ (1.2 g, 4.7 mmol, Aldrich). The reaction mixture was stirred for 2 h, filtered and concentrated in vacuo. Purification by silica gel chromatography (3% EtOAc/hexane) provided the title product as a white semi-solid in quantitative yield. MS (ESI, pos. ion) m/z: 401 (M+1).

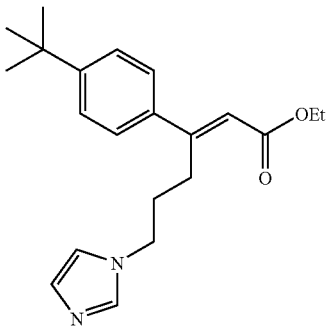

(e) Ethyl (2E)-3-[4-(tert-butyl)phenyl]-6-imidazolylhex-2-enoate. To a 100 mL round-bottomed flask charged with ethyl (2E)-3-[4-(tert-butyl)phenyl]-6-iodohex-2-enoate, Example 92(d), (1.1 g, 2.7 mmol), imidazole (0.20 g, 3.0 mmol, Aldrich), benzyltriethylammonium chloride (63 mg, 0.30 mmol, Aldrich), and CH₂Cl₂ (15 mL), stirred magnetically at room temperature, was added potassium hydroxide (50% aqueous solution, 1.5 mL). The reaction mixture was stirred at 50° C. overnight, then diluted with water. The reaction mixture was extracted with CH₂Cl₂. The organic solution was dried over Na₂SO₄, filtered, and concentrated in vacuo. Purification by silica gel chromatography (50% EtOAc/hexane) provided the title product as a pale yellow oil. MS (ESI, pos. ion) m/z: 341 (M+1).

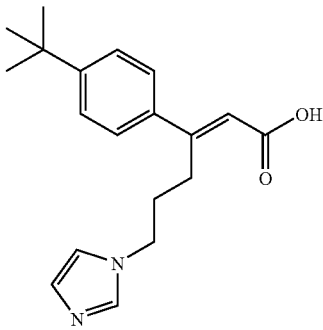

(f) (2E)-3-[4-(tert-Butyl)phenyl]-6-imidazolylhex-2-enoic acid. To a 50 mL round-bottomed flask equipped with a reflux condenser was added ethyl (2E)-3-[4-(tert-butyl)phenyl]-6-imidazolylhex-2-enoate, Example 92(e), (0.35 g, 1.0 mmol), THF (6 mL) and KOH (50% aqueous solution, 1.5 mL). The reaction mixture was heated and magnetically stirred under reflux overnight, then concentrated in vacuo and acidified with glacial acetic acid to pH ~4-5. The aqueous mixture was extracted with CH₂Cl₂ and the organic phase was dried over Na₂SO₄, filtered, and concentrated in vacuo. Purification by silica gel chromatography (5%-10% MeOH/CH₂Cl₂) provided the title product as a white solid. MS (ESI, pos. ion) m/z: 313 (M+1).

(g) (2E)-N-(2H,3H-Benzo[e]1,4-dioxan-6-yl)-3-[4-(tert-butyl)phenyl]-6-imidazolylhex-2-enamide. Analogous to the procedure used to prepare Example 1, (2E)-3-[4-(tert-butyl)phenyl]-6-imidazolylhex-2-enoic acid, Example 92(f), (76 mg, 0.24 mmol) and 1,4-benzodioxan-6-amine (36 mg, 0.24 mmol, Aldrich) provided, after purification by silica gel chromatography (3% -5% MeOH/CH₂Cl₂), the title product as an amorphous off-white solid. MS (ESI, pos. ion) m/z: 446 (M+1).

EXAMPLE 93

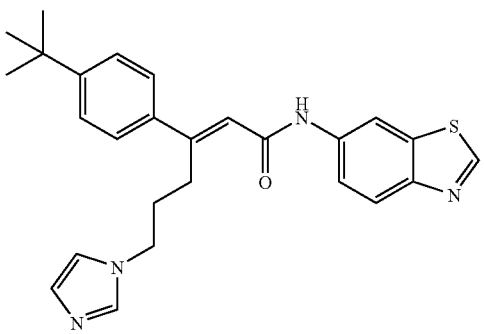

3-(4-tert-Butyl-phenyl)-6-imidazol-1-yl-hex-2-enoic acid benzothiazol-6-ylamide. Analogous to the procedure used to prepare Example 1, (2E)-3-[4-(tert-butyl)phenyl]-6-imidazolylhex-2-enoic acid, Example 92(f), (76 mg, 0.24 mmol) and 6-aminobenzothiazole (36 mg, 0.24 mmol, Lancaster) provided, after purification by silica gel chromatography (3%-5% MeOH/CH$_2$Cl$_2$), the title compound as a white solid. MS (ESI, pos. ion) m/z: 445 (M+1).

EXAMPLE 94

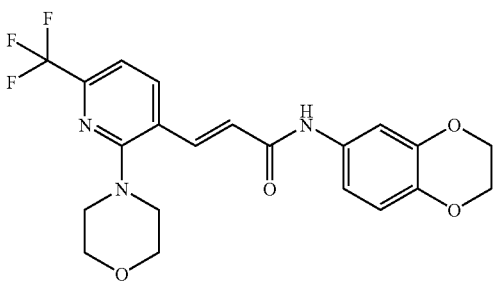

(2E)-N-(2H,3H-benzo[e]1,4-dioxan-6-yl)-3-[2-morpholin-4-yl-6-(trifluoromethyl)(3-pyridyl)]prop-2-enamide

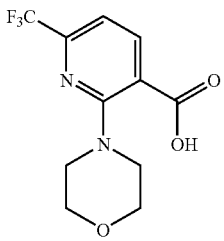

(a) 2-Morpholin-4-yl-6-(trifluoromethyl)pyridine-3-carboxylic acid. To a round-bottomed flask was added 2-chloro-6-trifluoromethylnicotinic acid (2.0 g, 8.9 mmol, Matrix) and morpholine (5.0 g, 57 mmol, Aldrich). The reaction mixture was magnetically stirred at 25° C. for 48 h, then diluted with 1 N HCl (100 mL) and extracted with EtOAc (100 mL). The aqueous phase was saturated with NaCl and extracted again with EtOAc (50 mL). The combined EtOAc extracts were washed with 1 N HCl (50 mL), satd NaCl (50 mL), dried over MgSO$_4$, filtered and concentrated in vacuo to afford the title product as an off-white waxy solid. MS (ESI, pos. ion) m/z: 277 (M+1).

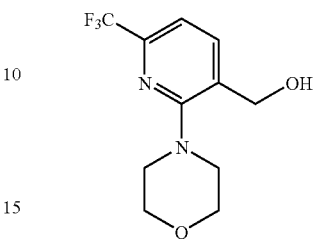

(b) [2-Morpholin-4-yl-6-(trifluoromethyl)-3-pyridyl]methan-1-ol. A solution of 2-morpholin-4-yl-6-(trifluoromethyl)pyridine-3-carboxylic acid, Example 94(a), (2.1 g, 7.6 mmol) in anhydrous THF (20 mL) was treated dropwise with lithium aluminum hydride (15 mL, 15 mmol, 1.0 M in THF, Aldrich) with stirring under N$_2$ at 25° C. The reaction mixture was stirred at 25° C. for 1.5 h, then quenched by the dropwise addition of a 10% aqueous solution of Rochelle salt (50 mL, potassium sodium tartrate, Aldrich). EtOAc (50 mL) was added and the bi-phasic mixture stirred vigorously for 2 h at 25° C. The mixture was diluted with water (100 mL) and the phases separated. The aqueous phase was extracted with EtOAc (2×75 mL), the organic phases were combined and washed with 1 N NaOH (2×75 mL), satd NaCl (75 mL), dried over MgSO$_4$, filtered and concentrated in vacuo to afford the title product as a viscous yellow oil. MS (ESI, pos. ion) m/z: 263 (M+1).

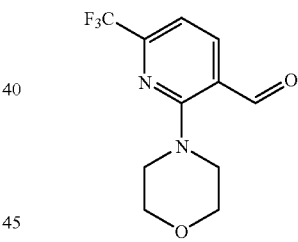

(c) 2-Morpholin-4-yl-6-(trifluoromethyl)pyridine-3-carbaldehyde. A solution of oxalyl chloride (3.6 mL, 7.2 mmol, 2.0 M in CH$_2$Cl$_2$, Aldrich) in anhydrous CH$_2$Cl$_2$ (20 mL) was magnetically stirred under N$_2$, in an oven-dried round-bottomed flask, at −60° C. The solution was treated dropwise with methyl sulfoxide (1.1 mL, 15 mmol, Aldrich) then stirred for 10 min. A solution of [2-morpholin-4-yl-6-(trifluoromethyl)-3-pyridyl]methan-1-ol, Example 94(b), (1.7 g, 6.5 mmol) in anhydrous CH$_2$Cl$_2$ (20 mL) was added via cannula, and the reaction mixture stirred at −60° C. for 15 min. Triethylamine (4.5 mL, 32 mmol, Aldrich) was added, the cooling bath was removed, and the reaction mixture allowed to warm to 25° C. and stirred at that temperature for 1 h. The mixture was washed with water (30 mL) and the aqueous wash was back-extracted with CH$_2$Cl$_2$ (2×20 mL). The combined organic phase was washed with water (30 mL), satd NaCl (30 mL), dried over MgSO$_4$, filtered and concentrated in vacuo. Purification by silica gel chromatography (9:1 hexane:EtOAc) provided the title product as a viscous yellow oil. MS (ESI, pos. ion) m/z: 261 (M+1).

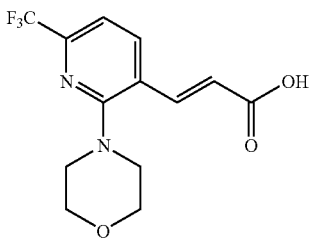

(d) (2E)-3-[2-Morpholin-4-yl-6-(trifluoromethyl)(3-pyridyl)]prop-2-enoic acid. Analogous to the procedure described for Example 40, step (a), 2-morpholin-4-yl-6-(trifluoromethyl)pyridine-3-carbaldehyde, Example 94(c), (1.2 g, 4.6 mmol) provided the title product as a yellow solid. MS (ESI, pos. ion) m/z: 303 (M+1).

(e) (2E)-N-(2H,3H-benzo[e]1,4-dioxan-6-yl)-3-[2-morpholin-4-yl-6-(trifluoromethyl)(3-pyridyl)]prop-2-enamide. (2E)-3-[2-Morpholin-4-yl-6-(trifluoromethyl)(3-pyridyl)]prop-2-enoic acid, Example 94(d), (200 mg, 0.66 mmol) was dissolved in anhydrous $CH_2Cl_2$ (10 mL) and treated with oxalyl chloride (0.36 mL, 0.72 mmol, 2.0 M in $CH_2Cl_2$, Aldrich) and anhydrous DMF (2 uL). The reaction mixture was stirred at reflux for 30 min, then concentrated in vacuo. The residue was dissolved in anhydrous $CH_2Cl_2$ (10 mL), treated with pyridine (0.27 mL, 3.5 mmol, Aldrich) and 1,4-benzodioxan-6-amine (120 mg, 0.79 mmol, Aldrich) and stirred at reflux for 15 min. The reaction mixture was concentrated in vacuo and the residue dissolved in EtOAc (75 mL). The mixture was washed with 1 N HCl (2×50 mL), 1 N NaOH (50 mL), water (50 mL), satd NaCl (50 mL), dried over $MgSO_4$, filtered and concentrated in vacuo. Recrystallization from EtOAc and hexane provided the title product as pale tan crystals. MP 200-201° C. MS (ESI, pos. ion) m/z: 436 (M+1).

EXAMPLE 95

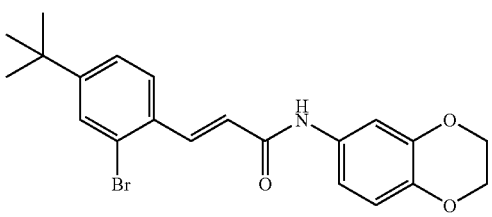

(2E)-N-(2H,3H-Benzo[e]1,4-dioxan-6-yl)-3-[4-(tert-butyl)-2-bromophenyl]prop-2-enamide

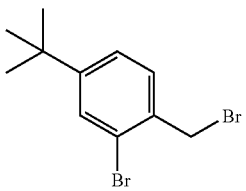

(a) 4-(tert-Butyl)-2-bromo-1-(bromomethyl)benzene. According to the procedure of Kikuchi, D. et al, *J. Org. Chem.* 1998, 63, 6023-6026, to a solution of sodium bromate (22 g, 145 mmol, Aldrich) in water (75 mL), magnetically stirred in an Erlenmeyer flask at 25° C., was added a solution of 4-t-butyltoluene (5.0 mL, 29 mmol, Aldrich) in acetonitrile (60 mL). The bi-phasic mixture was vigorously stirred while a solution of sodium bisulfite (15 g, 145 mmol, Baker) in water (150 mL) was added dropwise, via addition funnel, over 20 min. The reaction mixture was stirred for 6 h, then extracted with $Et_2O$ (300 mL). The organic phase was washed with satd aq. $Na_2S_2O_3$ (2×100 mL), satd NaCl (50 mL), dried over $MgSO_4$, filtered and concentrated in vacuo to afford of the title product as a pale orange oil.

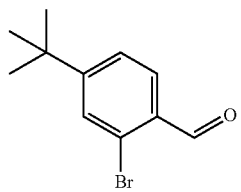

(b) 4-(tert-Butyl)-2-bromobenzaldehyde. According to the procedure of Mallory, et al, *Tetrahedron* 2001, 57, 3715-3724, a solution of sodium ethoxide (12 mL, 32 mmol, 21% in EtOH, Aldrich) in absolute EtOH (100 mL) was magnetically stirred under $N_2$ at 25° C. and treated with 2-nitropropane (2.9 mL, 32 mmol, Aldrich) followed by 4-(tert-butyl)-2-bromo-1-(bromomethyl)benzene, Example 95(a), (9.0 g, 29 mmol). The reaction mixture was stirred at 25° C. for 5 h, then concentrated in vacuo to an orange solid. The solid was partitioned between $Et_2O$ (150 mL) and water (100 mL). The layers were separated and the organic phase was washed with water (100 mL), 1 N NaOH (2×75 mL), satd NaCl (50 mL), dried over $MgSO_4$, filtered and concentrated in vacuo to afford the title product as an orange oil.

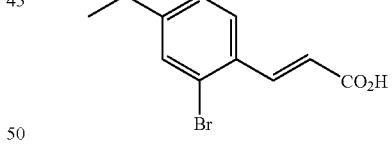

(c) (2E)-3-[4-(tert-Butyl)-2-bromophenyl]prop-2-enoic acid. Analogous to the procedure described for Example 40, step (a), 4-(tert-butyl)-2-bromobenzaldehyde, Example 95(b), (6.5 g, 27 mmol) provided the title product as a white solid. MS (ESI, pos. ion) m/z: 283, 285 (M, M+2).

(d) (2E)-N-(2H,3H-Benzo[e]1,4-dioxan-6-yl)-3-[4-(tert-butyl)-2-bromophenyl]prop-2-enamide. Analogous to the procedure described for Example 94, step (e), (2E)-3-[4-(tert-butyl)-2-bromophenyl]prop-2-enoic acid, Example 95(c), (3.0 g, 11 mmol) and 1,4-benzodioxan-6-amine (1.9 g, 13 mmol, Aldrich) provided, after recrystallization from $CH_2Cl_2$ and hexane, the title product as off-white crystals. MP 206-210° C. MS (ESI, pos. ion) m/z: 416, 418 (M, M+2).

EXAMPLE 96

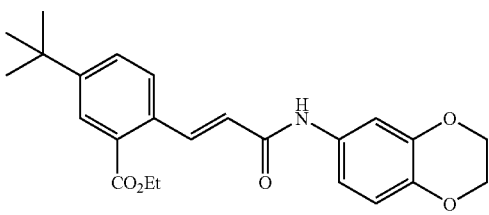

Ethyl 2-[(1E)-2-(N-(2H,3H-benzo[e]1,4-dioxan-6-yl)carbamoyl)vinyl]-5-(tert-butyl)benzoate According to the procedure of Ma, et al, *J. Org. Chem.* 1999, 64, 120-125, a solution of (2E)-N-(2H,3H-benzo[e]1,4-dioxan-6-yl)-3-[4-(tert-butyl)-2-bromophenyl]prop-2-enamide, Example 95, (200 mg, 0.48 mmol) in anhydrous EtOH (5 mL) and methyl sulfoxide (5 mL) was treated with triethylamine (0.67 mL, 0.48 mmol, Aldrich) and 1,3-bis(diphenylphosphino)propane (50 mg, 0.12 mmol, Aldrich). The mixture was purged with a stream of carbon monoxide, then treated with palladium acetate (22 mg, 0.10 mmol, Aldrich), and stirred under a balloon of carbon monoxide in a 70° C. oil bath for 3 h. The reaction mixture was allowed to cool to 25° C. and partitioned between EtOAc (50 mL) and water (20 mL). The organic phase was washed with water (10 mL), satd NaCl (10 mL), dried over MgSO₄, filtered and concentrated in vacuo. Purification by silica gel chromatography (step gradient, 4:1 then 3:1, hexane:EtOAc), followed by recrystallization from EtOAc and hexane, provided the title product as white crystals. MP 155° C. MS (ESI, pos. ion) m/z: 410 (M+1).

EXAMPLE 97

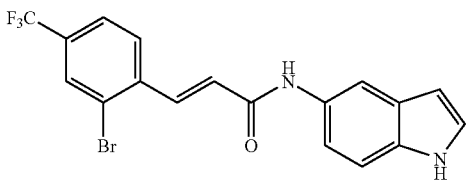

(2E)-3-[2-Bromo-4-(trifluoromethyl)phenyl]-N-indol-5-ylprop-2-enamide

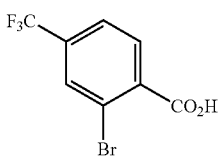

(a) 2-Bromo-4-(trifluoromethyl)benzoic acid. To a solution of 2-bromo-1-methyl-4-trifluoromethylbenzene (7.6 g, 32 mmol, ABCR) in pyridine (75 mL) was added tetraethylammonium permanganate (24 g, 96 mmol, prepared according to the procedure of Sala, et al. *J. Chem. Soc., Chem. Comm.* 1978, 253). The reaction mixture was warmed to 70° C. and stirred at that temperature for 30 h. The reaction mixture was allowed to cool to 25° C. and poured into an ice bath containing cond HCl (150 mL) and NaHSO₃ (150 g). The mixture turned to a clear aqueous solution and was extracted with EtOAc (4×200 mL). The combined extracts were washed with satd NaCl (200 mL), dried over Na₂SO₄, filtered and concentrated in vacuo to provide the title product as a white solid. MS (ESI, neg. ion) m/z: 267 (M−1).

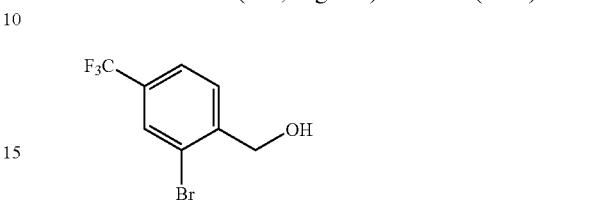

(b) [2-Bromo-4-(trifluoromethyl)phenyl]methan-1-ol. Analogous to the procedure used to prepare Example 46, step (a), 2-bromo-4-(trifluoromethyl)benzoic acid, Example 97(a), (5.4 g, 20 mmol) provided, after purificaton by silica gel chromatography (gradient: 0-10% EtOAc in hexane), the title product as a white solid. MS (ESI, neg. ion) m/z: 313 (M+acetate).

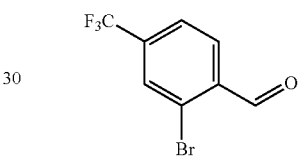

(c) 2-Bromo-4-(trifluoromethyl)benzaldehyde. Analogous to the procedure used to prepare Example 46, step (b), [2-bromo-4-(trifluoromethyl)phenyl]methan-1-ol, Example 97(b), (4.6 g, 18 mmol) provided, after purificaton by silica gel chromatography (gradient: 0-4% EtOAc in hexane), the title product as a colorless oil.

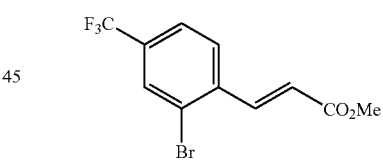

(d) Methyl (2E)-3-[2-bromo-4-(trifluoromethyl)phenyl]prop-2-enoate.

Analogous to the procedure used to prepare Example 46, step (c), 2-bromo-4-(trifluoromethyl)benzaldehyde, Example 97(c), (2.3 g, 8.9 mmol) and carbomethoxymethylene triphenylphosphorane (4.2 g, 12.5 mmol, Aldrich) provided, after purificaton by silica gel chromatography (gradient: 0-3% EtOAc in hexane), the title product as a white solid.

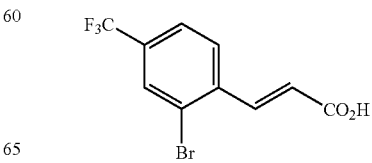

(e) (2E)-3-[2-Bromo-4-(trifluoromethyl)phenyl]prop-2-enoic acid. Analogous to the procedure used to prepare Example 46, step (d), methyl (2E)-3-[2-bromo-4-(trifluoromethyl)phenyl]prop-2-enoate, Example 97(d), (2.25 g, 8.9 mmol) provided the title product.

(f) (2E)-3-[2-Bromo-4-(trifluoromethyl)phenyl]-N-indol-5-ylprop-2-enamide.

Analogous to the procedure used to prepare Example 1, (2E)-3-[2-bromo-4-(trifluoromethyl)phenyl]prop-2-enoic acid, Example 97(e), (140 mg, 0.48 mmol) and 5-aminoindole (75 mg, 0.57 mmol, Aldrich) provided, after purification by silica gel chromatography (gradient: 0-25% EtOAc in hexane), the title compound as a yellow solid. MP 205-207° C. MS (ESI, pos. ion) m/z: 409 (M+1).

EXAMPLE 98

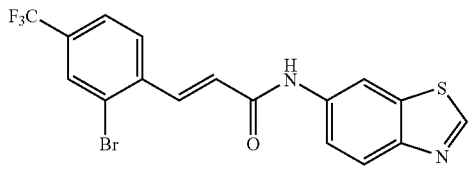

(2E)-N-Benzothiazol-6-yl-3-[2-bromo-4-(trifluoromethyl)phenyl]prop-2-enamide

Analogous to the procedure used to prepare Example 1, (2E)-3-[2-bromo-4-(trifluoromethyl)phenyl]prop-2-enoic acid, Example 97(e), (140 mg, 0.47 mmol) and 6-aminobenzothiazole (86 mg, 0.57 mmol, Lancaster) provided, after purification by silica gel chromatography (gradient: 0-30% EtOAc in hexane), the title product as an off-white solid. MP 214-215° C. MS (ESI, pos. ion) m/z: 427 (M+1).

EXAMPLE 99

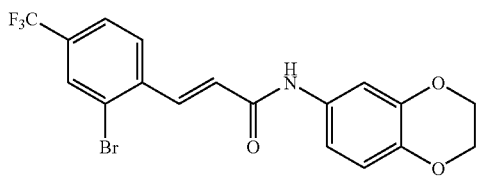

(2E)-N-(2H,3H-Benzo[e]1,4-dioxan-6-yl)-3-[2-bromo-4-(trifluoromethyl)-phenyl]prop-2-enamide Analogous to the procedure used to prepare Example 1, (2E)-3-[2-bromo-4-(trifluoromethyl)phenyl]prop-2-enoic acid, Example 97(e), (140 mg, 0.47 mmol) and 1,4-benzodioxan-6-amine (86 mg, 0.57 mmol, Aldrich) provided, after purification by silica gel chromatography (gradient: 0-18%EtOAc in hexane), the title product as an off-white solid. MP 212-213° C. MS (ESI, pos. ion) m/z: 428 (M+1).

EXAMPLE 100

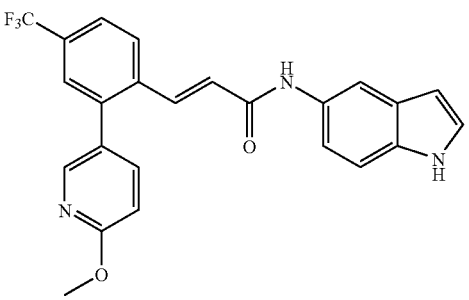

(2E)-N-indol-5-yl-3-[2-(6-methoxy(3-pyridyl))-4-(trifluoromethyl)phenyl]-prop-2-enamide A mixture of (2E)-3-[2-bromo-4-(trifluoromethyl)phenyl]-N-indol-5-ylprop-2-enamide, Example 97, (100 mg, 0.24 mmol), 2-methoxy-5-pyridineboronic acid (60 mg, 0.39 mmol, Digital Specialty Chemicals), tris(dibenzylideneacetone)-dipalladium(0) (22 mg, 0.024 mmol, Aldrich) and triphenylphosphine (26 mg, 0.098 mmol, Aldrich) in toluene (1.2 mL), 2.0M aqueous $Na_2CO_3$ (0.4 mL) and ethanol (0.4 mL) was stirred at 120° C. overnight. The reaction mixture was filtered through a pad of Celite and diluted with water (50 mL). The aqueous phase was extracted with EtOAc (3×60 mL). The combined extracts were washed with satd NaCl (100 mL), dried over $Na_2SO_4$, filtered and concentrated in vacuo. Purification by silica gel chromatography (gradient: 0-20% EtOAc in hexane) provided the title product as a yellow solid. MP 219-221° C. MS (ESI, pos. ion) m/z: 438 (M+1).

EXAMPLE 101

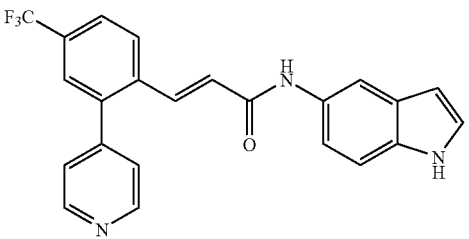

(2E)-N-Indol-5-yl-3-[2-(4-pyridyl)-4-(trifluoromethyl)phenyl]prop-2-enamide

Analogous to the procedure used to prepare Example 100, (2E)-3-[2-bromo-4-(trifluoromethyl)phenyl]-N-indol-5-yl-prop-2-enamide, Example 97, (120 mg, 0.29 mmol) and pyridine-4-boronic acid (72 mg, 0.59 mmol, Frontier Scientific) provided, after purification by silica gel chromatography (gradient: 0-60%EtOAc in hexane), the title product as a yellow solid. MP 229-234° C. MS (ESI, pos. ion) m/z: 408 (M+1).

EXAMPLE 102

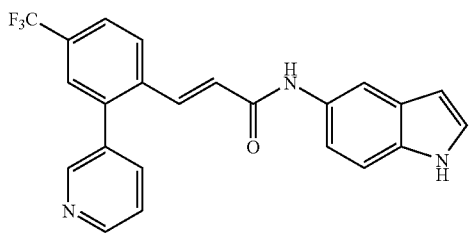

(2E)-N-Indol-5-yl-3-[2-(3-pyridyl)-4-(trifluoromethyl)phenyl]prop-2-enamide

Analogous to the procedure used to prepare Example 100, (2E)-3-[2-bromo-4-(trifluoromethyl)phenyl]-N-indol-5-yl-prop-2-enamide, Example 97, (120 mg, 0.29 mmol) and pyridine-3-boronic acid (58 mg, 0.47 mmol, Frontier Scientific) provided, after purification by silica gel chromatography (gradient: 0-20%EtOAc in hexane), the title product as a yellow solid. MP 196-197° C. MS (ESI, pos. ion) m/z: 408 (M+1).

EXAMPLE 103

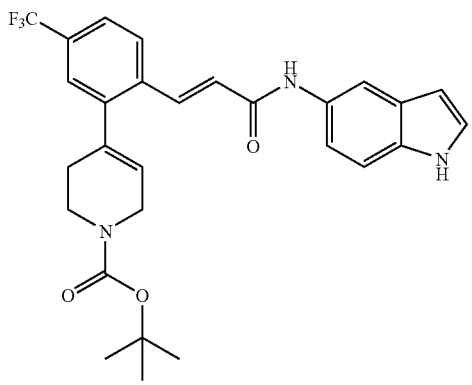

tert-Butyl 4-{2-[(1E)-2-(N-indol-5-ylcarbamoyl)vinyl]-5-(trifluoromethyl)phenyl}-1,2,5,6-tetrahydropyridinecarboxylate Analogous to the procedure used to prepare Example 100, (2E)-3-[2-bromo-4-(trifluoromethyl)phenyl]-N-indol-5-yl-prop-2-enamide, Example 97, (100 mg, 0.24 mmol) and 4-(4,4,5,5-tetramethyl-[1,3,2]dioxaborolan-2-yl)-3,6-dihydro-2H-pyridine-1-carboxylic acid tert-butyl ester (130 mg, 0.42 mmol, prepared according to the procedures of Wustrow, D. J. et al, *Synthesis* 1991, 993 and Ishiyama, T. et al, *J. Org. Chem.* 1995, 60, 7508) provided, after purification by silica gel chromatography (gradient: 0-35%EtOAc in hexane), the title product as an amorphous yellow solid. MS (ESI, pos. ion) m/z: 512 (M+1).

EXAMPLE 104

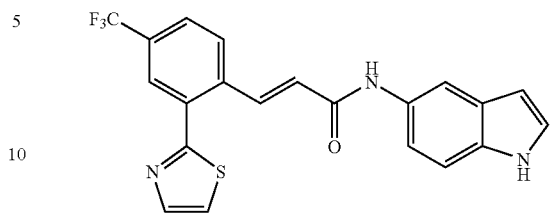

(2E)-N-Indol-5-yl-3-[2-(I,3-thiazol-2-yl)-4-(trifluoromethyl)phenyl]prop-2-enamide Analogous to the procedure used to prepare Example 100, (2E)-3-[2-bromo-4-(trifluoromethyl)phenyl]-N-indol-5-yl-prop-2-enamide, Example 97, (100 mg, 0.24 mmol) and 2-tributylstannylthiazole (155 mg, 0.42 mmol, Frontier Scientific) provided, after purification by silica gel chromatography (gradient: 0-35%EtOAc in hexane), the title product as an orange solid. MP 203-204° C. MS (ESI, pos. ion) m/z: 414 (M+1).

EXAMPLE 105

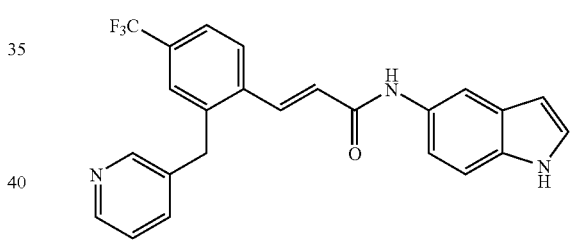

(2E)-N-Indol-5-yl-3-[2-(3-pyridylmethyl)-4-(trifluoromethyl)phenyl]prop-2-enamide A mixture of (2E)-3-[2-bromo-4-(trifluoromethyl)phenyl]-N-indol-5-ylprop-2-enamide, Example 97, (110 mg, 0.27 mmol), 3-(tributylstannanylmethyl)pyridine, Example 90(a), (160 mg, 0.43 mmol), tris(dibenzylideneacetone)dipalladium(0) (24 mg, 0.027 mmol, Aldrich) and triphenylphosphine (28 mg, 0.11 mmol, Aldrich) in 1-methyl-2-pyrrolidinone (1.5 mL) was stirred at 100° C. overnight. The reaction mixture was filtered through a pad of Celite and diluted with water (50 mL). The aqueous phase was extracted with EtOAc (3×60 mL). The combined organic extracts were washed with satd NaCl (100 mL), dried over Na$_2$SO$_4$, filtered and concentrated in vacuo. Purification by silica gel chromatography (gradient: 0-70% EtOAc in hexane) provided the title compound as an orange solid. MP 202-203° C. MS (ESI, neg. ion) m/z: 420 (M−1).

EXAMPLE 106

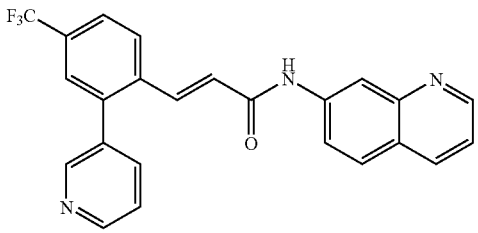

(2E)-3-[2-(3-Pyridyl)-4-(trifluoromethyl)phenyl]-N-(7-quinolyl)prop-2-enamide

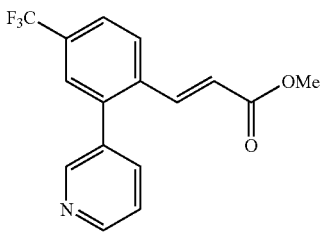

(a) Methyl (2E)-3-[2-(3-pyridyl)-4-(trifluoromethyl)phenyl]prop-2-enoate. A mixture of methyl (2E)-3-[2-bromo-4-(trifluoromethyl)phenyl]prop-2-enoate, Example 97(d), (585 mg, 1.89 mmol), pyridine-3-boronic acid (950 mg, 2.8 mmol, Frontier Scientific), tris(dibenzylideneacetone)dipalladium (0) (170 mg, 0.19 mmol, Aldrich) and triphenylphosphine (200 mg, 0.76 mmol, Aldrich) in toluene (5 mL), 1.0 M aqueous Na$_2$CO$_3$ (2 mL) and ethanol (2 mL) was stirred at 80° C. under N$_2$ overnight. The reaction mixture was filtered through a pad of Celite and diluted with water (60 mL). The aqueous phase was extracted with EtOAc (3×60 mL). The combined organic extracts were washed with satd NaCl (100 mL), dried over Na$_2$SO$_4$, filtered and concentrated in vacuo. Purification by silica gel chromatography (gradient: 0-35% EtOAc in hexane) provided the title product as a yellow solid. MS (ESI, pos. ion) m/z: 308 (M+1).

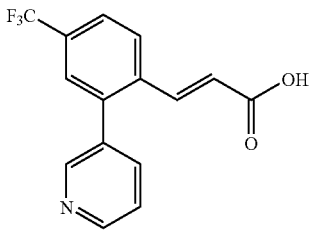

(b) (2E)-3-[2-(3-Pyridyl)-4-(trifluoromethyl)phenyl]prop-2-enoic acid. A mixture of methyl (2E)-3-[2-(3-pyridyl)-4-(trifluoromethyl)phenyl]prop-2-enoate, Example 106(a), (540 mg, 1.8 mmol) and LiOH monohydrate (370 mg, 8.8 mmol) in wet ethanol (5 mL) was stirred at room temperature overnight. The reaction mixture was neutralized with aqueous HCl (2.0 M, 4.4 mL, 8.8 mmol) and concentrated under reduced pressure. The material was dried under vacuum at 60° C. for 4 h to provide 955 mg of the crude material, which contained LiCl as a byproduct. MS (ESI, pos. ion) m/z: 294 (M+1).

(c) (2E)-3-[2-(3-Pyridyl)-4-(trifluoromethyl)phenyl]-N-(7-quinolyl)prop-2-enamide. Analogous to the procedure used to prepare Example 1, (2E)-3-[2-(3-pyridyl)-4-(trifluoromethyl)phenyl]prop-2-enoic acid, Example 106(b), (185 mg) and 7-aminoquinoline (64 mg, 0.44 mmol, Specs) provided, after purification by silica gel chromatography (gradient: 0-75% EtOAc in hexane), the title compound as an amorphous off-white solid. MS (ESI, pos. ion) m/z: 420 (M+1).

EXAMPLE 107

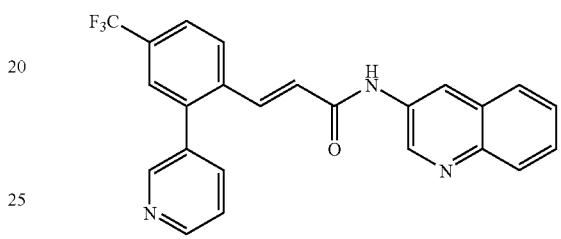

(2E)-3-[2-(3-Pyridyl)-4-(trifluoromethyl)phenyl]-N-(3-quinolyl)prop-2-enamide

Analogous to the procedure used to prepare Example 1, (2E)-3-[2-(3-pyridyl)-4-(trifluoromethyl)phenyl]prop-2-enoic acid, Example 106(b), (185 mg) and 3-aminoquinoline (64 mg, 0.44 mmol, Aldrich) provided, after purification by silica gel chromatography (gradient: 0-45% EtOAc in hexane), the title compound as a white solid. MP 196-199° C. MS (ESI, pos. ion) m/z: 420 (M+1).

EXAMPLE 108

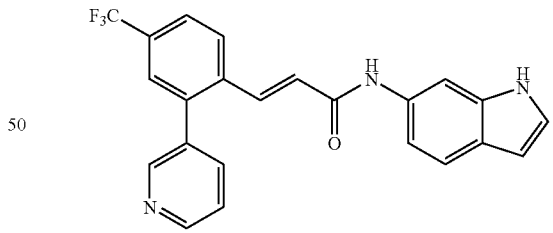

(2E)-N-Indol-6-yl-3-[2-(3-pyridyl)-4-(trifluoromethyl)phenyl]prop-2-enamide

Analogous to the procedure used to prepare Example 1, (2E)-3-[2-(3-pyridyl)-4-(trifluoromethyl)phenyl]prop-2-enoic acid, Example 106(b), (185 mg) and 6-aminoindole (59 mg, 0.44 mmol, Aldrich) provided, after purification by silica gel chromatography (gradient: 0-50% EtOAc in hexane), the title compound as an amorphous orange solid. MS (ESI, pos. ion) m/z: 408 (M+1).

EXAMPLE 109

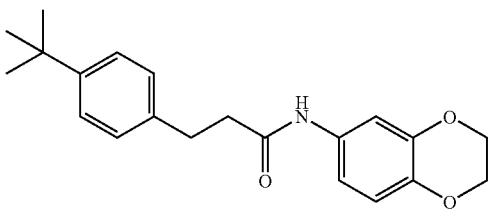

N-(2H,3H-Benzo[3,4-e]1,4-dioxan-6-yl)-3-[4-(tert-butyl)phenyl]propanamide

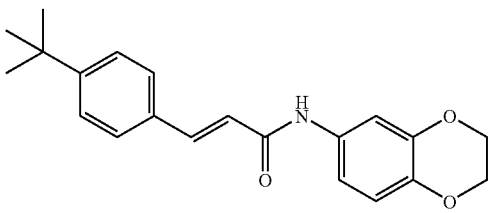

(a) (2E)-N-(2H,3H-Benzo[3,4-e]1,4-dioxan-6-yl)-3-[4-(tert-butyl)phenyl]-prop-2-enamide. A solution of 4-t-butyl-trans-cinnamic acid (500 mg, 2.45 mmol, EMKA-Chemie) in anhydrous $CH_2Cl_2$ (10 mL) was magnetically stirred and treated with oxalyl chloride (0.22 mL, 2.5 mmol, Aldrich) and DMF (0.005 mL). The reaction mixture was stirred at reflux for 30 min, then concentrated in vacuo. The residue was dissolved in acetone (1 mL) and added to a mixture of 1,4-benzodioxan-6-amine (370 mg, 2.45 mmol, Aldrich) and $K_2CO_3$ (500 mg) in acetone (2 mL) and water (4 mL), stirred at 0° C. The reaction mixture was vigorously stirred at 0° C. for 30 min, then diluted with ice water (50 mL). The resulting solid precipitate was collected by filtration and dissolved in $CH_2Cl_2$ (20 mL) and $Et_2O$ (150 mL). The organic solution was washed with 1 N HCl (3×75 mL), satd NaCl (50 mL), dried over $MgSO_4$, filtered and concentrated to afford the title product as an off-white foam. MS (ESI, pos. ion) m/z: 338 (M+1).

(b) N-(2H,3H-Benzo[3,4-e]1,4-dioxan-6-yl)-3-[4-(tert-butyl)phenyl]propanamide. (2E)-N-(2H,3H-Benzo[3,4-e]1,4-dioxan-6-yl)-3-[4-(tert-butyl)phenyl]prop-2-enamide, Example 109(a), (200 mg, 0.59 mmol) was dissolved in EtOH (25 mL), purged with $N_2$, treated with 10% Pd on carbon (50 mg, Aldrich) then purged with $H_2$ and the suspension stirred at 25° C., under 1 atm $H_2$, for 16 hr. The suspension was purged with $N_2$, filtered through a pad of Celite, and concentrated in vacuo to a white foam. Purification by silica gel chromatography (45:45:10 hexane:$CH_2Cl_2$:EtOAc) provided the title product as a clear glass. MS (ESI, pos. ion) m/z: 340 (M+1).

General Scheme I

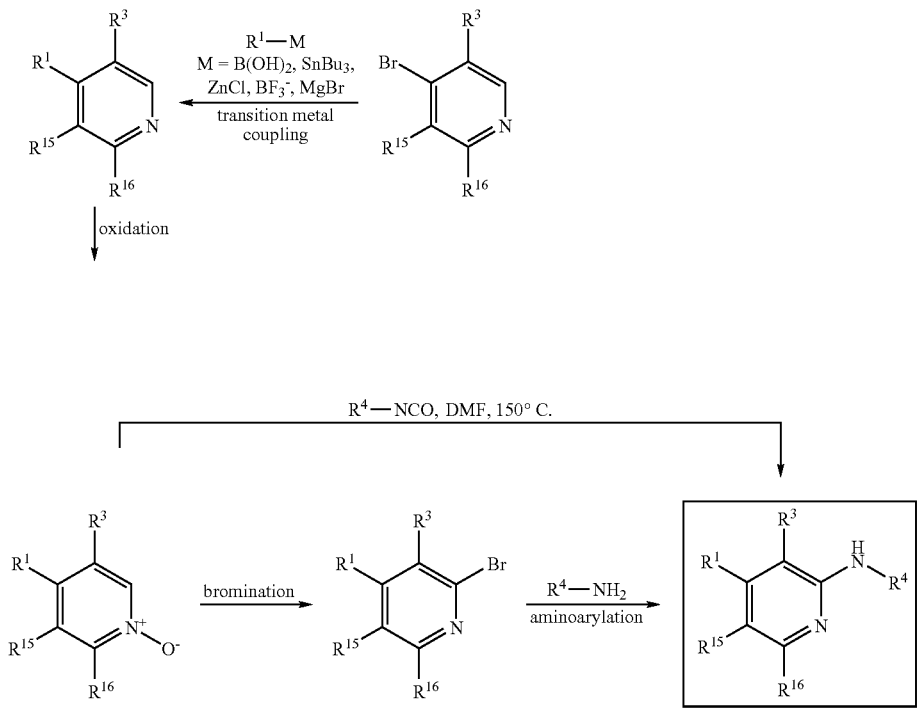

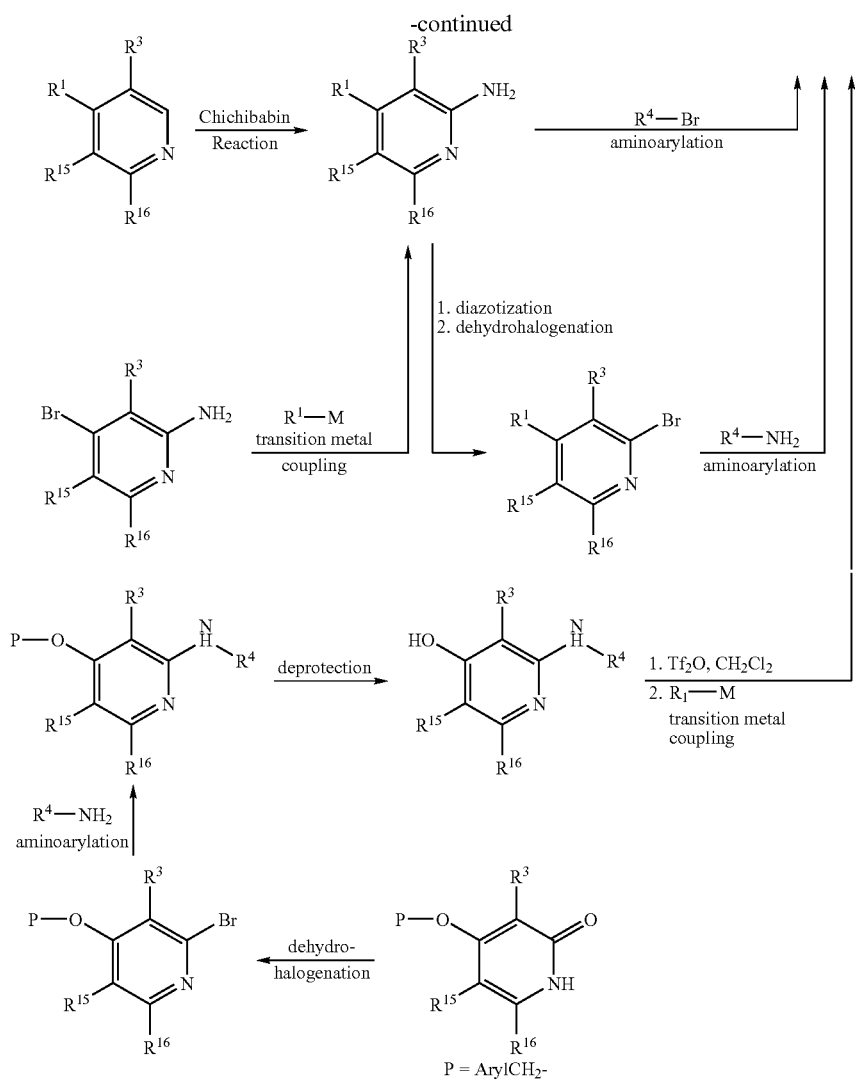
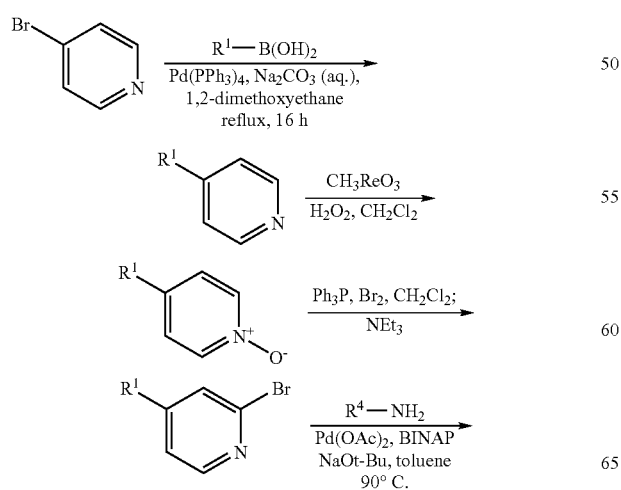
EXAMPLE 110
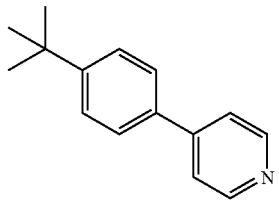

(a) 4-[4-(tert-Butyl)phenyl]pyridine

To 4-bromopyridine hydrochloride (Aldrich) (8.9 g, 46 mmol) and tetrakis(triphenylphosphine)palladium(0) (Aldrich) (1.6 g, 1.4 mmol) was added 1,2-dimethoxyethane (250 mL) with stirring under nitrogen. After 20 min, a solution of $Na_2CO_3$ (9.7 g in 70 mL of water) and 4-tert-butylbenzeneboronic acid (9.8 g, 55 mmol) were added sequentially to the mixture. The reaction was stirred at reflux overnight. The reaction mixture was concentrated in vacuo to approximately ⅓ its original volume, and the mixture was extracted with EtOAc (2×100 mL). The combined EtOAc layers were washed with brine, dried over $Na_2SO_4$ and concentrated in vacuo. Purification by silica gel chromatography (1:5 EtOAc/hexanes) gave the title compound as a white solid. MS (ESI, pos. ion) m/z: 212 (M+1).

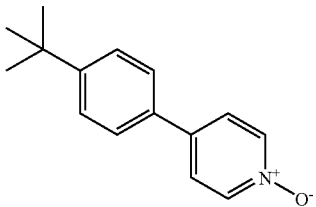

(b) 4-[4-(tert-Butyl)phenyl]pyridine 1-oxide

To the mixture of 4-[4-(tert-butyl)phenyl]pyridine (8.7 g, 41 mmol) and methyltrioxorhenium (VII) (Aldrich) (170 mg, 0.7 mmol) in a 100-mL round-bottomed flask was added $CH_2Cl_2$ (18 mL). The mixture was then treated with 12 mL of hydrogen peroxide (Aldrich) dropwise. The reaction was stirred at room temperature under nitrogen overnight. Methylene chloride and brine were then added, and the aqueous layer was extracted with $CH_2Cl_2$ (40 mL). The organic layer was dried over $Na_2SO_4$, concentrated in vacuo to give the title compound as an off-white solid. MS (ESI, pos. ion) m/z: 228 (M+1).

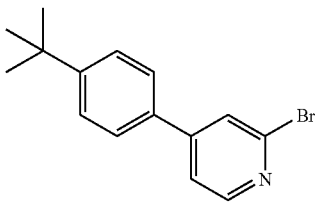

(c) 4-[4-(tert-Butyl)phenyl]-2-bromopyridine

To triphenylphosphine (Aldrich) (2.4 g, 9.1 mmol) dissolved in 10 mL of $CH_2Cl_2$ in a 50-mL round-bottomed flask was added bromine (Aldrich) (0.43 mL, 8.5 mmol). After stirring at 0° C. for 10 min, 4-[4-(tert-butyl)phenyl]pyridine 1-oxide (1.5 g, 6.5 mmol) was added dropwise, followed by $Et_3N$ (1.2 mL, 8.5 mmol). The reaction mixture was stirred at 0° C. for 1 h and then at room temperature overnight. Methylene chloride and brine were added, and the aqueous layer was extracted with $CH_2Cl_2$. The organic layer was collected and dried over $Na_2SO_4$, filtered and concentrated in vacuo. Following purification by silica gel chromatography (10:1 hexane:EtOAc), the title compound was obtained as a pale yellow oil. MS (ESI, pos. ion) m/z: 293 (M+1).

(d) 2H,3H-Benzo[e]1,4-dioxan-6-yl{4-[4-(tert-butyl)phenyl](2-pyridyl)}amine

To an oven-dried 50-mL round-bottomed flask were added 4-[4-(tert-butyl)phenyl]-2-bromopyridine (180 mg, 0.63 mmol) and 1,4-benzodioxan-6-amine (Aldrich) (191 mg, 1.3 mmol), followed by anhydrous toluene (60 mL) and DMF (6 mL). Nitrogen was bubbled through the above solution via a needle for 1 h. Then palladium acetate (Aldrich) (21 mg, 0.01 mmol) and BINAP (Aldrich) (59 mg, 0.01 mmol) were introduced to the reaction followed by sodium tert-butoxide (Aldrich) (170 mg, 1.8 mmol). The reaction mixture was heated in a 90 C. oil bath overnight. After cooling to room temperature, the reaction mixture was dissolved in ether, washed with brine, dried over $Na_2SO_4$ and concentrated in vacuo. Following purification by silica gel chromatography (3:1 hexane:EtOAc), the title compound was obtained as a pale tan solid. MS (ESI, pos. ion) m/z: 361 (M+1). MP: 162-163° C.

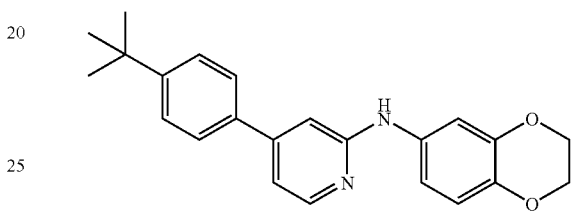

TABLE A

The following compounds were prepared according to General Schemes I and II:

| Example | Structure | MS (ESI, pos. ion) m/z | Melting Point ° C. |
|---|---|---|---|
| 111 | 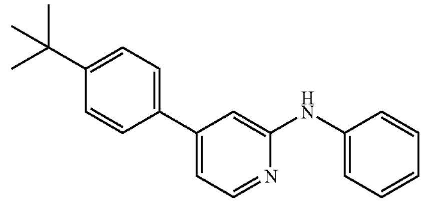 | 303 (M + 1) | 157 |

TABLE A-continued

The following compounds were prepared according to General Schemes I and II:

| Example | Structure | MS (ESI, pos. ion) m/z | Melting Point ° C. |
|---|---|---|---|
| 112 | 4-(4-tert-butylphenyl)-N-(3-methoxyphenyl)pyridin-2-amine | 333 (M + 1) | amorphous |
| 113 | 4-(4-tert-butylphenyl)-N-(benzo[d][1,3]dioxol-5-yl)pyridin-2-amine | 347 (M + 1) | 156 |
| 114 | 4-(4-tert-butylphenyl)-N-(3,4-dimethylphenyl)pyridin-2-amine | 331 (M + 1) | 133 |
| 115 | 4-(4-tert-butylphenyl)-N-(3,4,5-trimethoxyphenyl)pyridin-2-amine | 393 (M + 1) | amorphous |
| 116 | 4-(4-tert-butylphenyl)-N-(1H-indol-5-yl)pyridin-2-amine | 342 (M + 1) | 106 |
| 117 | 4-(4-tert-butylphenyl)-N-(benzo[d]thiazol-6-yl)pyridin-2-amine | 360 (M + 1) | 154 |

TABLE A-continued

The following compounds were prepared according to General Schemes I and II:

| Example | Structure | MS (ESI, pos. ion) m/z | Melting Point °C. |
|---|---|---|---|
| 118 | 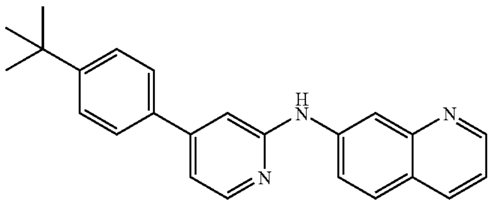 | 354 (M + 1) | 214 |
| 119 | 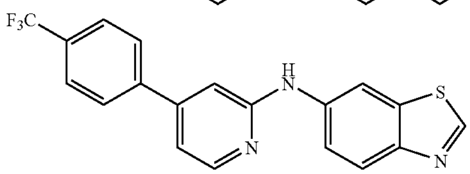 | 372 (M + 1) | 203 |
| 120 | 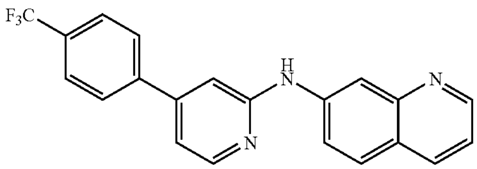 | 366 (M + 1) | 206 |
| 121 | 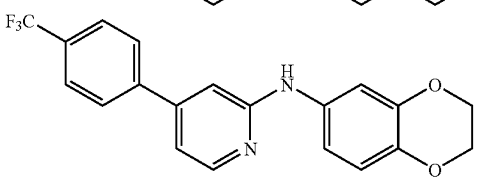 | 373 (M + 1) | 114 |
| 122 | 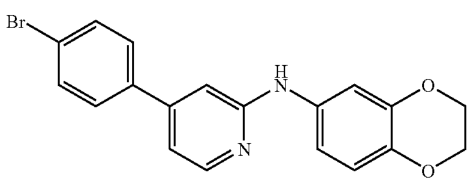 | 383, 385 (M, M + 2) | 124 |
| 123 | 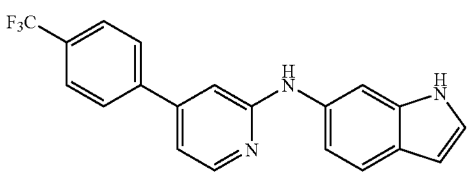 | 354 (M + 1) | ? |

EXAMPLE 124

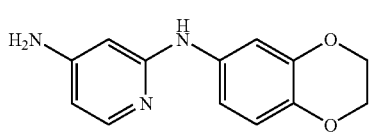

(a) N2-(2,3-Dihydro-benzo[1,4]dioxin-6-yl)-pyridine-2,4-diamine

In a 5-mL vial was added 4-amino-2-chloropyridine (Aldrich Chemical Company) (1.1 g, 8.7 mmol), 1,4-benzodioxane-6-amine (Aldrich Chemical Company) (5.3 g, 35 mmol) and copper (I) iodide (Aldrich Chemical Company) (0.17 g, 0.87 mmol). The content was sonicated at room temperature for 5 min and then heated in the Smith Microwave Synthesizer at 200° C. for 10 min. The residue was purified by flash chromatography (95:5 dichloromethane:2N NH3 in MeOH) to give the title compound as a dark solid. MS (ESI, pos. ion) m/z: 244 (M+1).

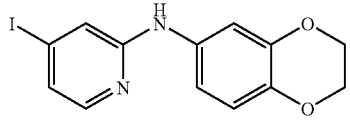

(b) (2,3-Dihydro-benzo[1,4]dioxin-6-yl)-(4-iodo-pyridin-2-yl)-amine

Isopentyl nitrile (Aldrich Chemical Company) (3.9 mL, 29 mmol) was added to a mixture of N2-(2,3-dihydro-benzo[1,4]dioxin-6-yl)-pyridine-2,4-diamine (Example 2(a), 2.4 g, 9.8 mmol), potassium iodide (Aldrich Chemical Company) (1.6 g, 9.8 mmol), iodine (Aldrich Chemical Company) (1.2 g, 4.9 mmol) and copper (I) iodide (Aldrich Chemical Company) (1.9 g, 9.8 mmol) in 1,2-dimethoxyethane (60 mL). The reaction mixture was heated at 60-65° C. for 1 hr.

After cooling to room temperature, the insoluble materials were removed by filtration and the filtrate was diluted with EtOAc, washed with 25% aqueous $NH_4OH$, 5% aqueous sodium bisulfite and then brine. The organic layer was separated, dried over $Na_2SO_4$ and concentrated in vacuo. The residue was purified on a Biotage 40 M column (2.5:1 hexane:EtOAc) to give the title compound as an off-white solid. MS (ESI, pos. ion) m/z: 355 (M+1).

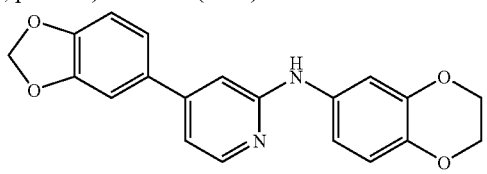

(c) (4-Benzo[1,3]dioxol-5-yl-pyridin-2-yl)-(2,3-dihydro-benzo[1,4]dioxin-6-yl)-amine In a 5 mL vial were added (2,3-dihydro-benzo[1,4]dioxin-6-yl)-(4-iodo-pyridin-2-yl)-amine (Example 2(b), 75 mg, 0.2 mmol), tetrakis (triphenylphosphine) palladium (0) (Aldrich Chemical Company) (12 mg, 0.011 mmol) and 1,2-dimethoxyethane (2 mL). After stirring under nitrogen for 10 min, aqueous $Na_2CO_3$ (22 mg in 0.5 mL of water) and 3,4-(methylenedioxy)phenylboronic acid (Aldrich Chemical Company) (42 mg, 0.25 mmol) were introduced. The reaction was heated in the Smith Microwave Synthesizer at 150° C. for 10 min. The residue was partitioned between EtOAc and brine. The aqueous layer was extracted with EtOAc and the combined EtOAc layer was washed with brine, dried over $Na_2SO_4$ and concentrated in vacuo. Purification on a Biotage 40 S column (4:1 hexane:EtOAc) gave the title compound as a light-yellow solid. MS (ESI, pos. ion) m/z: 349 (M+1). Mp: 116.0-118.0° C.

EXAMPLE 125

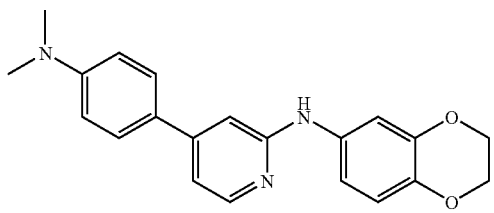

(2,3-Dihydro-benzo[1,4]dioxin-6-yl)-[4-(4-dimethylamino-phenyl)-pyridin-2-yl]-amine Following the same procedure described for Example 401 (c), the mixture of (2,3-dihydro-benzo[1,4]dioxin-6-yl)-(4-iodo-pyridin-2-yl)-amine (Example 401(b), 75 mg, 0.2 mmol), tetrakis (triphenylphosphine) palladium (0) (Aldrich Chemical Company) (12 mg, 0.011 mmol), N,N-dimethylaminobenzeneboronic acid (Aldrich Chemical Company) (41 mg, 0.25 mmol) and 1,2-dimethoxyethane (2 mL) gave, after heated in the Microwave Smith Synthesizer at 150° C. for 10 min and purification on a Biotage 40S column (1.5:1 hexane:EtOAc), the title compound as a tan solid. MS (ESI, pos. ion) m/z: 348 (M+1). Mp: 154.0-155.5° C.

EXAMPLE 126

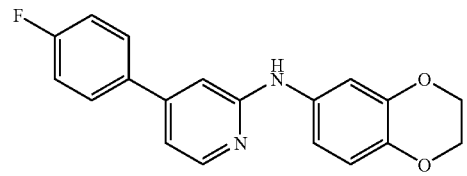

(2,3-Dihydro-benzo[1,4]dioxin-6-yl)-[4-(4-fluorophenyl)-pyridin-2-yl]-amine

Following the same procedure described for Example 401 (c), the mixture of (2,3-dihydro-benzo[1,4]dioxin-6-yl)-(4-iodo-pyridin-2-yl)-amine (Example 401 (b), 75 mg, 0.2 mmol), tetrakis (triphenylphosphine) palladium (0) (Aldrich Chemical Company) (12 mg, 0.011 mmol), 4-fluorobenzeneboronic acid (Avocado Chemical Company) (35 mg, 0.25 mmol) and 1,2-dimethoxyethane (2 mL) gave, after heated in the Microwave Smith Synthesizer at 150° C. for 10 min and purification on a Biotage 40S column (3:1 hexane:EtOAc), the title compound as an off-white solid. MS (ESI, pos. ion) n/z: 323 (M+1). Mp: 134.5-135.0° C.

EXAMPLE 127

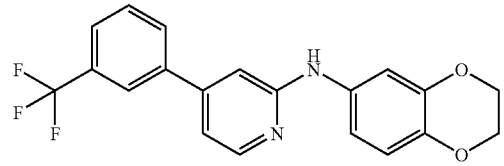

(2,3-Dihydro-benzo[1,4]dioxin-6-yl)-[4-(3-trifluoromethyl-phenyl)-pyridin-2-yl]-amine Following the same procedure described for Example 401 (c), the mixture of (2,3-dihydro-benzo[1,4]dioxin-6-yl)-(4-iodo-pyridin-2-yl)-amine (Example 401 (b), 75 mg, 0.2 mmol), tetrakis (triphenylphosphine) palladium (0) (Aldrich Chemical Company) (12 mg, 0.011 mmol), 3-(trifluoromethyl)phenylboronic acid (Aldrich Chemical Company) (47 mg, 0.25 mmol) and 1,2-dimethoxyethane (2 m]L) gave, after heated in the Microwave Smith Synthesizer at 150° C. for 10 min and purification on a Biotage 40S column (4:1 hexane:EtOAc), the title compound as a light-yellow solid. MS (ESI, pos. ion) m/z: 373 (M+1). Mp: 138.9-140.5° C.

EXAMPLE 128

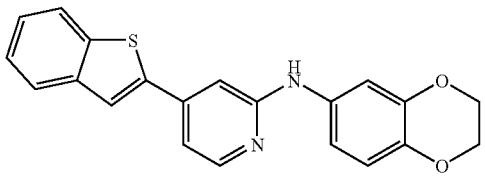

(4-Benzo[b]thiophen-2-yl-pyridin-2-yl)-(2,3-dihydro-benzo[1,4]dioxin-6-yl)-amine Following the same procedure described for Example 401 (c), the mixture of (2,3-dihydro-benzo[1,4]dioxin-6-yl)-(4-iodo-pyridin-2-yl)-amine (Example 401(b), 75 mg, 0.2 mmol), tetrakis (triphenylphosphine) palladium (0) (Aldrich Chemical Company) (12 mg, 0.011 mmol), benzothiophene-2-boronic acid (Frontier Scientific, Inc.) (45 mg, 0.25 mmol) and 1,2-dimethoxyethane (2 mL) gave, after heated in the Microwave Smith Synthesizer at 150° C. for 10 min and purification on a Biotage 40S column (4:1 hexane:EtOAc), the title compound as a light-yellow solid. MS (ESI, pos. ion) m/z: 361 (M+1). Mp: 154.0-154.1° C.

EXAMPLE 129

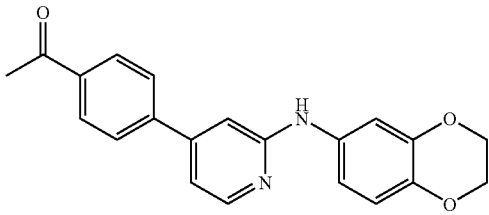

1-{4-[2-(2,3-Dihydro-benzo[1,4]dioxin-6-ylamino)-pyridin-4-yl]-phenyl}-ethanone

Following the similar procedure described for Example 401(c), the mixture of (2,3-dihydro-benzo[1,4]dioxin-6-yl)-(4-iodo-pyridin-2-yl)-amine (Example 401 (b), 0.73 g, 2.1 mmol), tetrakis (triphenylphosphine) palladium (0) (Aldrich Chemical Company) (0.12 g, 0.11 mmol), 4-actylphenylboronic acid (Aldrich Chemical Company) (0.41 g, 2.5 mmol) and 1,2-dimethoxyethane (20 mL) gave, after heated at 90° C. overnight and purification on a Biotage 40M column (3:1 hexane:EtOAc), the title compound as a light-orange solid. MS (ESI, pos. ion) m/z: 347 (M+1). Mp: 178.0-180.5° C.

EXAMPLE 130

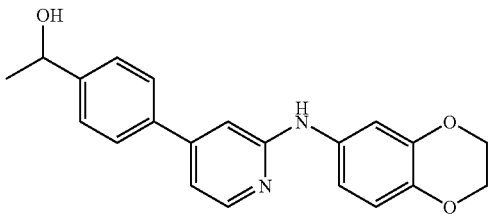

1-{4-[2-(2,3-Dihydro-benzo[1,4]dioxin-6-ylamino)-pyridin-4-yl]-phenyl}-ethanol

To the suspension of 1-{4-[2-(2,3-dihydro-benzo[1,4]dioxin-6-ylamino)-pyridin-4-yl]-phenyl}-ethanone (Example 7, 0.19 g, 0.55 mmol) in 2 mL of MeOH was added a solution of methylamine in MeOH (Aldrich Chemical Company) (2N, 0.55 mL, 1.1 mmol). The reaction was stirred at room temperature under nitrogen overnight. NaBH$_4$ (Aldrich Chemical Company) (25 mg, 0.66 mmol) was then added to the reaction and it was stirred for another 5 hrs. The solvent was dichloromethane:2N NH$_3$ in MeOH) to give the title compound as an off-white foam. MS (ESI, pos. ion) m/z: 349 (M+1). Mp: 55.9-61.5° C.

EXAMPLE 131

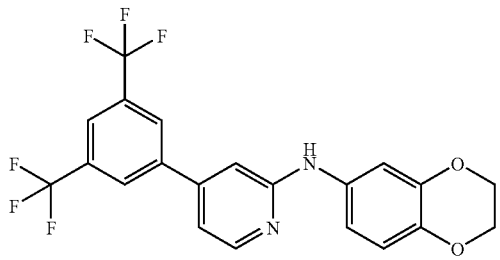

[4-(3,5-Bis-trifluoromethyl-phenyl)-pyridin-2-yl]-(2,3-dihydro-benzo[1,4]-dioxin-6-yl)-amine Following the same procedure described for Example 401 (c), the mixture of (2,3-dihydro-benzo[1,4]dioxin-6-yl)-(4-iodo-pyridin-2-yl)-amine (Example 401 (b), 75 mg, 0.2 mmol), tetrakis (triphenylphosphine) palladium (0) (Aldrich Chemical Company) (12 mg, 0.011 mmol), 3,5-bis(trifluoromethyl)phenylboronic acid (Aldrich Chemical Company) (64 mg, 0.25 mmol) and 1,2-dimethoxyethane (2 mL) gave, after heated in the Microwave Smith Synthesizer at 150° C. for 10 min and purification on a Biotage 40S column (4:1 hexane:EtOAc), the title compound as a light-yellow solid. MS (ESI, pos. ion) m/z: 441 (M+1). Mp: 130.0-131.5° C.

EXAMPLE 132

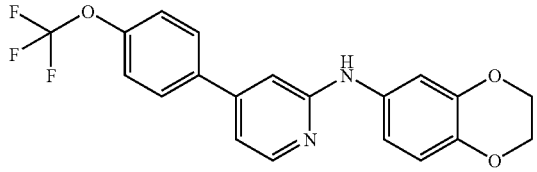

(2,3-Dihydro-benzo[1,4]dioxin-6-yl)-[4-(4-trifluoromethoxy-phenyl)-pyridin-2-yl]-amine Following the same procedure described for Example 401 (c), the mixture of (2,3-dihydro-benzo[1,4]dioxin-6-yl)-(4-iodo-pyridin-2-yl)-amine (Example 401 (b), 75 mg, 0.2 mmol), tetrakis (triphenylphosphine) palladium (0) (Aldrich Chemical Company) (12 mg, 0.011 mmol), 4-(trifluoromethoxy)phenylboronic acid (Lancaster Synthesis Ltd.) (51 mg, 0.25 mmol) and 1,2-dimethoxyethane (2 mL) gave, after heated in the Microwave Smith Synthesizer at 150° C. for 10 min and purification on a Biotage 40S column (4:1 hexane:EtOAc), the title compound as an orange glass. MS (ESI, pos. ion) m/z: 389 (M+1).

EXAMPLE 133

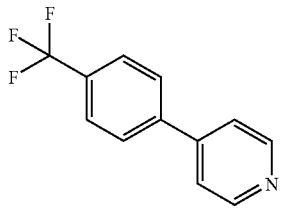

(a) 4-(4-Trifluoromethyl-phenyl)-pyridine

In a 250-mL, round-bottomed flask were added 4-bromopyridine hydrochloride (Aldrich) (4.7 g, 24 mmol), tetrakis (triphenylphosphine) palladium (0) (Aldrich) (1.4 g, 1.2 mmol) and 1,2-dimethoxyethane (120 mL). After stirring under nitrogen for 10 min, a solution of $Na_2CO_3$ (5.2 g in 30 mL of water) and 4-trifluoromethylbenzeneboronic acid (5.1 g, 27 mmol) were added sequentially to the mixture. The reaction was stirred in a 90° C. oil bath overnight. The 1,2-dimethoxyethane was evaporated in vacuo, and EtOAc was added to the residue. The aqueous layer was separated and extracted with EtOAc (2×50 mL). The combined EtOAc extracts were washed with brine, dried over $Na_2SO_4$ and concentrated in vacuo. Purification by silica gel flash chromatography using 1:5 EtOAc/hexanes as eluent gave the title compound as a light-tan solid. MS (ESI, pos. ion) m/z: 224 (M+1).

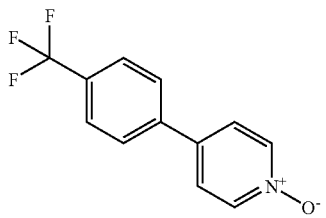

(b) 4-(4-Trifluoromethyl-phenyl)-pyridine 1-oxide

To a mixture of 4-(4-trifluoromethyl-phenyl)-pyridine (5.0 g, 22 mmol) and methyltrioxorhenium (VII) (Aldrich) (110 mg, 0.45 mmol) in a 100-mL, round-bottomed flask was added $CH_2Cl_2$ (10 mL). Hydrogen peroxide (5 mL, Aldrich) was added drop-wise, and the reaction was stirred at room temperature under $N_2$ for 48 h. The mixture was partitioned between $CH_2Cl_2$ and brine, and the aqueous layer was extracted with $CH_2Cl_2$ (40 mL). The combined organic layers were dried over $Na_2SO_4$, filtered, and concentrated in vacuo to give the title compound as an off-white solid. MS (ESI, pos. ion) m/z: 240 (M+1).

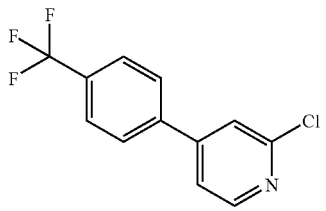

(c) 2-Chloro-4-(4-trifluoromethyl-phenyl)-pyridine

To 4-(4-trifluoromethyl-phenyl)-pyridine 1-oxide (2.4 g, 10 mmol) was added phosphorous oxychloride (12 mL) at room temperature. The reaction mixture was heated at reflux for 5 h. $POCl_3$ was removed under reduced pressure, and the residue was partitioned between EtOAc and aqueous ammonium hydroxide. The aqueous layer was extracted with EtOAc and the combined organic layers were dried over $Na_2SO_4$, filtered, and concentrated in vacuo. The crude material was purified by chromatography on a Biotage 40 M column (8:1 hexanes: EtOAc) to give the title compound as a white solid. MS (ESI, pos. ion) m/z: 258.5 (M+1).

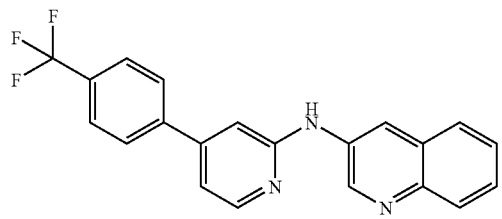

(d) Quinolin-3-yl-[4-(4-trifluoromethyl-phenyl)-pyridin-2-yl]-amine

To an oven-dried 50 mL round-bottomed flask were added 2-chloro-4-(4-trifluoromethyl-phenyl)-pyridine (138 mg, 0.54 mmol) and 3-aminoquinoline (Aldrich Chemical Company) (93 mg, 0.64 mmol), followed by anhydrous toluene (45 mL). Nitrogen was bubbled through the above solution via a needle for 1h. Then palladium acetate (Aldrich Chemical Company) (18 mg, 0.08 mmol) and BINAP (Aldrich Chemical Company) (50 mg, 0.08 mmol) were added to the reaction in one portion, followed by sodium tert-butoxide (Aldrich Chemical Company) (145 mg, 1.5 mmol). The reaction mixture was heated at 90° C. overnight. After cooling to room temperature, the reaction mixture was taken up to ether, and washed with brine. The aqueous layer was extracted with ether (2x) and the combined ether layer was dried over $Na_2SO_4$ and concentrated. The residue was purified on a Biotage 40 S column (2.5:1 hexane:EtOAc) to give the title compound as an off-white solid. MS (ESI, pos. ion) m/z: 366 (M+1). Mp: 207.4-207.5° C.

General Scheme III.a

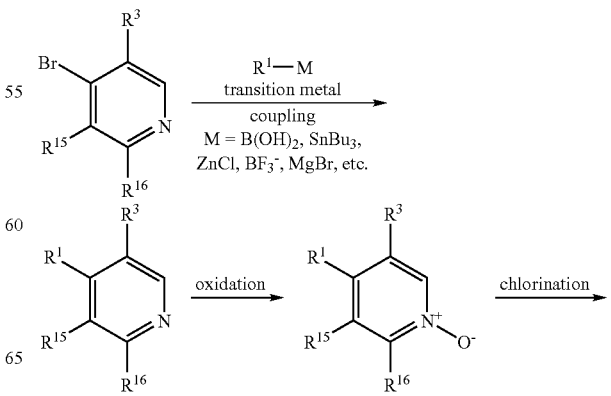

-continued

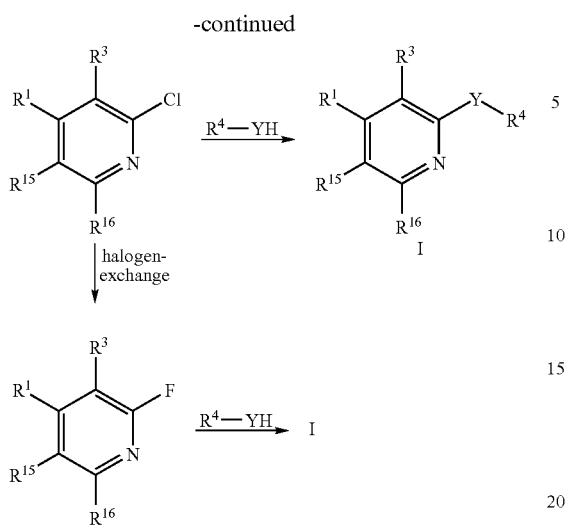

Scheme III.b

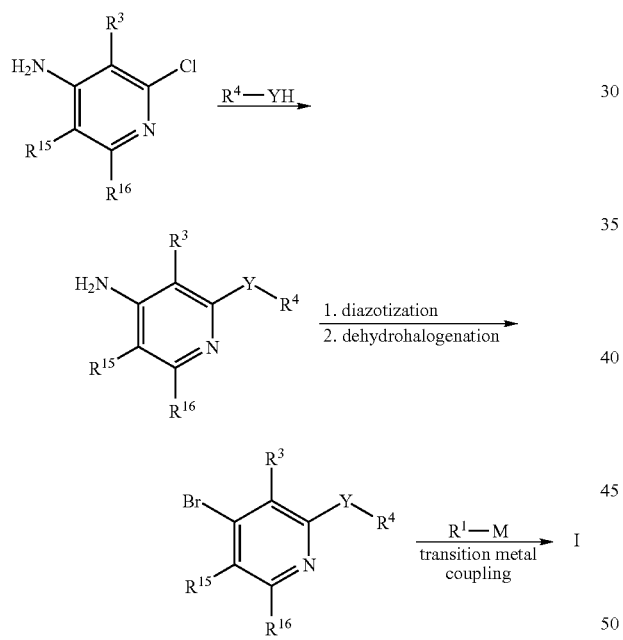

Scheme III.c

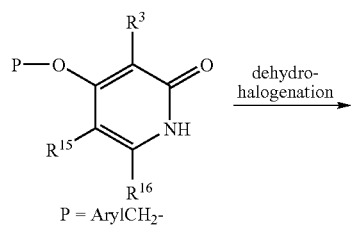

P = ArylCH₂-

-continued

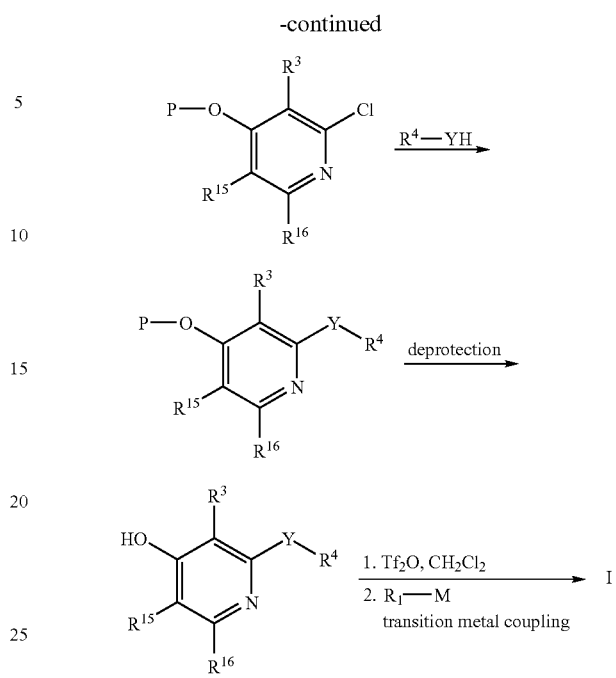

EXAMPLE 134

7-[4-(4-Trifluoromethyl-phenyl)-pyridin-2-yloxy]-quinoline

To an oven-dried, 50-mL, round-bottomed flask-were added 7-hydroxyquinoline (Aldrich) (87 mg, 0.6 mmol) and DMF (1 mL). The solution was place under nitrogen, and NaH (24 mg, 0.6 mmol) was added in one portion. After stirring for 10 min, 2-chloro-4-(4-trifluoromethylphenyl) pyridine (Example 410 (c), 129 mg, 0.5 mmol) was added. The reaction mixture was heated in a 155° C. oil bath for 72 h. After cooling to room temperature, the reaction mixture was partitioned between EtOAc and brine. The aqueous layer was extracted with EtOAc and the combined organic layers were dried over $Na_2SO_4$, concentrated in vacuo. The crude material was purified on a Biotage 40 S column (3:1 hexanes: EtOAc) to give the title compound as an off-white solid. MS (ESI, pos. ion) m/z: 367 (M+1). Mp: 156.5-158.5° C.

EXAMPLE 135

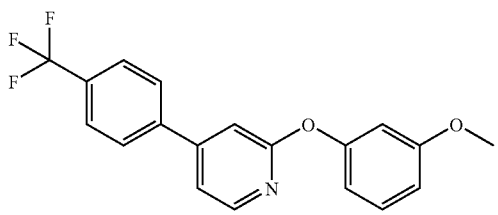

2-(3-Methoxy-phenoxy)-4-(4-trifluoromethyl-phenyl)-pyridine

This material was prepared according to the method described in Example 2 (d) using 2-chloro-4-(4-trifluoromethyl-phenyl)-pyridine (Example 410 (c), 129 mg, 0.5 mmol), 3-methoxyphenol (66 uL, 0.6 mmol), and sodium hydride (24 mg, 0.6 mmol) in DMF (1 mL). Purification on a Biotage 40S column (8:1 hexanes: EtOAc), provided the title compound as a white solid. MS (ESI, pos. ion) m/z: 346 (M+1). Mp: 77.5-79.6° C.

EXAMPLE 136

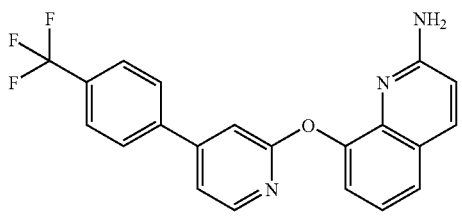

8-[4-(4-Trifluoromethyl-phenyl)-pyridin-2-yloxy]-quinolin-2-ylamine

A mixture of 2-azido-quinolin-8-ol (0.28 g, 1.5 mmol), 2-chloro-4-(4-trifluoromethyl-phenyl)-pyridine (Example 410 (c), 0.26 g, 1 mmol), and sodium hydride (64 mg, 1.6 mmol) in DMF (2 mL) was heated in a 180° C. oil bath for 48 h. The reaction mixture was then transferred to a 5-mL tube, and irradiated in the Microwave Smith Synthesizer at 250° C. for 10 min. EtOAc and brine were added, and the aqueous layer was extracted with EtOAc. Combined organic layers were dried over $Na_2SO_4$, filtered, and concentrated in vacuo. The compound was purified on a Biotage 40S column (98:2 dichloromethane: MeOH) followed by recrystallization from EtOAc/hexanes to give the title compound as a light-yellow shiny crystal. MS (ESI, pos. ion) m/z: 382 (M+1). Mp: 196.5-199.5° C. Anal. Calcd for $C_{21}H_{14}F_3N_3O$: C, 66.14; H, 3.70; N, 11.02. Found: C, 66.18; H, 3.69; N, 11.08.

EXAMPLE 137

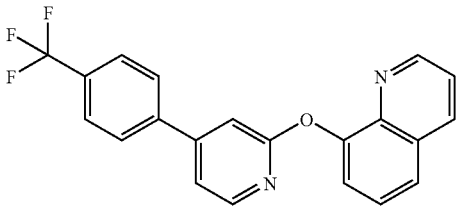

8-[4-(4-Trifluoromethyl-phenyl)-pyridin-2-yloxy]-quinoline

This material was prepared according to the method described in Example 413 using 2-chloro-4-(4-trifluoromethyl-phenyl)-pyridine (Example 410 (c), 0.16 g, 0.6 mmol), 8-hydroxyquinoline (0.1 g, 0.7 mmol), sodium hydride (38 mg, 1.0 mmol) and copper (I) iodide (12 mg, 0.06 mmol) in DMF (3 ML). Purification on a Biotage 40S column (3:1 hexanes: EtOAc), provided the title compound as a white solid. MS (ESI, pos. ion) nm/z: 367 (M+1). Anal. Calcd for $C_{21}H_{13}F_3N_2O$: C, 68.85; H, 3.58; N, 7.65. Found: C, 68.88; H, 3.59; N, 7.51.

EXAMPLE 138

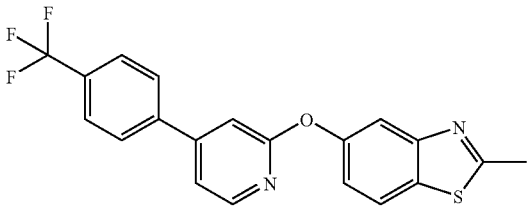

2-Methyl-5-[4-(4-trifluoromethyl-phenyl)-pyridin-2-yloxy]-benzothiazole

This material was prepared according to the method described in Example 413 using 2-chloro-4-(4-trifluoromethyl-phenyl)-pyridine (Example 410 (c), 0.16 g, 0.6 mmol), 2-methyl-5-benzothiazolol (0.12 g, 0.7 mmol), sodium hydride (38 mg, 1.0 mmol) and copper (I) iodide (12 mg, 0.06 mmol) in DMF (3 mL). Purification on a Biotage 40S column (3:1 hexanes: EtOAc), provided the title compound as a white solid. MS (ESI, pos. ion) m/z: 367 (M+1). Mp: 160.5-163.5° C. Anal. Calcd for $C_{20}H_{13}F_3N_2OS$. 0.25 $H_2O$: C, 61.45; H, 3.48; N, 7.17; S, 8.20.
Found: C, 61.45; H, 3.39; N, 7.17; S, 8.31.

TABLE B

The following compounds were prepared according to General Schemes III.a, III.b and III.c:

| Example | Structure | MS (ESI, pos. ion) m/z | Melting Point ° C. |
|---|---|---|---|
| 139 | 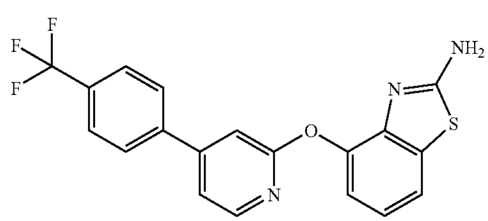 | 388 (M + 1) | 246.3-247.5 |

TABLE B-continued

The following compounds were prepared according to General Schemes III.a, III.b and III.c:

| Example | Structure | MS (ESI, pos. ion) m/z | Melting Point ° C. |
|---|---|---|---|
| 140 | 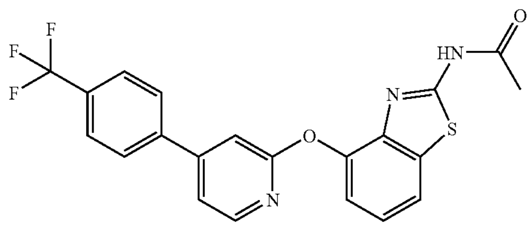 | 428 (M − 1)<br>430 (M + 1) | |

ADDITIONAL EXAMPLES

Following the procedures described above, or with slight modifications thereof, and following procedures familiar to one of ordinary skill in the art, the following examples were prepared from commercially available reagents:

| Example number | Structure | Melting Point (° C.) | Mass Spec. (ESI) m/z |
|---|---|---|---|
| 142 | 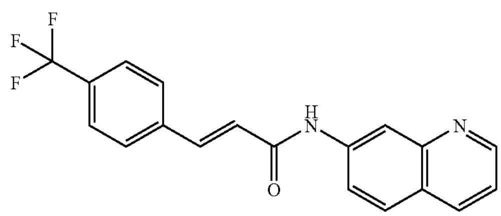 | 244 | 343 (M + 1) |
| 143 | 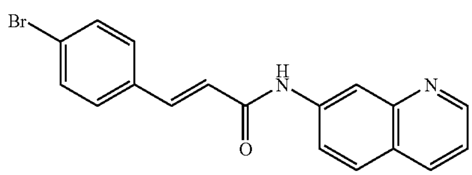 | 231 | 352, 354 (M, M + 2) |
| 144 | 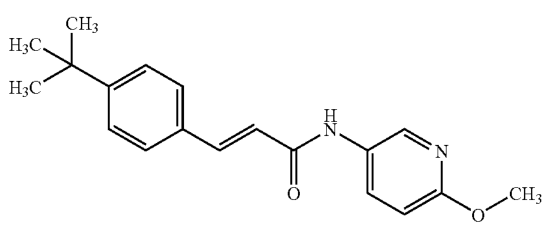 | 159 | 311 (M + 1) |
| 145 | 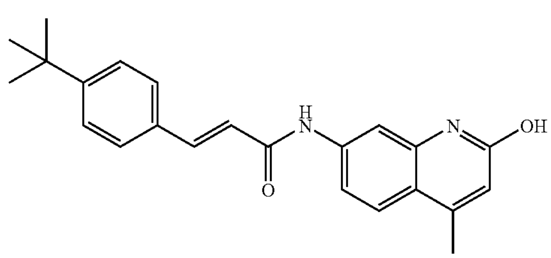 | >300 | 361 (M + 1) |

-continued

| Example number | Structure | Melting Point (° C.) | Mass Spec. (ESI) m/z |
|---|---|---|---|
| 146 | [Structure: 4-tert-butyl cinnamide with N-(3-methoxyphenyl)] | 59-61 | 310 (M + 1) |
| 147 | [Structure: 4-tert-butyl cinnamide with N-(4-methoxyphenyl)] | 174-175 | 310 (M + 1) |
| 148 | [Structure: 4-tert-butyl cinnamide with N-(3,5-dimethoxyphenyl)] | 97-102 | 340 (M + 1) |
| 149 | [Structure: 4-tert-butyl cinnamide with N-(benzothiazol-6-yl)] | 148-152 | 337 (M + 1) |
| 150 | [Structure: 4-tert-butyl cinnamide with N-(2,5-diethoxy-4-morpholinophenyl), HCl] | 233-237 | 453 (M + 1) |
| 151 | [Structure: 4-tert-butyl cinnamide with N-(2-hydroxyphenyl)] | oil | 296 (M + 1) |

-continued

| Example number | Structure | Melting Point (° C.) | Mass Spec. (ESI) m/z |
|---|---|---|---|
| 152 | 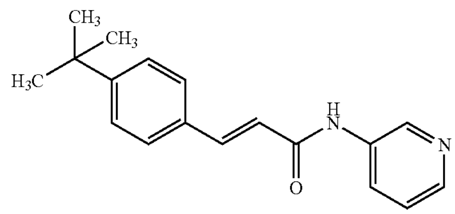 | 106-108 | 281 (M + 1) |
| 153 | 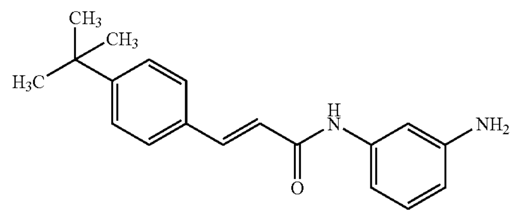 | 98-102 | 295 (M + 1) |
| 154 | 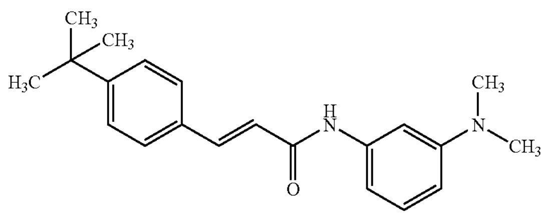 | 171-173 | 323 (M + 1) |
| 155 | 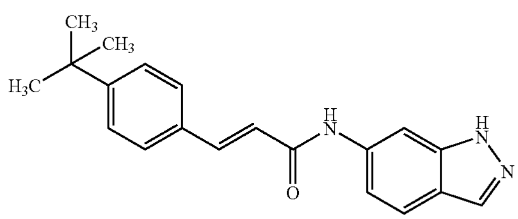 | 257 | 320 (M + 1) |
| 156 | 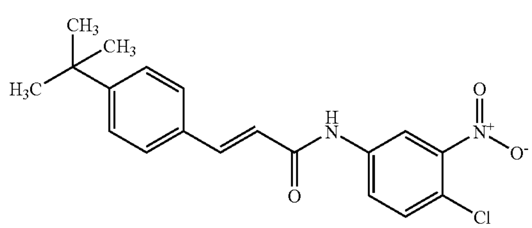 | 187-190 | 359 (M + 1) |
| 157 | 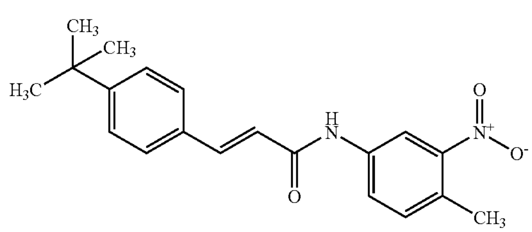 | 203 | 339 (M + 1) |

-continued

| Example number | Structure | Melting Point (° C.) | Mass Spec. (ESI) m/z |
|---|---|---|---|
| 158 | 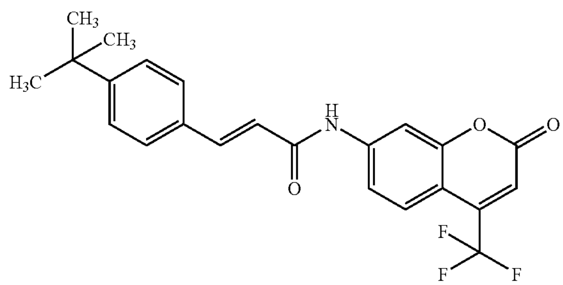 | 244-248 | 416 (M + 1) |
| 159 | 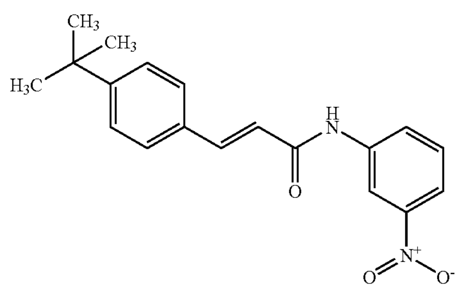 | 204 | 325 (M + 1) |
| 160 | 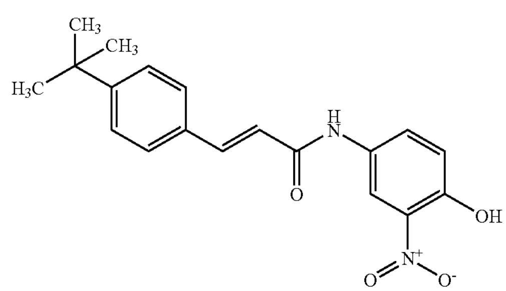 | 191 | 341 (M + 1) |
| 161 | 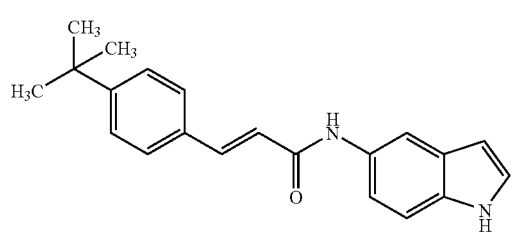 | thin film | 319 (M + 1) |
| 162 | 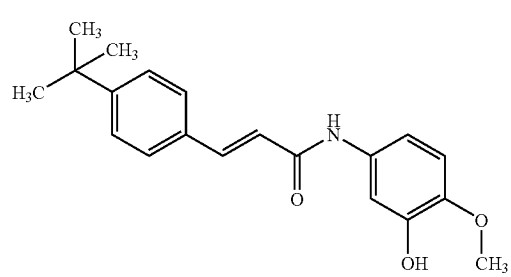 | 173 | 326 (M + 1) |

-continued
| Example number | Structure | Melting Point (° C.) | Mass Spec. (ESI) m/z |
|---|---|---|---|
| 163 | 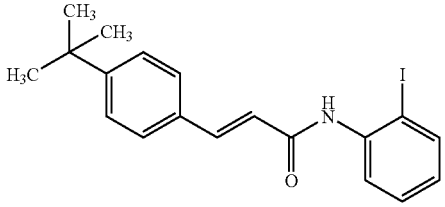 | 152 | 406 (M + 1) |
| 164 | 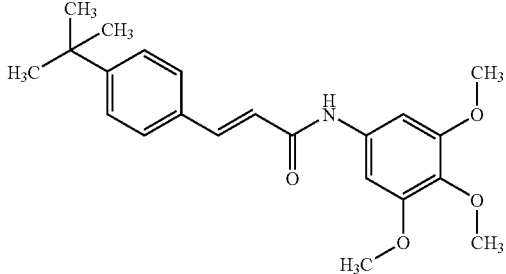 | 193 | 370 (M + 1) |
| 165 | 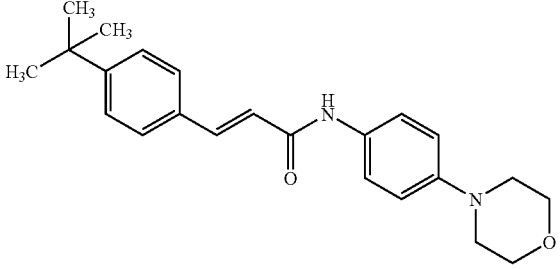 | 249 | 365 (M + 1) |
| 166 | 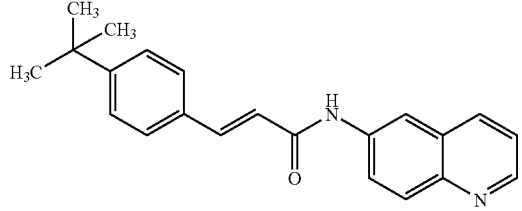 | 193 | 331 (M + 1) |
| 167 | 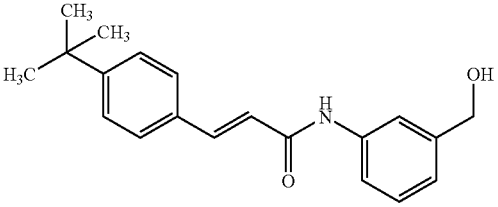 | 149 | 310 (M + 1) |
| 168 | 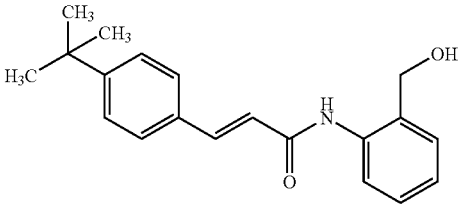 | 173 | 310 (M + 1) |

-continued

| Example number | Structure | Melting Point (° C.) | Mass Spec. (ESI) m/z |
|---|---|---|---|
| 169 | 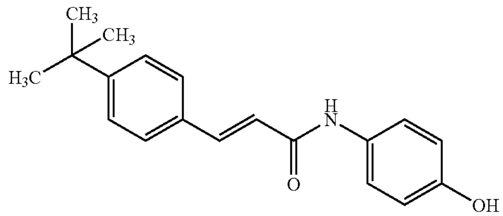 | 218 | 296 (M + 1) |
| 170 | 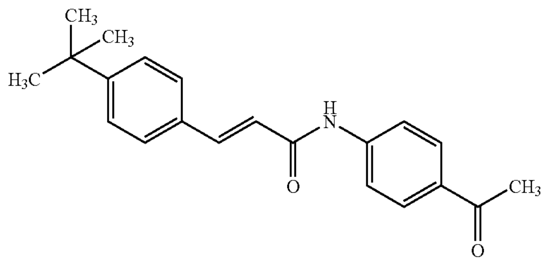 | 195 | 322 (M + 1) |
| 171 | 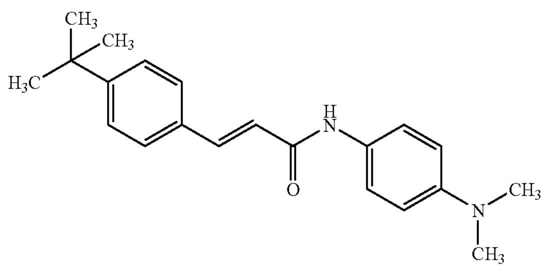 | 223 | 323 (M + 1) |
| 172 | 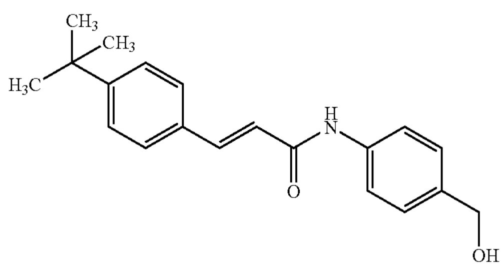 | 168 | 310 (M + 1) |
| 173 | 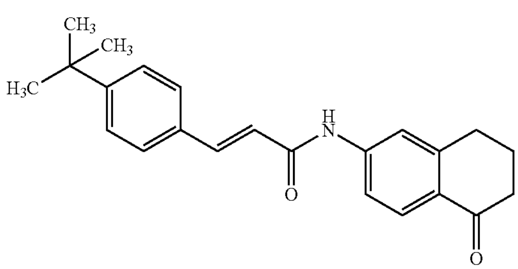 | 205 | 348 (M + 1) |
| 174 | 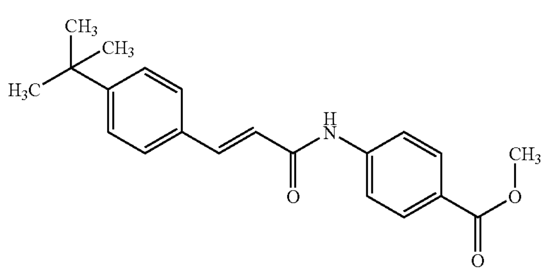 | 161 | 338 (M + 1) |

-continued

| Example number | Structure | Melting Point (° C.) | Mass Spec. (ESI) m/z |
|---|---|---|---|
| 175 | 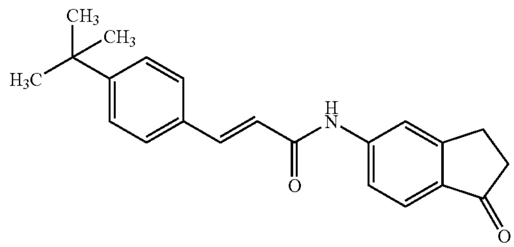 | 212 | 334 (M + 1) |
| 176 | 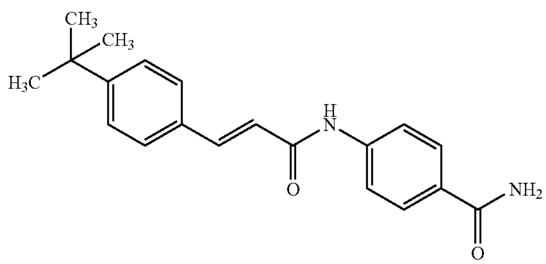 | 263 | 323 (M + 1) |
| 177 | 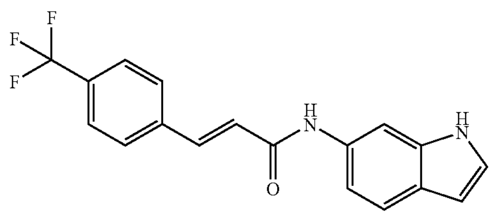 | 239 | 331 (M + 1) |
| 178 | 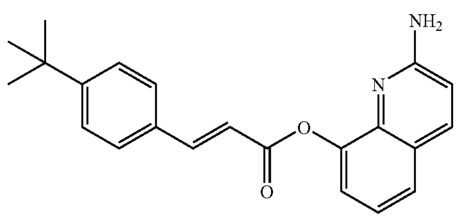 | 167 | 347 (M + 1) |
| 179 | 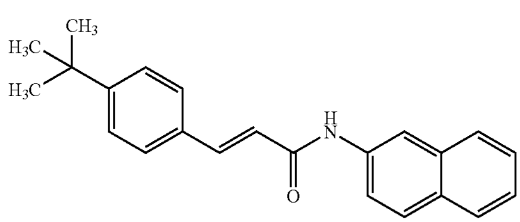 | 172 | 330 (M + 1) |
| 180 | 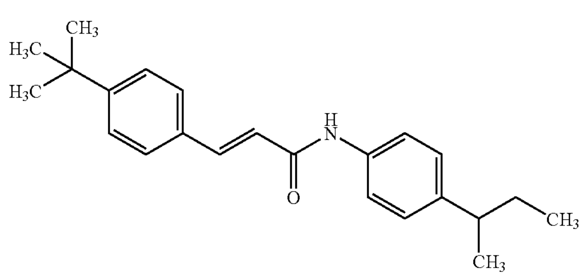 | 154 | 336 (M + 1) |

-continued

| Example number | Structure | Melting Point (° C.) | Mass Spec. (ESI) m/z |
|---|---|---|---|
| 181 | 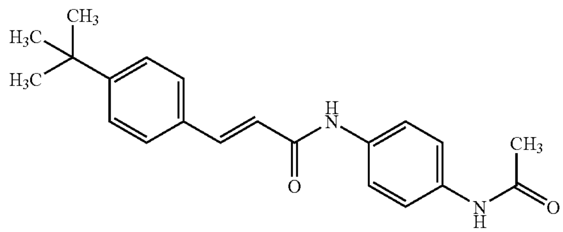 | 281 | 337 (M + 1) |
| 182 | 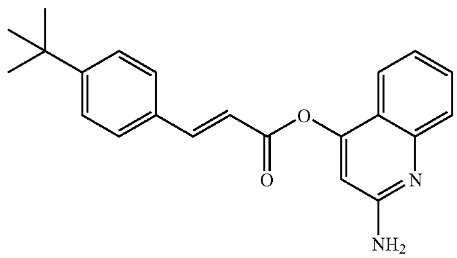 | 154 | 347 (M + 1) |
| 183 | 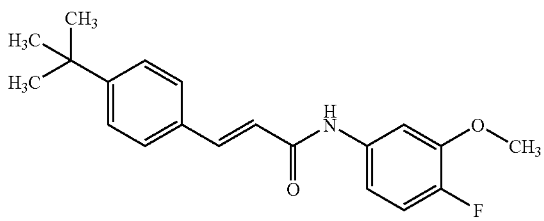 | 105 | 328 (M + 1) |
| 184 | 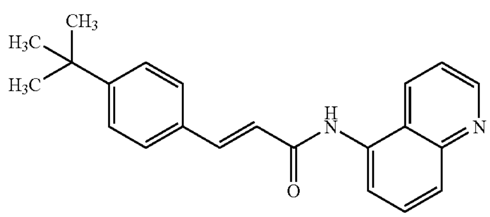 | 165 | 329 (M − 1) |
| 185 | 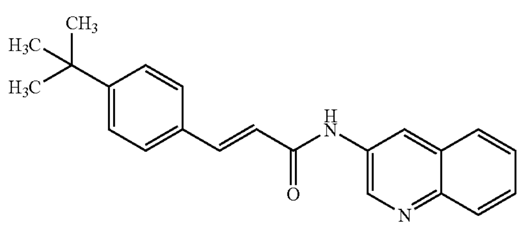 | 270 | 331 (M + 1) |
| 186 | 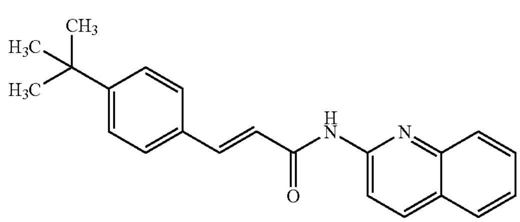 | 68 | 331 (M + 1) |

-continued

| Example number | Structure | Melting Point (° C.) | Mass Spec. (ESI) m/z |
|---|---|---|---|
| 187 | 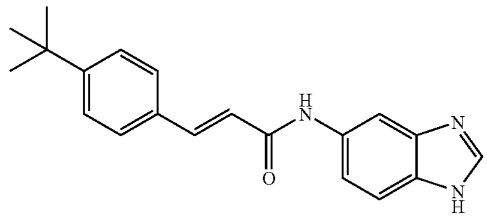 | 261 | 320 (M + 1) |
| 188 | 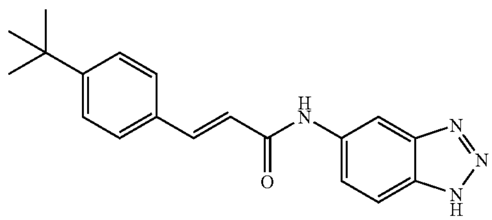 | 277 | 321 (M + 1) |
| 189 | 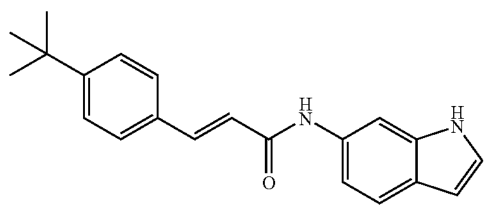 | 194 | 319 (M + 1) |
| 190 | 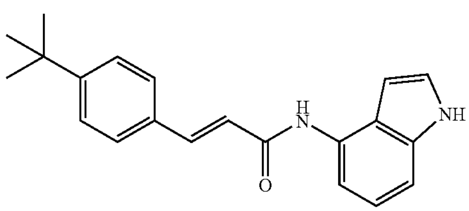 | 101 | 319 (M + 1) |
| 200 | 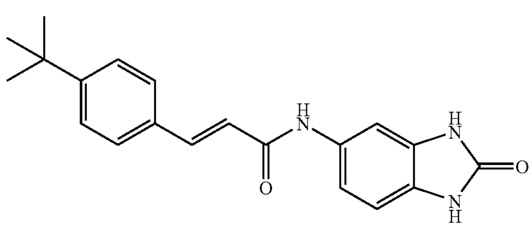 | 258 | 336 (M + 1) |
| 201 | 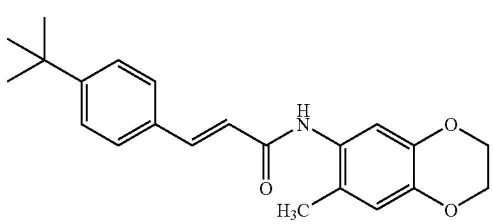 | 178 | 352 (M + 1) |

-continued

| Example number | Structure | Melting Point (° C.) | Mass Spec. (ESI) m/z |
|---|---|---|---|
| 202 | 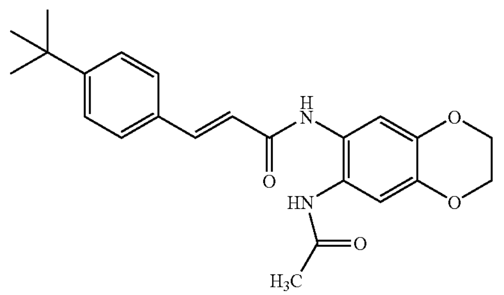 | 196 | 395 (M + 1) |
| 203 | 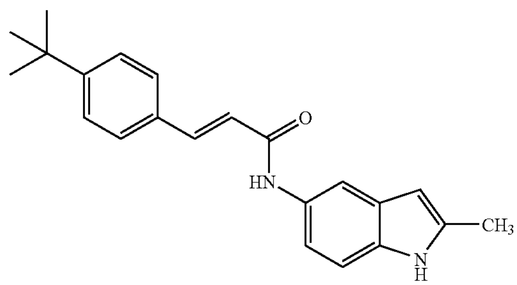 | 222 | 333 (M + 1) |
| 204 | 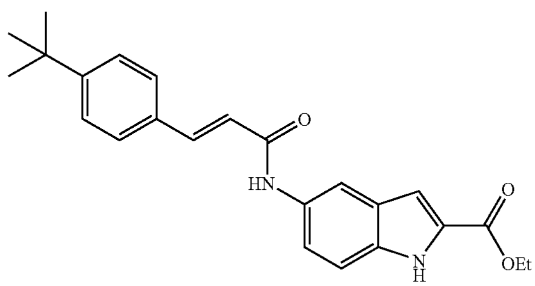 | 218 | 391 (M + 1) |
| 205 | 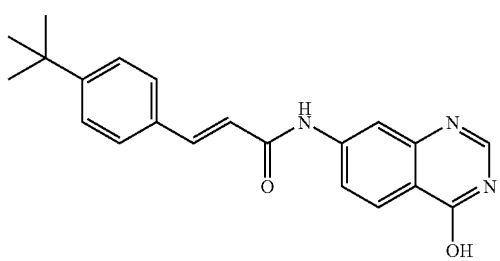 | 296-298 | 348 (M + 1) |
| 206 | 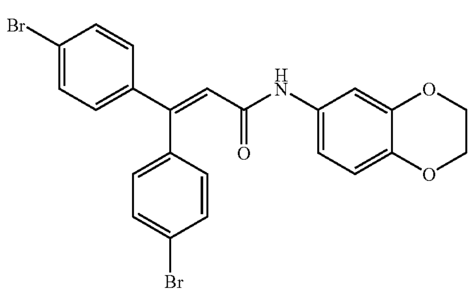 | 189 | 515 (M) |

-continued

| Example number | Structure | Melting Point (° C.) | Mass Spec. (ESI) m/z |
|---|---|---|---|
| 207 | 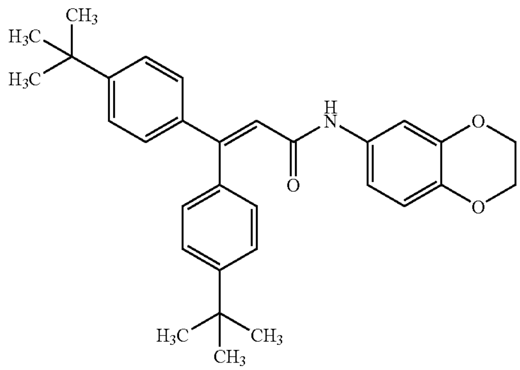 | 116-119 | 470 (M + 1) |
| 208 | 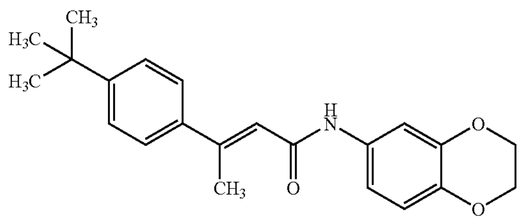 | 186 | 352 (M + 1) |
| 209 | 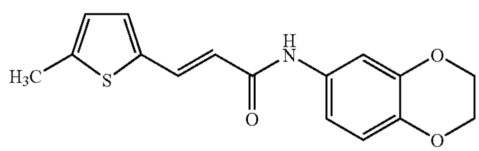 | 162-163 | 302 (M + 1) |
| 210 | 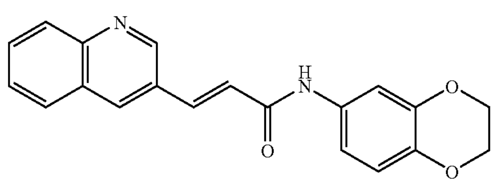 | 231-232 | 333 (M + 1) |
| 211 | 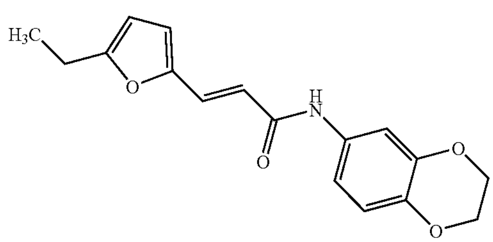 | 42-48 | 300 (M + 1) |
| 212 | 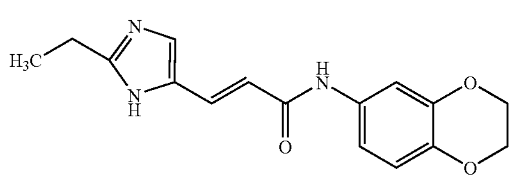 | 229-230 | 300 (M + 1) |

-continued

| Example number | Structure | Melting Point (° C.) | Mass Spec. (ESI) m/z |
|---|---|---|---|
| 213 | 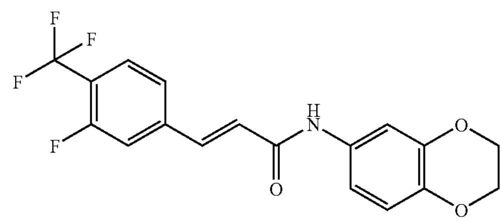 | 200-202 | 368 (M + 1) |
| 214 | 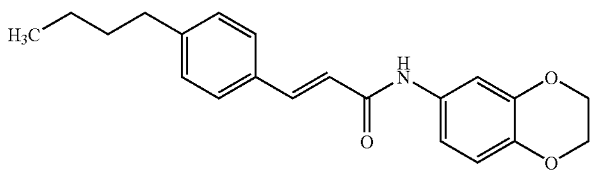 | 120 | 338 (M + 1) |
| 215 | 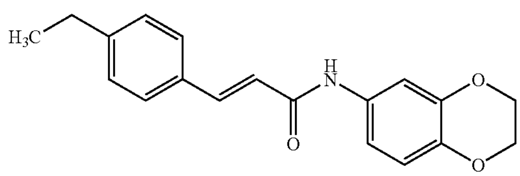 | 119 | 310 (M + 1) |
| 216 | 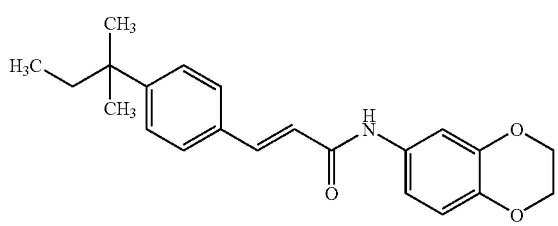 | 69 | 352 (M + 1) |
| 217 | 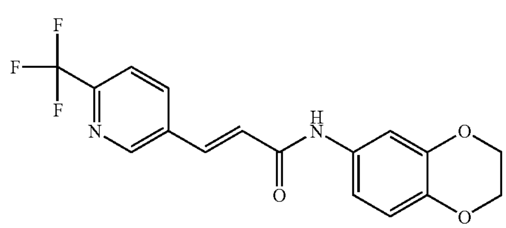 | amorphous glass | 351 (M + 1) |
| 218 | 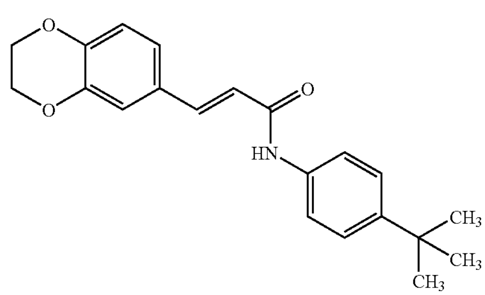 | 84-90 | 338 (M + 1) |

-continued

| Example number | Structure | Melting Point (° C.) | Mass Spec. (ESI) m/z |
|---|---|---|---|
| 219 | 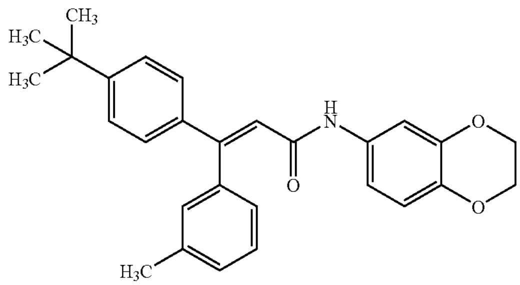 | 64-71 | 428 (M + 1) |
| 220 | 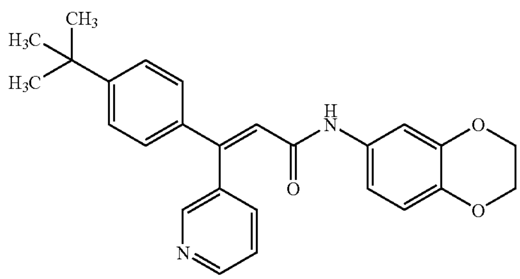 | 100-104 | 415 (M + 1) |
| 221 | 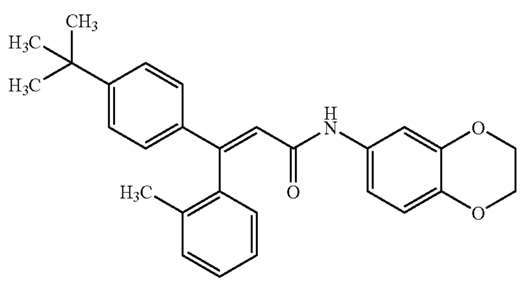 | 91-93 | 428 (M + 1) |
| 222 | 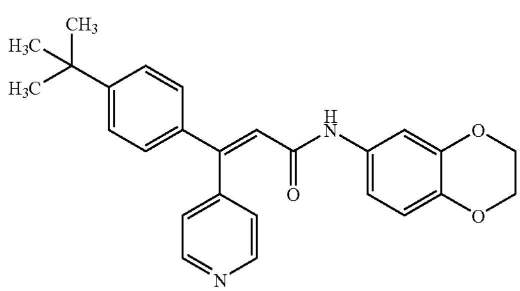 | 205-206 | 415 (M + 1) |
| 223 | 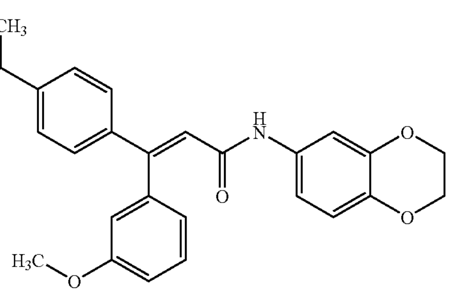 | 78-80 | 444 (M + 1) |

-continued

| Example number | Structure | Melting Point (° C.) | Mass Spec. (ESI) m/z |
|---|---|---|---|
| 224 | 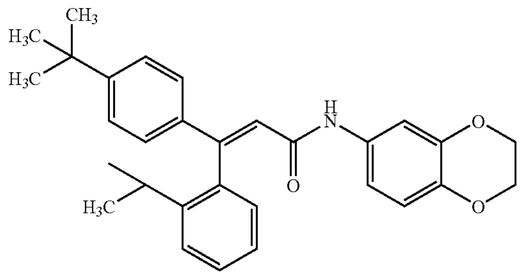 | 89-93 | 444 (M + 1) |
| 225 | 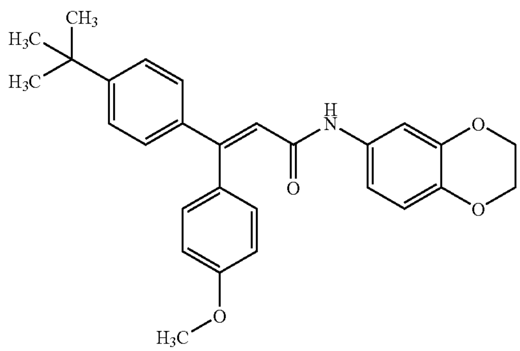 | 148-150 | 444 (M + 1) |
| 226 | 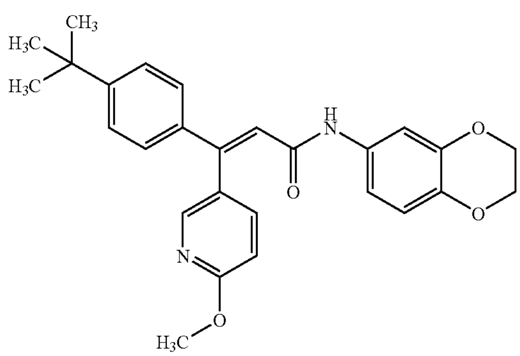 | 92-94 | 445 (M + 1) |
| 227 | 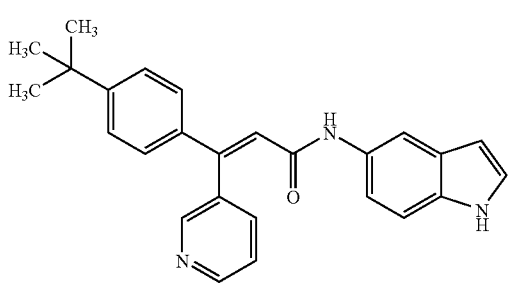 | 177-180 | 396 (M + 1) |

-continued

| Example number | Structure | Melting Point (° C.) | Mass Spec. (ESI) m/z |
|---|---|---|---|
| 228 | 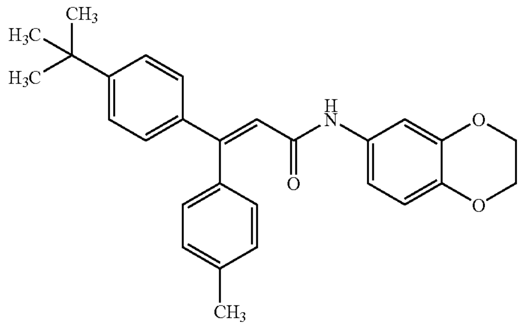 | 138-141 | 428 (M + 1) |
| 229 | 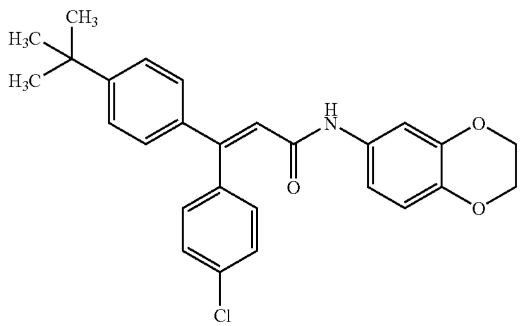 | 155 | 448 (M + 1) |
| 230 | 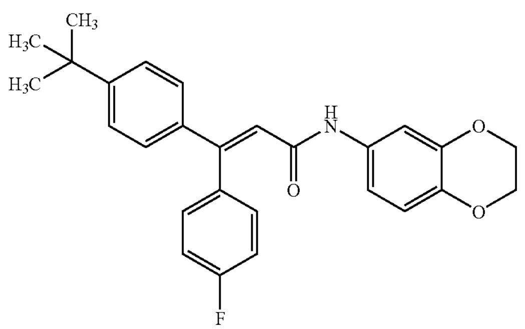 | 168 | 432 (M + 1) |
| 231 | 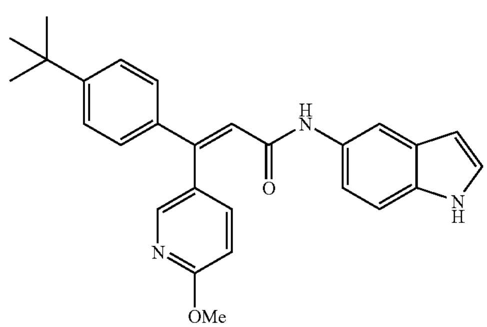 | 121-124 | 426 (M + 1) |
| 232 | 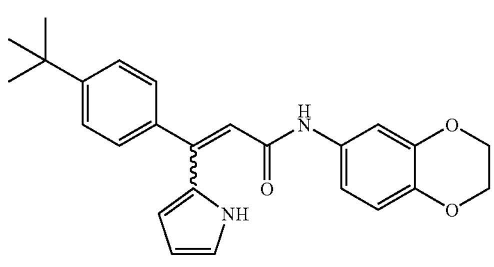 | | 403 (M + 1) |

-continued

| Example number | Structure | Melting Point (° C.) | Mass Spec. (ESI) m/z |
|---|---|---|---|
| 233 | 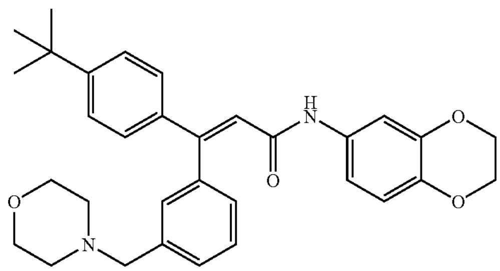 | 87 | 513 (M + 1) |
| 234 | 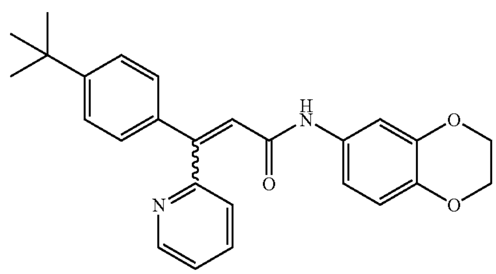 | | 415 (M + 1) |
| 235 | 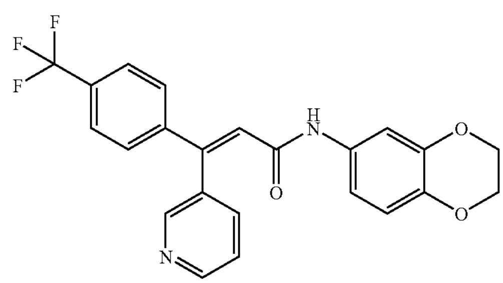 | amorphous | 427 (M + 1) |
| 236 | 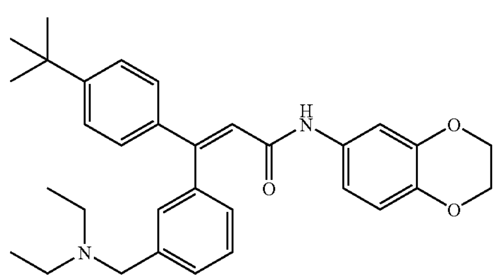 | 56 | 499 (M + 1) |
| 237 | 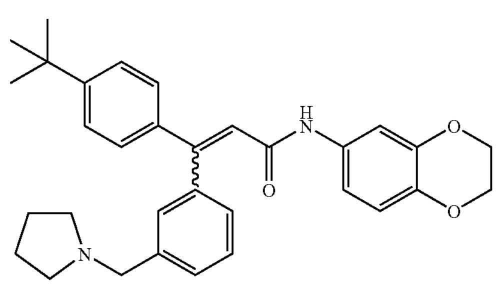 | | 497 (M + 1) |

-continued

| Example number | Structure | Melting Point (° C.) | Mass Spec. (ESI) m/z |
|---|---|---|---|
| 238 | 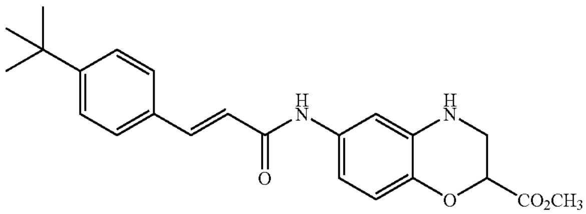 | 207-208 | 395 (M + 1) |
| 239 | 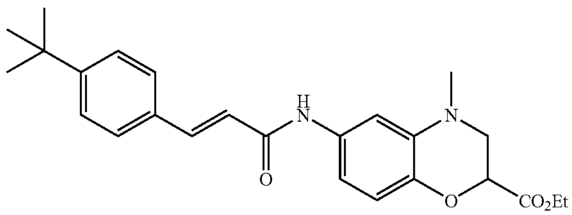 | 188-189 | 423 (M + 1) |
| 240 | 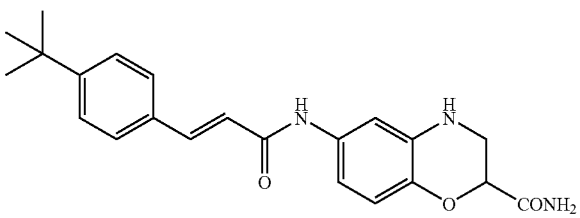 | 198-199 | 380 (M + 1) |
| 241 | 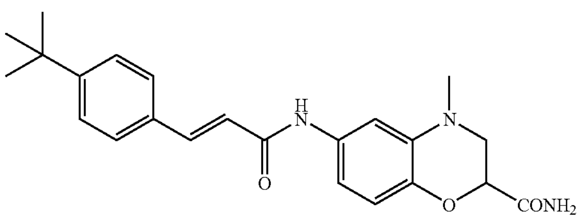 | 201-203 | 394 (M + 1) |
| 242 | 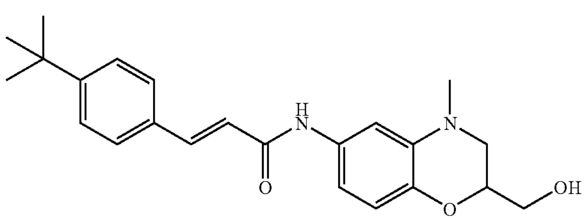 | 171-173 | 381 (M + 1) |
| 243 | 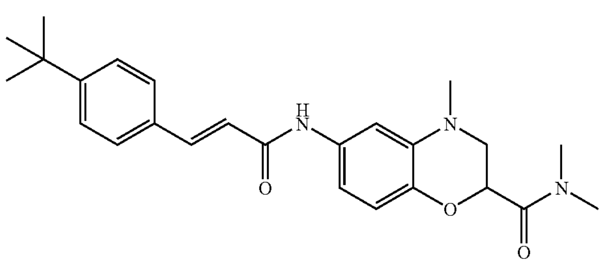 | 118-120 | 422 (M + 1) |

-continued

| Example number | Structure | Melting Point (° C.) | Mass Spec. (ESI) m/z |
|---|---|---|---|
| 244 | 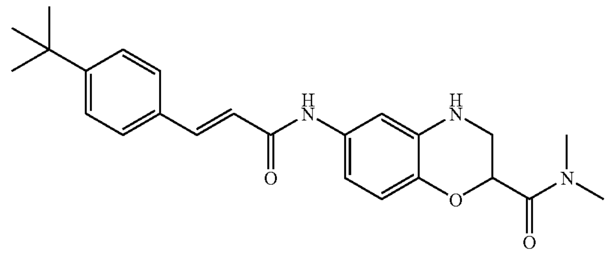 | 101-103 | 408 (M + 1) |
| 245 | 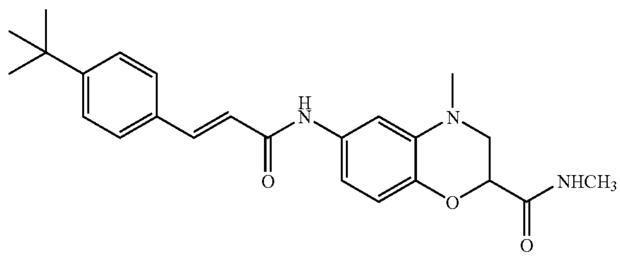 | 126-128 | 408 (M + 1) |
| 246 | 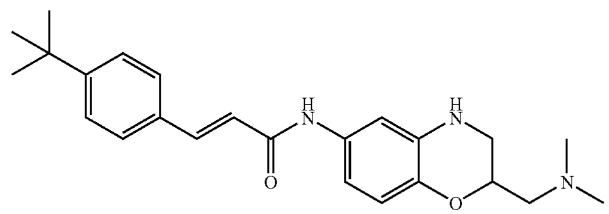 | 185-186 | 394 (M + 1) |
| 247 | 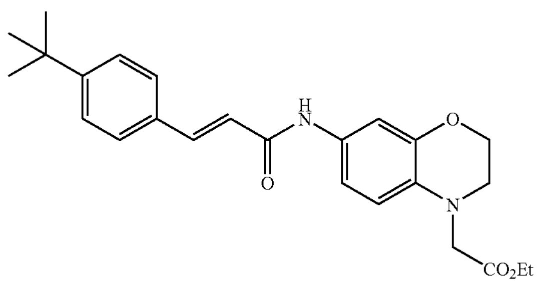 | 182-184 | 423 (M + 1) |
| 248 | 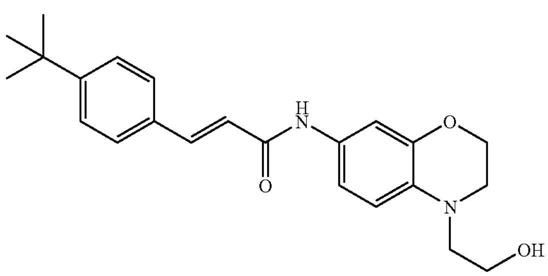 | 194-196 | 381 (M + 1) |
| 249 | 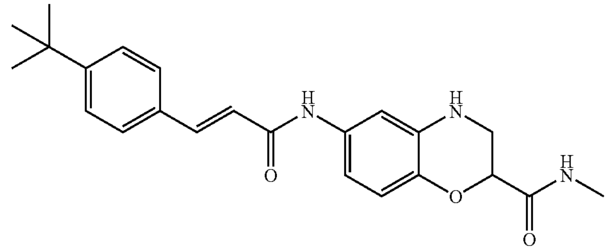 | 206-208 | 394 (M + 1) |

-continued

| Example number | Structure | Melting Point (° C.) | Mass Spec. (ESI) m/z |
|---|---|---|---|
| 250 | 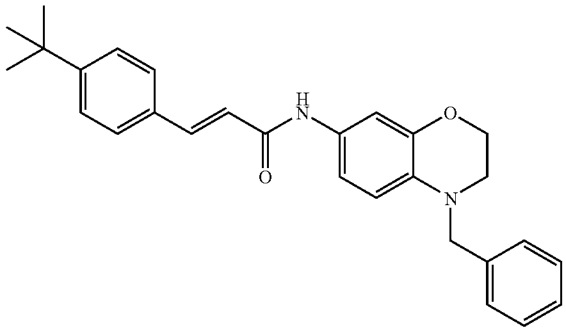 | 200-201 | 427 (M + 1) |
| 251 | 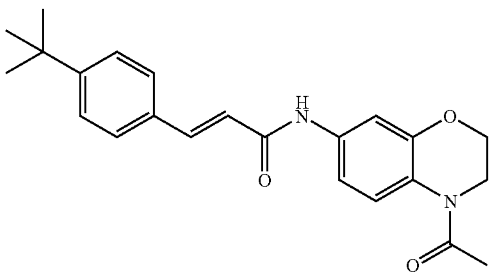 | 199-200 | 379 (M + 1) |
| 252 | 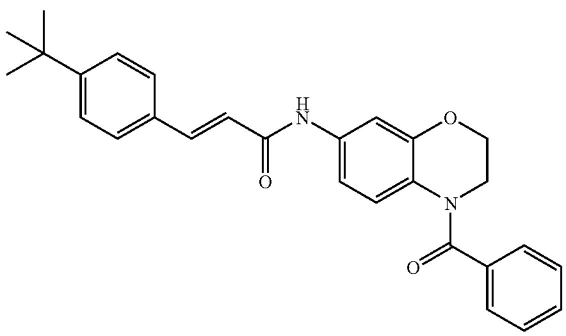 | 236-237 | 441 (M + 1) |
| 253 | 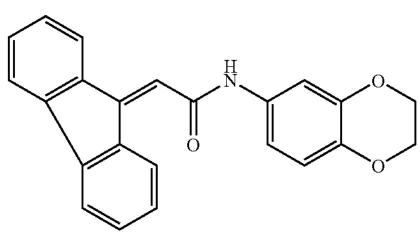 | 169 | 356 (M + 1) |
| 254 | 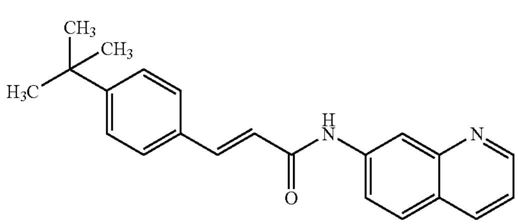 | 256-258 | 331 (M + 1) |

| Example number | Structure | Melting Point (° C.) | Mass Spec. (ESI) m/z |
|---|---|---|---|
| 255 | 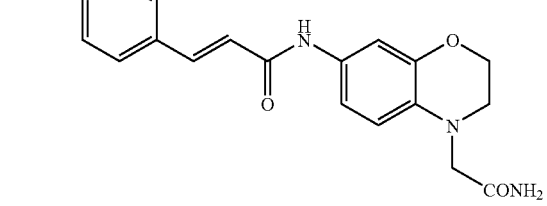 | 264-266 | 394 (M + 1) |
| 256 | 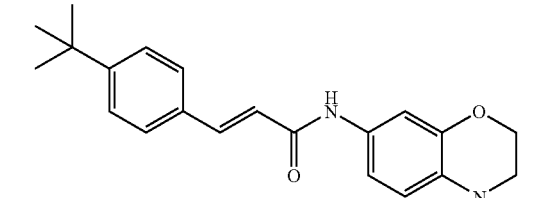 | 102-103 | 365 (M + 1) |
| 257 | 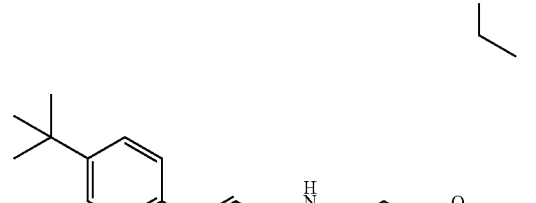 | 137-138 | 391 (M + 1) |
| 258 | 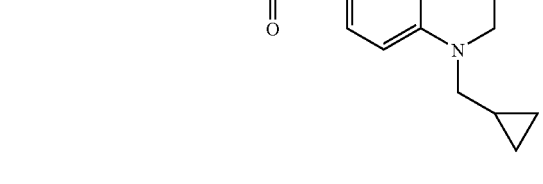 | 198-200 | 391 (M + 1) |
| 259 | 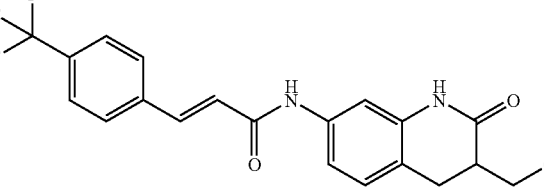 | 171-173 | 402 (M + 1) |
| 260 | 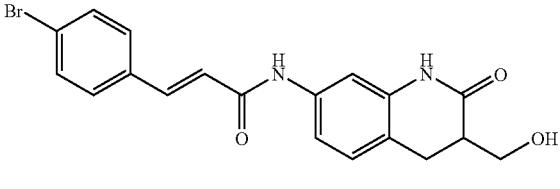 | 158-160 | 409 (M + 1) |

-continued
| Example number | Structure | Melting Point (° C.) | Mass Spec. (ESI) m/z |
|---|---|---|---|
| 261 | 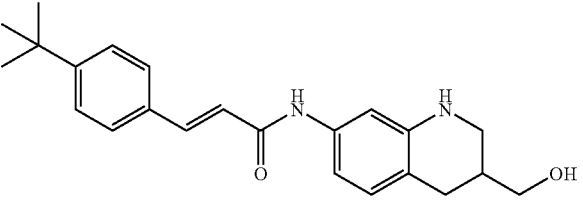 | 168-170 | 365 (M + 1) |
| 262 | 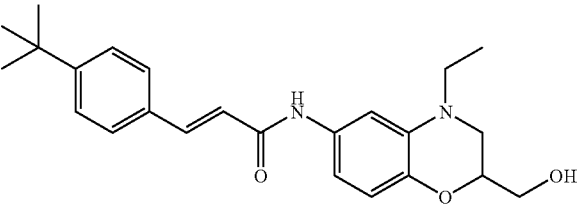 | 179-180 | 395 (M + 1) |
| 263 | 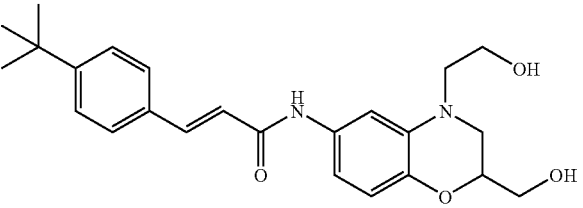 | 117-119 | 411 (M + 1) |
| 264 | 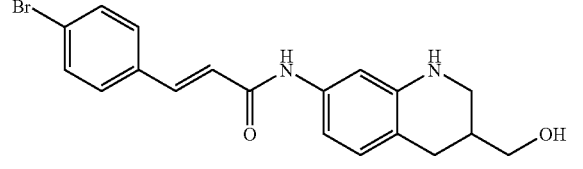 | 187-189 | 388 (M + 1) |
| 265 | 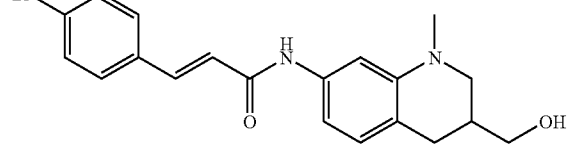 | 154-157 | 402 (M + 1) |
| 266 | 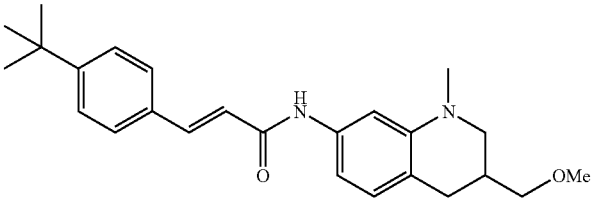 | 160-161 | 395 (M + 1) |
| 267 | 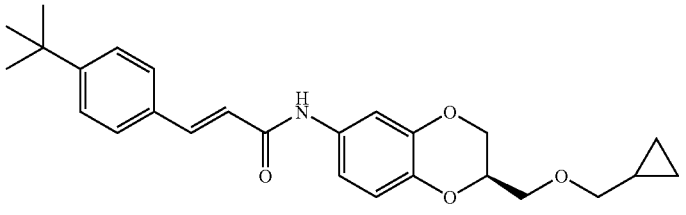 | 152-153 | 422 (M + 1) |

| Example number | Structure | Melting Point (°C.) | Mass Spec. (ESI) m/z |
|---|---|---|---|
| 268 | 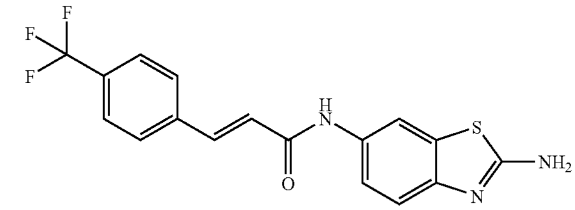 | 186-188 | 364 (M + 1) |
| 269 | 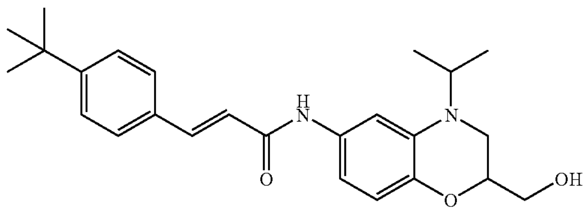 | 134-135 | 409 (M + 1) |
| 270 | 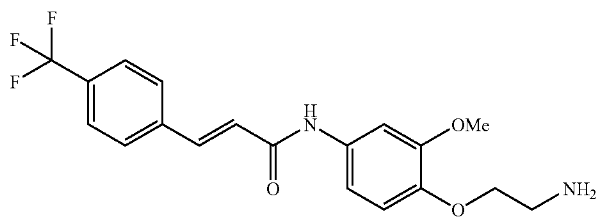 | 182-185 | 381 (M + 1) |
| 271 | 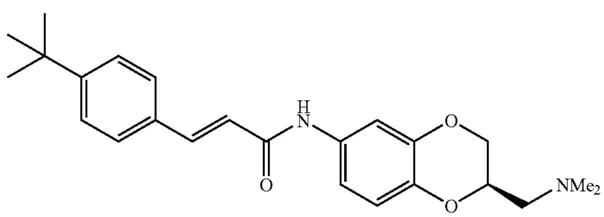 | 171-173 | 395 (M + 1) |
| 272 | 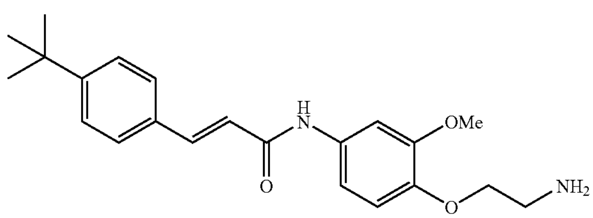 | 101-105 | 369 (M + 1) |
| 273 | 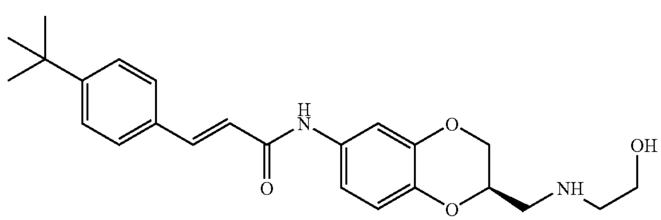 | 176-178 | 411 (M + 1) |
| 274 | 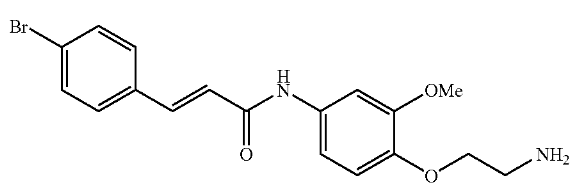 | 196-199 | 392 (M + 1) |

-continued

| Example number | Structure | Melting Point (° C.) | Mass Spec. (ESI) m/z |
|---|---|---|---|
| 275 | 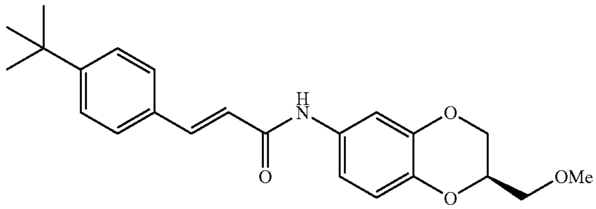 | 146-148 | 382 (M + 1) |
| 276 | 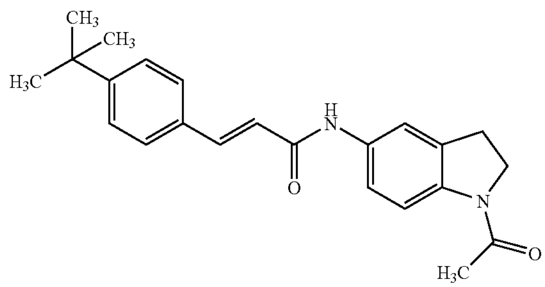 | 231 | 363 (M + 1) |
| 277 | 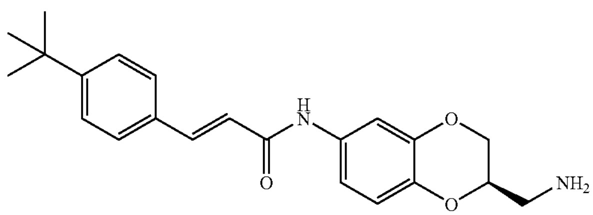 | 161-162 | 367 (M + 1) |
| 278 | 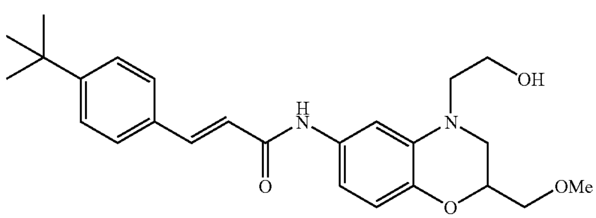 | 108-110 | 425 (M + 1) |
| 279 | 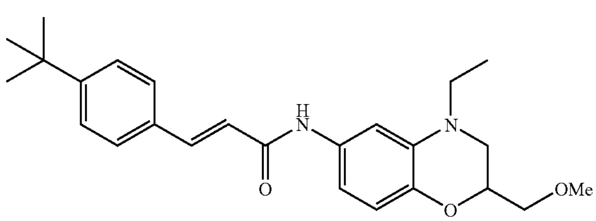 | 186-187 | 409 (M + 1) |
| 280 | 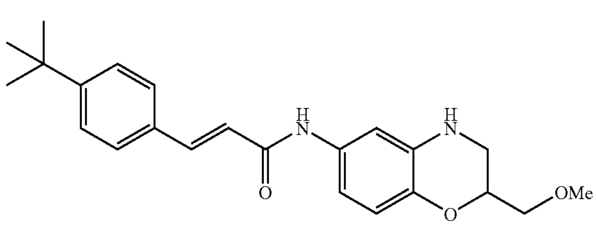 | 160-162 | 381 (M + 1) |

-continued

| Example number | Structure | Melting Point (°C.) | Mass Spec. (ESI) m/z |
|---|---|---|---|
| 281 | 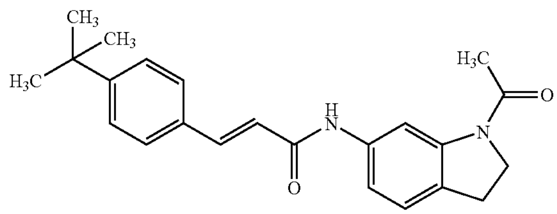 | 181 | 363 (M + 1) |
| 282 | 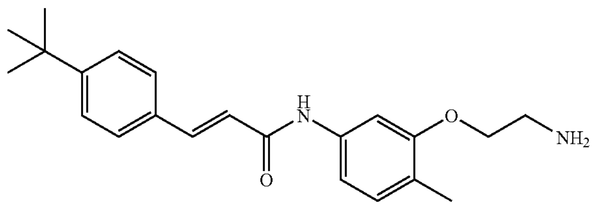 | amorphous | 353 (M + 1) |
| 283 | 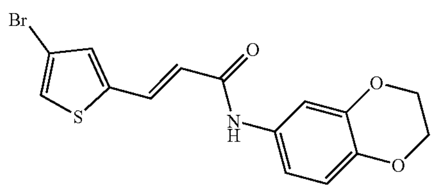 | (oil) | 366 (M) |
| 284 | 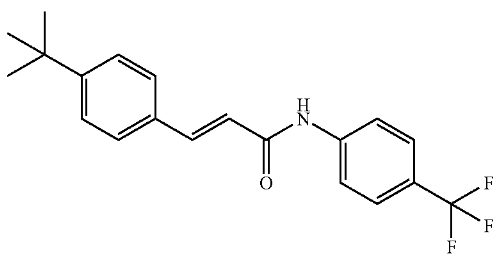 | | 348 (M + 1) |
| 285 | 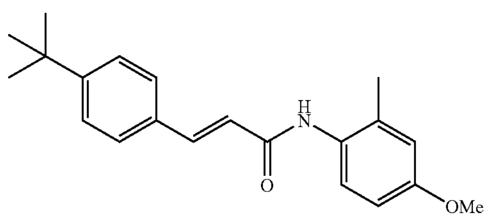 | | 324 (M + 1) |
| 286 | 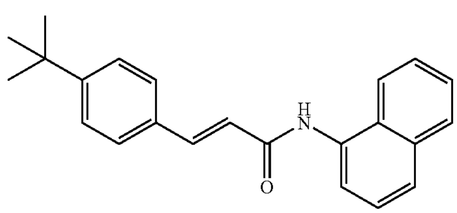 | | 330 (M + 1) |
| 287 | 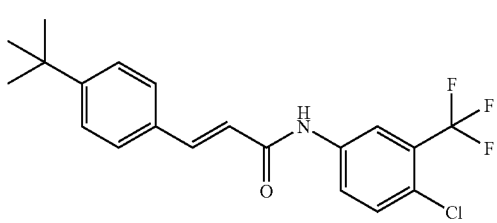 | | 382 (M + 1) |

-continued
| Example number | Structure | Melting Point (° C.) | Mass Spec. (ESI) m/z |
|---|---|---|---|
| 288 | 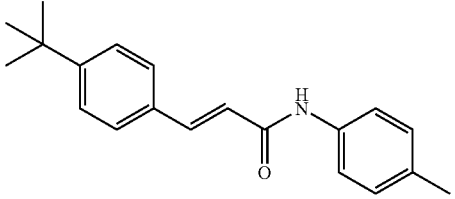 | | 294 (M + 1) |
| 289 | 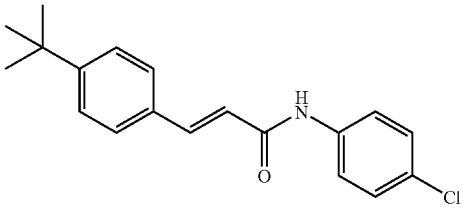 | | 314 (M + 1) |
| 290 | 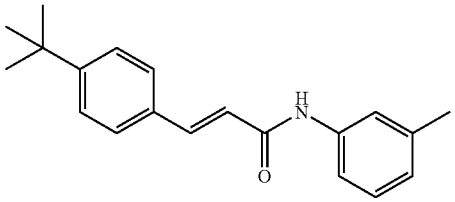 | | 294 (M + 1) |
| 291 | 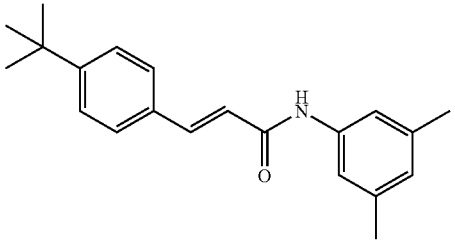 | | 308 (M + 1) |
| 292 | 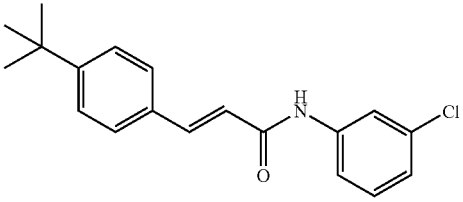 | | 314 (M + 1) |
| 293 | 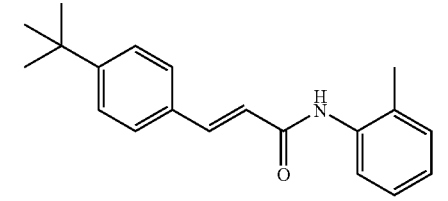 | | 294 (M + 1) |

-continued

| Example number | Structure | Melting Point (° C.) | Mass Spec. (ESI) m/z |
|---|---|---|---|
| 294 | 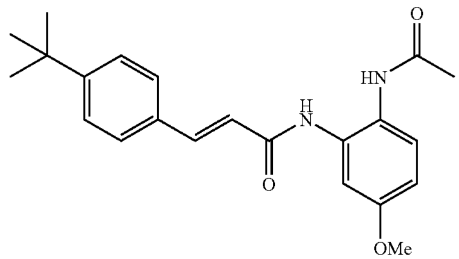 | | 367 (M + 1) |
| 295 | 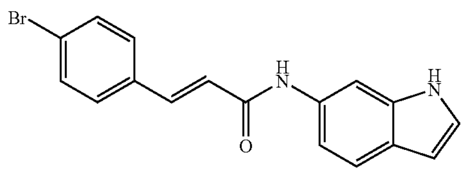 | 246-247 | 341 (M + 1) |
| 296 | 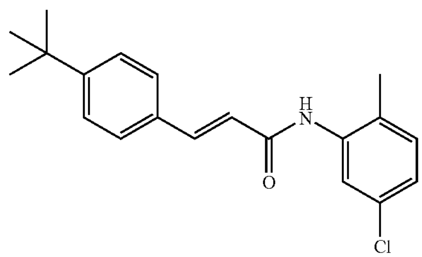 | | 328 (M + 1) |
| 297 | 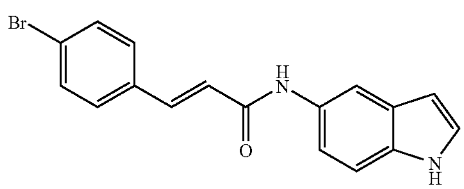 | 233-235 | 341 (M + 1) |
| 298 | 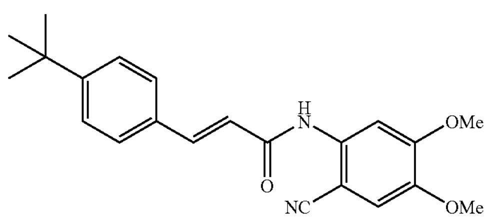 | | 365 (M + 1) |
| 299 | 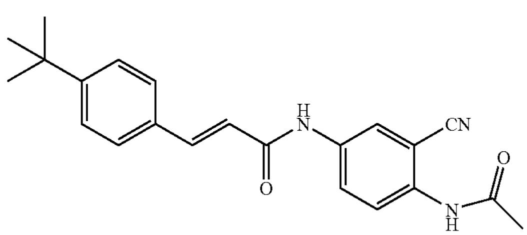 | | 362 (M + 1) |
| 300 | 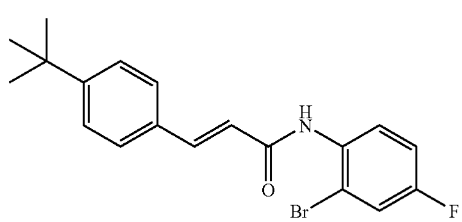 | | 376 (M + 1) |

-continued

| Example number | Structure | Melting Point (° C.) | Mass Spec. (ESI) m/z |
|---|---|---|---|
| 301 | 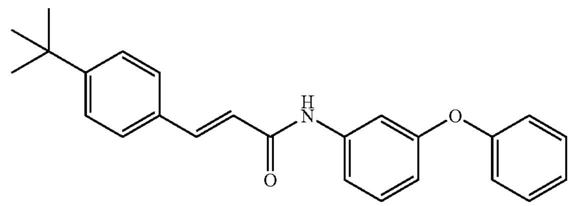 | | 372 (M + 1) |
| 302 | 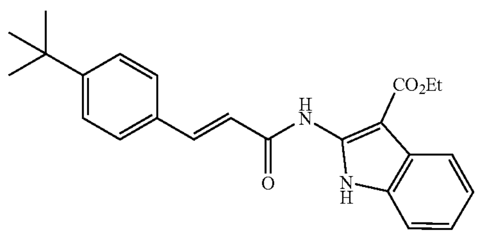 | 186-187 | 391 (M + 1) |
| 303 | 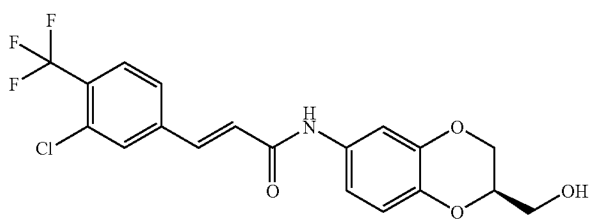 | 224-226 | 414 (M + 1) |
| 304 | 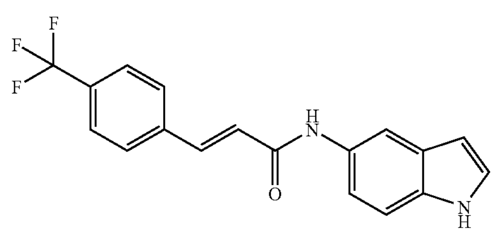 | 231-232 | 331 (M + 1) |
| 305 | 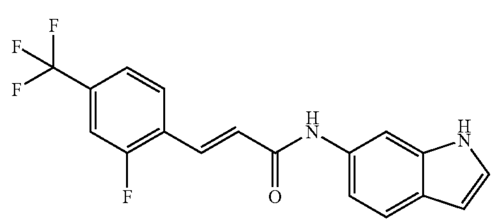 | 219-220 | 349 (M + 1) |
| 306 | 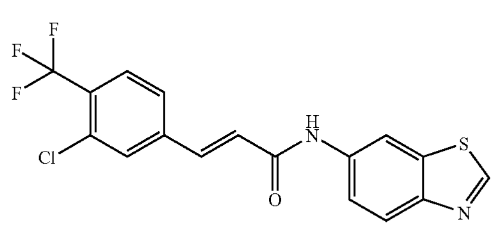 | 231-232 | 383 (M + 1) |

-continued

| Example number | Structure | Melting Point (° C.) | Mass Spec. (ESI) m/z |
|---|---|---|---|
| 307 | 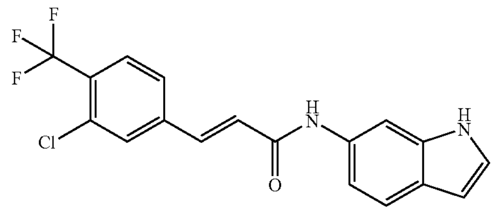 | 203-204 | 365 (M + 1) |
| 308 | 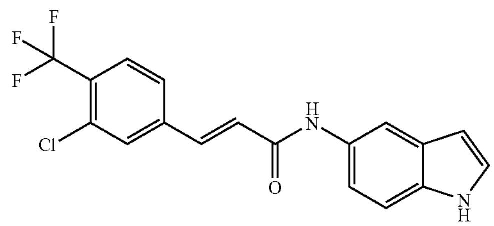 | 177-179 | 365 (M + 1) |
| 309 | 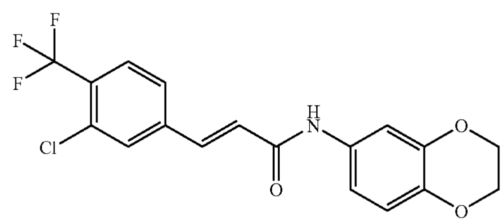 | 226-227 | 384 (M + 1) |
| 310 | 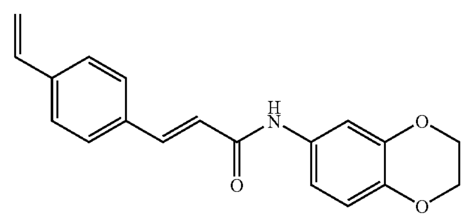 | Amorphous | 308 (M + 1) |
| 311 | 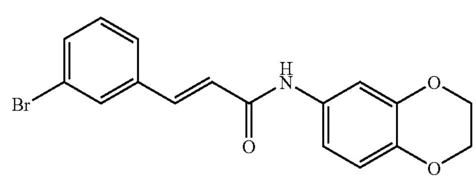 | 150 | 360 (M) |
| 312 | 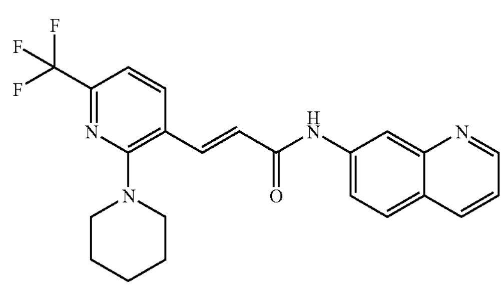 | 211 | 427 (M + 1) |

-continued
| Example number | Structure | Melting Point (° C.) | Mass Spec. (ESI) m/z |
|---|---|---|---|
| 313 | 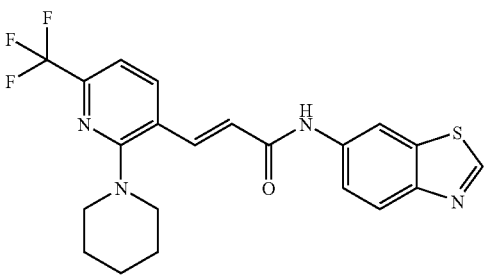 | 78 | 433 (M + 1) |
| 314 | 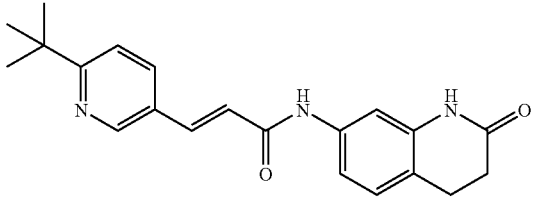 | 286 | 350 (M + 1) |
| 315 | 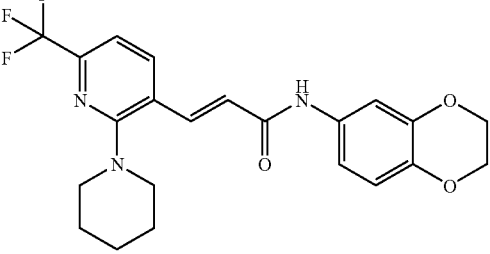 | Amorphous | 434 (M + 1) |
| 316 | 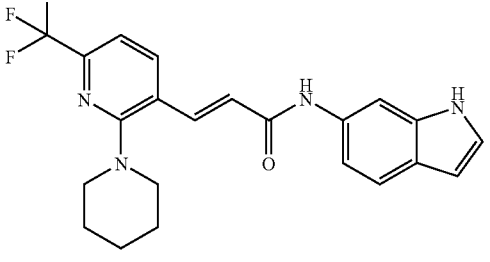 | 226 | 415 (M + 1) |
| 317 | 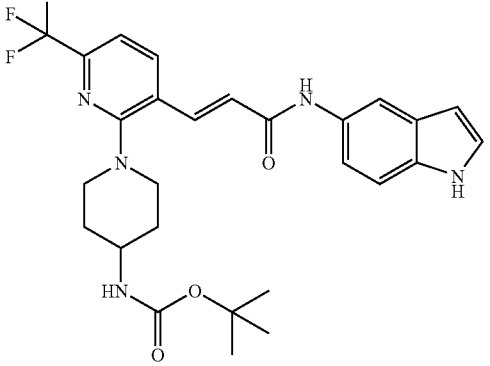 | 219 | 530 (M + 1) |

-continued

| Example number | Structure | Melting Point (° C.) | Mass Spec. (ESI) m/z |
|---|---|---|---|
| 318 | 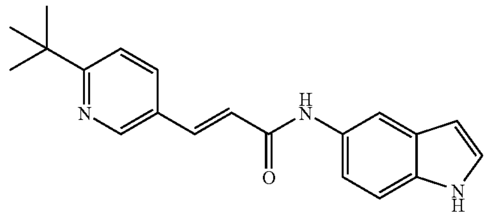 | Amorphous | 320 (M + 1) |
| 319 | 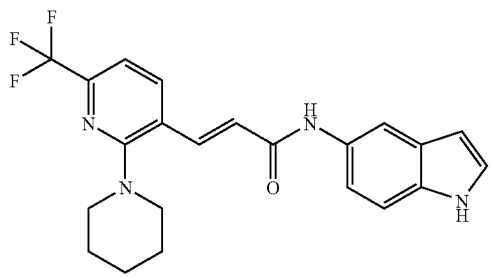 | Amorphous | 415 (M + 1) |
| 320 | 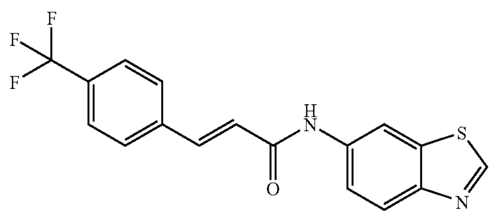 | 211 | 349 (M + 1) |
| 321 | 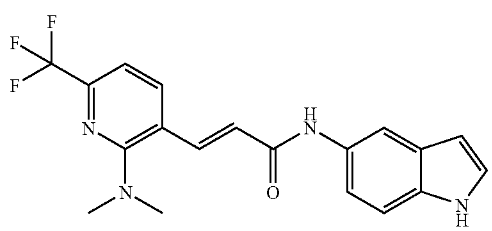 | Amorphous | 375 (M + 1) |
| 322 | 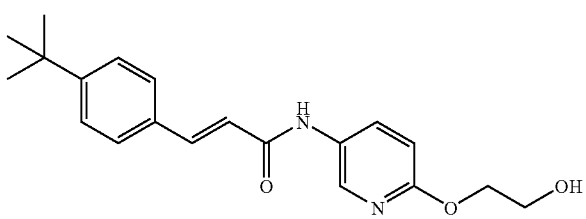 | Amorphous | 341 (M + 1) |
| 323 | 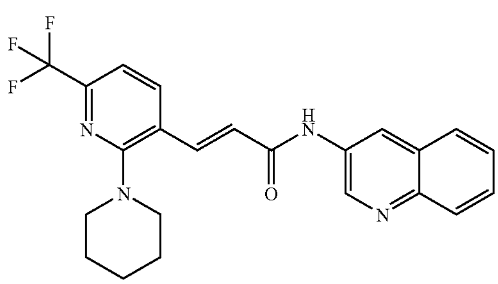 | Amorphous | 427 (M + 1) |

-continued

| Example number | Structure | Melting Point (° C.) | Mass Spec. (ESI) m/z |
|---|---|---|---|
| 324 | 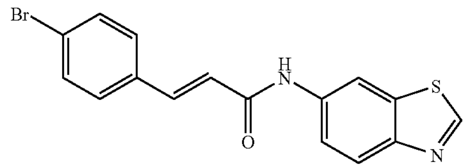 | 225 | 360 (M + 1) |
| 325 | 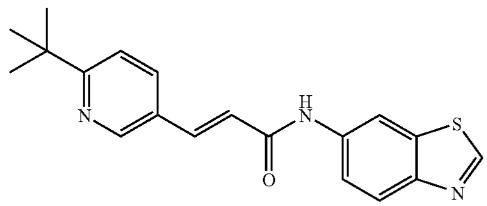 | Amorphous | 338 (M + 1) |
| 326 | 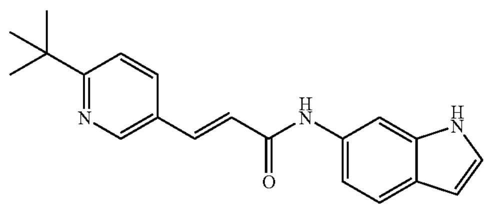 | 275 | 320 (M + 1) |
| 327 | 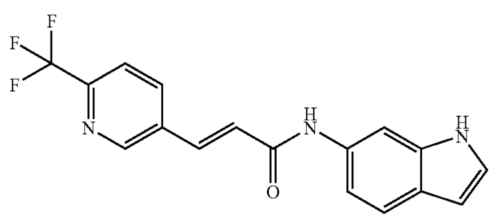 | 282 | 332 (M + 1) |
| 328 | 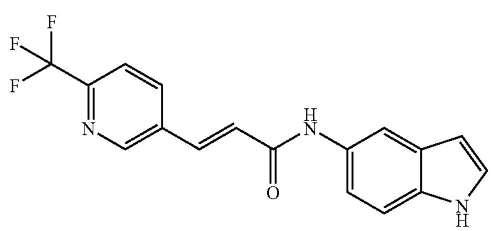 | 209 | 332 (M + 1) |
| 329 | 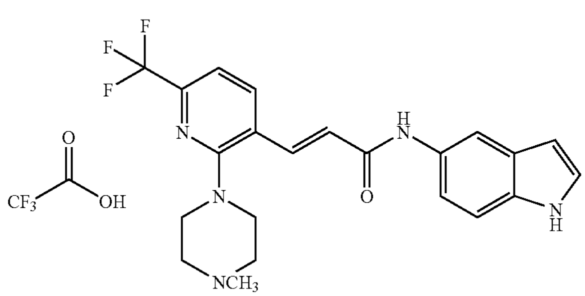 | Amorphous | 430 (M + 1) |

-continued

| Example number | Structure | Melting Point (° C.) | Mass Spec. (ESI) m/z |
|---|---|---|---|
| 330 | 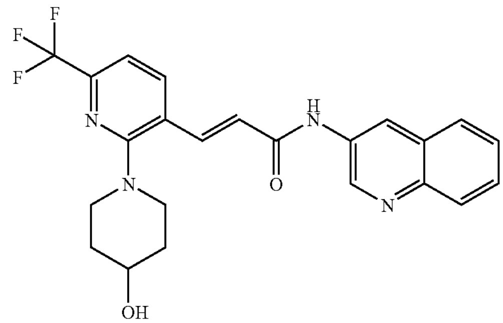 | 197 | 443 (M + 1) |
| 331 | 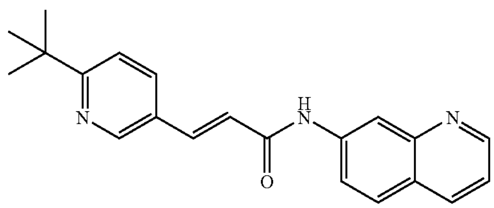 | Amorphous | 332 (M + 1) |
| 332 | 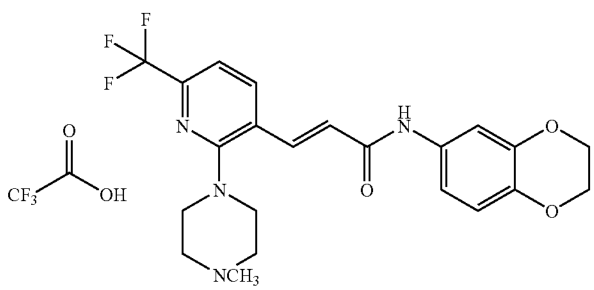 | Amorphous | 448 (M) |
| 333 | 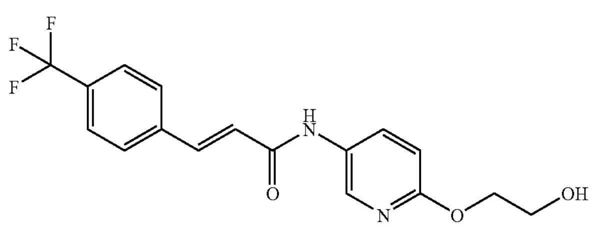 | 202 | 353 (M + 1) |
| 334 | 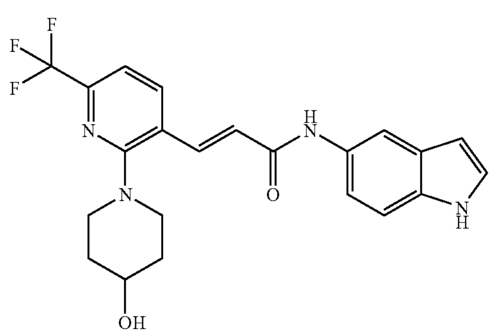 | 229 | 431 (M + 1) |

-continued

| Example number | Structure | Melting Point (° C.) | Mass Spec. (ESI) m/z |
|---|---|---|---|
| 335 | 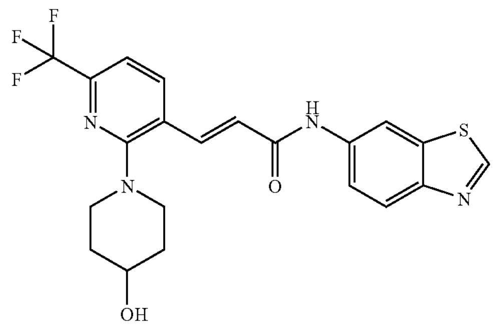 | 97 | 449 (M + 1) |
| 336 | 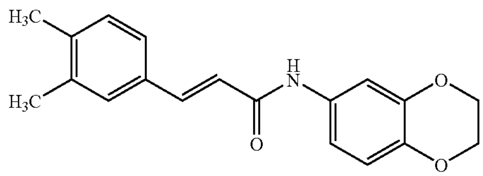 | 121 | 309 (M) |
| 337 | 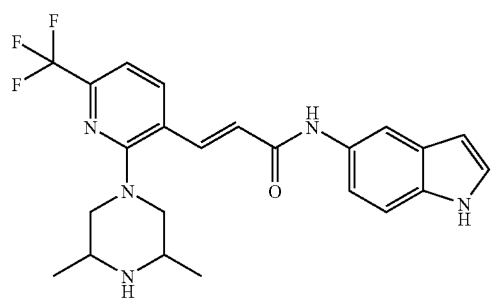 | Amorphous | 444 (M + 1) |
| 338 | 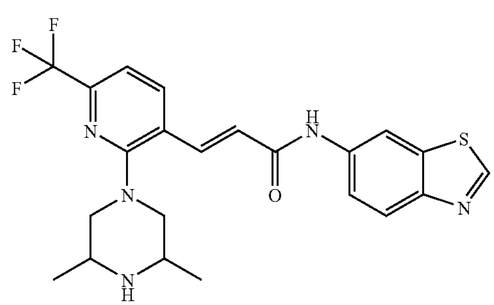 | Amorphous | 462 (M + 1) |
| 339 | 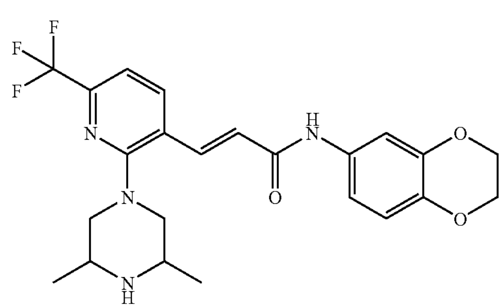 | Amorphous | 463 (M + 1) |

-continued

| Example number | Structure | Melting Point (° C.) | Mass Spec. (ESI) m/z |
|---|---|---|---|
| 340 | 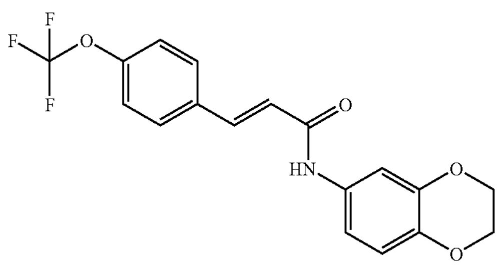 | 163 | 366 (M + 1) |
| 341 | 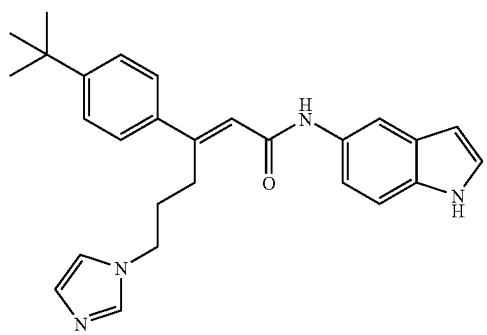 | 237-240 | 427 (M + 1) |
| 342 | 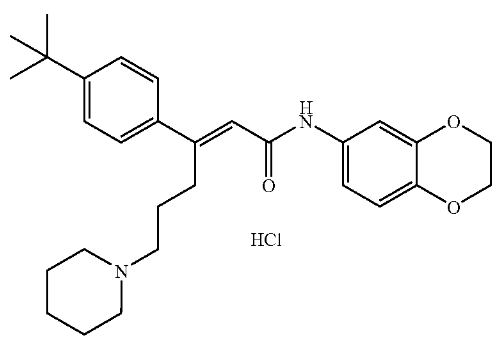 | 276-278 | 463 (M + 1) |
| 343 | 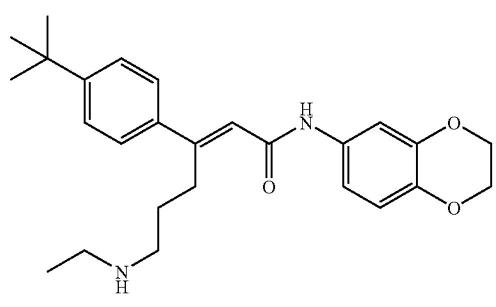 | amorphous | 423 (M + 1) |
| 344 | 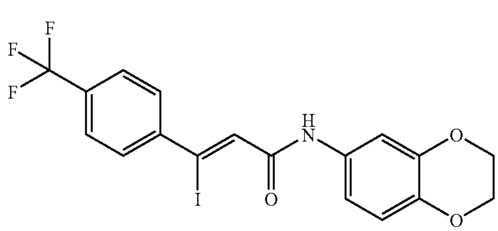 | 202-204 | 476 (M + 1) |

-continued
| Example number | Structure | Melting Point (° C.) | Mass Spec. (ESI) m/z |
|---|---|---|---|
| 345 | 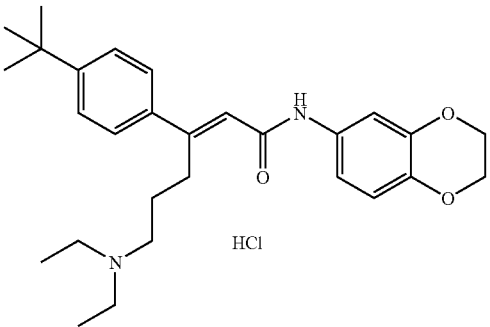 | 214-218 | 451 (M + 1) |
| 346 | 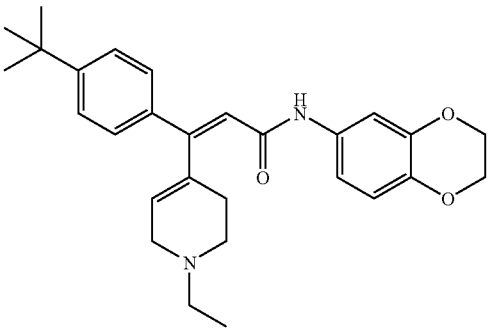 | amorphous | 447 (M + 1) |
| 347 | 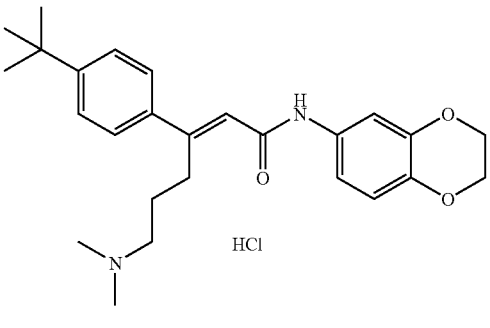 | 201-205 | 423 (M + 1) |
| 348 | 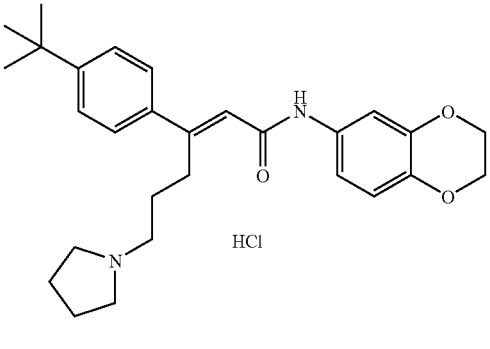 | 263-269 | 449 (M + 1) |

-continued

| Example number | Structure | Melting Point (° C.) | Mass Spec. (ESI) m/z |
|---|---|---|---|
| 349 | 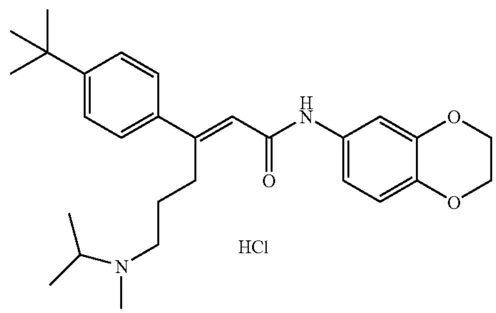 | 273-275 | 451 (M + 1) |
| 350 | 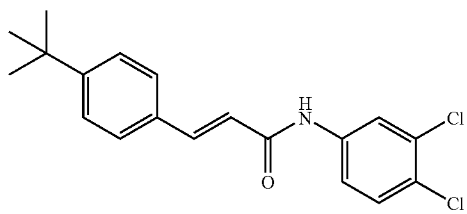 | | 348 (M + 1) |
| 351 | 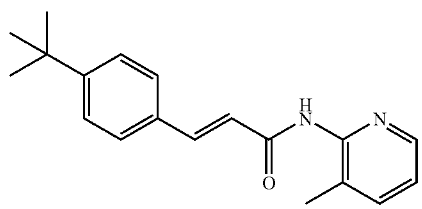 | | 295 (M + 1) |
| 352 | 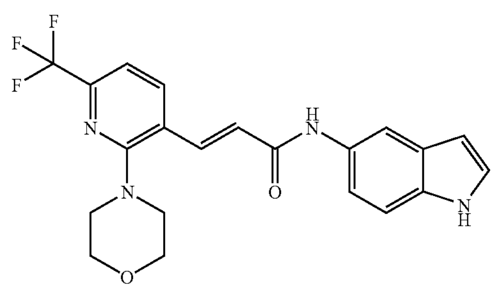 | amorphous | 417 (M + 1) |
| 353 | 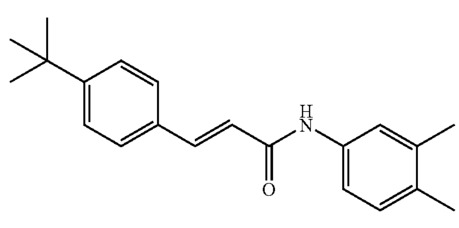 | | 308 (M + 1) |
| 354 | 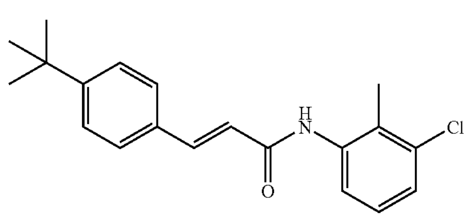 | | 328 (M + 1) |

| Example number | Structure | Melting Point (° C.) | Mass Spec. (ESI) m/z |
|---|---|---|---|
| 355 | 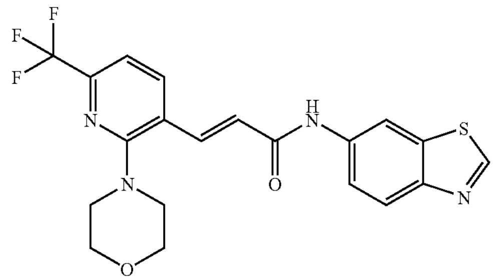 | amorphous | 435 (M + 1) |
| 356 | 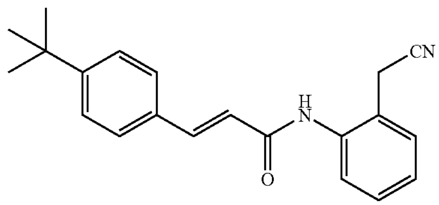 | | 319 (M + 1) |
| 357 | 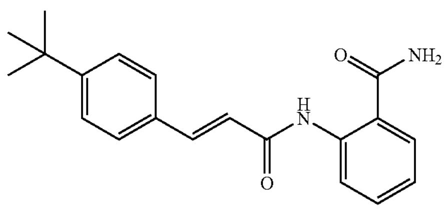 | | 323 (M + 1) |
| 358 | 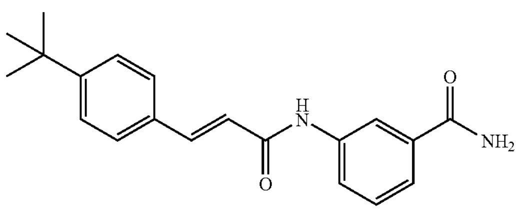 | | 323 (M + 1) |
| 359 | 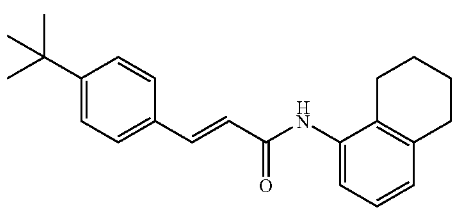 | | 334 (M + 1) |
| 360 | 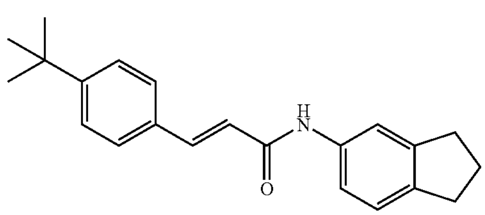 | | 320 (M + 1) |
| 361 | 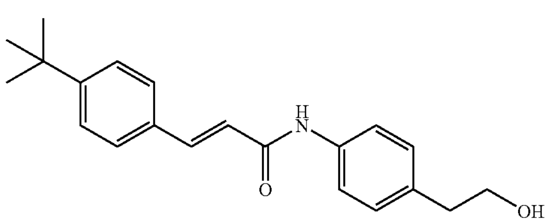 | | 324 (M + 1) |

-continued

| Example number | Structure | Melting Point (° C.) | Mass Spec. (ESI) m/z |
|---|---|---|---|
| 362 | 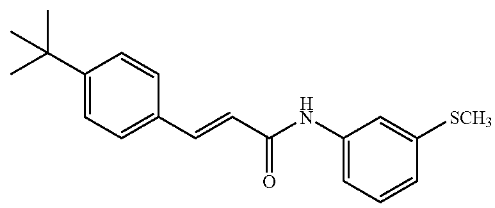 | | 294 (M + 1) |
| 363 | 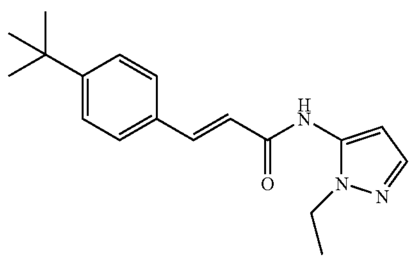 | | 298 (M + 1) |
| 364 | 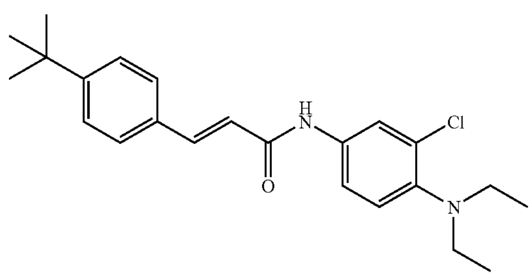 | | 385 (M + 1) |
| 365 | 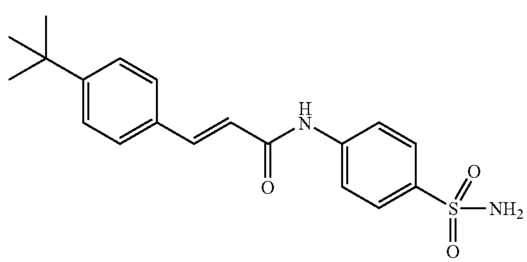 | | 359 (M + 1) |
| 366 | 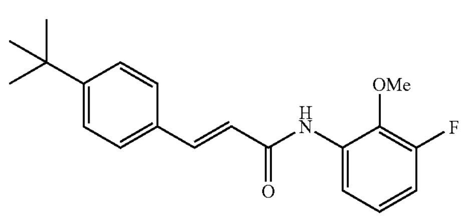 | | 328 (M + 1) |
| 367 | 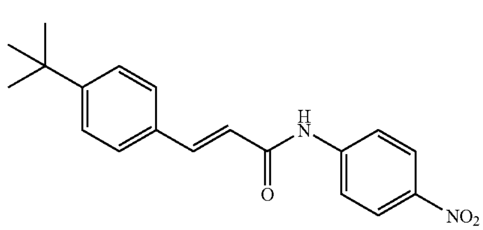 | | 325 (M + 1) |

-continued

| Example number | Structure | Melting Point (° C.) | Mass Spec. (ESI) m/z |
|---|---|---|---|
| 368 | 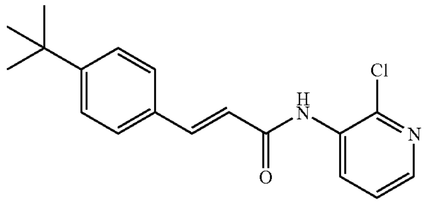 | | 315 (M + 1) |
| 369 | 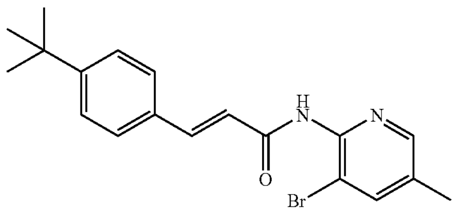 | | 374 (M + 1) |
| 370 | 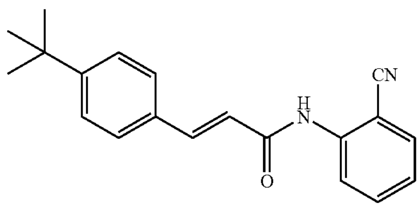 | | 305 (M + 1) |
| 371 | 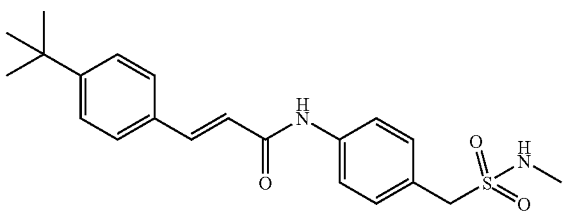 | | 387 (M + 1) |
| 372 | 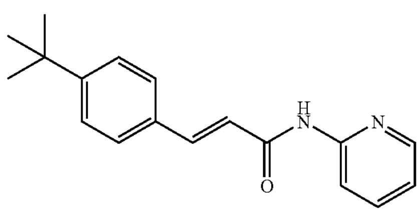 | | 281 (M + 1) |
| 373 | 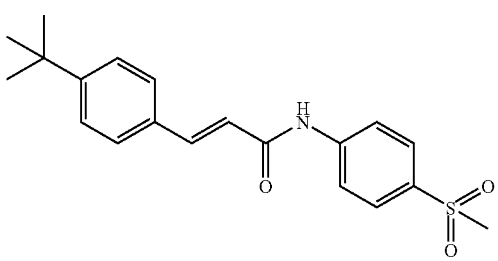 | | 358 (M + 1) |
| 374 | 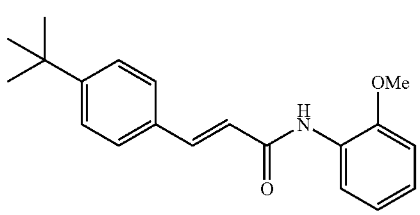 | | 310 (M + 1) |

-continued
| Example number | Structure | Melting Point (° C.) | Mass Spec. (ESI) m/z |
|---|---|---|---|
| 375 | 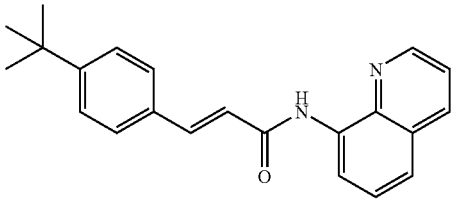 | | 331 (M + 1) |
| 376 | 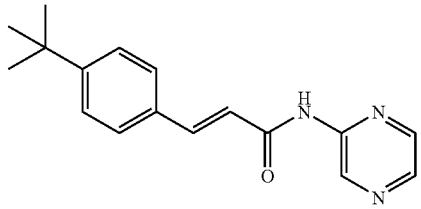 | | 282 (M + 1) |
| 377 | 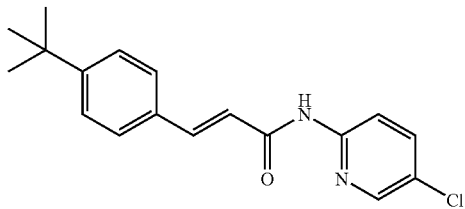 | | 315 (M + 1) |
| 378 | 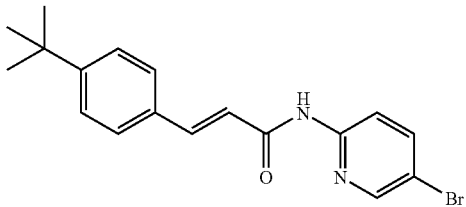 | | 360 (M + 1) |
| 379 | 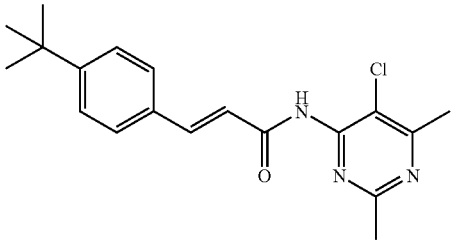 | | 344 (M + 1) |
| 380 | 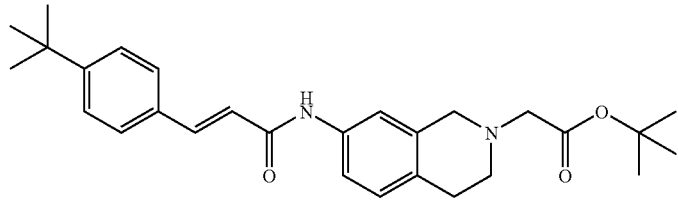 | amorphous | 449 (M + 1) |

-continued

| Example number | Structure | Melting Point (° C.) | Mass Spec. (ESI) m/z |
| --- | --- | --- | --- |
| 381 | 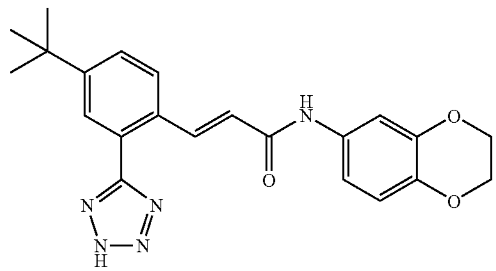 | amorphous | 401 (M + 1) |
| 382 | 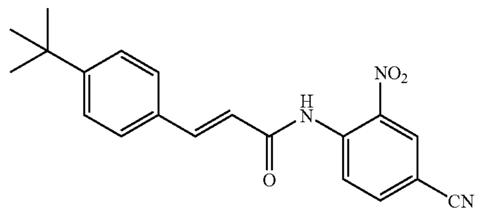 | | 350 (M + 1) |
| 383 | 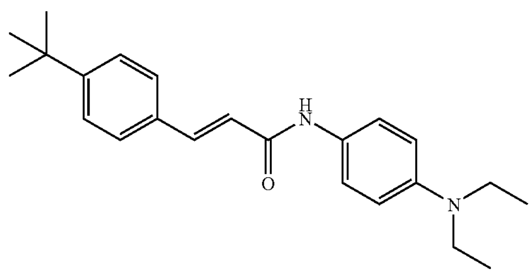 | | 351 (M + 1) |
| 384 | 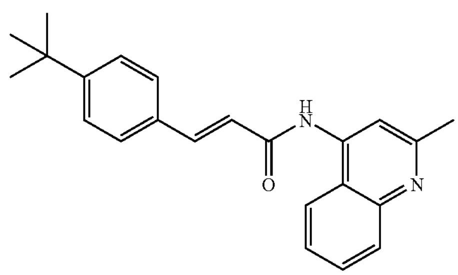 | | 345 (M + 1) |
| 385 | 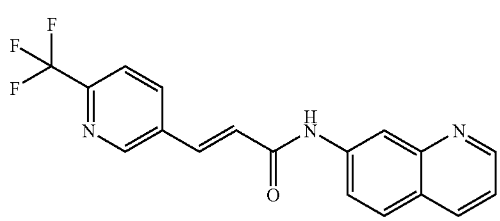 | | 344 (M + 1) |
| 386 | 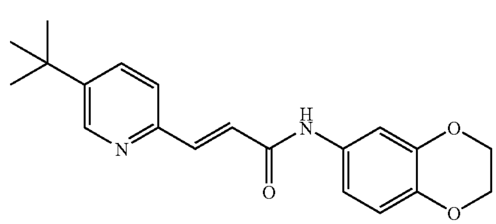 | | 339 (M + 1) |

-continued

| Example number | Structure | Melting Point (° C.) | Mass Spec. (ESI) m/z |
|---|---|---|---|
| 387 | 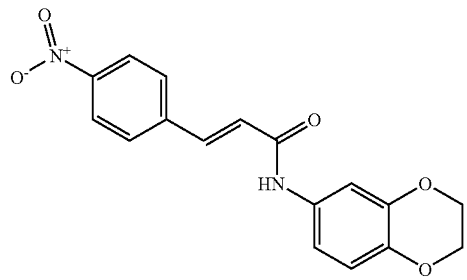 | 247-248 | 327 (M + 1) |
| 388 | 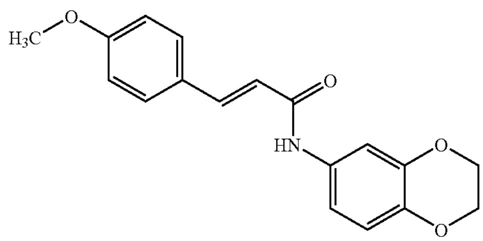 | 179-180 | 312 (M + 1) |
| 389 | 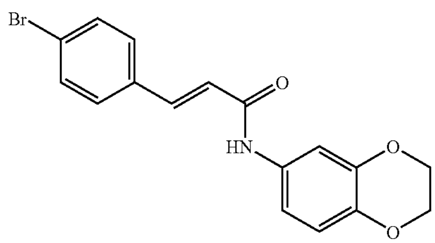 | 179-182 | 360, 362 (M, M + 2) |
| 390 | 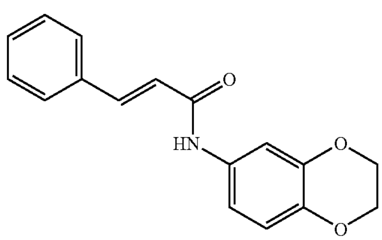 | 182-183 | 282 (M + 1) |
| 391 | 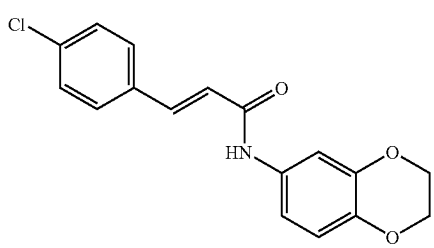 | 187-188 | 316 (M + 1) |
| 392 | 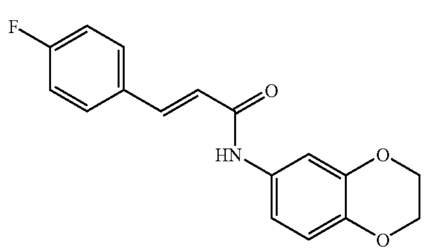 | 195-196 | 300 (M + 1) |

-continued
| Example number | Structure | Melting Point (° C.) | Mass Spec. (ESI) m/z |
|---|---|---|---|
| 393 | 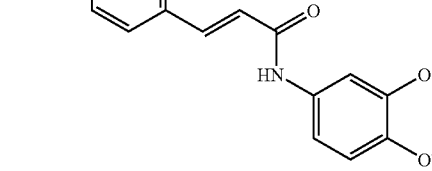 | 201-202 | 350 (M + 1) |
| 394 | 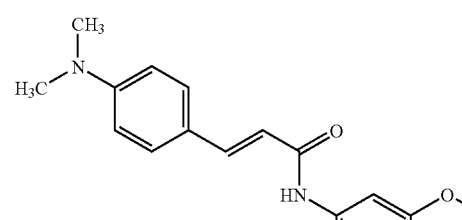 | 214-216 | 325 (M + 1) |
| 395 | 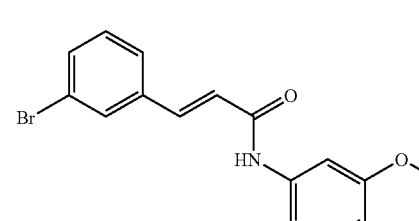 | 150 | 360 (M + 1) |
| 396 | 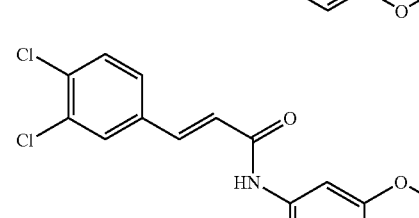 | 184-189 | 350 (M + 1) |
| 397 | 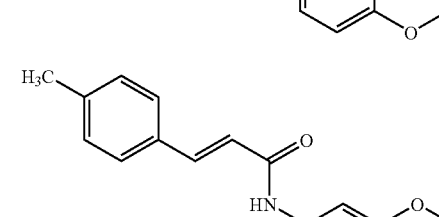 | 173-175 | 296 (M + 1) |
| 398 | 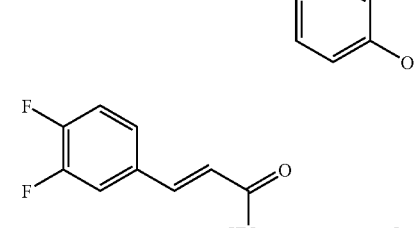 | 160-165 | 318 (M + 1) |

-continued
| Example number | Structure | Melting Point (° C.) | Mass Spec. (ESI) m/z |
|---|---|---|---|
| 399 | 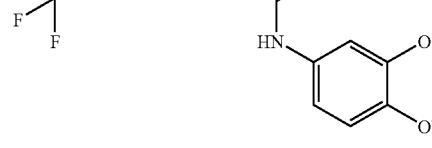 | 200 | 350 (M + 1) |
| 400 | 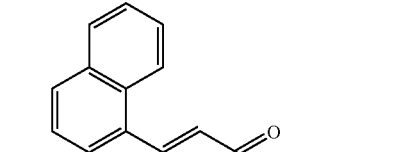 | 203-207 | 332 (M + 1) |
| 401 | 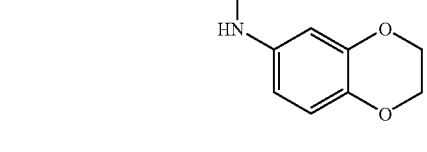 | 155-158 | 326 (M + 1) |
| 402 | 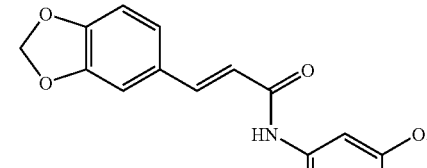 | 181-182 | 318 (M + 1) |
| 403 | 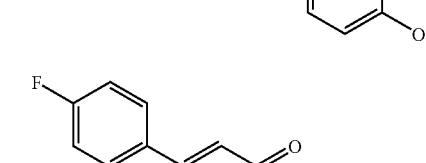 | 196 | 408 (M + 1) |
| 404 | 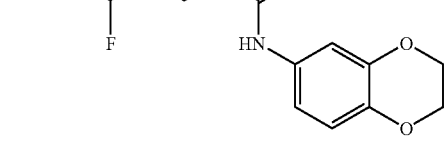 | 185-186 | 332 (M + 1) |

-continued
| Example number | Structure | Melting Point (° C.) | Mass Spec. (ESI) m/z |
|---|---|---|---|
| 405 | 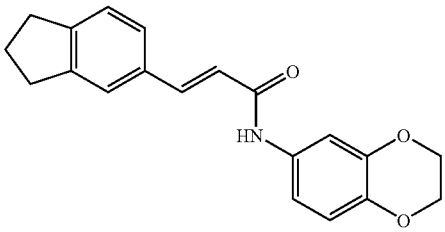 | (oil) | 322 (M + 1) |
| 406 | 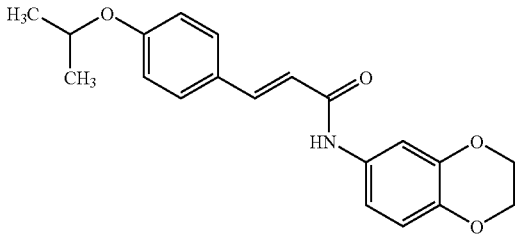 | 188 | 340 (M + 1) |
| 407 | 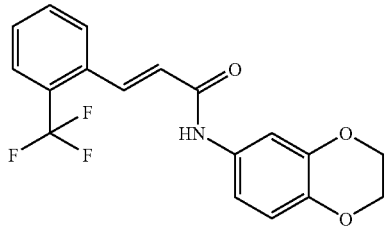 | 176 | 350 (M + 1) |
| 408 | 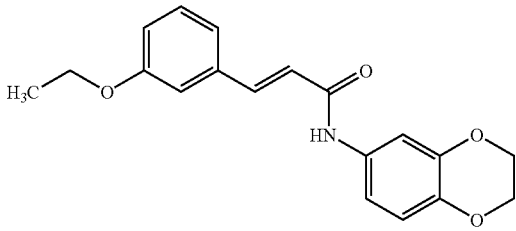 | (oil) | 326 (M + 1) |
| 409 | 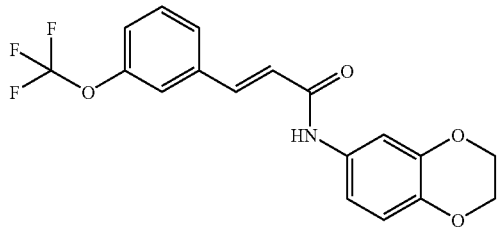 | 129 | 366 (M + 1) |
| 410 | 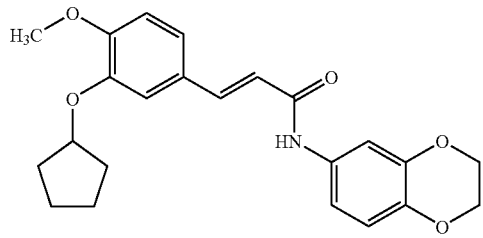 | 202 | 396 (M + 1) |

-continued
| Example number | Structure | Melting Point (° C.) | Mass Spec. (ESI) m/z |
|---|---|---|---|
| 411 | 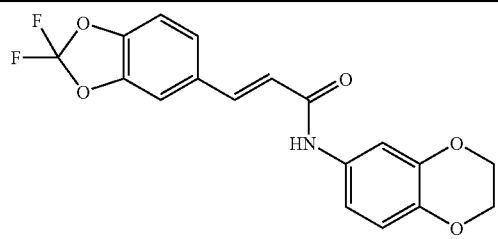 | 191 | 362 (M + 1) |
| 412 | 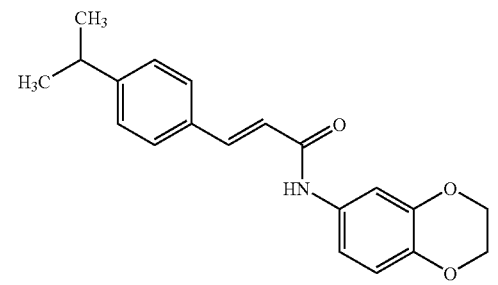 | 165 | 324 (M + 1) |
Table. The following compounds were prepared according to General Schemes I, II or III.
| Example number | Structure | MS (ESI, pos. ion) m/z | Melting Point ° C. |
|---|---|---|---|
| 413 | 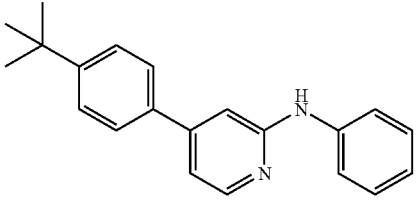 | 303 (M + 1) | 157 |
| 414 | 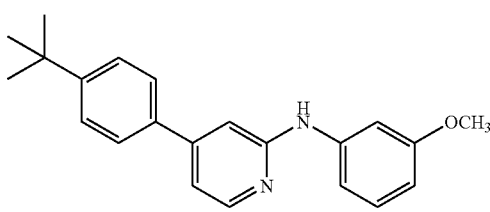 | 333 (M + 1) | amorphous |
| 415 | 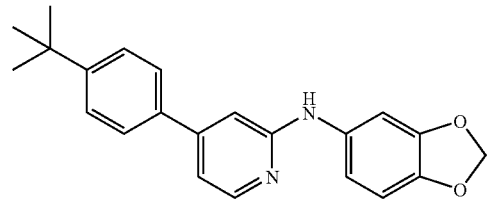 | 347 (M + 1) | 156 |

-continued

| Example number | Structure | MS (ESI, pos. ion) m/z | Melting Point ° C. |
|---|---|---|---|
| 416 | 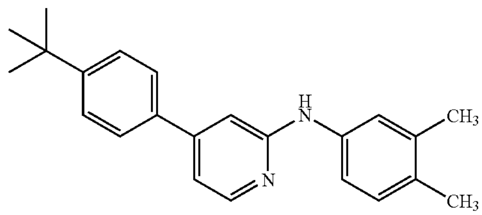 | 331 (M + 1) | 133 |
| 417 | 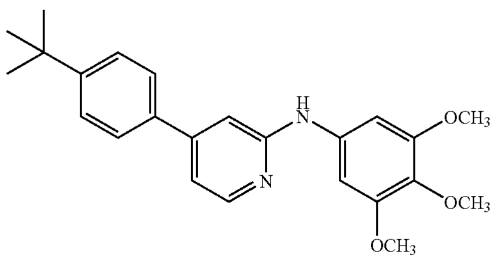 | 393 (M + 1) | amorphous |
| 418 | 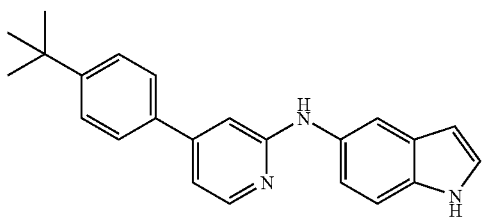 | 342 (M + 1) | 106 |
| 419 | 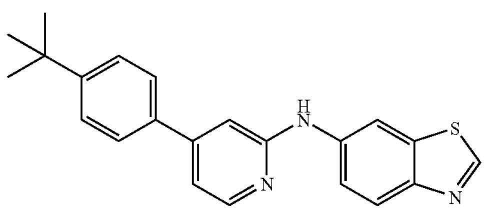 | 360 (M + 1) | 154 |
| 420 | 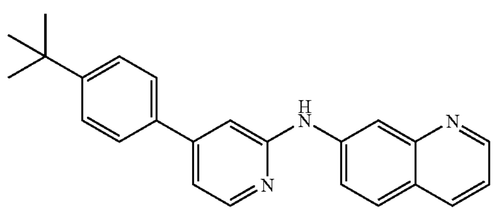 | 354 (M + 1) | 214 |
| 421 | 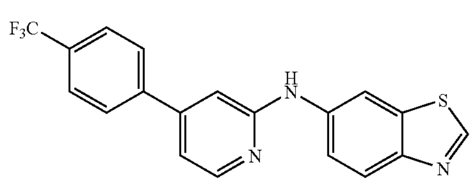 | 372 (M + 1) | 203 |
| 422 | 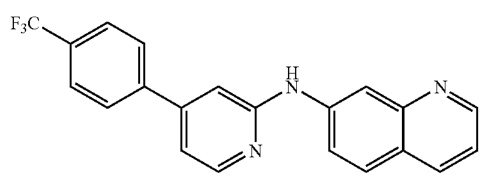 | 366 (M + 1) | 206 |

-continued

| Example number | Structure | MS (ESI, pos. ion) m/z | Melting Point ° C. |
|---|---|---|---|
| 423 | 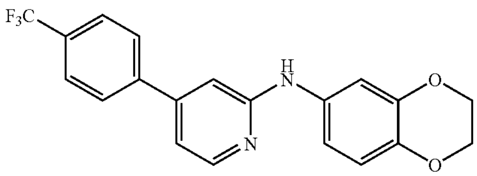 | 373 (M + 1) | 114 |
| 424 | 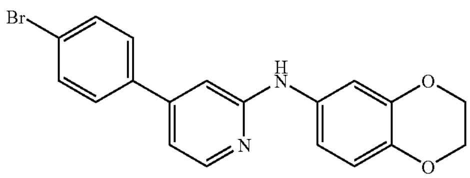 | 383, 385 (M, M + 2) | 124 |

ADDITIONAL EXAMPLES

Following the procedures described above, and applying the procedure in Example 109 to the cinnamides exemplified, or with slight modifications thereof, and following procedures familiar to one of ordinary skill in the art, the following examples may be prepared from commercially available reagents:

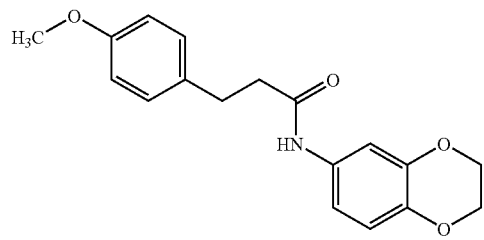

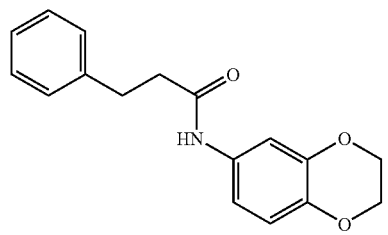

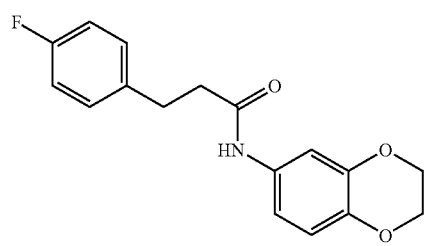

-continued

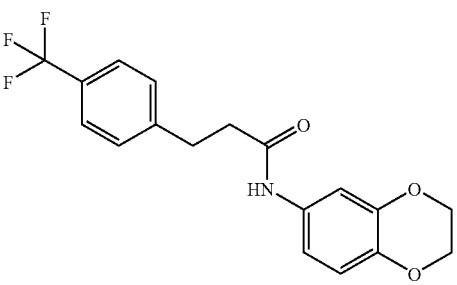

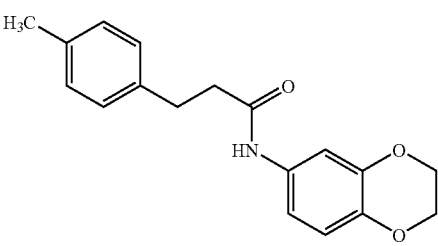

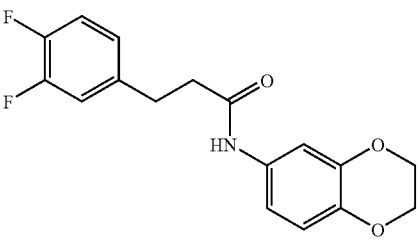

-continued
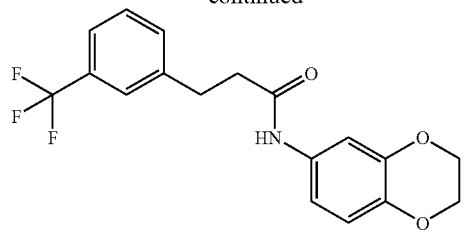
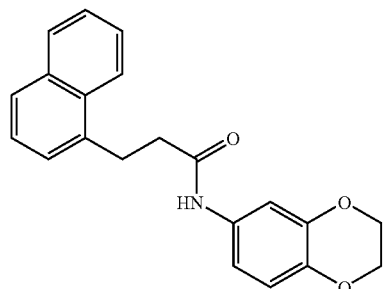
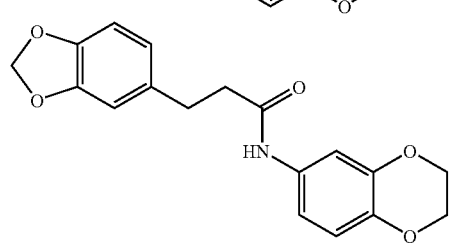
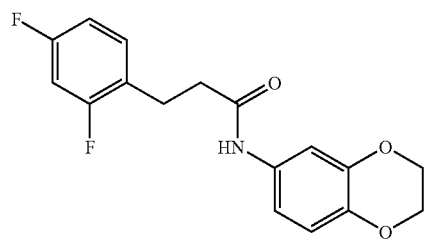
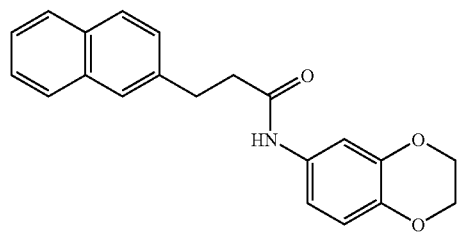
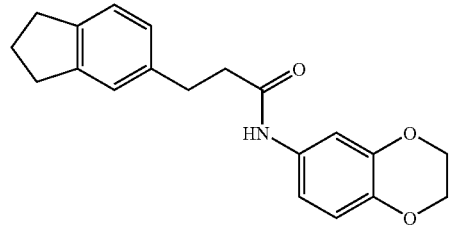
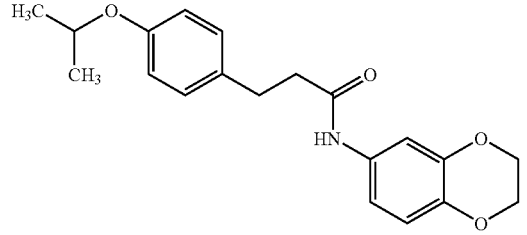
-continued
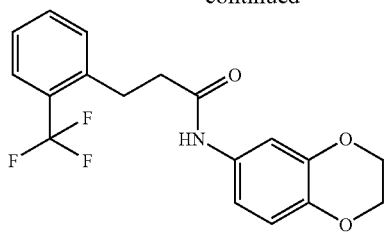
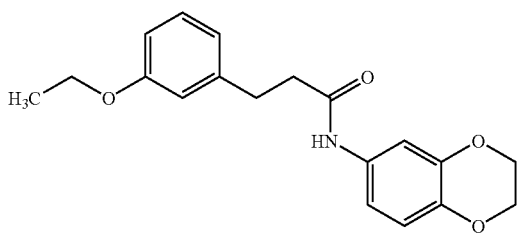
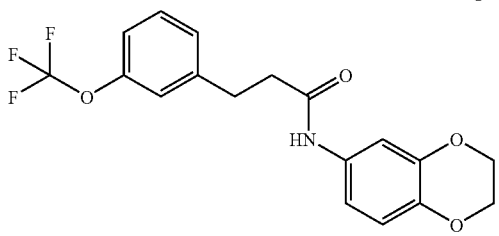
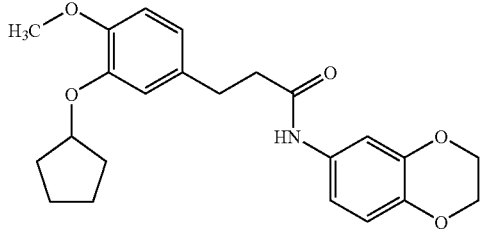
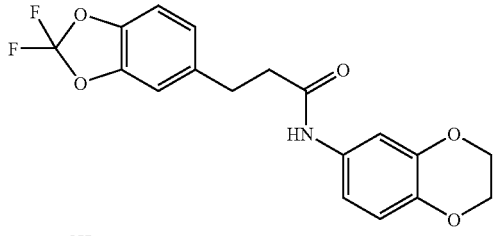
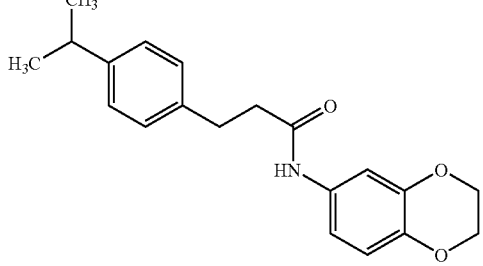
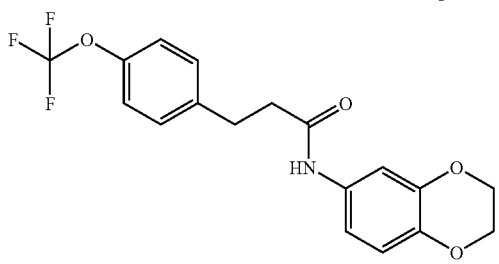

-continued
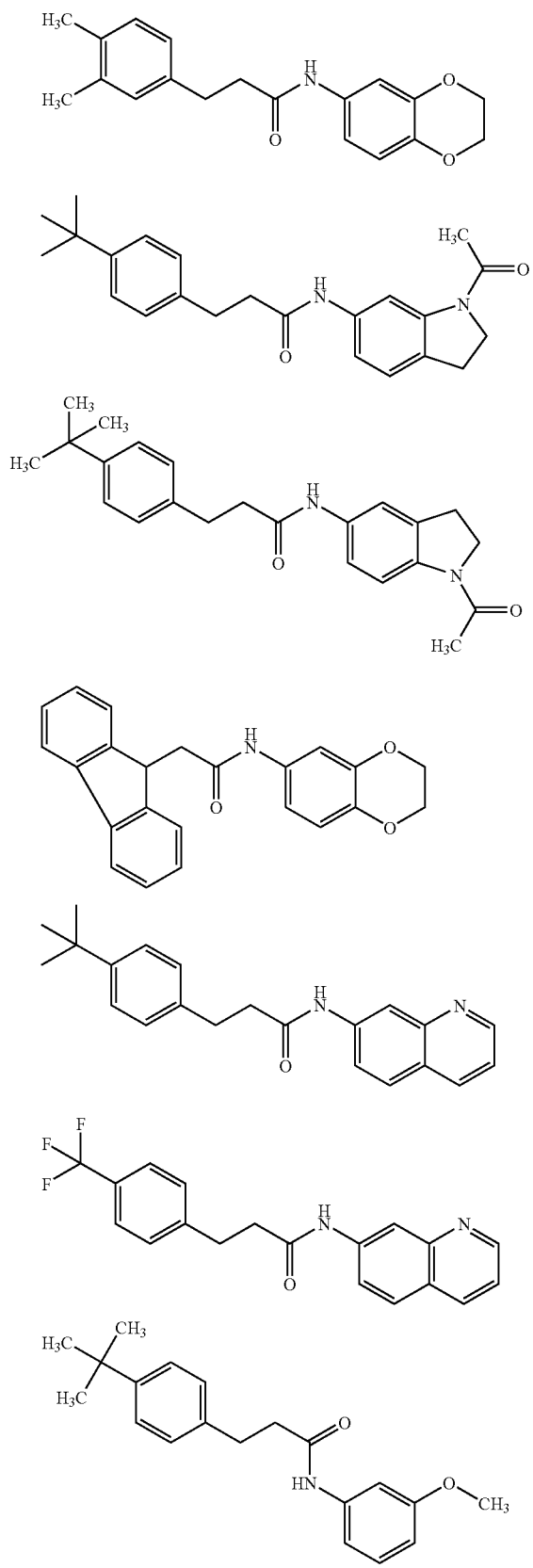
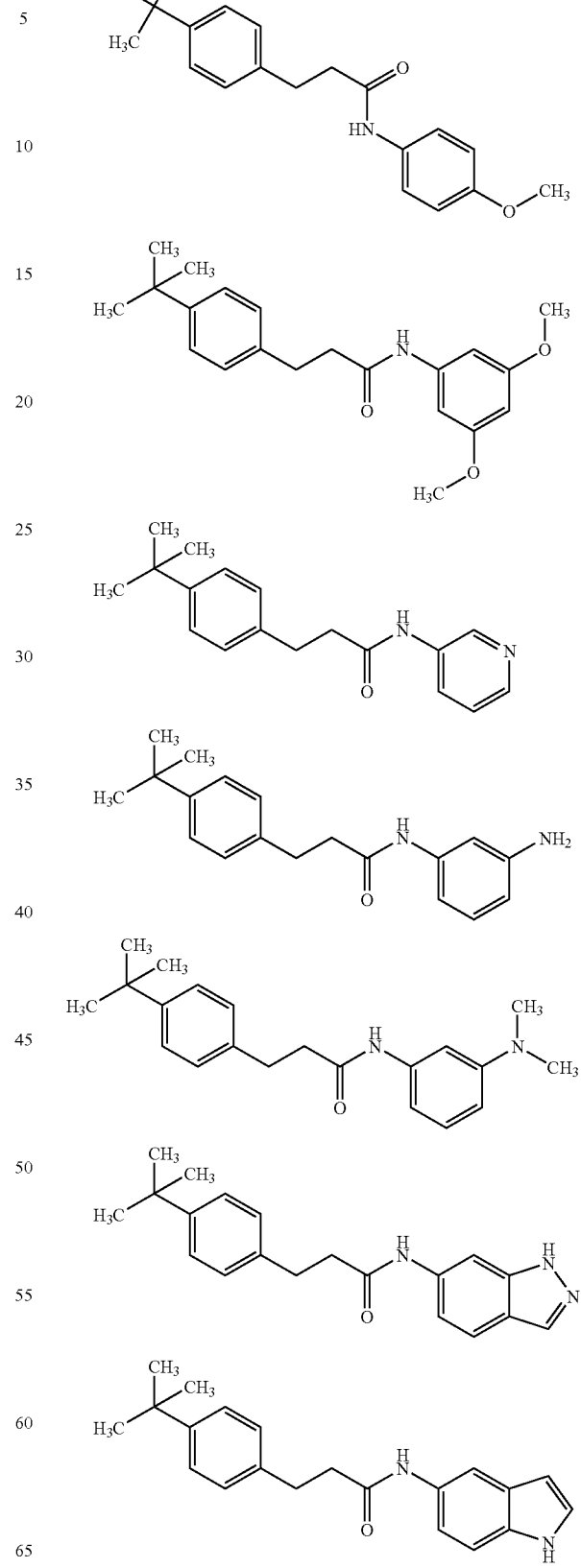

-continued
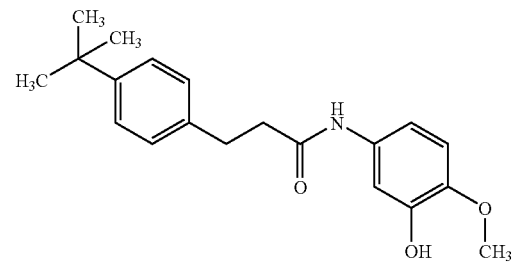
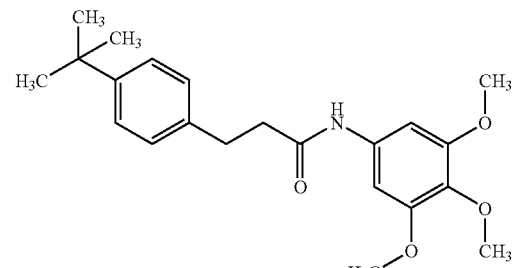
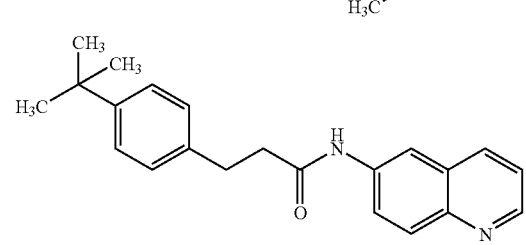
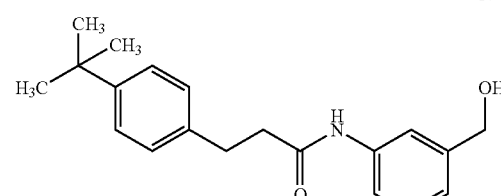
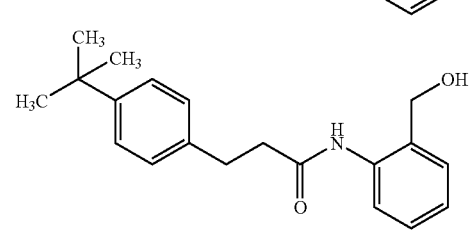
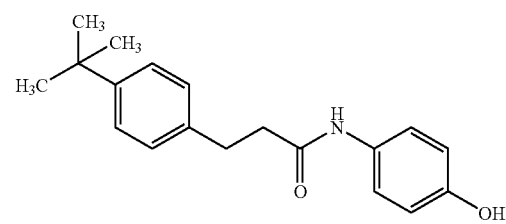
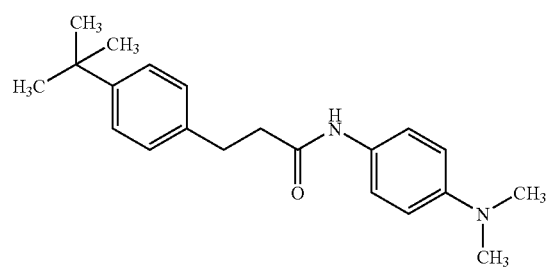
-continued
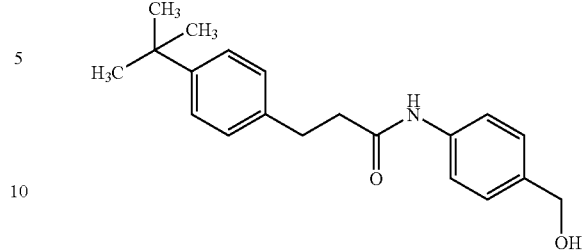
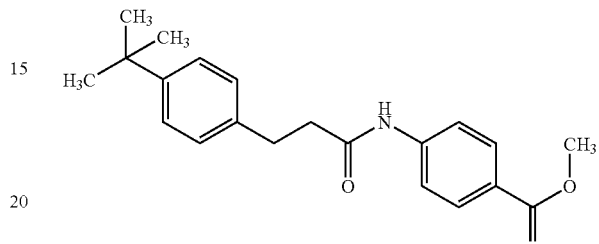
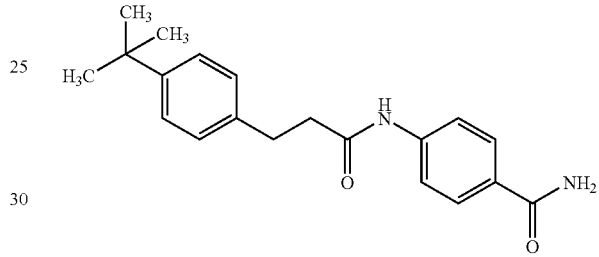
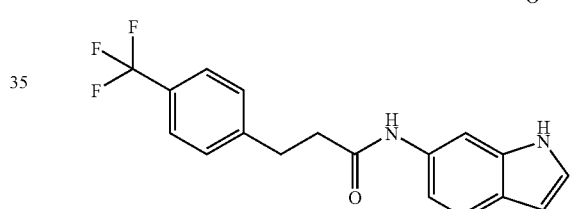
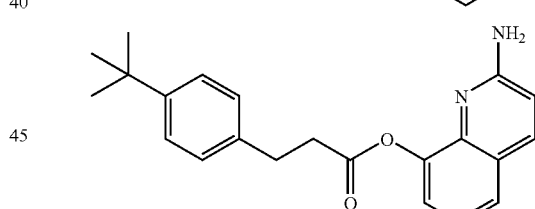
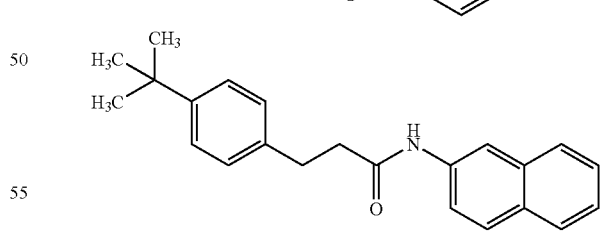
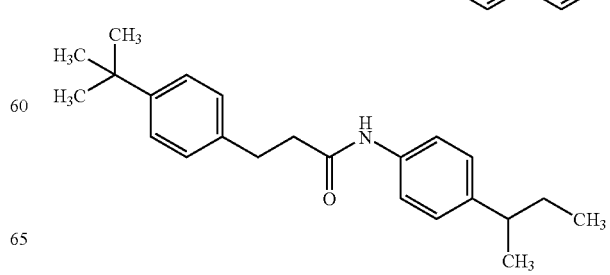

351
-continued
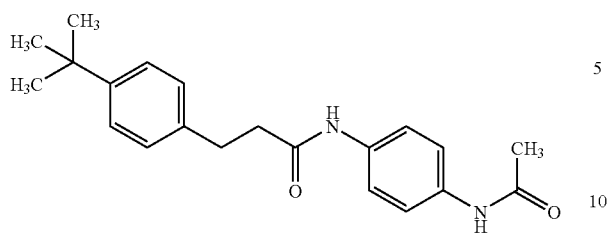
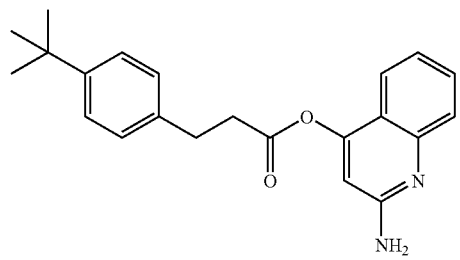
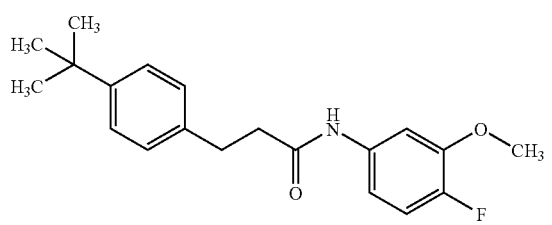
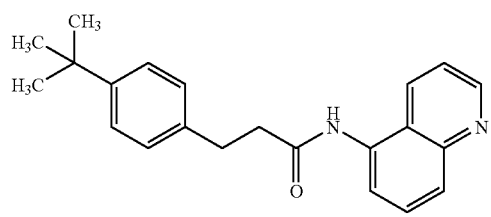
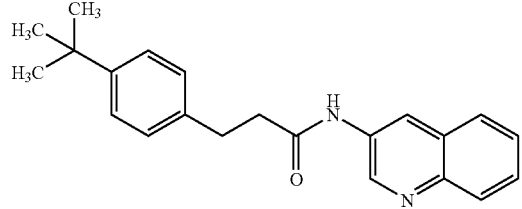
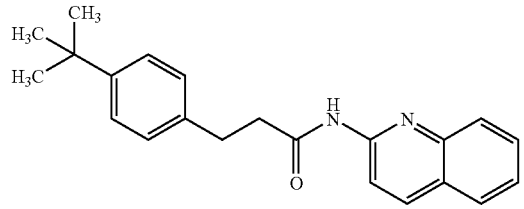
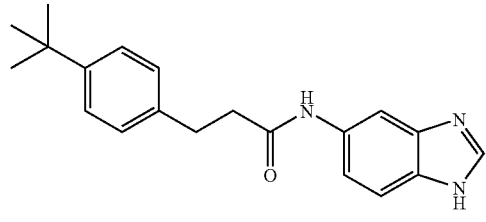
352
-continued
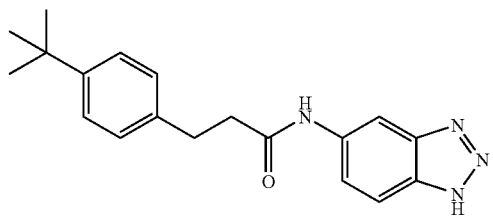
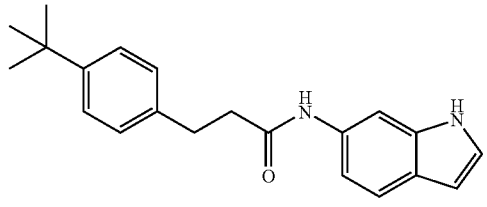
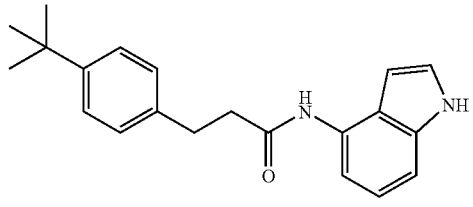
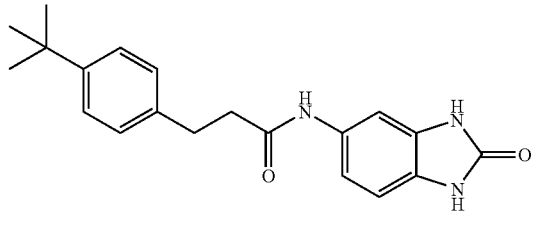
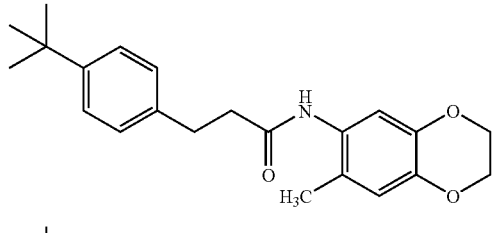
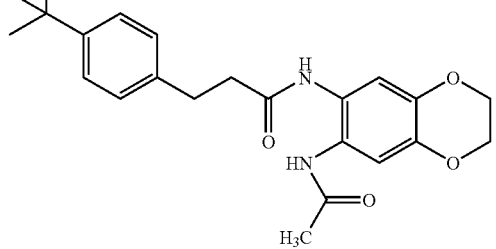
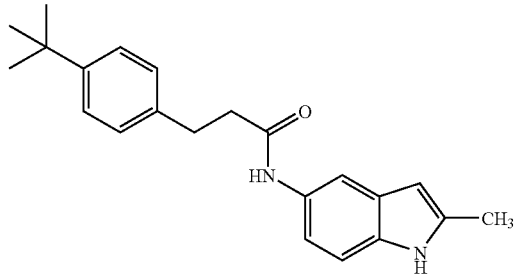

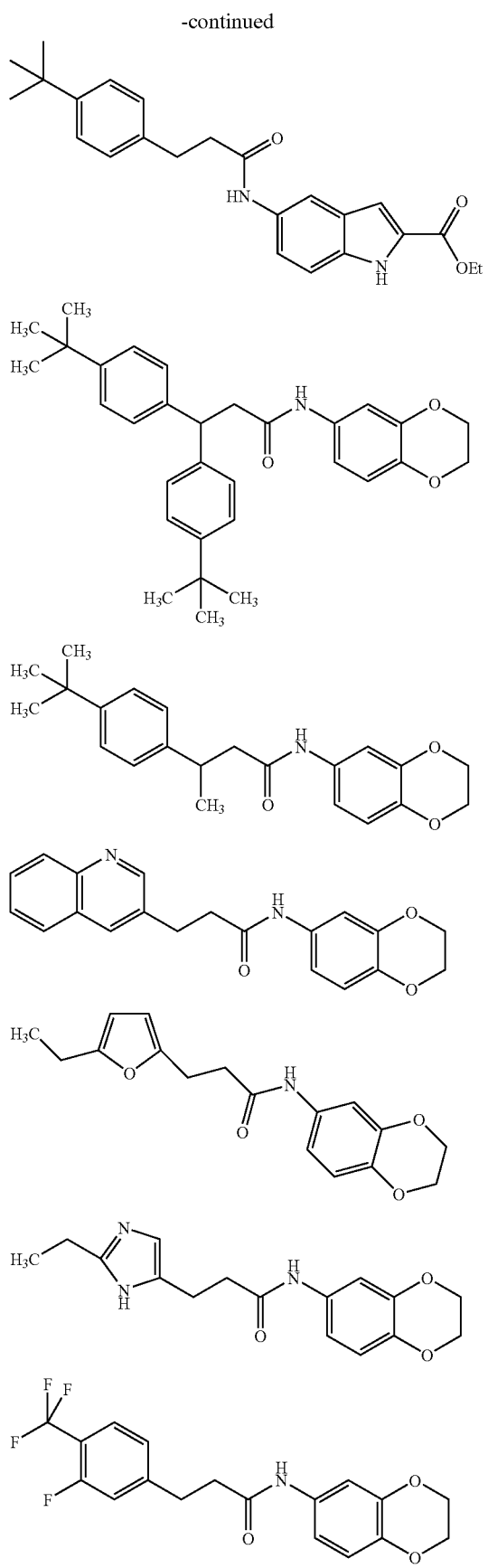
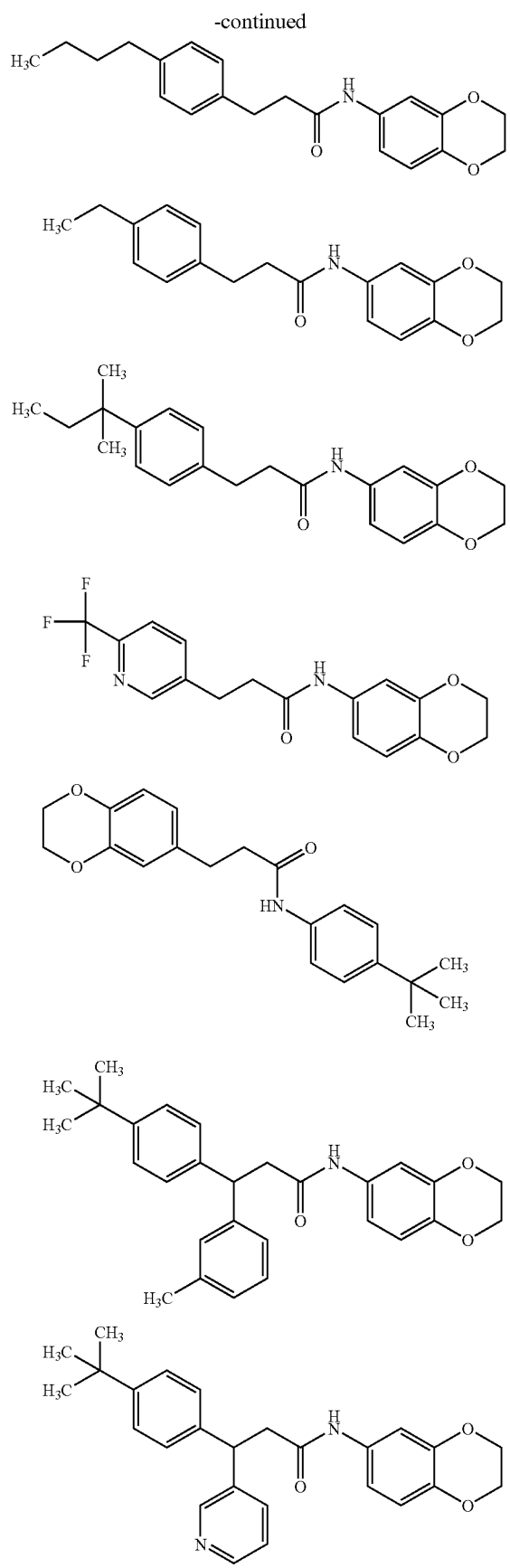

-continued
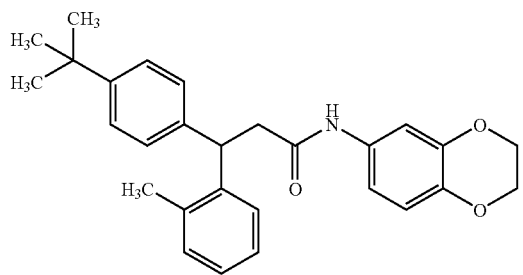
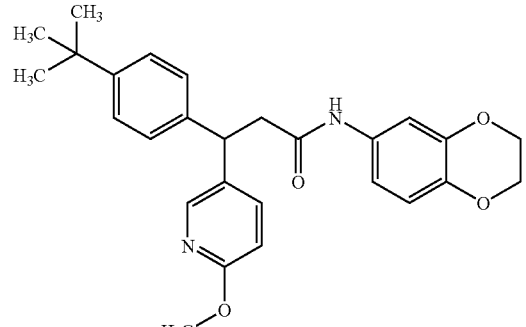
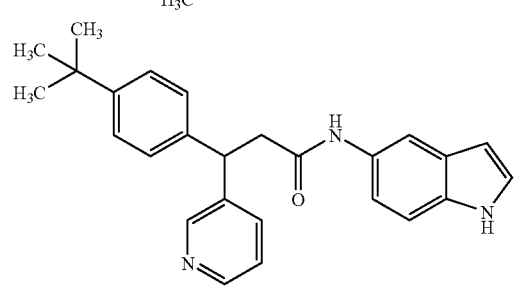
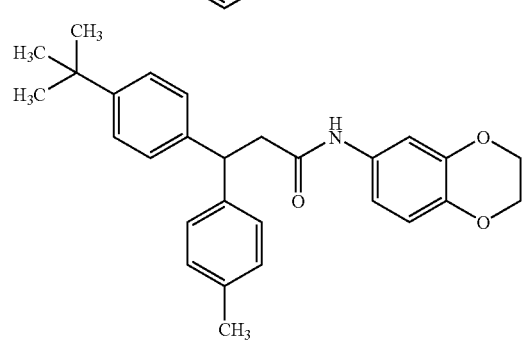
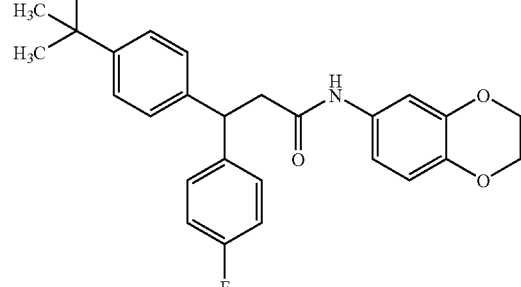
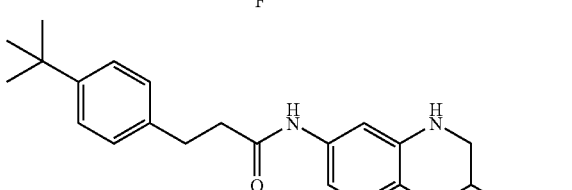
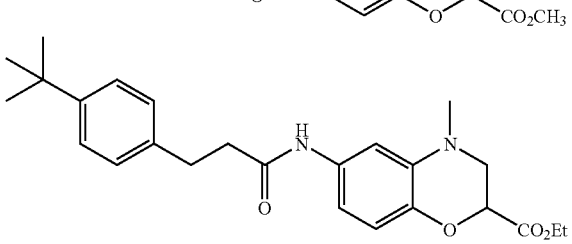

-continued
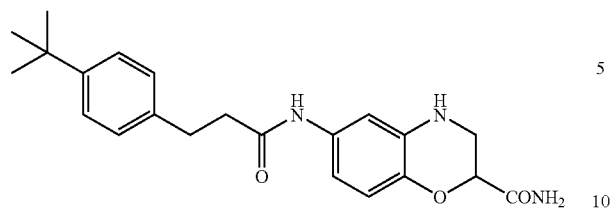
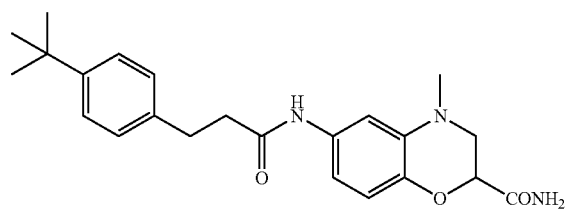
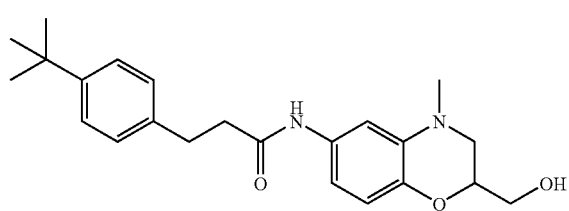
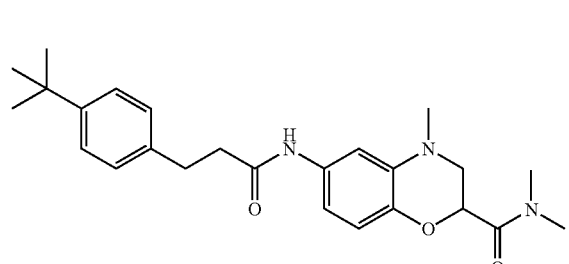
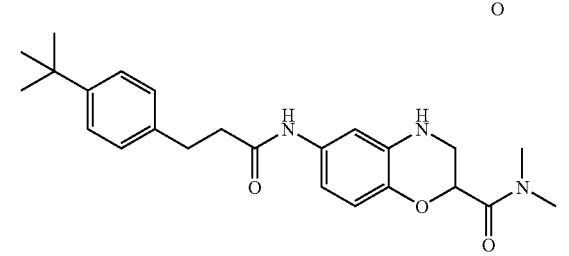
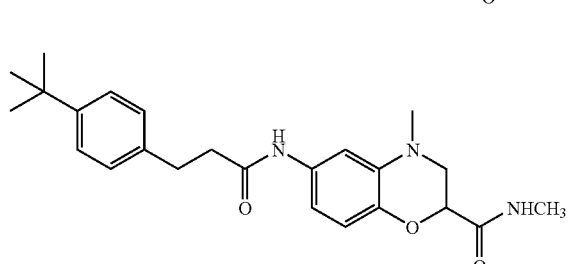
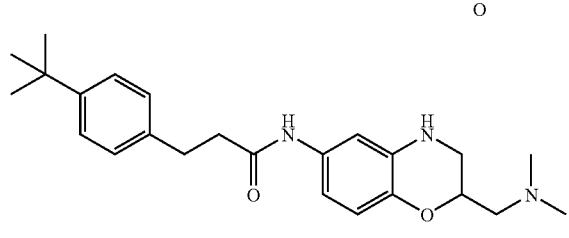
-continued
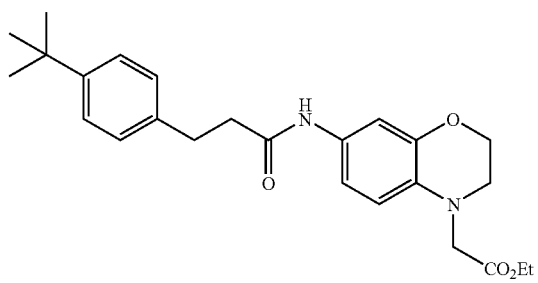
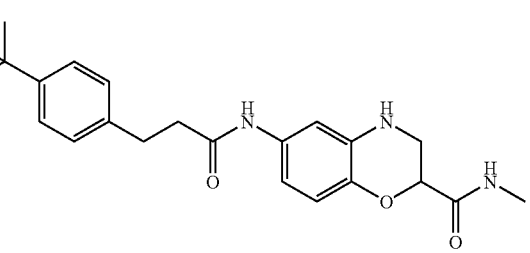
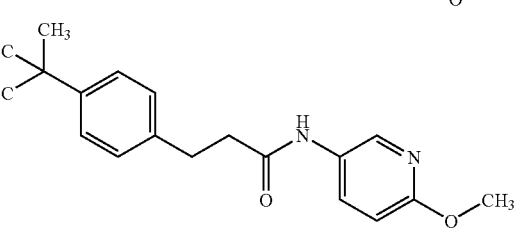
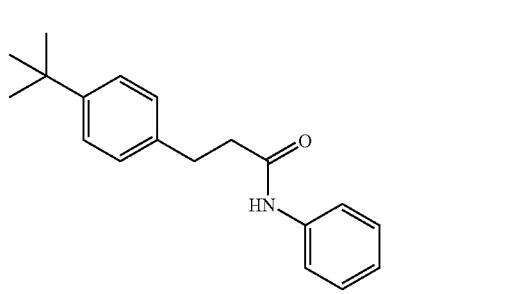
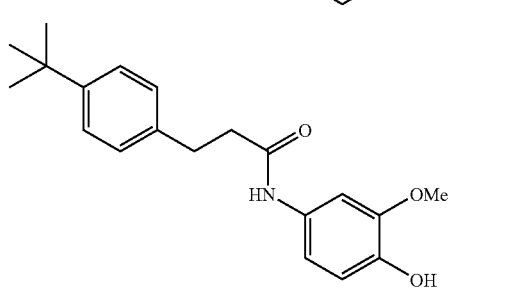
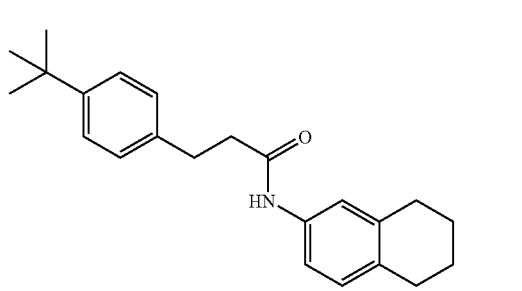

-continued
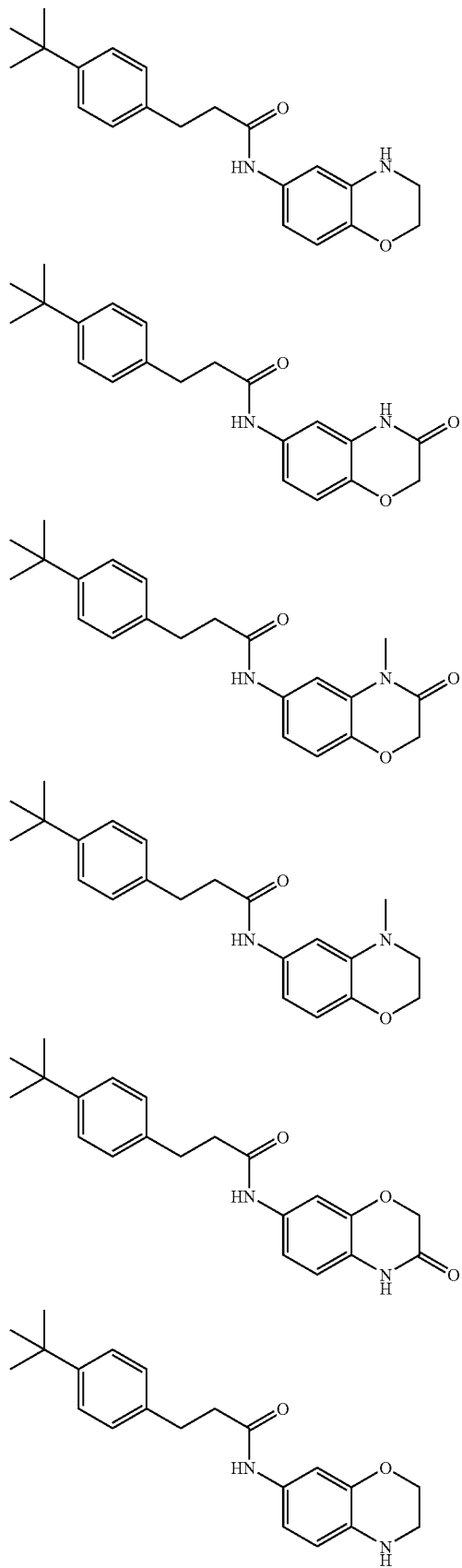
-continued
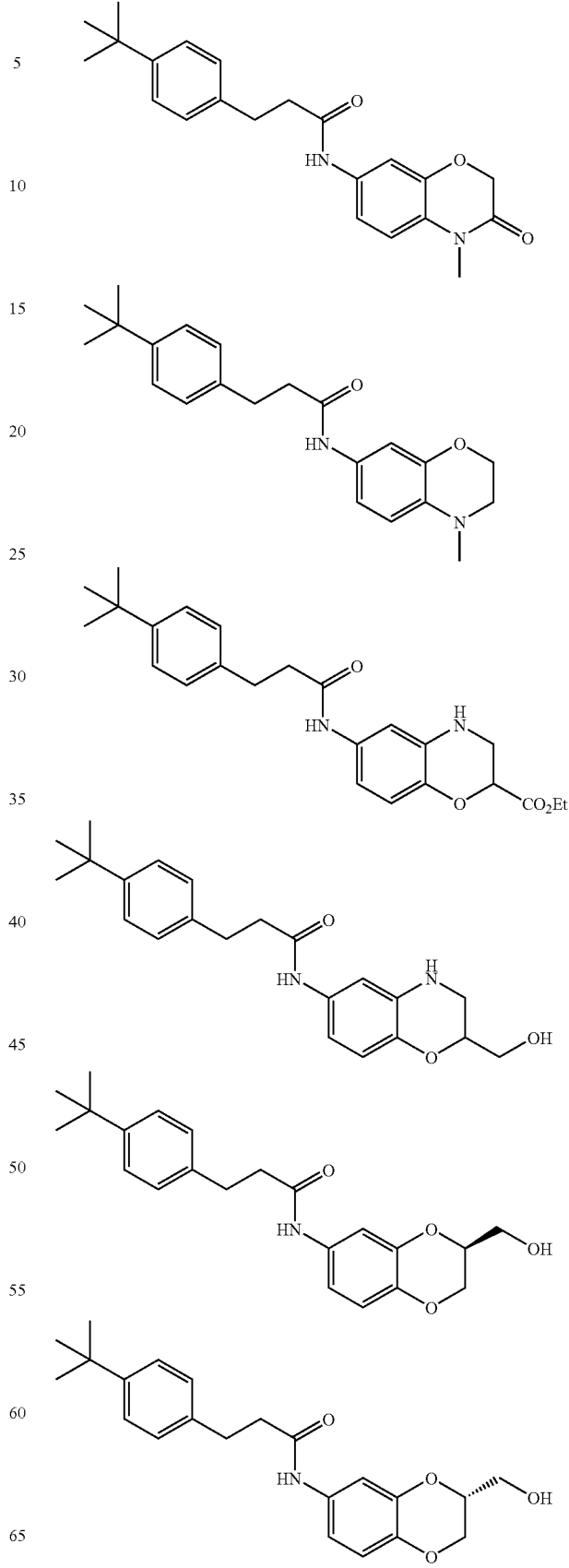

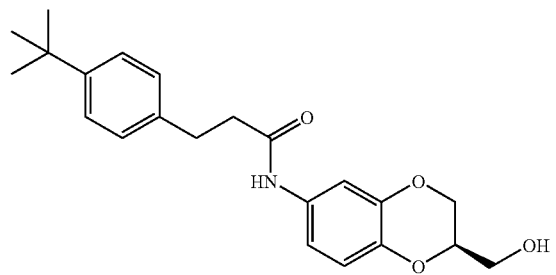
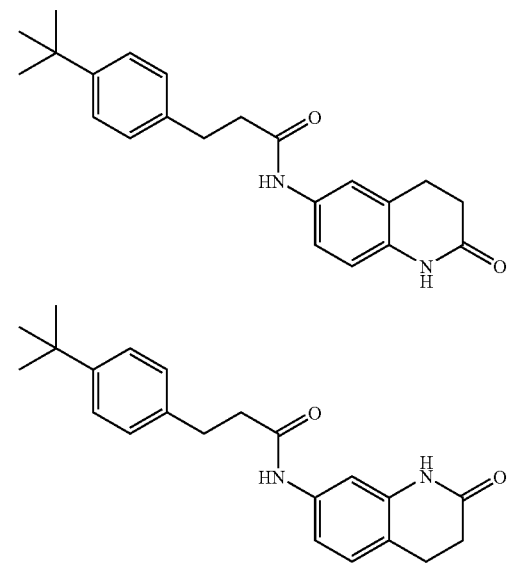
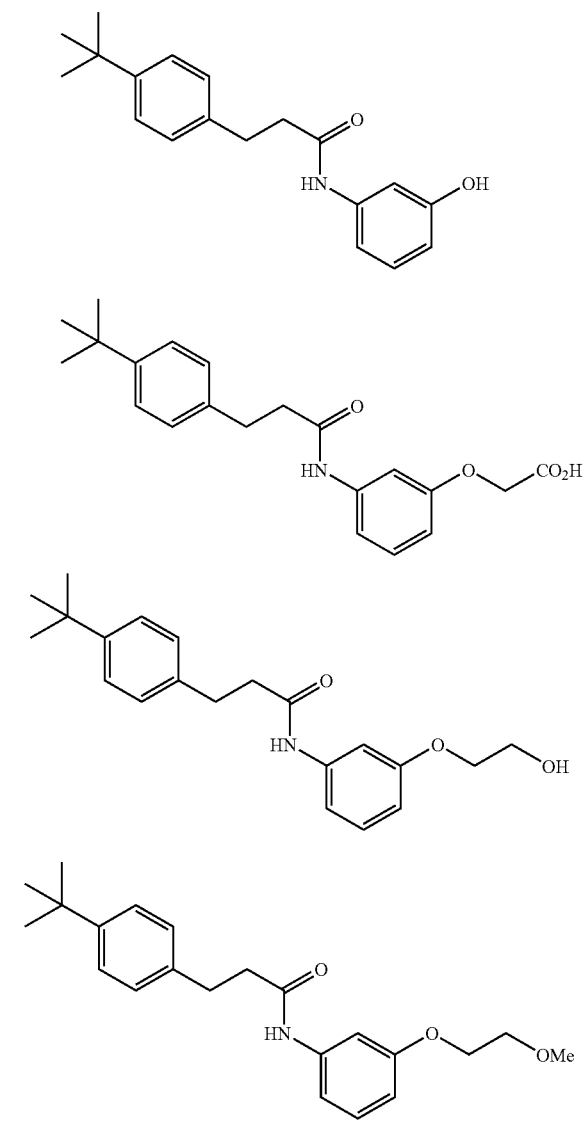

363
-continued
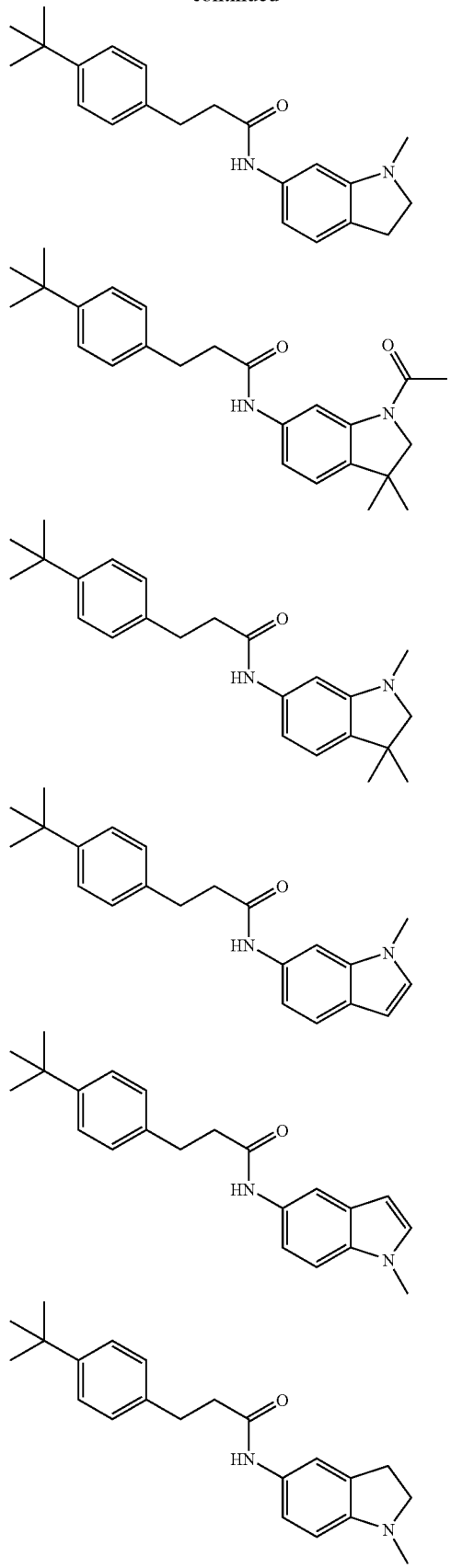
364
-continued
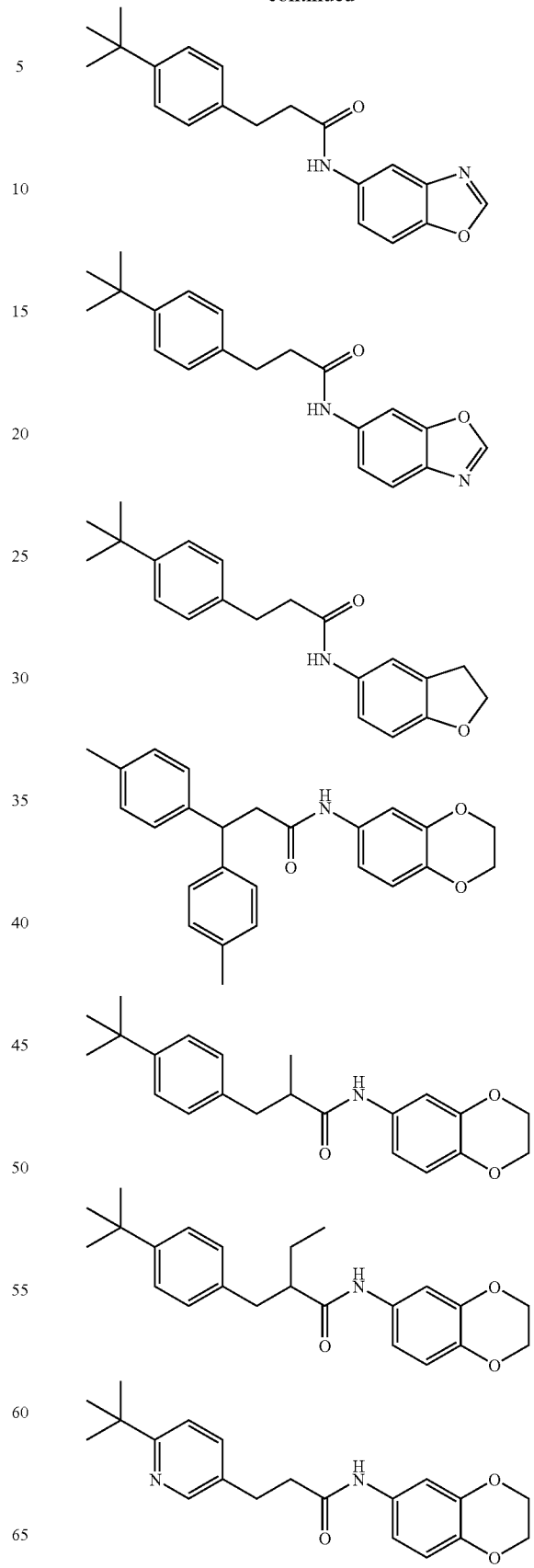

-continued
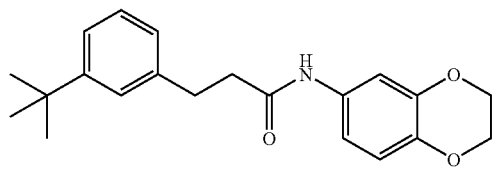
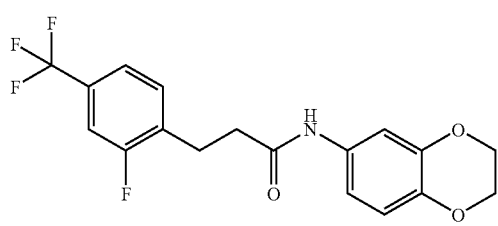
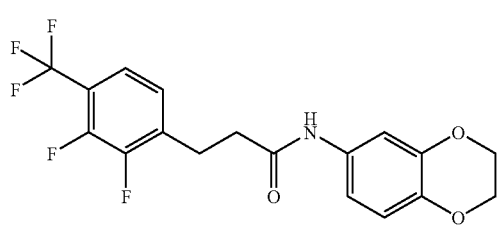
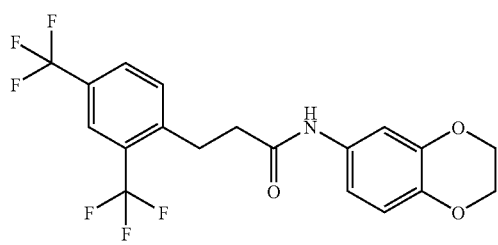
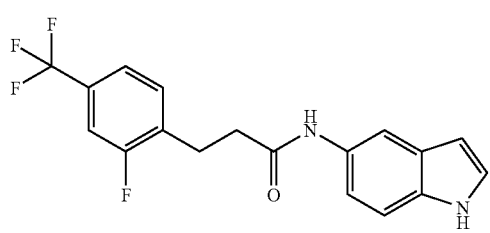
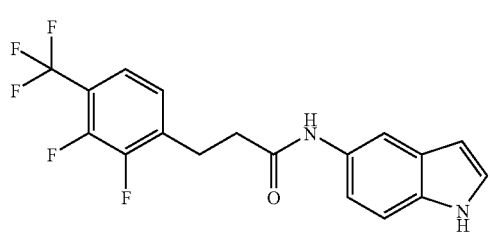
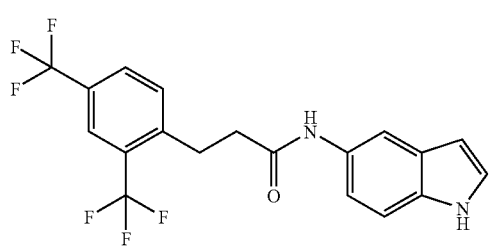
-continued
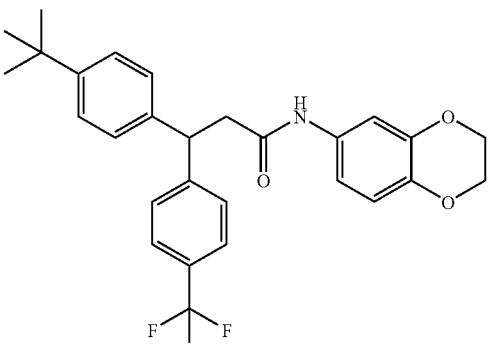
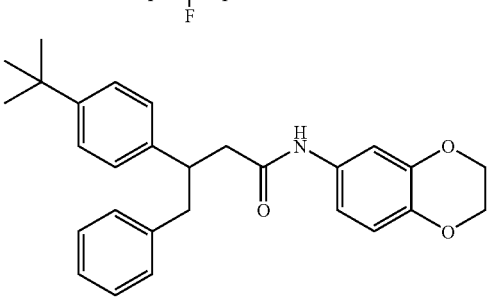
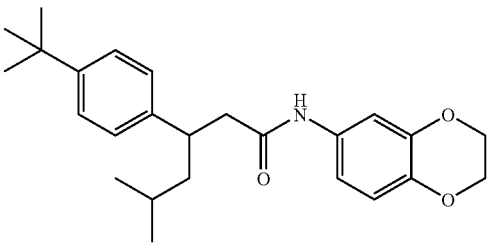
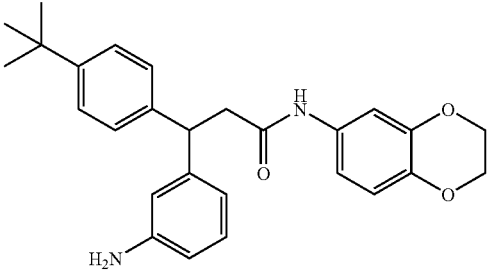
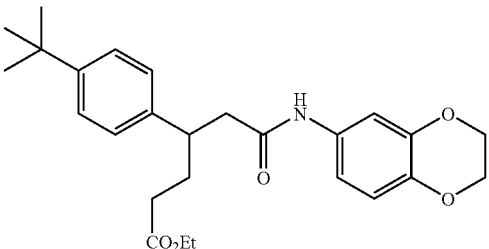
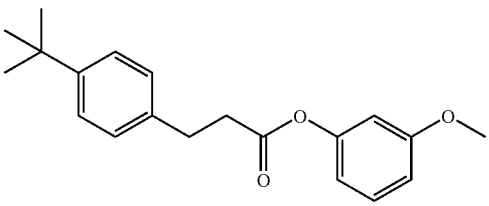

367
-continued
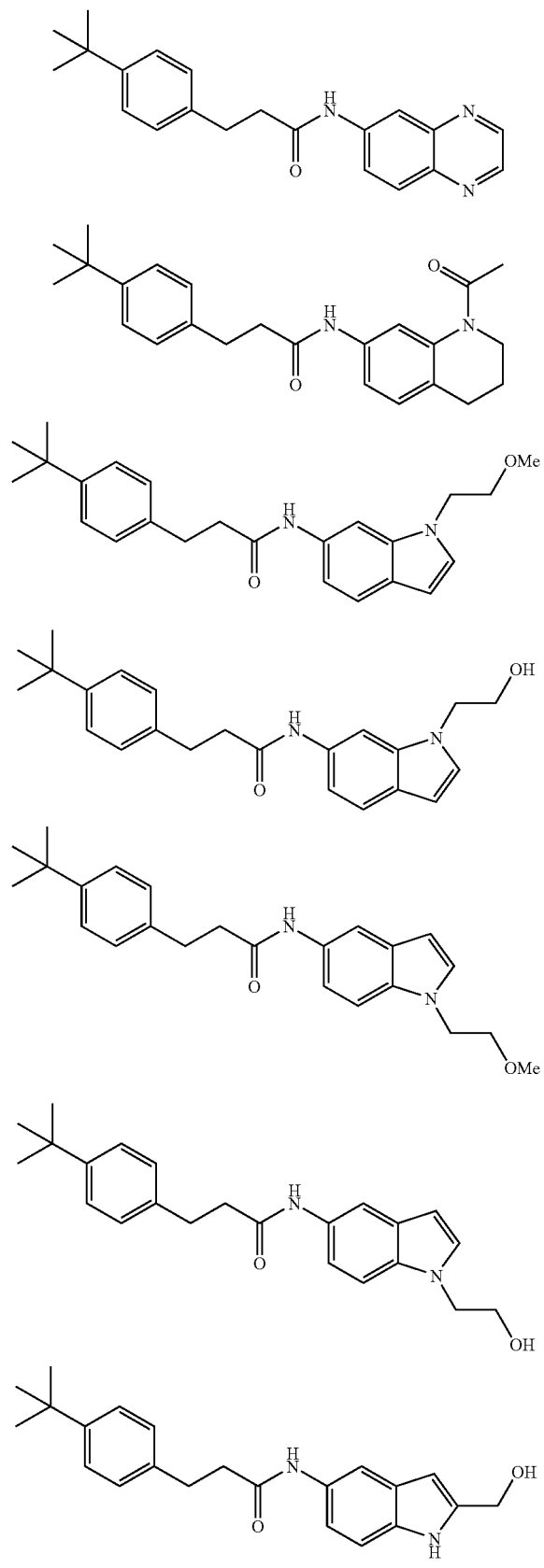
368
-continued
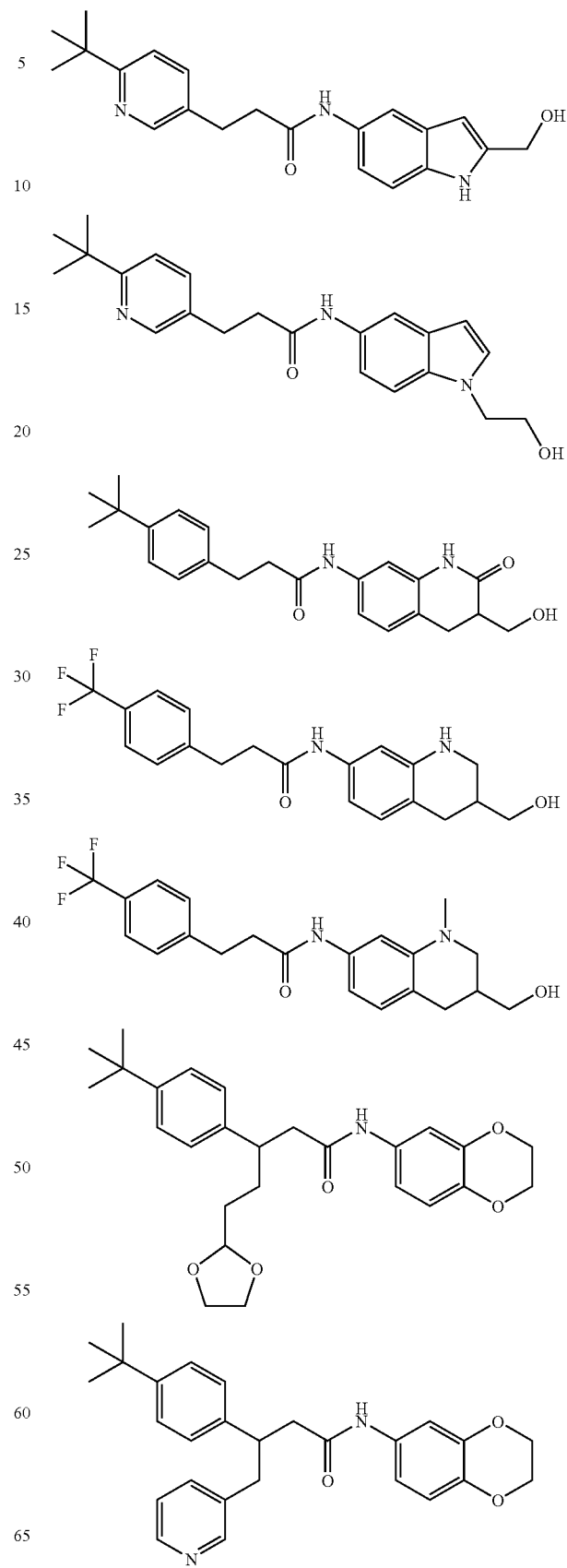

369
-continued
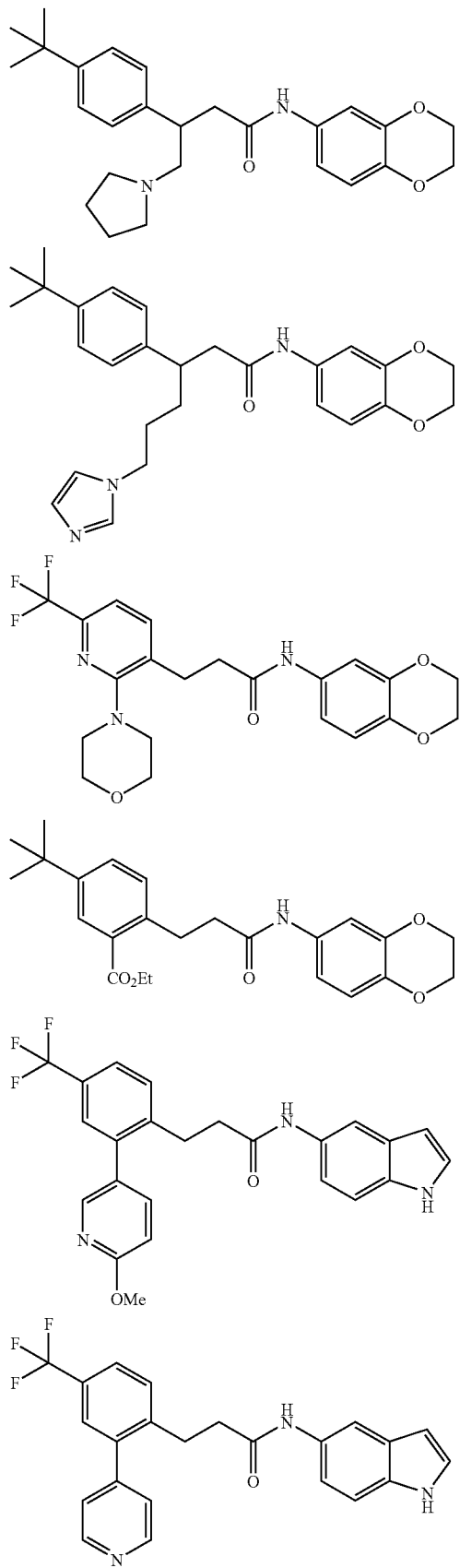
370
-continued
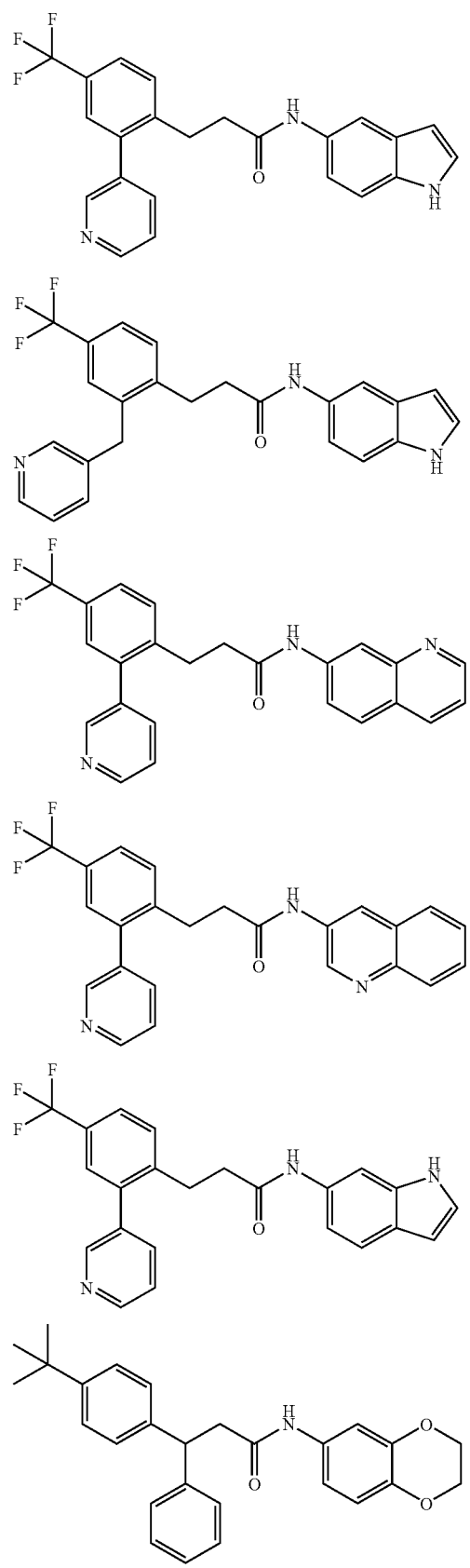

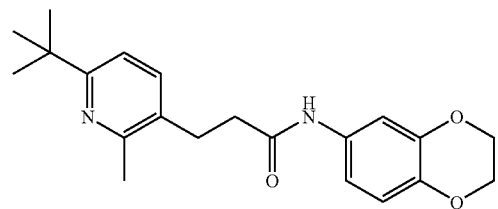
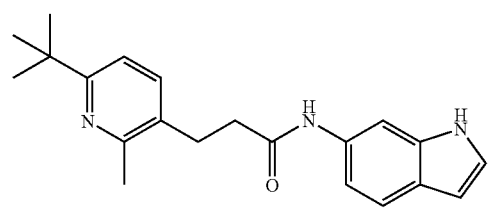
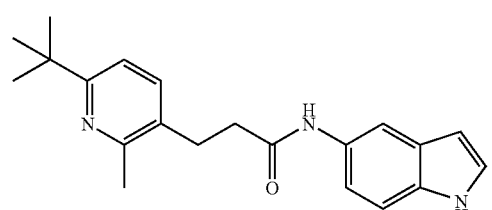
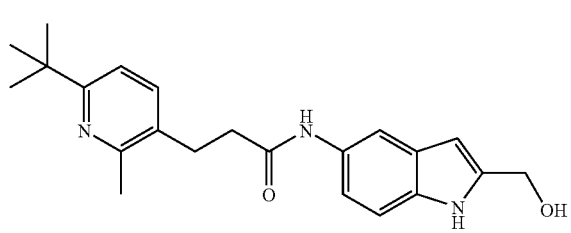
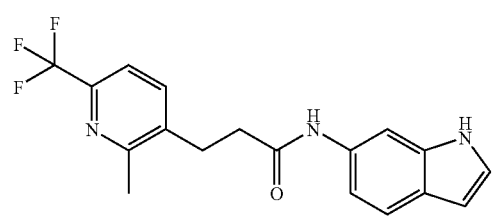
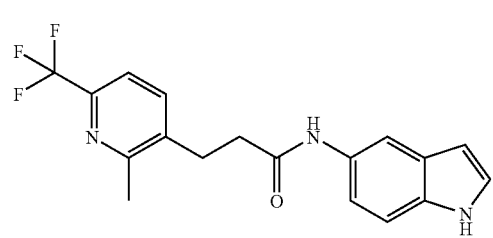
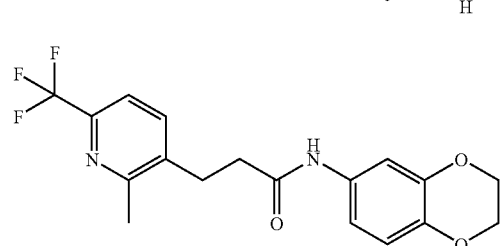
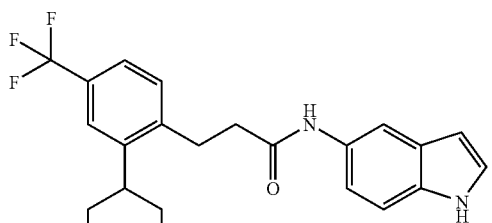
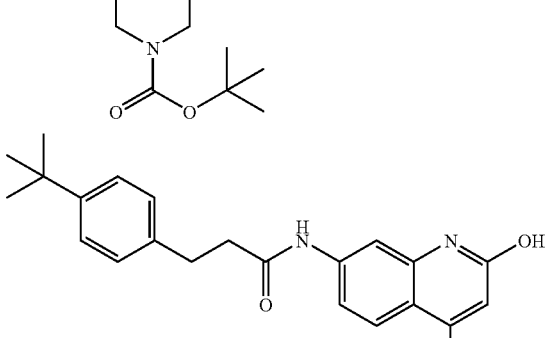
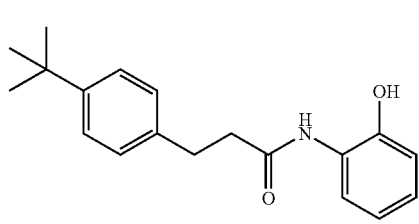
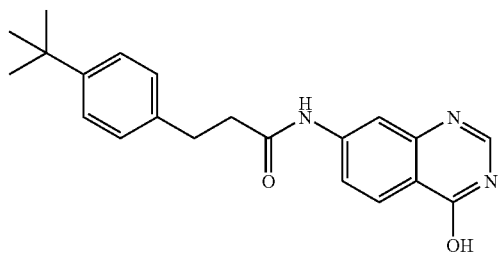
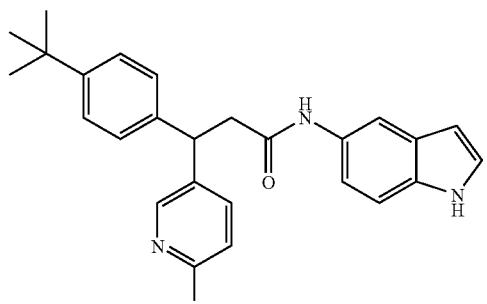
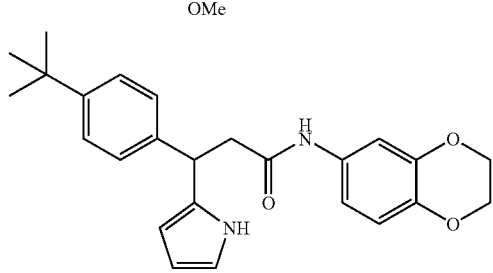

-continued
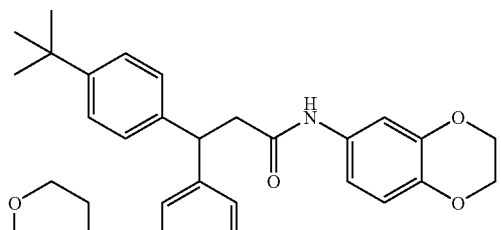
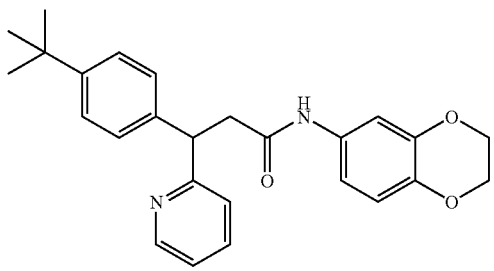
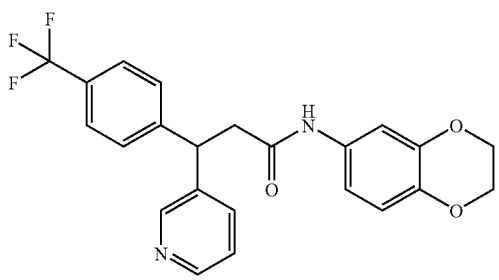
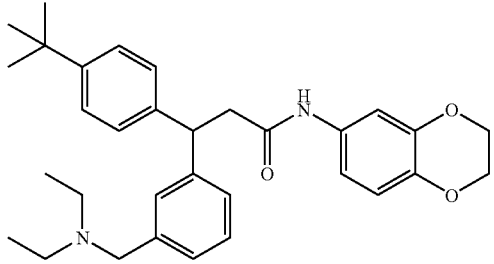
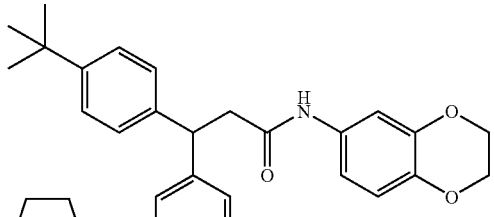
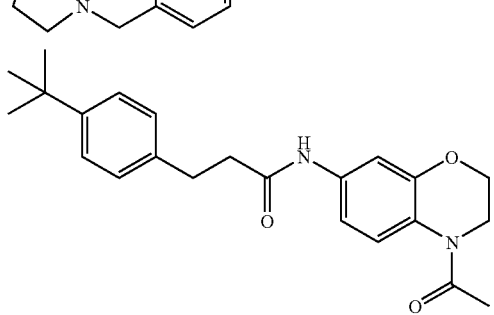
-continued
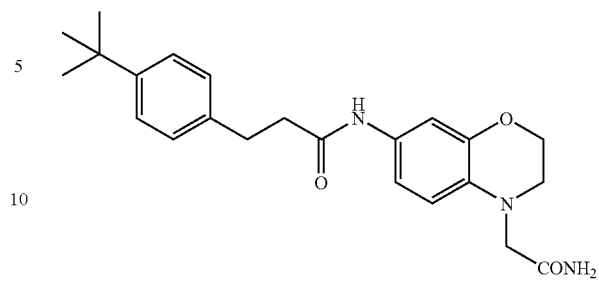
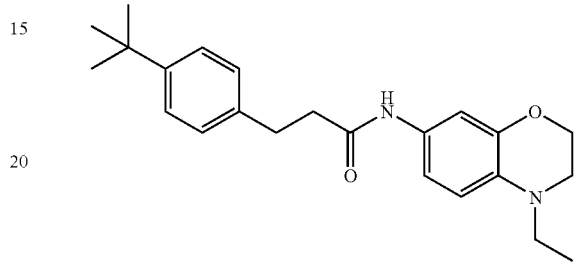
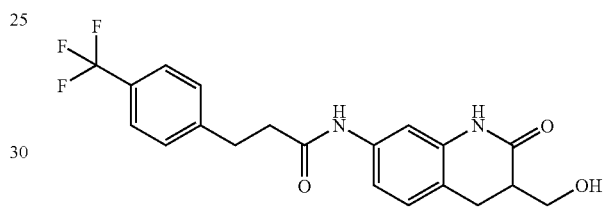
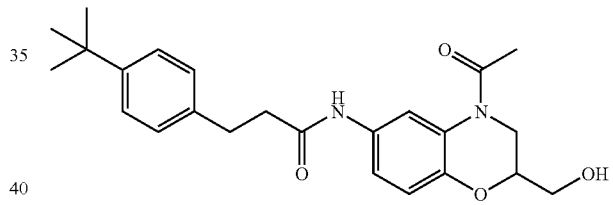
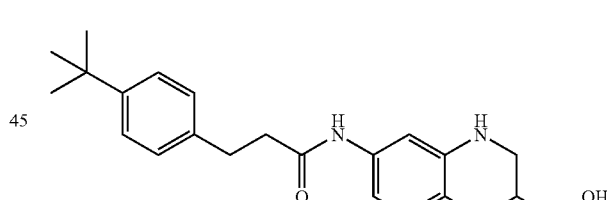
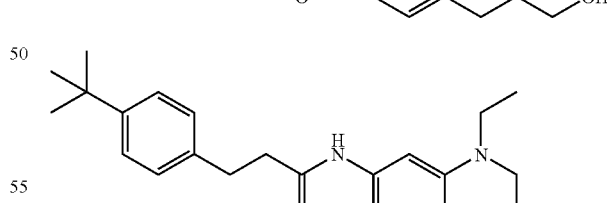
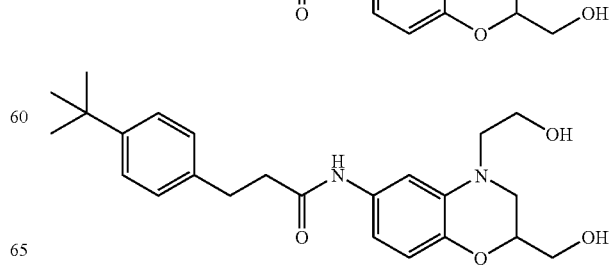

-continued
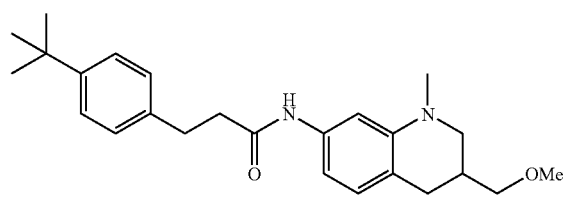
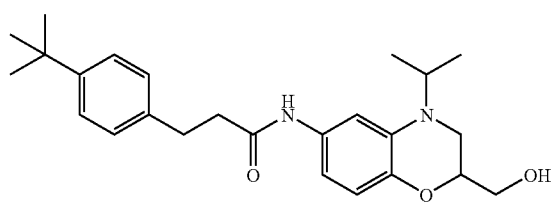
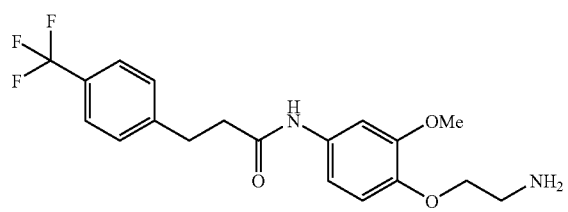
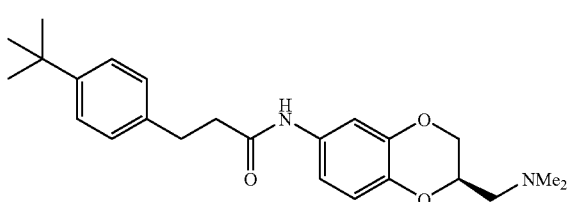
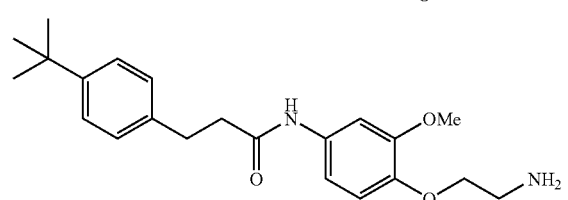
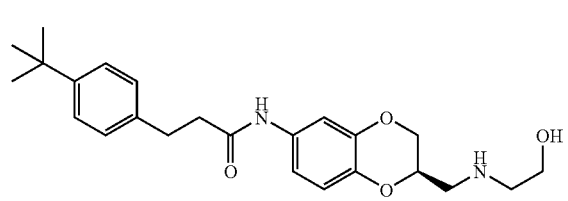
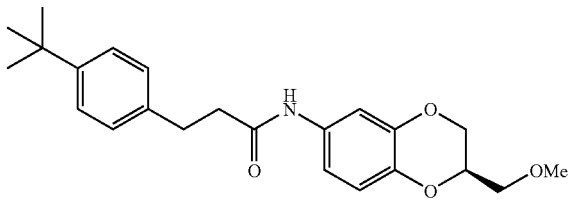
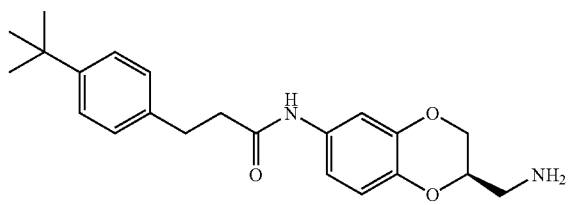
-continued
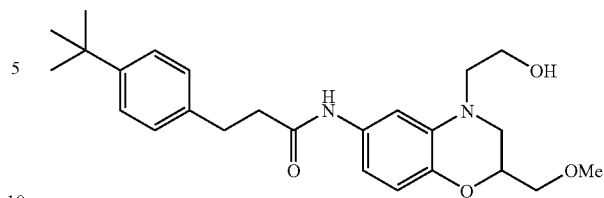
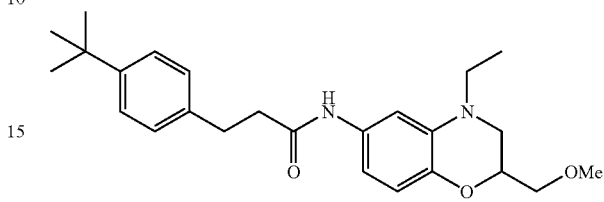
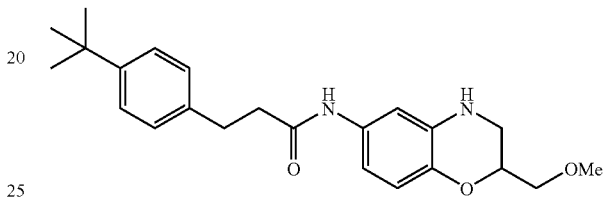
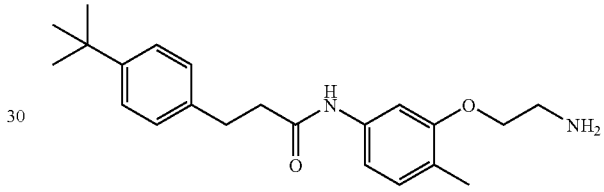
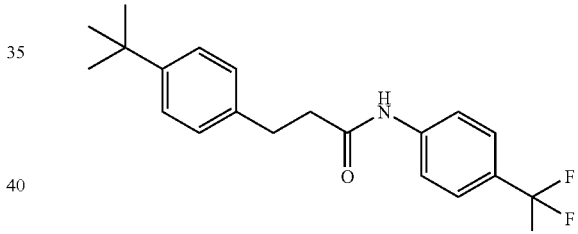
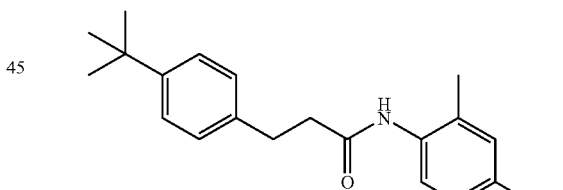
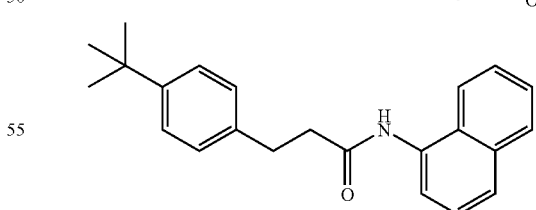
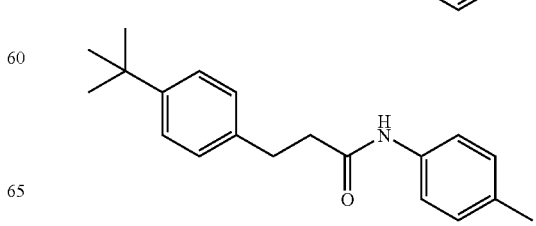

-continued
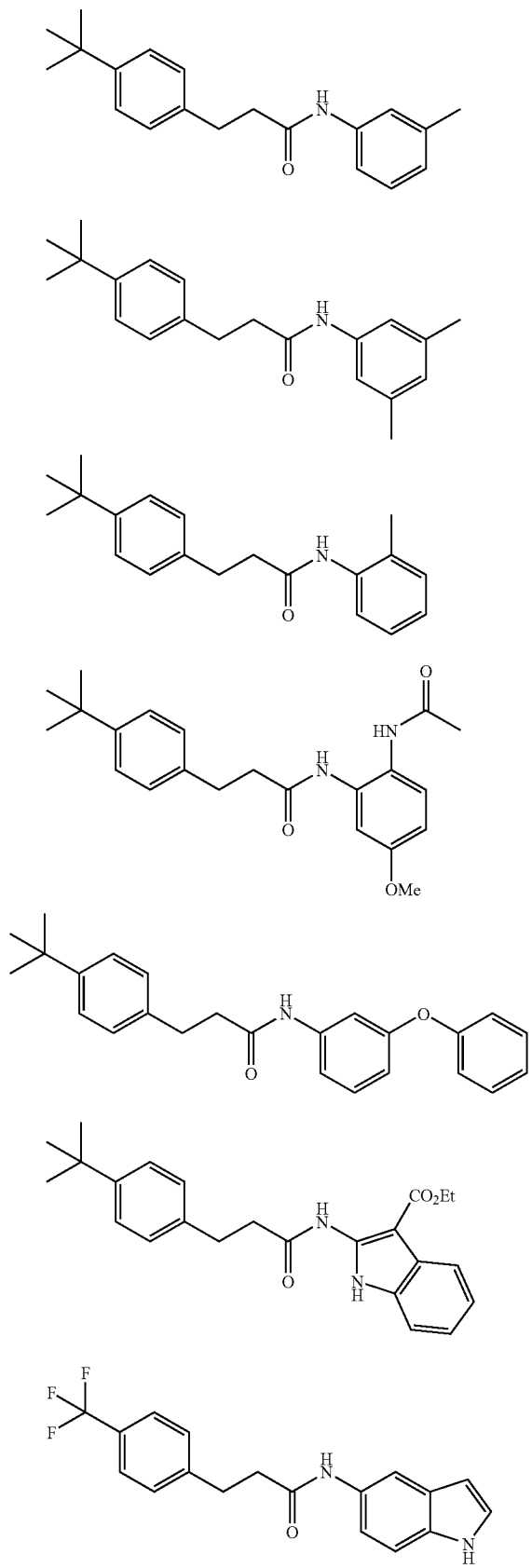
-continued
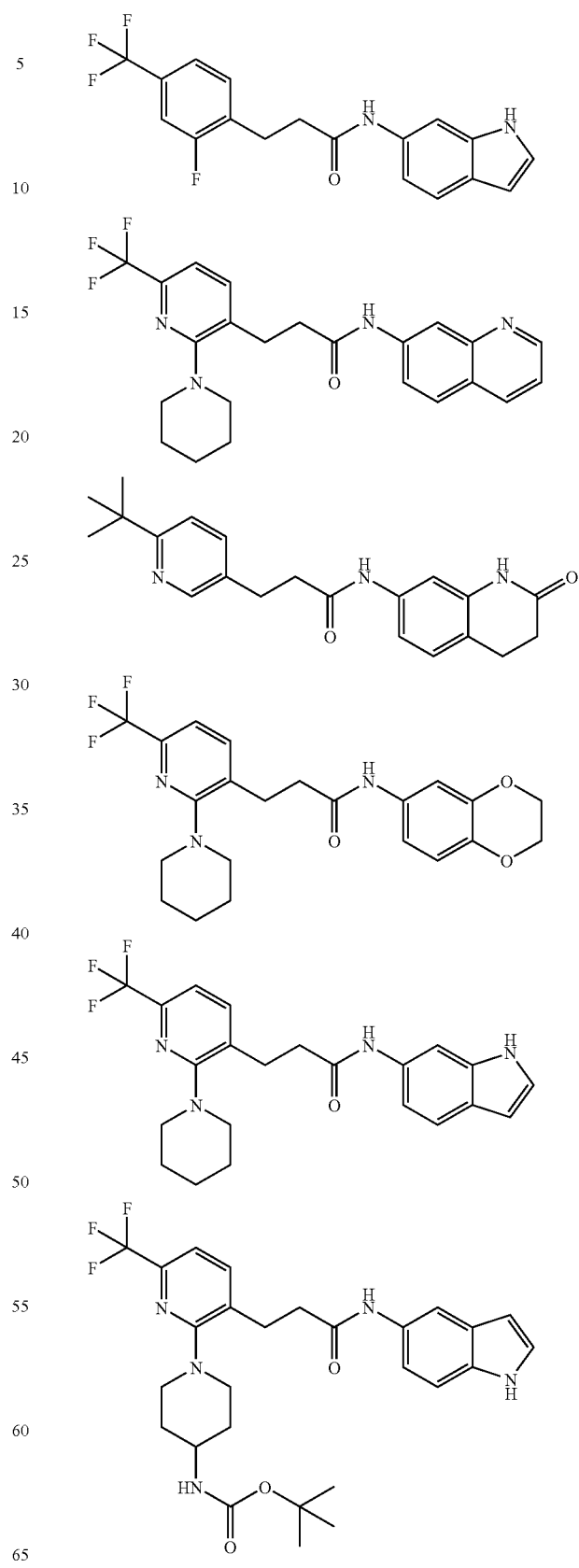

-continued
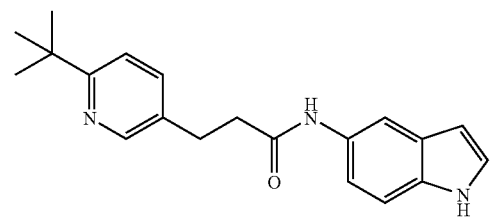
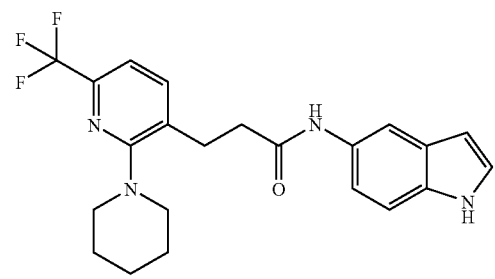
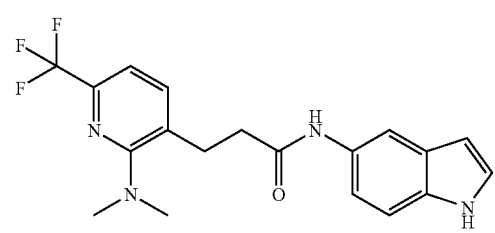
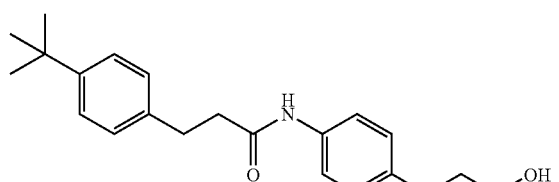
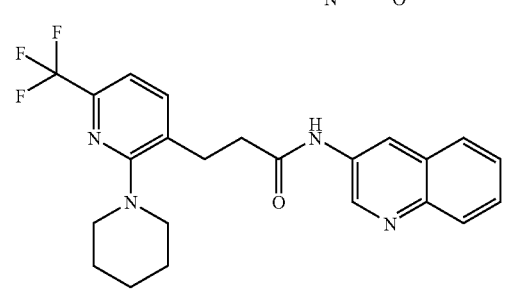
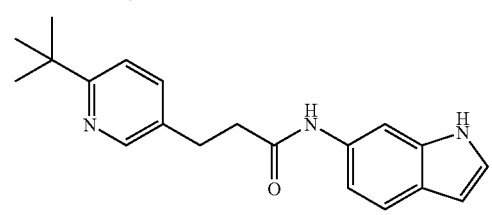
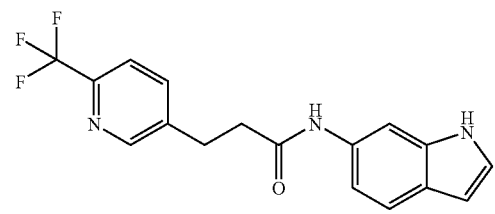
-continued
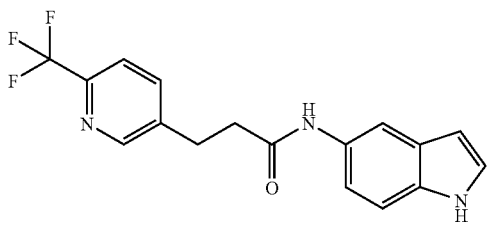
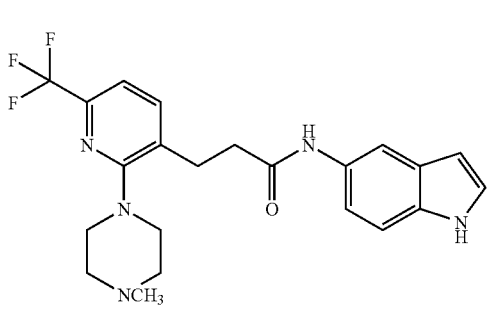
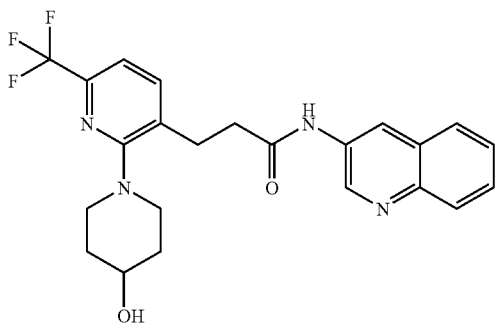
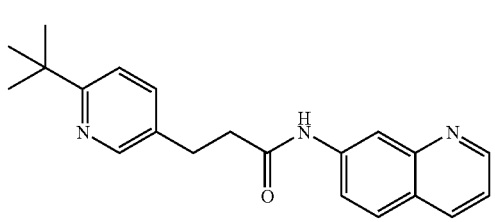
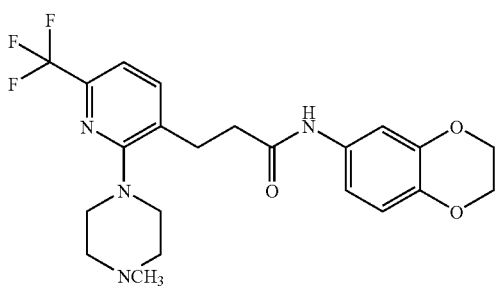
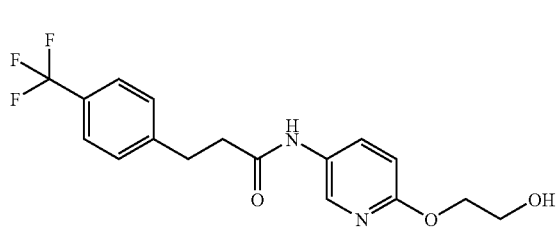

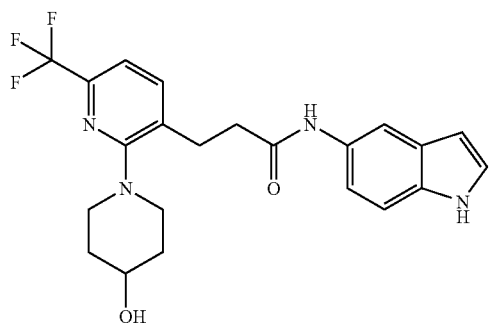
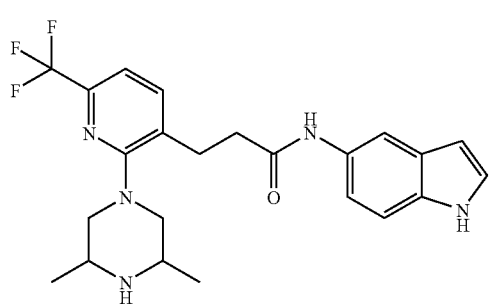
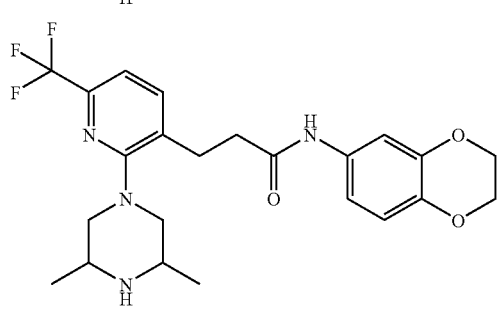
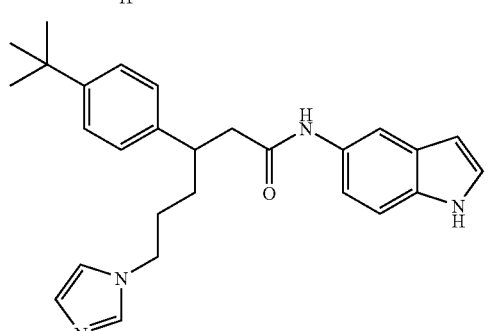
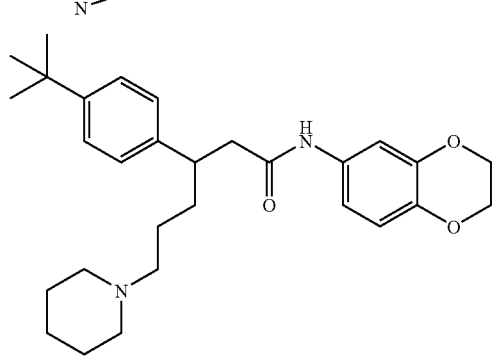
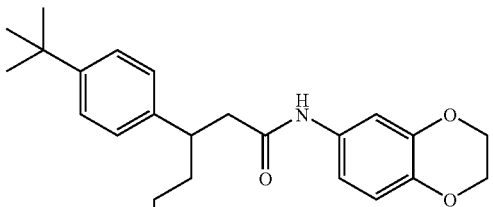
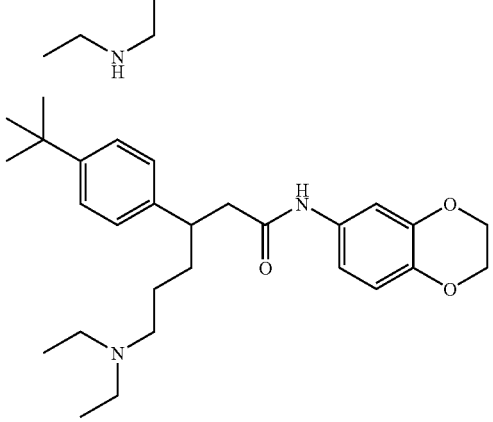
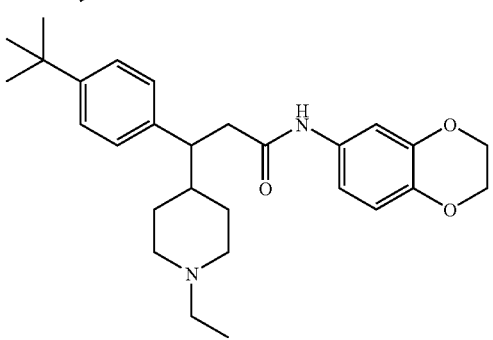
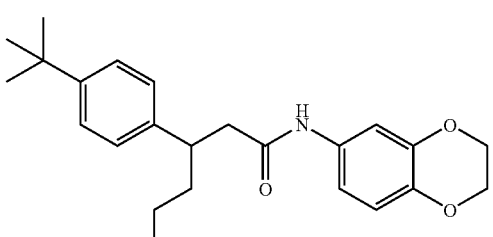
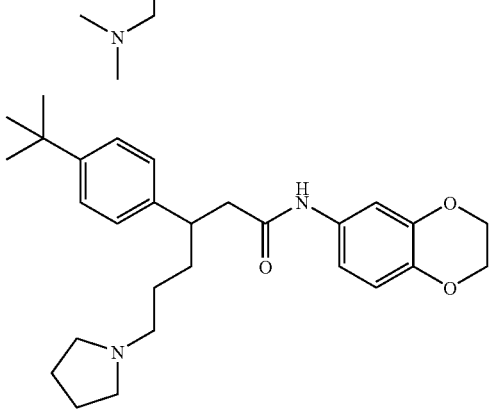

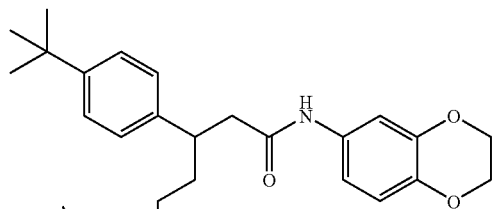
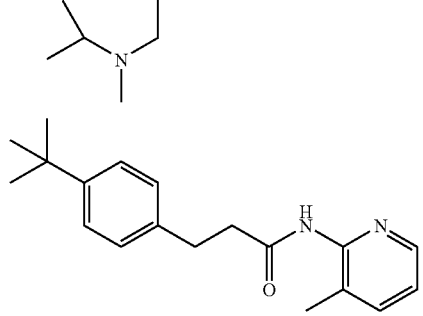
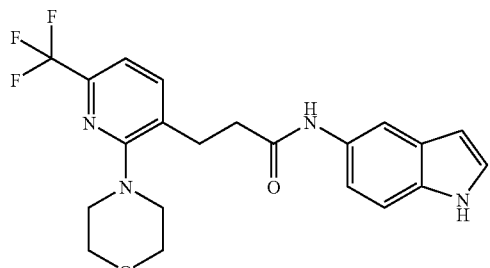
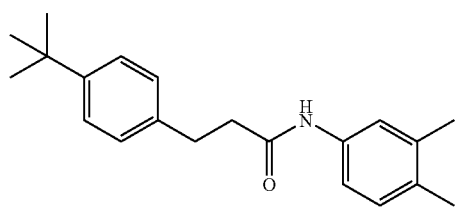
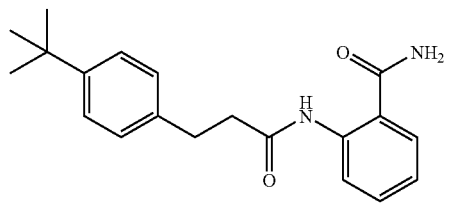
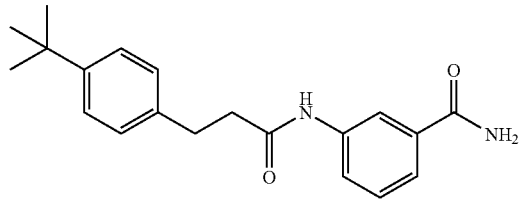
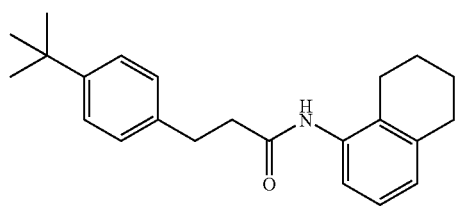
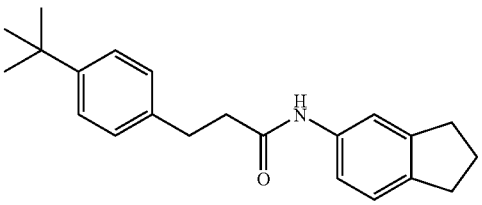
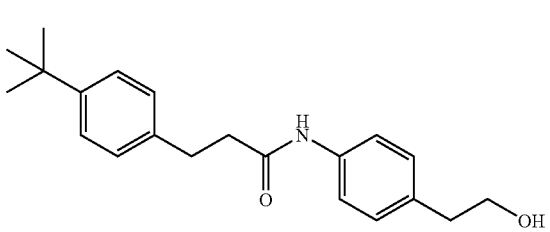
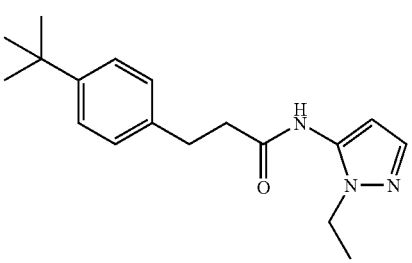
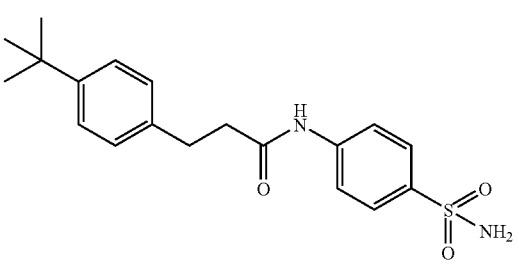
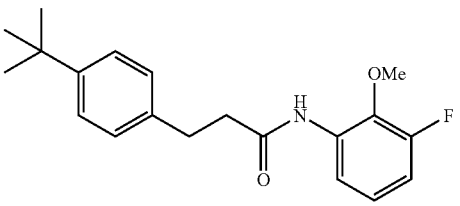
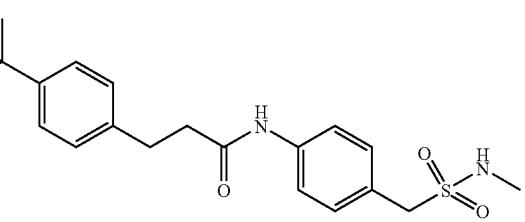
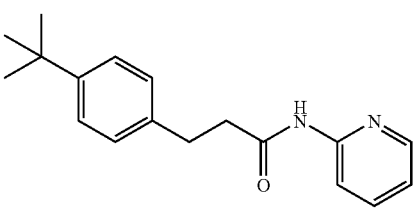

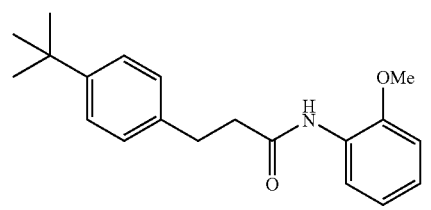
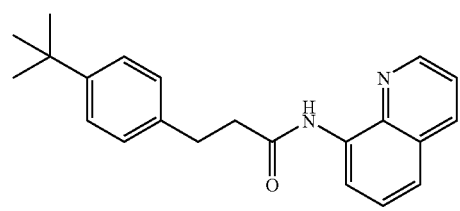
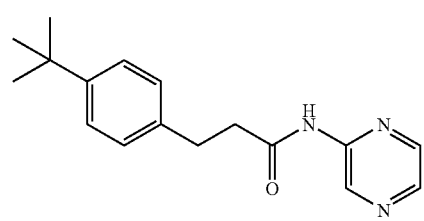
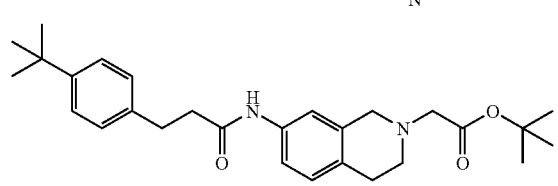
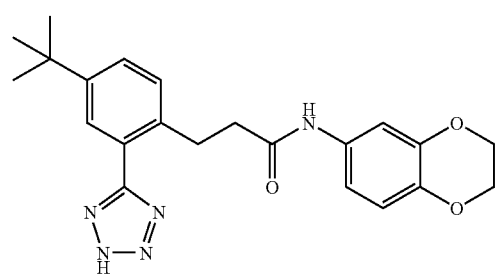
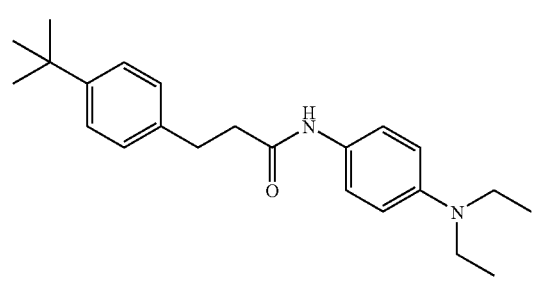
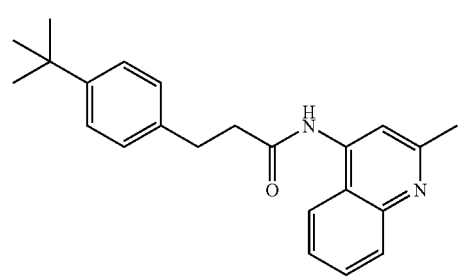
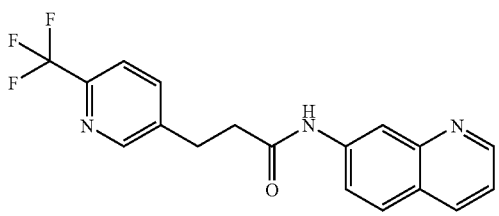
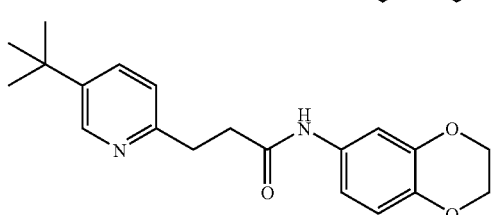
The following examples may also be made using the above generic schemes and synthetic examples:
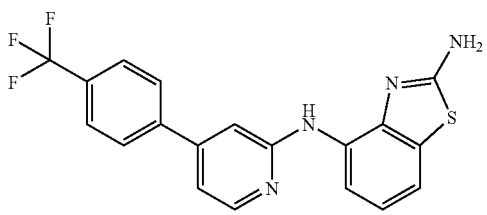
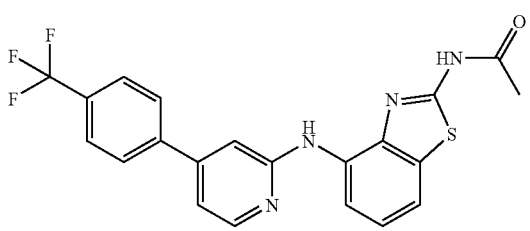
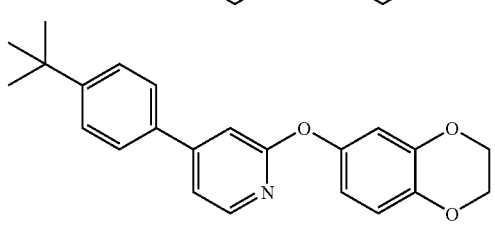
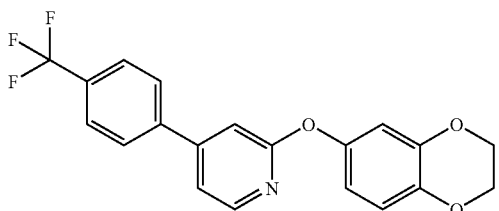
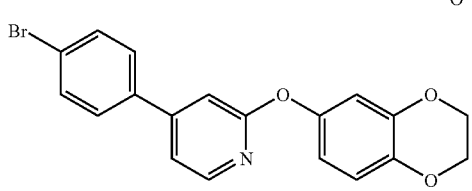

-continued

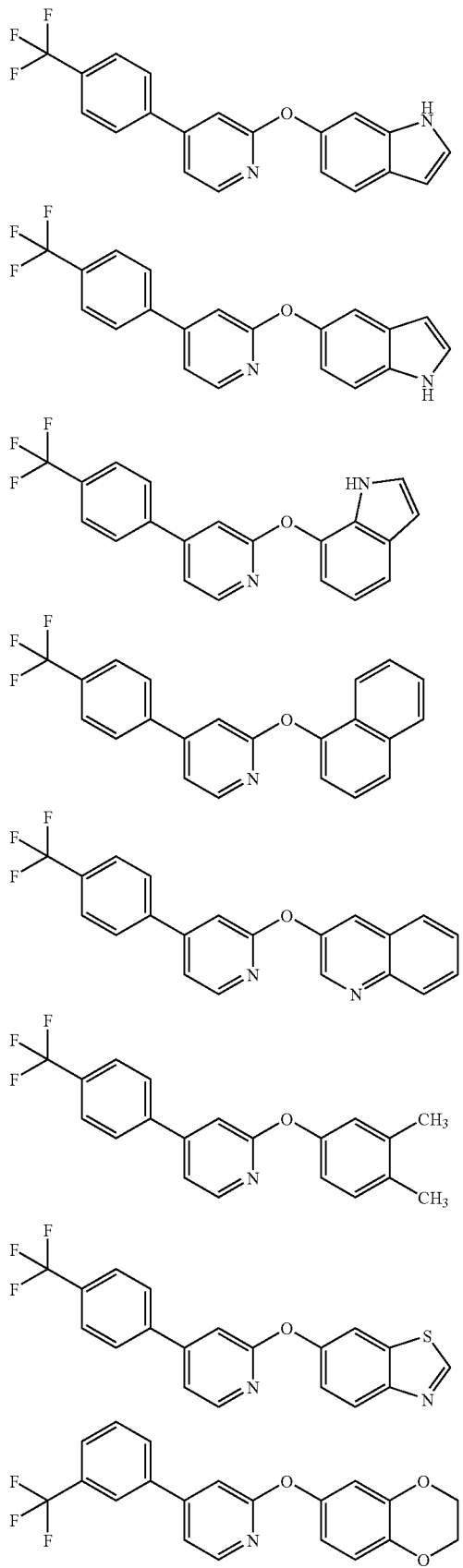

-continued

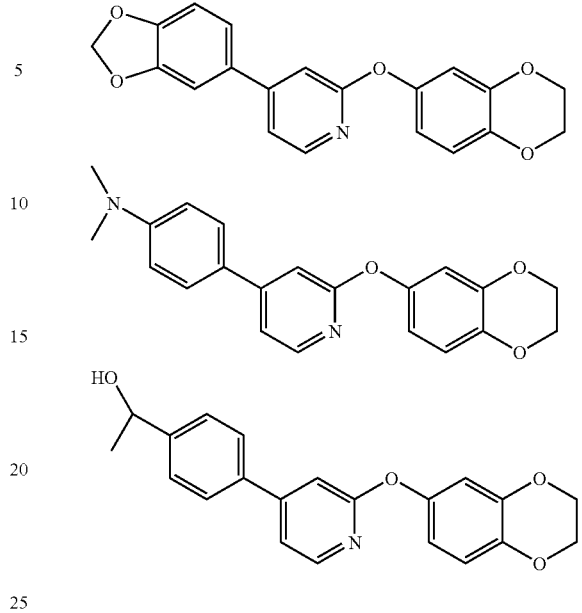

Capsaicin-Induced $Ca^{2+}$ Influx in Primary Dorsal Root Ganglion neurons

Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for 6 min to remove cell debris; and filtered through a 88-µm nylon mesh (Fisher Scientific, Pittsburgh, Pa.) to remove any clumps. Cell number was determined with a hemocytometer and cells were seeded into poly-ornithine 100 µg/ml (Sigma) and mouse laminin 1 µg/ml (Life Technologies)-coated 96-well plates at $10 \times 10^3$ cells/well in complete medium. The complete medium consists of minimal essential medium (MEM) and Ham's F12, 1:1, penicillin (100 U/ml), and streptomycin (100 µg/ml), and nerve growth factor (10 ng/ml), 10% heat inactivated horse serum (Life Technologies). The cultures were kept at 37° C., 5% $CO_2$ and 100% humidity. For controlling the growth of non-neuronal cells, 5-fluoro-2═-deoxyuridine (75 µM) and uridine (180 µM) were included in the medium. Activation of VR1 was achieved in these cellular assays using either a capsaicin stimulus (ranging from 0.01-10 µM) or by an acid stimulus (addition of 30 mM Hepes/Mes buffered at pH 4.1). Compounds were also tested in an assay format to evaluate their agonist properties at VR1. The activation of VR1 is followed as a function of cellular uptake of radioactive calcium ($^{45}Ca^{2+}$:Amersham CES3-2 mCi). Capsaicin Antagonist Assay: E-19 DRG cells at 3 days in culture are incubated with serial concentrations of VR1 antagonists, in HBSS (Hanks buffered saline solution supplemented with BSA 0.1 mg/ml and 1 mM Hepes at pH 7.4) for 15 min, room temperature. Cells are then challenged with a VR1 agonist, capsaicin (500 nM), in activation buffer containing 0.1 mg/ml BSA, 15 mM Hepes, pH 7.4, and 10 µCi/ml $^{45}Ca^{2+}$ (Amersham CES3-2 mCi) in Ham's F12 for 2 min at room temperature.

Acid Antagonist Assay: Compounds are pre-incubated with E-19 DRG cells at room temperature for 2 minutes prior to addition of $^{45}Ca^{2+}$ in 30 mM Hepes/Mes buffer (Final Assay pH 5) and then left for an additional 2 minutes prior to compound washout. Final concentration of $^{45}Ca^{2+}$ (Amersham CES3-2 mCi) is 10 µCi/mL.

Agonist Assay: Compounds are incubated with E-19 DRG cells at room temperature for 2 minutes in the presence of $^{45}Ca^{2+}$ prior to compound washout. Final $^{45}Ca^{2+}$ (Amersham CES3-2 mCi) at 10 µCi/mL.

Compound Washout and Analysis: Assay plates are washed using an ELX405 plate washer (Bio-Tek Instruments Inc.) immediately after functional assay. Wash 3× with PBS, 0.1 mg/mL BSA. Aspirate between washes. Read plates using a MicroBeta Jet (Wallac Inc.). Compound activity is then calculated using appropriate computational algorithms.

$^{45}Calcium^{2+}$ Assay Protocol

Compounds may be assayed using Chinese Hamster Ovary cell lines stably expressing either human VR1 or rat VR1 under a CMV promoter. Cells could be cultured in a Growth Medium, routinely passaged at 70% confluency using trypsin and plated in an assay plate 24 hours prior to compound evaluation.

Possible Growth Medium:
DMEM, high glucose (Gibco 11965-084).
10% Dialyzed serum (Hyclone SH30079.03).
1× Non-Essential Amino Acids (Gibco 11140-050).
1× Glutamine-Pen-Strep (Gibco 10378-016).
Geneticin, 450 µg/mL (Gibco 10131-035).

Compounds could be diluted in 100% DMSO and tested for activity over several log units of concentration [40 µM-2 pM]. Compounds may be further diluted in HBSS buffer (pH 7.4) 0.1 mg/mL BSA, prior to evaluation. Final DMSO concentration in assay would be 0.5-1%. Each assay plate could be controlled with a buffer only and a known antagonist compound (either capsazepine or one of the described VR1 antagonists).

Activation of VR1 could be achieved in these cellular assays using either a capsaicin stimulus (ranging from 0.1-1 µM) or by an acid stimulus (addition of 30 mM Hepes/Mes buffered at pH 4.1). Compounds could also be tested in an assay format to evaluate their agonist properties at VR1.

Capsaicin Antagonist Assay: Compounds may be pre-incubated with cells (expressing either human or rat VR1) at room temperature for 2 minutes prior to addition of $^{45}Ca^{2+}$ and Capsaicin and then left for an additional 2 minutes prior to compound washout. Capsaicin (200 nM) can be added in HAM's F12, 0.1 mg/mL BSA, 15 mM Hepes at pH 7.4. Final $^{45}Ca^{2+}$ (Amersham CES3-2 mCi) added could be 10 µCi/mL.

Acid Antagonist Assay: Compounds can be pre-incubated with cells (expressing either human or rat VR1) for 2 minutes prior to addition of $^{45}Ca^{2+}$ in 30 mM Hepes/Mes buffer (Final Assay pH 5) and then left for an additional 2 minutes prior to compound washout. Final $^{45}Ca^{2+}$ (Amersham CES3-2 mCi) added could be 10 µCi/mL.

Agonist Assay: Compounds can be incubated with cells (expressing either human or rat VR1) for 2 minutes in the presence of $^{45}Ca^{2+}$ prior to compound washout. Final $^{45}Ca^{2+}$ (Amersham CES3-2 mCi) added could be 10 µCi/mL. Compound Washout and Analysis: Assay plates would be washed using an ELX405 plate washer (Bio-Tek Instruments Inc.) immediately after the functional assay. One could wash 3× with PBS, 0.1 mg/mL BSA, aspirating between washes. Plates could then be read using a MicroBeta Jet (Wallac Inc.) and compound activity calculated using appropriate computational algorithms.

Useful nucleic acid sequences and proteins may be found in U.S. Pat. Nos. 6,335,180, 6,406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch.

Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalene-sulfonate, oxalate, palmoate, pectinate, persulfate, 2-phenyl-propionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one that is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, (x-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes, which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

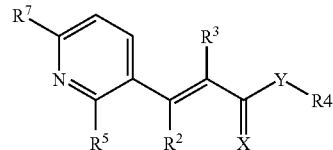

wherein:
$R^2$ is H;
$R^3$ is H or $C_{1-4}$alkyl;
(A) $R^4$ is

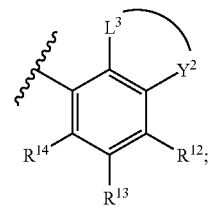

wherein
$L^3$ is a 2- or 3-atom, unsaturated, bridge containing 1, 2 or 3 carbon atoms and 1 atom independently selected from O, N and S, wherein the each of the carbon atoms in the bridge is substituted by H, =O, —$R^a$, —$C_{1-6}$alkylO$R^a$, —$C_{1-6}$alkyl, —C(=O)O$R^a$, —C(=O)N$R^aR^a$, —$C_{1-3}$alkylC(=O)O$R^a$, —$C_{1-3}$alkylC(=O)N$R^aR^a$, —OC(=O)$C_{1-6}$alkyl, —N$R^a$C(=O)$C_{1-6}$alkyl, —$C_{1-3}$alkylOC(=O)$C_{1-6}$alkyl or —$C_{1-3}$alkylN$R^a$C(=O)$C_{1-6}$alkyl, and any nitrogen atoms in the bridge are substituted by H, —$C_{1-6}$alkylO$R^a$, —$C_{1-6}$alkyl, —$C_{1-3}$alkylC(=O)O$R^a$, —$C_{1-3}$alkylC(=O)N$R^aR^a$, —$C_{1-3}$alkylOC(=O)$C_{1-6}$alkyl, —$C_{1-3}$alkylN$R^a$C(=O)$C_{1-6}$alkyl, —C(=O)$R^c$ or —$C_{1-3}$alkyl$R^c$;
$R^b$ is H, $C_{1-6}$alkyl, —C(=O)$C_{1-6}$alkyl, $C_{1-6}$alkyl-O—$R^a$; and
$Y^2$ is —N$R^b$— or —O—; or (B) R⁴ is

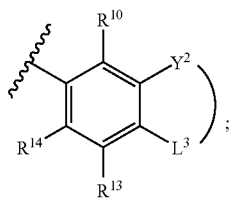

wherein
L³ is a 2- or 3-atom, unsaturated, bridge containing 1, 2 or 3 carbon atoms and 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;
R$^b$ is H, C$_{1-6}$alkyl, —C(=O)C$_{1-6}$alkyl, C$_{1-6}$alkyl-O—R$^a$; and
Y² is —NR$^b$— or —O—; or (C) R⁴ is

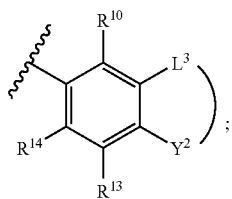

wherein
L³ is a 2- or 3-atom, unsaturated, bridge containing 1, 2 or 3 carbon atoms and 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;
R$^b$ is H, C$_{1-6}$alkyl, —C(=O)C$_{1-6}$alkyl, C$_{1-6}$alkyl-O—R$^a$; and
Y² is —NR$^b$— or —O—; and
R⁵ is independently, at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$^a$R$^a$, —O—C$_{1-6}$alkylOR$^a$, —NR$^a$R$^a$, —NR$^a$—C$_{1-4}$haloalkyl, —NR$^a$—C$_{1-6}$alkyl-NR$^a$R$^a$ or —NR$^a$—C$_{1-6}$alkylOR$^a$; or R⁵ is a saturated or unsaturated 5- or 6-membered ring heterocycle containing 1, 2 or 3 atoms selected from O, N and S;
R⁷ is tert-butyl or CF₃;

R¹⁰ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;
R¹² is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;
R¹³ is independently, at each instance, H, C$_{1-9}$alkyl, —C$_{1-3}$alkylOR$^a$, C$_{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;
R¹⁴ is independently, at each instance, H, C$_{1-9}$alkyl, —C$_{1-3}$alkylOR$^a$, C$^{1-4}$haloalkyl, halo, nitro, cyano, —OR$^a$, —S(=O)$_n$C$_{1-6}$alkyl, —O—C$_{1-4}$haloalkyl, —O—C$_{1-6}$alkylNR$^a$R$^a$, —O—C$_{1-6}$alkylOR$^a$, —O—C$_{1-6}$alkylC(=O)OR$^a$, —NR$^a$R$^a$, —NR$^a$—C$_{1-4}$haloalkyl, —NR$^a$—C$_{1-6}$alkylNR$^a$R$^a$, —NR$^a$—C$_{1-6}$alkylOR$^a$, —C(=O)C$_{1-6}$alkyl, —C(=O)OC$_{1-6}$alkyl, —OC(=O)C$_{1-6}$alkyl, —C(=O)NR$^a$C$_{1-6}$alkyl or —NR$^a$C(=O)C$_{1-6}$alkyl;
R$^a$ is independently, at each instance, H, phenyl, benzyl or C$_{1-6}$alkyl;
R$^b$ is H, C$_{1-6}$alkyl, —C(=O)C$_{1-6}$alkyl, C$_{1-6}$alkyl-O—R$^a$;
R$^c$ is phenyl substituted by 0, 1 or 2 groups selected from halo, C$_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, C$_{1-3}$haloalkyl, —OR$^a$ and —NR$^a$R$^a$;
X is O, S or NR$^a$;
Y is NH; and
n is independently, at each instance, 0, 1 or 2.
2. A compound according to claim 1, wherein:
R⁴ is

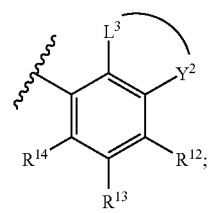

L³ is a 2- or 3-atom, unsaturated, bridge containing 1, 2 or 3 carbon atoms and 1 atom independently selected from O, N and S, wherein the each of the carbon atoms in the bridge is substituted by H, =O, —OR$^a$, —C$_{1-6}$alkylOR$^a$, C$_{1-6}$alkyl, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y² is —NR$^b$— or —O—.

3. A compound according to claim 1, wherein:
R⁴ is

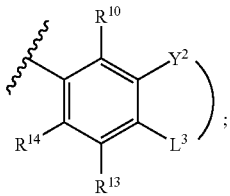

L³ is a 2- or 3-atom, unsaturated, bridge containing 1, 2 or 3 carbon atoms and 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y² is —NR$^b$— or —O—.

4. A compound according to claim 1, wherein:
R⁴ is

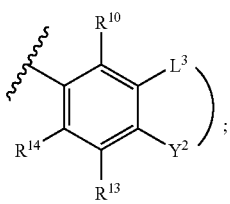

L³ is a 2- or 3-atom, unsaturated, bridge containing 1, 2 or 3 carbon atoms and 1 or 2 atoms independently selected from O, N and S, wherein the each of the carbon atoms in the bridge is substituted by H, =O, —OR$^a$, —C$_{1-6}$alkylOR$^a$, —C$_{1-6}$alkyl, —C(=O)OR$^a$, —C(=O)NR$^a$R$^a$, —C$_{1-3}$alkylC(=O)OR$^a$, —C$_{1-3}$alkylC(=O)NR$^a$R$^a$, —OC(=O)C$_{1-6}$alkyl, —NR$^a$C(=O)C$_{1-6}$alkyl, —C$_{1-3}$alkylOC(=O)C$_{1-6}$alkyl or —C$_{1-3}$alkylNR$^a$C(=O)C$_{1-6}$alkyl, and any nitrogen atoms in the bridge are substituted by H, —C$_{1-6}$alkylOR$^a$, —C$_{1-6}$alkyl, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^b$ is H, C$_{1-6}$alkyl, —C(=O)C$_{1-6}$alkyl, C$_{1-6}$alkyl-O—R$^a$; and

Y² is —NR$^b$— or —O—.

5. A pharmaceutical composition comprising a compound according to claim 1 and a pharmaceutically-acceptable diluent or carrier.

6. A compound having the structure

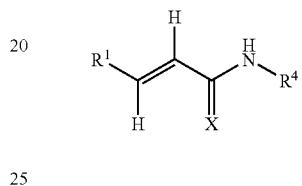

wherein:

X is O, S or NR$^m$;

n is independently, at each instance, 0, 1 or 2;

o is independently, at each instance, 0, 1, 2 or 3;

R$^m$ is independently at each instance H or R$^n$;

R$^n$ is independently at each instance C$_{1-8}$alkyl, phenyl or benzyl;

R$^q$ is independently in each instance H, C$_{1-4}$alkyl, C$_{1-4}$haloalkyl, halo, cyano, nitro, —C(=O)R$^n$, —C(=O)OR$^n$, —C(=O)NR$^m$R$^m$, —C(=NR$^m$)NR$^m$R$^m$, —OR$^m$, —OC(=O)R$^n$, —OC(=O)NR$^m$R$^m$, —OC(=O)N(R$^m$)S(=O)$_2$R$^n$, —OC$_{2-6}$alkylNR$^m$R$^m$, —OC$_{2-6}$alkylOR$^m$, —SR$^m$, —S(=O)R$^n$, —S(=O)$_2$R$^n$, —S(=O)$_2$NR$^m$R$^m$, —S(=O)$_2$N(R$^m$)C(=O)R$^n$, —S(=O)$_2$N(R$^m$)C(=O)OR$^n$, —S(=O)$_2$N(R$^m$)C(=O)NR$^m$R$^m$, —NR$^m$R$^m$, —N(R$^m$)C(=O)R$^n$, —N(R$^m$)C(=O)OR$^n$, —N(R$^m$)C(=O)NR$^m$R$^m$, —N(R$^m$)C(=NR$^m$)NR$^m$R$^m$, —N(R$^m$)S(=O)$_2$R$^n$, —N(R$^m$)S(=O)$_2$NR$^m$R$^m$, —NR$^m$C$_{2-6}$alkylNR$^m$R$^m$ or —NR$^m$C$_{2-6}$alkylOR$^m$;

R$^s$ is R$^n$ substituted by 0, 1, 2 or 3 substituents independently selected from R$^q$;

R⁵ is H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$^m$R$^m$, —O—C$_{1-6}$alkylOR$^m$, —NR$^m$R$^m$, —NR$^m$—C$_{1-4}$haloalkyl, —NR$^m$—C$_{1-6}$alkylNR$^m$R$^m$, —NR$^m$—C$_{1-6}$alkylOR$^m$, or —(CH$_2$)$_n$R$^c$ R⁶ is, independently at each instance, H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$^m$R$^m$, —O—C$_{1-6}$alkylOR$^m$, —NR$^m$R$^m$, —NR$^m$—C$_{1-4}$haloalkyl, —NR$^m$—C$_{1-6}$alkylNR$^m$R$^m$ or —NR$^m$—C$_{1-6}$alkylOR$^m$;

R⁸ is H, C$_{1-9}$alkyl, C$_{1-4}$haloalkyl, halo, nitro, cyano, —OC$_{1-6}$alkyl, —O—C$_{1-4}$haloalkyl, —O—C$_{1-6}$alkylNR$^m$R$^m$, —O—C$_{1-6}$alkylOR$^m$, —NR$^m$R$^m$, —NR$^m$—C$_{1-4}$haloalkyl, —NR$^m$—C$_{1-6}$alkylNR$^m$R$^m$ or —NR$^m$—C$_{1-6}$alkylOR$^m$; and (B) $R^1$ is

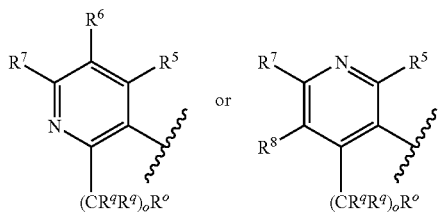

or $R^4$ is phenyl that is vicinally fused with a saturated or unsaturated 3- or 4-atom bridge containing 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)$_2$R″, —OC$_{2-6}$alkylOR′″, —SR′″, —S(=O)R″, —S(=O)$_2$R″, —S(=O)$_2$NR′″R′″, —S(=O)$_2$N(R′″)C(=O)R″, —S(=O)$_2$N(R′″)C(=O)OR″, —S(=O)$_2$N(R′″)C(=O)NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)$_2$R″, —N(R′″)S(=O)$_2$NR′″R′″, —NR′″C$_{2-6}$alkylOR′″, —C(=O)R$^s$, —C(=O)OR$^s$, —C(=O)NR′″R$^s$, —C(=NR′″)NR′″R$^s$, —OR$^s$, —OC(=O)R$^s$, —OC(=O)NR′″R$^s$, —OC(=O)N(R′″)S(=O)$_2$R$^s$, —OC$_{2-6}$alkylOR$^s$, —SR$^s$, —S(=O)R$^s$, —S(=O)$_2$R$^s$, —S(=O)$_2$NR′″R$^s$, —S(=O)$_2$N(R′″)C(=O)R$^s$, —S(=O)$_2$N(R′″)C(=O)OR$^s$, —S(=O)$_2$N(R′″)C(=O)NR′″R$^s$, —N(R′″)C(=O)R$^s$, —N(R′″)C(=O)OR$^s$, —N(R′″)C(=O)NR′″R$^s$, —N(R′″)C(=NR′″)NR′″R$^s$, —N(R′″)S(=O)$_2$R$^s$, —N(R′″)S(=O)$_2$NR′″R$^s$, —NR′″C$_{2-6}$alkylOR$^s$ and $C_{1-4}$alkyl substituted by 1 or 2 groups selected from $C_{1-2}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)$_2$R″, —OC$_{2-6}$alkylNR′″R′″, —OC$_{2-6}$alkylOR′″, —SR′″, —S(=O)R″, —S(=O)$_2$R″, —S(=O)$_2$NR′″R′″, —S(=O)$_2$N(R′″)C(=O)R″, —S(=O)$_2$N(R′″)C(=O)OR″, —S(=O)$_2$N(R′″)C(=O)NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)$_2$R″, —N(R′″)S(=O)$_2$NR′″R′″, —C(=O)R$^s$, —C(=O)OR$^s$, —C(=O)NR′″R$^s$, —C(=NR′″)NR′″R$^s$, —OR$^s$, —OC(=O)R$^s$, —OC(=O)NR′″R$^s$, —OC(=O)N(R′″)S(=O)$_2$R$^s$, —OC$_{2-6}$alkylOR$^s$, —SR$^s$, —S(=O)R$^s$, —S(=O)$_2$R$^s$, —S(=O)$_2$NR′″R$^s$, —S(=O)$_2$N(R′″)C(=O)R$^s$, —S(=O)$_2$N(R′″)C(=O)OR$^s$, —S(=O)$_2$N(R′″)C(=O)NR′″R$^s$, —N(R′″)C(=O)R$^s$, —N(R′″)C(=O)OR$^s$, —N(R′″)C(=O)NR′″R$^s$, —N(R′″)C(=NR′″)NR′″R$^s$, —N(R′″)S(=O)$_2$R$^s$, and —N(R′″)S(=O)$_2$NR′″R$^s$; and the ring and bridge carbon atoms are substituted with 0, 1 or 2 =O groups;

$R^7$ is tert-butyl or $CF_3$;

$R^o$ is a saturated, partially-saturated or unsaturated 5-, 6- or 7-membered monocyclic or 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, wherein the ring is substituted by 0, 1, 2 or 3 substituents independently selected from $R^p$; and $R^p$ is independently at each instance $C_{1-8}$alkyl, $C_{1-4}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)$_2$R″, —OC$_{2-6}$alkylNR′″R′″, —OC$_{2-6}$alkylOR′″, —SR′″, —S(=O)R″, —S(=O)$_2$R″, —S(=O)$_2$NR′″R′″, —S(=O)$_2$N(R′″)C(=O)R″, —S(=O)$_2$N(R′″)C(=O)OR″, —S(=O)$_2$N(R′″)C(=O)NR′″R′″, —NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)$_2$R″, —N(R′″)S(=O)$_2$NR′″R′″, —NR′″C$_{2-6}$alkylNR′″R′″ or —NR′″C$_{2-6}$alkylOR′″.

7. A compound according to claim 6, wherein $R^4$ is a phenyl ring that is vicinally fused with an unsaturated 3-atom bridge containing 1, 2 or 3 atoms selected from O, N and S with the remaining atoms being carbon, so long as the combination of O and S atoms is not greater than 2, wherein the ring and bridge are substituted by 0, 1, 2 or 3 substituents independently selected from $C_{1-8}$alkyl, $C_{1-4}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)$_2$R″, —OC$_{2-6}$alkylOR′″, —SR′″, —S(=O)R″, —S(=O)$_2$R″, —S(=O)$_2$NR′″R′″, —S(=O)$_2$N(R′″)C(=O)R″, —S(=O)$_2$N(R′″)C(=O)OR″, —S(=O)$_2$N(R′″)C(=O)NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)$_2$R″, —N(R′″)S(=O)$_2$NR′″R′″, —NR′″C$_{2-6}$alkylOR′″, —C(=O)R$^s$, —C(=O)OR$^s$, —C(=O)NR′″R$^s$, —C(=NR′″)NR′″R$^s$, —OR$^s$, —OC(=O)R$^s$, —OC(=O)NR′″R$^s$, —C(=O)N(R′″)S(=O)$_2$R$^s$, —OC$_{2-6}$alkylOR$^s$, —SR$^s$, —S(=O)R$^s$, —S(=O)$_2$R$^s$, —S(=O)$_2$NR′″R$^s$, —S(=O)$_2$N(R′″)C(=O)R$^s$, —S(=O)$_2$N(R′″)C(=O)OR$^s$, —S(=O)$_2$N(R′″)C(=O)NR′″R$^s$, —N(R′″)C(=O)R$^s$, —N(R′″)C(=O)OR$^s$, —N(R′″)C(=O)NR′″R$^s$, —N(R′″)C(=NR′″)NR′″R$^s$, —N(R′″)S(=O)$_2$R$^s$, —N(R′″)S(=O)$_2$NR′″R$^s$, —NR′″C$_{2-6}$alkylOR$^s$ and $C_{1-4}$alkyl substituted by 1 or 2 groups selected from $C_{1-2}$haloalkyl, halo, cyano, nitro, —C(=O)R″, —C(=O)OR″, —C(=O)NR′″R′″, —C(=NR′″)NR′″R′″, —OR′″, —OC(=O)R″, —OC(=O)NR′″R′″, —OC(=O)N(R′″)S(=O)$_2$R″, —OC$_{2-6}$alkylOR′″, —SR′″, —S(=O)R″, —S(=O)$_2$R″, —S(=O)$_2$NR′″R′″, —S(=O)$_2$N(R′″)C(=O)R″, —S(=O)$_2$N(R′″)C(=O)OR″, —S(=O)$_2$N(R′″)C(=O)NR′″R′″, —N(R′″)C(=O)R″, —N(R′″)C(=O)OR″, —N(R′″)C(=O)NR′″R′″, —N(R′″)C(=NR′″)NR′″R′″, —N(R′″)S(=O)$_2$R″, —N(R′″)S(=O)$_2$NR′″R′″, —C(=O)R$^s$, —C(=O)OR$^s$, —C(=O)NR′″R$^s$, —C(=NR′″)NR′″R$^s$, —OR$^s$, —OC(=O)R$^s$, —OC(=O)NR′″R$^s$, —OC(=O)N(R′″)S(=O)$_2$R$^s$, —OC$_{2-6}$alkylNR′″R$^s$, —OC$_{2-6}$alkylOR$^s$, —SR$^s$, —S(=O)R$^s$, —S(=O)$_2$R$^s$, —S(=O)$_2$NR′″R$^s$, —S(=O)$_2$N(R′″)C(=O)R$^s$, —S(=O)$_2$N(R′″)C(=O)OR$^s$, —S(=O)$_2$N(R′″)C(=O)NR′″R$^s$, —N(R′″)C(=O)R$^s$, —N(R′″)C(=O)OR$^s$, —N(R′″)C(=O)NR′″R$^s$, —N(R′″)C(=NR′″)NR′″R$^s$, —N(R′″)S(=O)$_2$R$^s$, and —N(R′″)S(=O)$_2$NR′″R$^{s,s}$, —NR′″C$_{2-6}$alkylOR$^s$ and —NR′″C$_{2-6}$alkylOR′″;

and the bridge carbon atoms are substituted with 0, 1 or 2 =O groups.

8. A pharmaceutical composition comprising a compound according to claim 6 and a pharmaceutically acceptable diluent or carrier.

9. A compound selected from the group of:
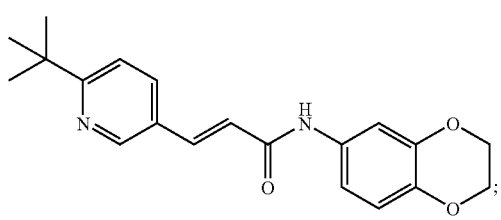
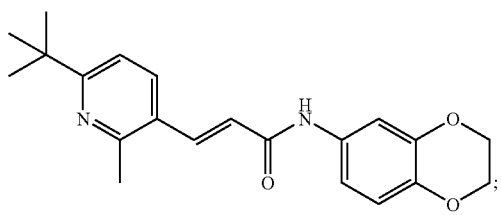
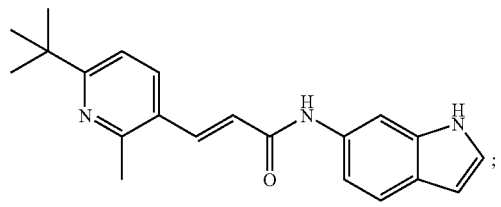
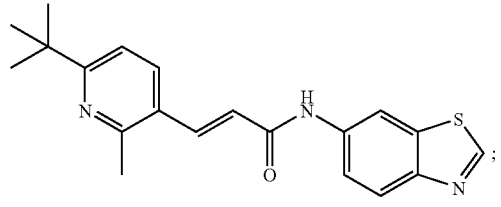
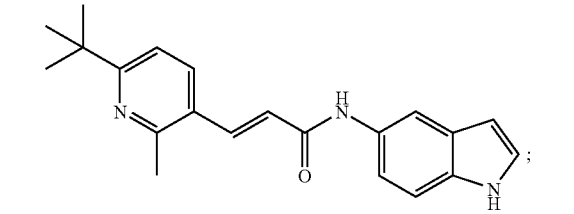
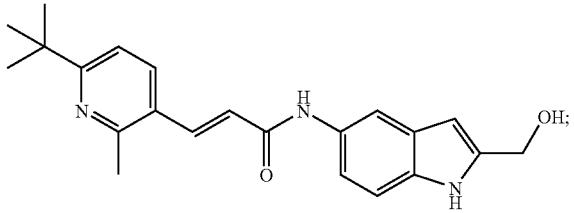
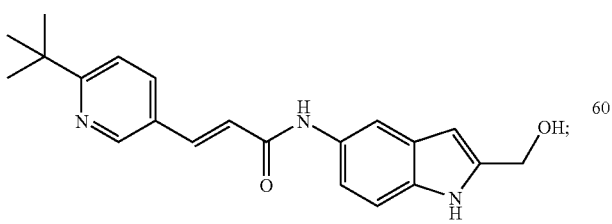
-continued
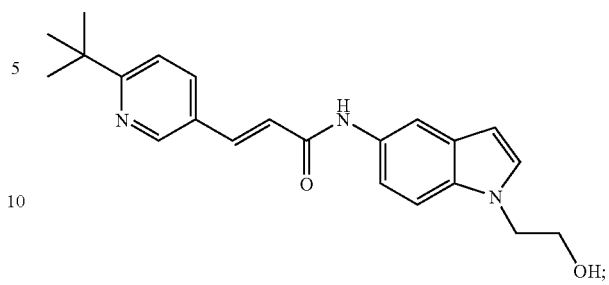
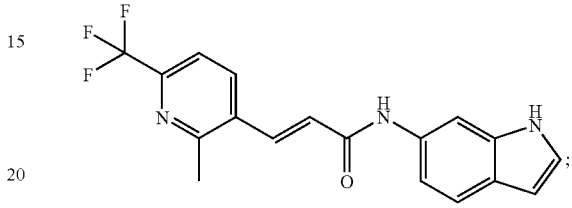
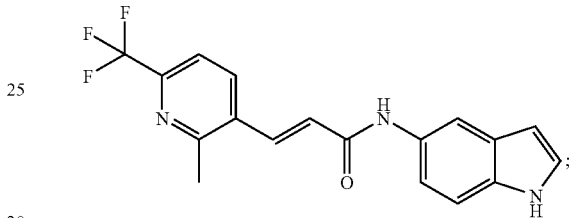
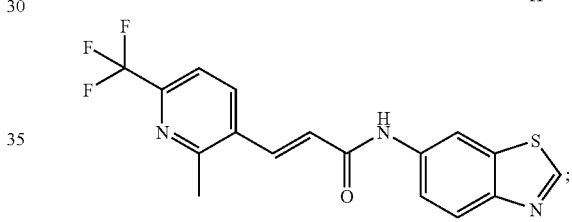
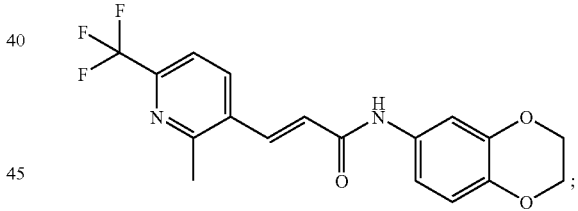
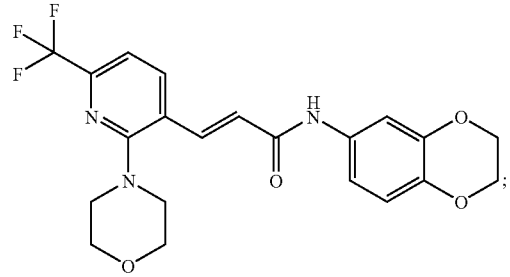
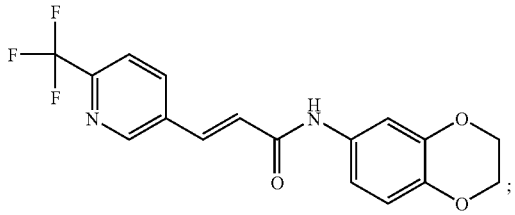

-continued
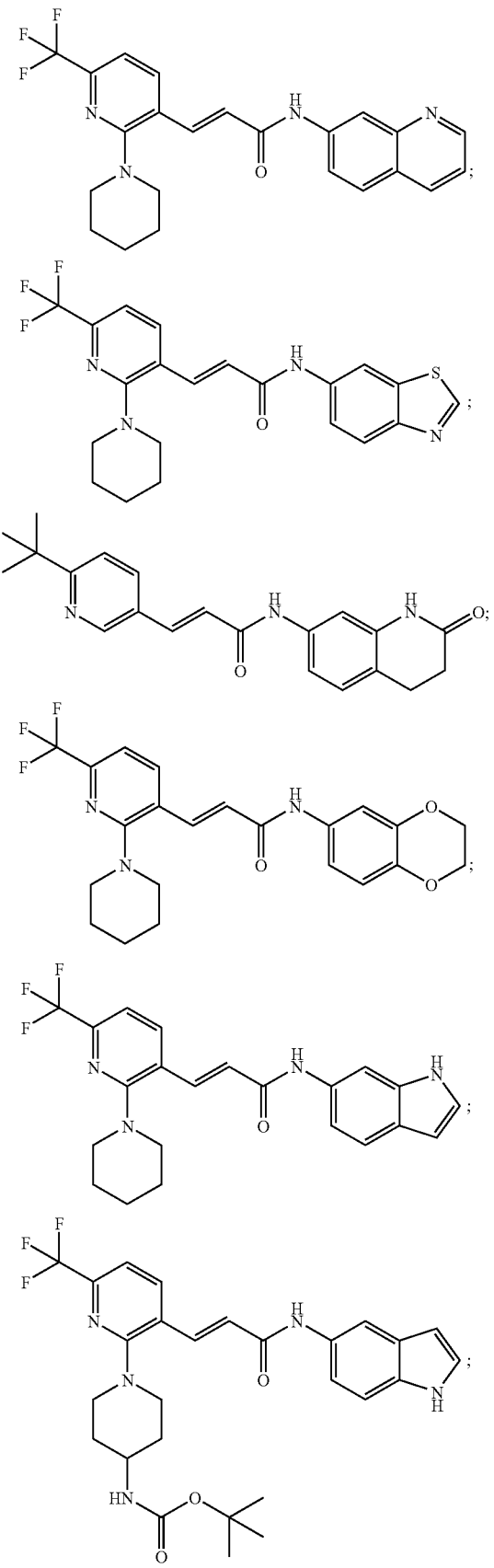
-continued
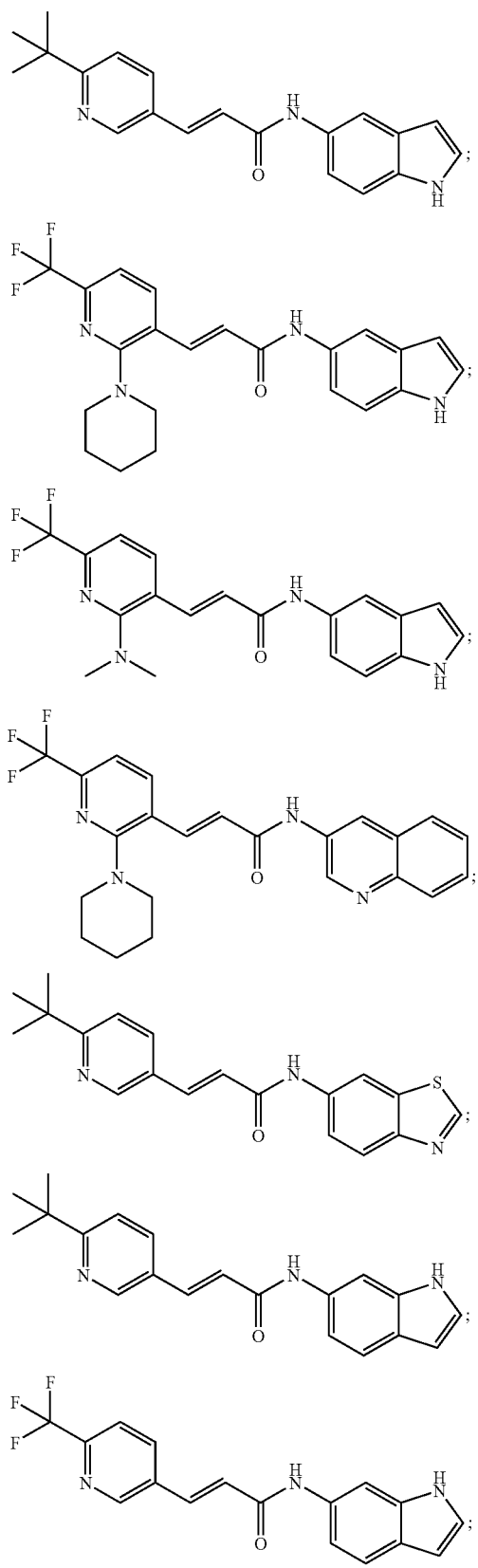

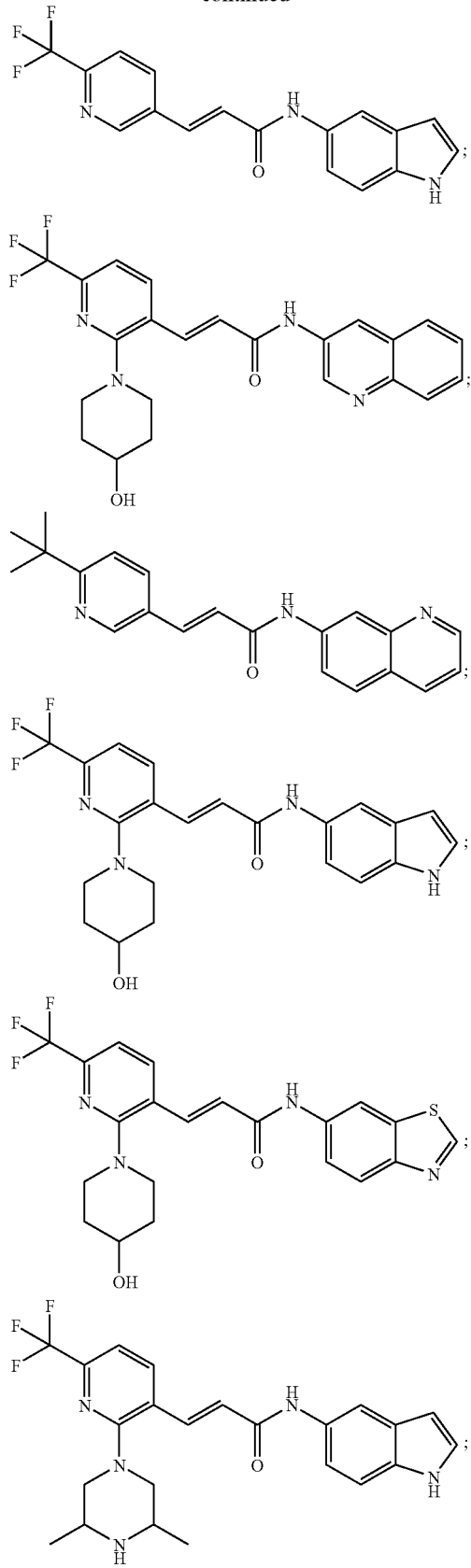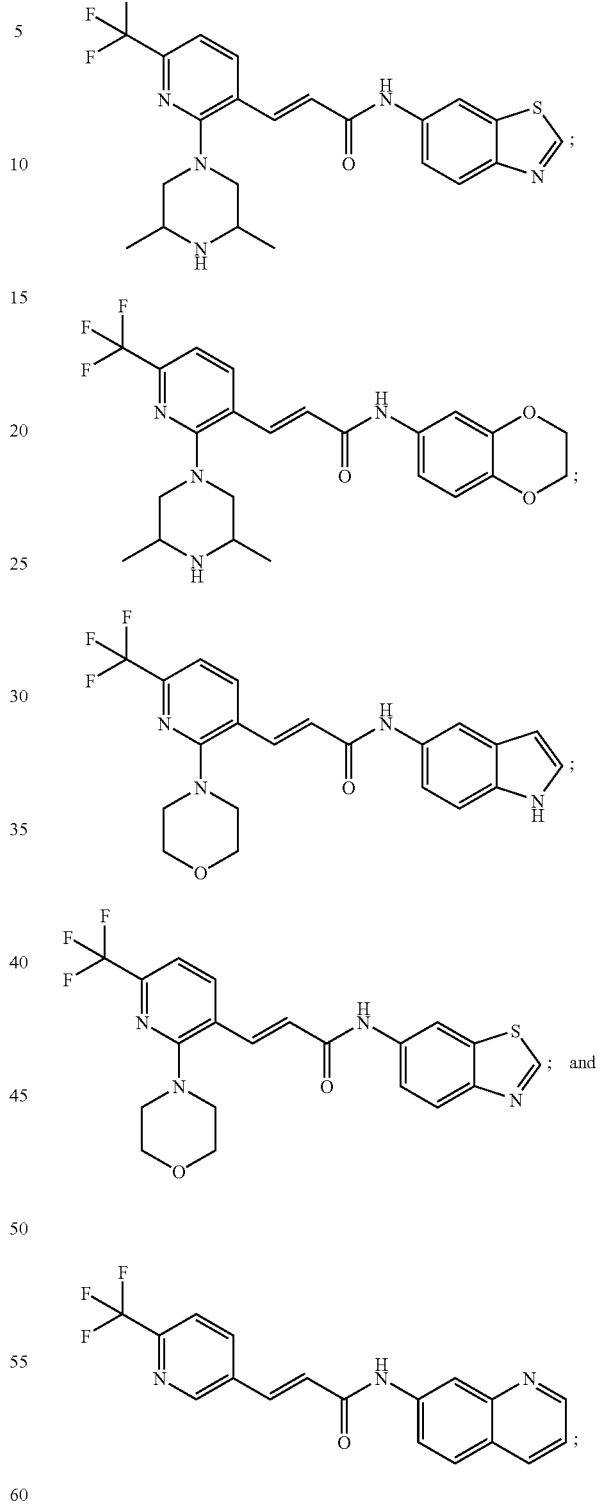
and any pharmaceutically-acceptable salts thereof.
* * * * *